US012643912B2

(12) United States Patent
Wéber et al.

(10) Patent No.: US 12,643,912 B2
(45) Date of Patent: Jun. 2, 2026

(54) MACROCYCLIC COMPOUNDS, A PROCESS FOR THEIR PREPARATION AND PHARMACEUTICAL COMPOSITIONS CONTAINING THEM

(71) Applicant: LES LABORATOIRES SERVIER, Suresnes Cedex (FR)

(72) Inventors: Csaba Wéber, Pilisszentlászló (HU); Klaus Seedorf, Hamburg (DE); Didier Durand, Chambourcy (FR); Márió Gyuris, Szeged (HU); Arpád Kiss, Budakalász (HU); Zoltán Madarász, Budapest (HU); Mark Molnár, Vâl (HU); Miklós Nyerges, Leányfalu (HU); Monika Rudasová, Budapest (HU); Attila Sápi, Hévízgyörk (HU); Sylvie Berger, Nanterre (FR); Valérie Duvivier, Orsay (FR); Virginie Martiny, Montgeron (FR); Isabelle Theret, Montesson (FR); Cédric Vinson, Olivet (FR)

(73) Assignee: LES LABORATOIRES SERVIER, Suresnes Cedex (FR)

( * ) Notice: Subject to any disclaimer, the term of this patent is extended or adjusted under 35 U.S.C. 154(b) by 820 days.

(21) Appl. No.: 17/904,514

(22) PCT Filed: Feb. 26, 2021

(86) PCT No.: PCT/EP2021/054780
§ 371 (c)(1),
(2) Date: Aug. 18, 2022

(87) PCT Pub. No.: WO2021/170774
PCT Pub. Date: Sep. 2, 2021

(65) Prior Publication Data

US 2023/0097678 A1 Mar. 30, 2023

(30) Foreign Application Priority Data

Feb. 28, 2020 (EP) .................................... 20305207

(51) Int. Cl.

| | |
|---|---|
| ***C07D 515/18*** | (2006.01) |
| ***A61K 9/20*** | (2006.01) |
| ***A61P 1/16*** | (2006.01) |
| ***A61P 3/10*** | (2006.01) |
| ***A61P 13/12*** | (2006.01) |

(52) U.S. Cl.
CPC .......... *C07D 515/18* (2013.01); *A61K 9/2009* (2013.01); *A61K 9/2013* (2013.01); *A61K 9/2018* (2013.01); *A61K 9/2054* (2013.01); *A61K 9/2059* (2013.01); *A61P 1/16* (2018.01); *A61P 3/10* (2018.01); *A61P 13/12* (2018.01)

(58) Field of Classification Search
CPC .................................................. C07D 515/18
See application file for complete search history.

(56) References Cited

FOREIGN PATENT DOCUMENTS

WO WO2015092733 6/2015

OTHER PUBLICATIONS

Ju, Organic Process Research and Development, 2014, vol. 18(6), pp. 827-830.*
Bartlett "Exploiting Chemical Diversity for Drug Discovery" Edited by Paul A Bartlett and Michael Entzeroth, The Royal Society of Chemistry, 2006, pp. 113-118.*
"Find ETDs Home » Thesis Resources » Find ETDs" Online: "https://ndltd.org/thesis-resources/find-etds/" Accessed Jan. 31, 2023.*
Irwin "ZINC—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
Registry/Zregistry (CAS Registrysm) Sep. 2016 2 pages.*
Dorwald F. A. Side Reactions in Organic Synthesis, 2005, Wiley: VCH, Weinheim p. IX of Preface p. 1-15.*
Venkatesh, J. Pharm. Sci. 89, 145-154 (2000) (p. 146, left column).*
J. G. Cannon, Chapter Nineteen in Burger's Medicinal Chemistry and Drug Discovery, Fifth Edition, vol. I: Principles and Practice, Wiley-Interscience 1995, pp. 783-802.*
International Search Report for PCT/EP2021/054788 dated Apr. 22, 2021.

* cited by examiner

*Primary Examiner* — Nizal S Chandrakumar
(74) *Attorney, Agent, or Firm* — HUESCHEN AND SAGE

(57) ABSTRACT

A compound of formula (I):

(I)

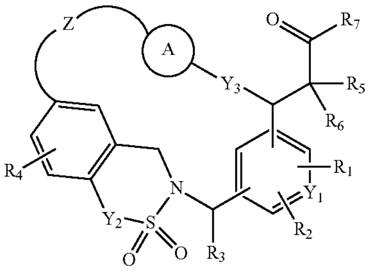

wherein Z, $Y_1$, $Y_2$,

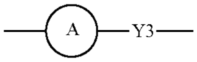

$R_1$ to $R_7$ are as defined in the description, its optical isomers, and addition salts thereof with a pharmaceutically acceptable base.
Medicaments.

5 Claims, No Drawings

MACROCYCLIC COMPOUNDS, A PROCESS FOR THEIR PREPARATION AND PHARMACEUTICAL COMPOSITIONS CONTAINING THEM

The present invention relates to new macrocyclic compounds, to a process for their preparation and to pharmaceutical compositions containing them.

The compounds of the present invention are new and have very valuable pharmacological characteristics.

BACKGROUND OF THE INVENTION

Nuclear factor erythroid 2-related factor 2 (Nrf2), also known as nuclear factor erythroid-derived 2-like 2, is a transcription factor that in humans is encoded by the NFE2L2 gene (Moi P, Chan K, Asunis I, Cao A, Kan Y W 1994. Proceedings of the National Academy of Sciences of the United States of America. 91 (21): 9926-30). Nrf2 is a basic leucine zipper (bZIP) protein that regulates and coordinates the basal and stress-inducible activation of a vast array of cytoprotective genes. Of particular importance in this regard is the transcription of components of the glutathione and thioredoxin antioxidant systems, as well as enzymes involved in phase I and phase II detoxification of exogenous and endogenous products, NADPH regeneration, and heme metabolism. As such, Nrf2 represents a crucial regulator of the cellular defense mechanisms against xenobiotic and oxidative stress (Vomund S, Schäfer, A, Parnham M J, Brüne B, and von Knethen A Int J Mol Sci. 2017 December; 18(12): 2772; Bischof L J M, Isoude A. Kuijperl Schimming J P, Wolters L, ter Braak B, Langenberg J P, Noort D, Beltman J B and van de Water B Archives of Toxicology (2019) 93:435-451). Of similar importance, Nrf2 is involved and modulating crucial cellular processes such as inflammation, autophagy, glucose and lipid metabolism, stem cell quiescence, and the unfolded protein response (reviewed in Yamamoto M, Kensler T W, Motohashi H (2018). Physiol Rev 98:1169-1203; Ahmed S M U, Luo L, Namani A, Wang X J, Tang X Biochimica et Biophysica Acta 1863 (2017) 585-597; Hayes J D and Dinkova-Kostova A T, Trends in Biochemical Sciences, vol. 39, no. 4, pp. 199-218, 2014).

Since alterations of these fundamental physiological processes are closely link to numerous diseases, the regulatory system of Nrf2 activity turned out to be an attractive drug target for a number of important medical indications such as metabolic, cardiovascular, neurodegenerative and autoimmune diseases (reviewed in Cuadrado A, Rojo A I, Wells G, Hayes J D, Cousin S P, Rumsey W L, ttucks O C, Franklin S, Levonen A-L, Kensler T W and Dinkova-Kostova A T Nature Reviews Drug Discovery 2019 volume 18, pages 295-317; Robledinos-Antón N, Fernández-Ginds R, Manda G, Cuadrado A. Oxid Med Cell Longev. 2019:9372182; Satta S, Mahmoud A M, Wilkinson F L, Alexander M Y and White S J. Oxidative Medicine and Cellular Longevity Volume 2017; Gao B., Doan A., Hybertson B. M. Clin. Pharmacol. 2014; 6:19-34).

Nrf2 is a crucial part of an evolutionarily conserved defense mechanism in mammals, and zebrafish, fruit fly and *Caenorhabditis elegans* have been shown to have similar anti-stress systems (reviewed by Fuse Y and Kobayashi M. Molecules. 2017 March; 22(3): 436). Nrf2 is ubiquitously and constitutively expressed in cells, thus ensuring their prompt protective response to oxidative, inflammatory, and metabolic stresses. The expression of Nrf2 is tightly regulated and under healthy/non-stressed conditions, low Nrf2 levels provide basal expression of its target genes. Under these conditions Nrf2 has a rapid turnover due to its constant degradation by the ubiquitin proteasome system (McMahon M, Thomas N, Itoh K, Yamamoto M, and Hayes J D, Journal of Biological Chemistry 2004 vol. 279, no. 30, pp. 31556-31567; Katoh Y, Iida K, Kang M I, Kobayashi A, Mizukami M, Tong K I, McMahon M, Hayes J D, Itoh K, Yamamoto M. Archives of Biochemistry and Biophysics, vol. 433, no. 2, pp. 342-350, 2005).

Degradation of Nrf2 is regulated through binding to KEAP1 (Kelch-like ECH-associated protein 1), an adapter protein of E3 ubiquitin ligase. In the presence of oxidative and xenobiotic stresses, Nrf2 degradation is blocked through liberation of Keap1, allowing Nrf2 accumulation and its translocation into the nucleus where it forms heterodimers with bZip proteins like small muscle aponeurosis fibromatosis (MAF) K, G, and F via the Neh1 containing CNC-bZIP domain (Ma Q. Annual Review of Pharmacology and Toxicology, vol. 53, no. 1, pp. 401-426, 2013; Hayes J D and Dinkova-Kostova A T, Trends in Biochemical Sciences, vol. 39, no. 4, pp. 199-218, 2014). In humans, these heterodimers directly regulate the expression of about 250 genes that present a regulatory enhancer sequence termed Antioxidant Response Element (ARE). These genes participate and regulate multiple homeostatic functions including redox homeostasis, detoxification, inflammation, proteostasis and metabolism (Pajares M, Jiménez-Moreno N, García-Yagüe A J et al., Autophagy 2016, vol. 12, no. 10, pp. 1902-1916; Pajares M, Cuadrado A, and Rojo A I, Redox Biology, 2017 vol. 11, pp. 543-553; Pajares M, Jiménez-Moreno N, Dias I H K et al., Redox Biology 2015, vol. 6, pp. 409-420; de la Vega M R, Dodson M, Gross C et al. Current Pharmacology Reports, vol. 2, no. 2, pp. 91-101, 2016).

KEAP1 harbors two discrete structural domains, the BTB (broad complex, tramtrack and bric-a-brac) domain in the N-terminal region and the double glycine repeat (DGR; also called the Kelch domain) in the C-terminal region (Itoh K, Wakabayashi N, Katoh Y, Ishii T, Igarashi K, Engel J D and Yamamoto M Genes Dev. 1999 Jan. 1; 13(1): 76-86). While the BTB domain contributes to the homodimerization of KEAP1 and its interaction with CUL3, the Kelch domain mediates KEAP1 binding to Nrf2 by interacting with the Neh2 domain. In this KEAP1-Nrf2 interaction, two specific motifs in the Neh2 domain of Nrf2, namely DLG and ETGE, individually bind to the Kelch domains of the KEAP1 homodimer. Identification of the two-site binding of the KEAP1 homodimer to Nrf2 led to propose the molecular mechanism of electrophilic stress sensing which has been described in detail by Tong et al. (Tong K I, Katoh Y, Kusunoki H, Itoh K, Tanaka T, Yamamoto M (2006) Mol Cell Biol 26:2887-2900; Tong K I, Padmanabhan B, Kobayashi A, Shang C, Hirotsu Y, Yokoyama S, Yamamoto M (2007). Mol Cell Biol 27:7511-7521. https://doi.org/10.1128/MCB.00753-072006) and reviewed in Yamamoto et al. (Yamamoto M, Kensler T W, Motohashi H (2018). Physiol Rev 98:1169-1203).

The intervening region (IVR) of KEAP1 resides between the BTB and the DGR/Kelch domains and is rich in reactive cysteine (Cys) residues that function as stress sensors. Twenty-seven and twenty-five Cys residues were identified in the human and mouse KEAP1 proteins, respectively. Among these, Cys151 in BTB domain and Cys273/288 in IVR are major sensor cysteine residues (Dinkova-Kostova, A. T., Holtzclaw, W. D., Cole, R. N., Itoh, K., Wakabayashi, N., Katoh, Y., Yamamoto, M., and Talalay, P. (2002). Proc. Natl. Acad. Sci. USA 99, 11908-11913; Zhang, D. D. and Hannink, M. (2003) Mol. Cell. Biol. 23, 8137-8151; Saito, R., Suzuki, T., Hiramoto, K., Asami, S., Naganuma, E., Suda, H., Iso, T., Yamamoto, H., Morita, M., Baird, L., et al. (2016). Mol. Cell. Biol. 36, 271-284; Suzuki T, Muramatsu A, Saito R, Iso T, Shibata T, Kuwata K, Kawaguchi S I, Iwawaki T, Adachi S, Suda H, Morita M, Uchida K, Baird L, Yamamoto M (2019) Cell Rep 28:746-758). The specificity of Keap1 cysteine residues against various chemical inducers of Nrf2 was investigated by using mutants of three major cysteine residues namely Cys 151, Cys273 and Cys288. These experiments led to the classification of Nrf2 inducers into four classes, namely class I (Cys151 preferring), class II (Cys288 preferring), class III (Cys151/Cys273/Cys288 collaboration preferring) and class IV (Cys151/Cys273/Cys288 independent) (Saito, R., Suzuki, T., Hiramoto, K., Asami, S., Naganuma, E., Suda, H., Iso, T., Yamamoto, H., Morita, M., Baird, L., et al. (2016). Mol. Cell. Biol. 36, 271-284). The cysteine code of Keap1 modification sites with various electrophiles has been summarized recently (Unoki T, Akiyama M, Kumagai Y. Int J Mol Sci. 2020 Jan. 15; 21(2)). It appears, however, challenging to define the chemical properties of each class as exemplified by 15-deoxy-prostaglandin J2 (15d-PGJ2) and prostaglandinA2 (PGA2). Despite sharing similar structural characteristics, 15d-PGJ2 and PGA2 belong to class II and class IV, respectively. Therefore, the complex properties such as structure and reactivity of electrophiles may determine the interaction with specific Keap1 reactive cysteine residues (Unoki T, Akiyama M, Kumagai Y. Int J Mol Sci. 2020 Jan. 15; 21(2)).

Nrf2 activators, or KEAP1 inhibitors as their molecular target is KEAP1 (Magesh S., Chen Y. and Hu L. Medicinal Research Reviews, 2012 vol. 32, no. 4, pp. 687-726), can be classified as electrophiles, protein-protein interaction (PPI) inhibitors, and multi target drugs. Most pharmacological Nrf2 activators are electrophilic molecules that covalently modify one or more cysteine residues present in the thiol-rich KEAP1 protein by oxidation or alkylation (Hur W., Gray N. S. Current Opinion in Chemical Biology. 2011; 15(1):162-173; Satoh T., McKercher S. R., Lipton S. A. Free Radical Biology & Medicine. 2013; 65:645-657; Wilson A. J., Kerns J. K., Callahan J. F., Moody C. J. Journal of Medicinal Chemistry. 2013; 56(19):7463-7476). The only marketed Nrf2 activators to date are dimethyl fumarate (BG-12 or Tecfidera) and diroximel fumarate (DRF) from Biogen. Dimethyl fumarate as been approved in 2013 and DRF in 2019 for relapsing-remitting multiple sclerosis (MS) (Schimrigk S., Brune N., Hellwig K., et al. European Journal of Neurology. 2006; 13(6):604-610; Gold R., Kappos L., Arnold D. L., et al. The New England Journal of Medicine. 2012; 367(12):1098-1107; Fox R. J., Miller D. H., Phillips J. T., et al. The New England Journal of Medicine. 2012; 367(12):1087-1097; Xu Z., Zhang F., Sun F., Gu K. F., Dong S., He D. Cochrane Database of Systematic Reviews. 2015; 4; Mills E. A., Ogrodnik M. A., Plave A., Mao-Draayer Y. Frontiers in Neurology. 2018; 9(5)). Previously, dimethyl fumarate was authorized for the treatment of psoriasis (Hoxtermann S., Nuchel C., Altmeyer P. Dermatology. 1998; 196 (2):223-230). The dimethyl fumarate-induced activation of Nrf2 in the central nervous system was described in the MS mice model of experimental allergic encephalomyelitis (Linker R. A., Lee D. H., Ryan S., et al. Brain. 2011; 134(3):678-692). In this model, dimethyl fumarate-dependent Nrf2 activation correlated with an improvement in the clinical course of MS, favored axon preservation, and increased astrocyte activation. These beneficial effects of dimethyl fumarate did not occur in Nrf2-null mice, hence indicating that dimethyl fumarate was acting mainly by targeting the Nrf2 pathway. dimethyl fumarate is mostly converted to monomethyl fumarate (MMF) by intestinal esterases, and only a small fraction of dimethyl fumarate is found in blood conjugated with glutathione (Dibbert S., Clement B., Skak-Nielsen T., Mrowietz U., Rostami-Yazdi M. Archives of Dermatological Research. 2013; 305(5):447-451). Since MMF is considered the active metabolite of dimethyl fumarate, several clinical trials are ongoing to assess the efficacy and safety of MMF.

Nrf2 activators interacting with the cysteine residues of Keap1 by virtue of their electrophilic nature inherently also react with glutathione or thiol in proteins. Since such thiol-reactive chemicals have the potential to cause electrophilic damage in cells, chemicals that directly inhibit the protein-protein interaction (PPI) of Keap1 and Nrf2 are emerging as attractive novel Nrf2 inducers (Bertrand, H. C., Schaap, M., Baird, L., Georgakopoulos, N. D., Fowkes, A., Thiollier, C., Kachi, H., Dinkova-Kostova, A. T., and Wells, G. (2015). J. Med. Chem. 58, 7186-7194; Davies, T. G., Wixted, W. E., Coyle, J. E., Griffiths-Jones, C., Hearn, K., McMenamin, R., Norton, D., Rich, S. J., Richardson, C., Saxty, G., Willems, H. M., Woolford, A. J., Cottom, J. E., Kou, J. P., Yonchuk, J. G., et al. (2016). J. Med. Chem. 59, 3991-4006; Jiang, Z Y, Lu, M C., and You, Q. D. (2016). J. Med. Chem. 59, 10837-10858; Lu, M. C., Ji, J. A., Jiang, Y. L., Chen, Z. Y., Yuan, Z. W., You, Q. D., and Jiang, Z. Y. (2016). Sci. Rep. 6, 26585; Yasuda, D., Nakajima, M., Yuasa, A., Obata, R., Takahashi, K., Ohe, T., Ichimura, Y., Komatsu, M., Yamamoto, M., Imamura, R., Kojima, H., Okabe, T., Nagano, T., and Mashino, T. (2016) Bioorg. Med. Chem. Lett. 26, 5956-5959). PPI inhibitors interfere with the docking of Nrf2 to the Kelch propeller of KEAP1 and most likely provide more selectivity over electrophilic compounds (Richardson B. G., Jain A. D., Speltz T. E., Moore T. W. Bioorganic & Medicinal Chemistry Letters. 2015; 25(11):2261-2268). Based on the X-ray crystal structure of KEAP1, small PPI inhibitors have been designed to impede the binding of the DLG and ETGE motifs to KEAP1. The ETGE motif adopts a β-hairpin structure that docks to the Kelch propeller of KEAP1 through specific hydrophobic and electrostatic interactions (Padmanabhan B., Tong K. I., Ohta T., et al. Molecular Cell. 2006; 21(5):689-700; Lo S. C., Li X., Henzl M. T., Beamer L. J., Hannink M. The EMBO Journal. 2006; 25(15):3605-3617). Up-to-date, no PPI inhibitor has entered clinical development, however, potent and selective PPI inhibitors of the KEAP1Kelch-Nrf2 interaction have been described and their activity was confirmed in in vitro and in vivo studies, respectively (Davies, T. G., Wixted, W. E., Coyle, J. E., Griffiths-Jones, C., Hearn, K., McMenamin, R., Norton, D., Rich, S. J., Richardson, C., Saxty, G., Willems, H. M., Woolford, A. J., Cottom, J. E., Kou, J. P., Yonchuk, J. G., et al. (2016). J. Med. Chem. 59, 3991-4006; Jiang, Z Y, Lu, M C., and You, Q. D. (2016). J. Med. Chem. 59, 10837-10858; Robledinos-Antón N, Fernández-Ginés R, Manda G, Cuadrado A. Oxid Med Cell Longev. 2019: 9372182).

Another mechanism of KEAP1 inhibition is related to the interaction with the CUL3/RBX1 complex, which is required for Nrf2 ubiquitination and degradation. Cys-151 located at the BTB domain influences the interaction of KEAP1 with CUL3. The crystal structure of the BTB domain bound to the pentacyclic triterpenoid 2-cyano-3,12-dioxo-oleana-1,9(11)-dien-28-oate (Bardoxolone, CDDO-Me or RTA 402) indicates that adduct formation with Cys-151 disrupts the interaction between KEAP1 and CUL3 (Cleasby A., Yon J., Day P. J., et al. Structure of the BTB domain of Keap1 and its interaction with the triterpenoid antagonist CDDO. PLoS One. 2014; 9 (6, article e98896); Iso T., Suzuki T., Baird L., Yamamoto M. Molecular and Cellular Biology. 2016; 36(24): 3100-3112; Dayalan Naidu S., Muramatsu A., Saito R., et al. Scientific Reports. 2018; 8(1): p. 8037). As a result, KEAP1 is locked in a Nrf2 bound conformation and newly expressed Nrf2 thereby escapes KEAP1-CUL3-mediated ubiquitination. Bardoxolone entered clinical trials for the treatment of advanced chronic kidney disease (CKD) and type 2 diabetes mellitus (Pergola P. E., Raskin P., Toto R. D., et al. The New England Journal of Medicine. 2011; 365(4):327-336). Although phase II clinical trials demonstrated long-term increment in glomerular filtration, the compound was halted at phase III due to cardiovascular safety issues (Zhang D. D. Antioxidants & Redox Signaling. 2013; 19(5):517-518. doi: 10.1089/ars.2012.5118). A new phase III clinical trial of Bardoxolone in patients with diabetic kidney disease (AYAME study) has recently started by Kyowa Kirin to better define the safety and efficacy profiles of CDDO-Me. Currently, Bardoxolone is also in clinical studies for the Alport syndrome (phase 2/3 CARDINAL trial) and pulmonary hypertension (phase 3 CATALYST trial). Furthermore, Reata is developing Bardoxolone in rare forms of CKD including autosomal dominant polycystic kidney disease (ADPKD), IgA nephropathy (IgAN), type 1 diabetic CKD (T1D CKD), and focal segmental glomerulosclerosis (FSGS). A second-generation derivative of Bardoxolone, called Omaveloxone (RTA-408), is under clinical investigation in the pivotal, registration, MOXIe trial for Friedreich's ataxia (Lynch D. R., Farmer J., Hauser L. et al. Annals of Clinical Translational Neurology. 2019; 6(1):15-26; https://www.reatapharma.com/our-science/pipeline/).

Several additional mechanisms have been proposed to explain the dissociation of Nrf2 from Keap1 under stress conditions. In addition to oxidation of the cysteine residues of Keap1 and targeting the DLG and ETGE binding sites, the binding of p62 to Keap1 and phosphorylation of Nrf2 by GSK3 have received particular attention.

p62, also known as sequestosome 1 (SQSTM1), is a ubiquitin-binding protein that targets protein aggregates for degradation via the autophagic pathway. p62 competes with Nrf2 for binding to Keap1, and binding of p62 to Keap1 leads to the degradation of Keap1 and the consequent Nrf2 stabilization (Komatsu M, Kurokawa H, Waguri S, Taguchi K, Kobayashi A, Ichimura Y, et al. Nat Cell Biol 2010; 12(3):213-23; Lau A, Wang X J, Zhao F, Villeneuve N F, Wu T, Jiang T, et al. Mol Cell Biol 2010; 30(13):3275-85). The p62 gene promoter contains an ARE and creates a Nrf2 driven positive feedback loop by inducing ARE-driven p62 gene transcription (Jain A, Lamark T, Sjottem E, Larsen K B, Awuh J A, Overvatn A, et al. J Biol Chem 2010; 285(29):22576-91). Since p62 is a cargo receptor for selective autophagy, Keap1-Nrf2 has an intriguing functional interaction with autophagy (Towers C G, Fitzwalter B E, Regan D, Goodspeed A, Morgan M J, Liu C W, et al. Dev Cell 2019. 23; 50(6):690-703. doi: 10.1016/j.devcel.2019.07.010).

Nrf2 stability is regulated also by glycogen synthase kinase (GSK)-3 mediated phosphorylation. GSK-3 phosphorylates the DSGIS motif located in the Neh6 domain of Nrf2 and thereby creates a recognition site for 0-transducin repeats containing E3 ubiquitin protein ligase (β-TrCP). This interaction targets Nrf2 to ubiquitin-dependent proteasome degradation (Rada P1, Rojo A I, Chowdhry S, McMahon M, Hayes J D, Cuadrado A. Mol Cell Biol. (2011) March; 31(6):1121-33). These data may suggest that GSK-3 inhibitors have utility as Nrf2 activators.

Besides dimethyl fumarate for the treatment of relapsing-remitting multiple sclerosis and psoriasis, respectively, the broad therapeutic potential of Nrf2 activators are supported by a number of studies.

The importance of Nrf2 in protection against reactive electrophiles was first demonstrated using acetaminophen. Nrf2 knockout mice displayed greater hepatotoxicity, manifested in increased serum ALT values and altered hepatic histology, following acetaminophen exposure, relative to WT mice (Chan K, Han X, Kan Y. Proc Natl Acad Sci USA 2001; 98:4611-4616; Enomoto A, Itoh K, Nagayoshi E, Haruta J, Kimura T, O'Connor T, Harada T, Yamamoto M. Toxicol Sci 2001; 59:169-177).

Acetaminophen was also shown to activate the nuclear translocation of Nrf2 at non-toxic doses thereby illustrating the role of Nrf2 in coordinating an adaptive response leading to attenuated acetaminophen toxicity (Goldring C, Kitteringham N, Elsby R, Randle L, Clement Y, Williams D, McMahon M, Hayes J, Itoh K, Yamamoto M, Park B. Hepatology 2004; 39:1267-1276). This adaptive response resulted in increased de novo synthesis of GSH and conjugation and excretion of reactive acetaminophen metabolites. This observation was further confirmed by the use of hepatocyte-specific conditional Keap1 knockout mice, a model in which the inhibitory component of the Nrf2 signaling pathway is absent resulting in elevated and sustained nuclear accumulation of Nrf2. These conditional knockout mice were considerably more resistant to acetaminophen toxicity than WT mice due to higher levels of Nrf2-regulated cytoprotective enzymes (Okawa H, Motohashi H, Kobayashi A, Aburatani H, Kensler T, Yamamoto M. Biochem Biophys Res Commun 2006; 339:79-88).

Activation of Nrf2 signaling by KEAP1 gene knockdown suppressed the onset of diabetes and when crossed with diabetic db/db mice, blood glucose levels became lower through improvement of both insulin secretion and insulin resistance. KEAP1 knockdown also prevented high-calorie-diet-induced diabetes and oral administration of the Nrf2 inducer CDDO-Im also attenuated diabetes in db/db mice. Interestingly, Nrf2 induction altered antioxidant-, energy consumption-, and gluconeogenesis-related gene expression in metabolic tissues. Overall, these data suggest that KEAP1-Nrf2 system is a critical target for preventing the onset of diabetes mellitus (Uruno A, Furusawa Y, Yagishita Y, Toshiaki Fukutomi T, Muramatsu H, Negishi T, Sugawara A, Kensler T W, Yamamotoa M. Molecular and Cellular Biology 2013; 2996-3010). In line with data obtained in db/db mice, Xue and colleagues investigated the impact of Nrf2 ablation in ob/ob mice. Global ablation led to reduced white adipose tissue (WAT) mass, but resulted in an even more severe metabolic syndrome with aggravated insulin resistance, hyperglycemia, and hypertriglyceridemia. Compared with wild-type mice, WAT of ob/ob mice expressed substantially higher levels of many genes related to antioxidant response, inflammation, adipogenesis, lipogenesis, glucose uptake, and lipid transport. Absence of Nrf2 in WAT resulted in reduced expression of most of these factors at mRNA or protein levels. These findings support a role for Nrf2 in regulating adipose development and function, by which Nrf2 controls the capacity of WAT expansion and insulin sensitivity and maintains glucose and lipid homeostasis (Xue P, Hou Y, Chen Y, Yang B, Fu J, Zheng H, Yarborough K, Woods C G, Liu D, Yamamoto M, Zhang Q, Andersen M E, Pi J. Diabetes. 2013 March; 62(3):845-54).

Recent data support a critical role of Nrf2 in β-cell survival and proliferation under stress conditions. Induction of Nrf2 is required for ChREBPα-mediated mitochondrial biogenesis and for glucose-stimulated and ChREBPα-augmented β-cell proliferation. Interestingly, overexpression of Nrf2 was sufficient to drive human β-cell proliferation in vitro, confirming the critical role of this pathway and its potential utility for therapeutic β-cell regeneration strategies (Kumar A, Katz L S, Schulz A M, Kim M, Honig L B, Li L, Davenport B, Homann D, Garcia-Ocaña A, Herman M A, Haynes C M, Chipuk J E, Scott D K. Diabetes. 2018 August; 67(8):1561-1575). Furthermore, Nrf2 activators like Oltipraz or dimethyl fumarate protect isolated mouse beta cells against glucolipotoxicity by preserving mitochondrial function, glucose-dependent ROS turnover, and antagonizing glucolipotoxicity-induced inhibition of insulin release and apoptosis (Schultheis J, Beckmann D, Mulac D, Müller L, Esselen M, Dufer M. Oxid Med Cell Longev. 2019 Nov. 11; 2019:7518510).

An important role of Nrf2 in preventing the onset of type 2 diabetes in humans is supported by the identification of the Nrf2 rs6721961 polymorphism, a variant of the Nrf2 gene in the upstream promoter region. In a Chinese cohort this polymorphism is significantly associated with oxidative stress, anti-oxidative status, and risk of newly-diagnosed T2DM (Wang X, Chen H, Liu J, Ouyang Y, Wang D, Bao W and Liu L. Int J Mol Sci. 2015; 16(7): 16483-16496). The SNP rs6721961, was initially identified to be associated with the risk of acute lung injury, an oxidative stress-mediated condition (Marzec J. M., Christie J. D., Reddy S. P., Jedlicka A. E., Vuong H., Lanken P. N., Aplenc R., Yamamoto T., Yamamoto M., Cho H.-Y. FASEB J. 2007; 21:2237-2246).

Nrf2 activation in the type 1 diabetes NOD mouse model by knocking down the expression of Keap1, inhibited T-cell infiltration within the islets, ameliorated impairment of insulin secretion and prevented the development of diabetes mellitus. Notably, Nrf2 activation decreased both the plasma interferon-7 (IFN-7) levels and the IFN-7-positive cell numbers in the pancreatic islets, demonstrating that activation of Nrf2 signaling prevented the onset of type 1 diabetes mellitus in NOD mice. Thus, Nrf2 appears to be a potential target for the prevention and treatment of type 1 diabetes (Yagishita Y. et al. J Endocrinol.: JOE-18-0355.R2. Published online 2019 Jan. 1. doi: 10.1530/JOE-18-0355).

Oxidative stress and inflammation are the most important pathogenic events in the development and progression of liver diseases and multiple studies have shown that activation or suppression of Nrf2 significantly affects the progression of liver diseases (Xu D, Xu M, Jeong S, Qian Y, Wu H, Xia Q and Kong X. Front Pharmacol. 2018; 9: 1428). Nrf2 has been found to be a key regulator to protect against the development of NASH (Gupte A. A., Lyon C. J., Hsueh W. A. (2013). Curr. Diabetes Rep. 13 362-371. 10.1007/s11892-013-0372-1), and conversely, loss or deletion of Nrf2 has been found to cause benign steatosis that progresses to NASH and contributes to the exacerbation of disease status (Chowdhry S., Nazmy M. H., Meakin P. J., Dinkova-Kostova A. T., Walsh S. V., Tsujita T., et al. (2010). Free Radic. Biol. Med. 48 357-371; Wang C., Cui Y., Li C., Zhang Y., Xu S., Li X., et al. (2013). Lipids Health Dis. 12:165. 10.1186/1476-511X-12-165; Ramadori P., Drescher H., Erschfeld S., Fragoulis A., Kensler T. W., Wruck C. J., et al. (2017). Oxid. Med. Cell. Longev. 2017:3420286). NASH development was also investigated in p62:Nrf2 double-knockout (DKO) mice. DKO mice showed massive hepatomegaly and steatohepatitis, hyperphagia-induced obesity coupled with insulin resistance and adipokine imbalance (Akiyama K, Warabi E, Okada K, Yanagawa T, Ishii T, Kose K, Tokushige K, Ishige K, Mizokami Y, Yamagata K, Onizawa K, Ariizumi S I, Yamamoto M, Shoda J. Exp Anim. 2018 May 10; 67(2):201-218).

A protective role of Nrf2 in NASH has been shown by Sharma and colleagues by using TBE-31, an Nrf2 activating small molecule. Treatment with TBE31 reversed insulin resistance in high fat high fructose fed wild-type mice, but not in Nrf2-null mice. Furthermore, TBE-31 treatment mice substantially decreased liver steatosis and expression of lipid synthesis genes, while increasing hepatic expression of fatty acid oxidation and lipoprotein assembly genes. Also, TBE-31 treatment decreased ER stress, expression of inflammation genes, and markers of apoptosis, fibrosis, and oxidative stress in the livers of high fat high fructose fed wild-type mice. By comparison, TBE-31 did not decrease steatosis, ER stress, lipogenesis, inflammation, fibrosis, or oxidative stress in livers of HFFr-fed Nrf2-null mice. The authors concluded that pharmacologic activation of Nrf2 in mice that had already been rendered obese and insulin resistant reversed insulin resistance, suppressed hepatic steatosis, and mitigated against NASH and liver fibrosis. These effects were mainly attributed to inhibition of ER, inflammatory, and oxidative stress (Sharma R S, Harrison D J, Kisielewski D, Cassidy D M, McNeilly A D, Gallagher J R, Walsh S V, Honda T, McCrimmon R J, Dinkova-Kostova A T, Ashford M L J, Dillon J F, Hayes J D Cell Mol Gastroenterol Hepatol. 2017 Dec. 13; 5(3):367-398).

A liver protective role of Nrf2 has also been demonstrated upon acute high doses of alcohol exposure using Nrf2-KO mice. Alcohol treatment resulted in substantially worsened liver and pancreatic injuries as well as pancreatic j-cell injury in these animals (Sun J, Fu J, Zhong Y, Li L, Chen C, Wang X, Wang L, Hou Y, Wang H, Zhao R, Zhang X, Yamamoto M, Xu Y, Pi J. Food Chem Toxicol. 2018 November; 121:495-503).

Nrf2 activators have potential utility for diseases/indications that are linked to increased oxidative stress and inflammation, impaired redox potential, impaired detoxification and deregulated metabolism.

Based on Nrf2 knockout, KEAP1 knockout, genetic polymorphisms and compound mediated Nrf2 activation studies, respectively, evidence is provided for indications including Type I diabetes and Type II diabetes and associated complications such as diabetic cardiomyopathy, diabetic retinopathy, diabetic neuropathy, diabetic nephropathy and diabetic wound healing; Maternal diabetes; Liver diseases such as Nonalcoholic Steatohepatitis (NASH), Non-Alcoholic Fatty Liver Disease, toxin-induced liver disease (e.g., acetaminophen-induced hepatic disease), Alcoholic Liver Disease (ALD), cholestasis, Primary Sclerosing Cholangitis (PSC), viral hepatitis, cirrhosis, Primary Biliary Cirrhosis (PBC), End Stage Liver Disease, Fibrosis; Kidney diseases such as Chronic kidney disease (CKD), Acute kidney injury, Contrast-induced nephropathy, Autosomal dominant polycystic kidney disease (ADPKD), Alstram and Alport syndromes, sepsis-induced acute kidney injury; kidney disease or malfunction seen during kidney transplantation, focal segmental glomerulosclerosis, IgA glomerulonephritis/nephropathy, fibrosis; Lung diseases such as pulmonary fibrosis, Idiopathic Pulmonary Fibrosis (IPF), cystic fibrosis, Acute lung injury, Lung infection, Chronic Obstructive Pulmonary Disease (COPD), Emphysema, Pulmonary Arterial Hypertension, Lung disease secondary to environmental exposures, chronic and acute asthma, acute respiratory distress syndrome; Cardiac diseases such as atherosclerosis, hypertension, heart failure, stroke, cardiomyopathy, coronary heart disease, Myocardial Ischemia; Neuronal damage, Traumatic brain injury, Depression, Epilepsy, Hepatic Encephalopathy, Huntington's disease, Parkinson's disease, Alzheimer's disease, autism, Friedreich's ataxia, Amyotrophic Lateral Sclerosis (ALS), Multiple Sclerosis (MS), Stroke, Cerebral infarction, Encephalopathy, neuronal damage/injury, Spinal cord injury; Inflammatory diseases such as inflammatory bowel disease, Ulcerative Colitis, Crohn's Disease, Pancreatitis, Arthritis, lupus nephritis; Eye diseases such as Age-related macular degeneration (AMD), Ocular Neurodegenerative Diseases, Age-related macular degeneration, cataracts, glaucoma, eye injury, Fuchs Endothelial Corneal Dystrophy (FECD), uveitis, Optic neuropathy/Ocular Neurodegenerative Diseases; Colon cancer; Autoimmune diseases; Psoriasis, dermatitis/topical effects of radiation, immunosuppression due to radiation exposure, Preeclampsia, High altitude sickness; Wound healing; Metabolic syndrome; Mitochondrial myopathies; Malaria; Ferroptosis/iron overload; Allergic contact dermatitis; Alcohol dependence; Amyloidosis; Anemia; Anxiety disorder; Asperger syndrome; Eczema; Brain edema; Brain ischemia; Cerebrovascular disorder; Chronic fatigue syndrome; Cognitive decline; Dermatitis/radiation-induced dermatitis; Duchenne muscular dystrophy; Edema; Encephalitis; Male/female fertility; Fracture healing; Gastroesophageal reflux disease; Hearing loss; influenza infections; Intestinal barrier dysfunction; Osteoarthritis; Osteoporosis; Radiation-induced injury; Reflux-Induced Esophagitis; Reperfusion injury (brain, heart, kidney, liver, retina); Schizophrenia; Seizures; Sjogren syndrome; Sickle cell disease; Skin ulcer; Vascular endothelial dysfunction; Blood-brain barrier dysfunction; Down syndrome.

WO 2015/092713 discloses bis aryl compounds as Nrf2 regulators.

The present invention relates more especially to compounds of formula (I)

(I)

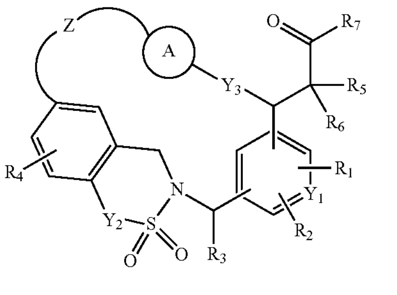

wherein

Z is —O—$(CH_2)n_1$-, —O—$(CH_2)n_1$-O—$(CH_2)n_2$, —O—$(CH_2)n_1$-S—$(CH_2)n_2$, O—$(CH_2)n_1$-S(O)—$(CH_2)n_2$, O—$(CH_2)n_1$-$S(O_2)$—$(CH_2)n_2$, —O—$(CH_2)$ $n_1$-NR—$(CH_2)n_2$, —O—$(CH_2)n_1$-CHR'—$(CH_2)n_2$, —NR—$(CH_2)n_1$-, —NR—(CO)—$(CH_2)n_1$-, —O—$(CH_2)n_1$-Ar—$(CH_2)n_2$, —O—$(CH_2)n_1$-Ar—O—$(CH_2)n_2$, —O—$(CH_2)n_1$-Ar—S—$(CH_2)n_2$, —O—$(CH_2)n_1$-Ar—S(O)—$(CH_2)n_2$, —O—$(CH_2)n_1$-Ar—S$(O_2)$—$(CH_2)n_2$, —O—$(CH_2)n_1$-Ar—CHR'—$(CH_2)n_2$, —O—$(CH_2)n_1$-Ar—CH═CH—, O—Ar—NR—$(CH_2)n_1$, —$(CH_2)n_1$-NR—(CO)—$(CH_2)n_2$- or Z is

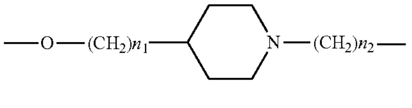 or

-continued

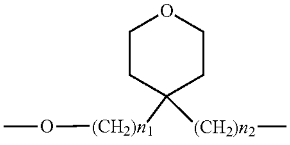

$Y_1$ is C or N, $Y_2$ is O or NR',

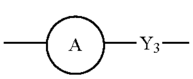 is 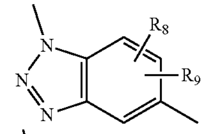, 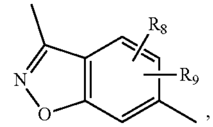, 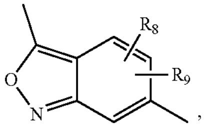, 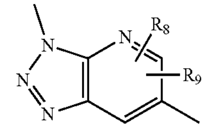, 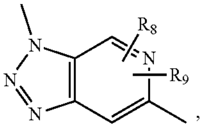, 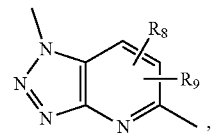, 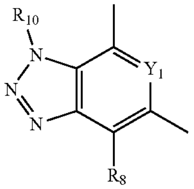, 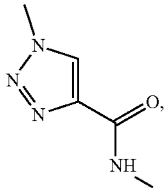, 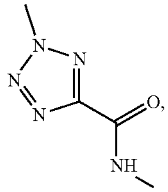, 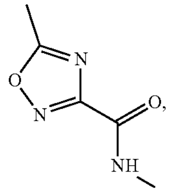, 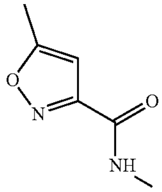, 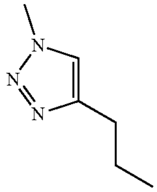, 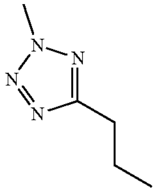, 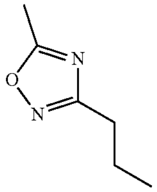 or 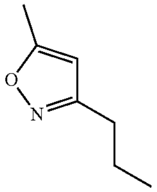

Ar is an optionally substituted aryl or heteroaryl group

R is a hydrogen atom, a linear or branched $C_1$-$C_3$ alkyl group or an optionally substituted aryl group, R' is a hydrogen atom or a group selected from hydroxyl, optionally substituted aryl and linear or branched $C_1$-$C_3$ alkyl optionally substituted by alkoxy or by one to three halogen atoms, $n_1$ and $n_2$ are each an integer from 1 to 6, $R_1$, $R_2$, $R_4$, $R_8$, $R_9$, which may be identical or different, are each a hydrogen atom or a group selected from halo, cyano, linear or branched $C_1$-$C_3$ alkyl optionally substituted by one to three halogen atoms, linear or branched $C_1$-$C_3$ alkoxy or optionally substituted aryl, $R_3$ is hydrogen or a linear or branched $C_1$-$C_3$ alkyl group optionally substituted by one to three halogen atoms, or $R_2$ and $R_3$ together form a ring with the atoms bearing them, $R_5$, $R_6$, identical or different, are each a hydrogen, deuterium or halogen atom or a linear or branched $C_1$-$C_3$ alkyl group, $R_7$ is a group selected from hydroxyl and NHR'$_7$, wherein R'$_7$ is a linear or branched $C_1$-$C_6$ alkyl group or an optionally substituted aryl or heteroaryl group, their optical isomers and addition salts thereof with a pharmaceutically acceptable base.

"Aryl group" means a phenyl, naphthyl, or biphenyl group optionally substituted by one or more identical or different groups selected from halogen, hydroxy, amino, linear or branched ($C_1$-$C_6$)-alkyl optionally substituted by one to 3 halogen atoms, carboxy, cyano, linear or branched ($C_1$-$C_6$)-alkoxy optionally substituted by one to 3 halogen atoms, linear or branched ($C_1$-$C_6$)-aminoalkyl optionally N-substituted by one or two linear or branched ($C_1$-$C_6$)-alkyl groups, linear or branched ($C_1$-$C_6$)-alkylsulfanyl optionally substituted by one to 3 halogen atoms, linear or branched ($C_1$-$C_6$)-alkylsulfinyl optionally substituted by one to 3 halogen atoms or linear or branched ($C_1$-$C_6$)-alkylsulfonyl optionally substituted by one to 3 halogen atoms.

"Heteroaryl group" means a monocyclic aromatic group or a bicyclic aromatic or partially aromatic group having from 5 to 12 ring members and containing one, two or three hetero atoms selected from oxygen, nitrogen and sulphur, it being understood that the heteroaryl may be optionally substituted by one or more identical or different groups selected from halogen, hydroxy, amino, cyano, linear or branched ($C_1$-$C_6$)-alkyl optionally substituted by one to 3 halogen atoms, linear or branched ($C_1$-$C_6$)-alkoxy optionally substituted by one to 3 halogen atoms, linear or branched ($C_1$-$C_6$)-aminoalkyl optionally N-substituted by one or two linear or branched ($C_1$-$C_6$)-alkyl groups, linear or branched ($C_1$-$C_6$)-alkylsulfanyl optionally substituted by one to 3 halogen atoms, linear or branched ($C_1$-$C_6$)-alkylsulfinyl optionally substituted by one to 3 halogen atoms or linear or branched ($C_1$-$C_6$)-alkylsulfonyl optionally substituted by one to 3 halogen atoms.

Among the heteroaryl groups there may be mentioned, without implying any limitation, pyrrolyl, furyl, thienyl, thiazolyl, isothiazolyl, oxazolyl, isoxazolyl, pyrazolyl, imidazolyl, pyridinyl (also known as pyridyl), pyrazinyl, pyridazinyl, pyrimidinyl, indolyl, dihydroisoindolyl, indazolyl, benzothienyl, benzofuranyl, imidazopyridinyl.

Optical isomers are understood as being the diastereoisomers and the enantiomers.

Among the pharmaceutically acceptable bases there may be mentioned, without implying any limitation, sodium hydroxide, potassium hydroxide, arginine, lysine, triethylamine and tert-butylamine.

One aspect of the present invention relates to the compounds of formula (IA), a particular case of the compounds of formula (I):

(IA)

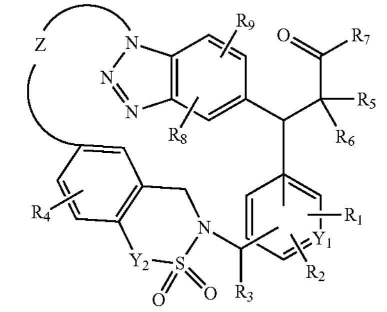

wherein Z, $Y_1$, $Y_2$, $R_1$ to $R_9$ are as defined for formula (I), their optical isomers, and addition salts thereof with a pharmaceutically acceptable base.

Another aspect of the present invention relates to the compounds of formula ($IA_1$), a particular case of the compounds of formula (I)

($IA_1$)

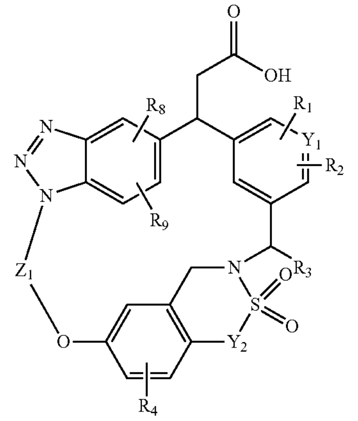

wherein $R_1$—$R_4$, $R_8$—$R_9$, $Y_1$, $Y_2$ are as defined before, and $Z_1$ is a group selected from —$(CH_2)n_1$, —$CH_2)n_1$-O—$(CH_2)n_2$, —$CH_2)n_1$-S—$(CH_2)n_2$, —$CH_2)n_1$-NR—$(CH_2)n_2$, —$CH_2)n_1$-CHR'—$(CH_2)n_2$, —$(CH_2)n_1$-$Ar_1$—$(CH_2)n_2$, —$CH_2)n_1$-$Ar_1$—O—$(CH_2)n_2$, —$(CH_2)n_1$-$Ar_1$—S—$(CH_2)n_2$, —$(CH_2)n_1$-$Ar_1$—CHR'—$(CH_2)n_2$, —$Ar_1$—NR—$(CH_2)n_1$, or $Z_1$ is

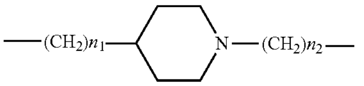

or

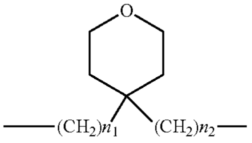

their optical isomers, and addition salts thereof with a pharmaceutically acceptable base.

Another aspect of the present invention relates to the compounds of formula (IB), a particular case of the compounds of formula (I)

(IB)

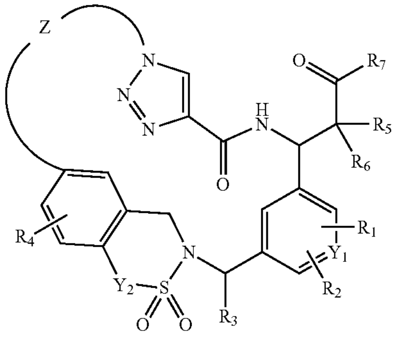

wherein Z, $Y_1$, $Y_2$, $R_1$ to $R_7$ are as defined before, their optical isomers, and addition salts thereof with a pharmaceutically acceptable base.

Another aspect of the present invention relates to the compounds of formula (IC), a particular case of the compounds of formula (I):

(IC)

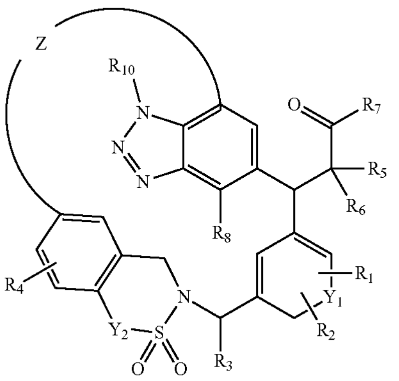

wherein Z, $Y_1$, $Y_2$, $R_1$ to $R_8$ and $R_{10}$ are as defined before, their optical isomers, and addition salts thereof with a pharmaceutically acceptable base.

Another aspect of the present invention relates to the compounds of formula (I) wherein Z is $-O-(CH_2)n_1-$, $-O-(CH_2)n_1-O-(CH_2)n_2$ or $-O-(CH_2)n_1-S-(CH_2)n_2$.

Another aspect of the present invention relates to the compounds of formula (I) wherein $Y_1$ is C.

Another aspect of the present invention relates to the compounds of formula (I) wherein $Y_2$ is O or $NCH_3$.

Another aspect of the present invention relates to the compounds of formula (I) wherein

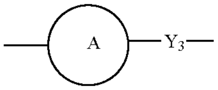 is 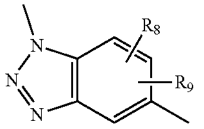

Another aspect of the present invention relates to the compounds of formula (I) wherein $R_7$ is hydroxyl.

Another aspect of the present invention relates to a process for the preparation of a compound of formula ($IA_1$), a particular case of the compounds of formula (I): starting from a compound of formula (II):

(II)

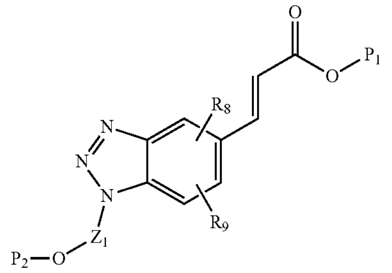

wherein $P_1$ is a protecting group of the acid function such as alkyl, and $P_2$ is a protecting group of the alcohol function, which is reacted with a compound of formula (III)

(III)

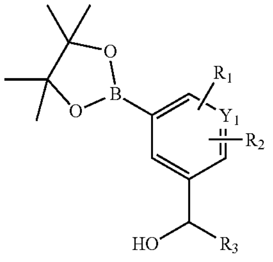

wherein $R_1$—$R_3$ and $Y_1$ are as defined for formula (I), to give a compound of formula (IV):

(IV)

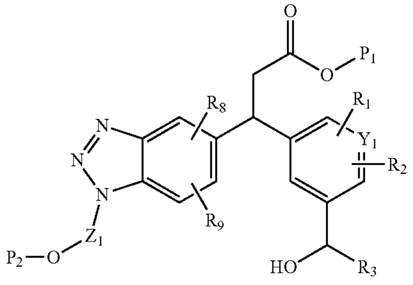

wherein $R_1$—$R_3$, $R_8$—$R_9$, $Y_1$, $Z_1$ and $P_1$-$P_2$ are as defined before, which is reacted with a compound of formula (V):

(V)

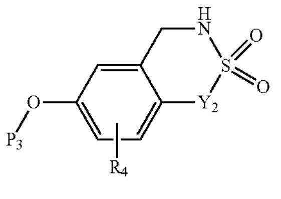

wherein $R_4$ and $Y_2$ are as defined for formula (I), and $P_3$ is a protecting group of the alcohol function, to give a compound of formula (VI):

(VI)

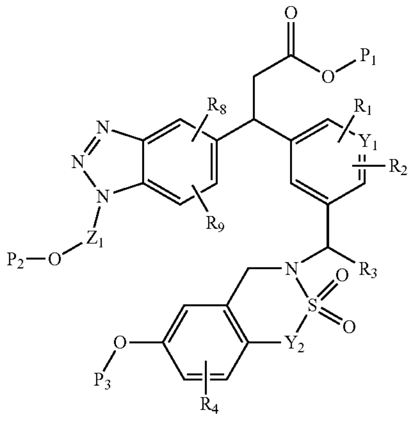

wherein $R_1$—$R_4$, $R_8$—$R_9$, $Y_1$, $Y_2$, $Z_1$ and $P_1$—$P_3$ are as defined before, which is deprotected to give a compound of formula (VII):

(VII)

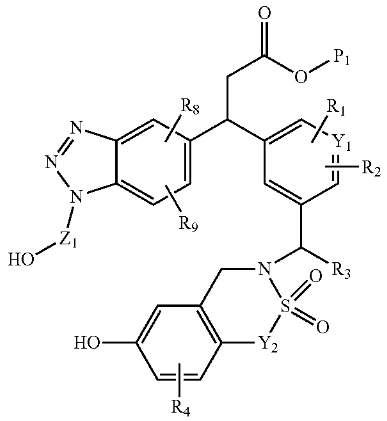

wherein $R_1$—$R_4$, $R_8$—$R_9$, $Y_1$, $Y_2$, $Z_1$ and $P_1$ are as defined before, which is halogenated to give a compound of formula (VIII):

(VIII)

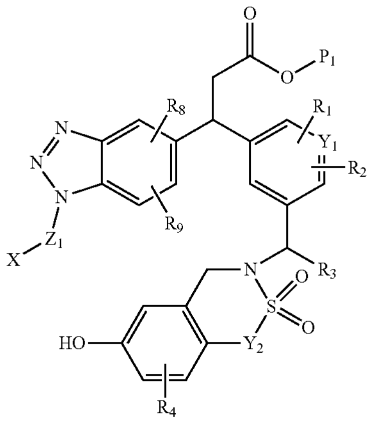

wherein $R_1$—$R_4$, $R_8$—$R_9$, $Y_1$, $Y_2$, $Z_1$ and $P_1$ are as defined before, and X is a halogen atom such as Br or Cl, which is reacted with a base (such as $Cs_2CO_3$) to give a compound of formula (IX)

(IX)

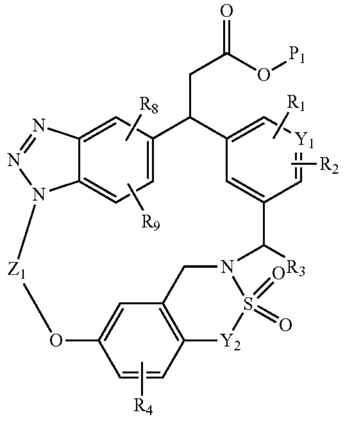

which is deprotected by reaction of a base such as LiOH to give a compound of formula ($IA_1$), the stereoisomers thereof are separated, if desired, using chiral separation techniques.

The compounds of the invention are Nrf2 activators.

As such, they can be used in the treatment of diseases that are linked to increased oxidative stress and inflammation, impaired redox potential, impaired detoxification and deregulated metabolism, including Type I diabetes and Type II diabetes and associated complications such as diabetic cardiomyopathy, diabetic retinopathy, diabetic neuropathy, diabetic nephropathy and diabetic wound healing; Maternal diabetes; Liver diseases such as Nonalcoholic Steatohepatitis (NASH), Non-Alcoholic Fatty Liver Disease, toxin-induced liver disease (e.g., acetaminophen-induced hepatic disease), Alcoholic Liver Disease (ALD), cholestasis, Primary Sclerosing Cholangitis (PSC), viral hepatitis, cirrhosis, Primary Biliary Cirrhosis (PBC), End Stage Liver Disease, Fibrosis; Kidney diseases such as Chronic kidney disease (CKD), Acute kidney injury, Contrast-induced nephropathy, Autosomal dominant polycystic kidney disease (ADPKD), Alstram and Alport syndromes, sepsis-induced acute kidney injury; kidney disease or malfunction seen during kidney transplantation, focal segmental glomerulosclerosis, IgA glomerulonephritis/nephropathy, fibrosis; Lung diseases such as pulmonary fibrosis, Idiopathic Pulmonary Fibrosis (IPF), cystic fibrosis, Acute lung injury, Lung infection, Chronic Obstructive Pulmonary Disease (COPD), Emphysema, Pulmonary Arterial Hypertension, Lung disease secondary to environmental exposures, chronic and acute asthma, acute respiratory distress syndrome; Cardiac diseases such as atherosclerosis, hypertension, heart failure, stroke, cardiomyopathy, coronary heart disease, Myocardial Ischemia; Neuronal damage, Traumatic brain injury, Depression, Epilepsy, Hepatic Encephalopathy, Huntington's disease, Parkinson's disease, Alzheimer's disease, autism, Friedreich's ataxia, Amyotrophic Lateral Sclerosis (ALS), Multiple Sclerosis (MS), Stroke, Cerebral infarction, Encephalopathy, neuronal damage/injury, Spinal cord injury; Inflammatory diseases such as inflammatory bowel disease, Ulcerative Colitis, Crohn's Disease, Pancreatitis, Arthritis, lupus nephritis; Eye diseases such as Age-related macular degeneration (AMD), Ocular Neurodegenerative Diseases, Age-related macular degeneration, cataracts, glaucoma, eye injury, Fuchs Endothelial Corneal Dystrophy (FECD), uveitis, Optic neuropathy/Ocular Neurodegenerative Diseases; Colon cancer; Autoimmune diseases; Psoriasis, dermatitis/topical effects of radiation, immunosuppression due to radiation exposure, Preeclampsia, High altitude sickness; Wound healing; Metabolic syndrome; Mitochondrial myopathies; Malaria; Ferroptosis/iron overload; Allergic contact dermatitis; Alcohol dependence; Amyloidosis; Anemia; Anxiety disorder; Asperger syndrome; Eczema; Brain edema; Brain ischemia; Cerebrovascular disorder; Chronic fatigue syndrome; Cognitive decline; Dermatitis/radiation-induced dermatitis; Duchenne muscular dystrophy; Edema; Encephalitis; Male/female fertility; Fracture healing; Gastroesophageal reflux disease; Hearing loss; influenza infections; Intestinal barrier dysfunction; Osteoarthritis; Osteoporosis; Radiation-induced injury; Reflux-Induced Esophagitis; Reperfusion injury (brain, heart, kidney, liver, retina); Schizophrenia; Seizures; Sjogren syndrome; Sickle cell disease; Skin ulcer; Vascular endothelial dysfunction; Blood-brain barrier dysfunction; Down syndrome.

The compounds according to the invention are especially useful for the treatment of Type II diabetes and NASH.

The present invention also relates to pharmaceutical compositions comprising a compound of formula (I) in combination with one or more inert, non-toxic, pharmaceutically acceptable excipients or carriers.

The useful dosage varies according to the age and weight of the patient, the administration route, the nature and severity of the disorder and any associated treatments, and ranges from 0.5 mg to 1000 mg per day in one or more administrations.

Among the pharmaceutical compositions according to the invention there may be mentioned more especially those that are suitable for oral, parenteral (intravenous, intramuscular or subcutaneous), per-or trans-cutaneous, nasal, rectal, perlingual, ocular or respiratory administration, and especially tablets or dragées, sublingual tablets, gelatin capsules, capsules, suppositories, creams, ointments, dermal gels, injectable or drinkable preparations, aerosols, and eye or nasal drops.

According to one aspect of the present invention, the pharmaceutical composition is a tablet for oral administration.

In addition to the compound of formula (I), the tablets according to the invention comprise one or more excipients or carriers, such as diluents, lubricants, binders, disintegrators, absorbents, colourants and sweeteners.

There may be mentioned as examples of excipients or carriers:

- for the diluents: lactose, dextrose, sucrose, mannitol, sorbitol, cellulose, glycerol,
- for the lubricants: silica, talc, stearic acid and its magnesium and calcium salts, polyethylene glycol,
- for the binders: aluminium and magnesium silicate, starch, gelatin, tragacanth, methylcellulose, sodium carboxymethylcellulose and polyvinylpyrrolidone,
- for the disintegrators: agar, alginic acid and its sodium salt, effervescent mixtures.

The percentage of active ingredient of formula (I) in the tablet is preferably between 5% and 50% by weight.

According to one aspect of the present invention, the compound of formula (I) according to the present invention is administered in association with one or more additional active ingredients.

The administration in association may be in the form of a simultaneous or successive co-administration of two or more separate pharmaceutical compositions each containing one of the active ingredients (free association), or in the form of the administration of a fixed association of the two or more active ingredients in the same pharmaceutical composition.

More specifically, the compounds of formula (I) and pharmaceutically acceptable salts thereof may be used in combination with one or more other active ingredients useful in the prevention or treatment of diabetes or NASH, including biguanides, sulfonylureas, DPP 4 inhibitors, SGLT2 inhibitors, GLP1 agonists, dual GLP1-GCG or GLP1-GIP agonists, FXR agonists, PPAR modulators, Thyroid hormone receptor agonists, FGF21 agonists, FGF19 agonists, DGAT2 inhibitors, ACC inhibitors or FAS inhibitors.

ABBREVIATIONS abs.: absolute
AcOH: acetic acid
aq.: aqueous
A $^{ta}$phos·$PdCl_2$: bis(di-tert-butyl(4-dimethylaminophenyl)phosphine)dichloropalladium(II)
$Cs_2CO_3$: cesium carbonate
° C.: degree Celsius
DCM: dichloromethane
DDQ: 2,3-dichloro-5,6-dicyano-1,4-benzoquinone
dia: diastereomer
DIAD: diisopropyl azodicarboxylate
Dioxane: 1,4-dioxane
DIPEA: diisopropylethyl amine, N-ethyl-N-(propan-2-yl)propan-2-amine
DMEM: Dulbecco's Modified Eagle Medium
DMF: N,N-dimethylformamide
DMSO: dimethyl sulfoxide
E1: first-eluted enantiomer
E2: second-eluted enantiomer
$Et_2O$: diethyl ether
EtOAc: ethyl acetate
EtOH: ethanol
FBS: Fetal Bovine Serum
g: gram(s)
h: hour(s)
HCl: hydrochloric acid
HCOOH: formic acid
HEC: HydroxyEthyl Cellulose
$H_2SO_4$: sulfuric acid
HPLC: high performance liquid chromatography
HRMS: high-resolution mass spectrometry
IPA: propan-2-ol
$K_2CO_3$: potassium carbonate
LC: liquid chromatography
LC-MS: liquid chromatography-mass spectroscopy
LiOH: lithium hydroxide
M: molar
MeOH: methanol
MeCN: acetonitrile
mg: milligram(s)
$MgSO_4$: magnesium sulfate
MHz: megahertz
min: minute(s)
mL: milliliter(s)
mmol: millimole(s)
MS: mass spectroscopy
MTBE: methyl-tert-butylether
$N_2$: nitrogen gas
NaCl: sodium chloride
NaH: sodium hydride NaOH: sodium hydroxide
$NaHCO_3$: sodium hydrogen carbonate
$Na_2SO_4$: sodium sulfate
NBS: N-bromosuccinimide
$NH_4HCO_3$: ammonium hydrogen carbonate
$NH_4Cl$: ammonium chloride
NMR: nuclear magnetic resonance
NMP: N-methyl pyrrolidone
Pd/C: palladium on activated carbon
$Pd_2(dba)_3$: tris(dibenzylideneacetone)dipalladium(0)
$PPh_3$: triphenylphosphine
quant.: quantitative yield
rac: racemic
RT: room temperature
sat.: saturated
tBuXPhos: 2-di-tert-butylphosphino-2',4',6'-triisopropylbiphenyl
TEA: triethylamine
TFA: trifluoroacetic acid
THF: tetrahydrofurane
wt %: weight percent General Information IUPAC chemical names were generated using ACD/Labs 2018 2.2 (File version C60H41, Build 106041, 7 Dec. 2018)

All reagents obtained from commercial sources were used without further purification. Anhydrous solvents were obtained from commercial sources and used without further drying.

Normal phase silica gel (flash) chromatography was performed on ISCO CombiFlash Rf 200i with pre-packed silica-gel cartridges (RediSep® Rf Gold High Performance).

Microwave heating was performed in an Anton Parr MonoWave or CEM Discover® instrument.

Reversed-phase (preparative) HPLC purifications were performed on a HANBON NP7000 Liquid Chromatography system with a Gemini-NX® 5 μM C18, 250 mm×50 mm i.d. column running at a flow rate of 99.9 mL $min^{-1}$ with UV diode array detection (210-400 nm) using pure water, or 5 mM aq. $NH_4HCO_3$ solution, or 5 mM aq. HCOOH solution, or 5 mM aq. TFA solution and MeCN as eluents unless specified otherwise.

Analytical LC-MS: The compounds of the present invention were characterized by high performance liquid chromatography-mass spectroscopy (HPLC-MS) on Agilent HP1200 with Agilent 6140 quadrupole LC/MS, operating in positive or negative ion electrospray ionisation mode. Molecular weight scan range is 100 to 1350. Parallel UV detection was done at 210 nm and 254 nm. Samples were supplied as a 1 mM solution in ACN, or in THF-water (1:1) with 5 L loop injection. LC-MS analyses were performed on two instruments, one of which was operated with basic, and the other with acidic eluents.

Basic LC-MS: Gemini-NX, 3 m, C18, 50 mm×3.00 mm i.d. column at 23° C., at a flow rate of 1 mL $min^{-1}$ using 5 mM $NH_4HCO_3$ (Solvent A) and acetonitrile (Solvent B) with a gradient starting from 100% Solvent A and finishing at 100% Solvent B over various/certain duration of time.

Acidic LCMS: ZORBAX Eclipse XDB-C18, 1.8 μm, 50 mm×4.6 mm i.d. column at 40° C., at a flow rate of 1 mL $min^{-1}$ using 0.02% v/v aq. HCOOH (Solvent A) and 0.02% v/v HCOOH in MeCN (Solvent B) with a gradient starting from 100% Solvent A and finishing at 100% Solvent B over various/certain duration of time.

$^1H$-NMR measurements were performed on Bruker Avance III 500 MHz spectrometer and Bruker Avance III 400 MHz spectrometer, using DMSO-d6 (hexadeutero-dimethylsulfoxide) or $CDCl_3$ (deuterochloroform) as solvent. $^1H$-NMR data is in the form of delta values, given in part per million (ppm), using the residual peak of the solvent (2.50 ppm for DMSO-d6 and 7.26 ppm for $CDCl_3$) as internal standard. Splitting patterns are designated as: s (singlet), 2s (2× singlet), d (doublet), 2d (2× doublet), t (triplet), 2t (2× triplet), q (quartet), 2q (2× quartet), quint (quintet), sept (septet), m (multiplet), 2m (2× multiplet), brs (broad singlet), brd (broad doublet), brt (broad triplet), brq (broad quartet), brm (broad multiplet), vbrs (very broad singlet), dd (doublet of doublets), td (triplet of doublets), dt (doublet of triplets), dq (doublet of quartets), ddd (doublet of doublet of doublets), dm (doublet of multiplets), tm (triplet of multiplets), qm (quartet of multiplets).

HRMS were determined on a Shimadzu IT-TOF, ion source temperature 200° C., ESI+/−, ionization voltage: (+−)4.5 kV. Mass resolution min. 10000.

The final products or final intermediates were separated to pure enantiomers/diastereomers using chiral supercritical fluid chromatography (SFC) in milligram scale using SFC-PICLAB-PREP 200 equipment (Pic Solution) by the following methods:

The mobile phase is carbon dioxide as a supercritical fluid or a mixture fluid (by adding a protic solvent, for example: isocratic 35-45% IPA or EtOH/supercritical $CO_2$)

The column was chosen according to the chromatography profile, for example:

Whelk 01 RR 30×250 mm×5 μm (particle size) or
LUX (Phenomenex) 30 mm×150 mm×5 μm (particle size) or
Chiralpak IG 30×250 mm×5 μm (particle size)

Temperature: 40° C.
Detection: at 230 nm
Flowrate: 120-150 mL/min.

The examples which follow illustrate the present invention.

General Procedure 1

General Procedure 1 STEP 1

To a solution of 1-fluoro-3-methyl-2-nitro-benzene (1 eq., 64.5 mmol) in MeCN (2 mL/mmol, 101.3 g, 128.92 mL) the amino alcohol (3 eq., 193.5 mmol) was added at RT. The reaction mixture was heated to 70° C. and stirred overnight. After completion of the reaction, the solvent was evaporated under reduced pressure. The residue was partitioned between 250 mL of water and 200 mL of EtOAc. The separated organic layer was washed with further 150 mL of brine. The combined aq. layers were washed with 100 mL EtOAc. The combined organic layers were dried over anhydrous $Na_2SO_4$, filtered, concentrated to dryness to give the crude product, which was purified by normal phase silica gel chromatography using heptane-EtOAc (for example 100:0 to 75:25) as an eluent to give the title compound.

General Procedure 1 STEP 2

To a solution of the General procedure 1 STEP 1 product (1 eq., 834 mmol) in AcOH (1.2 mL/mmol, 42 g, 40 mL) NBS (1 eq., 6 g, 34 mmol) was added at RT. The reaction mixture was heated to 110° C. and stirred for 2 h. After completion of the reaction, the mixture was cooled to RT and quenched with 200 ml of ice cold water. The pH was set to 14 by NaOH solution. The mixture was stirred at RT for 10 min. The mixture was extracted with 3×150 ml DCM. The combined organic layers were washed with brine. The organic phase was dried over anhydrous $Na_2SO_4$, filtered, concentrated to dryness to give the title compound, which was used in the next step without further purification or purified with reversed-phase chromatography using water-MeCN as an eluent.

General Procedure 1 STEP 3

To a solution of the General procedure 1 STEP 2 product (1 eq., 35.1 mmol) or an appropriate aryl nitro compound in EtOH (25 mL/mmol, 692 g, 877 mL) and water (3 mL/mmol, 105 g, 105 mL), iron powder (15 eq., 29.4 g, 526 mmol) and $NH_4Cl$ (5 eq., 9.38 g, 175 mmol) were added at RT. The reaction mixture was heated to 50° C. and stirred for 2 h. After completion of the reaction, the mixture was filtered through a pad of Celite, then washed with 2×100 ml of EtOH. The solvent was evaporated under reduced pressure, the evaporation residue was dissolved in 100 ml of DCM. The solution was dried over anhydrous $Na_2SO_4$, filtered, concentrated to dryness to give the title compound, which was used in the next step without further purification.

General Procedure 1 STEP 4

To a solution of General procedure 1 STEP 3 product (1 eq., 32 mmol) in AcOH (0.3 mL/mmol, 10 g, 9.6 mL) and water (3 mL/mmol, 96 g, 96 mL) $H_2SO_4$ (0.3 mL/mmol, 18 g, 9.6 mL) was added at 0° C. Sodium nitrite (1.5 eq., 3.3 g, 48 mmol) was added by portions and the reaction mixture was stirred at 0° C. for 10 min. The resulted dark heterogeneous mixture was allowed to warm to RT and stirred for further 30 min. After completion of the reaction, the mixture was quenched with 300 mL water and the pH was set to ~12 using concentrated NaOH solution. The mixture was extracted with 3×70 ml DCM. The organic layer was washed with 150 mL of brine. The organic layer was dried over anhydrous $Na_2SO_4$, filtered, concentrated to dryness to give a black oil, which was purified by normal phase silica gel chromatography using DCM-EtOAc (100:0 to 70:30) eluents to give the title compound.

General Procedure 1 STEP 5

To a solution of General procedure 1 STEP 4 product (1 eq., 22 mmol) in THF (10 mL/mmol, 200 g, 220 mL), water (5 mL/mmol, 110 g, 110 mL) and MeOH (2.5 mL/mmol, 44 g, 55 mL) LiOH (3 eq., 1.6 g, 66 mmol) was added at RT and the mixture was stirred for further 30 min. After completion of the reaction, the mixture was quenched with 400 mL water and 50 mL of 2 M aq. HCl solution. The mixture was extracted with 3×20 ml EtOAc. The organic layer was washed with brine and dried over anhydrous $Na_2SO_4$, filtered, concentrated to dryness to give an oil, which was purified by normal phase silica gel chromatography using DCM-EtOH (100:0 to 80:20) as an eluent to give the title compound.

General Procedure 1 STEP 6

To a solution of General procedure 1 STEP 5 product (1 eq., 10 mmol) in THF (7 mL/mmol, 63 g, 70 mL) NaH (1.2 eq., 480 mg, 12 mmol, 60 wt % in mineral oil) was added at 0° C. The mixture was allowed to warm to RT and was stirred at this temperature for 30 min. The reaction mixture was cooled to 0° C., 4-methoxy-benzylchloride (1.2 eq., 1.9 g, 12 mmol) was added and the mixture was stirred overnight at RT. After completion of the reaction, the mixture was quenched with 100 mL water and extracted with 3×100 ml EtOAc. The combined organic layers were washed with brine. The organic layer was dried over anhydrous $Na_2SO_4$, filtered, concentrated to dryness to give an orange oil, which was purified by normal phase silica gel chromatography using heptane-EtOAc (100:0 to 75:25) as an eluent to give the title compound.

General Procedure 1 STEP 7

To a solution of General procedure 1 STEP 6 product (1 eq., 7.1 mmol) in DMF (7 mL/mmol, 47.4 g, 50 mL) ethyl prop-2-enoate (2 eq., 1.44 g, 1.56 mL, 14.2 mmol), DIPEA (3 eq., 2.78 g, 3.75 ml, 21.5 mmol), tris-o-tolylphosphine (0.2 eq., 0.44 g, 1.4 mmol) and palladium diacetate (0.1 eq. 0.161 g, 0.71 mmol) were added at RT. The mixture was flushed twice with argon and heated in a closed Schlenk tube overnight at 100° C. After completion of the reaction, the solvent was evaporated to dryness under reduced pressure to afford a black oil, which was purified by normal phase silica gel chromatography using heptane-EtOAc (100:0 to 75:25) as an eluent to give the title compound.

General Procedure 2

General Procedure 2 STEP 1

To a solution of 1-fluoro-3-methyl-2-nitro-benzene (1 eq., 1.93 mmol) in MeCN (2 mL/mmol, 101.3 g, 128.92 mL), the O-benzyl-amino alcohol (1.2 eq., 2.32 mmol) was added followed by addition of $Cs_2CO_3$ (2 eq., 1.26 g, 3.87 mmol) or TEA (2 eq., 3.87 mmol) at RT. The reaction mixture was heated to 70° C. and stirred at this temperature overnight. After completion of the reaction, the mixture was filtered, the mother liquor was evaporated under reduced pressure. The crude product was purified by reversed-phase chromatography using water-MeCN gradient elution (95:5 to 0:100) to give the title compound.

General Procedure 2 STEP 2

To a solution of the General procedure 2 STEP 1 product (1 eq., 22 mmol) in AcOH (26 mL) NBS (1.2 eq., 4.6 g, 26 mmol) was added at RT. The reaction mixture was heated to 110° C. and stirred for 1.5 h. After completion of the reaction, the mixture was cooled to RT, quenched with 200 ml of ice cold water. The pH was adjusted to 14 using NaOH solution. The mixture was stirred at RT for 10 min. The mixture was extracted with 3×150 ml DCM. The combined organic layers were washed with brine. The organic phase was dried over anhydrous $Na_2SO_4$, filtered, concentrated to dryness to give the title compound, which was purified by reversed-phase chromatography using water-MeCN gradient elution (95:5 to 0:100) to give the title compound.

General Procedure 2 STEP 3

To a solution of the General procedure 2 STEP 2 product (1 eq., 17 mmol) in EtOH (430 mL) (or IPA) and water (50 mL), iron powder (15 eq., 14 g, 260 mmol) and $NH_4Cl$ (5.5 eq., 5 g, 93.5 mmol) were added at RT. The reaction mixture was heated to 50° C. and stirred at this temperature overnight. After completion of the reaction, the mixture was filtered through a pad of Celite and washed with 2×100 ml of EtOH. The mother liquor was concentrated under reduced pressure. The crude product was purified by reversed-phase chromatography using water-MeCN gradient elution (95:5 to 0:100) to give the title compound.

General Procedure 2 STEP 4

To a solution of General procedure 2 STEP 3 product (1 eq., 13 mmol) in AcOH (30 mL) and water (30 mL), $H_2SO_4$ (8.9 g, 4.6 mL, 90 mmol) was added at 0° C. Sodium nitrite (1.5 eq., 3.3 g, 48 mmol) was added in small portions and the reaction mixture was stirred at 0° C. for 10 min. The resulted dark heterogeneous mixture was allowed to warm to RT and was stirred at this temperature for further 30 min. After completion of the reaction, the mixture was quenched with 300 mL water and the pH was set to ~12 using 2 M aq. NaOH solution. The mixture was extracted with 3×70 ml DCM. The combined organic layers were washed with 150 mL of brine. The organic layer was dried over anhydrous $Na_2SO_4$, filtered, concentrated to dryness to give the crude product, which was purified by normal phase silica gel chromatography using DCM-EtOAc (100:0 to 95:5) as an eluent to give the title compound.

General Procedure 2 STEP 5

To a solution of General procedure 2 STEP 4 product (1 eq., 2.91 mmol) in DMF (20 mL) ethyl prop-2-enoate (2.2 eq., 642 g, 0.699 mL, 6.41 mmol), DIPEA (3 eq., 1.13 g, 1.52 ml, 8.74 mmol), tris-o-tolylphosphine (0.2 eq., 0.177 g, 0.583 mmol) and palladium acetate (0.1 eq. 0.65 g, 0.291 mmol) were added at RT. The mixture was flushed twice with argon and heated in a closed Schlenk tube overnight at 100° C. After completion of the reaction the solvent was evaporated to dryness under reduced pressure. The crude product was purified by normal phase silica gel chromatography using DCM-EtOH (100:0 to 95:5) as an eluent to give the title compound.

General Procedure 3

The aryl-bromide derivative (1 eq., 10 mmol) was introduced into a round bottom flask and dissolved in dioxane (5 mL/mmol, 50 mL). 4,4,5,5-Tetramethyl-2-(4,4,5,5-tetramethyl-1,3,2-dioxaborolan-2-yl)-1,3,2-dioxaborolane (1.1 eq., 2.79 g, 11 mmol) and dry potassium acetate (3.5 eq., 3.43 g, 35 mmol) were added at RT. The mixture was flushed with argon or nitrogen.

Finally [1,1'-bis(diphenylphosphino)ferrocene]dichloropalladium(II) catalyst (0.02 eq., 146 mg, 0.2 mmol) was added and the mixture was flushed again with argon or nitrogen before heating at 75° C. overnight under inert atmosphere. After completion of the reaction, the mixture was filtered through a pad of Celite and the mother liquor was evaporated to dryness under reduced pressure. The crude product was purified by normal phase silica gel chromatography using DCM-EtOAc (100:0 to 90:10) as an eluent, or by reversed-phase chromatography using water-MeCN (95:5 to 0:100) as an eluent to give the title compound.

General Procedure 4

General Procedure 4 STEP 1

Paraformaldehyde (3 eq., 12.8 mmol), magnesium dichloride (2 eq., 0.812 mg, 8.5 mmol) and TEA (2 eq., 1.18 mL, 8.5 mmol) were introduced into a round bottom flask. The mixture was dissolved in THF (20 mL) and stirred for 30 min at RT. The substituted phenol (1 eq., 4.3 mmol) was added and the mixture was stirred at reflux temperature overnight. After completion of the reaction the solvent was evaporated to dryness under reduced pressure. The residue was diluted with 50 mL EtOAc, washed with 50 mL 1 M HCl solution, then with 50 mL brine. The organic layer was dried over anhydrous $MgSO_4$, filtered, concentrated to obtain the crude product, which was purified by normal phase silica gel chromatography using heptane-EtOAc as an eluent to give the title compound.

General Procedure 4 STEP 2

Chlorosulfonyl isocyanate (4 eq., 13 g, 8.1 mL, 93 mmol) was introduced into a round bottom flask at 0° C. HCOOH (4 eq., 3.5 mL, 93 mmol) was added dropwise over a period of 40 min at 0° C. The mixture was allowed to warm to RT over a period of 30 min and the stirring at RT was continued for additional 1 h. The mixture was cooled to 0° C. and General procedure 4 STEP 1 product (1 eq., 23 mmol) dissolved in NMP (3.5 mL/mmol, 81 mL) was added dropwise over a period of 10 min. The mixture was allowed to warm to RT and stirred at this temperature overnight. After completion of the reaction, the mixture was quenched with 500 mL aq. sat. $NH_4Cl$ solution. The mixture was extracted with 2×200 mL EtOAc, the combined organic layers were dried over anhydrous $Na_2SO_4$, filtered, concentrated to dryness to give the crude product, which was purified by normal phase silica gel chromatography using heptane-EtOAc (100:0 to 50:50) as an eluent to give the title compound.

General Procedure 4 STEP 3

To a cooled solution of General procedure 4 STEP 2 product (1 eq., 22.4 mmol) in MeOH (8 mL/mmol, 179 mL) at −5° C. sodium borohydride (1.2 eq., 1.02 g, 26.9 mmol) was added slowly over a period of 20 min. The mixture was stirred for 1 h at −5° C. After completion of the reaction, the mixture was allowed to warm to RT and concentrated to dryness to give the crude product, which was purified by normal phase silica gel chromatography using DCM-EtOH (100:0 to 99:1) as an eluent, or by reversed-phase chromatography using water-MeCN gradient elution (95:5 to 0:100) to give the title compound.

General Procedure 5

General Procedure 5 STEP 1

To a stirred solution of the 6-bromo-3,4-dihydro-1,2$\lambda^6$,3-benzoxathiazine 2,2-dioxide derivative (1 eq., 17 mmol) in DCM (92 mL), TEA (1.1 eq., 2.5 mL, 18 mmol), N,N-dimethylpyridin-4-amine (0.1 eq., 0.2 g, 1.7 mmol) and di-tert-butyl-dicarbonate (1.1 eq., 4 g, 18 mmol) were added at RT. The mixture was stirred overnight at RT. After completion of the reaction the mixture was extracted with 3×50 ml 10 wt % aq. citric acid solution, then with 50 ml water. The organic layer was dried over anhydrous $Na_2SO_4$, filtered, concentrated to dryness to give the title compound, which was used in a next step without further purification.

General Procedure 5 STEP 2

General Procedure 5 STEP 1 product (1 eq., 16 mmol) was introduced into a round bottom flask and dissolved in dioxane (7.5 mL/mmol, 120 mL). 4,4,5,5-Tetramethyl-2-(4,4,5,5-tetramethyl-1,3,2-dioxaborolan-2-yl)-1,3,2-dioxaborolane (1.1 eq., 4.6 g, 18 mmol) and dry potassium acetate (3.5 eq., 5.6 g, 57 mmol) were added to the mixture at RT. The mixture was flushed with argon or nitrogen. Finally [1,1'-bis(diphenylphosphino) ferrocene]dichloropalladium (II) catalyst (0.02 eq., 160 mg, 0.33 mmol) was added and the mixture was flushed again with argon or nitrogen. After heating at 75° C. overnight under inert atmosphere. The mixture was filtered through a Celite pad, and the mother liquor was concentrated to dryness under reduced pressure. The crude product was purified by normal phase silica gel chromatography using heptane-EtOAc (100:0 to 80:20) as an eluent to give the title compound.

General Procedure 5 STEP 3

To a stirred solution of General procedure 5 STEP 2 product (1 eq., 11.5 mmol) in EtOH (15 mL/mmol, 73 mL) and water (7.5 mL/mmol, 37 mL), m-chloro-perbenzoic acid (1 eq., 2.84 g, 11.5 mmol) was added at RT in portions. The mixture was stirred overnight at RT. After completion of the reaction the mixture was quenched with 100 mL sat. aq. $NaHCO_3$ solution. The mixture was extracted with 3×50 ml of EtOAc. The combined organic layers were washed with 50 mL sat. aq. $NaHCO_3$ solution, then with 50 mL water. The organic layer was dried over anhydrous $Na_2SO_4$, filtered, concentrated to dryness to give the crude product, which was purified by normal phase silica gel chromatography using heptane-EtOAc (100:0 to 50:50) as an eluent to give the title compound.

General Procedure 5 STEP 4

To a solution of General procedure 5 STEP 3 product (1 eq., 9.2 mmol) in MeCN (58 mL), $Cs_2CO_3$ (2.4 eq., 7.2 g, 22 mmol) and benzylbromide (2.2 eq., 3.4 g, 2.4 mL, 20 mmol) were added and the mixture was stirred overnight at RT. After completion of the reaction the solvent was evaporated under reduced pressure, then diluted with 40 ml EtOAc. The mixture was washed with 40 mL brine, then with 40 mL water. The organic layer was dried over anhydrous $Na_2SO_4$, filtered, concentrated to dryness to give the crude product, which was used in the next step without further purification.

General Procedure 5 STEP 5

To a solution of General procedure 5 STEP 4 product (1 eq., 9.2 mmol) in DCM (75 mL), TFA (8 eq., 8.4 g, 5.66 mL, 74 mmol) was added dropwise and the mixture was stirred overnight at RT. The pH of the mixture was set to 9 using sat. aq. $NaHCO_3$ solution. The layers were separated, the organic layer was extracted with 30 mL brine, then 30 mL water. The organic layer was dried over anhydrous $Na_2SO_4$, filtered, concentrated to dryness to give the crude product, which was purified by normal phase silica gel chromatography using heptane-EtOAc (100:0 to 70:30) as an eluent to afford the title compound.

General Procedure 6

To a stirred solution of the ethyl aryl(prop-2-enoate) derivative or ethyl heteroaryl(prop-2-enoate) derivative (1 eq., 4.6 mmol) in dioxane (5-8 mL/mmol, 23 mL) and water (1-2.7 mL/mmol, 4.6 mL), the [3-(4,4,5,5-tetramethyl-1,3,2-dioxaborolan-2-yl)aryl derivative (1.5-2 eq., 6.9 mmol) and TEA (1.5 eq., 0.96 mL, 6.9 mmol) were added. The suspension was flushed and degassed with argon or nitrogen. Finally chloro(1,5-cyclooctadiene)rhodium(I) dimer catalyst (0.05 eq., 56 mg, 0.23 mmol) was added and the mixture was heated at 80° C. for 4-16 h under inert atmosphere. After completion of the reaction the mixture was diluted with 100 mL water, the layers were separated, the aq. layer was extracted with 2×50 mL EtOAc. The combined organic layers were washed with 50 mL brine, before drying over anhydrous $Na_2SO_4$. Filtration and concentration to dryness afforded the crude product, which was purified by normal phase silica gel chromatography using heptane-EtOAc (100:0 to 50:50) as an eluent, or by reversed-phase chromatography using water-MeCN gradient elution (95:5 to 0:100) to give the title compound.

General Procedure 7

To a stirred solution of the hydroxymethylphenyl derivative (1 eq., 1.6 mmol) in THF (22 mL/mmol, 35 mL), the substituted benzoxathiazine 2,2-dioxide, or 1,3-benzothiadiazine 2,2-dioxide derivative (1-2.5 eq., 2.4 mmol) and $PPh_3$ (2.2 eq., 0.93 g, 3.5 mmol) were added. The reaction mixture was cooled to 15° C. and DIAD (2 eq., 0.63 mL, 3.2 mmol) was added dropwise over a period of 5 min. The mixture was allowed to warm to RT and was stirred at this temperature overnight. After completion of the reaction the mixture was concentrated to dryness and purified by normal phase silica gel chromatography using DCM-EtOAc (100:0 to 80:20) eluent, or by reversed-phase chromatography using water-MeCN gradient elution (95:5 to 0:100) to give the title compound.

General Procedure 8

A stainless steel hydrogenation autoclave was charged with the ethyl 3-[3-[(6-benzyloxy-2,2-dioxo-4H-1,2$\lambda^6$,3-benzoxathiazin-3-yl)methyl]phenyl]-3-(4-methyl-1H-benzotriazol-5-yl)propanoate or ethyl 3-[3-[(6-benzyloxy-2,2-dioxo-1,4-dihydro-2,1,3-benzothiadiazin-3-yl)methyl]phenyl]-3-(4-methyl-1H-benzotriazol-5-yl)propanoate (1 eq., 0.883 mmol), Pd/C catalyst (0.1 eq., 0.0883 mmol), dioxane (3 mL), MeOH or EtOH (10 mL) and DCM (4 mL) and the autoclave was sealed, inertised, and filled with hydrogen (1-8 bar). After stirring at RT for 10-40 h, the reaction mixture was filtered through a Celite pad and the volatiles of the filtrate were evaporated to give the title compound. The crude product was purified by normal phase silica gel chromatography or by reversed-phase chromatography using water-MeCN gradient elution (95:5 to 0:100) to give the title compound.

General Procedure 9

To a stirred solution of the N-hydroxyalkyl ethyl 3-[3-[(6-hydroxy-2,2-dioxo-4H-1,2$\lambda^6$,3-benzoxathiazin-3-yl)methyl]phenyl]-3-(4-methyl-1H-benzotriazol-5-yl)propanoate or N-hydroxyalkyl ethyl 3-[3-[(6-hydroxy-2,2-dioxo-1,4-dihydro-2,1,3-benzothiadiazin-3-yl)methyl]phenyl]-3-(4-methyl-1H-benzotriazol-5-yl)propanoate (1 eq., 0.122 mmol) in DCM (1 mL), carbon-tetrabromide (7 eq., 69 mg, 0.2074 mmol) and $PPh_3$ (1.7 eq., 54.4 mg, 0.2074 mmol) were added. After stirring at RT for 5-20 h, the reaction mixture was concentrated under reduced pressure, and the crude product was purified by normal phase silica gel chromatography using hexane-EtOAc gradient elution to give the title compound.

General Procedure 10

The N-hydroxyalkyl ethyl 3-[3-[(6-hydroxy-2,2-dioxo-4H-1,2)$^6$,3-benzoxathiazin-3-yl)methyl]phenyl]-3-(4-methyl-1H-benzotriazol-5-yl)propanoate or N-hydroxyalkyl ethyl 3-[3-[(6-hydroxy-2,2-dioxo-1,4-dihydro-2,1,3-benzothiadiazin-3-yl)methyl]phenyl]-3-(4-methyl-1H-benzotriazol-5-yl)propanoate (1 eq., 88.7 mmol) was dissolved in DCM (355 mL) under $N_2$ atmosphere. The solution was cooled to 0° C. and thionyl chloride (1.2-4 eq., 12.7 g, 7.77 mL, 106.5 mmol) was added dropwise under $N_2$ atmosphere. After stirring at 40° C. for 4 h, the reaction mixture was cooled to 0° C. Water (155 mL) and aq. sat. $NaHCO_3$ solution (155 mL) were added slowly. and the layers were separated. The organic layer was washed with water, dried over $MgSO_4$, and the solvents were removed under reduced pressure. The crude product was used without further purification, or was purified if needed by normal phase silica gel chromatography using DCM-MeOH or hexane-EtOAc gradient elution to give the title compound.

General Procedure 11

To the stirred solution of the chloro or bromoalkyl ethyl 3-[3-[(6-hydroxy-2,2-dioxo-4H-1,2$\lambda^6$,3-benzoxathiazin-3-yl)methyl]phenyl]-3-(4-methyl-1H-benzotriazol-5-yl)propanoate or chloro or bromoalkyl ethyl 3-[3-[(6-hydroxy-2,2-dioxo-1,4-dihydro-2,1,3-benzothiadiazin-3-yl)methyl]phenyl]-3-(4-methyl-1H-benzotriazol-5-yl)propanoate (1 eq., 0.055 mmol) in MeCN (16 mL), $Cs_2CO_3$ (1-3 eq., 11 mg, 0.055 mmol) was added and the mixture was stirred at RT-80° C. for 4-36 h. After completion of the reaction, water (10 mL) was added to the mixture, and the MeCN was evaporated under reduced pressure. The residue was extracted with DCM (3×10 mL) and the combined organic layers were washed with water. The organic layer was dried over $Na_2SO_4$, filtered, the filtrate was concentrated to dryness to give the title compound, which was purified by normal phase silica gel chromatography, or by reversed-phase chromatography using water-MeCN gradient elution (95:5 to 0:100) to give the title compound.

General Procedure 12

To the solution of the macrocyclic ester (1 eq., 0.067 mmol) in a mixture of THF (0.67 mL), MeOH or EtOH (0.17 mL) and water (0.34 mL), lithium hydroxyde (3 eq.-4 eq., 4.8 mg, 0.20 mmol) was added. The reaction mixture was stirred at RT-80° C. for 2-30 h. After completion of the reaction, citric acid solution (10%) or 1 M aq. HCl was added to the reaction mixture, and the neutralized mixture was extracted with DCM three times. The organic layer was dried over $Na_2SO_4$, filtered, and the filtrate was concentrated. The residue was purified by preparative reversed-phase chromatography using water-MeCN gradient elution (95:5 to 0:100) to give the title compound.

EXAMPLE 1: [4,32-dimethyl-28,28-dioxo-22,27-dioxa-28λ$^6$-thia-1,14,15,16-tetraazahexacyclo [21.5.3.1$^{3,7}$0.1$^{9,13}$0.0$^{12,16}$0.0$^{26,30}$]tritriaconta-3(33),4,6,9(32),10,12,14,23,25,30-decaen-8-yl]acetic acid

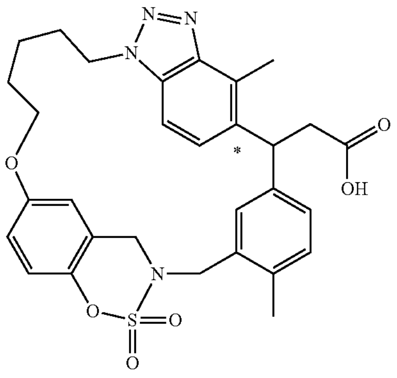

* = RorS

Step A1: Preparation of 5-(3-methyl-2-nitroanilino)pentan-1-ol

Using General Procedure 1 STEP 1 starting from 1-fluoro-3-methyl-2-nitro-benzene (1 eq., 10.0 g, 7.85 mL, 64.5 mmol) and 5-aminopentan-1-ol (3 eq., 19.950 g, 21 mL, 193.5 mmol) as reactants, the title compound (12.6 g, 82% yield) was obtained.

$^1$H-NMR (400 MHz, DMSO-d6) δ ppm: 7.26 (t, 1H), 6.76 (d, 1H), 6.54 (d, 1H), 6.39 (t, 2H), 4.34 (t, 1H), 3.39 (q, 2H), 3.16 (q, 2H), 2.3 (s, 2H), 1.55 (s, 2H), 1.44 (m, 2H), 1.34 (m, 2H)

Step A2: Preparation of 5-(4-bromo-3-methyl-2-nitroanilino)pentyl acetate

Using General Procedure 1 STEP 2 starting from 5-(3-methyl-2-nitroanilino)pentan-1-ol (8 g, 34 mmol) as a reactant, the title compound (12.6 g orange oil, quant.) was obtained.

$^1$H-NMR (400 MHz, DMSO-d6) δ ppm: 7.5 (d, 1H), 6.72 (d, 1H), 6.12 (t1, 1H), 4 (t, 2H), 3.15 (q, 2H), 2.25 (s, 3H), 2 (s, 3H), 1.6-1.3 (m, 6H)

Step A3: Preparation of 5-(2-amino-4-bromo-3-methylanilino)pentyl acetate

Using General Procedure 1 STEP 3 starting from 5-(4-bromo-3-methyl-2-nitroanilino)pentyl acetate (12.6 g, 35.1 mmol) as a reactant, the title compound (11.7 g orange solid, 91% yield) was obtained.

$^1$H-NMR (400 MHz, DMSO-d6) δ ppm: 6.7 (d, 1H), 6.25 (d, 1H), 5.8 (m, 3H), 4 (t, 2H), 3 (t, 2H), 2.2 (s, 3H), 2.01 (s, 3H), 1.65-1.4 (m, 6H)

Step A4: Preparation of 5-(5-bromo-4-methyl-1H-benzotriazol-1-yl)pentyl acetate

Using General Procedure 1 STEP 4 starting from 5-(2-amino-4-bromo-3-methylanilino)pentyl acetate (12 g, 32 mmol) as a reactant, the title compound (7.5 g orange oil, 69% yield) was obtained.

$^1$H-NMR (400 MHz, DMSO-d6) δ ppm: 7.7 (2d, 2H), 4.7 (t, 2H), 3.97 (t, 2H), 2.71 (s, 3H), 1.99 (s, 3H), 1.95 (m, 2H), 1.6 (m, 2H), 1.29 (m, 2H)

Step A5: Preparation of 5-(5-bromo-4-methyl-1H-benzotriazol-1-yl)pentan-1-ol

Using General Procedure 1 STEP 5 starting from 5-(5-bromo-4-methyl-1H-benzotriazol-1-yl)pentyl acetate (7.5 g, 22 mmol) as a reactant, the title compound (6.7 g orange oil, quant.) was obtained.

$^1$H-NMR (400 MHz, DMSO-d6) δ ppm: 7.7 (2d, 2H), 4.7 (t, 2H), 4.35 (m, 1H), 3.35 (t, 2H), 2.71 (s, 3H), 1.9 (m, 2H), 1.45 (m, 2H), 1.28 (m, 2H)

Step A6: Preparation of 5-bromo-1-{5-[(4-methoxy-phenyl)methoxy]pentyl}-4-methyl-1H-benzotriazole Using General Procedure 1 STEP 6 starting from 5-(5-bromo-4-methyl-1H-benzotriazol-1-yl)pentan-1-ol (3.0 g, 10 mmol) as a reactant, the title compound (3 g yellow oil, 72% yield) was obtained.

$^1$H-NMR (400 MHz, DMSO-d6) δ ppm: 7.7 (2d, 2H), 7.15 (d, 2H), 6.85 (d, 2H), 4.7 (t, 2H), 4.3 (s, 2H), 3.75 (s, 3H), 3.32 (t, 2H), 2.71 (s, 3H), 1.9 (m, 2H), 1.52 (m, 2H), 1.28 (m, 2H)

Step A7: Preparation of ethyl (2E)-3-(1-{5-[(4-methoxyphenyl)methoxy]pentyl}-4-methyl-1H-benzotriazol-5-yl)prop-2-enoate Using General Procedure 1 STEP 7 starting from 5-bromo-1-{5-[(4-methoxyphenyl)methoxy]pentyl}-4-methyl-1H-benzotriazole (3 g, 7.1 mmol) as a reactant, the title compound (3 g yellow solid, 91% yield) was obtained.

$^1$H-NMR (500 MHz, DMSO-d6) δ ppm: 8.03 (d, 1H), 7.96 (d, 1H), 7.73 (d, 1H), 7.16 (d, 2H), 6.86 (d, 2H), 6.64 (d, 1H), 4.7 (t, 2H), 4.3 (s, 2H), 4.22 (q, 2H), 3.73 (s, 3H), 3.33 (t, 2H), 2.81 (s, 3H), 1.9 (m, 2H), 1.53 (m, 2H), 1.28 (t, 3H), 1.26 (m, 2H)

Step C1: Preparation of 6-(benzyloxy)-2H-1,2)$^6$,3-benzoxathiazine-2,2-dione

Using General Procedure 4 STEP 2 starting from 5-(benzyloxy)-2-hydroxybenzaldehyde (1 eq., 5.3 g, 23 mmol) as a reactant, the title compound (6.48 g yellow solid, 96% yield) was obtained.

$^1$H-NMR (400 MHz, $CDCl_3$) δ ppm: 8.6 (s, 1H), 7.4 (m, 5H), 7.35 (dd, 1H), 7.3 (d, 1H), 7.15 (d, 1H), 5.1 (s, 2H)

Step C2: Preparation of 6-(benzyloxy)-3,4-dihydro-2H-1,2λ$^6$,3-benzoxathiazine-2,2-dione Using General Procedure 4 STEP 3 starting from 6-(benzyloxy)-2H-1,2λ$^6$,3-benzoxathiazine-2,2-dione (1 eq., 6.48 g, 22.4 mmol) as a reactant, the title compound (5.9 g, yellow solid, 90% yield) was obtained.

$^1$H-NMR (400 MHz, DMSO-d6) δ ppm: 8.4 (s1, 1H), 7.45 (d, 2H), 7.4 (t, 2H), 7.3 (t, 1H), 7 (m, m H), 5.1 (s, 2H), 4.5 (s, 2H)

Step 1: Preparation of ethyl 3-[3-(hydroxymethyl)-4-methylphenyl]-3-(1-{5-[(4-methoxyphenyl) methoxy]pentyl}-4-methyl-1H-benzotriazol-5-yl) propanoate Using General Procedure 6 starting from (ethyl(2E)-3-(1-{5-[(4-methoxyphenyl)methoxy]pentyl}-4-methyl-1H-benzotriazol-5-yl)prop-2-enoate (1 eq., 4 g, 4.6 mmol), and [2-methyl-5-(4,4,5,5-tetramethyl-1,3,2-dioxaborolan-2-yl) phenyl]methanol (1.5 eq., 1.7 g, 6.9 mmol) as reactants, the title compound (0.96 g, 38% yield) was obtained.

$^1$H-NMR (400 MHz, DMSO-d6) δ ppm: 7.6 (d, 1H), 7.48 (d, 1H), 7.25 (d, 1H), 7.18 (d, 2H), 7.08 (dd, 1H), 7 (d, 1H), 6.88 (d, 2H), 4.98 (t, 1H), 4.82 (t, 1H), 4.61 (t, 2H), 4.4 (d, 2H), 4.3 (s, 2H), 3.92 (q, 2H), 3.71 (s, 3H), 3.3 (t, 2H), 3.11 (2dd, 2H), 2.75 (s, 3H), 2.15 (s, 3H), 1.88 (m, 2H), 1.52 (m, 2H), 1.28 (m, 2H), 1 (t, 3H);

Step 2: Preparation of ethyl 3-(3-{[6-(benzyloxy)-2,2-dioxo-2H-1,2λ$^6$,3-benzoxathiazin-3(4H)-yl]methyl}-4-methylphenyl)-3-(1-{5-[(4-methoxyphenyl)methoxy]pentyl}-4-methyl-1H-benzotriazol-5-yl)propanoate Using General Procedure 7 starting from ethyl 3-[3-(hydroxymethyl)-4-methylphenyl]-3-(1-{5-[(4-methoxyphenyl)methoxy]pentyl}-4-methyl-1H-benzotriazol-5-yl) propanoate (1 eq., 0.96 g, 1.6 mmol), and 6-(benzyloxy)-3,4-dihydro-2H-1,2λ$^6$,3-benzoxathiazine-2,2-dione (1.5 eq., 0.7 g, 2.4 mmol) as reactants, the title compound (90% yield) was obtained.

$^1$H-NMR (400 MHz, DMSO-d6) δ ppm: 1.16 (m, 3H) 1.21-1.29 (m, 1H) 1.44-1.56 (m, 1H) 1.78-1.89 (m, 1H) 2.21 (s, 1H) 2.76 (s, 1H) 3.16 (dd, J=7.95, 4.77 Hz, 1H) 3.26-3.29 (m, 1H) 3.92 (q, J=7.09 Hz, 2H) 4.21 (s, 2H) 4.28 (s, 2H) 4.42 (s, 2H) 4.59 (t, J=6.91 Hz, 2H) 4.85 (t, J=7.95 Hz, 1H) 5.10 (s, 2H) 6.82-6.88 (m, 2H) 6.94 (d, J=2.81 Hz, 1H) 7.03-7.10 (m, 1H) 7.10-7.17 (m, 4H) 7.17-7.21 (m, 1H) 7.22 (s, 1H) 7.31-7.37 (m, 1H) 7.37-7.43 (m, 2H) 7.45 (s, 2H) 7.48 (d, J=8.44 Hz, 2H) 7.56-7.61 (m, 1H)

Step 3: Preparation of ethyl 3-{3-[(6-hydroxy-2,2-dioxo-2H-1,2λ$^6$,3-benzoxathiazin-3(4H)-yl)methyl]-4-methylphenyl}-3-[1-(5-hydroxypentyl)-4-methyl-1H-benzotriazol-5-yl]propanoate Using General Procedure 8 starting from ethyl 3-(3-{[6-(benzyloxy)-2,2-dioxo-2H-1,2λ$^6$,3-benzoxathiazin-3(4H)-yl]methyl}-4-methylphenyl)-3-(1-{5-[(4-methoxyphenyl) methoxy]pentyl}-4-methyl-1H-benzotriazol-5-yl) propanoate (1 eq., 2 g, 1.4 mmol) as a reactant, the title compound (830 mg yellow oil, 90% yield) was obtained.

$^1$H-NMR (400 MHz, DMSO-d6) δ ppm: 9.7/4.38 (2m, 2H), 7.61 (d, 1H), 7.5 (d, 1H), 7.21 (d, 1H), 7.2 (dd, 1H), 7.12 (d, 1H), 6.99 (d, 1H), 6.8 (dd, 1H), 6.6 (d, 1H), 4.82 (t, 1H), 4.61 (t, 2H), 4.39 (s, 2H), 4.29 (m, 2H), 3.95 (q, 2H), 3.31 (t, 2H), 3.18 (m, 2H), 2.75 (s, 3H), 2.2 (s, 3H), 1.88 (m, 2H), 1.4 (m, 2H), 1.25 (m, 2H), 1 (t, 3H)

Step 4: Preparation of ethyl 3-[1-(5-bromopentyl)-4-methyl-1H-benzotriazol-5-yl]-3-{3-[(6-hydroxy-2,2-dioxo-2H-1,2λ$^6$,3-benzoxathiazin-3(4H)-yl)methyl]-4-methylphenyl}propanoate Using General Procedure 9 starting from ethyl 3-{3-[(6-hydroxy-2,2-dioxo-2H-1,2λ$^6$,3-benzoxathiazin-3(4H)-yl)methyl]-4-methylphenyl}-3-[1-(5-hydroxypentyl)-4-methyl-1H-benzotriazol-5-yl]propanoate (1 eq., 0.8 g, 1.3 mmol) as a reactant, the title compound (710 mg white solid, 80% yield) was obtained.

$^1$H-NMR (400 MHz, DMSO-d6) δ ppm: 9.7 (m, 1H), 7.61 (d, 1H), 7.5 (d, 1H), 7.21 (d, 1H), 7.2 (dd, 1H), 7.12 (d, 1H), 6.99 (d, 1H), 6.8 (dd, 1H), 6.6 (d, 1H), 4.82 (t, 1H), 4.65 (t, 2H), 4.39 (s, 2H), 4.29 (m, 2H), 3.92 (q, 2H), 3.45 (t, 2H), 3.18 (m, 2H), 2.75 (s, 3H), 2.21 (s, 3H), 1.9 (m, 2H), 1.8 (m, 2H), 1.35 (m, 2H), 1 (t, 3H)

Step 5: Preparation of ethyl[4,32-dimethyl-28,28-dioxo-22,27-dioxa-28λ$^6$-thia-1,14,15,16-tetraazahexacyclo[21.5.3.1$^{3,7}$0.1$^{9,13}$0.0$^{12,16}$0.0$^{26,30}$]tritriaconta-3(33),4,6,9(32),10,12,14,23,25,30-decaen-8-yl]acetate Using General Procedure 11 starting from ethyl 3-[1-(5-bromopentyl)-4-methyl-1H-benzotriazol-5-yl]-3-{3-[(6-hydroxy-2,2-dioxo-2H-1,2λ$^6$,3-benzoxathiazin-3(4H)-yl) methyl]-4-methylphenyl}propanoate (1 eq., 0.7 g, 0.99 mmol) as a reactant, the title compound (620 mg yellow oil, 93% yield) was obtained.

$^1$H-NMR (400 MHz, DMSO-d6) δ ppm: 7.65 (d, 1H), 7.52 (d, 1H), 7.5 (dd, 1H), 7.3 (d, 1H), 7.05 (d, 1H), 6.9 (dd, 1H), 6.78 (d, 1H), 6.12 (d, 1H), 4.8 (t, 1H), 4.7 (t, 2H), 4.2/3.9 (m, 2H), 4.15/4 (m, 2H), 3.9 (m, 2H), 3.85 (m, 2H), 3.07 (m, 2H), 2.68 (s, 3H), 2.35 (s, 3H), 2 (m, 2H), 1.75 (m, 2H), 1.5/1.4 (m, 2H), 1 (t, 3H)

Step 6: Preparation of Example 1

Using General Procedure 12 starting from ethyl[4,32-dimethyl-28,28-dioxo-22,27-dioxa-28λ$^6$-thia-1,14,15,16-tetraazahexacyclo[21.5.3.1$^{3,7}$0.1$^{9,13}$0.0$^{12,16}$0.0$^{26,30}$]tritriaconta-3(33),4,6,9(32),10,12,14,23,25,30-decaen-8-yl] acetate (1 eq., 0.62 g, 0.92 mmol) as a reactant, the title compound (291 mg white solid, 55% yield) was obtained.

The enantiopure products were obtained by chromatographic separation on chiral column.

EXAMPLE 1a (E1)

HRMS calculated for $C_{30}H_{32}N_4O_6S$: 576.2042; $[M+H]^+$ found: 577.2115 (δ=−0.1 ppm).

EXAMPLE 1b (E2)

HRMS calculated for $C_{30}H_{32}N_4O_6S$: 576.2042; $[M+H]^+$ found: 577.2113 (δ=−0.4 ppm).

$^1$H-NMR (400 MHz, DMSO-d6) δ ppm: 11.55 (m, 1H), 7.62 (d, 1H), 7.5 (d, 2H), 7.29 (d, 1H), 7.02 (d, 1H), 6.9 (dd, 1H), 6.72 (d, 1H), 6.11 (d, 1H), 4.8 (t, 1H), 4.7 (t, 2H), 4.2/3.9 (2d, 2H), 4.11/4 (2d, 2H), 3.9/3.8 (2m, 2H), 2.92 (2dd, 2H), 2.65 (s, 3H), 2.31 (s, 3H), 1.99 (m, 2H), 1.72 (m, 2H), 1.48/1.38 (2m, 2H)

EXAMPLE 2: [4,30-Dimethyl-26,26-dioxo-20,25-dioxa-26λ$^6$-thia-1,14,15,16-tetraazahexacyclo[19.5.3.1$^{3,7}$0.1$^{9,13}$0.0$^{12,16}$0.0$^{24,28}$]hentriaconta-3(31),4,6,9(30),10,12,14,21,23,28-decaen-8-yl]acetic acid

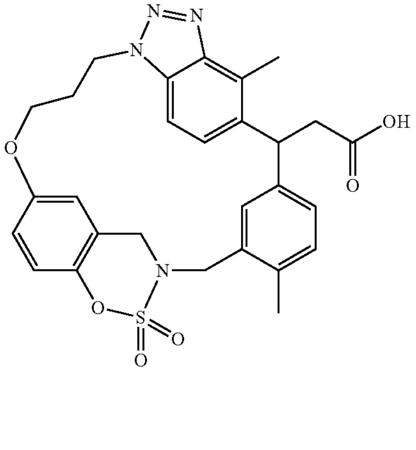 [SMILES: Cc1ccc2cc1CN1Cc3cc(ccc3OS1(=O)=O)OCCCn1nnc3c(C)c(ccc31)C2CC(=O)O]

Step A1: Preparation of N-[3-(benzyloxy)propyl]-3-methyl-2-nitroaniline

Using General Procedure 2 STEP 1 starting from 1-fluoro-3-methyl-2-nitro-benzene (1 eq., 1.93 mmol) and 3-benzyloxypropan-1-amine (1.2 eq., 383 mg, 2.32 mmol) as reactants, the title compound (375 mg, 64% yield) was obtained.

$^1$H-NMR (400 MHz, DMSO-d6) δ ppm: 7.37-7.26 (m, 5H), 7.26 (t, 1H), 6.77 (d, 1H), 6.55 (d, 1H), 6.47 (t, 1H), 4.47 (s, 2H), 3.51 (t, 2H), 2.29 (s, 2H), 2.26 (q, 2H), 1.83 (m, 2H)

Step A2: Preparation of N-[3-(benzyloxy)propyl]-4-bromo-3-methyl-2-nitroaniline

Using General Procedure 2 STEP 2 starting from N-[3-(benzyloxy)propyl]-3-methyl-2-nitroaniline (6.5 g, 22 mmol) as a reactant, the title compound (6.54 g, 80% yield) was obtained.

$^1$H-NMR (400 MHz, DMSO-d6) δ ppm: 7.5 (d, 1H), 7.3 (m, 5H), 6.72 (d, 1H), 6.18 (t), 4.45 (s, 2H), 3.48 (t, 2H), 3.22 (q, 2H), 2.25 (s, 3H), 1.8 (m, 2H)

Step A3: Preparation of N$^1$-[3-(benzyloxy)propyl]-4-bromo-3-methylbenzene-1,2-diamine Using General Procedure 2 STEP 3 starting from N-[3-(benzyloxy)propyl]-4-bromo-3-methyl-2-nitroaniline (6.5 g, 17 mmol) as a reactant, the title compound (5.4 g, 75% yield) was obtained.

$^1$H-NMR (400 MHz, DMSO-d6) δ ppm: 7.39-7.24 (s, 5H), 6.71 (d, 1H), 6.26 (d, 1H), 4.62-4.54 (m, 3H), 4.48 (s, 2H), 3.55 (t, 2H), 3.08 (q, 2H), 2.16 (s, 3H), 1.86 (m, 2H)

Step A4: Preparation of 1-[3-(benzyloxy)propyl]-5-bromo-4-methyl-1H-benzotriazole Using General Procedure 2 STEP 4 starting from N$^1$-[3-(benzyloxy)propyl]-4-bromo-3-methylbenzene-1,2-diamine (5.4 g, 13 mmol) as a reactant, the title compound (1.09 g, 23% yield) was obtained.

$^1$H-NMR (400 MHz, DMSO-d6) δ ppm: 7.68/7.65 (d, 2H), 7.34-7.2 (m, 5H), 4.78 (t, 2H), 4.38 (s, 2H), 3.41 (t, 2H), 2.71 (s, 3H), 2.18 (m, 2H)

Step A5: Preparation of ethyl (2E)-3-{1-[3-(benzyloxy)propyl]-4-methyl-1H-benzotriazol-5-yl}prop-2-enoate Using General Procedure 2 STEP 5 starting from 1-[3-(benzyloxy)propyl]-5-bromo-4-methyl-1H-benzotriazole (1.05 g, 2.91 mmol) as a reactant, the title compound (1.18 g, 70% yield) was obtained.

$^1$H-NMR (400 MHz, DMSO-d6) δ ppm: 1.28 (t, J=7.09 Hz, 2H) 2.14-2.23 (m, 3H) 3.41 (td, J=5.96, 3.00 Hz, 3H) 4.22 (q, J=7.17 Hz, 2H) 4.36-4.41 (m, 3H) 4.78 (t, J=6.79 Hz, 3H) 6.65 (d, J=15.77 Hz, 1H) 7.28 (s, 7H) 7.69 (d, J=8.80 Hz, 1H) 7.95-7.97 (m, 1H) 8.03 (d, J=15.89 Hz, 1H)

Step 1: Preparation of ethyl 3-{1-[3-(benzyloxy)propyl]-4-methyl-1H-benzotriazol-5-yl}-3-[3-(hydroxymethyl)-4-methylphenyl]propanoate Using General Procedure 6 starting from ethyl(2E)-3-{1-[3-(benzyloxy)propyl]-4-methyl-1H-benzotriazol-5-yl}prop-2-enoate (1 eq.), and [2-methyl-5-(4,4,5,5-tetramethyl-1,3,2-dioxaborolan-2-yl)phenyl]methanol (1.5 eq.) as reactants, the title compound (yellow oil, 44% yield) was obtained.

$^1$H-NMR (400 MHz, DMSO-d6) δ ppm: 7.55 (d, 1H), 7.45 (d, 1H), 7.25 (m, 6H), 7.1 (dd, 1H), 7.01 (d, 1H), 4.81 (t, 1H), 4.81 (t, 1H), 4.7 (t, 2H), 4.4 (d+s, 4H), 3.92 (q, 2H), 3.4 (t, 2H), 3.12 (2dd, 2H), 2.75 (s, 3H), 2.15 (m+s, 5H), 1 (t, 3H)

Step 2: Preparation of ethyl 3-(3-{[6-(benzyloxy)-2,2-dioxo-2H-1,2λ$^6$,3-benzoxathiazin-3(4H)-yl]methyl}-4-methylphenyl)-3-{1-[3-(benzyloxy)propyl]-4-methyl-1H-benzotriazol-5-yl}propanoate Using General Procedure 7 starting from ethyl 3-{1-[3-(benzyloxy)propyl]-4-methyl-1H-benzotriazol-5-yl}-3-[3-(hydroxymethyl)-4-methylphenyl]propanoate (1 eq.), and 6-(benzyloxy)-3,4-dihydro-2H-1,2λ$^6$,3-benzoxathiazine-2,2-dione (1.5 eq.) as reactants, the title compound (94% yield) was obtained.

$^1$H-NMR (400 MHz, DMSO-d6) δ ppm: 0.98 (t, J=7.09 Hz, 3H) 2.13 (quint, J=6.36 Hz, 2H) 2.22 (s, 3H) 2.76 (s, 3H) 3.17 (dd, J=8.01, 3.36 Hz, 2H) 3.36 (t, J=6.05 Hz, 2H) 3.92 (q, J=7.13 Hz, 2H) 4.21 (s, 2H) 4.37 (s, 2H) 4.41 (s, 2H) 4.68 (t, J=6.79 Hz, 2H) 4.85 (t, J=8.01 Hz, 1H) 5.10 (s, 2H) 6.94 (d, J=2.81 Hz, 1H) 7.03-7.09 (m, 1H) 7.10-7.16 (m, 2H) 7.16-7.31 (m, 7H) 7.32-7.37 (m, 1H) 7.37-7.43 (m, 1H) 7.44-7.47 (m, 1H) 7.48 (d, J=8.80 Hz, 1H) 7.53-7.59 (m, 1H)

Step 3: Preparation of ethyl 3-[1-(3-bromopropyl)-4-methyl-1H-benzotriazol-5-yl]-3-{3-[(6-hydroxy-2,2-dioxo-2H-1,2λ$^6$,3-benzoxathiazin-3(4H)-yl)methyl]-4-methylphenyl}propanoate Using General Procedure 8 starting from ethyl 3-(3-{[6-(benzyloxy)-2,2-dioxo-2H-1,2λ$^6$,3-benzoxathiazin-3(4H)-yl]methyl}-4-methylphenyl)-3-{1-[3-(benzyloxy)propyl]-4-methyl-1H-benzotriazol-5-yl}propanoate (1 eq.) as reactant ethyl 3-{3-[(6-hydroxy-2,2-dioxo-2H-1,2λ$^6$,3-benzoxathiazin-3(4H)-yl)methyl]-4-methylphenyl}-3-[1-(3-hydroxypropyl)-4-methyl-1H-benzotriazol-5-yl]propanoate (65% yield) was obtained. The crude product was reacted using General Procedure 9, resulting in the title compound (69% yield).

$^1$H-NMR (400 MHz, DMSO-d6) δ ppm: 9.65 (s, 1H), 7.62 (d, 1H), 7.51 (d, 1H), 7.2 (d, 1H), 7.18 (dd, 1H), 7.1 (d, 1H), 7 (d, 1H), 6.8 (dd, 1H), 6.6 (d, 1H), 4.85 (t, 1H), 4.75 (t, 2H), 4.38 (s, 2H), 4.2 (m, 2H), 3.92 (q, 2H), 3.48 (t, 2H), 3.18 (d, 2H), 2.75 (s, 3H), 2.42 (m, 2H), 2.21 (s, 3H), 1 (t, 3H)

Step 4: Preparation of ethyl[4,30-dimethyl-26,26-dioxo-20,25-dioxa-26λ$^6$-thia-1,14,15,16-tetraazahexacyclo[19.5.3.1$^{3,7}$0.1$^{9,13}$0.0$^{12,16}$0.0$^{24,28}$]hentriaconta-3(31),4,6,9(30),10,12,14,21,23,28-decaen-8-yl]acetate Using General Procedure 11 starting from ethyl 3-[1-(3-bromopropyl)-4-methyl-1H-benzotriazol-5-yl]-3-{3-[(6-hydroxy-2,2-dioxo-2H-1,2λ$^6$,3-benzoxathiazin-3(4H)-yl)methyl]-4-methylphenyl}propanoate (1 eq.) as a reactant, the title compound (96% yield) was obtained.

$^1$H-NMR (400 MHz, DMSO-d6) δ ppm: 7.54 (d, 1H), 7.48 (dd, 1H), 7.44 (d, 1H), 7.28 (d, 1H), 7.01 (d, 1H), 6.85 (dd, 1H), 6.47 (d, 1H), 5.2 (d, 1H), 4.87 (m, 2H), 4.76 (t, 1H), 4.36/3.64 (d, 2H), 4.13/3.44 (d, 2H), 4.01/3.7 (tt, 2H), 3.91 (q, 2H), 3.03 (d, 2H), 2.63 (s, 3H), 2.47/2.38 (m, 2H), 2.32 (s, 3H), 1 (t, 3H)

Step 5: Preparation of Example 2

Using General Procedure 12 starting from ethyl[4,30-dimethyl-26,26-dioxo-20,25-dioxa-26λ$^6$-thia-1,14,15,16-tetraazahexacyclo[19.5.3.1$^{3,7}$0.1$^{9,13}$0.0$^{12,16}$0.0$^{24,28}$]hentriaconta-3(31),4,6,9(30),10,12,14,21,23,28-decaen-8-yl] acetate (1 eq.) as a reactant, the title compound (white solid, 70% yield) was obtained as a racemic compound.

HRMS calculated for $C_{28}H_{28}N_4O_6S$: 548.1730; $[M+H]^+$ found: 549.1805 (δ=0.5 ppm).

$^1$H-NMR (400 MHz, DMSO-d6) δ ppm: 12.2 (m, 1H), 7.55 (d, 1H), 7.45 (dd, 1H), 7.4 (d, 1H), 7.25 (d, 1H), 7 (d, 1H), 6.85 (dd, 1H), 6.43 (d, 1H), 5.22 (d, 1H), 4.85 (m, 2H), 4.75 (t, 1H), 4.35/3.65 (m, 2H), 4.15/3.45 (m, 2H), 4/3.7 (m, 2H), 2.95 (d, 2H), 2.65 (s, 3H), 2.4 (m, 2H), 2.3 (s, 3H)

EXAMPLE 3: [(2R,8R)-2,4,31-Trimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid and [(2R,8S)-2,4,31-trimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid

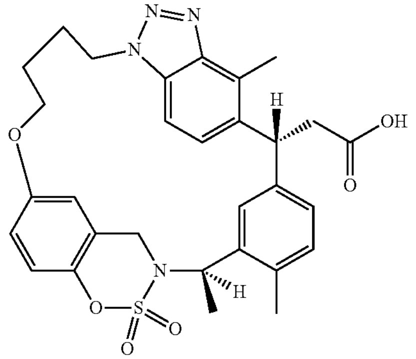

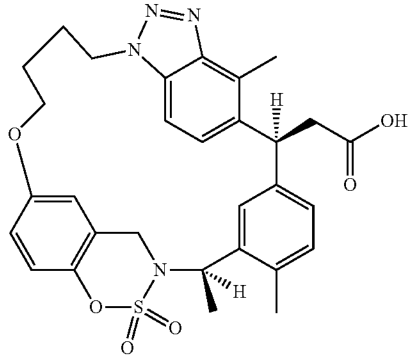

Step A1: Preparation of 4-(3-methyl-2-nitroanilino)butan-1-ol

Using General Procedure 1 STEP 1 starting from 1-fluoro-3-methyl-2-nitro-benzene (1 eq.) and 4-aminobutan-1-ol (3 eq.) as reactants, the title compound (44% yield) was obtained.

$^1$H-NMR (400 MHz, DMSO-d6) δ ppm: 7.28 (t, 1H), 6.78 (d, 1H), 6.52 (d, 1H), 6.4 (t, 1H), 4.4 (t, 1H), 3.41 (q, 2H), 3.2 (q, 2H), 2.3 (s, 3H), 1.58 (m, 2H), 1.48 (m, 2H)

Step A2: Preparation of 4-(4-bromo-3-methyl-2-nitroanilino)butyl acetate

Using General Procedure 1 STEP 2 starting from 4-(3-methyl-2-nitroanilino)butan-1-ol (1 eq.) as a reactant, the title compound (orange oil, 93% yield) was obtained.

$^1$H-NMR (400 MHz, DMSO-d6) δ ppm: 7.52 (d, 1H), 6.72 (d, 1H), 6.15 (t, 1H), 4 (t, 2H), 3.15 (q, 2H), 2.25 (s, 3H), 2 (s, 3H), 1.55 (m, 4H)

Step A3: Preparation of 4-(2-amino-4-bromo-3-methylanilino)butyl acetate

Using General Procedure 1 STEP 3 starting from 4-(4-bromo-3-methyl-2-nitroanilino)butyl acetate (1 eq.) as a reactant, the title compound (72% yield) was obtained.

$^1$H-NMR (400 MHz, DMSO-d6) δ ppm: 6.7 (d, 1H), 6.25 (d, 1H), 5.2-4.5 (ml, 3H), 4.01 (t, 2H), 3 (t, 2H), 2.19 (s, 3H), 2 (s, 3H), 1.7-1.5 (m, 4H)

Step A4: Preparation of 4-(5-bromo-4-methyl-1H-benzotriazol-1-yl)butyl acetate

Using General Procedure 1 STEP 4 starting from 4-(2-amino-4-bromo-3-methylanilino)butyl acetate (1 eq.) as a reactant, the title compound (orange oil, 49% yield) was obtained.

HRMS calculated for $C_{13}H_{16}BrN_3O_2$: 325.0426; $[M+H]^+$ found: 326.0502 (δ=1.0 ppm).

Step A5: Preparation of 4-(5-bromo-4-methyl-1H-benzotriazol-1-yl)butan-1-ol

Using General Procedure 1 STEP 5 starting from 4-(5-bromo-4-methyl-1H-benzotriazol-1-yl)butyl acetate (1 eq.) as a reactant, the title compound (orange oil, 85% yield) was obtained.

$^1$H-NMR (400 MHz, DMSO-d6) δ ppm: 7.7 (m, 2H), 4.75 (t, 2H), 4.45 (t, 1H), 3.45 (q, 2H), 2.75 (s, 3H), 1.95 (m, 2H), 1.4 (m, 2H)

Step A6: Preparation of 5-bromo-1-{4-[(4-methoxyphenyl)methoxy]butyl}-4-methyl-1H-benzotriazole Using General Procedure 1 STEP 6 starting from 4-(5-bromo-4-methyl-1H-benzotriazol-1-yl)butan-1-ol (1 eq.) as a reactant, the title compound (yellow oil, 74% yield) was obtained.

$^1$H-NMR (400 MHz, DMSO-d6) δ ppm: 7.68 (s, 2H), 7.19 (d, 2H), 6.88 (d, 2H), 4.71 (t, 2H), 4.32 (s, 2H), 3.73 (s, 3H), 3.39 (t, 2H), 2.72 (s, 3H), 1.95 (quint, 2H), 1.48 (quint, 2H)

Step A7: Preparation of ethyl (2E)-3-(1-{4-[(4-methoxyphenyl)methoxy]butyl}-4-methyl-1H-benzotriazol-5-yl)prop-2-enoate Using General Procedure 1 STEP 7 starting from 5-bromo-1-{4-[(4-methoxyphenyl)methoxy]butyl}-4-methyl-1H-benzotriazole (1 eq.) as a reactant, the title compound (yellow solid, 74% yield) was obtained.

$^1$H-NMR (400 MHz, DMSO-d6) δ ppm: 8.02 (d, 1H), 7.95 (d, 1H), 7.7 (d, 1H), 7.19 (d, 2H), 6.88 (d, 2H), 6.65 (d, 1H), 4.71 (t, 2H), 4.32 (s, 2H), 4.22 (q, 2H), 3.73 (s, 3H), 3.39 (t, 2H), 2.81 (s, 3H), 1.95 (m, 2H), 1.49 (m, 2H), 1.28 (t, 3H)

Step 1: Preparation of ethyl 3-{3-[(1S)-1-hydroxyethyl]-4-methylphenyl}-3-(1-{4-[(4-methoxyphenyl)methoxy]butyl}-4-methyl-1H-benzotriazol-5-yl)propanoate Using General Procedure 6 starting from ethyl(2E)-3-(1-{4-[(4-methoxyphenyl)methoxy]butyl}-4-methyl-1H-benzotriazol-5-yl)prop-2-enoate (1 eq.), and (1S)-1-[2-methyl-5-(4,4,5,5-tetramethyl-1,3,2-dioxaborolan-2-yl)phenyl]ethan-1-ol (2 eq.) as reactants, the title compound (yellow oil, 82% yield) was obtained.

$^1$H-NMR (400 MHz, DMSO-d6) δ ppm: 0.99 (t, J=7.09 Hz, 3H) 1.22 (dd, J=8.74, 6.42 Hz, 3H) 1.42-1.53 (m, 2H) 1.92 (quin, J=7.21 Hz, 2H) 1.99 (s, 2H) 2.19 (s, 3H) 2.76 (d, J=3.79 Hz, 3H) 3.09-3.16 (m, 2H) 3.38 (t, J=6.30 Hz, 2H) 3.73 (s, 3H) 3.92 (q, J=7.09 Hz, 2H) 4.32 (s, 2H) 4.64 (t, J=6.91 Hz, 2H) 4.83 (dt, J=7.64, 3.88 Hz, 2H) 4.92-5.01 (m, 1H) 6.83-6.90 (m, 2H) 6.95-7.01 (m, 1H) 7.02-7.08 (m, 1H) 7.19 (d, J=8.56 Hz, 2H) 7.40 (d, J=1.71 Hz, 1H) 7.43-7.49 (m, 1H) 7.55-7.60 (m, 1H)

Step 2: Preparation of ethyl 3-(3-{(1R)-1-[6-(benzyloxy)-2,2-dioxo-2H-1,2λ$^6$,3-benzoxathiazin-3(4H)-yl]ethyl}-4-methylphenyl)-3-(1-{4-[(4-methoxyphenyl) methoxy]butyl}-4-methyl-1H-benzotriazol-5-yl)propanoate Using General Procedure 7 starting from ethyl 3-{3-[(1S)-1-hydroxyethyl]-4-methylphenyl}-3-(1-{4-[(4-methoxyphenyl)methoxy]butyl}-4-methyl-1H-benzotriazol-5-yl)propanoate (1 eq.), and 6-(benzyloxy)-3,4-dihydro-2H-1,2λ$^6$,3-benzoxathiazine-2,2-dione (1.5 eq.) as reactants, the title compound (69% yield) was obtained.

$^1$H-NMR (400 MHz, DMSO-d6) δ ppm: 0.93-1.01 (m, 3H) 1.36-1.49 (m, 5H) 1.83-1.94 (m, 2H) 2.28 (s, 3H) 2.77 (d, J=4.65 Hz, 3H) 3.17-3.24 (m, 2H) 3.32-3.38 (m, 2H) 3.72 (s, 3H) 3.88-3.95 (m, 2H) 4.29 (d, J=2.69 Hz, 2H) 4.37-4.46 (m, 1H) 4.56-4.65 (m, 2H) 4.82-4.91 (m, 1H) 5.03-5.13 (m, 2H) 5.27 (q, J=6.77 Hz, 1H) 6.80-6.91 (m, 3H) 6.95-7.07 (m, 2H) 7.07-7.15 (m, 2H) 7.18 (d, J=8.44 Hz, 2H) 7.30-7.48 (m, 6H)

Step 3: Preparation of ethyl 3-[1-(4-hydroxybutyl)-4-methyl-1H-benzotriazol-5-yl]-3-{3-[(1R)-1-(6-hydroxy-2,2-dioxo-2H-1,2λ$^6$,3-benzoxathiazin-3(4H)-yl)ethyl]-4-methylphenyl}propanoate Using General Procedure 8 starting from ethyl 3-(3-{(1R)-1-[6-(benzyloxy)-2,2-dioxo-2H-1,2λ$^6$,3-benzoxathiazin-3(4H)-yl]ethyl}-4-methylphenyl)-3-(1-[{4-[(4-methoxyphenyl)methoxy]butyl}-4-methyl-1H-benzotriazol-5-yl)propanoate (1 eq.) as a reactant, the title compound (79% yield) was obtained.

$^1$H-NMR (400 MHz, DMSO-d6) δ ppm: 1.00 (q, J=7.01 Hz, 3H) 1.29-1.39 (m, 2H) 1.39-1.46 (m, 3H) 1.85-1.96 (m, 2H) 2.28 (s, 3H) 2.77 (s, 3H) 3.22 (d, J=7.83 Hz, 2H) 3.35-3.41 (m, 3H) 3.94 (qd, J=7.11, 2.02 Hz, 2H) 4.23-4.36 (m, 1H) 4.37 (s, 1H) 4.41 (t, J=5.14 Hz, 1H) 4.65 (t, J=7.03 Hz, 2H) 4.78-4.95 (m, 1H) 5.26 (q, J=6.64 Hz, 1H) 6.53-6.62 (m, 1H) 6.69-6.76 (m, 1H) 6.79-6.84 (m, 1H) 6.88-6.94 (m, 1H) 7.05-7.15 (m, 3H) 7.47 (d, J=10.64 Hz, 1H) 9.57-9.72 (m, 1H)

Step 4: Preparation of ethyl 3-[1-(4-bromobutyl)-4-methyl-1H-benzotriazol-5-yl]-3-{3-[(1R)-1-(6-hydroxy-2,2-dioxo-2H-1,2λ$^6$,3-benzoxathiazin-3(4H)-yl)ethyl]-4-methylphenyl}propanoate Using General Procedure 9 starting from ethyl 3-[1-(4-hydroxybutyl)-4-methyl-1H-benzotriazol-5-yl]-3-{3-[(1R)-1-(6-hydroxy-2,2-dioxo-2H-1,2λ$^6$,3-benzoxathiazin-3(4H)-yl)ethyl]-4-methylphenyl}propanoate (1 eq.) as a reactant, the title compound (colorless solid, 91% yield) was obtained.

$^1$H-NMR (400 MHz, DMSO-d6) δ ppm: 9.63/9.62 (2s, 1H), 7.64/7.59 (4d, 2H), 7.48/7.45 (2s, 1H), 7.11 (m, 2H), 6.91 (d, 1H), 6.73 (m, 1H), 6.6/6.56 (2d, 1H), 5.26 (m, 1H), 4.88 (m, 1H), 4.69 (t, 2H), 4.37/4.31 (s+m, 2H), 3.94 (2q, 2H), 3.54 (t, 2H), 3.23 (d1, 2H), 2.77 (s, 3H), 2.28 (s, 3H), 1.99 (quint, 2H), 1.77 (quint, 2H), 1.43/1.41 (2d, 3H)

Step 5: Preparation of ethyl[(2R)-2,4,31-trimethyl-27,27-dioxo-21,26-dioxa-27λ$^6$-thia-1,14,15,16-tetraazahexacyclo[$20.5.3.1^{3,7}0.1^{9,13}0.0^{12,16}0.0^{25,29}$]dotriaconta-3(32),4,6,9(31),10,12,14,22,24,29-decaen-8-yl]acetate Using General Procedure 11 starting from ethyl 3-[1-(4-bromobutyl)-4-methyl-1H-benzotriazol-5-yl]-3-{3-[(1R)-1-(6-hydroxy-2,2-dioxo-2H-1,2λ$^6$,3-benzoxathiazin-3(4H)-yl)ethyl]-4-methylphenyl}propanoate (1 eq.) as a reactant, the title compound (white solid, 91% yield) was obtained.

$^1$H-NMR (400 MHz, DMSO-d6) δ ppm: 1.03 (td, J=7.09, 3.30 Hz, 9H) 1.23-1.30 (m, 7H) 1.33-1.94 (m, 12H) 2.25-2.35 (m, 11H) 2.67 (s, 6H) 2.96-3.15 (m, 5H) 3.34-3.53 (m, 9H) 3.62-3.75 (m, 4H) 3.88-3.98 (m, 5H) 3.99-4.11 (m, 4H) 4.70-4.85 (m, 10H) 4.92 (t, J=7.95 Hz, 2H) 5.18-5.31 (m, 2H) 5.72 (d, J=2.81 Hz, 1H) 5.89 (br. s., 1H) 6.74-6.78 (m, 1H) 6.88-6.98 (m, 2H) 7.17 (s, 1H) 7.31 (d, J=8.07 Hz, 1H) 7.44 (d, J=7.58 Hz, 2H) 7.75 (d, J=8.68 Hz, 1H) 7.89 (d, J=8.68 Hz, 1H)

The diastereo-pure final intermediates were obtained by chromatographic separation on chiral column.

Step 6: Preparation of Example 3

Using General Procedure 12 starting from ethyl[(2R,8R)-2,4,31-trimethyl-27,27-dioxo-21,26-dioxa-27λ$^6$-thia-1,14,15,16-tetraazahexacyclo[$20.5.3.1^{3,7}0.1^{9,13}0.0^{12,16}0.0^{25,29}$]dotriaconta-3(32),4,6,9(31),10,12,14,22,24,29-decaen-8-yl]acetate (1 eq.) or ethyl[(2R,8S)-2,4,31-trimethyl-27,27-dioxo-21,26-dioxa-27λ$^6$-thia-1,14,15,16-tetraazahexacyclo[$20.5.3.1^{3,7}0.1^{9,13}0.0^{12,16}0.0^{25,29}$]dotriaconta-3(32),4,6,9(31),10,12,14,22,24,29-decaen-8-yl]acetate (1 eq.) as reactants, the title compounds (34%-78% yields respectively) were obtained.

EXAMPLE 3a (2R,8R)

HRMS calculated for $C_{30}H_{32}N_4O_6S$: 576.2042; $[M+H]^+$ found: 577.2119 (δ=0.6 ppm).

$^1$H-NMR (400 MHz, DMSO-d6) δ ppm: 12.21 (m, 1H), 7.7 (d, 1H), 7.43 (d, 1H), 7.3 (d, 1H), 7.1 (d, 1H), 6.9 (d, 1H), 6.7 (m, 2H), 5.89 (m, 1H), 5.21 (q, 1H), 4.9 (t, 1H), 4.73 (m, 2H), 4.05/3.48 (m, 2H), 3.7 (m, 2H), 3.25/2.89 (2dd, 2H), 2.8 (s, 3H), 2.3 (s, 3H), 2.2/2 (2m, 2H), 1.61/1.29 (2m, 2H), 1.1 (d, 3H)

EXAMPLE 3b (2R,8S)

HRMS calculated for $C_{30}H_{32}N_4O_6S$: 576.2042; $[M+H]^+$ found: 577.2118 (δ=0.5 ppm).

$^1$H-NMR (400 MHz, DMSO-d6) δ ppm: 12.5-11.8 (m, 1H), 7.88 (d, 1H), 7.73 (d, 1H), 7.43 (d, 1H), 7.2 (d, 1H), 7.11 (d, 1H), 6.93 (d, 1H), 6.78 (dd, 1H), 5.69 (d, 1H), 5.25 (q, 1H), 4.82-4.67 (m, 2H), 4.78 (t, 1H), 4.01/3.4 (m, 2H), 3.68/3.47 (m, 2H), 3.19/2.99 (2dd, 2H), 2.62 (s, 3H), 2.29 (s, 3H), 2.23-2 (2m, 2H), 1.92-1.68 (2m, 2H), 1.23 (d, 3H)

EXAMPLE 4: [5-Fluoro-31-methyl-27,27-dioxo-21,26-dioxa-27$\lambda^6$-thia-1,14,15,16-tetraazahexacyclo[20.5.3.$1^{3,7}$0.$1^{9,13}$0.$0^{12,16}$0.$0^{25,29}$]dotriaconta-3(32),4,6,9(31),10,12,14,22,24,29-decaen-8-yl]acetic acid

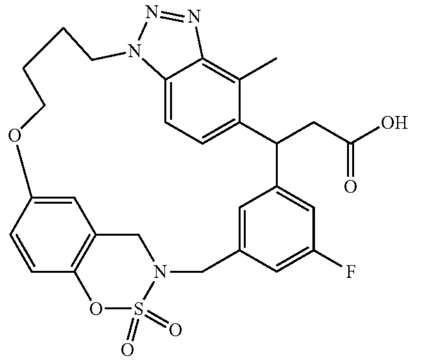 [SMILES: Cc1c2ccc3c1nnn3CCCCOc1ccc3c(c1)CN(Cc1cc(F)cc(c1)C2CC(=O)O)S(=O)(=O)O3]

Step 1: Preparation of ethyl 3-[3-fluoro-5-(hydroxymethyl)phenyl]-3-(1-{4-[(4-methoxyphenyl)methoxy]butyl}-4-methyl-1H-benzotriazol-5-yl)propanoate Using General Procedure 6 starting from ethyl(2E)-3-(1-{4-[(4-methoxyphenyl)methoxy]butyl}-4-methyl-1H-benzotriazol-5-yl)prop-2-enoate (1 eq.) and [3-fluoro-5-(4,4,5,5-tetramethyl-1,3,2-dioxaborolan-2-yl)phenyl]methanol (1.5 eq.) as reactants, the title compound (yellow oil, 30% yield) was obtained.

$^1$H-NMR (400 MHz, DMSO-d6) δ ppm: 7.6 (d, 1H), 7.5 (d, 1H), 7.2 (d, 2H), 7.1-6.9 (m, 3H), 6.88 (d, 2H), 5.22 (t, 1H), 4.85 (t, 1H), 4.62 (t, 2H), 4.41 (d, 2H), 4.3 (s, 2H), 3.95 (q, 2H), 3.71 (s, 3H), 3.39 (t, 2H), 3.18 (m, 2H), 2.78 (s, 3H), 1.9 (m, 2H), 1.5 (m, 2H), 1 (t, 3H)

Step 2: Preparation of ethyl 3-(3-{[6-(benzyloxy)-2,2-dioxo-2H-1,2$\lambda^6$,3-benzoxathiazin-3(4H)-yl]methyl}-5-fluorophenyl)-3-(1-{4-[(4-methoxyphenyl)methoxy]butyl}-4-methyl-1H-benzotriazol-5-yl)propanoate Using General Procedure 7 starting from ethyl 3-[3-fluoro-5-(hydroxymethyl)phenyl]-3-(1-{4-[(4-methoxyphenyl)methoxy]butyl}-4-methyl-1H-benzotriazol-5-yl)propanoate (1 eq.) and 6-(benzyloxy)-3,4-dihydro-2H-1,2$\lambda^6$,3-benzoxathiazine-2,2-dione (1.1 eq.) as reactants, the title compound (64% yield) was obtained.

$^1$H-NMR (400 MHz, DMSO-d6) δ ppm: 7.6 (d, 1H), 7.48 (d, 1H), 7.4-7.3 (m, 5H), 7.2-7 (m, 3H), 7.18 (d, 2H), 7-6.9 (m, 3H), 6.85 (d, 2H), 5.05 (s, 2H), 4.87 (t, 1H), 4.62 (s+t, 4H), 4.3 (s, 4H), 3.92 (q, 2H), 3.71 (s, 3H), 3.38 (t, 2H), 3.18 (d, 2H), 2.78 (s, 3H), 1.92 (m, 2H), 1.5 (m, 2H), 1 (t, 3H)

Step 3: Preparation of ethyl 3-{3-fluoro-5-[(6-hydroxy-2,2-dioxo-2H-1,2$\lambda^6$,3-benzoxathiazin-3(4H)-yl)methyl]phenyl}-3-[1-(4-hydroxybutyl)-4-methyl-1H-benzotriazol-5-yl]propanoate Using General Procedure 8 starting from ethyl 3-(3-{[6-(benzyloxy)-2,2-dioxo-2H-1,2$\lambda^6$,3-benzoxathiazin-3(4H)-yl]methyl}-5-fluorophenyl)-3-(1-[{4-[(4-methoxyphenyl)methoxy]butyl}-4-methyl-1H-benzotriazol-5-yl)propanoate (1 eq.) as a reactant, the title compound (96% yield) was obtained.

$^1$H-NMR (400 MHz, DMSO-d6) δ ppm: 9.6/4.4 (s+t, 2H), 7.62 (d, 1H), 7.5 (d, 1H), 7.21 (d, 1H), 7.1 (dd, 1H), 7.02 (dd, 1H), 6.81 (d, 1H), 6.7 (dd, 1H), 6.6 (d, 1H), 4.85 (t, 1H), 4.65 (t, 2H), 4.52 (s, 2H), 4.29 (s, 2H), 3.95 (q, 2H), 3.4 (q, 2H), 3.2 (d, 2H), 2.79 (s, 3H), 1.9 (m, 2H), 1.38 (m, 2H), 1 (t, 3H)

Step 4: Preparation of ethyl 3-[1-(4-bromobutyl)-4-methyl-1H-benzotriazol-5-yl]-3-{3-fluoro-5-[(6-hydroxy-2,2-dioxo-2H-1,2$\lambda^6$,3-benzoxathiazin-3(4H)-yl)methyl]phenyl}propanoate Using General Procedure 9 starting from ethyl 3-{3-fluoro-5-[(6-hydroxy-2,2-dioxo-2H-1,2$\lambda^6$,3-benzoxathiazin-3(4H)-yl)methyl]phenyl}-3-[1-(4-hydroxybutyl)-4-methyl-1H-benzotriazol-5-yl]propanoate (1 eq.) as a reactant, the title compound (66% yield) was obtained.

$^1$H-NMR (400 MHz, DMSO-d6) δ ppm: 9.6 (s, 1H), 7.64 (d, 1H), 7.51 (d, 1H), 7.2 (t, 1H), 7.13/7 (2dt, 2H), 6.88 (d, 1H), 6.7 (dd, 1H), 6.59 (d, 1H), 4.87 (t, 1H), 4.69 (t, 2H), 4.57 (s, 2H), 4.29 (s, 2H), 3.92 (q, 2H), 3.52 (t, 2H), 3.19 (d, 2H), 2.78 (s, 3H), 1.99 (m, 2H), 1.78 (m, 2H), 1 (t, 3H)

Step 5: Preparation of ethyl[5-fluoro-31-methyl-27,27-dioxo-21,26-dioxa-27$\lambda^6$-thia-1,14,15,16-tetraazahexacyclo[20.5.3.$1^{3,7}$0.$1^{9,13}$0.$0^{12,16}$0.$0^{25,29}$]dotriaconta-3(32),4,6,9(31),10,12,14,22,24,29-decaen-8-yl]acetate Using General Procedure 11 starting from ethyl 3-[1-(4-bromobutyl)-4-methyl-1H-benzotriazol-5-yl]-3-{3-fluoro-5-[(6-hydroxy-2,2-dioxo-2H-1,2)$^6$,3-benzoxathiazin-3(4H)-yl)methyl]phenyl}propanoate (1 eq.) as a reactant, the title compound (white solid, 72% yield) was obtained.

$^1$H-NMR (400 MHz, DMSO-d6) δ ppm: 7.59 (d, 1H), 7.4/7.06 (2m, 2H), 7.32 (d, 1H), 6.91 (d, 1H), 6.74 (m, 1H), 6.69 (dd, 1H), 6 (d, 1H), 4.87-4.67 (m, 3H), 4.15/4.05 (2dd, 4H), 3.93 (m, 2H), 3.67/3.37 (2m, 2H), 3.27/3.11 (2m, 2H), 2.75 (s, 3H), 2.18/1.96 (2m, 2H), 1.68/1.45 (2m, 2H), 1.01 (t, 3H)

Step 6: Preparation of Example 4

Using General Procedure 12 starting from ethyl[5-fluoro-31-methyl-27,27-dioxo-21,26-dioxa-27$\lambda^6$-thia-1,14,15,16-tetraazahexacyclo[20.5.3.$1^{3,7}$0.$1^{9,13}$0.$0^{12,16}$0.$0^{25,29}$]dotriaconta-3(32),4,6,9(31),10,12,14,22,24,29-decaen-8-yl]acetate (1 eq.) as a reactant, the title compound (white solid, 98% yield) was obtained.

HRMS calculated for $C_{28}H_{27}FN_4O_6S$: 566.1635; $[M+H]^+$ found: 567.1710 (δ=0.3 ppm).

$^1$H-NMR (400 MHz, DMSO-d6) δ ppm: 12.19 (m, 1H), 7.59 (d, 1H), 7.4/7.06 (2m, 2H), 7.3 (d, 1H), 6.91 (d, 1H), 6.71 (m, 1H), 6.69 (dd, 1H), 6 (d, 1H), 4.87-4.67 (m, 3H), 4.14/4.04 (2dd, 4H), 3.68/3.38 (2m, 2H), 3.17/2.91 (2m, 2H), 2.75 (s, 3H), 2.19/1.97 (2m, 2H), 1.69/1.46 (2m, 2H)

EXAMPLE 5: [5,31-Dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid

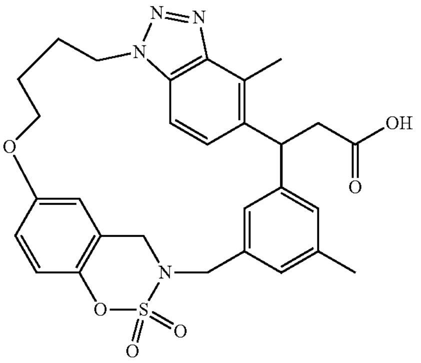 [SMILES: Cc1cc2cc(c1)C(CC(=O)O)c1ccc3c(nnn3CCCCOc3ccc4c(c3)CN(C2)S(=O)(=O)O4)c1C]

Step B1: Preparation of [3-methyl-5-(4,4,5,5-tetramethyl-1,3,2-dioxaborolan-2-yl)phenyl]methanol Using General Procedure 3 starting from (3-bromo-5-methylphenyl)methanol (1 eq., 2.01 g, 10 mmol) as a reactant, the title compound (1.13 g, 45% yield) was obtained.

$^1$H-NMR (400 MHz, DMSO-d6) δ ppm: 7.44/7.35/7.23 (3tf, 3H), 5.12 (t, 1H), 4.46 (d, 2H), 2.29 (s, 3H), 1.28 (s, 12H)

Step 1: Preparation of ethyl 3-[3-(hydroxymethyl)-5-methylphenyl]-3-(1-{4-[(4-methoxyphenyl)methoxy]butyl}-4-methyl-1H-benzotriazol-5-yl)propanoate Using General Procedure 6 starting from ethyl(2E)-3-(1-{4-[(4-methoxyphenyl)methoxy]butyl}-4-methyl-1H-benzotriazol-5-yl)prop-2-enoate (1 eq.) and [3-methyl-5-(4,4,5,5-tetramethyl-1,3,2-dioxaborolan-2-yl)phenyl]methanol (2 eq.) as reactants, the title compound (68% yield) was obtained.

$^1$H-NMR (400 MHz, DMSO-d6) δ ppm: 7.58 (d, 1H), 7.47 (d, 1H), 7.2 (d, 2H), 7.04/7/6.93 (3s1, 3H), 6.87 (d, 2H), 5.05 (t, 1H), 4.82 (t, 1H), 4.64 (t, 2H), 4.39 (d, 2H), 4.32 (s, 2H), 3.92 (qd, 2H), 3.73 (s, 3H), 3.38 (t, 2H), 3.13 (m, 2H), 2.76 (s, 3H), 2.23 (s, 3H), 1.92 (m, 2H), 1.48 (m, 2H), 0.99 (t, 3H)

Step 2: Preparation of ethyl 3-(3-{[6-(benzyloxy)-2,2-dioxo-2H-1,2λ$^6$,3-benzoxathiazin-3(4H)-yl]methyl}-5-methylphenyl)-3-(1-{4-[(4-methoxyphenyl)methoxy]butyl}-4-methyl-1H-benzotriazol-5-yl)propanoate Using General Procedure 7 starting from ethyl 3-[3-(hydroxymethyl)-5-methylphenyl]-3-(1-{4-[(4-methoxyphenyl)methoxy]butyl}-4-methyl-1H-benzotriazol-5-yl)propanoate (1 eq.) and 6-(benzyloxy)-3,4-dihydro-2H-1,2λ$^6$,3-benzoxathiazine-2,2-dione (1.5 eq.) as reactants the title compound (86% yield) was obtained.

$^1$H-NMR (400 MHz, DMSO-d6) δ ppm: 7.57 (d, 1H), 7.45-7.3 (m, 5H), 7.45 (d, 1H), 7.18 (d, 2H), 7.14/7.07/6.98 (3tf, 3H), 7.03/7/6.94 (dd+d+d, 3H), 6.86 (d, 2H), 5.05 (s, 2H), 4.82 (t, 1H), 4.63 (t, 2H), 4.55 (s, 2H), 4.31 (s, 2H), 4.23 (s, 2H), 3.92 (q, 2H), 3.73 (s, 3H), 3.36 (t, 2H), 3.12 (d, 2H), 2.76 (s, 3H), 2.22 (s, 3H), 1.91 (m, 2H), 1.47 (m, 2H), 0.98 (t, 3H)

Step 3: Preparation of ethyl 3-[1-(4-hydroxybutyl)-4-methyl-1H-benzotriazol-5-yl]-3-{3-[(6-hydroxy-2,2-dioxo-2H-1,2λ$^6$,3-benzoxathiazin-3(4H)-yl)methyl]-5-methylphenyl}propanoate Using General Procedure 8 starting from ethyl 3-(3-{[6-(benzyloxy)-2,2-dioxo-2H-1,2λ$^6$,3-benzoxathiazin-3(4H)-yl]methyl}-5-methylphenyl)-3-(1-[{4-[(4-methoxyphenyl)methoxy]butyl}-4-methyl-1H-benzotriazol-5-yl)propanoate (1 eq.) as a reactant, the title compound (99% yield) was obtained.

$^1$H-NMR (400 MHz, DMSO-d6) δ ppm: 9.63 (m, 1H), 7.62 (d, 1H), 7.47 (d, 1H), 7.15/7.08/6.99 (3tf, 3H), 6.91 (d, 1H), 6.73 (dd, 1H), 6.6 (d, 1H), 4.83 (t, 1H), 4.65 (t, 2H), 4.5/4.22 (2s, 4H), 3.94 (q, 2H), 3.39 (t, 2H), 3.14 (d, 2H), 2.77 (s, 3H), 2.24 (s, 3H), 1.91 (m, 2H), 1.37 (m, 2H), 1 (t, 3H)

Step 4: Preparation of ethyl 3-[1-(4-bromobutyl)-4-methyl-1H-benzotriazol-5-yl]-3-{3-[(6-hydroxy-2,2-dioxo-2H-1,2λ$^6$,3-benzoxathiazin-3(4H)-yl)methyl]-5-methylphenyl}propanoate Using General Procedure 9 starting from ethyl 3-[1-(4-hydroxybutyl)-4-methyl-1H-benzotriazol-5-yl]-3-{3-[(6-hydroxy-2,2-dioxo-2H-1,2)$^6$,3-benzoxathiazin-3(4H)-yl)methyl]-5-methylphenyl}propanoate (1 eq.) as a reactant, the title compound (78% yield) was obtained.

$^1$H-NMR (400 MHz, DMSO-d6) δ ppm: 9.61 (m, 1H), 7.63 (d, 1H), 7.49 (d, 1H), 7.14/7.07/6.98 (3tf, 3H), 6.9 (d, 1H), 6.73 (dd, 1H), 6.59 (d, 1H), 4.82 (t, 1H), 4.69 (t, 2H), 4.49/4.2 (2s, 4H), 3.93 (q, 2H), 3.54 (t, 2H), 3.14 (d, 2H), 2.76 (s, 3H), 2.22 (s, 3H), 1.99 (m, 2H), 1.77 (m, 2H), 0.99 (t, 3H)

Step 5: Preparation of ethyl[5,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate Using General Procedure 11 starting from ethyl 3-[1-(4-bromobutyl)-4-methyl-1H-benzotriazol-5-yl]-3-{3-[(6-hydroxy-2,2-dioxo-2H-1,2)$^6$,3-benzoxathiazin-3(4H)-yl)methyl]-5-methylphenyl}propanoate (1 eq.) as a reactant, the title compound (98% yield) was obtained.

$^1$H-NMR (400 MHz, DMSO-d6) δ ppm: 7.6 (d, 1H), 7.35 (d, 1H), 7.34/7.09/6.58 (3m, 3H), 6.93 (d, 1H), 6.73 (dd, 1H), 5.98 (d, 1H), 4.84-4.66 (2m, 3H), 4.03/3.98 (2s, 4H), 3.93 (m, 2H), 3.68/3.45 (2m, 2H), 3.21/3.09 (2m, 2H), 2.71 (s, 3H), 2.36 (s, 3H), 2.19/1.99 (2m, 2H), 1.68/1.48 (2m, 2H), 1.01 (t, 3H)

Step 6: Preparation of Example 5

Using General Procedure 12 starting from ethyl[5,31-dimethyl-27,27-dioxo-21,26-dioxa-27λ$^6$-thia-1,14,15,16- tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl] acetate (1 eq.) as a reactant, the title compound (white solid, 50% yield) was obtained.

HRMS calculated for $C_{29}H_{30}N_4O_6S$: 562.1886; $[M+H]^+$ found: 563.1963 (δ=0.7 ppm).

$^1$H-NMR (400 MHz, DMSO-d6) δ ppm: 12.15 (m, 1H), 7.6 (d, 1H), 7.34/7.09/6.57 (3s1, 3H), 7.33 (d, 1H), 6.94 (d, 1H), 6.73 (dd, 1H), 5.98 (d, 1H), 4.85-4.67 (2m, 3H), 4.03/3.98 (2s, 4 H), 3.68/3.45 (2m, 2H), 3.11/2.97 (2m, 2H), 2.71 (s, 3H), 2.36 (s, 3H), 2.19/1.99 (2m, 2H), 1.71/1.47 (2m, 2H)

EXAMPLE 6: [31-Methyl-27,27-dioxo-21,26-dioxa-27λ$^6$-thia-1,14,15,16-tetraazahexacyclo [20.5.3.1$^{3,7}$0.1$^{9,13}$0.0$^{12,16}$0.0$^{25,29}$]dotriaconta-3(32), 4,6,9(31),10,12,14,22,24,29-decaen-8-yl]acetic acid

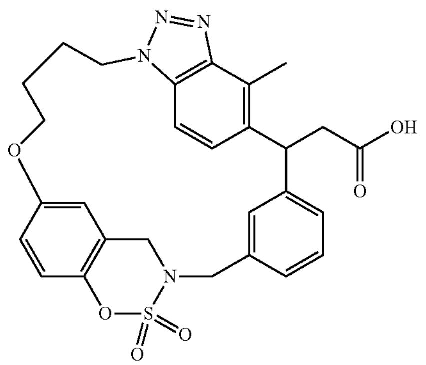 [SMILES: Cc1c2ccc3c1nnn3CCCCOc1ccc3c(c1)CN(Cc1cccc(c1)C2CC(=O)O)S(=O)(=O)O3]

Step 1: Preparation of ethyl 3-[3-(hydroxymethyl) phenyl]-3-(1-{4-[(4-methoxyphenyl) methoxy] butyl}-4-methyl-1H-benzotriazol-5-yl)propanoate Using General Procedure 6 starting from ethyl(2E)-3-(1-{4-[(4-methoxyphenyl)methoxy]butyl}-4-methyl-1H-benzotriazol-5-yl)prop-2-enoate (1 eq.) and [3-(4,4,5,5-tetramethyl-1,3,2-dioxaborolan-2-yl)phenyl]methanol (2 eq.) as reactants the title compound (75% yield) was obtained.

$^1$H-NMR (400 MHz, DMSO-d6) δ ppm: 7.58 (d, 1H), 7.48 (d, 1H), 7.26-7.1 (m, 4H), 7.2 (d, 2H), 6.88 (d, 2H), 5.09 (t, 1H), 4.86 (t, 1H), 4.64 (t, 2H), 4.42 (d, 2H), 4.32 (s, 2H), 3.92 (q, 2H), 3.73 (s, 3H), 3.38 (t, 2H), 3.18/3.13 (2dd, 2H), 2.77 (s, 3H), 1.92 (m, 2H), 1.48 (m, 2H), 0.99 (t, 3H)

Step 2: Preparation of ethyl 3-[1-(4-hydroxybutyl)-4-methyl-1H-benzotriazol-5-yl]-3-{3-[(6-hydroxy-2,2-dioxo-2H-1,2λ$^6$,3-benzoxathiazin-3(4H)-yl) methyl]phenyl}propanoate Using General Procedure 7 starting from ethyl 3-[3-(hydroxymethyl)phenyl]-3-(1-{4-[(4-methoxyphenyl) methoxy]butyl}-4-methyl-1H-benzotriazol-5-yl)propanoate (1 eq.) and 6-(benzyloxy)-3,4-dihydro-2H-1,2λ$^6$,3-benzoxathiazine-2,2-dione (1.5 eq.) as reactants ethyl 3-(3-{[6-(benzyloxy)-2,2-dioxo-2H-1,2λ$^6$,3-benzoxathiazin-3(4H)-yl]methyl}phenyl)-3-(1-[{4-[(4-methoxyphenyl)methoxy] butyl}-4-methyl-1H-benzotriazol-5-yl)propanoate was obtained.

The crude product was used without further purification using General Procedure 8. The title compound was obtained (77% yield).

$^1$H-NMR (400 MHz, DMSO-d6) δ ppm: 9.61 (m, 1H), 7.61 (d, 1H), 7.48 (d, 1H), 7.36 (m, 1H), 7.28-7.14 (m, 3H), 6.89 (d, 1H), 6.72 (dd, 1H), 6.59 (d, 1H), 4.86 (t, 1H), 4.65 (t, 2H), 4.51/4.26 (2s, 4H), 4.41 (t, 2H), 3.93 (q, 2H), 3.38 (q, 2H), 3.16 (d, 2H), 2.76 (s, 3H), 1.9 (m, 2H), 1.37 (m, 2H), 1 (t, 3H)

Step 3: Preparation of ethyl 3-[1-(4-bromobutyl)-4-methyl-1H-benzotriazol-5-yl]-3-{3-[(6-hydroxy-2,2-dioxo-2H-1,2λ$^6$,3-benzoxathiazin-3(4H)-yl)methyl] phenyl}propanoate Using General Procedure 9 starting from ethyl 3-[1-(4-hydroxybutyl)-4-methyl-1H-benzotriazol-5-yl]-3-{3-[(6-hydroxy-2,2-dioxo-2H-1,2)$^6$,3-benzoxathiazin-3(4H)-yl) methyl]phenyl}propanoate (1 eq.) as a reactant, the title compound (99% yield) was obtained.

$^1$H-NMR (400 MHz, DMSO-d6) δ ppm: 9.61 (m, 1H), 7.61 (d, 1H), 7.49 (d, 1H), 7.25-7.14 (m, 3H), 7.22 (m, 1H), 6.89 (d, 1H), 6.72 (dd, 1H), 6.59 (d, 1H), 4.88 (t, 1H), 4.7 (t, 2H), 4.5/4.26 (2s, 4H), 3.91 (q, 2H), 3.52 (t, 2H), 3.16 (d, 2H), 2.76 (s, 3H), 2 (m, 2H), 1.78 (m, 2H), 1 (t, 3H)

Step 4: Preparation of ethyl[31-methyl-27,27-dioxo-21,26-dioxa-27λ$^6$-thia-1,14,15,16-tetraazahexacyclo [20.5.3.1$^{3,7}$0.1$^{9,13}$0.0$^{12,16}$0.0$^{25,29}$]dotriaconta-3(32), 4,6,9(31),10,12,14,22,24,29-decaen-8-yl]acetate Using General Procedure 11 starting from ethyl 3-[1-(4-bromobutyl)-4-methyl-1H-benzotriazol-5-yl]-3-{3-[(6-hydroxy-2,2-dioxo-2H-1,2)$^6$,3-benzoxathiazin-3(4H)-yl) methyl]phenyl}propanoate (1 eq.) as a reactant, the title compound (78% yield) was obtained.

$^1$H-NMR (400 MHz, DMSO-d6) δ ppm: 7.6 (d, 1H), 7.5 (d, 1H), 7.4 (t, 1H), 7.31 (d, 1H), 7.25 (d, 1H), 6.95 (d, 1H), 6.81 (s1, 1H), 6.7 (dd, 1H), 6 (d, 1H), 4.8/4.71 (2m, 2H), 4.8 (m, 1H), 4.11/4 (2s, 4H), 3.92 (q, 2H), 3.7/3.4 (2m, 2H), 3.2/3.1 (2dd, 2H), 2.71 (s, 3H), 2.2/2 (2m, 2H), 1.7/1.5 (2m, 2H), 1 (t, 3H)

Step 5: Preparation of Example 6

Using General Procedure 12 starting from ethyl[31-methyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl] acetate (1 eq.) as a reactant, the title compound (white solid, 21% yield) was obtained.

HRMS calculated for $C_{28}H_{28}N_4O_6S$: 548.1730; $[M+H]^+$ found: 549.1809 (δ=1.2 ppm).

$^1$H-NMR (400 MHz, DMSO-d6) δ ppm: 7.58 (d, 1H), 7.5 (d, 1H), 7.41 (t, 1H), 7.32 (d, 1H), 7.26 (d, 1H), 6.92 (d, 1H), 6.8 (s1, 1H), 6.72 (dd, 1H), 5.98 (d, 1H), 4.8/4.72 (2m, 2H), 4.8 (m, 1H), 4.1 (s, 2H), 4 (s, 2H), 3.68/3.4 (2m, 2H), 3.12/3 (2dd, 2H), 2.7 (s, 3H), 2.2/1.98 (2m, 2H), 1.7/1.48 (2m, 2H)

EXAMPLE 7: [(8S)-4,31-Dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid and [(8R)-4,31-dimethyl-27,27-dioxo-21,26-dioxa-27λ$^6$-thia-1,14,15,16-tetraazahexacyclo[20.5.3.1$^{3,}$$_7$0.1$^{9,13}$0.0$^{12,16}$0.0$^{25,29}$]dotriaconta-3(32),4,6,9(31),10,12,14,22,24,29-decaen-8-yl]acetic acid

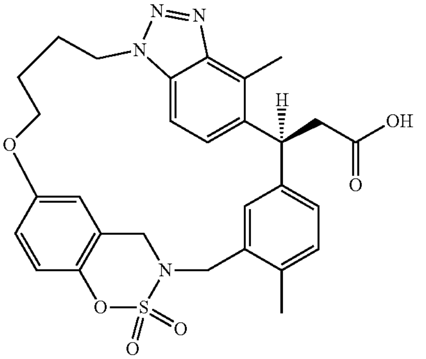

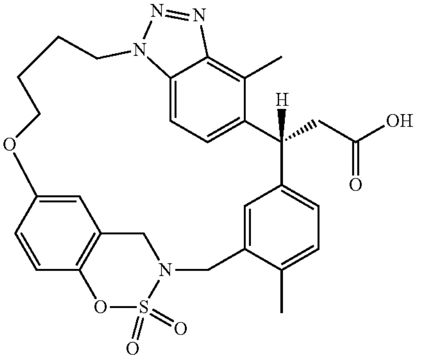

Step A1: Preparation of N-[4-(benzyloxy)butyl]-4-bromo-3-methyl-2-nitroaniline

The mixture of 4-bromo-3-methyl-2-nitro-aniline (1 eq., 10 g, 43 mmol), NaOH (1.2 eq., 2.1 g, 52 mmol) and acetone (2 mL/mmol, 87 mL) was heated to 65° C. in 15 min. 4-Bromobutoxymethylbenzene (1.2 eq.) was added to the mixture over a period of 5 min. The mixture was stirred at 65° C. for 72 h. After completion of the reaction, the mixture was quenched with 400 mL water. The mixture was extracted with 3×150 ml EtOAc. The organic layer was dried over anhydrous $Na_2SO_4$, filtered, concentrated to dryness to give the crude product, which was purified by normal phase silica gel chromatography using heptane-DCM (20:80) as an eluent to give the title compound (6.5 g, orange oil, 38% yield).

$^1$H-NMR (400 MHz, DMSO-d6) δ ppm: 7.5 (d, 1H), 7.3 (m, 5H), 6.7 (d, 1H), 6.15 (t, 1H), 4.4 (s, 2H), 3.45 (t, 2H), 3.1 (q, 2H), 2.2 (s, 3H), 1.6 (m, 4H)

Step A2: Preparation of N$^1$-[4-(benzyloxy)butyl]-4-bromo-3-methylbenzene-1,2-diamine To a solution of N-[4-(benzyloxy)butyl]-4-bromo-3-methyl-2-nitroaniline (1 eq., 6.1 g, 16 mmol) in EtOH (4 mL/mmol, 62 mL) tin(II) dichloride dihydrate (4 eq., 13 g, 62 mmol) was added at RT. The reaction mixture was heated to 70° C. and stirred at this temperature for 3 h.

After completion of the reaction 5N aq. NaOH solution (40 mL), then 160 ml EtOAc were added. The mixture was filtered, the mother liquor was separated. The organic layer was dried over anhydrous $Na_2SO_4$, filtered, concentrated to dryness to give the crude product, which was purified by reversed-phase chromatography using water-MeCN as an eluent (4 g, 71% yield).

$^1$H-NMR (400 MHz, DMSO-d6) δ ppm: 7.35-7.25 (m, 5H), 6.7 (d, 1H), 6.22 (d, 1H), 4.6 (s, 2H), 4.52 (t, 1H), 4.42 (s, 2H), 3.49 (t, 2H), 3 (q, 2H), 2.15 (s, 3H), 1.65 (m, 4H)

Step A3: Preparation of 1-[4-(benzyloxy)butyl]-5-bromo-4-methyl-1H-benzotriazole Using General Procedure 2 STEP 4 starting from N$^1$-[4-(benzyloxy)butyl]-4-bromo-3-methylbenzene-1,2-diamine (1 eq.) as a reactant, the title compound (orange oil, 79% yield) was obtained.

$^1$H-NMR (400 MHz, DMSO-d6) δ ppm: 7.68 (s, 2H), 7.3-7.2 (m, 5H), 4.7 (t, 2H), 4.4 (s, 2H), 3.42 (t, 2H), 2.7 (s, 3H), 1.98 (m, 2H), 1.5 (m, 2H)

Step A4: Preparation of ethyl (2E)-3-{1-[4-(benzyloxy)butyl]-4-methyl-1H-benzotriazol-5-yl}prop-2-enoate Using General Procedure 2 STEP 5 starting from 1-[4-(benzyloxy)butyl]-5-bromo-4-methyl-1H-benzotriazole (1 eq.) as a reactant, the title compound (black oil, 96% yield) was obtained.

$^1$H-NMR (400 MHz, DMSO-d6) δ ppm: 8 (d, 1H), 7.9 (d, 1H), 7.7 (d, 1H), 7.35-7.2 (m, 5H), 6.65 (d, 1H), 4.72 (t, 2H), 4.4 (s, 2H), 4.2 (q, 2H), 3.45 (t, 2H), 2.8 (s, 3H), 1.95 (quint, 2H), 1.52 (quint, 2H), 1.3 (t, 3H)

Step 1: Preparation of ethyl 3-{1-[4-(benzyloxy)butyl]-4-methyl-1H-benzotriazol-5-yl}-3-[3-(hydroxymethyl)-4-methylphenyl]propanoate Using General Procedure 6 starting from ethyl(2E)-3-{1-[4-(benzyloxy)butyl]-4-methyl-1H-benzotriazol-5-yl}prop-2-enoate (1 eq.) and [2-methyl-5-(4,4,5,5-tetramethyl-1,3,2-dioxaborolan-2-yl)phenyl]methanol (1.5 eq.) as reactants the title compound (49% yield) was obtained.

$^1$H-NMR (400 MHz, DMSO-d6) δ ppm: 7.6 (d, 1H), 7.45 (d, 1H), 7.35-7.2 (m, 6H), 7.1 (dd, 1H), 7.01 (d, 1H), 4.99 (t, 1H), 4.82 (t, 1H), 4.65 (t, 2H), 4.4 (d+s, 4H), 3.91 (q, 2H), 3.45 (t, 2H), 3.15 (d, 2H), 2.75 (s, 3H), 2.15 (s, 3H), 1.95 (m, 2H), 1.5 (m, 2H), 1 (t, 3H)

Step 2: Preparation of ethyl 3-{1-[4-(benzyloxy)butyl]-4-methyl-1H-benzotriazol-5-yl}-3-(3-{[6-(benzyloxy)-2,2-dioxo-2H-1,2λ$^6$,3-benzoxathiazin-3(4H)-yl]methyl}-4-methylphenyl)propanoate Using General Procedure 7 starting from ethyl 3-{1-[4-(benzyloxy)butyl]-4-methyl-1H-benzotriazol-5-yl}-3-[3-(hydroxymethyl)-4-methylphenyl]propanoate (1 eq.) and 6-(benzyloxy)-3,4-dihydro-2H-1,2λ$^6$,3-benzoxathiazine-2,2-dione (2.2 eq.) as reactants the title compound (60% yield) was obtained.

$^1$H-NMR (400 MHz, DMSO-d6) δ ppm: 7.58 (d, 1H), 7.48 (d, 1H), 7.45-7.2 (m, 13H), 7.15 (d, 1H), 7.05 (dd, 1H), 6.95 (d, 1H), 5.1 (s, 2H), 4.85 (t, 1H), 4.65 (t, 2H), 4.45/4.4

(2s, 4H), 4.22 (s, 2H), 3.92 (q, 2H), 3.42 (t, 2H), 3.15 (m, 2H), 2.75 (s, 3H), 2.2 (s, 3H), 1.92 (m, 2H), 1.48 (m, 2H), 1.2 (t, 3H)

Step 3: Preparation of ethyl 3-[1-(4-hydroxybutyl)-4-methyl-1H-benzotriazol-5-yl]-3-{3-[(6-hydroxy-2,2-dioxo-2H-1,2λ$^6$,3-benzoxathiazin-3(4H)-yl)methyl]-4-methylphenyl}propanoate Using General Procedure 8 starting from ethyl 3-{1-[4-(benzyloxy)butyl]-4-methyl-1H-benzotriazol-5-yl}-3-(3-{[6-(benzyloxy)-2,2-dioxo-2H-1,2λ$^6$,3-benzoxathiazin-3(4H)-yl]methyl}-4-methylphenyl)propanoate (1 eq.) as a reactant, the title compound (white solid, quant.) was obtained.

$^1$H-NMR (400 MHz, DMSO-d6) δ ppm: 7.62 (d, 1H), 7.5 (d, 1H), 7.22 (s, 1H), 7.2 (d, 1H), 7.15 (d, 1H), 7 (s, 1H), 6.8 (dd, 1H), 6.6 (d, 1H), 4.85 (t, 1H), 4.65 (t, 2H), 4.4 (m, 1H), 4.4 (s, 2H), 4.2 (m, 2H), 3.95 (q, 2H), 3.38 (t1, 2H), 3.15 (m, 2H), 2.75 (s, 3H), 2.32 (s, 3H), 1.9 (m, 2H), 1.35 (m, 2H), 1 (t, 3H)

Step 4: Preparation of ethyl 3-[1-(4-bromobutyl)-4-methyl-1H-benzotriazol-5-yl]-3-{3-[(6-hydroxy-2,2-dioxo-2H-1,2λ$^6$,3-benzoxathiazin-3(4H)-yl)methyl]-4-methylphenyl}propanoate Using General Procedure 9 starting from ethyl 3-[1-(4-hydroxybutyl)-4-methyl-1H-benzotriazol-5-yl]-3-{3-[(6-hydroxy-2,2-dioxo-2H-1,2)$^6$,3-benzoxathiazin-3(4H)-yl)methyl]-4-methylphenyl}propanoate (1 eq.) as a reactant, the title compound (73% yield) was obtained.

$^1$H-NMR (400 MHz, DMSO-d6) δ ppm: 9.68 (s, 1H), 7.63 (d, 1H), 7.52 (d, 1H), 7.22 (d, 1H), 7.2 (dd, 1H), 7.13 (d, 1H), 6.99 (d, 1H), 6.79 (dd, 1H), 6.6 (d, 1H), 4.84 (t, 1H), 4.69 (t, 2H), 4.38 (s, 2H), 4.2 (m, 2H), 3.94 (q, 2H), 3.54 (t, 2H), 3.19 (m, 2H), 2.76 (s, 3H), 2.22 (s, 3H), 1.99 (quint, 2H), 1.77 (quint, 2H), 1 (t, 3H)

Step 5: Preparation of ethyl[4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate Using General Procedure 11 starting from ethyl 3-[1-(4-bromobutyl)-4-methyl-1H-benzotriazol-5-yl]-3-{3-[(6-hydroxy-2,2-dioxo-2H-1,2λ$^6$,3-benzoxathiazin-3(4H)-yl)methyl]-4-methylphenyl}propanoate (1 eq.) as a reactant, the title compound (white solid, 79% yield) was obtained.

$^1$H-NMR (400 MHz, DMSO-d6) δ ppm: 7.7 (d, 1H), 7.5 (dd, 1H), 7.45 (d, 1H), 7.3 (d, 1H), 7 (d, 1H), 6.8 (dd, 1H), 6.55 (d, 1H), 5.85 (d, 1H), 4.8 (m, 3H), 4.1/3.95 (m, 2H), 4/3.8 (m, 2H), 3.9 (m, 2H), 3.7/3.45 (m, 2H), 3.15/3.08 (m, 2H), 2.63 (s, 3H), 2.31 (s, 3H), 2.2/2 (m, 2H), 1.8/1.6 (m, 2H), 1.02 (t, 3H)

Step 6: Preparation of Example 7

Using General Procedure 12 starting from ethyl[4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (1 eq.) as a reactant, the title compound (white solid, 93% yield) was obtained.

The enantiopure final products or final intermediates were obtained by chromatographic separation on chiral column.

EXAMPLE 7a (8S)

HRMS calculated for $C_{29}H_{30}N_4O_6S$: 562.1886; $[M+H]^+$ found: 563.1962 (δ=0.6 ppm).

EXAMPLE 7b (8R)

HRMS calculated for $C_{29}H_{30}N_4O_6S$: 562.1886; $[M+H]^+$ found: 563.1962 (δ=0.6 ppm).

$^1$H-NMR (400 MHz, DMSO-d6) δ ppm: 12.12 (m, 1H), 7.69 (d, 1H), 7.49 (dd, 1H), 7.41 (d, 1H), 7.3 (d, 1H), 7 (d, 1H), 6.8 (dd, 1H), 6.55 (d, 1H), 5.85 (d, 1H), 4.75 (m, 3H), 4.11-3.92 (d, 2H), 4-3.85 (d, 2H), 3.62/3.4 (m, 2H), 3.05/2.95 (dd, 2H), 2.65/2.31 (s, 6H), 2.2/2.08 (m, 2H), 1.8/1.65 (m, 2H)

EXAMPLE 8: [5-Methoxy-31-methyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid

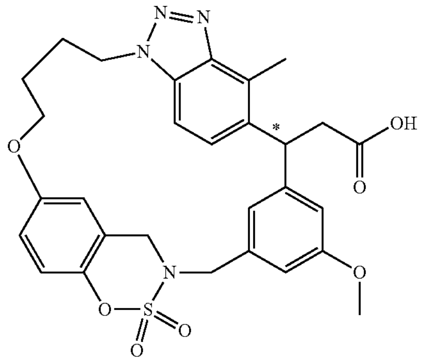

* = RorS enantiomer 2

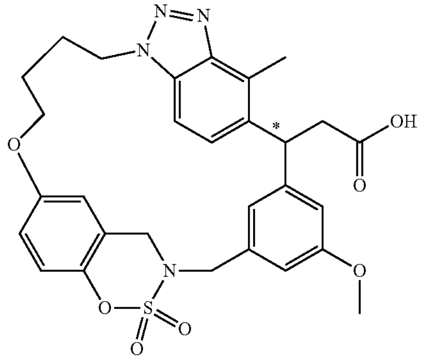

* = RorS

Step 1: Preparation of ethyl 3-[3-(hydroxymethyl)-5-methoxyphenyl]-3-(1-{4-[(4-methoxyphenyl)methoxy]butyl}-4-methyl-1H-benzotriazol-5-yl)propanoate Using General Procedure 6 starting from ethyl(2E)-3-(1-{4-[(4-methoxyphenyl)methoxy]butyl}-4-methyl-1H-benzotriazol-5-yl)prop-2-enoate (1 eq.) and [3-methoxy-5-(4,4, 5,5-tetramethyl-1,3,2-dioxaborolan-2-yl)phenyl]methanol (1 eq.) as reactants, the title compound (yellow oil, 30% yield) was obtained.

$^1$H-NMR (400 MHz, DMSO-d6) δ ppm: 7.59 (d, 1H), 7.5 (d, 1H), 7.2 (d, 2H), 6.88 (d, 2H), 6.3-6.15 (3s1, 3H), 5.1 (t, 1H), 4.81 (t, 1H), 4.62 (t, 2H), 4.4 (d, 2H), 4.3 (s, 2H), 3.95 (q, 2H), 3.71 (s, 6H), 3.39 (t, 2H), 3.12 (m, 2H), 2.75 (s, 3H), 1.92 (m, 2H), 1.5 (m, 2H), 1 (t, 3H)

Step 2: Preparation of ethyl 3-(3-{[6-(benzyloxy)-2,2-dioxo-2H-1,2λ$^6$,3-benzoxathiazin-3(4H)-yl]methyl}-5-methoxyphenyl)-3-(1-{4-[(4-methoxyphenyl)methoxy]butyl}-4-methyl-1H-benzotriazol-5-yl)propanoate Using General Procedure 7 starting from ethyl 3-[3-(hydroxymethyl)-5-methoxyphenyl]-3-(1-{4-[(4-methoxyphenyl)methoxy]butyl}-4-methyl-1H-benzotriazol-5-yl) propanoate (1 eq.) and 6-(benzyloxy)-3,4-dihydro-2H-1,2λ$^6$,3-benzoxathiazine-2,2-dione (1.1 eq.) as reactants, the title compound (88% yield) was obtained.

$^1$H-NMR (400 MHz, DMSO-d6) δ ppm: 7.72-7.3 (m, 5H), 7.58 (d, 1H), 7.48 (d, 1H), 7.2 (d, 2H), 7-6.9 (m, 3H), 6.91/6.8/6.72 (3d, 3H), 6.87 (d, 2H), 5.05 (s, 2H), 4.81 (t, 1H), 4.62 (t, 2H), 4.55 (s, 2H), 4.3/4.23 (2s, 4H), 3.91 (q, 2H), 3.7 (2s, 6H), 3.35 (t, 2H), 3.12 (d, 2H), 2.78 (s, 3H), 1.9 (m, 2H), 1.48 (m, 2H), 1 (t, 3H)

Step 3: Preparation of ethyl 3-[1-(4-hydroxybutyl)-4-methyl-1H-benzotriazol-5-yl]-3-{3-[(6-hydroxy-2,2-dioxo-2H-1,2λ$^6$,3-benzoxathiazin-3(4H)-yl)methyl]-5-methoxyphenyl}propanoate Using General Procedure 8 starting from ethyl 3-(3-{[6-(benzyloxy)-2,2-dioxo-2H-1,2λ$^6$,3-benzoxathiazin-3(4H)-yl]methyl}-5-methoxyphenyl)-3-(1-{4-[(4-methoxyphenyl) methoxy]butyl}-4-methyl-1H-benzotriazol-5-yl)propanoate (1 eq.) as a reactant, the title compound (white solid, 96% yield) was obtained.

$^1$H-NMR (400 MHz, DMSO-d6) δ ppm: 9.6/4.4 (s+t, 2H), 7.6 (d, 1H), 7.5 (d, 1H), 6.91 (d, 1H), 6.9 (d, 1H), 6.8/6.72/6.6 (3s1, 3H), 6.71 (dd, 1H), 4.81 (t, 1H), 4.62 (t, 2H), 4.52 (s, 2H), 4.21 (s, 2H), 3.92 (q, 2H), 3.7 (s, 3H), 3.4 (q, 2H), 3.17 (d, 2H), 2.78 (s, 3H), 1.9 (m, 2H), 1.38 (m, 2H), 1 (t, 3H)

Step 4: Preparation of ethyl 3-[1-(4-bromobutyl)-4-methyl-1H-benzotriazol-5-yl]-3-{3-[(6-hydroxy-2,2-dioxo-2H-1,2λ$^6$,3-benzoxathiazin-3(4H)-yl)methyl]-5-methoxyphenyl}propanoate Using General Procedure 9 starting from ethyl 3-[1-(4-hydroxybutyl)-4-methyl-1H-benzotriazol-5-yl]-3-{3-[(6-hydroxy-2,2-dioxo-2H-1,2λ$^6$,3-benzoxathiazin-3(4H)-yl) methyl]-5-methoxyphenyl}propanoate (1 eq.) as a reactant, the title compound (white solid, 82% yield) was obtained.

$^1$H-NMR (400 MHz, DMSO-d6) δ ppm: 9.61 (m, 1H), 7.64 (d, 1H), 7.51 (d, 1H), 6.91/6.81 (2s1, 2H), 6.88 (d, 1H), 6.73 (s1, 1H), 6.71 (dd, 1H), 6.58 (d, 1H), 4.82 (t, 1H), 4.69 (t, 2H), 4.51/4.21 (2s, 4H), 3.93 (q, 2H), 3.69 (s, 3H), 3.54 (t, 2H), 3.15 (d, 2H), 2.76 (s, 3H), 1.99 (m, 2H), 1.78 (m, 2H), 1 (t, 3H)

Step 5: Preparation of ethyl[5-methoxy-31-methyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$] dotriaconta-3(32),4,6,9(31),10,12,14,22,24,29-decaen-8-yl]acetate Using General Procedure 11 starting from ethyl 3-[1-(4-bromobutyl)-4-methyl-1H-benzotriazol-5-yl]-3-{3-[(6-hydroxy-2,2-dioxo-2H-1,2λ$^6$,3-benzoxathiazin-3(4H)-yl) methyl]-5-methoxyphenyl}propanoate (1 eq.) as a reactant, the title compound (95% yield) was obtained.

$^1$H-NMR (400 MHz, DMSO-d6) δ ppm: 7.6 (d, 1H), 7.33 (d, 1H), 7.09/6.78/6.37 (3s1, 3H), 6.93 (d, 1H), 6.71 (dd, 1H), 5.98 (d, 1H), 4.85-4.67 (m, 3H), 4.12-3.9 (2dd, 4H), 3.94 (m, 2H), 3.81 (s, 3H), 3.52/3.42 (2m, 2H), 3.2/3.08 (2dd, 2H), 2.72 (s, 3H), 2.19/1.98 (2m, 2H), 1.68/1.48 (2m, 2H), 1.02 (t, 3H)

Step 6: Preparation of Example 8

Using General Procedure 12 starting from ethyl[5-methoxy-31-methyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (1 eq.) as a reactant, the title compound (white solid, 28% yield) was obtained.

The enantiopure products were obtained by chromatographic separation on chiral column.

EXAMPLE 8a (E1)

HRMS calculated for $C_{29}H_{30}N_4O_7S$: 578.1835; $[M+H]^+$ found: 579.1911 (δ=0.5 ppm).

EXAMPLE 8b (E2)

HRMS calculated for $C_{29}H_{34}O_7S$: 578.1835; $[M+H]^+$ found: 579.1912 (δ=0.7 ppm).

$^1$H-NMR (400 MHz, DMSO-d6) δ ppm: 12.15 (m, 1H), 7.6 (d, 1H), 7.31 (d, 1H), 7.31 (2dd, 4H), 7.1/6.8/6.38 (3s1, 3H), 6.95 (d, 1H), 6.71 (dd, 1H), 5.98 (d, 1H), 4.85-4.67 (m, 3H), 3.81 (s, 3H), 3.68/3.41 (2m, 2H), 3.1/2.98 (2dd, 2H), 2.71 (s, 3H), 2.19/1.98 (2m, 2H), 1.68/1.48 (2m, 2H)

EXAMPLE 9: [4-Chloro-31-methyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid enantiomer 1

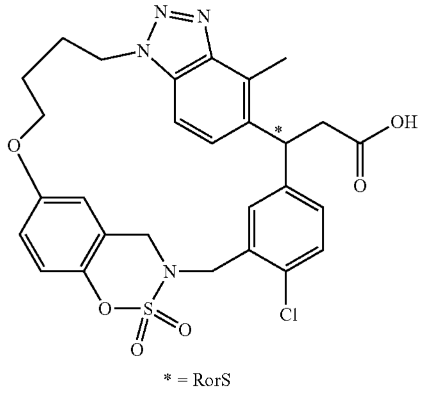

* = RorS

-continued enantiomer 2

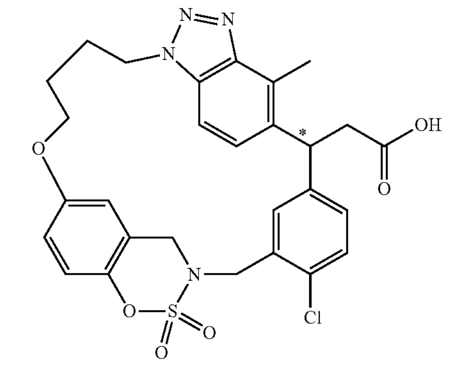

* = RorS

Step 1: Preparation of ethyl 3-[4-chloro-3-(hydroxymethyl)phenyl]-3-(1-{4-[(4-methoxyphenyl)methoxy]butyl}-4-methyl-1H-benzotriazol-5-yl)propanoate Using General Procedure 6 starting from ethyl(2E)-3-(1-{4-[(4-methoxyphenyl)methoxy]butyl}-4-methyl-1H-benzotriazol-5-yl)prop-2-enoate (1 eq.) and [2-chloro-5-(4,4,5,5-tetramethyl-1,3,2-dioxaborolan-2-yl)phenyl]methanol (2 eq.) as reactants, the title compound (yellow oil, 83% yield) was obtained.

$^1$H-NMR (400 MHz, DMSO-d6) δ ppm: 7.6 (d, 1H), 7.48 (d, 1H), 7.47 (d, 1H), 7.3 (d, 1H), 7.22 (dd, 1H), 7.19 (d, 2H), 6.88 (d, 2H), 5.3 (t, 1H), 4.89 (t, 1H), 4.63 (t, 2H), 4.49 (d, 2H), 4.3 (s, 2H), 3.92 (q, 2H), 3.71 (s, 3H), 3.39 (t, 2H), 3.17 (m, 2H), 2.75 (s, 3H), 1.91 (m, 2H), 1.49 (m, 2H), 1 (t, 3H)

Step 2: Preparation of ethyl 3-(3-{[6-(benzyloxy)-2,2-dioxo-2H-1,2λ$^6$,3-benzoxathiazin-3(4H)-yl]methyl}-4-chlorophenyl)-3-(1-{4-[(4-methoxyphenyl)methoxy]butyl}-4-methyl-1H-benzotriazol-5-yl)propanoate Using General Procedure 7 starting from ethyl 3-[4-chloro-3-(hydroxymethyl)phenyl]-3-(1-{4-[(4-methoxyphenyl)methoxy]butyl}-4-methyl-1H-benzotriazol-5-yl)propanoate (1 eq.) and 6-(benzyloxy)-3,4-dihydro-2H-1,2λ$^6$,3-benzoxathiazine-2,2-dione (1.5 eq.) as reactants, the title compound (92% yield) was obtained.

$^1$H-NMR (400 MHz, DMSO-d6) δ ppm: 7.6 (d, 1H), 7.5-7.3 (m, 8H), 7.49 (d, 1H), 7.18 (d, 2H), 7.09 (d, 1H), 7.04 (dd, 1H), 6.96 (d, 1H), 6.86 (d, 2H), 5.09 (s, 2H), 4.89 (t, 1H), 4.63 (t, 2H), 4.56/4.34 (2s, 4H), 4.3 (s, 2H), 3.94 (q, 2H), 3.72 (s, 3H), 3.36 (t, 2H), 3.2 (2ddd, 2H), 2.77 (s, 3H), 1.9 (m, 2H), 1.46 (m, 2H), 1 (t, 3H)

Step 3: Preparation of ethyl 3-{4-chloro-3-[(6-hydroxy-2,2-dioxo-2H-1,2λ$^6$,3-benzoxathiazin-3(4H)-yl)methyl]phenyl}-3-[1-(4-hydroxybutyl)-4-methyl-1H-benzotriazol-5-yl]propanoate Using General Procedure 8 starting from ethyl 3-(3-{[6-(benzyloxy)-2,2-dioxo-2H-1,2λ$^6$,3-benzoxathiazin-3(4H)-yl]methyl}-4-chlorophenyl)-3-(1-{4-[(4-methoxyphenyl)methoxy]butyl}-4-methyl-1H-benzotriazol-5-yl)propanoate (1 eq.) as a reactant, the title compound (77% yield) was obtained.

$^1$H-NMR (400 MHz, DMSO-d6) δ ppm: 9.68 (m, 1H), 7.64 (d, 1H), 7.51 (d, 1H), 7.49 (d, 1H), 7.39 (dd, 1H), 7.31 (d, 1H), 6.95 (d, 1H), 6.77 (dd, 1H), 6.63 (d, 1H), 4.89 (t, 1H), 4.66 (t, 2H), 4.51/4.33 (2s, 4H), 4.41 (t, 2H), 3.95 (q, 2H), 3.38 (q, 2H), 3.23/3.17 (2dd, 2H), 2.76 (s, 3H), 1.91 (m, 2H), 1.37 (m, 2H), 1.01 (t, 3H)

Step 4: Preparation of ethyl 3-[1-(4-bromobutyl)-4-methyl-1H-benzotriazol-5-yl]-3-{4-chloro-3-[(6-hydroxy-2,2-dioxo-2H-1,2)$^6$,3-benzoxathiazin-3(4H)-yl)methyl]phenyl}propanoate Using General Procedure 9 starting from ethyl 3-{4-chloro-3-[(6-hydroxy-2,2-dioxo-2H-1,2)$^6$,3-benzoxathiazin-3(4H)-yl)methyl]phenyl}-3-[1-(4-hydroxybutyl)-4-methyl-1H-benzotriazol-5-yl]propanoate (1 eq.) as a reactant, the title compound (79% yield) was obtained.

$^1$H-NMR (400 MHz, DMSO-d6) δ ppm: 9.67 (s), 7.66 (d, 1H), 7.53 (d, 1H), 7.49 (d, 1H), 7.39 (d, 1H), 7.32 (dd, 1H), 6.95 (d, 1H), 6.77 (dd, 1H), 6.62 (d, 1H), 4.89 (t, 1H), 4.7 (t, 2H), 4.52 (s, 2H), 4.33 (s, 2H), 3.95 (q, d H), 3.55 (t, 2H), 3.2 (m, 2H), 2.77 (s, 3H), 2 (m, 2H), 1.78 (m, 2H), 1.01 (t, 3H)

Step 5: Preparation of ethyl[4-chloro-31-methyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate Using General Procedure 11 starting from ethyl 3-[1-(4-bromobutyl)-4-methyl-1H-benzotriazol-5-yl]-3-{4-chloro-3-[(6-hydroxy-2,2-dioxo-2H-1,2)$^6$,3-benzoxathiazin-3(4H)-yl)methyl]phenyl}propanoate (1 eq.) as a reactant, the title compound (97% yield) was obtained.

$^1$H-NMR (400 MHz, DMSO-d6) δ ppm: 7.69 (d, 1H), 7.64 (dd, 1H), 7.57 (d, 1H), 7.45 (d, 1H), 6.99 (d, 1H), 6.8 (dd, 1H), 6.8 (d, 1H), 5.86 (d, 1H), 4.82 (m, 2H), 4.79 (m, 1H), 4.24/4.05 (dd, 2H), 4.01/3.84 (dd, 2H), 3.93 (q, 2H), 3.67/3.47 (2m, 2H), 3.21/3.08 (2dd, 2H), 2.63 (s, 3H), 2.2/2.05 (2m, 2H), 1.8/1.64 (2m, 2H), 1 (t, 3H)

Step 6: Preparation of Example 9

Using General Procedure 12 starting from ethyl[4-chloro-31-methyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (1 eq.) as a reactant, the title compound (white solid, 56% yield) was obtained.

The enantiopure products were obtained by chromatographic separation on chiral column.

EXAMPLE 9a (E1)

HRMS calculated for $C_{28}H_{27}ClN_4O_6S$: 582.1340; $[M+H]^+$ found: 583.1418 (δ=0.9 ppm).

EXAMPLE 9b (E2)

HRMS calculated for $C_{28}H_{27}ClN_4O_6S$: 582.1340; $[M+H]^+$ found: 583.1417 (δ=0.8 ppm).

$^1$H-NMR (400 MHz, DMSO-d6) δ ppm: 12.28 (m, 1H), 7.69 (d, 1H), 7.64 (dd, 1H), 7.57 (d, 1H), 7.44 (d, 1H), 6.99 (d, 1H), 6.79 (dd, 1H), 6.78 (d, 1H), 5.85 (d, 1H), 4.84-4.7 (m, 1H), 4.8 (t, 2H), 4.23/4.05 (dd, 2H), 4/3.83 (dd, 2H), 3.67/3.45 (2m, 2H), 3.09/2.96 (2dd, 2H), 2.63 (s, 3H), 2.2/2.08 (2m, 2H), 1.82/1.63 (2m, 2H)

EXAMPLE 10: [4-Methoxy-31-methyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid enantiomer 1

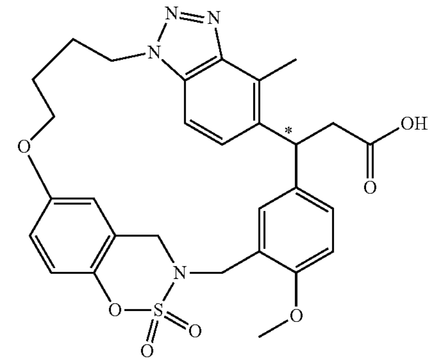

* = RorS enantiomer 2

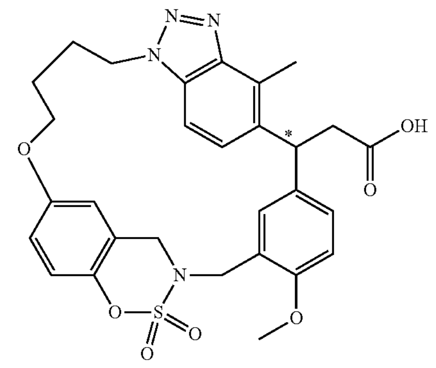

* = RorS

Step 1: Preparation of ethyl 3-[3-(hydroxymethyl)-4-methoxyphenyl]-3-(1-{4-[(4-methoxyphenyl)methoxy]butyl}-4-methyl-1H-benzotriazol-5-yl)propanoate Using General Procedure 6 starting from ethyl (2E)-3-(1-{4-[(4-methoxyphenyl)methoxy]butyl}-4-methyl-1H-benzotriazol-5-yl)prop-2-enoate (1 eq.) and [2-methoxy-5-(4,4,5,5-tetramethyl-1,3,2-dioxaborolan-2-yl)phenyl]methanol (1.4 eq.) as reactants, the title compound (yellow oil, 68% yield) was obtained.

$^1$H-NMR (400 MHz, DMSO-d6) δ ppm: 7.6 (d, 1H), 7.45 (d, 1H), 7.28 (d, 1H), 7.2 (d, 2H), 7.19 (dd, 1H), 6.9 (d, 2H), 6.82 (d, 1H), 4.9 (t, 1H), 4.82 (t, 1H), 4.65 (t, 2H), 4.41 (d, 2H), 4.31 (s, 2H), 3.92 (q, 2H), 3.71 (2s, 6H), 3.4 (t, 2H), 3.12 (dd, 2H), 2.78 (s, 3H), 1.91 (m, 2H), 1.5 (m, 2H), 1 (t, 3H)

Step 2: Preparation of ethyl 3-(3-{[6-(benzyloxy)-2,2-dioxo-2H-1,2λ$^6$,3-benzoxathiazin-3(4H)-yl]methyl}-4-methoxyphenyl)-3-(1-{4-[(4-methoxyphenyl)methoxy]butyl}-4-methyl-1H-benzotriazol-5-yl)propanoate Using General Procedure 7 starting from 3-[3-(hydroxymethyl)-4-methoxyphenyl]-3-(1-{4-[(4-methoxyphenyl)methoxy]butyl}-4-methyl-1H-benzotriazol-5-yl)propanoate (1 eq.) and 6-(benzyloxy)-3,4-dihydro-2H-1,2λ$^6$,3-benzoxathiazine-2,2-dione (1.1 eq.) as reactants, the title compound (79% yield) was obtained.

$^1$H-NMR (400 MHz, DMSO-d6) δ ppm: 7.6 (d, 1H), 7.49 (d, 1H), 7.45-7.3 (m, 5H), 7.28 (d, 1H), 7.21 (dd, 1H), 7.18 (d, 2H), 7-6.9 (m, 3H), 6.85 (d, 3H), 5.08 (s, 2H), 4.8 (t, 1H), 4.65 (t, 2H), 4.52 (s, 2H), 4.31 (s, 2H), 4.2 (s, 2H), 3.92 (q, 2H), 3.72/3.65 (2s, 6H), 3.38 (t, 2H), 3.12 (d, 2H), 2.79 (s, 3H), 1.9 (m, 2H), 1.45 (m, 2H), 1 (t, 3H)

Step 3: Preparation of ethyl 3-[1-(4-hydroxybutyl)-4-methyl-1H-benzotriazol-5-yl]-3-{3-[(6-hydroxy-2,2-dioxo-2H-1,2λ$^6$,3-benzoxathiazin-3(4H)-yl)methyl]-4-methoxyphenyl}propanoate Using General Procedure 8 starting from ethyl 3-(3-{[6-(benzyloxy)-2,2-dioxo-2H-1,2λ$^6$,3-benzoxathiazin-3(4H)-yl]methyl}-4-methoxyphenyl)-3-(1-{4-[(4-methoxyphenyl)methoxy]butyl}-4-methyl-1H-benzotriazol-5-yl)propanoate (1 eq.) as a reactant, the title compound (white solid, 81% yield) was obtained.

$^1$H-NMR (400 MHz, DMSO-d6) δ ppm: 9.6/4.41 (s+t, 2H), 7.65 (d, 1H), 7.5 (d, 1H), 7.28 (d, 1H), 7.21 (dd, 1H), 6.9 (d, 1H), 6.87 (d, 1H), 6.71 (dd, 1H), 6.6 (d, 1H), 4.82 (t, 1H), 4.65 (t, 2H), 4.5 (s, 2H), 4.2 (s, 2H), 3.95 (q, 2H), 3.7 (s, 3H), 3.4 (q, 2H), 3.15 (d, 2H), 2.75 (s, 3H), 1.91 (m, 2H), 1.38 (m, 2H), 1.02 (t, 3H)

Step 4: Preparation of ethyl 3-[1-(4-bromobutyl)-4-methyl-1H-benzotriazol-5-yl]-3-{3-[(6-hydroxy-2,2-dioxo-2H-1,2λ$^6$,3-benzoxathiazin-3(4H)-yl)methyl]-4-methoxyphenyl}propanoate Using General Procedure 9 starting from ethyl 3-[1-(4-hydroxybutyl)-4-methyl-1H-benzotriazol-5-yl]-3-{3-[(6-hydroxy-2,2-dioxo-2H-1,2λ$^6$,3-benzoxathiazin-3(4H)-yl)methyl]-4-methoxyphenyl}propanoate (1 eq.) as a reactant, the title compound (white solid, 69% yield) was obtained.

$^1$H-NMR (400 MHz, DMSO-d6) δ ppm: 9.6 (s, 1H), 7.65 (d, 1H), 7.51 (d, 1H), 7.25 (d, 1H), 7.22 (dd, 1H), 6.9 (d, 1H), 6.82 (d, 1H), 6.71 (dd, 1H), 6.59 (d, 1H), 4.85 (t, 1H), 4.7 (t, 2H), 4.49 (s, 2H), 4.21 (s, 2H), 3.92 (q, 2H), 3.7 (s, 3H), 3.55 (t, 2H), 3.15 (d, 2H), 2.75 (s, 3H), 2 (m, 2H), 1.8 (m, 2H), 1 (t, 3H)

Step 5: Preparation of ethyl[4-methoxy-31-methyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate Using General Procedure 11 starting from ethyl 3-[1-(4-bromobutyl)-4-methyl-1H-benzotriazol-5-yl]-3-{3-[(6-hydroxy-2,2-dioxo-2H-1,2λ$^6$,3-benzoxathiazin-3(4H)-yl)methyl]-4-methoxyphenyl}propanoate (1 eq.) as a reactant, the title compound (70% yield) was obtained.

$^1$H-NMR (400 MHz, DMSO-d6) δ ppm: 7.69 (d, 1H), 7.55 (dd, 1H), 7.45 (d, 1H), 7.09 (d, 1H), 6.95 (d, 1H), 6.78

(dd, 1H), 6.59 (d, 1H), 5.8 (d, 1H), 4.78 (m, 3H), 4.12/3.92 (2d, 2H), 4.02/3.8 (2d, 2H), 3.92 (q, 2H), 3.81 (s, 3H), 3.61/3.4 (2m, 2H), 3.12/3.02 (2dd, 2H), 2.62 (s, 3H), 2.2/2.1 (2m, 2H), 1.8/1.62 (2m, 2H), 1.02 (t, 3H)

Step 6: Preparation of Example 10

Using General Procedure 12 starting from ethyl[4-methoxy-31-methyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (1 eq.) as a reactant, the title compound (white solid, 88% yield) was obtained.

The enantiopure products were obtained by chromatographic separation on chiral column.

EXAMPLE 10a (E1)

HRMS calculated for $C_{29}H_{30}N_4O_7S$: 578.1835; $[M+H]^+$ found: 579.1911 (δ=0.5 ppm).

EXAMPLE 10b (E2)

HRMS calculated for $C_{29}H_{30}N_4O_7S$: 578.1835; $[M+H]^+$ found: 579.1911 (δ=0.5 ppm).

$^1$H-NMR (400 MHz, DMSO-d6) δ ppm: 12.15 (m, 1H), 7.69 (d, 1H), 7.55 (dd, 1H), 7.41 (d, 1H), 7.09 (d, 1H), 6.95 (d, 1H), 6.78 (dd, 1H), 6.55 (d, 1H), 5.79 (d, 1H), 4.75 (m, 3H), 4.12/3.92 (2d, 2H), 4.02/3.8 (2d, 2H), 3.8 (s, 3H), 3.61/3.4 (2m, 2H), 3.12/2.95 (2dd, 2H), 2.62 (s, 3H), 2.2/2.1 (2m, 2H), 1.8/1.62 (2m, 2H)

EXAMPLE 11: [4,33-Dimethyl-29,29-dioxo-23,28-dioxa-29λ$^6$-thia-1,14,15,16-tetraazahexacyclo[22.5.3.1$^{3,7}$0.1$^{9,13}$0.0$^{12,16}$0.0$^{27,31}$]tetratriaconta-3(34),4,6,9(33),10,12,14,24,26,31-decaen-8-yl]acetic acid enantiomer 1

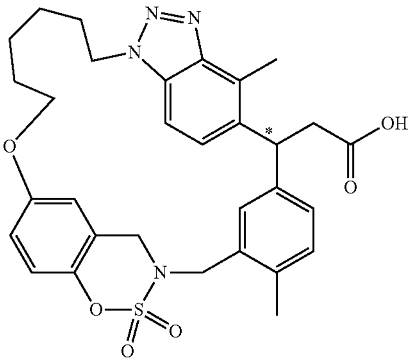

* = RorS

-continued enantiomer 2

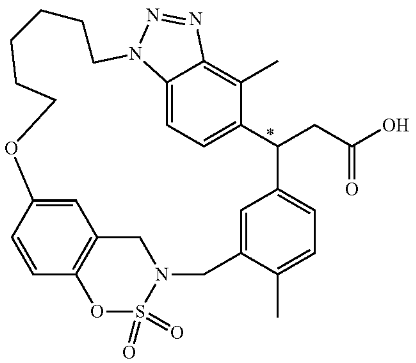

* = RorS

Step A1: Preparation of N-[6-(benzyloxy)hexyl]-3-methyl-2-nitroaniline

Using General Procedure 2 STEP 1 starting from 1-fluoro-3-methyl-2-nitrobenzene (1 eq.) and 6-benzyloxy-hexan-1-amine (1.2 eq.) as reactants, the title compound (53% yield) was obtained.

$^1$H-NMR (400 MHz, DMSO-d6) δ ppm: 7.35-7.2 (m, 6H), 6.78 (d, 1H), 6.52 (d, 1H), 6.39 (t, 1H), 4.42 (s, 2H), 3.41 (t, 2H), 3.15 (q, 2H), 2.29 (s, 3H), 1.55 (m, 4H), 1.32 (m, 4H)

Step A2: Preparation of N-[6-(benzyloxy)hexyl]-4-bromo-3-methyl-2-nitroaniline

Using General Procedure 2 STEP 2 starting from N-[6-(benzyloxy)hexyl]-3-methyl-2-nitroaniline (1 eq.) as a reactant, the title compound (99% yield) was obtained.

$^1$H-NMR (400 MHz, DMSO-d6) δ ppm: 7.5 (d, 1H), 7.3 (m, 5H), 6.7 (d, 1H), 6.12 (t), 4.43 (s, 2H), 3.4 (t, 2H), 3.1 (q, 2H), 2.25 (s, 3H), 1.53/1.34 (2m, 8H)

Step A3: Preparation of N$^1$-[6-(benzyloxy)hexyl]-4-bromo-3-methylbenzene-1,2-diamine Using General Procedure 2 STEP 3 starting from N-[6-(benzyloxy)hexyl]-4-bromo-3-methyl-2-nitroaniline (1 eq., 25.3 mmol) as a reactant, the title compound (67% yield) was obtained.

$^1$H-NMR (400 MHz, DMSO-d6) δ ppm: 7.3 (m, 5H), 6.7 (d, 1H), 6.23 (d, 1H), 4.59 (s1, 2H), 4.51 (t, 1H), 4.44 (s, 2H), 3.42 (t, 2H), 2.96 (q, 2H), 2.16 (s, 3H), 1.56 (m, 4H), 1.37 (m, 4H)

Step A4: Preparation of 1-[6-(benzyloxy)hexyl]-5-bromo-4-methyl-1H-benzotriazole Using General Procedure 2 STEP 4 starting from N$^1$-[6-(benzyloxy)hexyl]-4-bromo-3-methylbenzene-1,2-diamine (1 eq.) as a reactant, the title compound (28% yield) was obtained.

$^1$H-NMR (400 MHz, DMSO-d6) δ ppm: 7.68 (2d, 2H), 7.35-7.2 (m, 5H), 4.68 (t, 2H), 4.4 (s, 2H), 3.39 (t, 2H), 2.71 (s, 3H), 1.9 (m, 2H), 1.5 (m, 2H), 1.32 (m, 2H), 1.22 (m, 2H)

Step A5: Preparation of ethyl (2E)-3-{1-[6-(benzyloxy)hexyl]-4-methyl-1H-benzotriazol-5-yl}prop-2-enoate Using General Procedure 2 STEP 5 starting from 1-[6-(benzyloxy)hexyl]-5-bromo-4-methyl-1H-benzotriazole (1 eq.) as a reactant, the title compound (22% yield) was obtained.

$^1$H-NMR (400 MHz, DMSO-d6) δ ppm: 8 (dJ=16 Hz, 1H), 7.91 (d, 1H), 7.7 (d, 1H), 7.32-7.22 (m, 5H), 6.62 (d, 1H), 4.69 (t, 2H), 4.4 (s, 2H), 4.2 (q, 2H), 3.38 (t, 2H), 2.8 (s, 3H), 1.9 (m, 2H), 1.5 (m, 2H), 1.35-1.2 (m, 4H), 1.28 (t, 3H)

Step 1: Preparation of ethyl 3-{1-[6-(benzyloxy)hexyl]-4-methyl-1H-benzotriazol-5-yl}-3-[3-(hydroxymethyl)-4-methylphenyl]propanoate Using General Procedure 6 starting from ethyl (2E)-3-{1-[6-(benzyloxy)hexyl]-4-methyl-1H-benzotriazol-5-yl}prop-2-enoate (1 eq.) and [2-methyl-5-(4,4,5,5-tetramethyl-1,3,2-dioxaborolan-2-yl)phenyl]methanol (1.5 eq.) as reactants, the title compound (14% yield) was obtained.

$^1$H-NMR (400 MHz, DMSO-d6) δ ppm: 7.6 (d, 1H), 7.45 (d, 1H), 7.3 (s, 1H), 7.3 (m, 5H), 7.1 (d, 1H), 7 (d, 1H), 5 (t, 1H), 4.85 (t, 1H), 4.65 (t, 2H), 4.4 (2s, 4H), 3.95 (q, 2H), 3.35 (t, 2H), 3.15 (m, 2H), 2.75 (s, 3H), 2.15 (s, 3H), 1.85 (m, 2H), 1.5 (m, 2H), 1.35-1.2 (m, 4H), 1 (t, 3H)

Step 2: Preparation of ethyl 3-(3-{[6-(benzyloxy)-2,2-dioxo-2H-1,2λ$^6$,3-benzoxathiazin-3(4H)-yl]methyl}-4-methylphenyl)-3-{1-[6-(benzyloxy)hexyl]-4-methyl-1H-benzotriazol-5-yl}propanoate Using General Procedure 7 starting from ethyl 3-{1-[6-(benzyloxy)hexyl]-4-methyl-1H-benzotriazol-5-yl}-3-[3-(hydroxymethyl)-4-methylphenyl]propanoate (1 eq.) and 6-(benzyloxy)-3,4-dihydro-2H-1,2λ$^6$,3-benzoxathiazine-2,2-dione (1.2 eq.) as reactants, the title compound (84% yield) was obtained.

$^1$H-NMR (400 MHz, DMSO-d6) δ ppm: 7.61-6.93 (m, 18H), 5.1 (s, 2H), 4.84 (t, 1H), 4.58 (t, 2H), 4.42/4.21 (s, 2H), 4.42/4.21 (s, 2H), 4.38 (s, 2H), 3.92 (q, 2H), 3.32 (m, 2H), 3.16 (m, 2H), 2.76 (s, 3H), 2.21 (s, 3H), 1.83 (m, 2H), 1.45 (m, 2H), 1.3 (m, 2H), 1.19 (m, 2H), 0.97 (t, 3H)

Step 3: Preparation of ethyl 3-{3-[(6-hydroxy-2,2-dioxo-2H-1,2)$^6$,3-benzoxathiazin-3(4H)-yl)methyl]-4-methylphenyl}-3-[1-(6-hydroxyhexyl)-4-methyl-1H-benzotriazol-5-yl]propanoate Using General Procedure 8 starting from ethyl 3-(3-{[6-(benzyloxy)-2,2-dioxo-2H-1,2λ$^6$,3-benzoxathiazin-3(4H)-yl]methyl}-4-methylphenyl)-3-{1-[6-(benzyloxy)hexyl]-4-methyl-1H-benzotriazol-5-yl}propanoate (1 eq.) as a reactant, the title compound (95% yield) was obtained.

$^1$H-NMR (400 MHz, DMSO-d6) δ ppm: 9.68 (m, 1H), 7.61 (d, 1H), 7.5 (d, 1H), 7.21 (d, 1H), 7.19 (dd, 1H), 7.13 (d, 1H), 6.99 (d, 1H), 6.79 (dd, 1H), 6.6 (d, 1H), 4.84 (t, 1H), 4.63 (t, 2H), 4.38 (s, 2H), 4.29 (t, 1H), 4.2 (dd, 2H), 3.94 (q, 2H), 3.32 (m, 2H), 3.17 (m, 2H), 2.75 (s, 3H), 2.22 (s, 3H), 1.87 (m, 2H), 1.38-1.15 (m, 6H), 0.99 (t, 3H)

Step 4: Preparation of ethyl 3-[1-(6-bromohexyl)-4-methyl-1H-benzotriazol-5-yl]-3-{3-[(6-hydroxy-2,2-dioxo-2H-1,2λ$^6$,3-benzoxathiazin-3(4H)-yl)methyl]-4-methylphenyl}propanoate Using General Procedure 9 starting from ethyl 3-{3-[(6-hydroxy-2,2-dioxo-2H-1,2)$^6$,3-benzoxathiazin-3(4H)-yl)methyl]-4-methylphenyl}-3-[1-(6-hydroxyhexyl)-4-methyl-1H-benzotriazol-5-yl]propanoate (1 eq.) as a reactant, the title compound (87% yield) was obtained.

$^1$H-NMR (400 MHz, DMSO-d6) δ ppm: 9.68 (m, 1H), 7.61 (d, 1H), 7.5 (d, 1H), 7.21 (d, 1H), 7.2 (dd, 1H), 7.13 (d, 1H), 6.99 (d, 1H), 6.78 (dd, 1H), 6.6 (d, 1H), 4.84 (t, 1H), 4.63 (t, 2H), 4.38 (s, 2H), 4.19 (dd, 2H), 3.94 (q, 2H), 3.46 (t, 2H), 3.16 (dd, 2H), 2.75 (s, 3H), 2.22 (s, 3H), 1.88 (m, 2H), 1.74 (m, 2H), 1.39 (m, 2H), 1.24 (m, 2H), 1 (t, 3H)

Step 5: Preparation of ethyl[4,33-dimethyl-29,29-dioxo-23,28-dioxa-29λ$^6$-thia-1,14,15,16-tetraazahexacyclo[22.5.3.1$^{3,7}$0.1$^{9,13}$0.0$^{12,16}$0.0$^{27,31}$]tetratriaconta-3(34),4,6,9(33),10,12,14,24,26,31-decaen-8-yl]acetate Using General Procedure 11 starting from ethyl 3-[1-(6-bromohexyl)-4-methyl-1H-benzotriazol-5-yl]-3-{3-[(6-hydroxy-2,2-dioxo-2H-1,2λ$^6$,3-benzoxathiazin-3(4H)-yl)methyl]-4-methylphenyl}propanoate (1 eq.) as a reactant, the title compound (88% yield) was obtained.

$^1$H-NMR (400 MHz, DMSO-d6) δ ppm: 7.64 (d, 1H), 7.46 (d, 1H), 7.4 (dd, 1H), 7.21 (d, 1H), 7.15 (d, 1H), 7.07 (d, 1H), 6.9 (dd, 1H), 6.45 (d, 1H), 4.81 (t, 1H), 4.48 (t, 2H), 4.4/4.11 (dd, 2H), 4.23/4.03 (dd, 2H), 3.89 (q, 2H), 3.8 (m, 2H), 3.07 (d, 2H), 2.74 (s, 3H), 2.31 (s, 3H), 1.97 (m, 2H), 1.7 (m, 2H), 1.53 (m, 2H), 1.32 (m, 2H), 0.99 (t, 3H)

Step 6: Preparation of Example 11

Using General Procedure 12 starting from ethyl[4,33-dimethyl-29,29-dioxo-23,28-dioxa-29λ$^6$-thia-1,14,15,16-tetraazahexacyclo[22.5.3.1$^{3,7}$0.1$^{9,13}$0.0$^{12,16}$0.0$^{27,31}$]tetratriaconta-3(34),4,6,9(33),10,12,14,24,26,31-decaen-8-yl]acetate (1 eq.) as a reactant, the title compound (white solid, 62% yield) was obtained.

The enantiopure products were obtained by chromatographic separation on chiral column.

EXAMPLE 11a (E1)

HRMS calculated for $C_{31}H_4O_6S$: 590.2199; $[M+H]^+$ found: 591.2274 (δ=0.4 ppm).

EXAMPLE 11b (E2)

HRMS calculated for $C_{31}H_4O_6S$: 590.2199; $[M+H]^+$ found: 591.2274 (δ=0.4 ppm).

$^1$H-NMR (400 MHz, DMSO-d6) δ ppm: 12.13 (m, 1H), 7.64 (d, 1H), 7.45 (d, 1H), 7.4 (dd, 1H), 7.21 (d, 1H), 7.13 (d, 1H), 7.07 (d, 1H), 6.9 (dd, 1H), 6.43 (d, 1H), 4.9 (t, 1H), 4.66 (t, 2H), 4.39/4.11 (dd, 2H), 4.23/4.04 (dd, 2H), 3.91-3.76 (m, 2H), 2.96 (m, 2H), 2.74 (s, 3H), 2.31 (s, 3H), 1.97 (m, 2H), 1.7 (m, 2H), 1.53 (m, 2H), 1.32 (m, 2H)

EXAMPLE 12: [31-Methyl-27,27-dioxo-5-(trifluoromethyl)-21,26-dioxa-27λ$^{6}$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid enantiomer 1

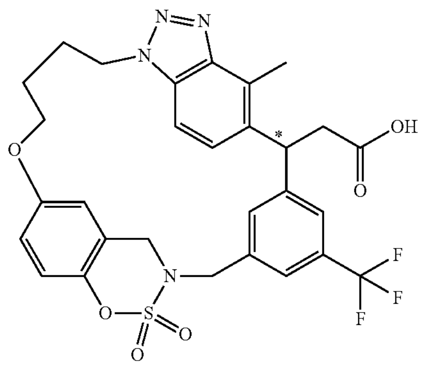

* = RorS enantiomer 2

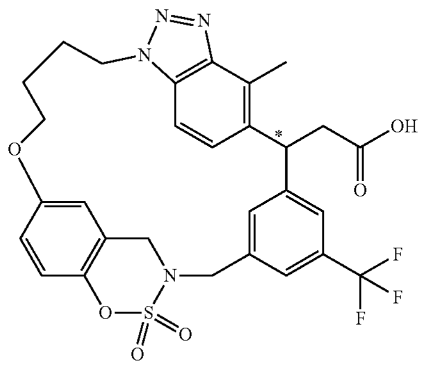

* = RorS

Step B1: Preparation of [3-(4,4,5,5-tetramethyl-1,3,2-dioxaborolan-2-yl)-5-(trifluoromethyl)phenyl]methanol Using General Procedure 3 starting from [3-bromo-5-(trifluoromethyl)phenyl]methanol (1 eq., 2.5 g, 9.8 mmol) as a reactant, the title compound (2.7 g, 91% yield) was obtained.

$^{1}$H-NMR (400 MHz, DMSO-d6) δ ppm: 7.9/7.87 (m, 3H), 5.4 (t, 1H), 4.6 (d, 2H), 1.3 (s, 12H)

Step 1: Preparation of ethyl 3-[3-{[6-(benzyloxy)-2,2-dioxo-2H-1,2λ$^{6}$,3-benzoxathiazin-3(4H)-yl]methyl}-5-(trifluoromethyl)phenyl]-3-(1-{4-[(4-methoxyphenyl)methoxy]butyl}-4-methyl-1H-benzotriazol-5-yl)propanoate Using General Procedure 6 starting from ethyl (2E)-3-(1-{4-[(4-methoxyphenyl)methoxy]butyl}-4-methyl-1H-benzotriazol-5-yl)prop-2-enoate (1 eq.) and [3-(4,4,5,5-tetramethyl-1,3,2-dioxaborolan-2-yl)-5-(trifluoromethyl)phenyl]methanol (1 eq.) as reactants, ethyl 3-[3-(hydroxymethyl)-5-(trifluoromethyl)phenyl]-3-(1-{4-[(4-methoxyphenyl)methoxy]butyl}-4-methyl-1H-benzotriazol-5-yl)propanoate (colorless oil, 16% yield) was obtained. The crude product was reacted using General Procedure 7 with 6-(benzyloxy)-3,4-dihydro-2H-1,2λ$^{6}$,3-benzoxathiazine-2,2-dione (1.1 eq.) affording the title compound (85% yield).

$^{1}$H-NMR (400 MHz, DMSO-d6) δ ppm: 7.68 (s, 1H), 7.61 (d, 1H), 7.6 (s, 1H), 7.52 (s, 1H), 7.5 (d, 1H), 7.42-7.3 (m, 5H), 7.19 (d, 2H), 7-6.9 (m, 3H), 6.88 (d, 2H), 5.05 (s, 2H), 4.95 (t, 1H), 4.7 (t, 2H), 4.62 (s, 2H), 4.42/4.3 (2s, 4H), 3.92 (q, 2H), 3.71 (s, 3H), 3.38 (t, 2H), 3.21 (d, 2H), 2.79 (s, 3H), 1.9 (m, 2H), 1.48 (m, 2H), 1 (t, 3H)

Step 2: Preparation of ethyl 3-[1-(4-hydroxybutyl)-4-methyl-1H-benzotriazol-5-yl]-3-{3-[(6-hydroxy-2,2-dioxo-2H-1,2λ$^{6}$,3-benzoxathiazin-3(4H)-yl)methyl]-5-(trifluoromethyl)phenyl}propanoate Using General Procedure 8 starting from ethyl 3-[3-{[6-(benzyloxy)-2,2-dioxo-2H-1,2λ$^{6}$,3-benzoxathiazin-3(4H)-yl]methyl}-5-(trifluoromethyl)phenyl]-3-(1-{4-[(4-methoxyphenyl) methoxy]butyl}-4-methyl-1H-benzotriazol-5-yl)propanoate (1 eq.) as a reactant, the title compound (white solid, 89% yield) was obtained.

$^{1}$H-NMR (400 MHz, DMSO-d6) δ ppm: 9.59 (s), 7.67 (s1, 1H), 7.65 (d, 1H), 7.61 (s1, 1H), 7.53 (s1, 1H), 7.52 (d, 1H), 6.8 (d, 1H), 6.68 (dd, 1H), 6.58 (d, 1H), 4.95 (t, 1H), 4.65 (t, 2 H), 4.63 (s, 2H), 4.41 (t), 4.4 (s, 2H), 3.95 (q, 2H), 3.38 (q, 2H), 3.23 (d, 2H), 2.78 (s, 3H), 1.91 (m, 2H), 1.37 (m, 2H), 1.01 (t, 3H)

Step 3: Preparation of ethyl 3-[1-(4-bromobutyl)-4-methyl-1H-benzotriazol-5-yl]-3-{3-[(6-hydroxy-2,2-dioxo-2H-1,2λ$^{6}$,3-benzoxathiazin-3(4H)-yl)methyl]-5-(trifluoromethyl)phenyl}propanoate Using General Procedure 9 starting from ethyl 3-[1-(4-hydroxybutyl)-4-methyl-1H-benzotriazol-5-yl]-3-{3-[(6-hydroxy-2,2-dioxo-2H-1,2λ$^{6}$,3-benzoxathiazin-3(4H)-yl)methyl]-5-(trifluoromethyl)phenyl}propanoate (1 eq.) as a reactant, the title compound (white solid, 50% yield) was obtained.

$^{1}$H-NMR (400 MHz, DMSO-d6) δ ppm: 9.6 (s, 1H), 7.69/7.6/7.52 (3s1, 3H), 7.69 (d, 1H), 7.55 (d, 1H), 6.8 (d, 1H), 6.7 (dd, 1H), 6.58 (d, 1H), 4.98 (t, 1H), 4.7 (t, 2H), 4.6 (s, 2H), 4.4 (s, 2H), 3.92 (q, 2H), 3.55 (t, 2H), 3.22 (d, 2H), 2.79 (s, 3H), 2 (m, 2H), 1.78 (m, 2H), 1.02 (t, 3H)

Step 4: Preparation of ethyl[31-methyl-27,27-dioxo-5-(trifluoromethyl)-21,26-dioxa-27λ$^{6}$-thia-1,14,15,16-tetraazahexacyclo[20.5.3.1$^{3,7}$0.1$^{9,13}$0.0$^{12,16}$0.0$^{25,}$$_{29}$]dotriaconta-3(32),4,6,9(31),10,12,14,22,24,29-decaen-8-yl]acetate Using General Procedure 11 starting from ethyl 3-[1-(4-bromobutyl)-4-methyl-1H-benzotriazol-5-yl]-3-{3-[(6-hydroxy-2,2-dioxo-2H-1,2λ$^{6}$,3-benzoxathiazin-3(4H)-yl)methyl]-5-(trifluoromethyl)phenyl}propanoate (1 eq.) as a reactant, the title compound (93% yield) was obtained.

$^{1}$H-NMR (400 MHz, DMSO-d6) δ ppm: 7.81/7.6/7.25 (3s, 3H), 7.71/4.81 (2m, 2H), 7.6 (d, 1H), 7.35 (d, 1H), 6.9 (d, 1H), 6.69 (dd, 1H), 6.02 (d, 1H), 4.81 (t, 1H), 4.28 (s, 2H), 4.05 (m, 2H), 3.95 (m, 2H), 3.88/3.68 (2m, 2H), 3.32/3.18 (2dd, 2H), 2.78 (s, 3H), 2.2/1.98 (2m, 2H), 1.68/1.45 (2m, 2H), 1 (t, 3H)

Step 5: Preparation of Example 12

Using General Procedure 12 starting from ethyl[31-methyl-27,27-dioxo-5-(trifluoromethyl)-21,26-dioxa-27λ$^{6}$- thia-1,14,15,16-tetraazahexacyclo[20.5.3.$1^{3,7}$0.$1^{9,13}$0.$0^{12,16}$0.$0^{25,29}$]dotriaconta-3(32),4,6,9(31),10,12,14,22,24,29-decaen-8-yl]acetate (1 eq.) as a reactant, the title compound (white solid, quant.) was obtained.

The enantiopure products were obtained by chromatographic separation on chiral column.

EXAMPLE 12a (E1)

HRMS calculated for $C_{29}H_{27}F_3N_4O_6S$: 616.1603; $[M+H]^+$ found: 617.1677 (δ=0.1 ppm).

EXAMPLE 12b (E2)

HRMS calculated for $C_{29}H_{27}F_3N_4O_6S$: 616.1603; $[M+H]^+$ found: 617.1678 (δ=0.3 ppm).

$^1$H-NMR (400 MHz, DMSO-d6) δ ppm: 12.3 (m, 1H), 7.84/7.58/7.23 (3s, 3H), 7.6 (d, 1H), 7.33 (d, 1H), 6.89 (d, 1H), 6.68 (dd, 1H), 6.02 (d, 1H), 4.89 (t, 1H), 4.81/4.72 (2m, 2H), 4.27 (s, 2H), 4.06 (m, 2H), 3.68/3.34 (2m, 2H), 3.32/3.18 (2dd, 2H), 2.78 (s, 3H), 2.2/1.98 (2m, 2H), 1.69/1.45 (2m, 2H)

EXAMPLE 13: [(2R,8R)-2,4,32-Trimethyl-28,28-dioxo-19,22,27-trioxa-28λ$^6$-thia-1,14,15,16-tetraazahexacyclo[21.5.3.$1^{3,7}$0.$1^{9,13}$0.$0^{12,16}$0.$0^{26,30}$]tritriaconta-3(33),4,6,9(32),10,12,14,23,25,30-decaen-8-yl]acetic acid and [(2R,8S)-2,4,32-trimethyl-28,28-dioxo-19,22,27-trioxa-28λ$^6$-thia-1,14,15,16-tetraazahexacyclo[21.5.3.$1^{3,7}$0.$1^{9,13}$0.$0^{12,16}$0.$0^{26,30}$]tritriaconta-3(33),4,6,9(32),10,12,14,23,25,30-decaen-8-yl]acetic acid

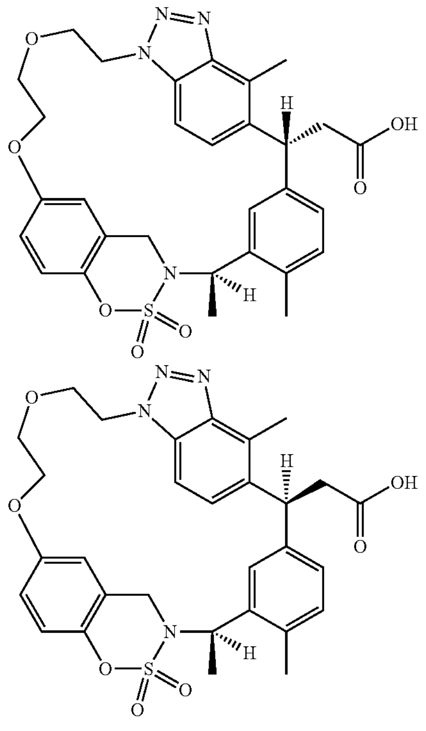

Step A1: Preparation of 2-[2-(3-methyl-2-nitroanilino)ethoxy]ethan-1-ol

Using General Procedure 1 STEP 1 starting from 1-fluoro-3-methyl-2-nitrobenzene (1 eq.) and 2-(2-aminoethoxy)ethan-1-ol (3 eq.) as reactants, the title compound (24% yield) was obtained.

$^1$H-NMR (400 MHz, DMSO-d6) δ ppm: 7.28 (t, 1H), 6.83 (d, 1H), 6.58 (d, 1H), 6.43 (t, 1H), 4.59 (t, 1H), 3.6 (t, 2H), 3.5 (m, 2H), 3.45 (m, 2H), 3.34 (q, 2H), 2.31 (s, 3H)

Step A2: Preparation of 2-[2-(4-bromo-3-methyl-2-nitroanilino)ethoxy]ethan-1-ol

Using General Procedure 1 STEP 2 starting from 2-[2-(3-methyl-2-nitroanilino)ethoxy]ethan-1-ol (1 eq.) as a reactant, the title compound (67% yield) was obtained.

$^1$H-NMR (400 MHz, DMSO-d6) δ ppm: 7.53 (d, 1H), 6.8 (d, 1H), 6.1 (t), 4.56 (t), 3.56 (t, 2H), 3.5 (q, 2H), 3.44 (t, 2H), 3.3 (q, 2H), 2.28 (s, 3H)

Step A3: Preparation of 2-[2-(2-amino-4-bromo-3-methylanilino)ethoxy]ethan-1-ol

Using General Procedure 1 STEP 3 starting from 2-[2-(4-bromo-3-methyl-2-nitroanilino)ethoxy]ethan-1-ol (1 eq.) as a reactant, the title compound (80% yield) was obtained.

$^1$H-NMR (400 MHz, DMSO-d6) δ ppm: 6.72 (d, 1H), 6.3 (d, 1H), 4.64-4.52 (m, 4H), 3.6 (t, 2H), 3.51 (m, 2H), 3.46 (m, 2H), 3.17 (m, 2H), 2.16 (s, 3H)

Step A4: Preparation of 2-[2-(5-bromo-4-methyl-1H-benzotriazol-1-yl)ethoxy]ethan-1-ol Using General Procedure 1 STEP 4 starting from 2-[2-(2-amino-4-bromo-3-methylanilino)ethoxy]ethan-1-ol (1 eq.) as a reactant, the title compound (yellow solid, 45% yield) was obtained.

$^1$H-NMR (400 MHz, DMSO-d6) δ ppm: 7.69 (d, 2H), 4.87 (t, 2H), 4.52 (m, 1H), 3.9 (t, 2H), 3.4-3.36 (m, 4H), 2.72 (s, 3H)

Step A5: Preparation of 1-{2-[2-(benzyloxy)ethoxy]ethyl}-5-bromo-4-methyl-1H-benzotriazole To a solution of 2-[2-(5-bromo-4-methyl-1H-benzotriazol-1-yl)ethoxy]ethan-1-ol (1 eq., 4.1 g, 13 mmol) in DMF (7 mL/mmol, 92 mL) NaH (1.2 eq., 630 mg, 16 mmol, 60 wt % in mineral oil) was added at 0° C. The mixture was allowed to warm to RT and stirred at this temperature for 30 min. The reaction mixture was cooled to 0° C. Benzylbromide (1.2 eq., 2.7 g, 1.9 mL, 16 mmol) was added and the stirring was continued overnight at RT. The mixture was quenched with 500 mL water, extracted with 4×1000 ml EtOAc and the organic layer was washed with brine, dried over anhydrous $Na_2SO_4$, filtered and concentrated to dryness to give a black oil, which was purified by normal phase silica gel chromatography using heptane-EtOAc (20:80) as an eluent to give the title compound (3.65 g, 71% yield).

$^1$H-NMR (400 MHz, DMSO-d6) δ ppm: 7.69/7.6 (dd, 2H), 7.33-7.23 (m, 3H), 7.16 (m, 2H), 4.88 (t, 2H), 4.31 (s, 2H), 3.91 (t, 2H), 3.53/3.43 (2m, 4H), 2.7 (s, 3H)

Step A6: Preparation of ethyl (2E)-3-(1-{2-[2-(benzyloxy)ethoxy]ethyl}-4-methyl-1H-benzotriazol-5-yl)prop-2-enoate Using General Procedure 1 STEP 7 starting from 1-{2-[2-(benzyloxy)ethoxy]ethyl}-5-bromo-4-methyl-1H-benzotriazole (1 eq., 3.65 g, 9.35 mmol) as a reactant, the title compound (1.7 g, 28% yield) was obtained.

$^1$H-NMR (400 MHz, DMSO-d6) δ ppm: 8 (d, 1H), 7.87 (d, 1H), 7.72 (d, 1H), 7.32-7.15 (m, 5H), 6.6 (d, 1H), 4.88 (t, 2H), 4.32 (s, 2H), 4.23 (q, 2H), 3.92 (t, 2H), 3.54/3.45 (2m, 4H), 2.79 (s, 3H), 1.29 (t, 3H)

Step 1: Preparation of ethyl 3-(1-{2-[2-(benzyloxy)ethoxy]ethyl}-4-methyl-1H-benzotriazol-5-yl)-3-{3-[(1S)-1-hydroxyethyl]-4-methylphenyl}propanoate Using General Procedure 6 starting from ethyl (2E)-3-(1-{2-[2-(benzyloxy)ethoxy]ethyl}-4-methyl-1H-benzotriazol-5-yl)prop-2-enoate (1 eq.) and (1S)-1-[2-methyl-5-(4,4,5,5-tetramethyl-1,3,2-dioxaborolan-2-yl)phenyl]ethan-1-ol (2 eq.) as reactants, the title compound (44% yield) was obtained.

$^1$H-NMR (400 MHz, DMSO-d6) δ ppm: 7.61 (d, 1H), 7.41 (d, 1H), 7.4 (s1, 1H), 7.32-7.18 (m, 5H), 7.02 (dd, 1H), 6.97 (d, 1H), 4.98/4.97 (2d, 1H), 4.85-4.78 (m, 4H), 4.33/4.32 (2s, 2H), 3.92 (q, 2H), 3.89 (m, 2H), 3.53/3.43 (2m, 4H), 3.16-3.01 (m, 2H), 2.75 (2s, 3H), 2.18 (2s, 3H), 1.22/1.2 (2d, 3H), 1 (t, 3H)

Step 2: Preparation of ethyl 3-(3-{(1R)-1-[6-(benzyloxy)-2,2-dioxo-2H-1,2λ$^6$,3-benzoxathiazin-3(4H)-yl]ethyl}-4-methylphenyl)-3-(1-{2-[2-(benzyloxy)ethoxy]ethyl}-4-methyl-1H-benzotriazol-5-yl)propanoate Using General Procedure 7 starting from ethyl 3-(1-{2-[2-(benzyloxy)ethoxy]ethyl}-4-methyl-1H-benzotriazol-5-yl)-3-{3-[(1S)-1-hydroxyethyl]-4-methylphenyl}propanoate (1 eq.) and 6-(benzyloxy)-3,4-dihydro-2H-1,2λ$^6$,3-benzoxathiazine-2,2-dione (1.5 eq.) as reactants, the title compound (79% yield) was obtained.

$^1$H-NMR (400 MHz, DMSO-d6) δ ppm: 7.62 (d, 1H), 7.5 (d, 1H), 7.48-7 (m, 13H), 7.1-6.96 (m, 2H), 6.89/6.83 (2d, 1H), 5.26 (m, 1H), 5.08 (m, 2H), 4.86 (m, 1H), 4.78 (m, 2H), 4.41 (s, 2H), 4.28 (s, 2H), 3.91 (q, 2H), 3.88 (m, 2H), 3.49/3.39 (2m, 4H), 3.18 (m, 2H), 2.76 (s, 3H), 2.27 (s, 3H), 1.4 (d, 3H), 0.98 (t, 3H)

Step 3: Preparation of ethyl 3-{3-[(1R)-1-(6-hydroxy-2,2-dioxo-2H-1,2)$^6$,3-benzoxathiazin-3(4H)-yl)ethyl]-4-methylphenyl}-3-{1-[2-(2-hydroxyethoxy)ethyl]-4-methyl-1H-benzotriazol-5-yl}propanoate Using General Procedure 8 starting from ethyl 3-(3-{(1R)-1-[6-(benzyloxy)-2,2-dioxo-2H-1,2λ$^6$,3-benzoxathiazin-3(4H)-yl]ethyl}-4-methylphenyl)-3-(1-{12-[2-(benzyloxy)ethoxy]ethyl}-4-methyl-1H-benzotriazol-5-yl)propanoate (1 eq.) as a reactant, the title compound (white solid, 94% yield) was obtained.

$^1$H-NMR (400 MHz, DMSO-d6) δ ppm: 9.63 (m, 1H), 7.65-7.53 (2dd, 2H), 7.47 (m, 1H), 7.14-7.08 (m, 2H), 6.91 (2, 1H), 6.76-6.7 (m, 1H), 6.6/6.56 (2d, 1H), 5.26 (q, 1H), 4.88 (q, 1H), 4.8 (t, 2H), 4.37/4.31 (s+dd, 2H), 3.95 (2q, 2H), 3.89 (m, 2H), 3.48-3.27 (m, 4H), 3.22 (2d, 2H), 2.77 (s, 3H), 2.28 (s, 3H), 1.43/1.41 (2d, 3H), 1.02/1 (2t, 3H)

Step 4: Preparation of ethyl 3-{1-[2-(2-bromoethoxy)ethyl]-4-methyl-1H-benzotriazol-5-yl}-3-{3-[(1R)-1-(6-hydroxy-2,2-dioxo-2H-1,2λ$^6$,3-benzoxathiazin-3(4H)-yl)ethyl]-4-methylphenyl}propanoate Using General Procedure 9 starting from ethyl 3-{3-[(1R)-1-(6-hydroxy-2,2-dioxo-2H-1,2λ$^6$,3-benzoxathiazin-3(4H)-yl)ethyl]-4-methylphenyl}-3-{11-[2-(2-hydroxyethoxy)ethyl]-4-methyl-1H-benzotriazol-5-yl}propanoate (1 eq.) as a reactant, the title compound (71% yield) was obtained.

$^1$H-NMR (400 MHz, DMSO-d6) δ ppm: 9.64 (m, 1H), 7.67-7.55 (2dd, 2H), 7.47 (m, 1H), 7.14-7.08 (m, 2H), 6.91 (m, 1H), 6.76-6.7 (m, 1H), 6.6/6.56 (2d, 1H), 5.26 (q, 1H), 4.88 (q, 1H), 4.83 (t, 2H), 4.36/4.31 (s+dd, 2H), 3.95 (2q, 2H), 3.93 (m, 2H), 3.66 (m, 2H), 3.44 (t, 2H), 3.3/3.22 (2d, 2H), 2.77 (s, 3H), 2.28 (s, 3H), 1.43/1.41 (2d, 3H), 1.02/1 (2t, 3H)

Step 5: Preparation of ethyl[(2R)-2,4,32-trimethyl-28,28-dioxo-19,22,27-trioxa-28λ$^6$-thia-1,14,15,16-tetraazahexacyclo[21.5.3.1$^{3,7}$0.1$^{9,13}$0.0$^{12,16}$0.0$^{26,30}$]tritriaconta-3(33),4,6,9(32),10,12,14,23,25,30-decaen-8-yl]acetate Using General Procedure 11 starting from ethyl 3-{1-[2-(2-bromoethoxy)ethyl]-4-methyl-1H-benzotriazol-5-yl}-3-{3-[(1R)-1-(6-hydroxy-2,2-dioxo-2H-1,2λ$^6$,3-benzoxathiazin-3(4H)-yl)ethyl]-4-methylphenyl}propanoate (1 eq.) as a reactant, the title compound (99% yield) was obtained.

$^1$H-NMR (400 MHz, DMSO-d6) δ ppm: 7.72/7.65 (2d, 1H), 7.52/6.91 (2s, 1H), 7.52/7.16 (2d, 1H), 7.45/7.09 (2d, 1H), 7.28/6.98 (2d, 1H), 6.93/6.88 (2d, 1H), 6.8/6.75 (2d, 1H), 6.36/5.99 (2s1, 1H), 5.4/5.26 (2m, 1H), 4.93/4.85 (2m, 1H), 4.83 (m, 2H), 4.71/4.17/3.81 (2m, 2H), 4.14-3.58 (m, 6H), 4.03/3.93 (2q, 2H), 3.23/2.96 (m+dd, 2H), 2.81/2.8 (2s, 3H), 2.33/2.29 (2s, 3H), 1.53/1.42 (s+s1, 3H), 1.17/1.02 (2m, 3H)

Step 6: Preparation of Example 13

Using General Procedure 12 starting from ethyl[(2R)-2,4,32-trimethyl-28,28-dioxo-19,22,27-trioxa-28λ$^6$-thia-1,14,15,16-tetraazahexacyclo[21.5.3.1$^{3,7}$0.1$^{9,13}$0.0$^{12,16}$0.0$^{26,30}$]tritriaconta-3(33),4,6,9(32),10,12,14,23,25,30-decaen-8-yl]acetate (1 eq.) as a reactant, the title compound (white solid, 59% yield) was obtained.

The diastereo-pure final products or final intermediates were obtained by chromatographic separation on chiral column.

EXAMPLE 13a (2R,8R)

HRMS calculated for $C_{30}H_{32}N_4O_7S$: 592.1992; $[M+H]^+$ found: 593.2072 (δ=1.3 ppm).

$^1$H-NMR (400 MHz, DMSO-d6) δ ppm: 13.6-11 (m, 1H), 7.64 (d, 1H), 7.48 (dd, 1H), 7.27 (d, 1H), 7.11 (d, 1H), 6.94 (d, 1H), 6.88 (s1, 1H), 6.8 (dd, 1H), 6.01 (d, 1H), 5.24 (q, 1H), 4.92 (t, 1H), 4.81 (t, 2H), 4.14/3.78 (dd, 2H), 4.1/4.04 (2m, 2H), 3.99-3.63 (m, 4H), 3.06/2.75 (2dd, 2H), 2.79 (s, 3H), 2.33 (s, 3H), 1.15 (d, 3H)

EXAMPLE 13b (2R,8S)

HRMS calculated for $C_{30}H_{32}N_4O_7S$: 592.1992; $[M+H]^+$ found: 593.2071 (δ=1.1 ppm).

$^1$H-NMR (400 MHz, DMSO-d6) δ ppm: 13.6-11 (m, 1H), 7.71 (d, 1H), 7.51 (d, 1H), 7.49 (d, 1H), 7.1 (dd, 1H), 6.99 (d, 1H), 6.89 (d, 1H), 6.76 (dd, 1H), 6.33 (d, 1H), 5.37 (q, 1H), 4.88-4.77 (m, 3H), 4.64/4.13 (dd, 2H), 3.96 (m, 2H), 3.96-3.58 (m, 4H), 3.08 (d, 2H), 2.79 (s, 3H), 2.28 (s, 3H), 1.49 (d, 3H)

Preparation of the Sodium Salt

The compound of Example 13b (2.03 g) and sodium hydroxide (0.14 g) were suspended in water (235 mL) at 25°

C. Tert-butanol (100 mL) was added to the suspension and the reaction mixture was heated at 60° C. for at least 1 hour (until complete dissolution). The solution was then cooled to −20° C. for fast solidification before the lyophilization step for 96 hours. After isolation from the lyophilization vessel, 2.10 g of the amorphous sodium salt of [(2R,8S)-2,4,32-trimethyl-28,28-dioxo-19,22,27-trioxa-28λ$^6$-thia-1,14,15,16-tetraazahexacyclo[21.5.3.1$^{3,7}$0.1$^{9,13}$0.0$^{12,16}$0.0$^{26,30}$]tritriaconta-3(33),4,6,9(32),10,12,14,23,25,30-decaen-8-yl] acetic acid (water content: 3.0%) were obtained.

IR: 2980 to 2860 $cm^{-1}$ ($CH_2$, $CH_3$), 1574 $cm^{-1}$ ($COO^-$ asym), 1492 $cm^{-1}$ (C═C), 1391 $cm^{-1}$ ($COO^-$ sym and $SO_2$ asym), 1200 to 1130 $cm^{-1}$ ($SO_2$ sym, ═C—O—C asym and C—O—C asym).

EXAMPLE 14: [4-Fluoro-31-methyl-27,27-dioxo-21,26-dioxa-27λ$^6$-thia-1,14,15,16-tetraazahexacyclo [20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid

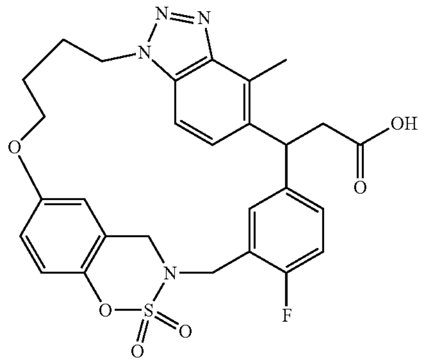 [SMILES: Cc1c2ccc3c1nnn3CCCCOc1ccc3c(c1)CN(Cc1cc(ccc1F)C2CC(=O)O)S(=O)(=O)O3]

Step 1: Preparation of ethyl 3-(3-{[6-(benzyloxy)-2,2-dioxo-2H-1,2λ$^6$,3-benzoxathiazin-3(4H)-yl] methyl}-4-fluorophenyl)-3-(1-{4-[(4-methoxyphenyl)methoxy]butyl}-4-methyl-1H-benzotriazol-5-yl) propanoate Using General Procedure 6 starting from ethyl (E)-3-[1-[4-[(4-methoxyphenyl)methoxy]butyl]-4-methyl-benzotriazol-5-yl]prop-2-enoate (1 eq.) and [2-fluoro-5-(4,4,5,5-tetramethyl-1,3,2-dioxaborolan-2-yl)phenyl]methanol (1 eq.) as reactants, ethyl 3-[4-fluoro-3-(hydroxymethyl)phenyl]-3-(1-{4-[(4-methoxyphenyl)methoxy]butyl}-4-methyl-1H-benzotriazol-5-yl)propanoate (17% yield) was obtained. The crude product was reacted using General Procedure 7 with 6-(benzyloxy)-3,4-dihydro-2H-1,2λ$^6$,3-benzoxathiazine-2,2-dione (1.1 eq.) resulting the title compound (85% yield).

$^1$H-NMR (400 MHz, DMSO-d6) δ ppm. 7.6 (d, 1H), 7.5-7.35 (m, 5H), 7.49 (d, 1H), 7.35/7.3 (m, 2H), 7.2 (d, 2H), 7.08 (t, 1H), 7-6.95 (m, 3H), 6.88 (d, 2H), 5.08 (s, 2H), 4.88 (t, 1H), 4.65 (t, 2H), 4.58 (s, 2H), 4.31 (2s, 4H), 3.92 (q, 2H), 3.71 (s, 3H), 3.38 (t, 2H), 3.18 (d, 2H), 2.79 (s, 3H), 1.91 (m, 2H), 1.48 (m, 2H), 1 (t, 3H)

Step 2: Preparation of ethyl 3-{4-fluoro-3-[(6-hydroxy-2,2-dioxo-2H-1,2),6,3-benzoxathiazin-3(4H)-yl)methyl]phenyl}-3-[1-(4-hydroxybutyl)-4-methyl-1H-benzotriazol-5-yl]propanoate Using General Procedure 8 starting from ethyl 3-(3-{[6-(benzyloxy)-2,2-dioxo-2H-1,2λ$^6$,3-benzoxathiazin-3 (4H)-yl]methyl}-4-fluorophenyl)-3-(1-{4-[(4-methoxyphenyl) methoxy]butyl}-4-methyl-1H-benzotriazol-5-yl)propanoate (1 eq.) as a reactant, the title compound (white solid, 77% yield) was obtained.

$^1$H-NMR (400 MHz, DMSO-d6) δ ppm: 9.4/4.4 (s+t, 2H), 7.63 (d, 1H), 7.5 (d, 1H), 7.45 (dd, 1H), 7.3 (m, 1H), 7.1 (t, 1H), 6.88 (d, 1H), 6.71 (dd, 1H), 6.61 (d, 1H), 4.88 (t, 1H), 4.67 (t, 2H), 4.53 (s, 2H), 4.3 (s, 2H), 3.95 (q, 2H), 3.4 (q, 2H), 3.2 (d, 2H), 2.78 (s, 3H), 1.9 (m, 2H), 1.38 (m, 2H), 1.02 (t, 3H)

Step 3: Preparation of ethyl 3-[1-(4-bromobutyl)-4-methyl-1H-benzotriazol-5-yl]-3-{4-fluoro-3-[(6-hydroxy-2,2-dioxo-2H-1,2λ$^6$,3-benzoxathiazin-3 (4H)-yl)methyl]phenyl}propanoate Using General Procedure 9 starting from ethyl 3-{4-fluoro-3-[(6-hydroxy-2,2-dioxo-2H-1,2λ$^6$,3-benzoxathiazin-3(4H)-yl)methyl]phenyl}-3-[1-(4-hydroxybutyl)-4-methyl-1H-benzotriazol-5-yl]propanoate (1 eq.) as a reactant, the title compound (31% yield) was obtained.

$^1$H-NMR (400 MHz, DMSO-d6) δ ppm: 9.6 (s, 1H), 7.65 (d, 1H), 7.51 (d, 1H), 7.45 (dd, 1H), 7.3 (m, 1H), 7.1 (t, 1H), 6.88 (d, 1H), 6.71 (dd, 1H), 6.6 (d, 1H), 4.88 (t, 1H), 4.7 (t, 2H), 4.52 (s, 2H), 4.31 (s, 2H), 3.93 (q, 2H), 3.55 (t, 2H), 3.2 (d, 2H), 2.79 (s, 3H), 2 (m, 2H), 1.8 (m, 2H), 1 (t, 3H)

Step 4: Preparation of ethyl[4-fluoro-31-methyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate Using General Procedure 11 starting from ethyl 3-[1-(4-bromobutyl)-4-methyl-1H-benzotriazol-5-yl]-3-{4-fluoro-3-[(6-hydroxy-2,2-dioxo-2H-1,2λ$^6$,3-benzoxathiazin-3 (4H)-yl)methyl]phenyl}propanoate (1 eq.) as a reactant, the title compound (white solid, 75% yield) was obtained.

$^1$H-NMR (400 MHz, DMSO-d6) δ ppm: 7.7 (d, 1H), 7.61 (dd, 1H), 7.45 (d, 1H), 7.29 (t, 1H), 6.98 (d, 1H), 6.81 (dd, 1H), 6.78 (dd, 1H), 6.4 (d, 1H), 4.85-4.7 (m, 3H), 4.21/4.05 (2d, 2H), 4.02/3.92 (2d, 2H), 3.95 (q, 2H), 3.68/3.42 (2m, 2H), 3.2/3.1 (2dd, 2H), 2.65 (s, 3H), 2.2/2.02 (2m, 2H), 1.8/1.65 (2m, 2H), 1.01 (t, 3H)

Step 5: Preparation of Example 14

Using General Procedure 12 starting from ethyl[4-fluoro-31-methyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl] acetate (1 eq.) as a reactant, the title compound (white solid, 81% yield) was obtained.

HRMS calculated for $C_{28}H_{27}FN_4O_6S$: 566.1635; $[M+H]^+$ found: 567.1712 (δ=0.7 ppm).

$^1$H-NMR (400 MHz, DMSO-d6) δ ppm: 12.3 (m, 1H), 7.67 (d, 1H), 7.63 (m, 1H), 7.42 (d, 1H), 7.27 (t, 1H), 6.97 (d, 1H), 6.76 (m, 1H), 6.76 (m, 1H), 5.88 (d, 1H), 4.8 (t, 2H), 4.77 (m, 1H), 4.21/4.05 (dd, 2H), 4.06/3.92 (dd, 2H), 3.66/3.4 (2m, 2H), 3.06/2.95 (2dd, 2H), 2.65 (s, 3H), 2.21/2.05 (2m, 2H), 1.79/1.59 (2m, 2H)

EXAMPLE 15: [4,24,31-Trimethyl-27,27-dioxo-21,26-dioxa-27λ6-thia-1,14,15,16-tetraazahexacyclo[20.5.3.1^3,7 0.1^9,13 0.0^12,16 0.0^25,29]dotriaconta-3(32),4,6,9(31),10,12,14,22,24,29-decaen-8-yl]acetic acid enantiomer 1

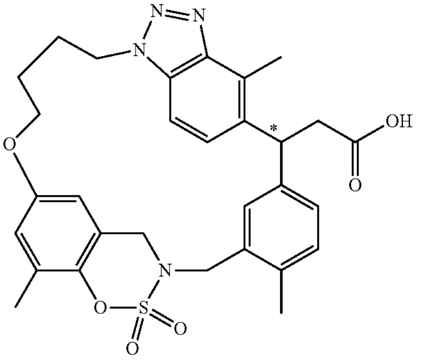

* = RorS enantiomer 2

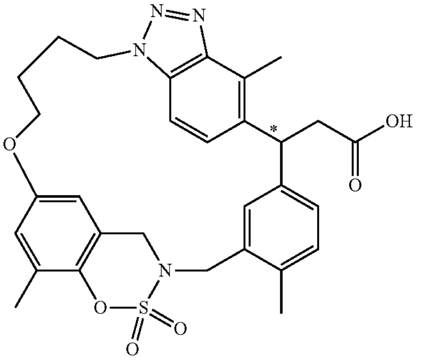

* = RorS

Step C1: Preparation of 6-bromo-8-methyl-2H-1,2)6,3-benzoxathiazine-2,2-dione

Using General Procedure 4 STEP 2 starting from 5-bromo-2-hydroxy-3-methylbenzaldehyde (1 eq., 3.65 g, 9.35 mmol) as a reactant, the title compound (2.85 g, 30% yield) was obtained.

$^1$H-NMR (400 MHz, DMSO-d6) δ ppm: 9.14 (s1, 1H), 8.09/8.05 (d1+dd, 2H), 2.33 (s, 3H)

Step C2: Preparation of 6-bromo-8-methyl-3,4-dihydro-2H-1,2λ$^6$,3-benzoxathiazine-2,2-dione Using General Procedure 4 STEP 3 starting from 6-bromo-8-methyl-2H-1,2λ$^6$,3-benzoxathiazine-2,2-dione (1 eq., 4.52 g, 16.37 mmol) as a reactant, the title compound (4.64 g, 99% yield) was obtained.

$^1$H-NMR (400 MHz, DMSO-d6) δ ppm: 8.59 (t, 1H), 7.5/7.38 (2d, 2H), 4.55 (s1, 2H), 2.2 (s, 3H)

Step C3: Preparation of tert-butyl 6-bromo-8-methyl-2,2-dioxo-2H-1,2λ$^6$,3-benzoxathiazine-3(4H)-carboxylate Using General Procedure 5 STEP 1 starting from 6-bromo-8-methyl-3,4-dihydro-2H-1,2λ$^6$,3-benzoxathiazine-2,2-dione (1 eq., 4.6 g, 16.539 mmol) as a reactant, the title compound (6.2 g, 99% yield) was obtained.

$^1$H-NMR (400 MHz, DMSO-d6) δ ppm: 7.7/7.64 (2d, 2H), 5.04 (s, 2H), 2.27 (s, 3H), 1.48 (s, 9H)

Step C4: Preparation of tert-butyl 8-methyl-2,2-dioxo-6-(4,4,5,5-tetramethyl-1,3,2-dioxaborolan-2-yl)-2H-1,2λ$^6$,3-benzoxathiazine-3(4H)-carboxylate Using General Procedure 5 STEP 2 starting from tert-butyl 6-bromo-8-methyl-2,2-dioxo-2H-1,2λ$^6$,3-benzoxathiazine-3(4H)-carboxylate (1 eq., 6.2 g, 16.39 mmol) as a reactant, the title compound (4.9 g, 70% yield) was obtained.

$^1$H-NMR (400 MHz, DMSO-d6) δ ppm: 7.69/7.65 (2s1, 2H), 5.06 (s, 2H), 2.29 (s, 3H), 1.48 (s, 9H), 1.3 (s, 12H)

Step C5: Preparation of tert-butyl 6-hydroxy-8-methyl-2,2-dioxo-2H-1,2λ$^6$,3-benzoxathiazine-3(4H)-carboxylate Using General Procedure 5 STEP 3 starting from tert-butyl 8-methyl-2,2-dioxo-6-(4,4,5,5-tetramethyl-1,3,2-dioxaborolan-2-yl)-2H-1,2λ$^6$,3-benzoxathiazine-3(4H)-carboxylate (1 eq., 4.9 g, 11.52 mmol) as a reactant, the title compound (3.9 g, 97% yield) was obtained.

$^1$H-NMR (400 MHz, DMSO-d6) δ ppm: 9.81 (m, 1H), 6.74/6.7 (2d, 2H), 4.9 (s, 2H), 2.19 (s, 3H), 1.48 (s, 9H)

Step C6: Preparation of tert-butyl 6-(benzyloxy)-8-methyl-2,2-dioxo-2H-1,2λ$^6$,3-benzoxathiazine-3(4H)-carboxylate Using General Procedure 5 STEP 4 starting from tert-butyl 6-hydroxy-8-methyl-2,2-dioxo-2H-1,2λ$^6$,3-benzoxathiazine-3(4H)-carboxylate (1 eq., 2.9 g, 9.19 mmol) as a reactant, the title compound (5 g, quant.) was obtained.

$^1$H-NMR (400 MHz, DMSO-d6) δ ppm: 7.46-7.29 (m, 5H), 7.12/7.03 (2d, 2H), 5.1 (s, 2H), 4.97 (s, 2H), 2.26 (s, 3H), 1.48 (s, 9H)

Step C7 Preparation of 6-(benzyloxy)-8-methyl-3,4-dihydro-2H-1,2λ$^6$,3-benzoxathiazine-2,2-dione Using General Procedure 5 STEP 5 starting from tert-butyl 6-(benzyloxy)-8-methyl-2,2-dioxo-2H-1,2λ$^6$,3-benzoxathiazine-3(4H)-carboxylate (1 eq., 5.0 g, 12.33 mmol) as a reactant, the title compound (1.85 g, 65% yield) was obtained.

$^1$H-NMR (400 MHz, DMSO-d6) δ ppm: 8.37 (m, 1H), 7.46-7.3 (m, 5H), 6.92/6.79 (2d, 2H), 5.06 (s, 2H), 4.47 (s, 2H), 2.16 (s, 3H)

Step 1: Preparation of ethyl 3-[3-(hydroxymethyl)-4-methylphenyl]-3-(1-{4-[(4-methoxyphenyl)methoxy]butyl}-4-methyl-1H-benzotriazol-5-yl)propanoate Using General Procedure 6 starting from ethyl (E)-3-[1-[4-[(4-methoxyphenyl)methoxy]butyl]-4-methyl-benzotriazol-5-yl]prop-2-enoate (1 eq.) and [2-methyl-5-(4,4,5,5-tetramethyl-1,3,2-dioxaborolan-2-yl)phenyl]methanol (2 eq.) as reactants, the title compound (43% yield) was obtained.

$^1$H-NMR (400 MHz, DMSO-d6) δ ppm: 7.58 (d, 1H), 7.45 (d, 1H), 7.28 (d, 1H), 7.2 (d, 2H), 7.1 (dd, 1H), 7.01 (d, 1H), 6.88 (d, 2H), 4.98 (t, 1H), 4.82 (t, 1H), 4.65 (t, 2H), 4.4

(d, 2H), 4.3 (s, 2H), 3.91 (q, 2H), 3.71 (s, 3H), 3.4 (t, 2H), 3.11 (dd, 2H), 2.75 (s, 3H), 2.15 (s, 3H), 1.91 (m, 2H), 1.48 (m, 2H), 1 (t, 3H)

Step 2: Preparation of ethyl 3-(3-{[6-(benzyloxy)-8-methyl-2,2-dioxo-2H-1,2$\lambda^6$,3-benzoxathiazin-3(4H)-yl]methyl}-4-methylphenyl)-3-(1-{4-[(4-methoxyphenyl)methoxy]butyl}-4-methyl-1H-benzotriazol-5-yl)propanoate Using General Procedure 7 starting from ethyl 3-[3-(hydroxymethyl)-4-methylphenyl]-3-(1-{4-[(4-methoxyphenyl)methoxy]butyl}-4-methyl-1H-benzotriazol-5-yl) propanoate (1 eq.) and 6-(benzyloxy)-8-methyl-3,4-dihydro-2H-1,2$\lambda^6$,3-benzoxathiazine-2,2-dione (1.5 eq.) as reactants, the title compound (88% yield) was obtained.

$^1$H-NMR (400 MHz, DMSO-d6) δ ppm: 7.56 (d, 1H), 7.47 (d, 1H), 7.46-7.31 (m, 5H), 7.46-7.12 (m, 3H), 7.19 (d, 2H), 7/6.75 (2d, 2H), 6.86 (d, 2H), 5.08 (s, 2H), 4.85 (t, 1H), 4.6 (t, 2H), 4.38 (s, 2H), 4.23 (s, 2H), 4.21 (s, 2H), 3.92 (q, 2H), 3.72 (s, 3H), 3.35 (t, 2H), 3.16 (m, 2H), 2.76 (s, 3H), 2.22/2.21 (2s, 6H), 1.89 (m, 2H), 1.44 (m, 2H), 0.97 (t, 3H)

Step 3: Preparation of ethyl 3-[1-(4-hydroxybutyl)-4-methyl-1H-benzotriazol-5-yl]-3-{3-[(6-hydroxy-8-methyl-2,2-dioxo-2H-1,2$\lambda^6$,3-benzoxathiazin-3(4H)-yl)methyl]-4-methylphenyl}propanoate Using General Procedure 8 starting from ethyl 3-(3-{[6-(benzyloxy)-8-methyl-2,2-dioxo-2H-1,2$\lambda^6$,3-benzoxathiazin-3(4H)-yl]methyl}-4-methylphenyl)-3-(1-{4-[(4-methoxyphenyl) methoxy]butyl}-4-methyl-1H-benzotriazol-5-yl)propanoate (1 eq.) as a reactant, the title compound (white solid, 97% yield) was obtained.

$^1$H-NMR (400 MHz, DMSO-d6) δ ppm: 9.55 (m, 1H), 7.61 (d, 1H), 7.49 (d, 1H), 7.22-7.11 (3m, 3H), 6.68/6.42 (2d, 2H), 4.84 (t, 1H), 4.65 (t, 2H), 4.34 (s, 2H), 4.19 (dd, 2H), 3.94 (q, 2H), 3.38 (t, 2H), 3.18/3.13 (2dd, 2H), 2.75 (s, 3H), 2.22/2.17 (2s, 6H), 1.9 (m, 2H), 1.36 (m, 2H), 1 (t, 3H)

Step 4: Preparation of ethyl 3-[1-(4-bromobutyl)-4-methyl-1H-benzotriazol-5-yl]-3-{3-[(6-hydroxy-8-methyl-2,2-dioxo-2H-1,2$\lambda^6$,3-benzoxathiazin-3(4H)-yl)methyl]-4-methylphenyl}propanoate Using General Procedure 9 starting from ethyl 3-[1-(4-hydroxybutyl)-4-methyl-1H-benzotriazol-5-yl]-3-{3-[(6-hydroxy-8-methyl-2,2-dioxo-2H-1,2$\lambda^6$,3-benzoxathiazin-3 (4H)-yl)methyl]-4-methylphenyl}propanoate (1 eq.) as a reactant, the title compound (78% yield) was obtained.

$^1$H-NMR (400 MHz, DMSO-d6) δ ppm: 9.55 (s, 1H), 7.65 (d, 1H), 7.5 (d, 1H), 7.2 (m, 2H), 7.11 (d, 1H), 6.7/6.41 (2d, 2H), 4.85 (t, 1H), 4.7 (t, 2H), 4.38 (s, 2H), 4.2 (m, 2H), 3.95 (q, 2H), 3.55 (t, 2H), 3.18 (m, 2H), 2.78 (s, 3H), 2.22/2.18 (2s, 6H), 1.98 (m, 2H), 1.78 (m, 2H), 1 (t, 3H)

Step 5: Preparation of ethyl[4,24,31-trimethyl-27,27-dioxo-21,26-dioxa-27$\lambda^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate Using General Procedure 11 starting from ethyl 3-[1-(4-bromobutyl)-4-methyl-1H-benzotriazol-5-yl]-3-{3-[(6-hydroxy-8-methyl-2,2-dioxo-2H-1,2$\lambda^6$,3-benzoxathiazin-3 (4H)-yl)methyl]-4-methylphenyl}propanoate (1 eq.) as a reactant, the title compound (quant.) was obtained.

$^1$H-NMR (400 MHz, DMSO-d6) δ ppm: 7.67 (d, 1H), 7.47 (dd, 1H), 7.43 (d, 1H), 7.43 (d, 1H), 6.71 (d, 1H), 6.55 (d, 1H), 5.67 (d, 1H), 4.84-4.7 (m, 3H), 4.13-3.79 (2dd, 4H), 3.92 (q, 2H), 3.63-3.43 (2m, 2H), 3.17/3.04 (2dd, 2H), 2.63 (s, 3H), 2.33 (s, 3H), 2.25-2 (m, 2H), 2.11 (s, 3H), 1.79/1.6 (2m, 2H), 1 (t, 3H)

Step 6: Preparation of Example 15

Using General Procedure 12 starting from ethyl[4,24,31-trimethyl-27,27-dioxo-21,26-dioxa-27$\lambda^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl] acetate (1 eq.) as a reactant, the title compound (white solid, 66% yield) was obtained.

The enantiopure products were obtained by chromatographic separation on chiral column.

EXAMPLE 15a (E1)

HRMS calculated for $C_{30}H_{32}N_4O_6S$: 576.2042; [M+H]$^+$ found: 577.2119 (δ=0.6 ppm).

EXAMPLE 15b (E2)

HRMS calculated for $C_{30}H_{32}N_4O_6S$: 576.2042; [M+H]$^+$ found: 577.2117 (δ=0.3 ppm).

$^1$H-NMR (400 MHz, DMSO-d6) δ ppm: 12.14 (m, 1H), 7.67 (d, 1H), 7.49 (dd, 1H), 7.42 (d, 1H), 7.29 (d, 1H), 6.71 (d, 1H), 6.53 (d, 1H), 5.66 (d, 1H), 4.84-4.7 (m, 3H), 4.13-3.79 (2dd, 4H), 3.63-3.43 (2m, 2H), 3.07/2.94 (2dd, 2H), 2.63 (s, 3H), 2.33 (s, 3H), 2.19/2.08 (2m, 2H), 2.11 (s, 3H), 1.8/1.6 (2m, 2H)

EXAMPLE 16: [24-Methoxy-4,31-dimethyl-27,27-dioxo-21,26-dioxa-27$\lambda^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid enantiomer 1

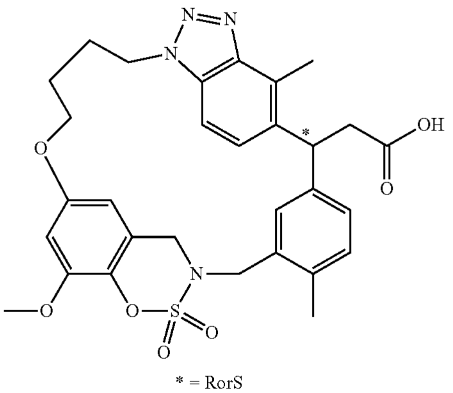

* = RorS

-continued enantiomer 2

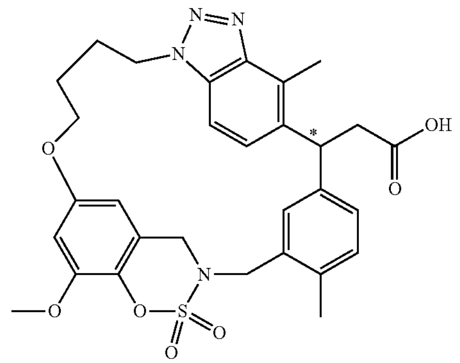

* = RorS

Step C1: Preparation of 6-bromo-8-methoxy-2H-1,2)6,3-benzoxathiazine-2,2-dione

Using General Procedure 4 STEP 2 starting from 5-bromo-2-hydroxy-3-methoxy-benzaldehyde (1 eq.) as a reactant, the title compound (32% yield) was obtained.

$^1$H-NMR (400 MHz, DMSO-d6) δ ppm: 9.14 (s, 1H), 7.83/7.79 (2d, 2H), 3.98 (s, 3H)

Step C2: Preparation of 6-bromo-8-methoxy-3,4-dihydro-2H-1,2)6,3-benzoxathiazine-2,2-dione Using General Procedure 4 STEP 3 starting from 6-bromo-8-methoxy-2H-1,2λ$^6$,3-benzoxathiazine-2,2-dione (1 eq.) as a reactant, the title compound (95% yield) was obtained.

$^1$H-NMR (400 MHz, DMSO-d6) δ ppm: 8.6 (s1, 1H), 7.26 (d, 1H), 7.1 (d, 1H), 4.55 (s, 2H), 3.85 (s, 3H)

Step C3: Preparation of tert-butyl 6-bromo-8-methoxy-2,2-dioxo-2H-1,2)6,3-benzoxathiazine-3(4H)-carboxylate Using General Procedure 5 STEP 1 starting from 6-bromo-8-methoxy-3,4-dihydro-2H-1,2λ$^6$,3-benzoxathiazine-2,2-dione (1 eq.) as a reactant, the title compound (88% yield) was obtained.

$^1$H-NMR (400 MHz, DMSO-d6) δ ppm: 7.48 (s, 1H), 7.4 (s, 1H), 5.05 (s, 2H), 3.9 (s, 3H), 1.5 (s, 9H)

Step C4: Preparation of tert-butyl 8-methoxy-2,2-dioxo-6-(4,4,5,5-tetramethyl-1,3,2-dioxaborolan-2-yl)-2H-1,2λ$^6$,3-benzoxathiazine-3(4H)-carboxylate Using General Procedure 5 STEP 2 starting from tert-butyl 6-bromo-8-methoxy-2,2-dioxo-2H-1,2λ$^6$,3-benzoxathiazine-3(4H)-carboxylate (1 eq.) as a reactant, the title compound (80% yield) was obtained.

$^1$H-NMR (400 MHz, DMSO-d6) δ ppm: 7.41 (d, 1H), 7.31 (d, 1H), 5.09 (s, 2H), 3.9 (s, 3H), 1.49 (s, 9H), 1.3 (s, 12H)

Step C5: Preparation of tert-butyl 6-hydroxy-8-methoxy-2,2-dioxo-2H-1,2λ$^6$,3-benzoxathiazine-3(4H)-carboxylate Using General Procedure 5 STEP 3 starting from tert-butyl 8-methoxy-2,2-dioxo-6-(4,4,5,5-tetramethyl-1,3,2-dioxaborolan-2-yl)-2H-1,2λ$^6$,3-benzoxathiazine-3(4H)-carboxylate (1 eq.) as a reactant, the title compound (81% yield) was obtained.

$^1$H-NMR (400 MHz, DMSO-d6) δ ppm: 9.92 (m, 1H), 6.52 (d, 1H), 6.43 (d, 1H), 4.9 (s, 2H), 3.8 (s, 3H), 1.48 (s, 9H)

Step C6: Preparation of tert-butyl 6-(benzyloxy)-8-methoxy-2,2-dioxo-2H-1,2λ$^6$,3-benzoxathiazine-3(4H)-carboxylate Using General Procedure 5 STEP 4 starting from tert-butyl 6-hydroxy-8-methoxy-2,2-dioxo-2H-1,2λ$^6$,3-benzoxathiazine-3(4H)-carboxylate (1 eq.) as a reactant, the title compound (74% yield) was obtained.

$^1$H-NMR (400 MHz, DMSO-d6) δ ppm: 7.5-7.28 (m, 5H), 6.83 (s1, 2H), 5.12 (s, 2H), 4.98 (s, 2H), 3.86 (s, 3H), 1.5 (s, 9H)

Step C7: Preparation of 6-(benzyloxy)-8-methoxy-3,4-dihydro-2H-1,2λ$^6$,3-benzoxathiazine-2,2-dione Using General Procedure 5 STEP 5 starting from tert-butyl 6-(benzyloxy)-8-methoxy-2,2-dioxo-2H-1,2λ$^6$,3-benzoxathiazine-3(4H)-carboxylate (1 eq.) as a reactant, the title compound (89% yield) was obtained.

$^1$H-NMR (400 MHz, DMSO-d6) δ ppm: 8.4 (s1, 1H), 7.48-7.3 (m, 5H), 6.71 (d, 1H), 6.5 (d, 1H), 5.08 (s, 2H), 4.49 (s, 2H), 3.8 (s, 3H)

Step 1: Preparation of ethyl 3-(3-{[6-(benzyloxy)-8-methoxy-2,2-dioxo-2H-1,2λ$^6$,3-benzoxathiazin-3(4H)-yl]methyl}-4-methylphenyl)-3-(1-{4-[(4-methoxyphenyl)methoxy]butyl}-4-methyl-1H-benzotriazol-5-yl)propanoate Using General Procedure 7 starting from ethyl 3-[3-(hydroxymethyl)-4-methylphenyl]-3-(1-{4-[(4-methoxyphenyl)methoxy]butyl}-4-methyl-1H-benzotriazol-5-yl) propanoate (1 eq.) and 6-(benzyloxy)-8-methoxy-3,4-dihydro-2H-1,2λ$^6$,3-benzoxathiazine-2,2-dione (1.2 eq.) as reactants, the title compound (yellow solid, 88% yield) was obtained.

$^1$H-NMR (400 MHz, DMSO-d6) δ ppm: 7.57 (d, 1H), 7.48 (d, 2H), 7.48 (d, 1H), 7.4 (t, 2H), 7.33 (t, 1H), 7.22-7.1 (m, 5H), 6.87 (d, 2H), 6.8 (d, 1H), 6.47 (d, 1H), 5.09 (s, 2H), 4.83 (t, 1H), 4.6 (t, 2H), 4.39 (s, 2H), 4.29 (s, 2H), 4.2 (s, 2H), 3.9 (q, 2H), 3.82 (s, 3H), 3.7 (s, 3H), 3.33 (t, 2H), 3.18 (m, 2H), 2.73 (s, 3H), 2.2 (s, 3H), 1.89 (m, 2H), 1.42 (m, 2H), 0.98 (t, 3H)

Step 2: Preparation of ethyl 3-[1-(4-hydroxybutyl)-4-methyl-1H-benzotriazol-5-yl]-3-{3-[(6-hydroxy-8-methoxy-2,2-dioxo-2H-1,2λ$^6$,3-benzoxathiazin-3(4H)-yl)methyl]-4-methylphenyl}propanoate Using General Procedure 8 starting from ethyl 3-(3-{[6-(benzyloxy)-8-methoxy-2,2-dioxo-2H-1,2λ$^6$,3-benzoxathiazin-3(4H)-yl]methyl}-4-methylphenyl)-3-(1-{4-[(4-methoxyphenyl) methoxy]butyl}-4-methyl-1H-benzotriazol-5-yl)propanoate (1 eq.) as a reactant, the title compound (white solid, 97% yield) was obtained.

$^1$H-NMR (400 MHz, DMSO-d6) δ ppm: 9.7/4.41 (s+t, 2H), 7.61 (d, 1H), 7.5 (d, 1H), 7.2 (d+dd, 2H), 7.15 (d, 1H), 6.52 (d, 1H), 6.15 (d, 1H), 4.85 (t, 1H), 4.68 (t, 2H), 4.35 (s, 2 H), 4.2 (m, 2H), 3.95 (q, 2H), 3.8 (s, 3H), 3.4 (q, 2H), 3.18 (m, 2H), 2.78 (s, 3H), 2.22 (s, 3H), 1.9 (m, 2H), 1.39 (m, 2H), 1 (t, 3H)

Step 3: Preparation of ethyl 3-[1-(4-bromobutyl)-4-methyl-1H-benzotriazol-5-yl]-3-{3-[(6-hydroxy-8-methoxy-2,2-dioxo-2H-1,2λ$^6$,3-benzoxathiazin-3(4H)-yl)methyl]-4-methylphenyl}propanoate Using General Procedure 9 starting from ethyl 3-[1-(4-hydroxybutyl)-4-methyl-1H-benzotriazol-5-yl]-3-{3-[(6-hydroxy-8-methoxy-2,2-dioxo-2H-1,2λ$^6$,3-benzoxathiazin-3(4H)-yl)methyl]-4-methylphenyl}propanoate (1 eq.) as a reactant, the title compound (yellow solid, 86% yield) was obtained.

$^1$H-NMR (400 MHz, DMSO-d6) δ ppm: 9.69 (s, 1H), 7.62 (d, 1H), 7.5 (d, 1H), 7.2 (d, 1H), 7.19 (dd, 1H), 7.11 (d, 1H), 6.5 (d, 1H), 6.11 (d, 1H), 4.82 (t, 1H), 4.68 (t, 2H), 4.32 (s, 2H), 4.19 (m, 2H), 3.91 (q, 2H), 3.79 (s, 3H), 3.51 (t, 2H), 3.18 (m, 2H), 2.73 (s, 3H), 2.2 (s, 3H), 1.99 (m, 2H), 1.78 (m, 2H), 1 (t, 3H)

Step 4: Preparation of ethyl[24-methoxy-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,}$$_{29}$]dotriaconta-3(32),4,6,9(31),10,12,14,22,24,29-decaen-8-yl]acetate Using General Procedure 11 starting from ethyl 3-[1-(4-bromobutyl)-4-methyl-1H-benzotriazol-5-yl]-3-{3-[(6-hydroxy-8-methoxy-2,2-dioxo-2H-1,2λ$^6$,3-benzoxathiazin-3(4H)-yl)methyl]-4-methylphenyl}propanoate (1 eq.) as a reactant, the title compound (white solid, 73% yield) was obtained.

The enantiopure final intermediates were obtained by chromatographic separation on chiral column.

$^1$H-NMR (400 MHz, DMSO-d6) δ ppm: 7.69 (d, 1H), 7.48 (dd, 1H), 7.42 (d, 1H), 7.29 (d, 1H), 6.57/6.51 (2d, 2H), 5.32 (d, 1H), 4.79 (m, 3H), 4.12/3.8 (2d, 2H), 3.91/3.8 (2d, 2H), 3.91 (q, 2H), 3.74 (s, 3H), 3.6/3.39 (m, 2H), 3.14/3.03 (m, 2H), 2.61 (s, 3H), 2.3 (s, 3H), 2.2/2.05 (m, 2H), 1.8/1.6 (m, 2H), 1 (t, 3H)

Step 5: Preparation of Example 16

Using General Procedure 12 starting from ethyl[24-methoxy-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,}$$_{16}$0.0$^{25,29}$]dotriaconta-3(32),4,6,9(31),10,12,14,22,24,29-decaen-8-yl]acetate E1 (1 eq.) or E2 (1 eq.) as reactants, the title compounds (85%-67% yields respectively) were obtained.

EXAMPLE 16a (E1)

HRMS calculated for $C_{30}H_{32}N_4O_7S$: 592.1992; [M+H]$^+$ found: 593.2070 (δ=0.9 ppm).

EXAMPLE 16b (E2)

HRMS calculated for $C_{30}H_{32}N_4O_7S$: 592.1992; [M+H]$^+$ found: [M+H]+=593.2073 (5=1.4 ppm).

$^1$H-NMR (400 MHz, DMSO-d6) δ ppm: 12.2 (m, 1H), 7.68 (d, 1H), 7.49 (dd, 1H), 7.41 (d, 1H), 7.29 (d, 1H), 5.31 (d, 1H), 4.75 (m, 3H), 4.11/3.92 (2d, 2H), 3.98/3.8 (2d, 2H), 3.73 (s, 3H), 3.59/3.33 (2m, 2H), 3.52/3.51 (2d, 2H), 3.05/2.92 (2dd, 2H), 2.6 (s, 3H), 2.3 (s, 3H), 2.19/2.07 (2m, 2H), 1.8/1.6 (2m, 2H)

EXAMPLE 17: [24-Fluoro-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid enantiomer

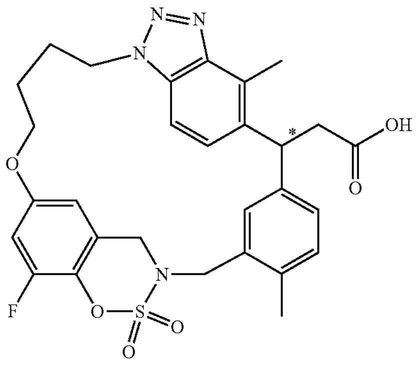

* = RorS enantiomer 2

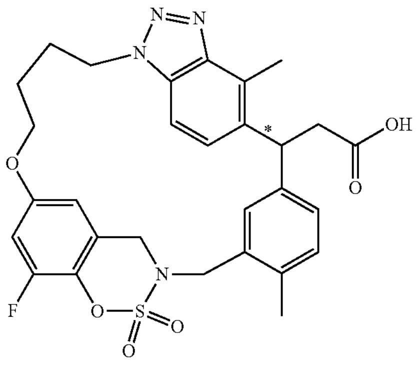

* = RorS

Step C1: Preparation of 6-bromo-8-fluoro-2H-1,2),6,3-benzoxathiazine-2,2-dione

Using General Procedure 4 STEP 2 starting from 5-bromo-3-fluoro-2-hydroxybenzaldehyde (1 eq.) as a reactant, the title compound (25% yield) was obtained.

$^1$H-NMR (400 MHz, DMSO-d6) δ ppm: 9.2 (s, 1H), 8.3 (dd, 1H), 8.1 (s, 1H)

Step C2: Preparation of 6-bromo-8-fluoro-3,4-dihydro-2H-1,2λ$^6$,3-benzoxathiazine-2,2-dione Using General Procedure 4 STEP 3 starting from 6-bromo-8-fluoro-2H-1,26,3-benzoxathiazine-2,2-dione (1 eq.) as a reactant, the title compound (87% yield) was obtained.

$^1$H-NMR (400 MHz, DMSO-d6) δ ppm: 8.91 (s1, 1H), 7.72 (dd, 1H), 7.41 (tf, 1H), 4.68 (s, 2H)

Step C3: Preparation of tert-butyl 6-bromo-8-fluoro-2,2-dioxo-2H-1,2λ$^6$,3-benzoxathiazine-3 (4H)-carboxylate Using General Procedure 5 STEP 1 starting from 6-bromo-8-fluoro-3,4-dihydro-2H-1,2λ$^6$,3-benzoxathiazine-2,2-dione (1 eq.) as a reactant, the title compound (85% yield) was obtained.

$^1$H-NMR (400 MHz, DMSO-d6) δ ppm: 7.88 (d, 1H), 7.74 (s, 1H), 5.18 (s, 2H), 1.5 (s, 9H)

Step C4: Preparation of tert-butyl 8-fluoro-2,2-dioxo-6-(4,4,5,5-tetramethyl-1,3,2-dioxaborolan-2-yl)-2H-1,2λ$^6$,3-benzoxathiazine-3(4H)-carboxylate Using General Procedure 5 STEP 2 starting from tert-butyl 6-bromo-8-fluoro-2,2-dioxo-2H-1,2λ$^6$,3-benzoxathiazine-3(4H)-carboxylate (1 eq.) as a reactant, the title compound (71% yield) was obtained.

$^1$H-NMR (400 MHz, DMSO-d6) δ ppm: 7.69 (s, 1H), 7.57 (d, 1H), 5.21 (s, 2H), 1.49 (s, 9H), 1.31 (s, 12H)

Step C5: Preparation of tert-butyl 8-fluoro-6-hydroxy-2,2-dioxo-2H-1,2λ$^6$,3-benzoxathiazine-3(4H)-carboxylate Using General Procedure 5 STEP 3 starting from tert-butyl 8-fluoro-2,2-dioxo-6-(4,4,5,5-tetramethyl-1,3,2-dioxaborolan-2-yl)-2H-1,2λ$^6$,3-benzoxathiazine-3(4H)-carboxylate (1 eq.) as a reactant, the title compound (81% yield) was obtained.

$^1$H-NMR (400 MHz, DMSO-d6) δ ppm: 10.4 (m, 1H), 6.79 (dd, 1H), 6.78 (d, 1H), 5.02 (s, 2H), 1.49 (s, 9H)

Step C6: Preparation of 6-(benzyloxy)-8-fluoro-3,4-dihydro-2H-1,2λ$^6$,3-benzoxathiazine-2,2-dione Using General Procedure 5 STEP 4 starting from tert-butyl 8-fluoro-6-hydroxy-2,2-dioxo-2H-1,2λ$^6$,3-benzoxathiazine-3(4H)-carboxylate (1 eq.) as a reactant, tert-butyl 6-(benzyloxy)-8-fluoro-2,2-dioxo-2H-1,2λ$^6$,3-benzoxathiazine-3(4H)-carboxylate (36% yield) was obtained.

The crude product was reacted using General Procedure 5 STEP 5 resulting the title compound (91% yield).

$^1$H-NMR (400 MHz, DMSO-d6) δ ppm: 8.7 (m, 1H), 7.48-7.3 (m, 5H), 7.1 (dd, 1H), 6.8 (d, 1H), 5.09 (s, 2H), 4.58 (s, 2H)

Step 1: Preparation of ethyl 3-(3-{[6-(benzyloxy)-8-fluoro-2,2-dioxo-2H-1,2λ$^6$,3-benzoxathiazin-3(4H)-yl]methyl}-4-methylphenyl)-3-(1-{4-[(4-methoxyphenyl)methoxy]butyl}-4-methyl-1H-benzotriazol-5-yl)propanoate Using General Procedure 7 starting from ethyl 3-[3-(hydroxymethyl)-4-methylphenyl]-3-(1-{4-[(4-methoxyphenyl)methoxy]butyl}-4-methyl-1H-benzotriazol-5-yl) propanoate (1 eq.) and 6-(benzyloxy)-8-fluoro-3,4-dihydro-2H-1,2λ$^6$,3-benzoxathiazine-2,2-dione (1 eq.) as reactants, the title compound (85% yield) was obtained.

$^1$H-NMR (400 MHz, DMSO-d6) δ ppm: 0.97 (t, J=7.09 Hz, 3H) 1.39-1.51 (m, 2H) 1.89 (quint, J=7.27 Hz, 2H) 1.99 (s, 2H) 2.22 (s, 3H) 2.76 (s, 3H) 3.16 (dd, J=8.07, 2.69 Hz, 2H) 3.35 (t, J=6.30 Hz, 2H) 3.72 (s, 3H) 3.92 (q, J=7.05 Hz, 2H) 4.24-4.32 (m, 4H) 4.49 (s, 2H) 4.60 (t, J=6.97 Hz, 2H) 4.84 (t, J=8.07 Hz, 1H) 5.11 (s, 2H) 6.79 (s, 1H) 6.82-6.89 (m, 2H) 7.10-7.22 (m, 5H) 7.24 (s, 1H) 7.32-7.50 (m, 6H) 7.53-7.59 (m, 1H)

Step 2: Preparation of ethyl 3-{3-[(8-fluoro-6-hydroxy-2,2-dioxo-2H-1,2)$^6$,3-benzoxathiazin-3(4H)-yl)methyl]-4-methylphenyl}-3-[1-(4-hydroxybutyl)-4-methyl-1H-benzotriazol-5-yl]propanoate Using General Procedure 8 starting from ethyl 3-(3-{[6-(benzyloxy)-8-fluoro-2,2-dioxo-2H-1,2λ$^6$,3-benzoxathiazin-3(4H)-yl]methyl}-4-methylphenyl)-3-(1-{4-[(4-methoxyphenyl) methoxy]butyl}-4-methyl-1H-benzotriazol-5-yl)propanoate (1 eq.) as a reactant, the title compound (white solid, 97% yield) was obtained.

$^1$H-NMR (400 MHz, DMSO-d6) δ ppm: 10.1/4.4 (s+t, 2H), 7.62 (d, 1H), 7.5 (d, 1H), 7.28 (d, 1H), 7.2 (dd, 1H), 7.15 (d, 1H), 6.78 (dd, 1H), 6.48 (d, 1H), 4.85 (t, 1H), 4.65 (t, 2H), 4.49 (s, 2H), 4.28 (m, 2H), 3.95 (q, 2H), 3.4 (q, 2H), 3.18 (d, 2H), 2.78 (s, 3H), 2.22 (s, 3H), 1.9 (m, 2H), 1.38 (m, 2H), 1 (t, 3H)

Step 3: Preparation of ethyl 3-[1-(4-bromobutyl)-4-methyl-1H-benzotriazol-5-yl]-3-{3-[(8-fluoro-6-hydroxy-2,2-dioxo-2H-1,2λ$^6$,3-benzoxathiazin-3 (4H)-yl)methyl]-4-methylphenyl}propanoate Using General Procedure 9 starting from ethyl 3-{3-[(8-fluoro-6-hydroxy-2,2-dioxo-2H-1,2)$^6$,3-benzoxathiazin-3 (4H)-yl)methyl]-4-methylphenyl}-3-[l-(4-hydroxybutyl)-4-methyl-1H-benzotriazol-5-yl]propanoate (1 eq.) as a reactant, the title compound (off-white solid, 65% yield) was obtained.

$^1$H-NMR (400 MHz, DMSO-d6) δ ppm: 10.1 (s, 1H), 7.62 (d, 1H), 7.5 (d, 1H), 7.22 (d, 1H), 7.19 (dd, 1H), 7.12 (d, 1H), 6.78 (d, 1H), 6.45 (d, 1H), 4.83 (t, 1H), 4.69 (t, 2H), 4.48 (s, 2H), 4.26 (m, 2H), 3.91 (q, 2H), 3.51 (t, 2H), 3.15 (m, 2H), 2.73 (s, 3H), 2.21 (s, 3H), 2 (m, 2H), 1.78 (m, 2H), 1 (t, 3H)

Step 4: Preparation of ethyl[24-fluoro-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate Using General Procedure 11 starting from ethyl 3-[1-(4-bromobutyl)-4-methyl-1H-benzotriazol-5-yl]-3-{3-[(8-fluoro-6-hydroxy-2,2-dioxo-2H-1,2)$^6$,3-benzoxathiazin-3 (4H)-yl)methyl]-4-methylphenyl}propanoate (1 eq.) as a reactant, the title compound (off-white solid, 74% yield) was obtained.

The enantiopure final intermediates were obtained by chromatographic separation on chiral column.

$^1$H-NMR (400 MHz, DMSO-d6) δ ppm: 7.68 (d, 1H), 7.49 (dd, 1H), 7.41 (d, 1H), 7.3 (d, 1H), 6.9 (dd, 1H), 6.6 (d, 1H), 5.75 (d, 1H), 4.79 (m, 3H), 4.2/4.02 (2d, 2H), 4.02/3.95 (2d, 2H), 3.95 (q, 2H), 3.7/3.5 (2m, 2H), 3.18/3.05 (2dd, 2H), 2.63 (s, 3H), 2.32 (s, 3H), 2.2/2.05 (2m, 2H), 1.8/1.62 (2m, 2H), 1 (t, 3H)

Step 5: Preparation of Example 17

Using General Procedure 12 starting from ethyl[24-fluoro-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8- yl]acetate E1 (1 eq.) or E2 (1 eq.) as reactants, the title compounds (65%-99% yields respectively) were obtained.

EXAMPLE 17a (E1)

HRMS calculated for $C_{29}H_{29}FN_4O_6S$: 580.1792; $[M+H]^+$ found: 581.1871 (δ=1.1 ppm).

EXAMPLE 17b (E2)

HRMS calculated for $C_{29}H_{29}FN_4O_6S$: 580.1792; $[M+H]^+$ found: 581.1867 (δ=0.4 ppm).

$^1$H-NMR (400 MHz, DMSO-d6) δ ppm: 12.3 (m, 1H), 7.55 (d, 1H), 7.5 (dd, 1H), 7.4 (d, 1H), 7.3 (d, 1H), 6.9 (dd, 1H), 6.55 (d, 1H), 5.7 (s1, 1H), 4.8 (m, 3H), 4.15/4 (2d, 2H), 4/3.9 (2d, 2H), 3.7/3.5 (2m, 2H), 3/2.9 (2m, 2H), 2.6 (s, 3H), 2.3 (s, 3H), 2.2/2.1 (2m, 2H), 1.8/1.6 (2m, 2H)

$^{19}$F-NMR (376 MHz, DMSO-d6) δ ppm: 133

EXAMPLE 18: [5-Fluoro-4,31-dimethyl-27,27-dioxo-21,26-dioxa-27$\lambda^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid enantiomer 1

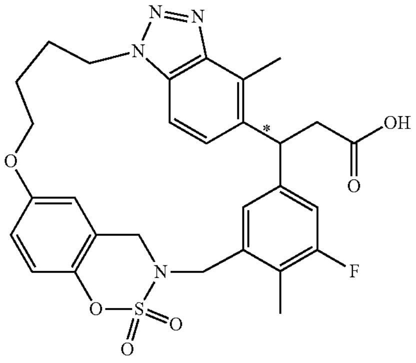

* = RorS enantiomer 2

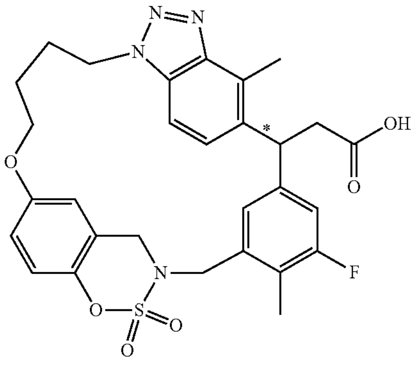

* = RorS

Step B1: Preparation of (5-bromo-3-fluoro-2-methylphenyl)methanol

Lithium aluminium hydride (4 eq., 3.07 g, 80.9 mmol) was placed into a round bottom flask. After addition of abs. THF (5 mL/mmol, 101 ml), the mixture was cooled to 0° C. A solution of methyl 5-bromo-3-fluoro-2-methylbenzoate (5 g, 20.2 mmol) in abs. THF (5 mL/mmol, 101 mL) was added dropwise at 0° C. while continuous stirring. The reaction mixture was allowed to warm to RT and was stirred at this temperature overnight. After completion of the reaction the mixture was quenched carefully with 150 mL of water and 100 mL 2M aq. NaOH solution was added. The mixture was concentrated to dryness, then it was purified by normal phase silica gel chromatography using DCM-EtOH (90:10) as an eluent to give the title compound (1.8 g, 41% yield).

$^1$H-NMR (400 MHz, DMSO-d6) δ ppm: 7.41 (d, 1H), 7.35 (dd, 1H), 5.35 (t, 1H), 4.5 (d, 2H), 2.1 (s, 3H)

Step B2: Preparation of [3-fluoro-2-methyl-5-(4,4,5,5-tetramethyl-1,3,2-dioxaborolan-2-yl)phenyl]methanol Using General Procedure 3 starting from (5-bromo-3-fluoro-2-methylphenyl)methanol (1 eq., 1.8 g, 8.2 mmol) as a reactant, the title compound (2.5 g, 73% yield) was obtained.

$^1$H-NMR (400 MHz, DMSO-d6) δ ppm: 7.55 (s, 1H), 7.2 (d, 1H), 5.2 (t, 1H), 4.52 (d, 2H), 2.18 (s, 3H), 1.31 (s, 12H)

Step 1: Preparation of ethyl 3-[3-fluoro-5-(hydroxymethyl)-4-methylphenyl]-3-(1-{4-[(4-methoxyphenyl)methoxy]butyl}-4-methyl-1H-benzotriazol-5-yl)propanoate Using General Procedure 6 starting from ethyl (2E)-3-(1-{4-[(4-methoxyphenyl)methoxy]butyl}-4-methyl-1H-benzotriazol-5-yl)prop-2-enoate (1 eq.) and [3-fluoro-2-methyl-5-(4,4,5,5-tetramethyl-1,3,2-dioxaborolan-2-yl)phenyl]methanol (1.4 eq.) as reactants, the title compound (32% yield) was obtained.

$^1$H-NMR (400 MHz, DMSO-d6) δ ppm: 7.6 (d, 1H), 7.5 (d, 1H), 7.2 (d, 2H), 7.12 (s1, 1H), 7.05 (d, 1H), 6.9 (d, 2H), 5.1 (t, 1H), 4.82 (t, 1H), 4.65 (t, 2H), 4.45 (d, 2H), 4.32 (s, 2H), 3.95 (q, 2H), 3.72 (s, 3H), 3.4 (t, 2H), 3.15 (t, 2H), 2.78 (s, 3H), 2.08 (s, 3H), 1.92 (m, 2H), 1.5 (m, 2H), 1 (t, 3H)

Step 2: Preparation of ethyl 3-(3-{[6-(benzyloxy)-2,2-dioxo-2H-1,2$\lambda^6$,3-benzoxathiazin-3(4H)-yl]methyl}-5-fluoro-4-methylphenyl)-3-(1-{4-[(4-methoxyphenyl) methoxy]butyl}-4-methyl-1H-benzotriazol-5-yl)propanoate Using General Procedure 7 starting from ethyl 3-[3-fluoro-5-(hydroxymethyl)-4-methylphenyl]-3-(1-{4-[(4-methoxyphenyl)methoxy]butyl}-4-methyl-1H-benzotriazol-5-yl)propanoate (1 eq.) and 6-(benzyloxy)-3,4-dihydro-2H-1,2$\lambda^6$,3-benzoxathiazine-2,2-dione (1.1 eq.) as reactants, the title compound (91% yield) was obtained.

$^1$H-NMR (400 MHz, DMSO-d6) δ ppm: 7.6/7.5 (2d, 2H), 7.45 (d1, 2H), 7.4 (t, 2H), 7.35 (t1, 1H), 7.2 (d, 2H), 7.1 (m, 3H), 7.05 (dd, 1H), 6.95 (d, 1H), 6.85 (d, 2H), 5.1 (s, 2H), 4.85 (t, 1H), 4.6 (t, 2H), 4.45-4.25 (3s, 6H), 3.95 (q, 2H), 3.7 (s, 3H), 3.35 (t, 2H), 3.2 (m, 2H), 2.8 (s1, 3H), 2.1 (s1, 3H), 1.9 (quint, 2H), 1.45 (quint, 2H), 1 (t, 3H)

Step 3: Preparation of ethyl 3-{3-fluoro-5-[(6-hydroxy-2,2-dioxo-2H-1,2$\lambda^6$,3-benzoxathiazin-3(4H)-yl)methyl]-4-methylphenyl}-3-[1-(4-hydroxybutyl)-4-methyl-1H-benzotriazol-5-yl]propanoate Using General Procedure 8 starting from ethyl 3-(3-{[6-(benzyloxy)-2,2-dioxo-2H-1,2$\lambda^6$,3-benzoxathiazin-3(4H)- yl]methyl}-5-fluoro-4-methylphenyl)-3-(1-{4-[(4-methoxyphenyl) methoxy]butyl}-4-methyl-1H-benzotriazol-5-yl) propanoate (1 eq.) as a reactant, the title compound (white solid, quant.) was obtained.

$^1$H-NMR (400 MHz, DMSO-d6) δ ppm: 9.7 (s, 1H), 7.6 (d, 1H), 7.5 (d, 1H), 7.15 (m, 2H), 7 (d, 1H), 6.8 (dd, 1H), 6.6 (d, 1H), 4.85 (t, 1H), 4.65 (t, 2H), 4.4 (m, 3H), 4.25 (2d, 2H), 3.9 (q, 2H), 3.4 (q, 2H), 3.2 (m, 2H), 2.8 (s, 3H), 2.1 (d, 3H), 1.9 (quint, 2H), 1.4 (quint, 2H), 1 (t, 3H)

Step 4: Preparation of ethyl 3-[1-(4-bromobutyl)-4-methyl-1H-benzotriazol-5-yl]-3-{3-fluoro-5-[(6-hydroxy-2,2-dioxo-2H-1,2$\lambda^6$,3-benzoxathiazin-3 (4H)-yl)methyl]-4-methylphenyl}propanoate Using General Procedure 9 starting from ethyl 3-{3-fluoro-5-[(6-hydroxy-2,2-dioxo-2H-1,2$\lambda^6$,3-benzoxathiazin-3(4H)-yl)methyl]-4-methylphenyl}-3-[1-(4-hydroxybutyl)-4-methyl-1H-benzotriazol-5-yl]propanoate (1 eq.) as a reactant, the title compound (white solid, 73% yield) was obtained.

$^1$H-NMR (400 MHz, DMSO-d6) δ ppm: 9.7 (s, 1H), 7.65/7.5 (2d, 2H), 7.15 (m, 2H), 7 (d, 1H), 6.8 (dd, 1H), 6.6 (d, 1H), 4.85 (t, 1H), 4.7 (t, 2H), 4.4 (2d, 2H), 4.25 (2d, 2H), 3.9 (q, 2H), 3.5 (t, 2H), 3.2 (m, 2H), 2.75 (s1, 3H), 2.1 (d, 3H), 2 (m, 2H), 1.8 (quint, 2H), 1 (t, 3H)

Step 5: Preparation of ethyl[5-fluoro-4,31-dimethyl-27,27-dioxo-21,26-dioxa-27$\lambda^6$-thia-1,14,15,16-tetraazahexacyclo[20.5.3.1$^{3,7}$0.1$^{9,13}$0.0$^{12,16}$0.0$^{25,29}$] dotriaconta-3(32),4,6,9(31),10,12,14,22,24,29-decaen-8-yl]acetate Using General Procedure 11 starting from ethyl 3-[1-(4-bromobutyl)-4-methyl-1H-benzotriazol-5-yl]-3-{3-fluoro-5-[(6-hydroxy-2,2-dioxo-2H-1,2$\lambda^6$,3-benzoxathiazin-3 (4H)-yl)methyl]-4-methylphenyl}propanoate (1 eq.) as a reactant, the title compound (96% yield) was obtained.

The enantiopure final intermediates were obtained by chromatographic separation on chiral column.

$^1$H-NMR (400 MHz, DMSO-d6) δ ppm: 1.17 (t, J=7.15 Hz, 3H) 1.58 (dt, J=13.63, 6.76 Hz, 1H) 1.70-1.86 (m, 1H) 2.20-2.27 (m, 3H) 2.65 (s, 3H) 3.05 (dd, J=15.83, 8.74 Hz, 1H) 3.16-3.26 (m, 1H) 3.43-3.57 (m, 1H) 3.62-3.73 (m, 1H) 3.83-4.00 (m, 7H) 4.03-4.17 (m, 4H) 4.63-4.89 (m, 4H) 5.89 (d, J=2.81 Hz, 1H) 6.45 (s, 1H) 6.79 (dd, J=9.05, 2.93 Hz, 1H) 6.97-7.01 (m, 1H) 7.39-7.47 (m, 2H) 7.68 (d, J=8.68 Hz, 1H)

Step 6: Preparation of Example 18

Using General Procedure 12 starting from ethyl[5-fluoro-4,31-dimethyl-27,27-dioxo-21,26-dioxa-27$\lambda^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl] acetate E1 (1 eq.) or E2 (1 eq.) as reactants the title compounds (80%-72% yields respectively) were obtained.

EXAMPLE 18a (E1)

HRMS calculated for $C_{29}H_{29}FN_4O_6S$: 580.1792; [M+H]$^+$ found: 581.1867 (δ=0.4 ppm).

EXAMPLE 18b (E2)

HRMS calculated for $C_{29}H_{29}FN_4O_6S$: 580.1792; [M+H]$^+$ found: 581.1866 (δ=0.2 ppm).

$^1$H-NMR (400 MHz, DMSO-d6) δ ppm: 12.2 (m, 1H), 7.7 (d, 1H), 7.41 (2d, 2H), 7 (d, 1H), 6.8 (dd, 1H), 6.45 (d, 1H), 5.9 (d, 1H), 4.79 (m, 3H), 4.09 (m, 2H), 3.91 (m, 2H), 3.68/3.45 (2m, 2H), 3.1/2.95 (2dd, 2H), 2.65 (s, 3H), 2.22 (s, 3H), 2.2/2.05 (2m, 2H), 1.8/1.6 (2m, 2H)

EXAMPLE 19: [(2R,8R)-2,4,33-Trimethyl-29,29-dioxo-23,28-dioxa-29$\lambda^6$-thia-1,14,15,16-tetraazahexacyclo[22.5.3.1$^{3,7}$0.1$^{9,13}$0.0$^{12,16}$0.0$^{27,31}$]tetratriaconta-3(34),4,6,9(33),10,12,14,24,26,31-decaen-8-yl]acetic acid and [(2R,8S)-2,4,33-trimethyl-29,29-dioxo-23,28-dioxa-29$\lambda^6$-thia-1,14,15,16-tetraazahexacyclo[22.5.3.1$^{3,7}$0.1$^{9,13}$0.0$^{12,16}$0.0$^{27,31}$] tetratriaconta-3(34),4,6,9(33),10,12,14,24,26,31-decaen-8-yl]acetic acid

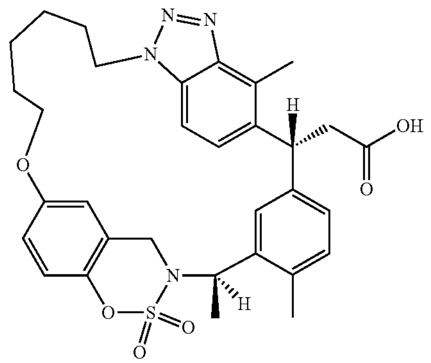

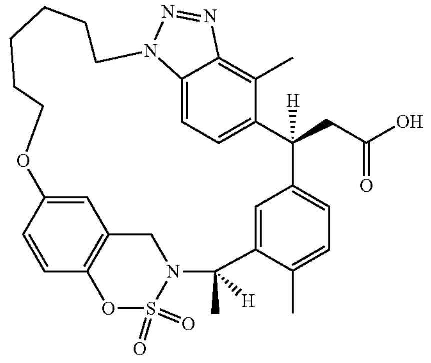

Step 1: Preparation of ethyl 3-{1-[6-(benzyloxy) hexyl]-4-methyl-1H-benzotriazol-5-yl}-3-{3-[(1S)-1-hydroxyethyl]-4-methylphenyl}propanoate Using General Procedure 6 starting from ethyl (2E)-3-{1-[6-(benzyloxy)hexyl]-4-methyl-1H-benzotriazol-5-yl}prop-2-enoate (1 eq.) (1S)-1-[2-methyl-5-(4,4,5,5-tetramethyl-1,3,2-dioxaborolan-2-yl)phenyl]ethan-1-ol (2 eq.) as reactants, the title compound (70% yield) was obtained.

$^1$H-NMR (400 MHz, DMSO-d6) δ ppm: 7.59 (d, 1H), 7.46 (d, 1H), 7.4 (d, 1H), 7.34-7.22 (br, 5H), 6.99 (d, 1H), 4.97 (d, 1H), 4.82 (m, 1H), 4.82 (m, 1H), 4.62 (dd, 2H), 4.4 (s, 2H), 4.05 (dd, 1H), 3.92 (q, 2H), 3.36 (t, 2H), 3.11 (m, 2H), 2.75 (s, 3H), 2.19 (s, 3H), 1.87 (quint, 2H), 1.48 (quint, 2H), 1.32 (quint, 2H), 1.22 (m, 3H), 1.22 (m, 2H), 0.99 (t, 3H)

Step 2: Preparation of ethyl 3-(3-{(1R)-1-[6-(benzyloxy)-2,2-dioxo-2H-1,2λ$^6$,3-benzoxathiazin-3(4H)-yl]ethyl}-4-methylphenyl)-3-{1-[6-(benzyloxy)hexyl]-4-methyl-1H-benzotriazol-5-yl}propanoate Using General Procedure 7 starting from ethyl 3-{1-[6-(benzyloxy)hexyl]-4-methyl-1H-benzotriazol-5-yl}-3-{3-[(1S)-1-hydroxyethyl]-4-methylphenyl}propanoate (1 eq.) and 6-(benzyloxy)-3,4-dihydro-2H-1,2λ$^6$,3-benzoxathiazine-2,2-dione (1.5 eq.) as reactants, the title compound (beige solid, 71% yield) was obtained.

$^1$H-NMR (400 MHz, DMSO-d6) δ ppm: 0.95-1.00 (m, 3H) 1.23-1.36 (m, 3H) 1.37-1.49 (m, 5H) 1.83 (sxt, J=6.85 Hz, 2H) 1.99 (s, 1H) 2.28 (s, 3H) 2.76 (d, J=3.67 Hz, 3H) 3.14-3.26 (m, 2H) 3.33-3.36 (m, 1H) 3.86-3.97 (m, 2H) 4.27-4.49 (m, 4H) 4.59 (q, J=6.64 Hz, 2H) 4.87 (td, J=7.98, 4.10 Hz, 1H) 5.02-5.14 (m, 2H) 5.27 (q, J=6.93 Hz, 1H) 6.96-7.16 (m, 4H) 7.24-7.48 (m, 11H) 7.49-7.55 (m, 1H) 7.57-7.63 (m, 1H)

Step 3: Preparation of ethyl 3-{3-[(1R)-1-(6-hydroxy-2,2-dioxo-2H-1,2λ$^6$,3-benzoxathiazin-3(4H)-yl)ethyl]-4-methylphenyl}-3-[1-(6-hydroxyhexyl)-4-methyl-1H-benzotriazol-5-yl]propanoate Using General Procedure 8 starting from ethyl 3-(3-{(1R)-1-[6-(benzyloxy)-2,2-dioxo-2H-1,2λ$^6$,3-benzoxathiazin-3(4H)-yl]ethyl}-4-methylphenyl)-3-{1-[6-(benzyloxy)hexyl]-4-methyl-1H-benzotriazol-5-yl}propanoate (1 eq.) as a reactant, the title compound (grey solid, 78% yield) was obtained.

$^1$H-NMR (400 MHz, DMSO-d6) δ ppm: 9.66 (m, 1H), 7.63/7.56 (2dd, 2H), 7.47/7.44 (2d, 1H), 7.15-7.08 (m, 2H), 6.92/6.9 (2d, 1H), 6.72 (2dd, 1H), 6.58 (2dd, 1H), 5.26 (m, 1H), 4.87 (m, 1H), 4.63 (t, 2H), 4.31 (m, 2H), 3.94 (2d, 2H), 3.32 (m, 2H), 3.22 (d, 2H), 2.76 (s, 3H), 2.28 (s, 3H), 1.87 (m, 2H), 1.43/1.41 (2d, 3H), 1.38-1.1 (m, 4H), 1.33 (m, 2H), 1/0.99 (2t, 3H)

Step 4: Preparation of ethyl 3-[1-(6-bromohexyl)-4-methyl-1H-benzotriazol-5-yl]-3-{3-[(1R)-1-(6-hydroxy-2,2-dioxo-2H-1,2λ$^6$,3-benzoxathiazin-3(4H)-yl)ethyl]-4-methylphenyl}propanoate Using General Procedure 9 starting from ethyl 3-{3-[(1R)-1-(6-hydroxy-2,2-dioxo-2H-1,2λ$^6$,3-benzoxathiazin-3(4H)-yl)ethyl]-4-methylphenyl}-3-[1-(6-hydroxyhexyl)-4-methyl-1H-benzotriazol-5-yl]propanoate (1 eq.) as a reactant, the title compound (84% yield) was obtained.

$^1$H-NMR (400 MHz, DMSO-d6) δ ppm: 9.61/9.6 (2s, 1H), 7.62 (dd, 1H), 7.58 (d, 1H), 7.48/7.42 (2d, 1H), 7.1 (m, 2H), 6.91 (d, 1H), 6.71 (m, 1H), 6.6/6.53 (2d, 1H), 5.26 (m, 1H), 4.89 (m, 1H), 4.62 (t, 2H), 4.4-4.2 (m, 2H), 3.92 (2d, 2H), 3.46 (m, 2H), 3.21 (d, 2H), 2.77 (s, 3H), 2.28 (s, 3H), 1.88 (m, 2H), 1.71 (m, 2H), 1.4 (2d, 3H), 1.38 (m, 2H), 1.21 (m, 3H), 1 (2t, 1H)

Step 5: Preparation of ethyl[(2R)-2,4,33-trimethyl-29,29-dioxo-23,28-dioxa-29λ$^6$-thia-1,14,15,16-tetraazahexacyclo[22.5.3.1$^{3,7}$0.1$^{9,13}$0.0$^{12,16}$0.0$^{27,31}$]tetratriaconta-3(34),4,6,9(33),10,12,14,24,26,31-decaen-8-yl]acetate Using General Procedure 11 starting from ethyl 3-[1-(6-bromohexyl)-4-methyl-1H-benzotriazol-5-yl]-3-{3-[(1R)-1-(6-hydroxy-2,2-dioxo-2H-1,2λ$^6$,3-benzoxathiazin-3(4H)-yl)ethyl]-4-methylphenyl}propanoate (1 eq.) as a reactant, the title compound (81% yield) was obtained.

$^1$H-NMR (400 MHz, DMSO-d6) δ ppm: 1.00 (dt, J=11.62, 7.09 Hz, 12H) 1.20-1.29 (m, 9H) 1.29-1.76 (m, 25H) 1.86-1.98 (m, 5H) 2.30 (d, J=9.05 Hz, 10H) 2.63-2.79 (m, 1H) 2.97 (dd, J=15.77, 7.46 Hz, 1H) 3.09-3.27 (m, 2H) 3.64-3.76 (m, 1H) 3.77-3.99 (m, 6H) 4.00-4.10 (m, 1H) 4.18 (d, J=17.48 Hz, 1H) 4.59-4.72 (m, 3H) 4.86 (t, J=8.01 Hz, 1H) 4.94 (t, J=7.95 Hz, 1H) 5.24-5.42 (m, 3H) 5.99 (d, J=2.81 Hz, 1H) 6.40 (d, J=2.81 Hz, 1H) 6.75-6.86 (m, 2H) 6.93-7.04 (m, 3H) 7.09-7.20 (m, 2H) 7.29 (dd, J=12.41, 7.76 Hz, 2H) 7.47 (d, J=7.58 Hz, 1H) 7.55 (s, 1H) 7.61 (d, J=8.80 Hz, 1H) 7.66 (d, J=8.68 Hz, 1H) 7.77 (d, J=8.93 Hz, 1H)

Step 6: Preparation of Example 19

Using General Procedure 12 starting from ethyl[(2R)-2,4,33-trimethyl-29,29-dioxo-23,28-dioxa-29λ$^6$-thia-1,14,15,16-tetraazahexacyclo[22.5.3.1$^{3,7}$0.1$^{9,13}$0.0$^{12,16}$0.0$^{27,31}$]tetratriaconta-3(34),4,6,9(33),10,12,14,24,26,31-decaen-8-yl]acetate (1 eq.) as a reactant, the title compound (white solid, 91% yield) was obtained.

The diastereo-pure products were obtained by chromatographic separation on chiral column.

EXAMPLE 19a (2R,8R)

HRMS calculated for $C_{32}H_{36}N_4O_6S$: 604.2356; $[M+H]^+$ found: 605.2430 (δ=0.3 ppm).

$^1$H-NMR (400 MHz, DMSO-d6) δ ppm: 12.2 (s1), 7.6 (d, 1H), 7.48 (dd, 1H), 7.3 (d, 1H), 7.14 (d, 1H), 7 (d, 1H), 6.96 (d, 1H), 6.78 (dd, 1H), 6 (d, 1H), 5.3 (q, 1H), 4.92 (t, 1H), 4.64 (m, 2H), 4.04/3.83 (2d, 2H), 3.7 (m, 2H), 3.11/2.85 (2dd, 2H), 2.82 (s, 3H), 2.32 (s, 3H), 2 (m, 2H), 1.6 (m, 2H), 1.4 (m, 2H), 1.25 (m, 2H), 1.25 (d, 3H) $^{13}$C-NMR (100 MHz, DMSO-d6) δ ppm: 131.6, 128.4, 128, 126.5, 119.5, 115.7, 111.4, 107.8, 68.4, 55.3, 47.8, 45, 41.6, 39.9, 29.5, 27.5, 25.7, 25.5, 18.7, 15.1, 13.6

EXAMPLE 19b (2R,8S)

HRMS calculated for $C_{32}H_{36}N_4O_6S$: 604.2356; $[M+H]^+$ found: 605.2431 (δ=0.4 ppm).

$^1$H-NMR (400 MHz, DMSO-d6) δ ppm: 12.1 (s1), 7.75 (d, 1H), 7.65 (d, 1H), 7.52 (d, 1H), 7.3 (dd, 1H), 7.12 (d, 1H), 7 (d, 1H), 6.82 (dd, 1H), 6.4 (d, 1H), 5.34 (q, 1H), 4.84 (t, 1H), 4.67 (m, 2H), 4.18/3.92 (2d, 2H), 3.82 (t, 2H), 3.15/3.05 (2dd, 2H), 2.82 (s, 3H), 2.3 (s, 3H), 1.85 (m, 2H), 1.7 (m, 2H), 1.6-1.4 (m, 2H), 1.5 (d, 3H), 1.35 (m, 2H)

$^{13}$C-NMR (100 MHz, DMSO-d6) δ ppm: 131.4, 129.9, 126.9, 125.2, 119.5, 116.1, 111.1, 107.9, 68.4, 55.4, 47.6, 45.4, 42.1, 40.9, 30, 28.2, 25.7, 24.8, 18.7, 15.7, 13.5

EXAMPLE 20: [(2R,8S)-2,4,32-Trimethyl-28,28-dioxo-22,27-dioxa-$28\lambda^6$-thia-1,14,15,16-tetraazahexacyclo[21.5.3.$1^{3,7}$0.$1^{9,13}$0.$0^{12,16}$0.$0^{26,30}$]tritriaconta-3(33),4,6,9(32),10,12,14,23,25,30-decaen-8-yl]acetic acid and [(2R,8R)-2,4,32-trimethyl-28,28-dioxo-22,27-dioxa-$28\lambda^6$-thia-1,14,15,16-tetraazahexacyclo[21.5.3.$1^{3,7}$0.$1^{9,13}$0.$0^{12,16}$0.$0^{26,30}$]tritriaconta-3(33),4,6,9(32),10,12,14,23,25,30-decaen-8-yl]acetic acid

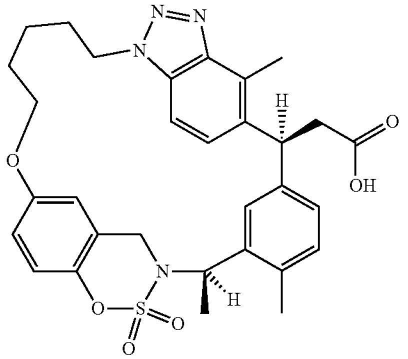

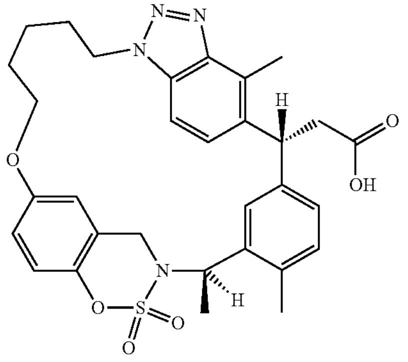

Step 1: Preparation of ethyl 3-{3-[(1S)-1-hydroxyethyl]-4-methylphenyl}-3-(1-{5-[(4-methoxyphenyl)methoxy]pentyl}-4-methyl-1H-benzotriazol-5-yl)propanoate Using General Procedure 6 starting from ethyl (2E)-3-(1-{5-[(4-methoxyphenyl)methoxy]pentyl}-4-methyl-1H-benzotriazol-5-yl)prop-2-enoate (1 eq.) and (1S)-1-[2-methyl-5-(4,4,5,5-tetramethyl-1,3,2-dioxaborolan-2-yl)phenyl]ethan-1-ol (2 eq.) as reactants, the title compound (77% yield) was obtained.

$^1$H-NMR (400 MHz, DMSO-d6) δ ppm: 7.59 (d, 1H), 7.45 (d, 1H), 7.41 (d, 1H), 7.18 (d, 2H), 7.04 (dd, 1H), 6.98 (d, 1H), 6.87 (d, 2H), 4.96 (d, 1H), 4.82 (m, 1H), 4.82 (m, 1H), 4.62 (dd, 2H), 4.31 (s, 2H), 3.92 (q, 2H), 3.73 (s, 3H), 3.31 (m, 2H), 3.15-3.09 (m, 2H), 2.77 (s, 3H), 2.19 (s, 3H), 1.87 (m, 2H), 1.51 (m, 2H), 1.27 (m, 2H), 1.23/1.21 (d, 3H), 0.99 (t, 3H)

Step 2: Preparation of ethyl 3-(3-{(1R)-1-[6-(benzyloxy)-2,2-dioxo-2H-1,$2\lambda^6$,3-benzoxathiazin-3(4H)-yl]ethyl}-4-methylphenyl)-3-(1-{5-[(4-methoxyphenyl)methoxy]pentyl}-4-methyl-1H-benzotriazol-5-yl)propanoate Using General Procedure 7 starting from ethyl 3-{3-[(1S)-1-hydroxyethyl]-4-methylphenyl}-3-(1-{15-[(4-methoxyphenyl)methoxy]pentyl}-4-methyl-1H-benzotriazol-5-yl)propanoate (1 eq.) and 6-(benzyloxy)-3,4-dihydro-2H-1,$2\lambda^6$,3-benzoxathiazine-2,2-dione (1.5 eq.) as reactants, the title compound (64% yield) was obtained.

$^1$H-NMR (400 MHz, DMSO-d6) δ ppm: 7.6 (d, 1H), 7.51 (2d, 1H), 7.5-6.8 (m, 15H), 5.27 (q, 1H), 5.09 (m, 2H), 4.88 (m, 1H), 4.59 (m, 2H), 4.41 (m, 2H), 4.29 (s, 2H), 3.9 (q, 2H), 3.71 (s, 3H), 3.29 (m, 2H), 3.2 (m, 2H), 2.76 (2s, 3H), 2.28 (s, 3H), 1.82 (m, 2H), 1.49 (m, 2H), 1.4 (m, 3H), 1.22 (m, 2H), 0.96 (m, 3H)

Step 3: Preparation of ethyl 3-{3-[(1R)-1-(6-hydroxy-2,2-dioxo-2H-1,$2\lambda^6$,3-benzoxathiazin-3(4H)-yl)ethyl]-4-methylphenyl}-3-[1-(5-hydroxypentyl)-4-methyl-1H-benzotriazol-5-yl]propanoate Using General Procedure 8 starting from ethyl 3-(3-{(1R)-1-[6-(benzyloxy)-2,2-dioxo-2H-1,$2\lambda^6$,3-benzoxathiazin-3(4H)-yl]ethyl}-4-methylphenyl)-3-(1-{5-[(4-methoxyphenyl)methoxy]pentyl}-4-methyl-1H-benzotriazol-5-yl)propanoate (1 eq.) as a reactant, the title compound (grey solid, 98% yield) was obtained.

$^1$H-NMR (400 MHz, DMSO-d6) δ ppm: 9.63/9.62 (2m, 3H), 7.62/7.56 (2dd, 2H), 7.47/7.45 (2s1, 1H), 7.1 (m, 2H), 6.92/6.9 (2d, 1H), 6.73 (m, 1H), 6.58 (2d, 1H), 5.25 (m, 1H), 4.88 (m, 1H), 4.63 (t, 2H), 4.32 (m, 2H), 3.94 (m, 2H), 3.32 (m, 2H), 3.22 (m, 2H), 2.77 (s, 3H), 2.28 (s, 3H), 1.88 (m, 2H), 1.46-1.37 (m+d, 5H), 1.24 (m, 2H), 1/0.99 (2t, 3H)

Step 4: Preparation of ethyl 3-[1-(5-bromopentyl)-4-methyl-1H-benzotriazol-5-yl]-3-{3-[(1R)-1-(6-hydroxy-2,2-dioxo-2H-1,$2\lambda^6$,3-benzoxathiazin-3(4H)-yl)ethyl]-4-methylphenyl}propanoate Using General Procedure 9 starting from ethyl 3-{3-[(1R)-1-(6-hydroxy-2,2-dioxo-2H-1,$2\lambda^6$,3-benzoxathiazin-3(4H)-yl)ethyl]-4-methylphenyl}-3-[l-(5-hydroxypentyl)-4-methyl-1H-benzotriazol-5-yl]propanoate (1 eq.) as a reactant, the title compound (white solid, 78% yield) was obtained.

$^1$H-NMR (400 MHz, DMSO-d6) δ ppm: 9.6/9.59 (2s, 1H), 7.62 (2d, 1H), 7.58 (d, 1H), 7.48/7.42 (2d, 1H), 7.1 (m, 2H), 6.9 (d, 1H), 6.71 (m, 1H), 6.59/6.55 (2d, 1H), 5.26 (m, 1H), 4.88 (m, 1H), 4.65 (t, 2H), 4.4-4.25 (m, 2H), 3.93 (q, 2H), 3.48 (t, 2H), 3.21 (m, 2H), 2.77 (s, 3H), 2.28 (s, 3H), 1.9 (m, 2H), 1.8 (m, 2H), 1.41 (2d, 3H), 1.32 (m, 2H), 1/0.99 (2t, 3H)

Step 5: Preparation of ethyl[(2R)-2,4,32-trimethyl-28,28-dioxo-22,27-dioxa-$28\lambda^6$-thia-1,14,15,16-tetraazahexacyclo[21.5.3.$1^{3,7}$0.$1^{9,13}$0.$0^{12,16}$0.$0^{26,30}$]tritriaconta-3(33),4,6,9(32),10,12,14,23,25,30-decaen-8-yl]acetate Using General Procedure 11 starting from ethyl 3-[1-(5-bromopentyl)-4-methyl-1H-benzotriazol-5-yl]-3-{3-[(1R)-1-(6-hydroxy-2,2-dioxo-2H-1,$2\lambda^6$,3-benzoxathiazin-3(4H)-yl)ethyl]-4-methylphenyl}propanoate (1 eq.) as a reactant, the title compound (78% yield) was obtained.

$^1$H-NMR (400 MHz, DMSO-d6) δ ppm: 0.92-1.07 (m, 7H) 1.27-1.53 (m, 9H) 1.55-1.81 (m, 5H) 1.85-1.98 (m, 3H) 1.99-2.09 (m, 2H) 2.23-2.36 (m, 7H) 2.75 (s, 4H) 2.80 (s, 3H) 2.94 (dd, J=15.71, 7.52 Hz, 1H) 3.10 (dd, J=16.08, 7.03 Hz, 2H) 3.21-3.29 (m, 2H) 3.57-3.78 (m, 3H) 3.80-3.98 (m, 8H) 4.04-4.21 (m, 2H) 4.56-4.76 (m, 4H) 4.81-4.89 (m, 1H) 4.95 (t, J=7.82 Hz, 1H) 5.21-5.36 (m, 2H) 5.99 (s, 2H) 6.76-6.88 (m, 3H) 6.91-6.99 (m, 2H) 7.13 (dd, J=10.51, 8.19

Hz, 2H) 7.24-7.38 (m, 3H) 7.48 (d, J=7.95 Hz, 1H) 7.60-7.71 (m, 2H) 7.84 (d, J=8.68 Hz, 1H)

Step 6: Preparation of Example 20

Using General Procedure 12 starting from ethyl[(2R)-2,4,32-trimethyl-28,28-dioxo-22,27-dioxa-28$\lambda^{6}$-thia-1,14,15,16-tetraazahexacyclo[21.5.3.$1^{3,7}$0.$1^{9,13}$0.$0^{12,16}$0.$0^{26,30}$]tritriaconta-3(33),4,6,9(32),10,12,14,23,25,30-decaen-8-yl] acetate (1 eq.) as a reactant, the title compound (white solid, 32% yield) was obtained.

The diastereo-pure products were obtained by chromatographic separation on chiral column.

EXAMPLE 20a (2R,8S)

HRMS calculated for $C_{31}H_{34}N_4O_6S$: 590.2199; $[M+H]^+$ found: 591.2273 (δ=0.2 ppm).

$^1$H-NMR (400 MHz, DMSO-d6) δ ppm: 12.4-11.9 (m, 1H), 7.62 (d, 1H), 7.49 (dd, 1H), 7.31 (d, 1H), 7.09 (d, 1H), 6.94 (d, 1H), 6.84 (d, 1H), 6.81 (dd, 1H), 5.99 (d, 1H), 5.28 (q, 1H), 4.91 (m, 1H), 4.75-4.6 (t, 2H), 4.08/3.7 (m, 2H), 3.89/3.7 (m, 2H), 3.16/2.8 (2m, 2H), 2.8 (s, 3H), 2.32 (s, 3H), 2.1-1.85 (m, 2H), 1.69 (m, 2H), 1.55-1.23 (m, 2H), 1.12 (d, 3H)

EXAMPLE 20b (2R,8R)

HRMS calculated for $C_{31}H_{34}N_4O_6S$: 590.2199; $[M+H]^+$ found: 591.2274 (δ=0.4 ppm).

$^1$H-NMR (400 MHz, DMSO-d6) δ ppm: 12.4-11.9 (m, 1H), 7.81 (d, 1H), 7.68 (d, 1H), 7.37 (dd, 1H), 7.29 (d, 1H), 7.13 (d, 1H), 6.98 (d, 1H), 6.83 (dd, 1H), 5.97 (d, 1H), 5.3 (q, 1H), 4.81 (m, 1H), 4.7 (t, 2H), 4.15/3.6 (m, 2H), 3.85 (m, 2H), 3.18/2.99 (2m, 2H), 2.71 (s, 3H), 2.29 (s, 3H), 2.1-1.85 (m, 2H), 1.8-1.55 (m, 2H), 1.5-1.2 (m, 5H)

EXAMPLE 21: [(2R,8S)-2,4,19,33-Tetramethyl-29,29-dioxo-23,28-dioxa-29$\lambda^{6}$-thia-1,14,15,16,19-pentaazahexacyclo[22.5.3.$1^{3,7}$0.$1^{9,13}$0.$0^{12,16}$0.$0^{27,31}$]tetratriaconta-3(34),4,6,9(33),10,12,14,24,26,31-decaen-8-yl]acetic acid and [(2R,8R)-2,4,19,33-tetramethyl-29,29-dioxo-23,28-dioxa-29$\lambda^{6}$-thia-1,14,15,16,19-pentaazahexacyclo[22.5.3.$1^{3,7}$0.$1^{9,13}$0.$0^{12,16}$0.$0^{27,31}$]tetratriaconta-3(34),4,6,9(33),10,12,14,24,26,31-decaen-8-yl]acetic acid

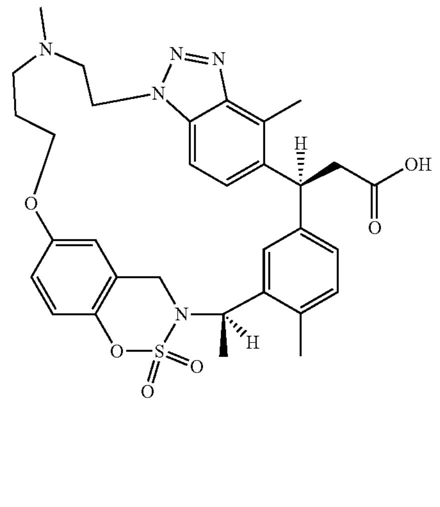

-continued

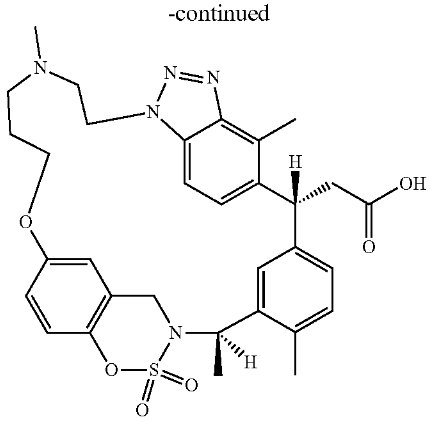

Step A1: Preparation of tert-butyl (2-{[3-(benzyloxy)propyl](methyl)amino}ethyl) carbamate To a solution of [(3-bromopropoxy)methyl]benzene (10 g, 43.6 mmol, 7.7 mL) in MeCN (3 mL/mmol, 131 mL) tert-butyl[2-(methylamino)ethyl]carbamate (1 eq., 7.61 g, 43.6 mmol) and $K_2CO_3$ (2 eq., 8.65 g, 87.3 mmol) were added at RT. The reaction mixture was heated to 50° C. and stirred for 2 h. After completion of the reaction the mixture was diluted with 500 ml of EtOAc, extracted with 500 ml of water, then with 500 ml of brine. The organic layer was dried over anhydrous $Na_2SO_4$, filtered, concentrated to dryness to give the crude product as a colorless oil, which was used in a next step without further purification (14 g, 99% yield).

$^1$H-NMR (400 MHz, DMSO-d6) δ ppm: 7.38-7.28 (m, 5H), 6.58 (t, 1H), 4.43 (s, 2H), 3.45 (t, 2H), 2.99 (q, 2H), 2.38 (t, 2H), 2.32 (t, 2H), 2.13 (s, 3H), 1.65 (quint, 2H), 1.37 (s, 9H)

Step A2: Preparation of $N^1$-[3-(benzyloxy)propyl]-$N^1$-methylethane-1,2-diamine To a solution of tert-butyl (2-{[3-(benzyloxy)propyl](methyl)amino}ethyl)carbamate (14 g, 43 mmol) in dioxane (5 mL/mmol, 220 mL) HCl (4N in dioxane) (4 eq., 43 mL) was added at RT and the reaction mixture was stirred overnight. After completion of the reaction the volatiles were evaporated to dryness under reduced pressure. The crude product was partitioned between 200 mL DCM and 300 ml sat. aq. $NaHCO_3$. The layers were separated, the aq. layer was evaporated to dryness under reduced pressure. 50 ml of MeCN was added, then the solid was filtered-off and washed with 2×20 ml MeCN. The mother liquor was concentrated to dryness to give the crude product as a yellow oil. The crude product was used without further purification (6.2 g, 62% yield).

$^1$H-NMR (400 MHz, DMSO-d6) δ ppm: 7.38-7.23 (m, 5H), 4.44 (s, 2H), 3.45 (t, 2H), 2.56 (t, 2H), 2.36 (t, 2H), 2.33 (t, 2H), 2.1 (s, 3H), 1.67 (quint, 2H)

Step A3: Preparation of $N^1$-[3-(benzyloxy)propyl]-$N^1$-methyl-$N_2$-(3-methyl-2-nitrophenyl)ethane-1,2-diamine Using General Procedure 2 STEP 1 starting from 1-fluoro-3-methyl-2-nitro-benzene (1 eq.) and the crude $N^1$-[3-(benzyloxy)propyl]-$N^1$-methylethane-1,2-diamine (1.2 eq.) as reactants, the title compound (58% yield) was obtained.

$^1$H-NMR (400 MHz, DMSO-d6) δ ppm: 7.35-7.22 (m, 1H), 7.35-7.22 (m, 5H), 6.78 (d, 1H), 6.61 (t, 1H), 6.58 (d, 1H), 4.41 (s, 2H), 3.49 (t, 2H), 3.2 (q, 2H), 2.55 (t, 2H), 2.41 (t, 2H), 2.32 (s, 3H), 2.19 (s, 3H), 1.69 (quint, 2H)

Step A4: Preparation of $N^1$-(2-{[3-(benzyloxy)propyl](methyl)amino}ethyl)-4-bromo-3-methylbenzene-1,2-diamine Using General Procedure 2 STEP 2 starting from $N^1$-[3-(benzyloxy)propyl]-$N^1$-methyl-$N^2$-(3-methyl-2-nitrophenyl)ethane-1,2-diamine (1 eq.) as a reactant, $N^1$-[3-(benzyloxy)propyl]-$N^2$-(4-bromo-3-methyl-2-nitrophenyl)-$N^1$-methylethane-1,2-diamine (71% yield) was obtained. The crude product was reacted using General Procedure 2 STEP 3 resulting the title compound (76% yield).

LC-MS calculated for $C_{20}H_{28}BrN_3O$: 405; $[M+H]^+$ found: 406/408.

Step A5: Preparation of 3-(benzyloxy)-N-[2-(5-bromo-4-methyl-1H-benzotriazol-1-yl)ethyl]-N-methylpropan-1-amine Using General Procedure 2 STEP 4 starting from $N^1$-(2-{[3-(benzyloxy)propyl](methyl)amino}ethyl)-4-bromo-3-methylbenzene-1,2-diamine (1 eq.) as a reactant, the title compound (85% yield) was obtained.

$^1$H-NMR (400 MHz, DMSO-d6) δ ppm: 8.19 (s, 1H), 7.4 (2d, 2H), 7.3 (t, 2H), 7.25 (t, 1H), 7.2 (d, 2H), 4.3 (t, 2H), 4.22 (s, 2H), 3.18 (t, 2H), 2.68 (t, 2H), 2.55 (s, 3H), 2.35 (t, 2H), 2.2 (s, 3H), 1.5 (m, 2H)

Step A6: Preparation of ethyl (2E)-3-[1-(2-{[3-(benzyloxy)propyl](methyl)amino}ethyl)-4-methyl-1H-benzotriazol-5-yl]prop-2-enoate Using General Procedure 2 STEP 5 starting from 3-(benzyloxy)-N-[2-(5-bromo-4-methyl-1H-benzotriazol-1-yl)ethyl]-N-methylpropan-1-amine (1 eq.) as a reactant, the title compound (93% yield) was obtained.

$^1$H-NMR (400 MHz, DMSO-d6) δ ppm: 8 (d, 1H), 7.91 (d, 1H), 7.7 (d, 1H), 7.3 (t, 2H), 7.22 (t, 1H), 7.19 (d, 2H), 6.61 (d, 1H), 4.77 (t, 2H), 4.2 (q, 2H), 4.18 (s, 2H), 3.08 (t, 2H), 2.82 (t, 2H), 2.79 (s, 3H), 2.31 (t, 2H), 2.19 (s, 3H), 1.42 (q, 2H), 1.28 (t, 3H)

Step 1: Preparation of ethyl 3-[1-(2-{[3-(benzyloxy)propyl](methyl)amino}ethyl)-4-methyl-1H-benzotriazol-5-yl]-3-{3-[(1S)-1-hydroxyethyl]-4-methylphenyl}propanoate Using General Procedure 6 starting from ethyl (2E)-3-[1-(2-{[3-(benzyloxy)propyl](methyl)amino}ethyl)-4-methyl-1H-benzotriazol-5-yl]prop-2-enoate (1 eq.) and (15)-1-[2-methyl-5-(4,4,5,5-tetramethyl-1,3,2-dioxaborolan-2-yl)phenyl]ethanol (1 eq.) as reactants, the title compound (33% yield) was obtained.

$^1$H-NMR (400 MHz, DMSO-d6) δ ppm: 7.59 (d, 1H), 7.45 (d, 1H), 7.41 (m, 1H), 7.35 (d, 1H), 7.31 (dd, 1H), 7.22 (m, 2H), 7.02 (m, 1H), 6.97 (m, 2H), 4.93 (d, 1H), 4.82 (m, 1H), 4.82 (m, 1H), 4.7 (t, 2H), 4.22 (s, 2H), 3.91 (q, 2H), 3.15 (m, 2H), 3.15-3.05 (m, 2H), 2.82 (t, 2H), 2.75 (s, 3H), 2.35 (t, 2H), 2.19 (s, 3H), 2.19 (s, 3H), 1.47 (quint, 2H), 1.21 (d, 3H), 0.99 (t, 3H)

Step 2: Preparation of ethyl 3-(3-{(1R)-1-[6-(benzyloxy)-2,2-dioxo-2H-1,2λ$^6$,3-benzoxathiazin-3(4H)-yl]ethyl}-4-methylphenyl)-3-[1-(2-{[3-(benzyloxy)propyl](methyl)amino}ethyl)-4-methyl-1H-benzotriazol-5-yl]propanoate Using General Procedure 7 starting from ethyl 3-[1-[2-[3-benzyloxypropyl(methyl)amino]ethyl]-4-methyl-benzotriazol-5-yl]-3-[3-[(1S)-1-hydroxyethyl]-4-methyl-phenyl]propanoate (1 eq.) and 6-(benzyloxy)-3,4-dihydro-2H-1,2λ$^6$,3-benzoxathiazine-2,2-dione (1.1 eq.) as reactants, the title compound (58% yield) was obtained.

LC-MS calculated for $C_{48}H_{55}N_5O_7S$: 845; $[M+H]^+$ found: 846.

Step 3: Preparation of ethyl 3-{3-[(1R)-1-(6-hydroxy-2,2-dioxo-2H-1,2λ$^6$,3-benzoxathiazin-3(4H)-yl)ethyl]-4-methylphenyl}-3-(1-{2-[(3-hydroxypropyl)(methyl)amino]ethyl}-4-methyl-1H-benzotriazol-5-yl)propanoate Using General Procedure 8 starting from ethyl 3-(3-{(1R)-1-[6-(benzyloxy)-2,2-dioxo-2H-1,2λ$^6$,3-benzoxathiazin-3(4H)-yl]ethyl}-4-methylphenyl)-3-[1-(2-{[3-(benzyloxy)propyl](methyl)amino}ethyl)-4-methyl-1H-benzotriazol-5-yl]propanoate (1 eq.) as a reactant, the title compound (yellow oil, 97% yield) was obtained.

LC-MS calculated for $C_{34}H_{43}N_5O_7S$: 665; $[M+H]^+$ found: 666.

Step 4: Preparation of ethyl 3-(1-{2-[(3-bromopropyl)(methyl)amino]ethyl}-4-methyl-1H-benzotriazol-5-yl)-3-{3-[(1R)-1-(6-hydroxy-2,2-dioxo-2H-1,2λ$^6$,3-benzoxathiazin-3(4H)-yl)ethyl]-4-methylphenyl}propanoate Using General Procedure 9 starting from ethyl 3-{3-[(1R)-1-(6-hydroxy-2,2-dioxo-2H-1,2λ$^6$,3-benzoxathiazin-3(4H)-yl)ethyl]-4-methylphenyl}-3-(1-{12-[(3-hydroxypropyl)(methyl)amino]ethyl}-4-methyl-1H-benzotriazol-5-yl)propanoate (1 eq.) as a reactant, the title compound (white solid, 20% yield) was obtained.

LC-MS calculated for $C_{34}H_{42}BrN_5O_6S$: 727; $[M+H]^+$ found: 728/730.

Step 5: Preparation of ethyl[(2R)-2,4,19,33-tetramethyl-29,29-dioxo-23,28-dioxa-29λ$^6$-thia-1,14,15,16,19-pentaazahexacyclo[22.5.3.1$^{3,7}$0.1$^{9,13}$0.0$^{12,16}$0.0$^{27,31}$]tetratriaconta-3(34),4,6,9(33),10,12,14,24,26,31-decaen-8-yl]acetate Using General Procedure 11 starting from ethyl 3-(1-{2-[(3-bromopropyl)(methyl)amino]ethyl}-4-methyl-1H-benzotriazol-5-yl)-3-{3-[(1R)-1-(6-hydroxy-2,2-dioxo-2H-1,2λ$^6$,3-benzoxathiazin-3(4H)-yl)ethyl]-4-methylphenyl}propanoate (1 eq.) as a reactant, the title compound (white solid, 99% yield) was obtained.

$^1$H-NMR (400 MHz, DMSO-d6) δ ppm: 7.74/7.63 (2d, 1H), 7.73/7.48 (2d, 1H), 7.58 (s, 1H), 7.27/7.04 (2d, 1H), 7.25/7.12 (d, 1H), 7.01/6.93 (2d, 1H), 6.84/6.73 (2d, 1H), 6.37/5.81 (2s1, 1H), 5.35/5.29 (2q, 1H), 4.93/4.87 (2t, 1H), 4.8/4.71/4.61/4.58 (4m, 2H), 4.24/4.02/3.98/3.87 (4d, 2H), 3.91 (q, 2H), 3.83 (m, 2H), 3.34-3.13/3.02 (4dd, 2H), 3.11/3.06/2.86/2.72 (4m, 2H), 2.84 (2s, 3H), 2.59-2.46/2.4 (2m, 2H), 2.29 (s, 3H), 2.19/2.13 (2s1, 3H), 1.85 (m, 2H), 1.52/1.27 (2d, 3H), 1.01 (2d, 3H)

Step 6: Preparation of Example 21

Using General Procedure 12 starting from ethyl[(2R)-2,4,19,33-tetramethyl-29,29-dioxo-23,28-dioxa-29$\lambda^6$-thia-1,14,15,16,19-pentaazahexacyclo[22.5.3.$1^{3,7}$0.$1^{9,13}$0.$0^{12,}$ ${}_{16}$0.$0^{27,31}$]tetratriaconta-3(34),4,6,9(33),10,12,14,24,26,31-decaen-8-yl]acetate (1 eq.) as a reactant, the title compound (white solid, 83% yield) was obtained.

The diastereo-pure products were obtained by chromatographic separation on chiral column.

EXAMPLE 21a (2R,8S)

HRMS calculated for $C_{32}H_{37}N_5O_6S$: 619.2464; $[M+H]^+$ found: 620.2538 (δ=0.1 ppm).

$^1$H-NMR (400 MHz, DMSO-d6) δ ppm: 12.05 (m, 1H), 7.71 (m, 2H), 7.55 (d, 1H), 7.29 (dd, 1H), 7.12 (d, 1H), 7 (d, 1H), 6.81 (dd, 1H), 6.38 (d, 1H), 5.35 (q, 1H), 4.85 (t, 1H), 4.78/4.58 (2m, 2H), 4.21/3.95 (2d, 2H), 3.82 (m, 2H), 3.1/3 (2dd, 2H), 3.05/2.7 (2m, 2H), 2.81 (s, 3H), 2.55 (m, 2H), 2.3 (s, 3H), 2.15 (s, 3H), 1.82 (m, 2H), 1.5 (d, 3H)

EXAMPLE 21b (2R,8R)

HRMS calculated for $C_{32}H_{37}N_5O_6S$: 619.2464; $[M+H]^+$ found: 620.2576 (δ=6.2 ppm).

$^1$H-NMR (400 MHz, DMSO-d6) δ ppm: 12.3 (m, 1H), 7.65/7.22 (2d, 2H), 7.5 (dd, 1H), 7.22 (d, 1H), 7 (d, 1H), 6.95 (d, 1H), 6.72 (dd, 1H), 5.82 (d, 1H), 5.3 (q, 1H), 4.91 (t, 1H), 4.7/4.6 (2m, 2H), 4.02/3.85 (2d, 2H), 3.48/3.32 (2m, 2H), 3.1 (m, 2H), 2.88 (m, 2H), 2.81 (s, 3H), 2.4 (t, 2H), 2.3 (s, 3H), 2.2 (s, 3H), 1.68 (m, 2H), 1.25 (d, 3H)

EXAMPLE 22: [23-Chloro-4,31-dimethyl-27,27-dioxo-21,26-dioxa-27$\lambda^6$-thia-1,14,15,16-tetraazahexacyclo[20.5.3.$1^{3,7}$0.$1^{9,13}$0.$0^{12,16}$0.$0^{25,29}$]dotriaconta-3(32),4,6,9(31),10,12,14,22,24,29-decaen-8-yl]acetic acid enantiomer 1

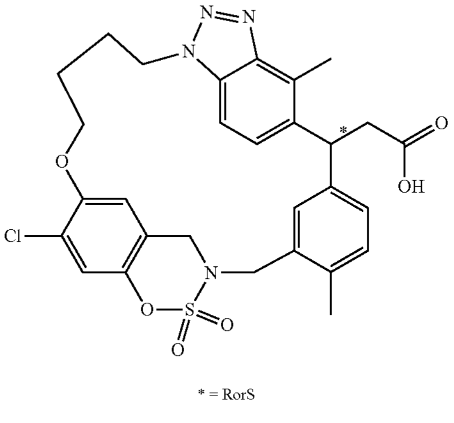

* = RorS

-continued enantiomer 2

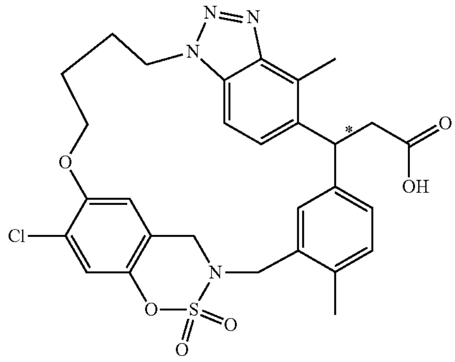

* = RorS

Step C1: Preparation of 5-(benzyloxy)-4-chloro-2-hydroxybenzaldehyde

Using General Procedure 4 STEP 1 starting from 4-(benzyloxy)-3-chlorophenol (1 eq.) as a reactant, the title compound (45% yield) was obtained.

$^1$H-NMR (500 MHz, DMSO-d6) δ ppm: 10.66 (s, 1H), 10.22 (s, 1H), 7.49-7.3 (m, 5H), 7.38 (s, 1H), 7.12 (s, 1H), 5.16 (s, 2H)

Step C2: Preparation of 6-(benzyloxy)-7-chloro-2H-1,2)$^6$,3-benzoxathiazine-2,2-dione Using General Procedure 4 STEP 2 starting from 5-(benzyloxy)-4-chloro-2-hydroxybenzaldehyde (1 eq.) as a reactant, the title compound (91% yield) was obtained.

$^1$H-NMR (500 MHz, DMSO-d6) δ ppm: 9.16 (s, 1H), 7.93 (s, 1H), 7.92 (s, 1H), 7.53-7.34 (m, 5H), 5.28 (s, 2H)

Step C3: Preparation of 6-(benzyloxy)-7-chloro-3,4-dihydro-2H-1,2$\lambda^6$,3-benzoxathiazine-2,2-dione Using General Procedure 4 STEP 3 starting from 6-(benzyloxy)-7-chloro-2H-1,2$\lambda^6$,3-benzoxathiazine-2,2-dione (1 eq.) as a reactant, the title compound (quant.) was obtained.

$^1$H-NMR (500 MHz, DMSO-d6) δ ppm: 8.5 (br., 1H), 7.47 (dm, 2H), 7.41 (tm, 2H), 7.35 (tm, 1H), 7.34 (s, 1H), 7.25 (s, 1H), 5.17 (s, 2H), 4.52 (s, 2H)

Step 1: Preparation of ethyl 3-(3-{[6-(benzyloxy)-7-chloro-2,2-dioxo-2H-1,2$\lambda^6$,3-benzoxathiazin-3(4H)-yl]methyl}-4-methylphenyl)-3-(1-{4-[(4-methoxyphenyl)methoxy]butyl}-4-methyl-1H-benzotriazol-5-yl)propanoate Using General Procedure 7 starting from ethyl 3-[3-(hydroxymethyl)-4-methylphenyl]-3-(1-{4-[(4-methoxyphenyl)methoxy]butyl}-4-methyl-1H-benzotriazol-5-yl) propanoate (1 eq.) and 6-(benzyloxy)-7-chloro-3,4-dihydro-2H-1,2$\lambda^6$,3-benzoxathiazine-2,2-dione (1.4 eq.) as reactants, the title compound (yellow oil, 50% yield) was obtained.

$^1$H-NMR (500 MHz, DMSO-d6) δ ppm: 7.57 (d, 1H), 7.51-7.33 (m, 5H), 7.48 (d, 1H), 7.45 (s, 1H), 7.26 (s, 1H), 7.26 (d, 1H), 7.19 (dd, 1H), 7.18 (dm, 2H), 7.13 (d, 1H), 6.86 (dm, 2H), 5.16 (s, 2H), 4.85 (t, 1H), 4.62 (t, 2H), 4.49/4.44 (d+d, 2H), 4.29 (s, 2H), 4.27/4.21 (d+d, 2H), 3.91 (q, 2H), 3.72 (s, 3H), 3.35 (t, 2H), 3.2/3.16 (dd+dd, 2H), 2.77 (s, 3H), 2.2 (s, 3H), 1.89 (m, 2H), 1.45 (m, 2H), 0.96 (t, 3H)

Step 2: Preparation of ethyl 3-{3-[(7-chloro-6-hydroxy-2,2-dioxo-2H-1,$2\lambda^6$,3-benzoxathiazin-3(4H)-yl)methyl]-4-methylphenyl}-3-[1-(4-hydroxybutyl)-4-methyl-1H-benzotriazol-5-yl]propanoate Using General Procedure 8 starting from ethyl 3-[3-[(6-benzyloxy-7-chloro-2,2-dioxo-4H-1,$2\lambda^6$,3-benzoxathiazin-3-yl)methyl]-4-methyl-phenyl]-3-[1-[4-[(4-methoxyphenyl) methoxy]butyl]-4-methyl-benzotriazol-5-yl]propanoate (1 eq.) as a reactant, the title compound (yellow oil, 74% yield) was obtained.

$^1$H-NMR (500 MHz, DMSO-d6) δ ppm: 10.48 (brs, 1H), 7.61 (d, 1H), 7.51 (d, 1H), 7.31 (s, 1H), 7.27 (d, 1H), 7.19 (dd, 1H), 7.13 (d, 1H), 6.85 (s, 1H), 4.83 (t, 1H), 4.64 (t, 2H), 4.45/4.42 (d+d, 2H), 4.43 (brs, 1H), 4.25/4.2 (d+d, 2H), 3.93 (q, 2H), 3.37 (t, 2H), 3.17 (d, 2H), 2.76 (s, 3H), 2.22 (s, 3H), 1.9 (m, 2H), 1.35 (m, 2H), 0.99 (t, 3H)

Step 3: Preparation of ethyl[23-chloro-4,31-dimethyl-27,27-dioxo-21,26-dioxa-$27\lambda^6$-thia-1,14,15,16-tetraazahexacyclo[20.5.3.$1^{3,7}$0.$1^{9,13}$0.$0^{12,16}$0.$0^{25,29}$]dotriaconta-3(32),4,6,9(31),10,12,14,22,24,29-decaen-8-yl]acetate Using General Procedure 10 starting from ethyl 3-{3-[(7-chloro-6-hydroxy-2,2-dioxo-2H-1,$2\lambda^6$,3-benzoxathiazin-3(4H)-yl)methyl]-4-methylphenyl}-3-[1-(4-hydroxybutyl)-4-methyl-1H-benzotriazol-5-yl]propanoate (1 eq.) as a reactant, ethyl 3-[1-(4-chlorobutyl)-4-methyl-1H-benzotriazol-5-yl]-3-{3-[(7-chloro-6-hydroxy-2,2-dioxo-2H-1,$2\lambda^6$, 3-benzoxathiazin-3(4H)-yl)methyl]-4-methylphenyl}propanoate (yellow solid foam, quant.) was obtained, which was reacted in the next step without further purification using General Procedure 11. The title compound (white solid) was obtained (64% yield).

$^1$H-NMR (500 MHz, DMSO-d6) δ ppm: 7.68 (d, 1H), 7.47 (dd, 1H), 7.47 (d, 1H), 7.35 (s, 1H), 7.27 (d, 1H), 6.67 (d, 1H), 6.1 (s, 1H), 4.85/4.74 (dm+dm, 2H), 4.77 (t, 1H), 4.27/3.9 (d+d, 2H), 4/3.76 (d+d, 2H), 3.92 (q, 2H), 3.7/3.44 (m+m, 2H), 3.13/3.06 (dd+dd, 2H), 2.64 (s, 3H), 2.31 (s, 3H), 2.22/1.99 (m+m, 2H), 1.82/1.62 (m+m, 2H), 1.01 (t, 3H)

Step 4: Preparation of [23-chloro-4,31-dimethyl-27,27-dioxo-21,26-dioxa-$27\lambda^6$-thia-1,14,15,16-tetraazahexacyclo[20.5.3.$1^{3,7}$0.$1^{9,13}$0.$0^{12,16}$0.$0^{25,29}$]dotriaconta-3(32),4,6,9(31),10,12,14,22,24,29-decaen-8-yl]acetic acid Using General Procedure 12 starting from ethyl[23-chloro-4,31-dimethyl-27,27-dioxo-21,26-dioxa-$27\lambda^6$-thia-1,14,15,16-tetraazahexacyclo[20.5.3.$1^{3,7}$0.$1^{9,13}$0.$0^{12,16}$0.$0^{25,29}$]dotriaconta-3(32),4,6,9(31),10,12,14,22,24,29-decaen-8-yl]acetate (1 eq.) as a reactant, the title compound (white solid, 94% yield) was obtained.

The enantiopure products were obtained by chromatographic separation on chiral column.

EXAMPLE 22a (E1)

HRMS calculated for $C_{29}H_{29}ClN_4O_6S$: 596.1497; $[M+H]^+$ found: 597.1564 (δ=−0.9 ppm).

EXAMPLE 22b (E2)

HRMS calculated for $C_{29}H_{29}ClN_4O_6S$: 596.1497; $[M+H]^+$ found: 597.1549 (δ=−3.4 ppm).

$^1$H-NMR (500 MHz, DMSO-d6) δ ppm: 12.23 (brs, 1H), 7.68 (d, 1H), 7.48 (dd, 1H), 7.46 (d, 1H), 7.35 (s, 1H), 7.27 (d, 1H), 6.65 (d, 1H), 6.09 (s, 1H), 4.85/4.74 (m+m, 2H), 4.75 (m, 1H), 4.26/3.91 (d+d, 2H), 4.01/3.77 (d+d, 2H), 3.69/3.42 (m+m, 2H), 3.02/2.96 (dd+dd, 2H), 2.64 (s, 3H), 2.31 (s, 3H), 2.22/2.01 (m+m, 2H), 1.83/1.63 (m+m, 2H)

$^{13}$C-NMR (125 MHz, DMSO-d6) δ ppm: 131.3, 131.2, 128.7, 127.2, 120.1, 111.5, 107.9, 68.7, 52.1, 48.7, 48.1, 41.8, 40.9, 26.7, 25.5, 18.5, 13.4

EXAMPLE 23: [(2R,8R)-24-Methoxy-2,4,31-trimethyl-27,27-dioxo-21,26-dioxa-$27\lambda^6$-thia-1,14,15,16-tetraazahexacyclo[20.5.3.$1^{3,7}$0.$1^{9,13}$0.$0^{12,16}$0.$0^{25,29}$]dotriaconta-3(32),4,6,9(31),10,12,14,22,24,29-decaen-8-yl]acetic acid and [(2R,8S)-24-methoxy-2,4,31-trimethyl-27,27-dioxo-21,26-dioxa-$27\lambda^6$-thia-1,14,15,16-tetraazahexacyclo[20.5.3.$1^{3,7}$0.$1^{9,13}$0.$0^{12,16}$0.$0^{25,29}$]dotriaconta-3(32),4,6,9(31),10,12,14,22,24,29-decaen-8-yl]acetic acid

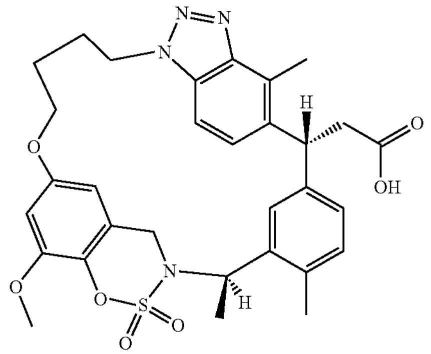

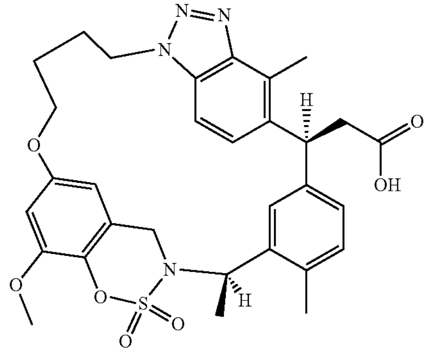

Step 1: Preparation of ethyl 3-(3-{(1R)-1-[6-(benzyloxy)-8-methoxy-2,2-dioxo-2H-1,$2\lambda^6$,3-benzoxathiazin-3(4H)-yl]ethyl}-4-methylphenyl)-3-(1-{4-[(4-methoxyphenyl)methoxy]butyl}-4-methyl-1H-benzotriazol-5-yl)propanoate Using General Procedure 7 starting from ethyl 3-{3-[(1R)-1-hydroxyethyl]-4-methylphenyl}-3-(1-{4-[(4-methoxyphenyl)methoxy]butyl}-4-methyl-1H-benzotriazol-5-yl)propanoate (1 eq.) and 6-(benzyloxy)-8-methoxy-3,4-dihydro-2H-1,$2\lambda^6$,3-benzoxathiazine-2,2-dione (1.05 eq.) as reactants, the title compound (79% yield) was obtained.

$^1$H-NMR (400 MHz, DMSO-d6) δ ppm: 0.88-1.05 (m, 14H) 1.13-1.30 (m, 10H) 1.36-1.49 (m, 20H) 1.82-1.94 (m, 9H) 2.27 (s, 11H) 2.74-2.81 (m, 11H) 3.12-3.26 (m, 8H) 3.34

(q, J=6.15 Hz, 8H) 3.72 (s, 13H) 3.81 (s, 11H) 3.92 (q, J=7.09 Hz, 8H) 4.23-4.36 (m, 11H) 4.39 (s, 4H) 4.55-4.65 (m, 8H) 4.87 (t, J=7.76 Hz, 4H) 5.01-5.14 (m, 7H) 5.21-5.30 (m, 3H) 6.35 (d, J=2.57 Hz, 1H) 6.42 (d, J=2.57 Hz, 1H) 6.72-6.78 (m, 1H) 6.86 (d, J=8.56 Hz, 2H) 7.07-7.14 (m, 2H) 7.17 (d, J=8.56 Hz, 2H) 7.28-7.38 (m, 1H) 7.38-7.44 (m, 3H) 7.44-7.49 (m, 2H) 7.49-7.55 (m, 1H) 7.56-7.62 (m, 1H)

Step 2: Preparation of ethyl 3-[1-(4-hydroxybutyl)-4-methyl-1H-benzotriazol-5-yl]-3-{3-[(1R)-1-(6-hydroxy-8-methoxy-2,2-dioxo-2H-1,2λ$^6$,3-benzoxathiazin-3(4H)-yl)ethyl]-4-methylphenyl}propanoate Using General Procedure 8 starting from ethyl 3-(3-{(1R)-1-[6-(benzyloxy)-8-methoxy-2,2-dioxo-2H-1,2λ$^6$,3-benzoxathiazin-3(4H)-yl]ethyl}-4-methylphenyl)-3-(1-{4-[(4-methoxyphenyl)methoxy]butyl}-4-methyl-1H-benzotriazol-5-yl)propanoate (1 eq.) as a reactant, the title compound (yellow solid, 98% yield) was obtained.

$^1$H-NMR (400 MHz, DMSO-d6) δ ppm: 0.92-1.06 (m, 6H) 1.10-1.48 (m, 13H) 1.90 (quin, J=7.18 Hz, 4H) 2.27 (s, 5H) 2.70-2.79 (m, 5H) 3.22 (d, J=7.70 Hz, 3H) 3.34-3.42 (m, 4H) 3.77 (s, 5H) 3.88-3.99 (m, 3H) 4.27 (d, J=5.26 Hz, 1H) 4.33 (d, J=2.32 Hz, 1H) 4.37-4.46 (m, 1H) 4.65 (t, J=6.97 Hz, 2H) 4.80-4.94 (m, 1H) 5.24 (q, J=6.77 Hz, 1H) 6.10 (d, J=2.45 Hz, 1H) 6.15 (d, J=2.57 Hz, 1H) 6.40-6.49 (m, 1H) 6.76-6.84 (m, 1H) 7.04-7.16 (m, 3H) 7.45 (d, J=10.15 Hz, 1H) 7.53-7.59 (m, 1H) 7.59-7.66 (m, 1H) 9.60-9.65 (m, 1H)

Step 3: Preparation of ethyl 3-[1-(4-bromobutyl)-4-methyl-1H-benzotriazol-5-yl]-3-{3-[(1R)-1-(6-hydroxy-8-methoxy-2,2-dioxo-2H-1,2λ$^6$,3-benzoxathiazin-3(4H)-yl)ethyl]-4-methylphenyl}propanoate Using General Procedure 9 starting from ethyl 3-[1-(4-hydroxybutyl)-4-methyl-1H-benzotriazol-5-yl]-3-{3-[(1R)-1-(6-hydroxy-8-methoxy-2,2-dioxo-2H-1,2λ$^6$,3-benzoxathiazin-3(4H)-yl)ethyl]-4-methylphenyl}propanoate (1 eq.) as a reactant, the title compound (65% yield) was obtained.

$^1$H-NMR (400 MHz, DMSO-d6) δ ppm: 1.00 (q, J=6.89 Hz, 5H) 1.35-1.46 (m, 3H) 1.77 (quin, J=7.03 Hz, 3H) 1.94-2.05 (m, 5H) 2.27 (s, 4H) 2.76 (s, 4H) 3.22 (d, J=7.70 Hz, 3H) 3.53 (t, J=6.66 Hz, 3H) 3.76 (s, 4H) 3.94 (qd, J=7.09, 2.32 Hz, 3H) 4.23-4.37 (m, 2H) 4.69 (t, J=6.79 Hz, 3H) 4.81-4.94 (m, 2H) 5.24 (d, J=6.72 Hz, 1H) 6.03-6.18 (m, 2H) 6.34-6.51 (m, 2H) 6.96-7.22 (m, 3H) 7.44 (d, J=11.37 Hz, 1H) 7.52-7.68 (m, 3H) 9.63 (d, J=5.14 Hz, 1H)

Step 4: Preparation of ethyl[(2R)-24-methoxy-2,4,31-trimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate Using General Procedure 11 starting from ethyl 3-[1-(4-bromobutyl)-4-methyl-1H-benzotriazol-5-yl]-3-{3-[(1R)-1-(6-hydroxy-8-methoxy-2,2-dioxo-2H-1,2λ$^6$,3-benzoxathiazin-3(4H)-yl)ethyl]-4-methylphenyl}propanoate (1 eq.) as a reactant, the title compound (white solid, 69% yield) was obtained.

$^1$H-NMR (400 MHz, DMSO-d6) δ ppm: 0.92-1.06 (m, 11H) 1.11 (d, J=6.85 Hz, 4H) 1.27 (d, J=6.85 Hz, 8H) 1.54-1.92 (m, 8H) 2.00-2.22 (m, 7H) 2.23-2.36 (m, 13H) 2.66 (s, 7H) 2.81 (s, 4H) 2.92-3.15 (m, 5H) 3.33-3.50 (m, 7H) 3.59-3.79 (m, 14H) 3.83-4.00 (m, 10H) 4.64-4.99 (m, 11H) 5.15-5.31 (m, 5H) 5.37 (br. s., 1H) 6.46 (dd, J=19.93, 2.45 Hz, 3H) 6.73 (s, 1H) 7.08-7.25 (m, 4H) 7.30 (d, J=8.07 Hz, 1H) 7.44 (d, J=7.70 Hz, 3H) 7.68 (d, J=8.68 Hz, 1H) 7.75 (d, J=8.80 Hz, 1H) 7.89 (d, J=8.80 Hz, 1H)

Step 5: Preparation of Example 23

Using General Procedure 12 starting from ethyl[(2R)-24-methoxy-2,4,31-trimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (1 eq.) as a reactant, the title compound (72% yield) was obtained.

The enantiopure products were obtained by chromatographic separation on chiral column.

EXAMPLE 23a (2R,8R)

HRMS calculated for $C_{31}H_{34}N_4O_7S$: 606.2148; $[M+H]^+$ found: 607.2223 (δ=0.3 ppm).

$^1$H-NMR (400 MHz, DMSO-d6) δ ppm: 12 (s1, 1H), 7.69 (d, 1H), 7.44 (dd, 1H), 7.39 (d, 1H), 7.09 (d, 1H), 6.72 (d, 1H), 6.42 (d, 1H), 5.38 (d1, 1H), 5.21 (q, 1H), 4.89 (t, 1H), 4.76 (m, 2H), 4.02/3.4 (2*d, 2H), 3.7 (m, 2H), 3.7 (s, 3H), 3.28/2.87 (dd, 2H), 2.81 (s, 3H), 2.31 (s, 3H), 2.2/2 (m, 2H), 1.61/1.28 (m, 2H), 1.11 (d, 3H)

EXAMPLE 23b (2R,8S)

HRMS calculated for $C_{31}H_{34}N_4O_7S$: 606.2148; $[M+H]^+$ found: 607.2224 (δ=0.5 ppm).

$^1$H-NMR (400 MHz, DMSO-d6) δ ppm: 12.2 (s1, 1H), 7.88/7.74 (d, 2H), 7.44 (dd, 1H), 7.2 (d, 1H), 7.11 (d, 1H), 6.49 (d, 1H), 5.23 (q, 1H), 5.19 (d, 1H), 4.8-4.67 (m, 1H), 4.8-4.67 (m, 2H), 3.99/3.36 (d, 2H), 3.73 (s, 3H), 3.63/3.41 (m, 2H), 3.28/2.96 (dd, 2H), 2.64 (s, 3H), 2.29 (s, 3H), 2.18/2.09 (m, 2H), 1.87/1.74 (m, 2H), 1.27 (d, 3H)

EXAMPLE 24: [(2R,8S)-18-(2-Methoxyethyl)-2,4,31-trimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid and [(2R,8R)-18-(2-methoxyethyl)-2,4,31-trimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid diastereoisomer 1

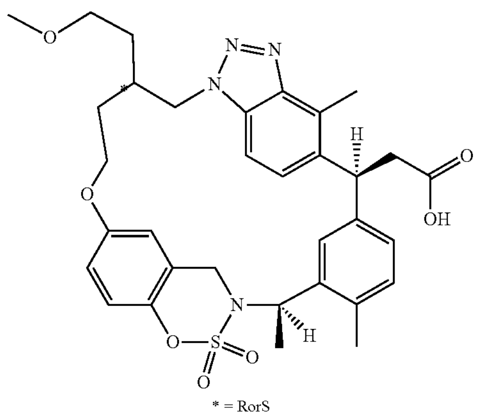

* = RorS

-continued diastereoisomer

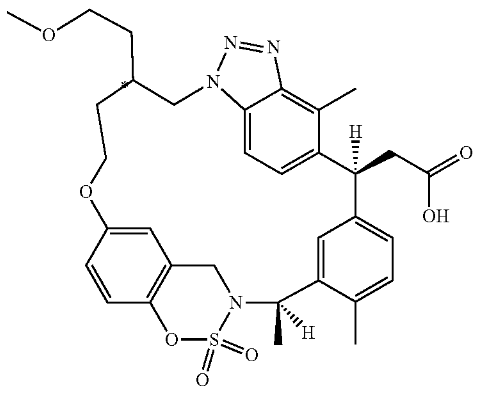

* = RorS diastereoisomer 1

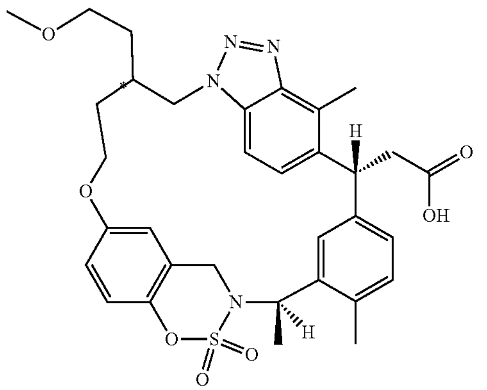

* = RorS diastereoisomer 2

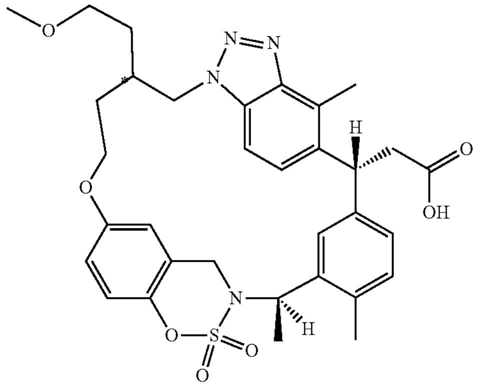

* = RorS

Step A1: Preparation of 2-[2-(benzyloxy)ethyl]-4-methoxybutanenitrile

To a solution of 4-methoxybutanenitrile (6.88 g, 69.4 mmol) in abs. THF (1 mL/mmol, 70 mL) lithium trimethyl-N-(trimethylsilyl)silanaminide (1.2 eq., 1 M in THF, 83.3 mL, 83.3 mmol) was added dropwise at −78° C. while continuous stirring. [(2-iodoethoxy)methyl]benzene (1.2 eq., 21.8 g, 83.3 mmol) dissolved in 35 mL of THF was added dropwise at −78° C. The reaction mixture was allowed to warm to RT and was stirred overnight. After completion of the reaction the mixture was quenched with water. 200 mL of EtOAc was added and the layers were separated. The organic layer was washed with 150 mL of brine and dried over anhydrous $Na_2SO_4$. Filtration and concentration to dryness afforded a crude product, which was purified by normal phase silica gel chromatography using heptane-EtOAc (100:0 to 70:30) as an eluent to give the title compound (8.1 g, 50% yield).

$^1$H-NMR (400 MHz, DMSO-d6) δ ppm: 7.4-7.25 (m, 5H), 4.5 (s, 2H), 3.55 (m, 2H), 3.45 (m, 2H), 3.25 (s, 3H), 2.95 (m, 1H), 1.9-1.7 (m, 4H)

Step A2: Preparation of 2-[2-(benzyloxy)ethyl]-4-methoxybutan-1-amine

Lithium aluminium hydride (1 eq., 1.3 g, 35 mmol) was placed into a round bottom flask. After addition of abs. THF (70 ml) the mixture was cooled to 10° C. A solution of 2-[2-(benzyloxy)ethyl]-4-methoxybutanenitrile (8.1 g, 35 mmol) in abs. THF (70 mL) was added dropwise at 10° C. while continuous stirring over a period of 15 min. The reaction mixture was allowed to warm to RT and stirred for further 3 h at this temperature. After completion of the reaction the mixture was cooled to 10° C. and quenched with aq. $Na_2SO_4$. The mixture was stirred overnight at RT and filtered. The filter cake was washed with THF. The mother liquor was concentrated to dryness to give the title compound (8.3 g, 96% yield).

$^1$H-NMR (400 MHz, DMSO-d6) δ ppm: 7.39-7.22 (m, 5H), 4.44 (s, 2H), 3.45 (t, 2H), 3.32 (t, 2H), 3.19 (s, 3H), 2.46 (d, 2H), 1.68-1.37 (m, 5H), 1.44-1.14 (m, 2H)

Step A3: Preparation of N-{2-[2-(benzyloxy)ethyl]-4-methoxybutyl}-3-methyl-2-nitroaniline Using General Procedure 2 STEP 1 starting from 1-fluoro-3-methyl-2-nitro-benzene (1 eq.) and 2-[2-(benzyloxy)ethyl]-4-methoxybutan-1-amine (1.2 eq) as reactants, the title compound (50% yield) was obtained.

$^1$H-NMR (400 MHz, DMSO-d6) δ ppm: 7.3 (m, 5H), 7.2 (t, 1H), 6.75 (d, 1H), 6.5 (d+t, 2H), 4.45 (s, 2H), 3.5 (m, 2H), 3.4 (m, 2H), 3.2 (s, 3H), 3.15 (m, 2H), 2.3 (s, 3H), 1.9 (sept., 1H), 1.55 (m, 4H)

Step A4: Preparation of N-{2-[2-(benzyloxy)ethyl]-4-methoxybutyl}-4-bromo-3-methyl-2-nitroaniline Using General Procedure 2 STEP 2 starting from N-{2-[2-(benzyloxy)ethyl]-4-methoxybutyl}-3-methyl-2-nitroaniline (1 eq.) as a reactant, the title compound (62% yield) was obtained.

$^1$H-NMR (400 MHz, DMSO-d6) δ ppm: 7.42 (d, 1H), 7.31 (t, 2H), 7.28 (d+t, 3H), 6.7 (d, 1H), 6.2 (t), 4.43 (s, 2H), 3.5 (m, 2H), 3.35 (m, 2H), 3.2 (s, 3H), 3.1 (m, 2H), 2.25 (s, 3H), 1.88 (m, 1H), 1.64-1.42 (m, 4H)

Step A5: Preparation of $N^1$-{2-[2-(benzyloxy)ethyl]-4-methoxybutyl}-4-bromo-3-methylbenzene-1,2-diamine Using General Procedure 2 STEP 3 starting from N-{2-[2-(benzyloxy)ethyl]-4-methoxybutyl}-4-bromo-3-methyl-2-nitroaniline (1 eq.) as a reactant, the title compound (quant.) was obtained.

$^{1}$H-NMR (400 MHz, DMSO-d6) δ ppm: 7.3 (m, 5H), 6.69 (d, 1H), 6.25 (d, 1H), 4.68 (m, 3H), 4.45 (s, 2H), 3.5 (m, 2H), 3.4 (m, 2H), 3.2 (s, 3H), 2.98 (d, 2H), 2.19 (s, 3H), 1.9 (m, 1H), 1.75-1.5 (m, 4H)

Step A6: Preparation of 1-{2-[2-(benzyloxy)ethyl]-4-methoxybutyl}-5-bromo-4-methyl-1H-benzotriazole Using General Procedure 2 STEP 4 starting from $N^1$-{2-[2-(benzyloxy)ethyl]-4-methoxybutyl}-4-bromo-3-methylbenzene-1,2-diamine (1 eq.) as a reactant, the title compound (78% yield) was obtained.

$^{1}$H-NMR (400 MHz, DMSO-d6) δ ppm: 7.69 (d, 1H), 7.6 (d, 1H), 7.35-7.2 (m, 5H), 4.68 (d, 2H), 4.39 (m, 2H), 3.48 (m, 2H), 3.35 (m, 2H), 3.18 (s, 3H), 2.71 (s, 3H), 2.3 (m, 1H), 1.6-1.4 (m, 4H)

Step A7: Preparation of ethyl (2E)-3-(1-{2-[2-(benzyloxy)ethyl]-4-methoxybutyl}-4-methyl-1H-benzotriazol-5-yl)prop-2-enoate Using General Procedure 2 STEP 5 starting from 1-{2-[2-(benzyloxy)ethyl]-4-methoxybutyl}-5-bromo-4-methyl-1H-benzotriazole (1 eq.) as a reactant, the title compound (34% yield) was obtained.

$^{1}$H-NMR (400 MHz, DMSO-d6) δ ppm: 8.02 (d, 1H), 7.95 (d, 1H), 7.65 (d, 1H), 7.35-7.2 (m, 5H), 6.65 (d, 1H), 4.68 (d, 2H), 4.4 (s, 2H), 4.22 (q, 2H), 3.49 (m, 2H), 3.35 (m, 2H), 3.19 (s, 3H), 2.8 (s, 3H), 2.3 (m, 1H), 1.6-1.4 (m, 4H), 1.3 (t, 3H)

Step 1: Preparation of ethyl 3-(1-{2-[2-(benzyloxy)ethyl]-4-methoxybutyl}-4-methyl-1H-benzotriazol-5-yl)-3-{3-[(1S)-1-hydroxyethyl]-4-methylphenyl}propanoate Using General Procedure 6 starting from ethyl (2E)-3-(1-{2-[2-(benzyloxy)ethyl]-4-methoxybutyl}-4-methyl-1H-benzotriazol-5-yl)prop-2-enoate (1 eq.) and (1S)-1-[2-methyl-5-(4,4,5,5-tetramethyl-1,3,2-dioxaborolan-2-yl)phenyl]ethan-1-ol (1.2 eq.) as reactants, the title compound (83% yield) was obtained.

$^{1}$H-NMR (400 MHz, DMSO-d6) δ ppm: 7.5 (d, 1H), 7.45 (2d, 1H), 7.4 (d, 1H), 7.32-7.2 (m, 5H), 7.05 (2dd, 1H), 6.98 (2d, 1H), 4.99 (2d, 1H), 4.81 (m, 2H), 4.6 (d, 2H), 4.4 (s, 2H), 3.92 (q, 2H), 3.48 (2t, 2H), 3.3 (m, 2H), 3.12 (s, 3H), 3.1 (m, 2H), 2.78 (s, 3H), 2.28 (m, 1H), 2.19 (s, 3H), 1.6-1.4 (m, 4H), 1.22 (2d, 3H), 1 (t, 3H)

Step 2: Preparation of ethyl 3-(3-{(1R)-1-[6-(benzyloxy)-2,2-dioxo-2H-1,2λ$^6$,3-benzoxathiazin-3(4H)-yl]ethyl}-4-methylphenyl)-3-(1-{2-[2-(benzyloxy)ethyl]-4-methoxybutyl}-4-methyl-1H-benzotriazol-5-yl)propanoate Using General Procedure 7 starting from ethyl 3-(1-{2-[2-(benzyloxy)ethyl]-4-methoxybutyl}-4-methyl-1H-benzotriazol-5-yl)-3-{3-[(1S)-1-hydroxyethyl]-4-methylphenyl}propanoate (1 eq.) and 6-(benzyloxy)-8-methoxy-3,4-dihydro-2H-1,2λ$^6$,3-benzoxathiazine-2,2-dione (1.1 eq.) as reactants, the title compound (59% yield) was obtained.

$^{1}$H-NMR (400 MHz, DMSO-d6) δ ppm: 7.6-7.2 (m, 15H), 7.12-6.95 (m, 2H), 6.9/6.85 (2d, 1H), 5.28 (m, 1H), 5.1 (2s, 2H), 4.9 (m, 1H), 4.6 (d, 2H), 4.45-4.3 (m, 4H), 3.9 (q, 2H), 3.45 (m, 2H), 3.3/3.2 (2m, 5H), 3.1 (m, 2H), 2.8/2.3 (s, 6H), 2.28 (m, 1H), 1.5 (m, 4H), 1.4 (d, 3H), 1.22 (t, 3H)

Step 3: Preparation of ethyl 3-[3-[(1R)-1-(6-hydroxy-2,2-dioxo-4H-1,2λ6,3-benzoxathiazin-3-yl)ethyl]-4-methyl-phenyl]-3-[1-[2-(2-hydroxyethyl)-4-methoxy-butyl]-4-methyl-benzotriazol-5-yl]propanoate Using General Procedure 8 starting from ethyl 3-(3-{(1R)-1-[6-(benzyloxy)-2,2-dioxo-2H-1,2λ$^6$,3-benzoxathiazin-3(4H)-yl]ethyl}-4-methylphenyl)-3-(1-{12-[2-(benzyloxy)ethyl]-4-methoxybutyl}-4-methyl-1H-benzotriazol-5-yl)propanoate (1 eq.) as a reactant, the title compound (81% yield) was obtained.

$^{1}$H-NMR (400 MHz, DMSO-d6) δ ppm: 9.6/4.35 (s+t, 2H), 7.6 (m, 2H), 7.5 (d, 1H), 7.12 (m, 2H), 6.91 (d, 1H), 6.75 (dd, 1H), 6.6/6.55 (2d, 1H), 5.25 (q, 1H), 4.9 (m, 1H), 4.6 (d, 2H), 4.35 (m, 2H), 3.92 (q, 2H), 3.45 (m, 4H), 3.21 (d, 2H), 3.12 (s, 3H), 2.8 (s, 3H), 2.3 (s, 3H), 2.25 (m, 1H), 1.5-1.3 (m, 4H), 1.45 (d, 3H), 1.2 (t, 3H)

Step 4: Preparation of ethyl 3-{1-[2-(2-bromoethyl)-4-methoxybutyl]-4-methyl-1H-benzotriazol-5-yl}-3-{3-[(1R)-1-(6-hydroxy-2,2-dioxo-2H-1,2)$^6$,3-benzoxathiazin-3(4H)-yl)ethyl]-4-methylphenyl}propanoate Using General Procedure 9 starting from ethyl 3-[3-[(1R)-1-(6-hydroxy-2,2-dioxo-4H-1,2λ$^6$,3-benzoxathiazin-3-yl)ethyl]-4-methyl-phenyl]-3-[1-[2-(2-hydroxyethyl)-4-methoxy-butyl]-4-methyl-benzotriazol-5-yl]propanoate (1 eq.) as a reactant, the title compound (39% yield) was obtained.

$^{1}$H-NMR (400 MHz, DMSO-d6) δ ppm: 9.6 (s, 1H), 7.6 (d, 1H), 7.55 (d, 1H), 7.45 (2d, 1H), 7.11 (m, 2H), 6.9 (d, 1H), 6.71 (dd, 1H), 6.59 (2d, 1H), 5.28 (q, 1H), 4.9 (m, 1H), 4.61 (d, 2H), 4.4-4.3 (m, 2H), 3.92 (q, 2H), 3.58 (m, 2H), 3.3 (m, 2H), 3.21 (d, 2H), 3.15 (s, 3H), 2.78 (s, 3H), 2.3 (m, 1H), 2.28 (s, 3H), 1.9-1.7 (2m, 2H), 1.5 (m, 2H), 1.4 (d, 3H), 1 (2t, 3H)

Step 5: Preparation of Example 24

Using General Procedure 11 starting from ethyl 3-{1-[2-(2-bromoethyl)-4-methoxybutyl]-4-methyl-1H-benzotriazol-5-yl}-3-{3-[(1R)-1-(6-hydroxy-2,2-dioxo-2H-1,2λ$^6$,3-benzoxathiazin-3(4H)-yl)ethyl]-4-methylphenyl}propanoate (1 eq.) as a reactant, ethyl[(2R)-18-(2-methoxyethyl)-2,4,31-trimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (white solid, 57% yield) was obtained. The crude product was reacted using General Procedure 12 resulting the title compound (quant.).

The diastereo-pure products were obtained by chromatographic separation on chiral column.

EXAMPLE 24a (2R,8S dia1)

HRMS calculated for $C_{33}H_{38}N_4O_7S$: 634.246; $[M+H]^+$ found: 635.2534.

$^{1}$H-NMR (400 MHz, DMSO-d6) δ ppm: 12.2 (ml, 1H), 7.79 (d, 1H), 7.61 (d, 1H), 7.45 (dd, 1H), 7.22 (d, 1H), 7.02 (d, 1H), 6.9 (d, 1H), 6.7 (dd, 1H), 5.4 (d, 1H), 5.22 (q, 1H), 4.79 (dd, 1H), 4.75/4.6 (2dd, 2H), 4.12/3.4 (2d, 2H), 3.58

(m, 3H), 3.3 (s, 3H), 3.2-3 (m, 2H), 2.9 (dd, 1H), 2.6 (s, 3H), 2.3 (s, 3H), 1.9-1.7 (m, 5H), 1.2 (d, 3H)

EXAMPLE 24b (2R,8S dia2)

HRMS calculated for $C_{33}H_3N_4O_7S$: 634.246; $[M+H]^+$ found: 635.2534.

$^1$H-NMR (400 MHz, DMSO-d6) δ ppm: 12.2 (ml, 1H), 7.89 (d, 1H), 7.78 (d, 1H), 7.45 (dd, 1H), 7.21 (d, 1H), 7.04 (d, 1H), 6.95 (d, 1H), 6.75 (dd, 1H), 5.4 (d, 1H), 5.25 (q, 1H), 4.79 (dd, 1H), 4.61/4.55 (2dd, 2H), 4.05/3.35 (2d, 2H), 3.55 (t, 2H), 3.45 (m, 1H), 3.3 (m, 4H), 3.1/2.9 (2m, 2H), 2.6 (s, 3H), 2.3 (s, 3H), 1.9-1.7 (m, 5H), 1.2 (d, 3H)

EXAMPLE 24c (2R,8R dia1)

HRMS calculated for $C_{33}H_{38}N_4O_7S$: 634.246; $[M+H]^+$ found: 635.2536 (δ=0.3 ppm).

$^1$H-NMR (400 MHz, DMSO-d6) δ ppm: 7.6 (d, 1H), 7.49 (dd, 1H), 7.28 (d, 1H), 7.2 (d, 1H), 6.9 (d, 1H), 6.89 (d, 1H), 6.7 (dd, 1H), 5.6 (d, 1H), 5.26 (q, 1H), 4.9 (dd, 1H), 4.7/4.6 (2dd, 2H), 4.1/3.55 (2d, 2H), 3.6-3.35 (m, 4H), 3.3 (s, 3H), 3.2/2.88 (2m, 2H), 2.8 (s, 3H), 2.3 (s, 3H), 1.8 (m, 3H), 1.68/1.5 (2m, 2H), 1.2 (d, 3H)

EXAMPLE 24d (2R,8R dia2)

HRMS calculated for $C_{33}H_{38}N_4O_7S$: 634.246; $[M+H]^+$ found: 635.2535 (δ=0.2 ppm).

$^1$H-NMR (400 MHz, DMSO-d6) δ ppm: 7.7 (d, 1H), 7.49 (dd, 1H), 7.31 (d, 1H), 7.09 (d, 1H), 6.91 (d, 1H), 6.82 (d, 1H), 6.7 (dd, 1H), 5.65 (d, 1H), 5.26 (q, 1H), 4.95 (t, 1H), 4.6 (m, 2H), 4.05/3.6 (2d, 2H), 3.6-3.35 (m, 4H), 3.23 (s, 3H), 3.15/2.82 (2m, 2H), 2.8 (s, 3H), 2.32 (s, 3H), 1.88/1.78 (2m, 2H), 1.7 (m, 3H), 1.1 (d, 3H)

EXAMPLE 25 [23-Methoxy-4,31-dimethyl-27,27-dioxo-21,26-dioxa-27λ$^6$-thia-1,14,15,16-tetraaza-hexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid enantiomer 1

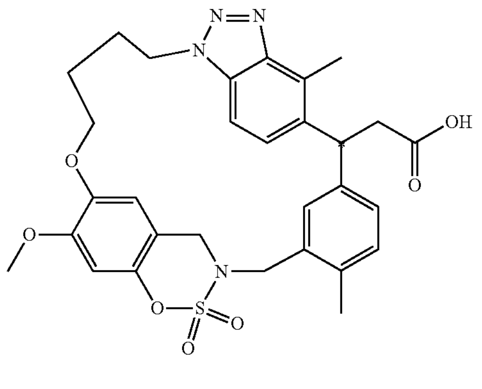

* = RorS

-continued enantiomer 2

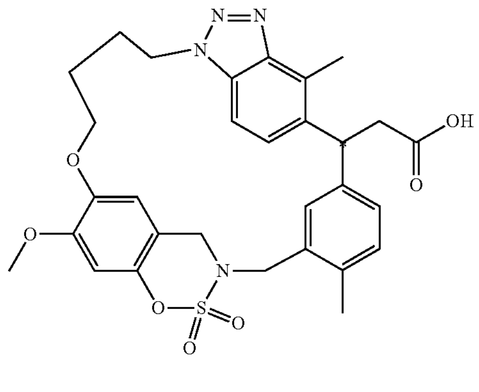

* = RorS

Step C1: Preparation of 5-(benzyloxy)-2-hydroxy-4-methoxybenzaldehyde

Using General Procedure 4 STEP 1 starting from 4-(benzyloxy)-3-methoxyphenol (1 eq.) as a reactant, the title compound (55% yield) was obtained.

$^1$H-NMR (500 MHz, DMSO-d6) δ ppm: 10.71 (s, 1H), 10.02 (s, 1H), 7.46-7.29 (m, 5H), 7.24 (s, 1H), 6.58 (s, 1H), 5.03 (s, 2H), 3.84 (s, 3H)

Step C2: Preparation of 6-(benzyloxy)-7-methoxy-2H-1,2)$^6$,3-benzoxathiazine-2,2-dione Using General Procedure 4 STEP 2 starting from 5-(benzyloxy)-2-hydroxy-4-methoxy-benzaldehyde (1 eq.) as a reactant, the title compound (67% yield) was obtained.

$^1$H-NMR (500 MHz, DMSO-d6) δ ppm: 8.96 (s, 1H), 7.64 (s, 1H), 7.5-7.33 (m, 5H), 7.26 (s, 1H), 5.14 (s, 2H), 3.95 (s, 3H)

Step C3: Preparation of 6-(benzyloxy)-7-methoxy-3,4-dihydro-2H-1,2λ$^6$,3-benzoxathiazine-2,2-dione Using General Procedure 4 STEP 3 starting from 6-(benzyloxy)-7-methoxy-2H-1,2λ$^6$,3-benzoxathiazine-2,2-dione (1 eq.) as a reactant, the title compound (white solid, 98% yield) was obtained.

$^1$H-NMR (500 MHz, DMSO-d6) δ ppm: 8.4 (t, 1H), 7.52-7.29 (m, 5H), 6.98 (s, 1H), 6.76 (s, 1H), 5.04 (s, 2H), 4.42 (d, 2H), 3.76 (s, 3H)

Step 1: Preparation of ethyl 3-(3-{[6-(benzyloxy)-7-methoxy-2,2-dioxo-2H-1,2λ$^6$,3-benzoxathiazin-3 (4H)-yl]methyl}-4-methylphenyl)-3-(1-{4-[(4-methoxyphenyl) methoxy]butyl}-4-methyl-1H-benzotriazol-5-yl)propanoate Using General Procedure 7 starting from ethyl 3-[3-(hydroxymethyl)-4-methylphenyl]-3-(1-{4-[(4-methoxy-phenyl)methoxy]butyl}-4-methyl-1H-benzotriazol-5-yl) propanoate (1 eq.) and 6-(benzyloxy)-7-methoxy-3,4-dihydro-2H-1,2λ$^6$,3-benzoxathiazine-2,2-dione (1.2 eq.) as reactants, the title compound (white solid, 74% yield) was obtained.

$^1$H-NMR (500 MHz, DMSO-d6) δ ppm: 7.57 (d, 1H), 7.48 (d, 1H), 7.48-7.31 (m, 5H), 7.22 (d, 1H), 7.19 (dd, 1H), 7.18 (m, 2H), 7.13 (d, 1H), 6.99 (s, 1H), 6.88 (s, 1H), 6.86 (m, 2H), 5.03 (s, 2H), 4.85 (t, 1H), 4.62 (t, 2H), 4.38/4.34 (d+d, 2H), 4.29 (s, 2H), 4.22/4.18 (d+d, 2H), 3.91 (q, 2H), 3.8 (s, 3H), 3.72 (s, 3H), 3.35 (t, 2H), 3.19/3.16 (dd+dd, 2H), 2.76 (s, 3H), 2.2 (s, 3H), 1.89 (m, 2H), 1.44 (m, 2H), 0.97 (t, 3H)

Step 2: Preparation of ethyl 3-[1-(4-hydroxybutyl)-4-methyl-1H-benzotriazol-5-yl]-3-{3-[(6-hydroxy-7-methoxy-2,2-dioxo-2H-1,2λ$^6$,3-benzoxathiazin-3(4H)-yl)methyl]-4-methylphenyl}propanoate Using General Procedure 8 starting from ethyl 3-(3-{[6-(benzyloxy)-7-methoxy-2,2-dioxo-2H-1,2λ$^6$,3-benzoxathiazin-3(4H)-yl]methyl}-4-methylphenyl)-3-(1-{4-[(4-methoxyphenyl) methoxy]butyl}-4-methyl-1H-benzotriazol-5-yl)propanoate (1 eq.) as a reactant, the title compound (quant.) was obtained.

$^1$H-NMR (500 MHz, DMSO-d6) δ ppm: 9.26 (s, 1H), 7.61 (d, 1H), 7.5 (d, 1H), 7.2 (s, 1H), 7.19 (dd, 1H), 7.13 (d, 1H), 6.8 (s, 1H), 6.6 (s, 1H), 4.83 (t, 1H), 4.65 (t, 2H), 4.63 (t, 1H), 4.3 (s, 2H), 4.19/4.16 (d+d, 2H), 3.93 (q, 2H), 3.79 (s, 3H), 3.37 (m, 2H), 3.18/3.14 (dd+dd, 2H), 2.75 (s, 3H), 2.21 (s, 3H), 1.9 (m, 2H), 1.35 (m, 2H), 1 (t, 3H)

Step 3: Preparation of ethyl 3-[1-(4-chlorobutyl)-4-methyl-1H-benzotriazol-5-yl]-3-{3-[(6-hydroxy-7-methoxy-2,2-dioxo-2H-1,2λ$^6$,3-benzoxathiazin-3(4H)-yl)methyl]-4-methylphenyl}propanoate hydrochloride Using General Procedure 10 starting from ethyl 3-[1-(4-hydroxybutyl)-4-methyl-1H-benzotriazol-5-yl]-3-{3-[(6-hydroxy-7-methoxy-2,2-dioxo-2H-1,2λ$^6$,3-benzoxathiazin-3(4H)-yl)methyl]-4-methylphenyl}propanoate (1 eq.) as a reactant, the title compound (quant.) was obtained.

$^1$H-NMR (500 MHz, DMSO-d6) δ ppm: 9.26 (s, 1H), 7.63 (d, 1H), 7.52 (d, 1H), 7.2 (m, 1H), 7.2 (m, 1H), 7.13 (d, 1H), 6.8 (s, 1H), 6.59 (s, 1H), 4.83 (t, 1H), 4.69 (t, 2H), 4.3 (s, 2H), 4.19/4.15 (d+d, 2H), 3.93 (q, 2H), 3.79 (s, 3H), 3.64 (t, 2H), 3.19/3.15 (dd+dd, 2H), 2.75 (s, 3H), 2.21 (s, 3H), 1.99 (m, 2H), 1.68 (m, 2H), 0.99 (t, 3H)

Step 4: Preparation of ethyl[23-methoxy-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate Using General Procedure 11 starting from ethyl 3-[1-(4-chlorobutyl)-4-methyl-1H-benzotriazol-5-yl]-3-{3-[(6-hydroxy-7-methoxy-2,2-dioxo-2H-1,2λ$^6$,3-benzoxathiazin-3(4H)-yl)methyl]-4-methylphenyl}propanoate hydrochloride (1 eq.) as a reactant, the title compound (white solid, 34% yield) was obtained.

$^1$H-NMR (500 MHz, DMSO-d6) δ ppm: 7.69 (d, 1H), 7.47 (dd, 1H), 7.46 (d, 1H), 7.28 (d, 1H), 6.75 (s, 1H), 6.56 (d, 1H), 5.77 (s, 1H), 4.82/4.75 (m+m, 2H), 4.78 (dd, 1H), 4.18/3.87 (d+d, 2H), 3.93 (q, 2H), 3.93/3.69 (d+d, 2H), 3.72 (s, 3H), 3.56/3.3 (m+m, 2H), 3.14/3.06 (dd+dd, 2H), 2.61 (s, 3H), 2.32 (s, 3H), 2.2/2.02 (m+m, 2H), 1.78/1.61 (m+m, 2H), 1.01 (t, 3H)

Step 5: Preparation of Example 25

Using General Procedure 12 starting from ethyl[23-methoxy-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (1 eq.) as a reactant, the title compound (white solid, 86% yield) was obtained.

The enantiopure products were obtained by chromatographic separation on chiral column.

EXAMPLE 25a (E1, optical purity: 99.9%)

HRMS calculated for $C_{30}H_{32}N_4O_7S$: 592.1992; $[M+H]^+$ found: 593.2048 (δ=−2.8 ppm).

EXAMPLE 25b (E2, optical purity-99.4%)

HRMS calculated for $C_{30}H_{32}N_4O_7S$: 592.1992; $[M+H]^+$ found: 593.2047 (δ=−2.9 ppm).

$^1$H-NMR (500 MHz, DMSO-d6) δ ppm: 12.54 (br., 1H), 7.68 (d, 1H), 7.48 (brd., 1H), 7.45 (d, 1H), 7.27 (d, 1H), 6.74 (s, 1H), 6.53 (brs., 1H), 5.75 (s, 1H), 4.81/4.74 (m+m, 2H), 4.75 (m, 1H), 4.16/3.87 (d+d, 2H), 3.93/3.69 (d+d, 2H), 3.72 (s, 3H), 3.55/3.28 (m+m, 2H), 2.99/2.92 (dd+dd, 2H), 2.6 (s, 3H), 2.32 (s, 3H), 2.2/2.03 (m+m, 2H), 1.78/1.61 (m+m, 2H)

$^{13}$C-NMR (125 MHz, DMSO-d6) δ ppm: 173.3, 131.3, 131.3, 128.8, 127.3, 110.8, 107.9, 102.9, 68.3, 56.3, 51.9, 48.4, 48.2, 42, 41.3, 27, 25.6, 18.5, 13.4

EXAMPLE 26: [(2R,8S)-2,4,33-Trimethyl-29,29-dioxo-20,23,28-trioxa-29λ$^6$-thia-1,14,15,16-tetraazahexacyclo[22.5.3.1$^{3,7}$0.1$^{9,13}$0.0$^{12,16}$0.0$^{27,31}$]tetratriaconta-3(34),4,6,9(33),10,12,14,24,26,31-decaen-8-yl]acetic acid and [(2R,8R)-2,4,33-trimethyl-29,29-dioxo-20,23,28-trioxa-29λ$^6$-thia-1,14,15,16-tetraazahexacyclo[22.5.3.1$^{3,7}$0.1$^{9,13}$0.0$^{12,16}$0.0$^{27,31}$]tetratriaconta-3(34),4,6,9(33),10,12,14,24,26,31-decaen-8-yl]acetic acid

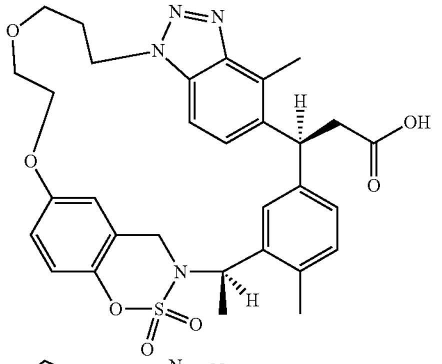

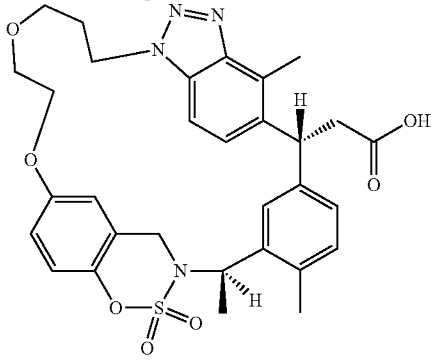

Step A1: Preparation of N-{3-[2-(benzyloxy)ethoxy]propyl}-3-methyl-2-nitroaniline Using General Procedure 2 STEP 1 starting from 1-fluoro-3-methyl-2-nitrobenzene (1 eq.) and 3-[2-(benzyloxy)ethoxy]propan-1-amine hydrochloride (1.2 eq) as a reactant, the title compound (85% yield) was obtained.

$^1$H-NMR (400 MHz, DMSO-d6) δ ppm: 7.38-7.27 (m, 5H), 7.24 (dd, 1H), 6.77 (d, 1H), 6.54 (d, 1H), 6.48 (t, 1H), 4.49 (s, 2H), 3.58 (m, 4H), 3.5 (t, 2H), 3.23 (q, 2H), 2.3 (s, 3H), 1.8 (quint, 2H)

Step A2: Preparation of N-{3-[2-(benzyloxy)ethoxy]propyl}-4-bromo-3-methyl-2-nitroaniline Using General Procedure 2 STEP 2 starting from N-{3-[2-(benzyloxy)ethoxy]propyl}-3-methyl-2-nitroaniline (1 eq.) as a reactant, the title compound (99% yield) was obtained.

$^1$H-NMR (400 MHz, DMSO-d6) δ ppm: 7.49 (d, 1H), 7.38-7.25 (m, 5H), 6.72 (d, 1H), 6.18 (t, 1H), 4.49 (s, 2H), 3.6-3.5 (m, 4H), 3.48 (t, 2H), 3.2 (q, 2H), 2.25 (s, 3H), 1.77 (quint, 2H)

Step A3: Preparation of N-{3-[2-(benzyloxy)ethoxy]propyl}-4-bromo-3-methylbenzene-1,2-diamine Using General Procedure 2 STEP 3 starting from N-{3-[2-(benzyloxy)ethoxy]propyl}-4-bromo-3-methyl-2-nitroaniline (1 eq.) as a reactant, the title compound (quant.) was obtained.

$^1$H-NMR (400 MHz, DMSO-d6) δ ppm: 7.37-7.24 (m, 5H), 6.71 (d, 1H), 6.27 (d, 1H), 4.9-4.5 (m, 3H), 4.49 (s, 2H), 3.56 (m, 4H), 3.52 (t, 2H), 3.06 (t, 2H), 2.16 (s, 3H), 1.82 (m, 2H)

Step A4: Preparation of 1-{3-[2-(benzyloxy)ethoxy]propyl}-5-bromo-4-methyl-1H-benzotriazole Using General Procedure 2 STEP 4 starting from N$^1$-{3-[2-(benzyloxy)ethoxy]propyl}-4-bromo-3-methylbenzene-1,2-diamine (1 eq.) as a reactant, the title compound (42% yield) was obtained.

$^1$H-NMR (400 MHz, DMSO-d6) δ ppm: 2.13 (quint, J=6.39 Hz, 2H) 2.71 (s, 3H) 3.35 (t, J=6.05 Hz, 2H) 3.41-3.58 (m, 6H) 4.43-4.47 (m, 3H) 4.74 (t, J=6.72 Hz, 2H) 7.20-7.37 (m, 9H) 7.55-7.68 (m, 3H)

Step A5: Preparation of ethyl (2E)-3-(1-{3-[2-(benzyloxy)ethoxy]propyl}-4-methyl-1H-benzotriazol-5-yl)prop-2-enoate Using General Procedure 2 STEP 5 starting from 1-{3-[2-(benzyloxy)ethoxy]propyl}-5-bromo-4-methyl-1H-benzotriazole (1 eq.) as a reactant, the title compound (98% yield) was obtained.

$^1$H-NMR (400 MHz, DMSO-d6) δ ppm: 8.01 (d, 1H), 7.89 (d, 1H), 7.69 (d, 1H), 7.38-7.25 (m+m, 5H), 6.61 (d, 1H), 4.74 (t, 2H), 4.47 (s, 2H), 4.22 (q, 2H), 3.54-3.47 (m+m, 4H), 3.37 (t, 2H), 2.8 (s, 3H), 2.23 (quint, 2H), 1.29 (t, 3H)

Step 1: Preparation of ethyl 3-(1-{3-[2-(benzyloxy)ethoxy]propyl}-4-methyl-1H-benzotriazol-5-yl)-3-{3-[(1S)-1-hydroxyethyl]-4-methylphenyl}propanoate Using General Procedure 6 starting from ethyl (2E)-3-(1-{3-[2-(benzyloxy)ethoxy]propyl}-4-methyl-1H-benzotriazol-5-yl)prop-2-enoate (1 eq.) and (1S)-1-[2-methyl-5-(4,4,5,5-tetramethyl-1,3,2-dioxaborolan-2-yl)phenyl]ethan-1-ol (1 eq.) as reactants, the title compound (59% yield) was obtained.

$^1$H-NMR (400 MHz, DMSO-d6) δ ppm: 7.56 (d, 1H), 7.41 (d, 1H), 7.39 (m, 1H), 7.35-7.22 (m, 5H), 7.02 (dd, 1H), 6.99 (d, 1H), 4.97 (m, 1H), 4.82 (m, 1H), 4.82 (m, 1H), 4.68 (t, 2H), 4.46 (s, 2H), 3.92 (q, 2H), 3.52/3.49 (m, 4H), 3.35 (t, 2H), 3.14-3.07 (m, 2H), 2.75 (s, 3H), 2.19 (s, 3H), 2.1 (quint, 2H), 1.21 (d, 3H), 1 (t, 3H)

Step 2: Preparation of ethyl 3-{3-[(1R)-1-(6-hydroxy-2,2-dioxo-2H-1,2λ$^6$,3-benzoxathiazin-3(4H)-yl)ethyl]-4-methylphenyl}-3-{1-[3-(2-hydroxyethoxy)propyl]-4-methyl-1H-benzotriazol-5-yl}propanoate Using General Procedure 7 starting from ethyl 3-(1-{3-[2-(benzyloxy)ethoxy]propyl}-4-methyl-1H-benzotriazol-5-yl)-3-{3-[(1S)-1-hydroxyethyl]-4-methylphenyl}propanoate (1 eq.) and 6-(benzyloxy)-3,4-dihydro-2H-1,2λ$^6$,3-benzoxathiazine-2,2-dione (1.1 eq.) as reactants, ethyl 3-(3-{(1R)-1-[6-(benzyloxy)-2,2-dioxo-2H-1,2λ$^6$,3-benzoxathiazin-3(4H)-yl]ethyl}-4-methylphenyl)-3-(1-{3-[2-(benzyloxy)ethoxy]propyl}-4-methyl-1H-benzotriazol-5-yl)propanoate (orange oil, 84% yield) was obtained. The crude product was reacted using General Procedure 8 resulting the title compound (white solid, 87% yield).

$^1$H-NMR (400 MHz, DMSO-d6) δ ppm: 9.62 (m, 1H), 7.64-7.54 (m, 2H), 7.47/7.47 (2s1, 1H), 7.14-7.08 (m, 2H), 6.92/6.9 (2d, 1H), 6.76-6.7 (m, 1H), 6.57 (2d, 1H), 5.25 (m, 1H), 4.88 (q, 1H), 4.7 (t, 2H), 4.57 (m, 1H), 4.36/4.31 (s+dd, 2H), 3.95 (2d, 2H), 3.47 (m, 2H), 3.39-3.28 (m, 4H), 3.22 (m, 2H), 2.77 (s, 3H), 2.28 (s, 3H), 2.1 (m, 2H), 1.43/1.41 (2d, 3H), 1.01/1 (2t, 3H)

Step 3: Preparation of ethyl 3-{1-[3-(2-bromoethoxy)propyl]-4-methyl-1H-benzotriazol-5-yl}-3-{3-[(1R)-1-(6-hydroxy-2,2-dioxo-2H-1,2λ$^6$,3-benzoxathiazin-3(4H)-yl)ethyl]-4-methylphenyl}propanoate Using General Procedure 9 starting from ethyl 3-{3-[(1R)-1-(6-hydroxy-2,2-dioxo-2H-1,2λ$^6$,3-benzoxathiazin-3(4H)-yl)ethyl]-4-methylphenyl}-3-{11-[3-(2-hydroxyethoxy)propyl]-4-methyl-1H-benzotriazol-5-yl}propanoate (1 eq.) as a reactant, the title compound (white solid, 60% yield) was obtained.

$^1$H-NMR (400 MHz, DMSO-d6) δ ppm: 9.55 (s, 1H), 7.7-7.5 (2d, 2H), 7.49 (2d, 1H), 7.11 (m, 2H), 6.91 (d, 1H), 6.71 (2dd, 1H), 6.48 (2d, 1H), 5.28 (m, 1H), 4.9 (m, 1H), 4.7 (t, 2H), 4.4-4.3 (m, 2H), 3.95 (q, 2H), 3.68 (t, 2H), 3.55 (t, 2H), 3.41 (t, 2H), 3.21 (d, 2H), 2.79 (s, 3H), 2.3 (s, 3H), 2.12 (m, 2H), 1.45 (2d, 3H), 1.02 (2t, 3H)

Step 4: Preparation of ethyl[(2R)-2,4,33-trimethyl-29,29-dioxo-20,23,28-trioxa-29)$^6$-thia-1,14,15,16-tetraazahexacyclo[22.5.3.1$^{3,7}$0.1$^{9,13}$0.0$^{12,16}$0.0$^{27,31}$]tetratriaconta-3(34),4,6,9(33),10,12,14,24,26,31-decaen-8-yl]acetate Using General Procedure 11 starting from ethyl 3-{1-[3-(2-bromoethoxy)propyl]-4-methyl-1H-benzotriazol-5-yl}-3-{3-[(1R)-1-(6-hydroxy-2,2-dioxo-2H-1,2λ$^6$,3-benzoxathiazin-3(4H)-yl)ethyl]-4-methylphenyl}propanoate (1 eq.) as a reactant, the title compound (white solid, quant.) was obtained.

$^1$H-NMR (400 MHz, DMSO-d6) δ ppm: 1.01 (td, J=7.09, 4.16 Hz, 6H) 1.18 (d, J=6.85 Hz, 2H) 1.55 (d, J=6.85 Hz, 3H) 2.18 (d, J=5.38 Hz, 3H) 2.26-2.36 (m, 6H) 2.79 (s, 2H)

2.85 (s, 3H) 2.95 (dd, J=15.77, 8.31 Hz, 1H) 3.14-3.26 (m, 3H) 3.39-3.54 (m, 3H) 3.55-3.61 (m, 1H) 3.61-3.73 (m, 2H) 3.74-3.85 (m, 2H) 3.87-3.98 (m, 5H) 4.01 (d, J=6.60 Hz, 1H) 4.08 (t, J=4.71 Hz, 2H) 4.19 (d, J=17.73 Hz, 1H) 4.35 (d, J=17.61 Hz, 1H) 4.53-4.82 (m, 4H) 4.83-4.96 (m, 2H) 5.23-5.31 (m, 1H) 5.33-5.42 (m, 1H) 6.25 (d, J=2.81 Hz, 1H) 6.50 (d, J=2.81 Hz, 1H) 6.78-6.94 (m, 2H) 6.96-7.04 (m, 2H) 7.10 (dd, J=19.38, 8.25 Hz, 2H) 7.17-7.25 (m, 2H) 7.42 (d, J=6.48 Hz, 1H) 7.54-7.65 (m, 4H)

Step 5: Preparation of Example 26

Using General Procedure 12 starting from ethyl[(2R)-2,4,33-trimethyl-29,29-dioxo-20,23,28-trioxa-29λ$^6$-thia-1,14,15,16-tetraazahexacyclo[22.5.3.1$^{3,7}$0.1$^{9,13}$0.0$^{12,16}$0.0$^{27,31}$]tetratriaconta-3(34),4,6,9(33),10,12,14,24,26,31-decaen-8-yl]acetate (1 eq.) as a reactant, the title compound (white solid, 85% yield) was obtained.

The diastereo-pure products were obtained by chromatographic separation on chiral column.

EXAMPLE 26a (2R,8S)

HRMS calculated for $C_{31}H_{34}N_4O_7S$: 606.2148; $[M+H]^+$ found: 607.2223 (δ=0.3 ppm).

$^1$H-NMR (400 MHz, DMSO-d6) δ ppm: 12.1 (s1, 1H), 7.62/7.59 (d, 2H), 7.59 (d, 1H), 7.19 (dd, 1H), 7.08 (d, 1H), 7.01 (d, 1H), 6.91 (dd, 1H), 6.49 (d, 1H), 5.37 (q, 1H), 4.87 (t, 1H), 4.77/4.67 (m, 2H), 4.33/3.95 (d, 2H), 4.08 (t, 2H), 3.79/3.66 (m, 2H), 3.49 (m, 2H), 3.11 (m, 2H), 2.83 (s, 3H), 2.29 (s, 3H), 2.19 (m, 2H), 1.54 (d, 3H)

EXAMPLE 26b (2R,8R)

HRMS calculated for $C_{31}H_{34}N_4O_7S$: 606.2148; $[M+H]^+$ found: 607.2223 (δ=0.3 ppm).

$^1$H-NMR (400 MHz, DMSO-d6) δ ppm: 12.11 (s1, 1H), 7.61 (d, 1H), 7.43 (dd, 1H), 7.23 (d, 1H), 7.11 (d, 1H), 6.99 (d, 1H), 6.88 (d, 1H), 6.85 (dd, 1H), 6.24 (d, 1H), 5.28 (q, 1H), 4.9 (t, 1H), 4.75/4.61 (m, 2H), 4.16/3.96 (d, 2H), 3.91/3.83 (m, 2H), 3.71/3.59 (m, 2H), 3.59/3.5 (m, 2H), 3.11/2.84 (dd, 2H), 2.8 (s, 3H), 2.3 (s, 3H), 2.29/2.18 (m, 2H), 1.19 (d, 3H)

EXAMPLE 27: [(2R,8R)-2,4,33-Trimethyl-29,29-dioxo-19,23,28-trioxa-29λ$^6$-thia-1,14,15,16-tetraazahexacyclo[22.5.3.1$^{3,7}$0.1$^{9,13}$0.1$^{12,16}$0.0$^{27,31}$]tetratriaconta-3(34),4,6,9(33),10,12,14,24,26,31-decaen-8-yl]acetic acid and [(2R,8S)-2,4,33-trimethyl-29,29-dioxo-19,23,28-trioxa-29λ$^6$-thia-1,14,15,16-tetraazahexacyclo[22.5.3.1$^{3,7}$0.1$^{9,13}$0.0$^{12,16}$0.0$^{27,31}$]tetratriaconta-3(34),4,6,9(33),10,12,14,24,26,31-decaen-8-yl]acetic acid

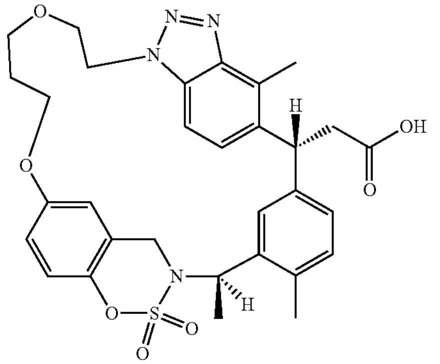

-continued

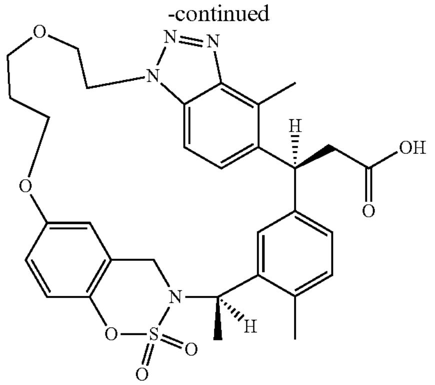

Step A1: Preparation of tert-butyl {2-[3-(benzyloxy)propoxy]ethyl}carbamate

To a solution of 3-(benzyloxy)propyl 4-methylbenzene-1-sulfonate (41 g, 130 mmol) in toluene (2 mL/mmol, 260 mL) tetrabutylammonium-hydrogenesulfate (0.1 eq., 4.3 g, 13 mmol), tert-butyl (2-hydroxyethyl)carbamate (1 eq., 21 g, 130 mmol) and 50 wt % aq. NaOH (9 eq., 92 g, 1.2 mol) were added. The mixture was heated at 85° C. for 16 h. After completion of the reaction the mixture was diluted with 1 L EtOAc. The mixture was washed with 2 L of sat. aq. $NH_4Cl$ solution, the layers were separated. The organic layer was dried over anhydrous $Na_2SO_4$, filtered, concentrated to dryness to give the crude product, which was purified by reverse-phase chromatography using water-MeCN eluent system to give the title compound (19.6 g, yellow oil, 47% yield).

$^1$H-NMR (400 MHz, DMSO-d6) δ ppm: 7.38-7.24 (m, 5H), 6.73 (t, 1H), 4.44 (s, 2H), 3.49 (t, 2H), 3.44 (t, 2H), 3.33 (t, 2H), 3.04 (q, 2H), 1.76 (quint, 2H), 1.38 (s, 9H)

Step A2: Preparation of 2-[3-(benzyloxy)propoxy]ethan-1-amine hydrochloride

To a solution of tert-butyl {2-[3-(benzyloxy)propoxy]ethyl}carbamate (19.6 g, 59.5 mmol) in dioxane (5 mL/mmol, 298 mL) HCl (4N in dioxane) (4 eq., 59.5 mL) was added at RT. The reaction mixture was stirred overnight at RT. After completion of the reaction the solvent was evaporated to dryness under reduced pressure. The crude product was used without further purification as an HCl salt (15.6 g, quant.).

$^1$H-NMR (400 MHz, DMSO-d6) δ ppm: 7.98 (s, 3H), 7.4-7.36 (m, 5H), 4.46 (s, 2H), 3.56 (t, 2H), 3.5 (t, 2H), 3.5 (t, 2H), 2.93 (t, 2H), 1.81 (quint, 2H)

Step A3: Preparation of N-{2-[3-(benzyloxy)propoxy]ethyl}-3-methyl-2-nitroaniline Using General Procedure 2 STEP 1 starting from 1-fluoro-3-methyl-2-nitrobenzene (1 eq.) and 2-[3-(benzyloxy)propoxy]ethan-1-amine hydrochloride (1.2 eq.) as reactants, the title compound (93% yield) was obtained.

$^1$H-NMR (400 MHz, DMSO-d6) δ ppm: 7.38-7.24 (m, 5H), 7.27 (m, 1H), 6.82 (d, 1H), 6.59 (d, 1H), 6.46 (t, 1H), 4.42 (s, 2H), 3.57 (t, 2H), 3.52-3.47 (m, 4H), 3.33 (dt, 2H), 2.31 (s, 3H), 1.79 (quint, 2H)

Step A4: Preparation of N-{2-[3-(benzyloxy)propoxy]ethyl}-4-bromo-3-methyl-2-nitroaniline Using General Procedure 2 STEP 2 starting from N-{2-[3-(benzyloxy)propoxy]ethyl}-3-methyl-2-nitroaniline (1 eq.) as a reactant, the title compound (58% yield) was obtained.

$^1$H-NMR (400 MHz, DMSO-d6) δ ppm: 7.54 (d, 1H), 7.38-7.23 (m, 5H), 6.8 (d, 1H), 6.09 (t, 1H), 4.42 (s, 2H), 3.51 (t, 2H), 3.47 (m, 4H), 3.3 (q, 2H), 2.38 (s, 3H), 1.77 (quint, 2H)

Step A5: Preparation of N-{2-[3-(benzyloxy)propoxy]ethyl}-4-bromo-3-methylbenzene-1,2-diamine Using General Procedure 2 STEP 3 starting from N-{2-[3-(benzyloxy)propoxy]ethyl}-4-bromo-3-methyl-2-nitroaniline (1 eq.) as a reactant, the title compound (quant.) was obtained.

$^1$H-NMR (400 MHz, DMSO-d6) δ ppm: 7.38-7.23 (m, 5H), 6.71 (d, 1H), 6.29 (d, 1H), 4.6 (s1, 3H), 4.42 (s, 2H), 3.56/3.5 (m, 2H), 3.56/3.5 (m, 4H), 3.16 (t, 2H), 2.17 (s, 3H), 1.79 (quint, 2H)

Step A6: Preparation of ethyl (2E)-3-(1-{2-[3-(benzyloxy)propoxy]ethyl}-4-methyl-1H-benzotriazol-5-yl)prop-2-enoate Using General Procedure 2 STEP 4 starting from N$^1$-{2-[3-(benzyloxy)propoxy]ethyl}-4-bromo-3-methylbenzene-1,2-diamine (1 eq.) as a reactant, 1-{12-[3-(benzyloxy)propoxy]ethyl}-5-bromo-4-methyl-1H-benzotriazole (29% yield) was obtained. The crude product was reacted using General Procedure 2 STEP 5 to give the title compound (91% yield).

$^1$H-NMR (400 MHz, DMSO-d6) δ ppm: 8.01 (d, 1H), 7.92 (d, 1H), 7.69 (d, 1H), 7.3 (t, 2H), 7.25 (t, 1H), 7.2 (d, 2H), 6.62 (d, 1H), 4.85 (t, 2H), 4.22 (s, 2H), 4.21 (q, 2H), 3.82 (t, 2H), 3.4 (t, 2H), 3.21 (t, 2H), 2.79 (s, 3H), 1.6 (quint, 2H), 1.28 (t, 3H)

Step 1: Preparation of ethyl 3-(1-{2-[3-(benzyloxy)propoxy]ethyl}-4-methyl-1H-benzotriazol-5-yl)-3-{3-[(1S)-1-hydroxyethyl]-4-methylphenyl}propanoate Using General Procedure 6 starting from ethyl (2E)-3-(1-{12-[3-(benzyloxy)propoxy]ethyl}-4-methyl-1H-benzotriazol-5-yl)prop-2-enoate (1 eq.) and (1S)-1-[2-methyl-5-(4,4,5,5-tetramethyl-1,3,2-dioxaborolan-2-yl)phenyl]ethan-1-ol (1 eq.) as reactants, the title compound (48% yield) was obtained.

$^1$H-NMR (400 MHz, DMSO-d6) δ ppm: 7.58 (d, 1H), 7.44 (d, 1H), 7.4 (d, 1H), 7.31 (t, 2H), 7.24 (t, 1H), 7.21 (d, 2H), 7.03 (dd, 1H), 6.97 (d, 1H), 4.83 (m, 1H), 4.83 (m, 1H), 4.8 (m, 2H), 4.25 (s, 2H), 3.97 (d, 1H), 3.92 (q, 2H), 3.82 (t, 2H), 3.4 (t, 2H), 3.25 (m, 2H), 3.15-3.05 (m, 2H), 2.76 (s, 3H), 2.18 (s, 3H), 1.61 (quint, 2H), 1.21 (d, 3H), 1 (t, 3H)

Step 2: Preparation of ethyl 3-{3-[(1R)-1-(6-hydroxy-2,2-dioxo-2H-1,2λ$^6$,3-benzoxathiazin-3(4H)-yl)ethyl]-4-methylphenyl}-3-{1-[2-(3-hydroxypropoxy)ethyl]-4-methyl-1H-benzotriazol-5-yl}propanoate Using General Procedure 7 starting from ethyl 3-(1-{2-[3-(benzyloxy)propoxy]ethyl}-4-methyl-1H-benzotriazol-5-yl)-3-{3-[(1S)-1-hydroxyethyl]-4-methylphenyl}propanoate (1.1 eq.) and 6-(benzyloxy)-3,4-dihydro-2H-1,2λ$^6$,3-benzoxathiazine-2,2-dione (1.1 eq.) as reactants, ethyl 3-(3-{(1R)-1-[6-(benzyloxy)-2,2-dioxo-2H-1,2λ$^6$,3-benzoxathiazin-3(4H)-yl]ethyl}-4-methylphenyl)-3-(1-{12-[3-(benzyloxy)propoxy]ethyl}-4-methyl-1H-benzotriazol-5-yl)propanoate (yellow oil, 86% yield) was obtained. The crude product was reacted using General Procedure 8 resulting the title compound (yellow oil, 83% yield).

$^1$H-NMR (400 MHz, DMSO-d6) δ ppm: 9.62 (2m, 2H), 7.65-7.42 (m, 2H), 7.47/7.45 (2s1, 1H), 7.14-7.07 (m, 2H), 6.92/6.9 (2d, 1H), 6.75-6.7 (m, 1H), 6.58 (2d, 1H), 5.25 (q, 1H), 4.87 (q, 1H), 4.8 (t, 2H), 4.36/4.32 (2s, 2H), 4.31-4.24 (m, 1H), 3.94 (2q, 2H), 3.82 (m, 2H), 3.39 (2t, 2H), 3.29 (q, 2H), 3.22 (m, 2H), 2.76 (s, 3H), 2.27 (s, 3H), 1.5 (m, 2H), 1.43/1.41 (2d, 3H), 1.01/1 (2t, 3H)

Step 3: Preparation of ethyl 3-{1-[2-(3-bromopropoxy)ethyl]-4-methyl-1H-benzotriazol-5-yl}-3-{3-[(1R)-1-(6-hydroxy-2,2-dioxo-2H-1,2)$^6$,3-benzoxathiazin-3(4H)-yl)ethyl]-4-methylphenyl}propanoate Using General Procedure 9 starting from ethyl 3-{3-[(1R)-1-(6-hydroxy-2,2-dioxo-2H-1,2)$^6$,3-benzoxathiazin-3(4H)-yl)ethyl]-4-methylphenyl}-3-{11-[2-(3-hydroxypropoxy)ethyl]-4-methyl-1H-benzotriazol-5-yl}propanoate (1 eq.) as a reactant, the title compound (white solid, 49% yield) was obtained.

$^1$H-NMR (400 MHz, DMSO-d6) δ ppm: 9.55 (s, 1H), 7.7-7.55 (2d, 2H), 7.49 (2d, 1H), 7.1 (m, 2H), 6.9 (d, 1H), 6.71 (2, 1H), 6.6 (2d, 1H), 5.25 (m, 1H), 4.9 (m, 1H), 4.81 (t, 2H), 4.4-4.25 (m, 2H), 3.95 (m, 2H), 3.85 (t, 2H), 3.41 (t, 2H), 3.3 (t, 2H), 3.21 (d, 2H), 2.76 (s, 3H), 2.3 (s, 3H), 1.85 (m, 2H), 1.45 (2d, 3H), 1.02 (2t, 3H)

Step 4: Preparation of ethyl[(2R)-2,4,33-trimethyl-29,29-dioxo-19,23,28-trioxa-29λ$^6$-thia-1,14,15,16-tetraazahexacyclo[22.5.3.1$^{3,7}$0.1$^{9,13}$0.0$^{12,16}$0.0$^{27,31}$]tetratriaconta-3(34),4,6,9(33),10,12,14,24,26,31-decaen-8-yl]acetate Using General Procedure 11 starting from ethyl 3-{1-[2-(3-bromopropoxy)ethyl]-4-methyl-1H-benzotriazol-5-yl}-3-{3-[(1R)-1-(6-hydroxy-2,2-dioxo-2H-1,2λ$^6$,3-benzoxathiazin-3(4H)-yl)ethyl]-4-methylphenyl}propanoate (1 eq.) as a reactant, the title compound (white solid, 83% yield) was obtained.

$^1$H-NMR (400 MHz, DMSO-d6) δ ppm: 1.00 (td, J=7.09, 5.50 Hz, 5H) 1.24 (d, J=6.85 Hz, 2H) 1.52 (d, J=6.85 Hz, 3H) 1.77-1.86 (m, 1H) 1.92 (dt, J=12.90, 6.39 Hz, 2H) 2.30 (d, J=1.59 Hz, 5H) 2.79 (s, 2H) 2.85 (s, 3H) 2.92-3.27 (m, 4H) 3.44-3.66 (m, 5H) 3.81-3.88 (m, 3H) 3.92-4.01 (m, 3H) 4.01-4.16 (m, 2H) 4.34 (d, J=17.85 Hz, 1H) 4.70-4.82 (m, 2H) 4.82-4.96 (m, 3H) 5.28 (d, J=7.09 Hz, 1H) 5.35 (q, J=6.64 Hz, 1H) 6.00 (d, J=2.81 Hz, 1H) 6.44 (d, J=2.81 Hz, 1H) 6.71-6.85 (m, 2H) 6.91-7.02 (m, 2H) 7.11 (d, J=7.82 Hz, 1H) 7.19-7.31 (m, 2H) 7.48 (d, J=6.85 Hz, 1H) 7.57 (s, 1H) 7.58-7.69 (m, 3H)

Step 5: Preparation of Example 27

Using General Procedure 12 starting from ethyl[(2R)-2,4,33-trimethyl-29,29-dioxo-19,23,28-trioxa-29)$^6$-thia-1,14,15,16-tetraazahexacyclo[22.5.3.1$^{3,7}$0.1$^{9,13}$0.0$^{12,16}$0.0$^{27,31}$]tetratriaconta-3(34),4,6,9(33),10,12,14,24,26,31-decaen-8- yl]acetate (1 eq.) as a reactant, the title compound (white solid, 97% yield) was obtained.

The diastereo-pure products were obtained by chromatographic separation on chiral column.

EXAMPLE 27a (2R,8R)

HRMS calculated for $C_{31}H_4O_7S$: 606.2148; $[M+H]^+$ found: 607.2224 (δ=0.5 ppm).

$^1$H-NMR (400 MHz, DMSO-d6) δ ppm: 12.2 (s1, 1H), 7.6 (d, 1H), 7.49 (dd, 1H), 7.26 (d, 1H), 7.19 (d, 1H), 7 (d, 1H), 6.95 (d, 1H), 6.76 (dd, 1H), 6.01 (d, 1H), 5.28 (q, 1H), 4.9 (t, 1H), 4.78 (m, 2H), 4.11/3.9 (d, 2H), 4 (m, 2H), 3.6 (m, 2H), 3.55 (m, 2H), 3.08/2.85 (dd, 2H), 2.79 (s, 3H), 2.3 (s, 3H), 1.83 (m, 2H), 1.23 (d, 3H)

EXAMPLE 27b (2R,8S)

HRMS calculated for $C_{31}H_{34}N_4O_7S$: 606.2148; $[M+H]^+$ found: 607.2222 (δ=0.2 ppm).

$^1$H-NMR (400 MHz, DMSO-d6) δ ppm: 12.1 (s1, 1H), 7.64 (d, 1H), 7.59 (d, 1H), 7.55 (d, 1H), 7.23 (dd, 1H), 7.11 (d, 1H), 6.99 (d, 1H), 6.81 (dd, 1H), 6.43 (d, 1H), 5.33 (q, 1H), 4.85/4.76 (m, 2H), 4.85 (t, 1H), 4.32/4.01 (d, 2H), 4-3.97 (m, 2H), 3.86 (m, 2H), 3.61/3.52 (m, 2H), 3.07 (m, 2H), 2.83 (s, 3H), 2.3 (s, 3H), 1.91 (m, 2H), 1.5 (d, 3H)

EXAMPLES 28a and 28b: [(2R,8R)-4-Methoxy-2,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid and [(2R,8S)-4-methoxy-2,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid

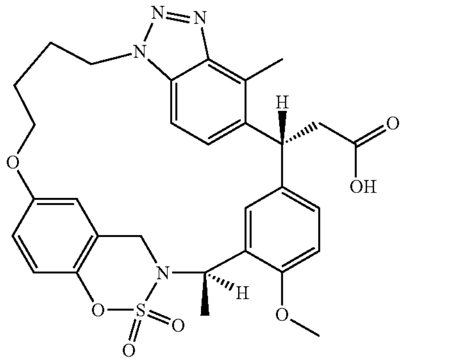

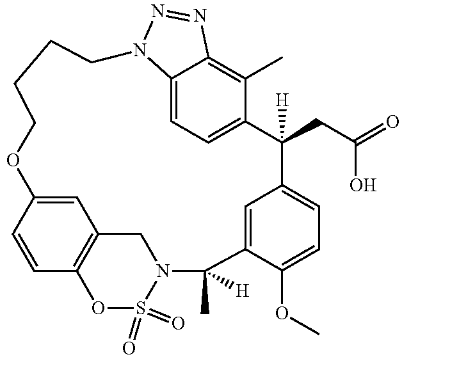

Step 1: Preparation of ethyl 3-{3-[(1S)-1-hydroxyethyl]-4-methoxyphenyl}-3-(1-{4-[(4-methoxyphenyl)methoxy]butyl}-4-methyl-1H-benzotriazol-5-yl) propanoate Using General Procedure 6 starting from ethyl (2E)-3-(1-{4-[(4-methoxyphenyl)methoxy]butyl}-4-methyl-1H-benzotriazol-5-yl)prop-2-enoate (1 eq.) and (1S)-1-[2-methoxy-5-(4,4,5,5-tetramethyl-1,3,2-dioxaborolan-2-yl)phenyl] ethan-1-ol (1.5 eq.) as reactants, the title compound (65% yield) was obtained.

$^1$H-NMR (400 MHz, DMSO-d6) δ ppm: 7.58 (2d, 1H), 7.45 (2d, 1H), 7.37 (d, 1H), 7.2 (d, 2H), 7.13 (2dd, 1H), 6.87 (d, 2H), 6.82 (d, 1H), 4.91 (m, 1H), 4.89 (d, 1H), 4.82 (m, 1H), 4.64 (m, 2H), 4.32 (s, 2H), 3.92 (q, 2H), 3.73/3.72 (2s, 6H), 3.38 (t, 2H), 3.11 (m, 2H), 2.76/2.75 (2s, 3H), 1.92 (m, 2H), 1.48 (m, 2H), 1.22-1.15 (2d, 3H), 0.99 (t, 3H)

Step 2: Preparation of ethyl 3-(3-{(1R)-1-[6-(benzyloxy)-2,2-dioxo-2H-1,2λ$^6$,3-benzoxathiazin-3(4H)-yl]ethyl}-4-methoxyphenyl)-3-(1-{4-[(4-methoxyphenyl)methoxy]butyl}-4-methyl-1H-benzotriazol-5-yl)propanoate Using General Procedure 7 starting from ethyl 3-{3-[(1S)-1-hydroxyethyl]-4-methoxyphenyl}-3-(1-{4-[(4-methoxyphenyl)methoxy]butyl}-4-methyl-1H-benzotriazol-5-yl) propanoate (1 eq.) and 6-(benzyloxy)-3,4-dihydro-2H-1,2λ$^6$,3-benzoxathiazine-2,2-dione (1.1 eq.) as reactants, the title compound (66% yield) was obtained.

$^1$H-NMR (400 MHz, DMSO-d6) δ ppm: 7.6 (d, 1H), 7.5 (2d, 1H), 7.45-7.3 (m, 6H), 7.2 (d, 2H), 7.1 (dd, 1H), 6.9 (m, 4H), 6.75 (m, 2H), 5.39 (m, 1H), 5 (m, 2H), 4.8 (m, 1H), 4.6 (2t, 2 H), 4.55 (m, 2H), 4.3 (s, 2H), 3.91 (q, 2H), 3.71/3.65 (2s, 6H), 3.48 (m, 2H), 3.18 (d, 2H), 2.79 (s, 3H), 1.91 (m, 2H), 1.5 (m, 2H), 1.45 (2d, 3H), 1 (t, 3H)

Step 3: Preparation of ethyl 3-[1-(4-hydroxybutyl)-4-methyl-1H-benzotriazol-5-yl]-3-{3-[(1R)-1-(6-hydroxy-2,2-dioxo-2H-1,2λ$^6$,3-benzoxathiazin-3(4H)-yl)ethyl]-4-methoxyphenyl}propanoate Using General Procedure 8 starting from ethyl 3-(3-{(1R)-1-[6-(benzyloxy)-2,2-dioxo-2H-1,2λ$^6$,3-benzoxathiazin-3(4H)-yl]ethyl}-4-methoxyphenyl)-3-(1-{4-[(4-methoxyphenyl) methoxy]butyl}-4-methyl-1H-benzotriazol-5-yl)propanoate (1 eq.) as a reactant, the title compound (off-white solid, 83% yield) was obtained.

$^1$H-NMR (400 MHz, DMSO-d6) δ ppm: 1.01 (td, J=7.09, 3.79 Hz, 3H) 1.21 (dd, J=13.69, 5.99 Hz, 1H) 1.31-1.39 (m, 2H) 1.42 (t, J=6.42 Hz, 3H) 1.91 (quint, J=7.31 Hz, 2H) 2.76 (d, J=3.67 Hz, 3H) 3.09-3.21 (m, 2H) 3.38 (t, J=5.93 Hz, 2H) 3.67 (s, 3H) 3.70 (s, 1H) 3.94 (q, J=7.09 Hz, 2H) 4.34-4.57 (m, 3H) 4.65 (t, J=6.97 Hz, 2H) 4.83 (q, J=7.62 Hz, 1H) 5.37 (quint, J=6.79 Hz, 1H) 6.51 (dd, J=13.14, 2.75 Hz, 1H) 6.64 (dd, J=8.99, 2.75 Hz, 1H) 6.73-6.85 (m, 3H) 7.08 (d, J=8.19 Hz, 1H) 7.13 (dd, J=8.56, 2.08 Hz, 1H) 7.42 (dd, J=9.35, 2.02 Hz, 1H) 7.53 (t, J=9.11 Hz, 1H) 7.59-7.67 (m, 1H) 9.54 (br. s., 1H)

Step 4: Preparation of ethyl 3-[1-(4-bromobutyl)-4-methyl-1H-benzotriazol-5-yl]-3-{3-[(1R)-1-(6-hydroxy-2,2-dioxo-2H-1,2λ$^6$,3-benzoxathiazin-3(4H)-yl)ethyl]-4-methoxyphenyl}propanoate Using General Procedure 9 starting from ethyl 3-[1-(4-hydroxybutyl)-4-methyl-1H-benzotriazol-5-yl]-3-{3-[(1R)-

1-(6-hydroxy-2,2-dioxo-2H-1,2λ$^6$,3-benzoxathiazin-3(4H)-yl)ethyl]-4-methoxyphenyl}propanoate (1 eq.) as a reactant, the title compound (73% yield) was obtained.

$^1$H-NMR (400 MHz, DMSO-d6) δ ppm: 1.00 (td, J=7.09, 3.79 Hz, 3H) 1.42 (t, J=6.66 Hz, 3H) 1.71-1.83 (m, 2H) 1.94-2.05 (m, 2H) 2.70-2.79 (m, 3H) 3.08-3.25 (m, 2H) 3.53 (t, J=6.66 Hz, 2H) 3.62-3.70 (m, 3H) 3.94 (q, J=7.13 Hz, 2H) 4.34-4.57 (m, 2H) 4.69 (t, J=6.85 Hz, 2H) 4.83 (q, J=7.83 Hz, 1H) 5.31-5.42 (m, 1H) 6.51 (dd, J=11.37, 2.81 Hz, 1H) 6.64 (dd, J=8.93, 2.81 Hz, 1H) 6.62-6.68 (m, 1H) 6.74-6.84 (m, 2H) 7.13 (dd, J=8.50, 2.02 Hz, 1H) 7.42 (dd, J=10.03, 2.08 Hz, 1H) 7.55 (t, J=8.74 Hz, 1H) 7.61-7.68 (m, 1H) 9.52 (d, J=5.01 Hz, 1H)

Step 5: Preparation of ethyl[(2R)-4-methoxy-2,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate Using General Procedure 11 starting from ethyl 3-[1-(4-bromobutyl)-4-methyl-1H-benzotriazol-5-yl]-3-{3-[(1R)-1-(6-hydroxy-2,2-dioxo-2H-1,2λ$^6$,3-benzoxathiazin-3(4H)-yl)ethyl]-4-methoxyphenyl}propanoate (1 eq.) as a reactant, the title compound (white solid, 73% yield) was obtained.

$^1$H-NMR (400 MHz, DMSO-d6) δ ppm: 1.02 (td, J=7.09, 2.81 Hz, 6H) 1.12-1.22 (m, 5H) 1.22-1.29 (m, 4H) 1.31 (d, J=7.21 Hz, 3H) 1.40 (d, J=7.46 Hz, 1H) 1.48-1.61 (m, 1H) 1.62-1.88 (m, 2H) 2.00-2.28 (m, 4H) 2.63-2.90 (m, 6H) 3.09 (td, J=15.62, 7.89 Hz, 2H) 3.24-3.37 (m, 10H) 3.46 (td, J=9.54, 6.11 Hz, 1H) 3.53-3.69 (m, 3H) 3.70-3.80 (m, 7H) 3.88-3.98 (m, 5H) 4.05-4.15 (m, 1H) 4.68-4.97 (m, 6H) 5.43 (dq, J=17.93, 7.19 Hz, 2H) 5.62 (d, J=2.57 Hz, 1H) 5.75 (d, J=2.81 Hz, 1H) 6.62-6.72 (m, 2H) 6.80-6.94 (m, 4H) 6.99 (d, J=8.56 Hz, 1H) 7.20-7.29 (m, 2H) 7.42 (dd, J=8.44, 1.96 Hz, 1H) 7.50 (dd, J=8.56, 1.83 Hz, 1H) 7.67 (d, J=8.68 Hz, 1H) 7.74-7.81 (m, 1H) 7.83-7.89 (m, 1H)

Step 6: Preparation of Examples 28a and 28b

Using General Procedure 12 starting from ethyl[(2R)-4-methoxy-2,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (1 eq.) as a reactant, the title compound (white solid, 77% yield) was obtained.

The diastereo-pure products were obtained by chromatographic separation on chiral column.

EXAMPLE 28a (2R,8R)

HRMS calculated for $C_{30}H_{32}N_4O_7S$: 592.1992; $[M+H]^+$ found: 593.2067 (δ=0.4 ppm).

$^1$H-NMR (400 MHz, DMSO-d6) δ ppm: 12.5-11.8 (m, 1H), 7.67 (d, 1H), 7.5 (dd, 1H), 7.19 (d, 1H), 7 (d, 1H), 6.83 (d, 1H), 6.8 (d, 1H), 6.65 (dd, 1H), 5.63 (d, 1H), 5.4 (q, 1H), 4.87 (dd, 1H), 4.72 (m, 2H), 4/3.71 (AM, 2H), 3.76 (s, 3H), 3.6/3.32 (2m, 2H), 3.2/2.9 (2dd, 2H), 2.81 (s, 3H), 2.2/2.01 (2m, 2H), 1.7/1.4 (2m, 2H), 1.17 (d, 3H)

EXAMPLE 28b (2R,8S)

HRMS calculated for $C_{30}H_{32}N_4O_7S$: 592.1992; $[M+H]^+$ found: 593.2066 (δ=0.3 ppm).

$^1$H-NMR (400 MHz, DMSO-d6) δ ppm: 12.3-11.6 (m, 1H), 7.92 (dd, 1H), 7.82 (d, 1H), 7.77 (d, 1H), 7.18 (d, 1H), 6.9 (d, 1H), 6.88 (d, 1H), 6.69 (dd, 1H), 5.7 (d, 1H), 5.42 (q, 1H), 4.75 (m, 3H), 4.08/3.69 (AM, 2H), 3.72 (s, 3H), 3.62/3.45 (2m, 2H), 3.2/2.99 (2dd, 2H), 2.68 (s, 3H), 2.2/2.1 (2m, 2H), 1.8/1.59 (2m, 2H), 1.29 (d, 3H)

EXAMPLES 28c and 28d: [(2S,8R)-4-Methoxy-2,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid and [(2S,8S)-4-methoxy-2,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid

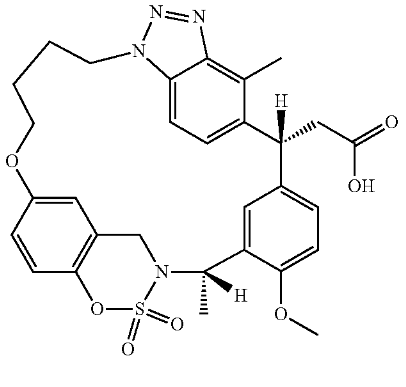

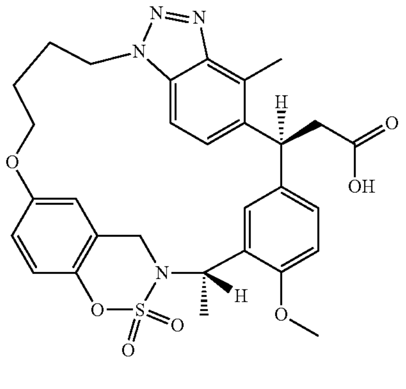

Step 1: Preparation of ethyl 3-{3-[(1R)-1-hydroxyethyl]-4-methoxyphenyl}-3-(1-{4-[(4-methoxyphenyl)methoxy]butyl}-4-methyl-1H-benzotriazol-5-yl)propanoate Using General Procedure 6 starting from ethyl (2E)-3-(1-{4-[(4-methoxyphenyl)methoxy]butyl}-4-methyl-1H-benzotriazol-5-yl)prop-2-enoate (1 eq.) and (1R)-1-[2-methoxy-5-(4,4,5,5-tetramethyl-1,3,2-dioxaborolan-2-yl)phenyl]ethan-1-ol (1.1 eq.) as reactants, the title compound (81% yield) was obtained.

$^1$H-NMR (400 MHz, DMSO-d6) δ ppm: 7.6 (2d, 1H), 7.45 (2d, 1H), 7.35 (d, 1H), 7.2 (d, 2H), 7.12 (dd, 1H), 6.88 (d, 2H), 6.81 (d, 1H), 4.9 (d, 1H), 4.9 (m, 1H), 4.8 (m, 1H), 4.65 (t, 2H), 4.32 (s, 2H), 3.91 (q, 2H), 3.71 (2s, 6H), 3.4 (t, 2H), 3.1 (2d, 2H), 2.79 (2s, 3H), 1.92 (m, 2H), 1.48 (m, 2H), 1.2 (2d, 3H), 1 (t, 3H)

Step 2: Preparation of ethyl 3-(3-{(1S)-1-[6-(benzyloxy)-2,2-dioxo-2H-1,2λ$^6$,3-benzoxathiazin-3(4H)-yl]ethyl}-4-methoxyphenyl)-3-(1-{4-[(4-methoxyphenyl)methoxy]butyl}-4-methyl-1H-benzotriazol-5-yl)propanoate Using General Procedure 7 starting from ethyl 3-{3-[(1R)-1-hydroxyethyl]-4-methoxyphenyl}-3-(1-{4-[(4-methoxyphenyl)methoxy]butyl}-4-methyl-1H-benzotriazol-5-yl)propanoate (1 eq.) and 6-benzyloxy-3,4-dihydro-1,2λ$^6$,3-benzoxathiazine 2,2-dioxide (1.1 eq.) as reactants, the title compound (60% yield) was obtained.

$^1$H-NMR (400 MHz, DMSO-d6) δ ppm: 7.6 (d, 1H), 7.5 (2d, 1H), 7.45-7.3 (m, 6H), 7.2 (d, 2H), 7.11 (dd, 1H), 6.9 (m, 2H), 6.88 (d, 2H), 6.78 (m, 2H), 5.39 (m, 1H), 5.05 (m, 2H), 4.81 (m, 1H), 4.65-4.5 (m, 2H), 4.61 (2t, 2H), 4.3 (s, 2H), 3.92 (q, 2H), 3.71/3.65 (2s, 6H), 3.38 (m, 2H), 3.15 (m, 2H), 2.78 (s, 3H), 1.9 (m, 2H), 1.48 (m+d, 5H), 0.99 (t, 3H)

Step 3: Preparation of ethyl 3-[1-(4-hydroxybutyl)-4-methyl-1H-benzotriazol-5-yl]-3-{3-[(1S)-1-(6-hydroxy-2,2-dioxo-2H-1,2λ$^6$,3-benzoxathiazin-3(4H)-yl)ethyl]-4-methoxyphenyl}propanoate Using General Procedure 8 starting from ethyl 3-(3-{(1S)-1-[6-(benzyloxy)-2,2-dioxo-2H-1,2λ$^6$,3-benzoxathiazin-3(4H)-yl]ethyl}-4-methoxyphenyl)-3-(1-{4-[(4-methoxyphenyl)methoxy]butyl}-4-methyl-1H-benzotriazol-5-yl)propanoate (1 eq.) as a reactant, the title compound (70% yield) was obtained.

$^1$H-NMR (400 MHz, DMSO-d6) δ ppm: 0.95-1.03 (m, 3H) 1.30-1.47 (m, 5H) 1.85-1.97 (m, 2H) 2.76 (d, J=3.55 Hz, 3H) 3.18 (d, J=8.19 Hz, 2H) 3.34-3.42 (m, 2H) 3.67 (s, 3H) 3.94 (q, J=7.13 Hz, 2H) 4.33 (t, J=5.07 Hz, 1H) 4.37-4.58 (m, 3H) 4.65 (t, J=6.97 Hz, 2H) 4.83 (q, J=7.87 Hz, 1H) 5.32-5.42 (m, 1H) 6.51 (dd, J=13.20, 2.81 Hz, 1H) 6.64 (dd, J=8.86, 2.75 Hz, 1H) 6.76 (d, J=1.59 Hz, 1H) 6.79-6.84 (m, 2H) 7.08 (d, J=8.31 Hz, 1H) 7.13 (dd, J=8.56, 2.08 Hz, 1H) 7.42 (dd, J=9.05, 1.96 Hz, 1H) 7.53 (t, J=9.17 Hz, 1H) 7.60-7.65 (m, 1H) 9.51 (s, 1H) 9.52 (s, 1H)

Step 4: Preparation of ethyl 3-[1-(4-bromobutyl)-4-methyl-1H-benzotriazol-5-yl]-3-{3-[(1S)-1-(6-hydroxy-2,2-dioxo-2H-1,2λ$^6$,3-benzoxathiazin-3(4H)-yl)ethyl]-4-methoxyphenyl}propanoate Using General Procedure 9 starting from ethyl 3-[1-(4-hydroxybutyl)-4-methyl-1H-benzotriazol-5-yl]-3-{3-[(1S)-1-(6-hydroxy-2,2-dioxo-2H-1,2λ$^6$,3-benzoxathiazin-3(4H)-yl)ethyl]-4-methoxyphenyl}propanoate (1 eq.) as a reactant, the title compound (white solid, quant.) was obtained.

$^1$H-NMR (400 MHz, DMSO-d6) δ ppm: 1.00 (td, J=7.09, 3.79 Hz, 3H) 1.42 (t, J=6.66 Hz, 3 H) 1.71-1.82 (m, 2H) 1.92-2.06 (m, 2H) 2.76 (d, J=3.91 Hz, 3H) 3.10-3.25 (m, 2H) 3.53 (t, J=6.66 Hz, 2H) 3.67 (d, J=1.10 Hz, 3H) 3.94 (q, J=7.13 Hz, 2H) 4.35-4.60 (m, 2H) 4.69 (t, J=6.85 Hz, 2H) 4.83 (q, J=7.83 Hz, 1H) 5.36 (quin, J=6.94 Hz, 1H) 6.51 (dd, J=11.37, 2.81 Hz, 1H) 6.64 (dd, J=8.93, 2.81 Hz, 1H) 6.76 (s, 1H) 6.78 (s, 1H) 6.81 (dd, J=8.68, 2.93 Hz, 1H) 7.13 (dd, J=8.50, 2.02 Hz, 1H) 7.42 (dd, J=10.03, 2.08 Hz, 1H) 7.55 (t, J=8.74 Hz, 1H) 7.61-7.69 (m, 1H) 9.52 (d, J=5.01 Hz, 1H)

Step 5: Preparation of ethyl[(2S)-4-methoxy-2,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate Using General Procedure 11 starting from ethyl 3-[1-(4-bromobutyl)-4-methyl-1H-benzotriazol-5-yl]-3-{3-[(1S)-1-(6-hydroxy-2,2-dioxo-2H-1,2λ$^6$,3-benzoxathiazin-3(4H)-yl)ethyl]-4-methoxyphenyl}propanoate (1 eq.) as a reactant, the title compound (white solid, 60% yield) was obtained.

$^1$H-NMR (400 MHz, DMSO-d6) δ ppm: 0.98-1.07 (m, 6H) 1.15-1.20 (m, 4H) 1.31 (d, J=7.21 Hz, 3H) 1.40 (d, J=7.46 Hz, 1H) 1.48-1.61 (m, 1H) 1.62-1.75 (m, 1H) 1.75-1.87 (m, 1H) 2.00-2.14 (m, 2H) 2.14-2.28 (m, 2H) 2.70 (s, 3H) 2.84 (s, 2H) 3.09 (td, J=15.62, 7.89 Hz, 2H) 3.32-3.38 (m, 1H) 3.46 (td, J=9.54, 6.11 Hz, 1H) 3.54-3.77 (m, 9H) 3.87-3.98 (m, 5H) 3.98-4.02 (m, 1H) 4.05-4.14 (m, 1H) 4.66-4.83 (m, 5H) 4.89 (t, J=7.89 Hz, 1H) 5.43 (dq, J=17.93, 7.19 Hz, 2H) 5.62 (d, J=2.57 Hz, 1H) 5.75 (d, J=2.81 Hz, 1H) 6.62-6.72 (m, 2H) 6.81-6.93 (m, 4H) 6.99 (d, J=8.56 Hz, 1H) 7.19-7.26 (m, 2H) 7.42 (dd, J=8.44, 1.96 Hz, 1H) 7.50 (dd, J=8.56, 1.83 Hz, 1H) 7.67 (d, J=8.68 Hz, 1H) 7.74-7.80 (m, 1H) 7.83-7.89 (m, 1H)

Step 6: Preparation of Examples 28c and 28d

Using General Procedure 12 starting from ethyl[(2S)-4-methoxy-2,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (1 eq.) as a reactant, the title compound (white solid, 89% yield) was obtained.

The diastereo-pure products were obtained by chromatographic separation on chiral column.

EXAMPLE 28c (2S,8R)

HRMS calculated for $C_{30}H_{32}N_4O_7S$: 592.1992; $[M+H]^+$ found: 593.2065 (δ=0.1 ppm).

EXAMPLE 28d (2S,8S)

HRMS calculated for $C_{30}H_{32}N_4O_7S$: 592.1992; $[M+H]^+$ found: 593.2070 (δ=0.9 ppm).

$^1$H-NMR (400 MHz, DMSO-d6) δ ppm: 12.3-11.6 (m, 1H), 7.92 (dd, 1H), 7.82 (d, 1H), 7.77 (d, 1H), 7.18 (d, 1H), 6.9 (d, 1H), 6.88 (d, 1H), 6.69 (dd, 1H), 5.7 (d, 1H), 5.42 (q, 1H), 4.75 (m, 3H), 4.08/3.69 (AM, 2H), 3.72 (s, 3H), 3.62/3.45 (m, 2H), 3.2/2.99 (dd, 2H), 2.68 (s, 3H), 2.2/2.1 (m, 2H), 1.8/1.59 (m, 2H), 1.29 (d, 3H)

EXAMPLE 29: [(2R,8R)-2,4,24,31-Tetramethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid and [(2R,8S)-2,4,24,31-tetramethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid

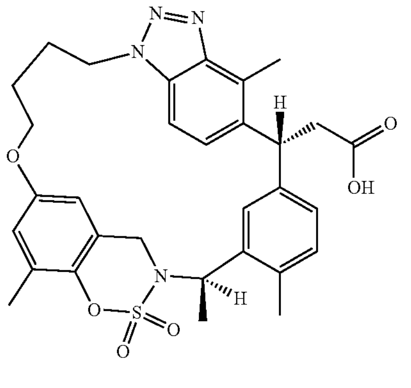

-continued

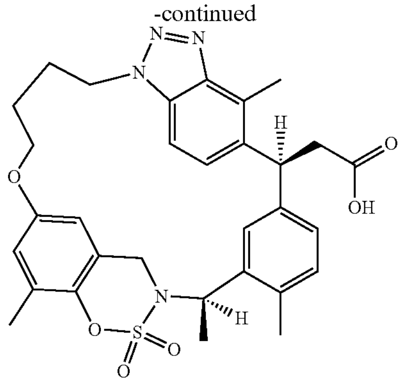

Step 1: Preparation of ethyl 3-{1-[4-(benzyloxy)butyl]-4-methyl-1H-benzotriazol-5-yl}-3-{3-[(1S)-1-hydroxyethyl]-4-methylphenyl}propanoate Using General Procedure 6 starting from ethyl (E)-3-[1-(4-benzyloxybutyl)-4-methyl-benzotriazol-5-yl]prop-2-enoate (1 eq.) and (1S)-1-[2-methyl-5-(4,4,5,5-tetramethyl-1,3,2-dioxaborolan-2-yl)phenyl]ethanol (1.2 eq.) as reactants, the title compound (50% yield) was obtained.

$^1$H-NMR (400 MHz, DMSO-d6) δ ppm: 7.58/7.46 (2dd, 1H), 7.41 (d, 1H), 7.35-7.22 (m, 5H), 7.06 (dd, 1H), 6.98 (d, 1H), 4.97/4.96 (2d, 1H), 4.83 (m, 1H), 4.83 (m, 1H), 4.65 (t, 2H), 4.4 (s, 2H), 3.92 (q, 2H), 3.42 (t, 2H), 3.12 (m, 2H), 2.77/2.76 (2s, 3H), 2.19 (s, 3H), 1.94 (m, 2H), 1.5 (m, 2H), 1.23/1.21 (2d, 3H), 1 (t, 3H)

Step 2: Preparation of ethyl 3-{1-[4-(benzyloxy)butyl]-4-methyl-1H-benzotriazol-5-yl}-3-(3-{(1R)-1-[6-(benzyloxy)-8-methyl-2,2-dioxo-2H-1,2λ$^6$,3-benzoxathiazin-3(4H)-yl]ethyl}-4-methylphenyl)propanoate Using General Procedure 7 starting from ethyl 3-{1-[4-(benzyloxy)butyl]-4-methyl-1H-benzotriazol-5-yl}-3-{3-[(1S)-1-hydroxyethyl]-4-methylphenyl}propanoate (1 eq.) and 6-(benzyloxy)-8-methyl-3,4-dihydro-2H-1,2λ$^6$,3-benzoxathiazine-2,2-dione (1.1 eq.) as reactants, the title compound (68% yield) was obtained.

$^1$H-NMR (400 MHz, DMSO-d6) δ ppm: 0.90-1.03 (m, 6H) 1.41 (d, J=6.97 Hz, 5H) 1.43-1.53 (m, 4H) 1.81-1.98 (m, 4H) 2.13-2.20 (m, 6H) 2.28 (s, 6H) 2.73-2.80 (m, 6H) 3.11-3.25 (m, 4H) 3.34-3.44 (m, 4H) 3.92 (q, J=7.05 Hz, 4H) 4.25-4.37 (m, 2H) 4.39 (d, J=3.67 Hz, 5H) 4.55-4.66 (m, 4H) 4.81-4.91 (m, 2H) 4.99-5.11 (m, 4H) 5.26 (q, J=6.93 Hz, 2H) 6.63 (d, J=2.81 Hz, 1H) 6.69 (d, J=2.81 Hz, 1H) 6.89-6.97 (m, 2H) 7.06-7.15 (m, 4H) 7.20-7.37 (m, 12H) 7.37-7.48 (m, 10H) 7.51-7.56 (m, 2H) 7.56-7.61 (m, 2H)

Step 3: Preparation of ethyl 3-[1-(4-hydroxybutyl)-4-methyl-1H-benzotriazol-5-yl]-3-{3-[(1R)-1-(6-hydroxy-8-methyl-2,2-dioxo-2H-1,2λ$^6$,3-benzoxathiazin-3(4H)-yl)ethyl]-4-methylphenyl}propanoate Using General Procedure 8 starting from ethyl 3-{1-[4-(benzyloxy)butyl]-4-methyl-1H-benzotriazol-5-yl}-3-(3-{(1R)-1-[6-(benzyloxy)-8-methyl-2,2-dioxo-2H-1,2λ$^6$,3-benzoxathiazin-3(4H)-yl]ethyl}-4-methylphenyl)propanoate (1 eq.) as a reactant, the title compound (63% yield) was obtained.

$^1$H-NMR (400 MHz, DMSO-d6) δ ppm: 9.5/4.4 (s+t, 2H), 7.61 (2d, 1H), 7.58 (2d, 1H), 7.45 (2d, 1H), 7.11 (m, 2H), 6.61 (2d, 1H), 6.41/6.39 (2d, 1H), 5.25 (m, 1H), 4.9 (m, 1H), 4.65 (t, 2H), 4.35/4.29 (2m, 2H), 3.95 (q, 2H), 3.4 (q, 2H), 3.21 (d, 2H), 2.79 (s, 3H), 2.3 (s, 3H), 2.11 (2s, 3H), 1.91 (m, 2H), 1.45 (2d, 3H), 1.38 (m, 2H), 1.01 (2t, 3H)

Step 4: Preparation of ethyl 3-[1-(4-bromobutyl)-4-methyl-1H-benzotriazol-5-yl]-3-{3-[(1R)-1-(6-hydroxy-8-methyl-2,2-dioxo-2H-1,2λ$^6$,3-benzoxathiazin-3(4H)-yl)ethyl]-4-methylphenyl}propanoate Using General Procedure 9 starting from ethyl 3-[1-(4-hydroxybutyl)-4-methyl-1H-benzotriazol-5-yl]-3-{3-[(1R)-1-(6-hydroxy-8-methyl-2,2-dioxo-2H-1,2λ$^6$,3-benzoxathiazin-3(4H)-yl)ethyl]-4-methylphenyl}propanoate (1 eq.) as a reactant, the title compound (white solid, 77% yield) was obtained.

$^1$H-NMR (400 MHz, DMSO-d6) δ ppm: 9.5 (s, 1H), 7.62 (d, 1H), 7.59 (d, 1H), 7.48/7.41 (d, 1H), 7.1 (m, 2H), 6.61 (d, 1H), 6.4/6.39 (d, 1H), 5.24 (m, 1H), 4.88 (m, 1H), 4.69 (t, 2H), 4.31/4.28 (m, 2H), 3.92 (q, 2H), 3.52 (q, 2H), 3.21 (d, 2H), 2.79 (s, 3H), 2.28 (s, 3H), 2.1 (s, 2H), 2 (m, 2H), 1.78 (d, 3H), 1.41 (m, 2H), 1 (t, 3H)

Step 5: Preparation of ethyl[(2R)-2,4,24,31-tetramethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate Using General Procedure 11 starting from ethyl 3-[1-(4-bromobutyl)-4-methyl-1H-benzotriazol-5-yl]-3-{3-[(1R)-1-(6-hydroxy-8-methyl-2,2-dioxo-2H-1,2λ$^6$,3-benzoxathiazin-3(4H)-yl)ethyl]-4-methylphenyl}propanoate (1 eq.) as a reactant, the title compound (white solid, 61% yield) was obtained.

$^1$H-NMR (400 MHz, DMSO-d6) δ ppm: 0.97-1.13 (m, 4H) 1.21-1.32 (m, 2H) 1.53-1.76 (m, 1H) 1.77-1.89 (m, 1H) 2.03-2.10 (m, 3H) 2.12-2.25 (m, 1H) 2.31 (d, J=11.86 Hz, 3H) 2.66 (s, 2H) 2.72-2.80 (m, 1H) 2.81 (s, 1H) 2.95-3.15 (m, 1H) 3.34-3.51 (m, 2H) 3.67 (td, J=9.75, 5.32 Hz, 1H) 3.88-4.01 (m, 3H) 4.62-4.85 (m, 3H) 4.92 (t, J=7.76 Hz, 1H) 5.24 (dq, J=13.89, 6.82 Hz, 1H) 5.53 (d, J=2.93 Hz, 1H) 5.69 (br. s., 1H) 6.56-6.76 (m, 1H) 7.08-7.24 (m, 2H) 7.30 (d, J=7.95 Hz, 1H) 7.44 (d, J=7.70 Hz, 1H) 7.68 (d, J=8.80 Hz, 1H) 7.74 (d, J=8.68 Hz, 1H) 7.88 (d, J=8.68 Hz, 1H)

Step 6: Preparation of Example 29

Using General Procedure 12 starting from ethyl[(2R)-2,4,24,31-tetramethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (1 eq.) as a reactant, the title compound (white solid, 73% yield) was obtained.

The diastereo-pure products were obtained by chromatographic separation on chiral column.

EXAMPLE 29a (2R,8R)

HRMS calculated for $C_{31}H_{34}N_4O_6S$: 590.2199; $[M+H]^+$ found: 591.2273 (δ=0.2 ppm).

$^1$H-NMR (400 MHz, DMSO-d6) δ ppm: 12.25 (m, 1H), 7.7 (d, 1H), 7.48 (dd, 1H), 7.3 (d, 1H), 7.1 (d, 1H), 6.72 (d, 1H), 6.61 (d, 1H), 5.7 (s1, 1H), 5.21 (q, 1H), 4.9 (t, 1H), 4.75 (m, 2H), 4.02/3.48 (2d, 2H), 3.75/3.7 (2m, 2H), 3.28/2.9

(2dd, 2H), 2.8 (s, 3H), 2.31 (s, 3H), 2.2/2.02 (2m, 2H), 2.08 (s, 3H), 1.61/1.28 (2m, 2H), 1.11 (d, 3H)

EXAMPLE 29b (2R,8S)

HRMS calculated for $C_{31}H_{34}N_4O_6S$: 590.2199; $[M+H]^+$ found: 591.2273 (δ=0.2 ppm).

$^1$H-NMR (400 MHz, DMSO-d6) δ ppm: 12.2 (m, 1H), 7.89 (d, 1H), 7.72 (d, 1H), 7.48 (dd, 1H), 7.2 (d, 1H), 7.11 (d, 1H), 6.69 (d, 1H), 5.51 (d, 1H), 5.28 (q, 1H), 4.8-4.7 (2m, 2H), 4.8 (t, 1H), 4/3.4 (2d, 2H), 3.65/3.47 (2m, 2H), 3.2/2.99 (2dd, 2H), 2.69 (s, 3H), 2.3 (s, 3H), 2.18/2.1 (2m, 2H), 2.1 (s, 3H), 1.82/1.71 (2m, 2H), 1.11 (d, 3H)

EXAMPLE 30: [5-Methoxy-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid enantiomer 1

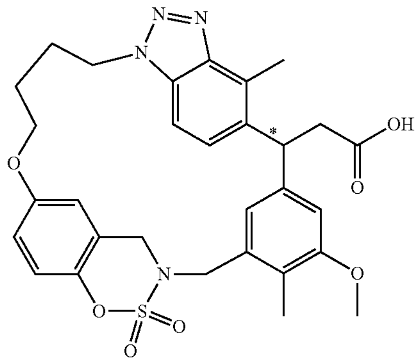

* = RorS enantiomer 2

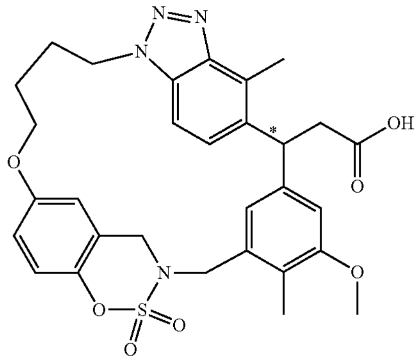

* = RorS

Step B1: Preparation of methyl 5-bromo-3-methoxy-2-methylbenzoate

Methyl 5-bromo-3-hydroxy-2-methylbenzoate (1.0 eq., 26.0 g, 106.1 mmol) was dissolved in DMF (300 mL), then methyl iodide (4 eq., 26.5 mL, 60.2 g, 424.5 mmol) and $Cs_2CO_3$ (4 eq., 137.9 g, 424.5 mmol) were added. The reaction mixture was stirred at RT for 12 h. After the completion of the reaction the mixture was poured into ice water, extracted with EtOAc, after separation the organic phase was dried over $MgSO_4$ and concentrated under reduced pressure.

The crude product was purified by normal phase silica gel chromatography using heptane-EtOAc eluent to give the title compound (light yellow solid, 19.1 g, 69% yield).

$^1$H-NMR (400 MHz, DMSO-d6) δ ppm: 7.44 (s, 1H), 7.34 (s, 1H), 3.88 (s, 3H), 3.83 (s, 3H), 2.25 (s, 3H)

Step B2: Preparation of (5-bromo-3-methoxy-2-methylphenyl)methanol

Methyl 5-bromo-3-methoxy-2-methylbenzoate (1 eq., 19.0 g, 73 mmol) was dissolved in THF (200 mL), the solution was cooled to 0° C. Lithium tetrahydrido aluminate (1.2 eq., 44 mL, 2M solution in THF) was added over 30 min. under $N_2$ atm. the mixture was allowed to warm to RT and stirred at RT for 2 h. The reaction mixture was quenched with aq. sat. $NH_4Cl$ solution, extracted with EtOAc, the organic phase was separated, dried over $MgSO_4$, concentrated under reduced pressure. The crude product was purified by normal phase silica gel chromatography using heptane-EtOAc eluent to give the title compound (yellow solid, 14.7 g, 87% yield).

$^1$H-NMR (400 MHz, DMSO-d6) δ ppm: 7.16 (s, 1H), 7.03 (s, 1H), 5.23 (t, 1H), 4.46 (d, 2H), 3.34 (s, 3H), 2.00 (s, 3H)

Step B3: Preparation of [3-methoxy-2-methyl-5-(4,4,5,5-tetramethyl-1,3,2-dioxaborolan-2-yl)phenyl]methanol Using General Procedure 3 starting from (5-bromo-3-methoxy-2-methylphenyl)methanol (1 eq., 14.6 g, 63 mmol) as a reactant, gave the title compound (12.53 g, 71% yield).

$^1$H-NMR (400 MHz, DMSO-d6) δ ppm: 7.37 (s1, 1H), 7.06 (s1, 1H), 5.04 (t, 1H), 4.47 (d, 2H), 3.79 (s, 3H), 2.09 (s, 3H), 1.29 (s, 12H)

Step 1: Preparation of ethyl 3-{1-[4-(benzyloxy)butyl]-4-methyl-1H-benzotriazol-5-yl}-3-[3-(hydroxymethyl)-5-methoxy-4-methylphenyl]propanoate Using General Procedure 6 starting from ethyl (2E)-3-{1-[4-(benzyloxy)butyl]-4-methyl-1H-benzotriazol-5-yl}prop-2-enoate (1 eq.) and [3-methoxy-2-methyl-5-(4,4,5,5-tetramethyl-1,3,2-dioxaborolan-2-yl)phenyl]methanol (1.15 eq.) as reactants, the title compound (76% yield) was obtained.

$^1$H-NMR (400 MHz, DMSO-d6) δ ppm: 7.59 (d, 1H), 7.49 (d, 1H), 7.35-7.2 (m, 5H), 6.89 (d, 2H), 4.95 (t, 1H), 4.82 (t, 1H), 4.67 (t, 2H), 4.41 (s, 2H), 4.4 (d, 2H), 3.91 (q, 2H), 3.75 (s, 3H), 3.45 (t, 2H), 3.15 (d, 2H), 2.8 (s, 3H), 2 (s, 3H), 1.95 (m, 2H), 1.5 (m, 2H), 1 (t, 3H)

Step 2: Preparation of ethyl 3-{1-[4-(benzyloxy)butyl]-4-methyl-1H-benzotriazol-5-yl}-3-(3-{[6-(benzyloxy)-2,2-dioxo-2H-1,2λ$^6$,3-benzoxathiazin-3(4H)-yl]methyl}-5-methoxy-4-methylphenyl)propanoate Using General Procedure 7 starting from ethyl 3-{1-[4-(benzyloxy)butyl]-4-methyl-1H-benzotriazol-5-yl}-3-[3-(hydroxymethyl)-5-methoxy-4-methylphenyl]propanoate (1 eq.) and 6-(benzyloxy)-3,4-dihydro-2H-1,2λ$^6$,3-benzoxathiazine-2,2-dione (1.1 eq.) as reactants, the title compound (87% yield) was obtained.

$^1$H-NMR (400 MHz, DMSO-d6) δ ppm: 7.59 (d, 1H), 7.54 (d, 1H), 7.49-7.2 (m, 10H), 7.11 (d, 1H), 7.08 (dd, 1H), 6.96 (d, 1H), 6.9 (d, 1H), 6.8 (d, 1H), 5.1 (s, 2H), 4.87 (t, 1H), 4.61 (t, 2H), 4.39 (s, 4H), 4.19 (m, 2H), 3.92 (q, 2H), 3.74 (s, 3H), 3.39 (t, 2H), 3.19 (d, 2H), 2.79 (s, 3H), 2.03 (s, 3H), 1.9 (m, 2H), 1.48 (m, 2H), 0.99 (t, 3H)

Step 3: Preparation of ethyl 3-[1-(4-hydroxybutyl)-4-methyl-1H-benzotriazol-5-yl]-3-{3-[(6-hydroxy-2,2-dioxo-2H-1,2λ$^6$,3-benzoxathiazin-3(4H)-yl)methyl]-5-methoxy-4-methylphenyl}propanoate Using General Procedure 8 starting from ethyl 3-{1-[4-(benzyloxy)butyl]-4-methyl-1H-benzotriazol-5-yl}-3-(3-{[6-(benzyloxy)-2,2-dioxo-2H-1,2λ$^6$,3-benzoxathiazin-3(4H)-yl]methyl}-5-methoxy-4-methylphenyl)propanoate (1 eq.) as a reactant, the title compound (95% yield) was obtained.

$^1$H-NMR (400 MHz, DMSO-d6) δ ppm: 9.7/4.85 (s+t, 2H), 7.6 (d, 1H), 7.52 (d, 1H), 7 (d, 1H), 6.95 (d, 1H), 6.8 (m, 2H), 6.59 (d, 1H), 4.65 (t, 2H), 4.41 (m, 1H), 4.31 (s, 2H), 4.18 (m, 2H), 3.95 (q, 2H), 3.78 (s, 3H), 3.4 (t, 2H), 3.2 (d, 2H), 2.8 (s, 3H), 2.05 (s, 3H), 1.91 (m, 2H), 1.38 (m, 2H), 1 (t, 3H)

Step 4: Preparation of ethyl 3-[1-(4-bromobutyl)-4-methyl-1H-benzotriazol-5-yl]-3-{3-[(6-hydroxy-2,2-dioxo-2H-1,2λ$^6$,3-benzoxathiazin-3(4H)-yl)methyl]-5-methoxy-4-methylphenyl}propanoate Using General Procedure 9 starting from ethyl 3-[1-(4-hydroxybutyl)-4-methyl-1H-benzotriazol-5-yl]-3-{3-[(6-hydroxy-2,2-dioxo-2H-1,2)$^6$,3-benzoxathiazin-3(4H)-yl)methyl]-5-methoxy-4-methylphenyl}propanoate (1 eq.) as a reactant, the title compound (white solid, 86% yield) was obtained.

$^1$H-NMR (400 MHz, DMSO-d6) δ ppm: 9.67 (s, 1H), 7.63 (d, 1H), 7.56 (d, 1H), 6.98 (d, 1H), 6.95 (d, 1H), 6.78 (m, 2H), 6.57 (d, 1H), 4.84 (t, 1H), 4.69 (t, 2H), 4.33 (s, 2H), 4.2/4.12 (2d, 2H), 3.94 (q, 2H), 3.75 (s, 3H), 3.53 (t, 2H), 3.19 (d, 2H), 2.78 (s, 3H), 2.05 (s, 3H), 2 (quint, 2H), 1.77 (quint, 2H), 1 (t, 3H)

Step 5: Preparation of ethyl[5-methoxy-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate Using General Procedure 11 starting from ethyl 3-[1-(4-bromobutyl)-4-methyl-1H-benzotriazol-5-yl]-3-{3-[(6-hydroxy-2,2-dioxo-2H-1,2λ$^6$,3-benzoxathiazin-3(4H)-yl)methyl]-5-methoxy-4-methylphenyl}propanoate (1 eq.) as a reactant, the title compound (quant.) was obtained.

$^1$H-NMR (400 MHz, DMSO-d6) δ ppm: 7.67 (d, 1H), 7.45 (d, 1H), 7.23 (s, 1H), 6.98 (d, 1H), 6.79 (dd, 1H), 6.12 (d, 1H), 5.81 (d, 1H), 4.83-4.74 (m, 3H), 4.16-3.78 (m, 6H), 3.9 (s, 3H), 3.64/3.4 (dt, 2H), 3.21/3.07 (dd, 2H), 2.64 (s, 3H), 2.24-2.03 (m, 2H), 2.14 (s, 3H), 1.82/1.65 (m, 2H), 1.02 (t, 3H)

Step 6: Preparation of Example 30

Using General Procedure 12 starting from ethyl[5-methoxy-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (1 eq.) as a reactant, the title compound (white solid, 66% yield) was obtained.

The enantiopure products were obtained by chromatographic separation on chiral column.

EXAMPLE 30a (E1)

HRMS calculated for $C_{30}H_{32}N_4O_7S$: 592.1992; $[M+H]^+$ found: 593.2069 (δ=0.8 ppm).

EXAMPLE 30b (E2)

HRMS calculated for $C_{30}H_{32}N_4O_7S$: 592.1992; $[M+H]^+$ found: 593.2066 (δ=0.3 ppm).

$^1$H-NMR (400 MHz, DMSO-d6) δ ppm: 12.2 (m, 1H), 7.7 (d, 1H), 7.45 (d, 1H), 7.25 (d, 1H), 7 (d, 1H), 6.8 (dd, 1H), 6.11 (d, 1H), 5.8 (d, 1H), 4.8 (m, 3H), 4.12/3.82 (d, 2H), 4.03/3.85 (d, 2H), 3.9 (s, 3H), 3.65/3.4 (m, 2H), 3.1/2.98 (dd, 2H), 2.62 (s, 3H), 2.21/2.1 (m, 2H), 2.18 (s, 3H), 1.88/1.68 (m, 2H)

EXAMPLE 31: [(2S,8S)-4-methoxy-2,32-dimethyl-28,28-dioxo-22,27-dioxa-28λ$^6$-thia-1,14,15,16-tetraazahexacyclo[21.5.3.1$^{3,7}$0.1$^{9,13}$0.0$^{12,16}$0.0$^{26,30}$]tritriaconta-3(33),4,6,9(32),10,12,14,23,25,30-decaen-8-yl]acetic acid, [(2R,8S)-4-methoxy-2,32-dimethyl-28,28-dioxo-22,27-dioxa-28λ$^6$-thia-1,14,15,16-tetraazahexacyclo[21.5.3.1$^{3,7}$0.1$^{9,13}$0.0$^{12,16}$0.0$^{26,30}$]tritriaconta-3(33),4,6,9(32),10,12,14,23,25,30-decaen-8-yl]acetic acid, [(2S,8R)-4-methoxy-2,32-dimethyl-28,28-dioxo-22,27-dioxa-28λ$^6$-thia-1,14,15,16-tetraazahexacyclo[21.5.3.1$^{3,7}$0.1$^{9,13}$0.0$^{12,16}$0.0$^{26,30}$]tritriaconta-3(33),4,6,9(32),10,12,14,23,25,30-decaen-8-yl]acetic acid and [(2R,8R)-4-methoxy-2,32-dimethyl-28,28-dioxo-22,27-dioxa-28λ$^6$-thia-1,14,15,16-tetraazahexacyclo[21.5.3.1$^{3,7}$0.1$^{9,13}$0.0$^{12,16}$0.0$^{26,30}$]tritriaconta-3(33),4,6,9(32),10,12,14,23,25,30-decaen-8-yl]acetic acid

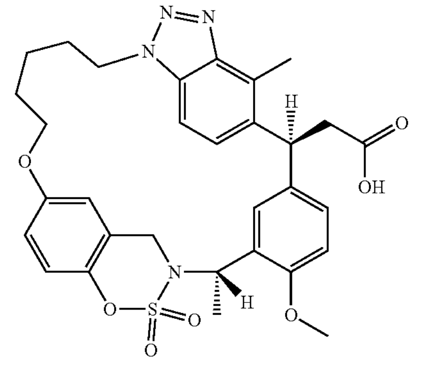

-continued

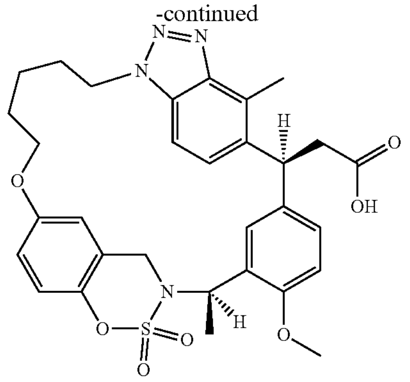

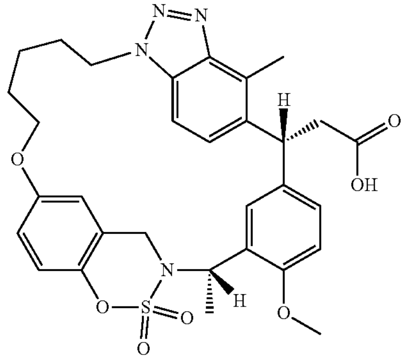

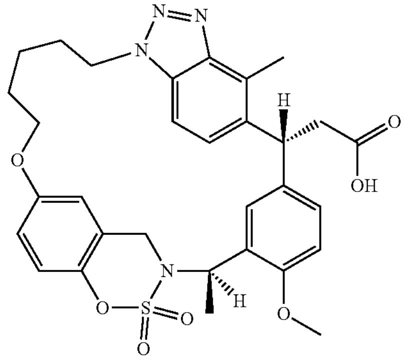

Step A1: Preparation of {[(5-iodopentyl)oxy]methyl}benzene

To a solution of 5-(benzyloxy)pentan-1-ol (1 eq., 1.15 kg, 5.92 mol) in DCM (8 L) $PPh_3$ (1.3 eq., 2.02 kg, 7.70 mol) and imidazole (1.3 eq., 524 g, 7.70 mol) were added at 15° C. Iodine (1.3 eq., 1.95 kg, 7.70 mol) was added to the mixture at 0-15° C. by portions. The mixture was stirred at 15° C. for 0.5 h. After the completion of the reaction, the mixture was quenched with sat. aq. $Na_2SO_3$ (5 L). The organic layer was separated, dried over anhydrous $Na_2SO_4$, filtered and concentrated under reduced pressure. The residue was cooled to 0° C. slowly. The precipitate formed was filtered out, the filter cake was washed with MTBE (2×1.3 L) and the filtrate was concentrated under reduced pressure. The residue was purified by normal phase silica gel chromatography using petroleum ether/EtOAc 0 to 50:1 eluent to give the title compound (pale yellow oil, 1.45 kg, 81% yield).

$^1$H-NMR (400 MHz, $CDCl_3$) δ ppm: 7.27-7.37 (m, 5H), 4.52 (m, 2H), 3.49 (t, J=6.4 Hz, 2H), 3.20 (t, J=7.2 Hz, 2H), 1.84-1.88 (m, 2H), 1.64-1.67 (m, 2H), 1.49-1.53 (m, 2H)

Step A2: Preparation of N-[5-(benzyloxy)pentyl]-4-bromo-3-methyl-2-nitroaniline

To a solution of 4-bromo-3-methyl-2-nitro-aniline (1 eq., 25 g, 108 mmol) and {[(5-iodopentyl)oxy]methyl}benzene (1.5 eq., 49.4 g, 162 mmol) in DMF (250 mL) potassium tert-butylate was added portion-wise (1.5 eq., 18.2 g, 162 mmol) at 0-5° C., then the mixture was stirred at RT for 3 h. The reaction mixture was poured into $H_2O$ (520 mL), extracted with MTBE (3×90 mL). The combined organic layers were dried over $Na_2SO_4$, filtered and concentrated to dryness. The residue was purified by normal phase silica gel chromatography using petroleum ether/EtOAc 0 to 7:1 eluent to give the title compound (red oil, 26.46 g, 65 mmol, 60% yield).

$^1$H-NMR (400 MHz, $CDCl_3$) δ ppm: 7.46 (d, J=9.2 Hz, 1H), 7.33-7.36 (m, 5H), 6.54 (d, J=9.2 Hz, 1H), 5.72 (s, 1H), 4.51 (s, 2H), 3.49 (t, J=6.4 Hz, 2H), 3.13-3.18 (m, 2H), 2.45 (s, 3H), 1.64-1.71 (m, 4H), 1.44-1.52 (m, 2H)

Step A3: Preparation of $N^1$-[5-(benzyloxy)pentyl]-4-bromo-3-methylbenzene-1,2-diamine To a solution of N-[5-(benzyloxy)pentyl]-4-bromo-3-methyl-2-nitroaniline (1 eq., 316 g, 776 mmol) in EtOH (1.9 L) and water (950 mL) $NH_4Cl$ (10 eq., 415 g, 7.76 mol) was added. The mixture was heated to 70° C., then iron (5 eq., 217 g, 3.88 mol) was added in small portions and the mixture was heated at 80° C. for 1 h. The reaction mixture was cooled to 50° C., bergmehl was added and the stirring was continued for 10 min. The reaction mixture was filtered through bergmehl. The filter cake was washed with hot EtOAc (2×2.5 L at 50° C.) and the filtrate was concentrated under reduced pressure. The aq. layer was extracted with EtOAc (3×1.3 L), the organic layer was washed with brine (3×0.5 L), dried over $Na_2SO_4$ and concentrated under reduced pressure. To the crude product (250 g) petroleum ether: EtOAc 10:1 (750 mL) was added, the mixture was stirred at 25° C. for 16 h. The precipitate was filtered out and the filter cake was washed with petroleum ether: EtOAc 10:1 (100 mL), then dried in vacuo. The crude product (161 g, 427 mmol, 55% yield) was obtained as light brown solid.

$^1$H-NMR (400 MHz, $CDCl_3$) δ ppm: 7.27-7.36 (m, 5H), 7.01 (d, J=8.8 Hz, 1H), 6.45 (d, J=8.4 Hz, 1H), 4.52 (s, 2H), 3.47-3.52 (m, 4H), 3.08 (t, J=6.8 Hz, 2H), 2.32 (s, 3H), 1.65-1.71 (m, 4H), 1.53-1.57 (m, 2H)

Step A4: Preparation of 1-[5-(benzyloxy)pentyl]-5-bromo-4-methyl-1H-benzotriazole To a solution of $N^1$-[5-(benzyloxy)pentyl]-4-bromo-3-methylbenzene-1,2-diamine (1 eq., 200 g, 530 mmol) in MeCN (1.40 L) 3-methylbutyl nitrite (2.5 eq., 155 g, 1.33 mol) was added at RT and the mixture was stirred for 16 h. After the reaction completed, the mixture was concentrated under reduced pressure. The residue was dissolved in EtOAc (1 L), washed with sat. $Na_2SO_3$ (3×340 mL), then the organic layer was washed with brine (0.5 L). The aq. layer was extracted with EtOAc (2×170 mL), the combined organic layers were dried over $Na_2SO_4$, filtered and concentrated under reduced pressure. The crude product was purified by normal phase silica gel chromatography using petroleum ether/EtOAc 0 to 50:1 to give the title compound (134 g, 346.7 mmol, 65% yield) as black oil.

$^1$H-NMR (400 MHz, $CDCl_3$) δ ppm: 7.49 (d, J=8.8 Hz, 1H), 7.20-7.26 (m, 5H), 7.12 (d, J=8.8 Hz, 1H), 4.52 (t, J=6.8 Hz, 2H), 4.39 (s, 2H), 3.36 (t, J=6.4 Hz, 2H), 2.76 (s, 3H), 1.92-1.97 (m, 2H), 1.56-1.60 (m, 2H), 1.33-1.37 (m, 2H)

Step A5: Preparation of ethyl (2E)-3-{1-[5-(benzyloxy)pentyl]-4-methyl-1H-benzotriazol-5-yl}prop-2-enoate Using General Procedure 2 STEP 5 starting from 1-[5-(benzyloxy)pentyl]-5-bromo-4-methyl-1H-benzotriazole (1 eq.) as a reactant, the title compound (58% yield) was obtained.

$^1$H-NMR (400 MHz, $CDCl_3$) δ ppm: 8.14 (d, J=16.4 Hz, 1H), 7.68 (d, J=9.2 Hz, 1H), 7.23-7.40 (m, 5H), 6.42 (d, J=15.6 Hz, 1H), 4.62 (t, J=7.2 Hz, 2H), 4.40-4.53 (m, 2H), 4.31 (q, J=7.2 Hz, 2H), 3.45 (t, J=6.4 Hz, 2H), 2.92 (s, 3H), 2.03 (m, 2H), 1.62-1.76 (m, 2H), 1.40-1.50 (m, 2H), 1.37 (t, J=7.2 Hz, 3H)

Step 1: Preparation of ethyl 3-{1-[5-(benzyloxy)pentyl]-4-methyl-1H-benzotriazol-5-yl}-3-[3-(1-hydroxyethyl)-4-methoxyphenyl]propanoate Using General Procedure 6 starting from ethyl (2E)-3-{1-[5-(benzyloxy)pentyl]-4-methyl-1H-benzotriazol-5-yl}prop-2-enoate (1 eq.) and 1-[2-methoxy-5-(4,4,5,5-tetramethyl-1,3,2-dioxaborolan-2-yl)phenyl]ethan-1-ol (1.1 eq.) as reactants, the title compound (70% yield) was obtained.

$^1$H-NMR (400 MHz, DMSO-d6) δ ppm: 7.61 (d, 1H), 7.45 (d, 1H), 7.38 (d, 1H), 7.32-7.2 (m, 5H), 7.12 (dd, 1H), 6.81 (d, 1H), 4.9 (d, 1H), 4.9 (m, 1H), 4.8 (m, 1H), 4.61 (t, 2H), 4.4 (s, 2H), 3.91 (q, 2H), 3.7 (s, 3H), 3.38 (t, 2H), 3.1 (d, 2H), 2.78 (2s, 3H), 1.89 (m, 2H), 1.55 (m, 2H), 1.3 (m, 2H), 1.2 (2d, 3H), 1 (t, 3H)

Step 2: Preparation of ethyl 3-(3-{1-[6-(benzyloxy)-2,2-dioxo-2H-1,2λ$^6$,3-benzoxathiazin-3(4H)-yl]ethyl}-4-methoxyphenyl)-3-{1-[5-(benzyloxy)pentyl]-4-methyl-1H-benzotriazol-5-yl}propanoate Using General Procedure 7 starting from ethyl 3-{1-[5-(benzyloxy)pentyl]-4-methyl-1H-benzotriazol-5-yl}-3-[3-(1-hydroxyethyl)-4-methoxyphenyl]propanoate (1 eq.) and 6-(benzyloxy)-3,4-dihydro-2H-1,2λ$^6$,3-benzoxathiazine-2,2-dione (1.1 eq.) as reactants, the title compound (58% yield) was obtained.

$^1$H-NMR (400 MHz, DMSO-d6) δ ppm: 7.6 (d, 1H), 7.5 (2d, 1H), 7.45-7.2 (m, 11H), 7.1 (2d, 1H), 6.9 (m, 2H), 6.75 (m, 2H), 5.39 (m, 1H), 5.02 (m, 2H), 4.81 (m, 1H), 4.6-4.5 (m, 2H), 4.6 (2t, 2H), 4.4 (s, 2H), 3.91 (q, 2H), 3.65 (s, 3H), 3.35 (m, 2H), 3.18 (d, 2H), 2.78 (s, 3H), 1.89 (m, 2H), 1.55 (m, 2H), 1.45 (2d, 3H), 1.28 (m, 2H), 0.99 (t, 3H)

Step 3: Preparation of ethyl 3-{3-[1-(6-hydroxy-2,2-dioxo-2H-1,2λ$^6$,3-benzoxathiazin-3(4H)-yl)ethyl]-4-methoxyphenyl}-3-[1-(5-hydroxypentyl)-4-methyl-1H-benzotriazol-5-yl]propanoate Using General Procedure 8 starting from ethyl 3-(3-{1-[6-(benzyloxy)-2,2-dioxo-2H-1,2λ$^6$,3-benzoxathiazin-3(4H)-yl]ethyl}-4-methoxyphenyl)-3-{1-[5-(benzyloxy)pentyl]-4-methyl-1H-benzotriazol-5-yl}propanoate (1 eq.) as a reactant, the title compound (84% yield) was obtained.

$^1$H-NMR (400 MHz, DMSO-d6) δ ppm: 9.5/4.3 (s+m, 2H), 7.62 (d, 1H), 7.52 (d, 1H), 7.41 (d, 1H), 7.15 (dd, 1H), 6.81 (d, 1H), 6.79 (d, 1H), 6.69 (dd, 1H), 6.5 (d, 1H), 5.39 (m, 1H), 4.81 (m, 1H), 4.65 (t, 2H), 4.6-4.4 (m, 2H), 3.92 (q, 2H), 3.68 (s, 3H), 3.3 (m, 2H), 3.2 (d, 2H), 2.79 (2s, 3H), 1.88 (m, 2H), 1.45 (m, 5H), 1.25 (m, 2H), 1 (2t, 3H)

Step 4: Preparation of ethyl 3-[1-(5-bromopentyl)-4-methyl-1H-benzotriazol-5-yl]-3-{3-[1-(6-hydroxy-2,2-dioxo-2H-1,2λ$^6$,3-benzoxathiazin-3(4H)-yl)ethyl]-4-methoxyphenyl}propanoate Using General Procedure 9 starting from ethyl 3-{3-[1-(6-hydroxy-2,2-dioxo-2H-1,2λ$^6$,3-benzoxathiazin-3(4H)-yl)ethyl]-4-methoxyphenyl}-3-[1-(5-hydroxypentyl)-4-methyl-1H-benzotriazol-5-yl]propanoate (1 eq.) as a reactant, the title compound (white solid, 66% yield) was obtained.

$^1$H-NMR (400 MHz, DMSO-d6) δ ppm: 9.42 (s, 1H), 7.65 (d, 1H), 7.55 (d, 1H), 7.41 (d, 1H), 7.12 (dd, 1H), 6.81 (d, 1H), 6.79 (d, 1H), 6.65 (dd, 1H), 6.5 (d, 1H), 5.39 (m, 1H), 4.81 (m, 1H), 4.65 (t, 2H), 4.6-4.4 (m, 2H), 3.92 (q, 2H), 3.68 (s, 3H), 3.49 (t, 2H), 3.2 (d, 2H), 2.79 (2s, 3H), 1.9 (m, 2H), 1.8 (m, 2H), 1.45 (d, 3H), 1.35 (m, 2H), 1 (t, 3H)

Step 5: Preparation of ethyl[4-methoxy-2,32-dimethyl-28,28-dioxo-22,27-dioxa-28λ$^6$-thia-1,14,15,16-tetraazahexacyclo[21.5.3.1$^{3,7}$0.1$^{9,13}$0.0$^{12,16}$0.0$^{26,}$$_{30}$]tritriaconta-3(33),4,6,9(32),10,12,14,23,25,30-decaen-8-yl]acetate Using General Procedure 11 starting from ethyl 3-[1-(5-bromopentyl)-4-methyl-1H-benzotriazol-5-yl]-3-{3-[1-(6-hydroxy-2,2-dioxo-2H-1,2)$^6$,3-benzoxathiazin-3(4H)-yl)ethyl]-4-methoxyphenyl}propanoate (1 eq.) as a reactant, the title compound (quant.) was obtained.

$^1$H-NMR (400 MHz, DMSO-d6) δ ppm: 1.01 (t, J=7.03 Hz, 7H) 1.25 (d, J=7.34 Hz, 4H) 1.35 (d, J=4.89 Hz, 5H) 1.50 (d, J=7.09 Hz, 5H) 1.55-1.74 (m, 5H) 1.88-1.97 (m, 3H) 2.70-2.78 (m, 2H) 2.81 (s, 3H) 2.86 (s, 3H) 3.01 (dd, J=15.53, 7.70 Hz, 1H) 3.17 (ddd, J=15.62, 7.61, 4.16 Hz, 4H) 3.62 (s, 4H) 3.65-3.74 (m, 6H) 3.76-3.84 (m, 1H) 3.92 (quin, J=7.24 Hz, 4H) 4.01 (d, J=2.32 Hz, 2H) 4.14 (d, J=17.97 Hz, 1H) 4.41 (d, J=17.61 Hz, 1H) 4.70 (d, J=6.24 Hz, 4H) 4.83 (t, J=8.13 Hz, 1H) 4.89 (t, J=7.58 Hz, 1H) 5.42-5.55 (m, 2H) 5.69 (d, J=2.69 Hz, 1H) 6.11 (d, J=2.81 Hz, 1H) 6.66-6.77 (m, 4H) 6.85 (dd, J=10.88, 9.05 Hz, 2H) 6.94 (d, J=8.68 Hz, 1H) 7.01 (d, J=1.96 Hz, 1H) 7.15-7.20 (m, 1H) 7.26 (d, J=8.80 Hz, 1H) 7.47-7.54 (m, 2H) 7.59-7.65 (m, 2H) 7.66-7.73 (m, 2H)

Step 6: Preparation of Example 31

Using General Procedure 12 starting from ethyl[4-methoxy-2,32-dimethyl-28,28-dioxo-22,27-dioxa-28λ$^6$-thia-1,14,15,16-tetraazahexacyclo[21.5.3.1$^{3,7}$0.1$^{9,13}$0.0$^{12,16}$0.0$^{26,30}$]tritriaconta-3(33),4,6,9(32),10,12,14,23,25,30-decaen-8-yl]acetate (1 eq.) as a reactant, the title compound (white solid, 67% yield) was obtained.

The diastereo-pure products were obtained by chromatographic separation on chiral column.

EXAMPLE 31a (2S,8S)

HRMS calculated for $C_{31}H_{34}N_4O_7S$: 606.2148; [M+H]$^+$ found: 607.2223 (δ=0.3 ppm).

$^1$H-NMR (400 MHz, DMSO-d6) δ ppm: 7.61 (d, 1H), 7.51 (dd, 1H), 7.21 (d, 1H), 7 (d, 1H), 6.99 (d, 1H), 6.88 (d, 1H), 6.75 (dd, 1H), 5.75 (d, 1H), 5.49 (q, 1H), 4.9 (t, 1H), 4.7 (m, 2H), 4 (s, 2H), 3.81/3.61 (2m, 2H), 3.72 (s, 3H), 3.09/2.88 (2dd, 2H), 2.81 (s, 3H), 2 (m, 2H), 1.65 (m, 2H), 1.38/1.18 (2m, 2H), 1.28 (d, 3H)

EXAMPLE 31b (2R,8S)

HRMS calculated for $C_{31}H_{34}N_4O_7S$: 606.2148; $[M+H]^+$ found: 607.2221 (δ=0.0 ppm).

$^1$H-NMR (400 MHz, DMSO-d6) δ ppm: 7.7 (s, 2H), 7.58 (d, 1H), 7.2 (dd, 1H), 6.82 (d, 1H), 6.71 (d, 1H), 6.7 (dd, 1H), 6.1 (d, 1H), 5.5 (q, 1H), 4.81 (t, 1H), 4.7 (t, 2H), 4.39/4.1 (2d, 2H), 3.7 (m, 2H), 3.61 (s, 3H), 3.15/3.05 (2dd, 2H), 2.8 (s, 3H), 2 (m, 2H), 1.7/1.52 (2m, 2H), 1.48 (d, 3H), 1.39/1.18 (2m, 2H)

EXAMPLE 31c (2S,8R)

HRMS calculated for $C_{31}H_{34}N_4O_7S$: 606.2148; $[M+H]^+$ found: 607.2232 (δ=1.8 ppm).

$^1$H-NMR (400 MHz, DMSO-d6) δ ppm: 12.07 (s1, 1H), 7.68 (s, 2H), 7.46 (d, 1H), 7.19 (dd, 1H), 6.84 (d, 1H), 6.73 (d, 1H), 6.71 (dd, 1H), 6.09 (d, 1H), 5.5 (q, 1H), 4.81 (t, 1H), 4.7 (t, 2H), 4.38/4.1 (2d, 2H), 3.71 (m, 2H), 3.63 (s, 3H), 3.15/3.05 (2dd, 2H), 2.8 (s, 3H), 1.99 (m, 2H), 1.69/1.53 (2m, 2H), 1.47 (d, 3H), 1.38/1.18 (2m, 2H)

EXAMPLE 31d (2R,8R)

HRMS calculated for $C_{31}H_{34}N_4O_7S$: 606.2148; $[M+H]^+$ found: 607.2221 (δ=0.0 ppm).

$^1$H-NMR (400 MHz, DMSO-d6) δ ppm: 12.2 (s1, 1H), 7.61 (d, 1H), 7.53 (dd, 1H), 7.2 (d, 1H), 6.99/6.97 (2d, 2H), 6.87 (d, 1H), 6.75 (dd, 1H), 5.74 (d, 1H), 5.46 (q, 1H), 4.88 (t, 1H), 4.69 (m, 2H), 3.99 (s, 2H), 3.82/3.63 (2m, 2H), 3.74 (s, 3H), 3.07/2.87 (dd+m, 2H), 2.85 (s, 3H), 1.99 (m, 2H), 1.63 (m, 2H), 1.37/1.18 (2m, 2H), 1.24 (d, 3H)

EXAMPLE 32: [23-Fluoro-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid enantiomer 1

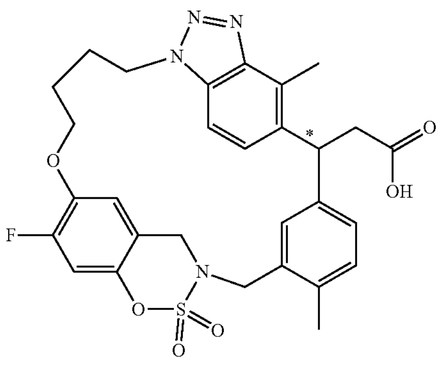

* = RorS

-continued enantiomer 2

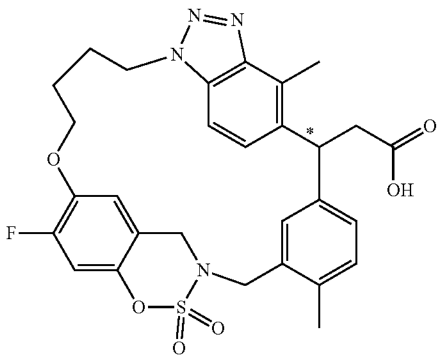

* = RorS

Step C1: Preparation of 5-(benzyloxy)-4-fluoro-2-hydroxybenzaldehyde

Using General Procedure 4 STEP 1 starting from 4-(benzyloxy)-3-fluorophenol (1 eq.) as a reactant, the title compound (95% yield) was obtained.

$^1$H-NMR (500 MHz, DMSO-d6) δ ppm: 10.78 (s, 1H), 10.18 (s, 1H), 7.48-7.29 (m, 5H), 7.43 (d, 1H), 6.87 (d, 1H), 5.13 (s, 2H)

Step C2: Preparation of 6-(benzyloxy)-7-fluoro-2H-1,2)$^6$,3-benzoxathiazine-2,2-dione Using General Procedure 4 STEP 2 starting from 5-(benzyloxy)-4-fluoro-2-hydroxybenzaldehyde (1 eq.) as a reactant, the title compound (94% yield) was obtained.

$^1$H-NMR (500 MHz, DMSO-d6) δ ppm: 9.11 (s, 1H), 7.97 (d, 1H), 7.76 (d, 1H), 7.52-7.36 (m, 5H), 5.25 (s, 2H)

Step C3: Preparation of 6-(benzyloxy)-7-fluoro-3,4-dihydro-2H-1,2λ$^6$,3-benzoxathiazine-2,2-dione Using General Procedure 4 STEP 3 starting from 6-(benzyloxy)-7-fluoro-2H-1,2λ$^6$,3-benzoxathiazine-2,2-dione (1 eq.) as a reactant, the title compound (yellow solid, 86% yield) was obtained.

$^1$H-NMR (500 MHz, DMSO-d6) δ ppm: 8.56 (brs, 1H), 7.48-7.32 (m, 5H), 7.25 (d, 1H), 7.19 (d, 1H), 5.14 (s, 2H), 4.5 (s, 2H)

Step 1: Preparation of ethyl 3-{1-[4-(benzyloxy)butyl]-4-methyl-1H-benzotriazol-5-yl}-3-(3-{[6-(benzyloxy)-7-fluoro-2,2-dioxo-2H-1,2λ$^6$,3-benzoxathiazin-3(4H)-yl]methyl}-4-methylphenyl)propanoate Using General Procedure 7 starting from ethyl (2E)-3-{1-[4-(benzyloxy)butyl]-4-methyl-1H-benzotriazol-5-yl}prop-2-enoate (1 eq.) and 6-(benzyloxy)-7-fluoro-3,4-dihydro-2H-1,2λ$^6$,3-benzoxathiazine-2,2-dione (1.2 eq.) as reactants, the title compound (66% yield) was obtained.

$^1$H-NMR (500 MHz, DMSO-d6) δ ppm: 7.58 (d, 1H), 7.49 (d, 1H), 7.47 (dm, 2H), 7.41 (tm, 2H), 7.36 (tm, 1H), 7.3 (d, 1H), 7.3 (m, 2H), 7.27 (d, 1H), 7.25 (m, 2H), 7.25 (d, 1H), 7.24 (m, 1H), 7.2 (dd, 1H), 7.13 (d, 1H), 5.14 (s, 2H), 4.86 (t, 1H), 4.64 (t, 2H), 4.47/4.42 (d+d, 2H), 4.38 (s, 2H), 4.26/4.21 (d+d, 2H), 3.92 (q, 2H), 3.39 (t, 2H), 3.2/3.16 (dd+dd, 2H), 2.77 (s, 3H), 2.2 (s, 3H), 1.92 (m, 2H), 1.47 (m, 2H), 0.97 (t, 3H)

Step 2: Preparation of ethyl 3-{3-[(7-fluoro-6-hydroxy-2,2-dioxo-2H-1,2)$^6$,3-benzoxathiazin-3(4H)-yl)methyl]-4-methylphenyl}-3-[1-(4-hydroxybutyl)-4-methyl-1H-benzotriazol-5-yl]propanoate Using General Procedure 8 starting from ethyl 3-{1-[4-(benzyloxy)butyl]-4-methyl-1H-benzotriazol-5-yl}-3-(3-{[6-(benzyloxy)-7-fluoro-2,2-dioxo-2H-1,2λ$^6$,3-benzoxathiazin-3(4H)-yl]methyl}-4-methylphenyl)propanoate (1 eq.) as a reactant, the title compound (white solid foam, 95% yield) was obtained.

$^1$H-NMR (500 MHz, DMSO-d6) δ ppm: 10.17 (s, 1H), 7.62 (d, 1H), 7.52 (d, 1H), 7.26 (d, 1H), 7.2 (dd, 1H), 7.18 (d, 1H), 7.14 (d, 1H), 6.84 (d, 1H), 4.84 (t, 1H), 4.65 (t, 2H), 4.44 (brt., 1H), 4.4 (s, 2H), 4.25/4.2 (d+d, 2H), 3.94 (q, 2H), 3.38 (m, 2H), 3.18 (d, 2H), 2.77 (s, 3H), 2.22 (s, 3H), 1.9 (m, 2H), 1.36 (m, 2H), 1 (t, 3H)

Step 3: Preparation of ethyl 3-[1-(4-chlorobutyl)-4-methyl-benzotriazol-5-yl]-3-[3-[(7-fluoro-6-hydroxy-2,2-dioxo-4H-1,2λ$^6$,3-benzoxathiazin-3-yl)methyl]-4-methyl-phenyl]propanoate Using General Procedure 10 starting from ethyl 3-{3-[(7-fluoro-6-hydroxy-2,2-dioxo-2H-1,2λ$^6$,3-benzoxathiazin-3(4H)-yl)methyl]-4-methylphenyl}-3-[1-(4-hydroxybutyl)-4-methyl-1H-benzotriazol-5-yl]propanoate (1 eq.) as a reactant, the title compound (yellow oil, quant.) was obtained.

$^1$H-NMR (500 MHz, DMSO-d6) δ ppm: 10.17 (s, 1H), 7.64 (d, 1H), 7.53 (d, 1H), 7.25 (d, 1H), 7.2 (dd, 1H), 7.18 (d, 1H), 7.14 (d, 1H), 6.84 (d, 1H), 4.85 (t, 1H), 4.7 (t, 2H), 4.4 (s, 2H), 4.25/4.19 (d+d, 2H), 3.94 (q, 2H), 3.65 (t, 2H), 3.18 (d, 2H), 2.77 (s, 3H), 2.22 (s, 3H), 1.99 (m, 2H), 1.68 (m, 2H), 1 (t, 3H)

Step 4: Preparation of ethyl[23-fluoro-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate Using General Procedure 11 starting from ethyl 3-[1-(4-chlorobutyl)-4-methyl-benzotriazol-5-yl]-3-[3-[(7-fluoro-6-hydroxy-2,2-dioxo-4H-1,2λ$^6$,3-benzoxathiazin-3-yl)methyl]-4-methyl-phenyl]propanoate (1 eq.) as a reactant, the title compound (white solid foam, 69% yield) was obtained.

$^1$H-NMR (500 MHz, DMSO-d6) δ ppm: 7.69 (d, 1H), 7.47 (dd, 1H), 7.47 (d, 1H), 7.27 (d, 1H), 7.2 (d, 1H), 6.64 (d, 1H), 6.1 (d, 1H), 4.83/4.76 (m+m, 2H), 4.78 (t, 1H), 4.24/3.9 (d+d, 2H), 3.99/3.76 (d+d, 2H), 3.92 (q, 2H), 3.7/3.42 (m+m, 2H), 3.14/3.06 (dd+dd, 2H), 2.64 (s, 3H), 2.32 (s, 3H), 2.21/2.01 (m+m, 2H), 1.8/1.62 (m+m, 2H), 1.01 (t, 3H)

Step 5: Preparation of Example 32

Using General Procedure 12 starting from ethyl[23-fluoro-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (1 eq.) as a reactant, the title compound (white solid, 55% yield) was obtained.

The enantiopure products were obtained by chromatographic separation on chiral column.

EXAMPLE 32a (E1)

HRMS calculated for $C_{29}H_{29}FN_4O_6S$: 580.1792; [M+H]$^+$ found: 581.1863 (δ=−0.3 ppm).

EXAMPLE 32b (E2)

HRMS calculated for $C_{29}H_{29}FN_4O_6S$: 580.1792; [M+H]$^+$ found: 581.1867 (δ=0.4 ppm).

$^1$H-NMR (500 MHz, DMSO-d6) δ ppm: 7.68 (d, 1H), 7.48 (s, 1H), 7.45 (d, 1H), 7.27 (s, 1H), 7.2 (d, 1H), 6.61 (s, 1H), 6.08 (d, 1H), 4.84/4.74 (m+m, 2H), 4.75 (t, 1H), 4.23/3.91 (d+d, 2H), 3.99/3.76 (d+d, 2H), 3.69/3.4 (m+m, 2H), 3.01/2.94 (dd+dd, 2H), 2.63 (s, 3H), 2.31 (s, 3H), 2.22/2.01 (m+m, 2H), 1.81/1.62 (m+m, 2H)

$^{13}$C-NMR (125 MHz, DMSO-d6) δ ppm: 131.3, 131.3, 128.8, 127.2, 112.6, 107.9, 107.4, 68.7, 52, 48.5, 48.2, 41.9, 41.1, 26.8, 25.4, 16.5, 13.4

EXAMPLE 33: [5-Chloro-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid enantiomer 1

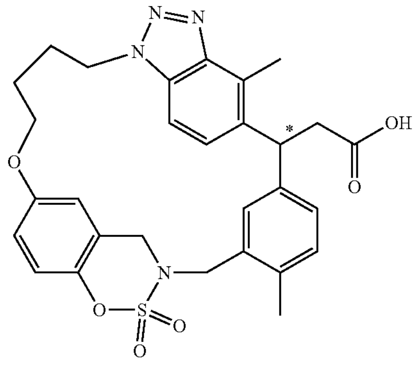

* = RorS enantiomer 2

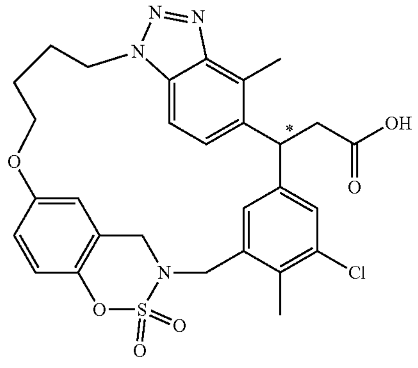

* = RorS

Step B1: Preparation of (5-bromo-3-chloro-2-methylphenyl)methanol

Methyl 5-bromo-3-chloro-2-methyl-benzoate (1 eq., 20.0 g, 75.9 mmol) was dissolved in EtOH (500 mL), then sodium borohydride (3 eq., 8.6 g, 227.7 mmol) was added to the stirred mixture at 0° C. The mixture was stirred at this temperature for 10 min and calcium chloride (3 eq., 25.3 g, 227.7 mmol) was added over a period of 30 min. Then it was allowed to warm to RT and stirred at RT for 2 h. The reaction mixture was quenched with cold 1M aq. HCl solution, extracted with EtOAc, the organic phase was separated, dried over $MgSO_4$, concentrated under reduced pressure to give the crude product (17.0 g, 95% yield) as white solid, which was used in the next step without further purification.

$^1$H-NMR (400 MHz, DMSO-d6) δ ppm: 7.58 (s, 1H), 7.53 (s, 1H), 5.42 (t, 1H), 4.52 (d, 2H), 2.21 (s, 3H)

Step B2: Preparation of [3-chloro-2-methyl-5-(4,4,5,5-tetramethyl-1,3,2-dioxaborolan-2-yl)phenyl]methanol Using General Procedure 3 starting from (5-bromo-3-chloro-2-methylphenyl)methanol (1 eq., 20.0 g, 84.9 mmol) as a reactant, gave the title compound (11.6 g, 48% yield).

$^1$H-NMR (400 MHz, DMSO-d6) δ ppm: 7.68 (d, 1H), 7.5 (d, 1H), 5.25 (t, 1H), 4.52 (d, 2H), 2.3 (s, 3H), 1.3 (s, 12H)

Step 1: Preparation of ethyl 3-{1-[4-(benzyloxy)butyl]-4-methyl-1H-benzotriazol-5-yl}-3-[3-chloro-5-(hydroxymethyl)-4-methylphenyl]propanoate Using General Procedure 6 starting from ethyl (2E)-3-{1-[4-(benzyloxy)butyl]-4-methyl-1H-benzotriazol-5-yl}prop-2-enoate (1 eq.) and [3-chloro-2-methyl-5-(4,4,5,5-tetramethyl-1,3,2-dioxaborolan-2-yl)phenyl]methanol (1.1 eq.) as reactants, the title compound (98% yield) was obtained.

$^1$H-NMR (400 MHz, DMSO-d6) δ ppm: 7.6 (d, 1H), 7.49 (d, 1H), 7.29 (m, 7H), 5.16 (t, 1H), 4.84 (t, 1H), 4.66 (t, 2H), 4.44 (d, 2H), 4.4 (s, 2H), 3.94 (q, 2H), 3.42 (t, 2H), 3.16 (t, 2H), 2.76 (s, 3H), 2.19 (s, 3H), 1.95 (quint, 2H), 1.5 (quint, 2H), 1 (t, 3H)

Step 2: Preparation of ethyl 3-{1-[4-(benzyloxy)butyl]-4-methyl-1H-benzotriazol-5-yl}-3-(3-{[6-(benzyloxy)-2,2-dioxo-2H-1,2$\lambda^6$,3-benzoxathiazin-3(4H)-yl]methyl}-5-chloro-4-methylphenyl)propanoate Using General Procedure 7 starting from ethyl 3-{1-[4-(benzyloxy)butyl]-4-methyl-1H-benzotriazol-5-yl}-3-[3-chloro-5-(hydroxymethyl)-4-methylphenyl]propanoate (1 eq.) and 6-(benzyloxy)-3,4-dihydro-2H-1,2$\lambda^6$,3-benzoxathiazine-2,2-dione (1.1 eq.) as reactants, the title compound (85% yield) was obtained.

$^1$H-NMR (400 MHz, DMSO-d6) δ ppm: 7.6 (d, 1H), 7.51 (d, 1H), 7.46 (d, 2H), 7.42-7.22 (m, 10H), 7.13 (d, 1H), 7.06 (dd, 1H), 6.93 (d, 1H), 5.1 (s, 2H), 4.85 (t, 1H), 4.63 (t, 2H), 4.44 (s1, 2H), 4.38 (s, 2H), 4.29 (s1, 2H), 3.93 (q, 2H), 3.4 (t, 2H), 3.2 (m, 2H), 2.76 (s, 3H), 2.26 (s, 3H), 1.92 (quint, 2H), 1.48 (quint, 2H), 0.99 (t, 3H)

Step 3: Preparation of ethyl 3-{3-chloro-5-[(6-hydroxy-2,2-dioxo-2H-1,2$\lambda^6$,3-benzoxathiazin-3(4H)-yl)methyl]-4-methylphenyl}-3-[1-(4-hydroxybutyl)-4-methyl-1H-benzotriazol-5-yl]propanoate Using General Procedure 8 starting from ethyl 3-{1-[4-(benzyloxy)butyl]-4-methyl-1H-benzotriazol-5-yl}-3-(3-{[6-(benzyloxy)-2,2-dioxo-2H-1,2$\lambda^6$,3-benzoxathiazin-3(4H)-yl]methyl}-5-chloro-4-methylphenyl)propanoate (1 eq.) as a reactant, the title compound (white solid, 81% yield) was obtained.

$^1$H-NMR (400 MHz, DMSO-d6) δ ppm: 9.7/4.41 (s+t, 2H), 7.65 (d, 1H), 7.55 (d, 1H), 7.4/7.28 (2d, 2H), 7 (d, 1H), 6.8 (dd, 1H), 6.6 (d, 1H), 4.85 (t, 1H), 4.65 (t, 2H), 4.41 (s, 2H), 4.28 (d, 2H), 3.95 (q, 2H), 3.38 (q, 2H), 3.2 (m, 2H), 2.78 (s, 3H), 2.29 (s, 3H), 1.9 (m, 2H), 1.39 (m, 2H), 1.02 (t, 3H)

Step 4: Preparation of ethyl 3-[1-(4-bromobutyl)-4-methyl-1H-benzotriazol-5-yl]-3-{3-chloro-5-[(6-hydroxy-2,2-dioxo-2H-1,2$\lambda^6$,3-benzoxathiazin-3(4H)-yl)methyl]-4-methylphenyl}propanoate Using General Procedure 9 starting from ethyl 3-{3-chloro-5-[(6-hydroxy-2,2-dioxo-2H-1,2$\lambda^6$,3-benzoxathiazin-3(4H)-yl)methyl]-4-methylphenyl}-3-[1-(4-hydroxybutyl)-4-methyl-1H-benzotriazol-5-yl]propanoate (1 eq.) as a reactant, the title compound (white solid, 74% yield) was obtained.

$^1$H-NMR (400 MHz, DMSO-d6) δ ppm: 9.68 (s, 1H), 7.65/7.55 (2d, 2H), 7.39/7.26 (2d, 2H), 6.99 (d, 1H), 6.78 (dd, 1H), 6.6 (d, 1H), 4.84 (t, 1H), 4.69 (t, 2H), 4.4 (s, 2H), 4.27 (d, 2H), 3.95 (q, 2H), 3.54 (t, 2H), 3.2 (t, 2H), 2.76 (s, 3H), 2.26 (s, 3H), 2 (m, 2H), 1.78 (m, 2H), 1.01 (t, 3H)

Step 5: Preparation of ethyl[5-chloro-4,31-dimethyl-27,27-dioxo-21,26-dioxa-27$\lambda^6$-thia-1,14,15,16-tetraazahexacyclo[20.5.3.$1^{3,7}$0.$1^{9,13}$0.$0^{12,16}$0.$0^{25,29}$]dotriaconta-3(32),4,6,9(31),10,12,14,22,24,29-decaen-8-yl]acetate Using General Procedure 11 starting from ethyl 3-[1-(4-bromobutyl)-4-methyl-1H-benzotriazol-5-yl]-3-{3-chloro-5-[(6-hydroxy-2,2-dioxo-2H-1,2)$^6$,3-benzoxathiazin-3(4H)-yl)methyl]-4-methylphenyl}propanoate (1 eq.) as a reactant, the title compound (white solid, 45% yield) was obtained.

$^1$H-NMR (400 MHz, DMSO-d6) δ ppm: 7.68/5.88 (m+d, 2H), 7.67/7.43 (2d, 2H), 6.99 (d, 1H), 6.79 (dd, 1H), 6.6 (d, 1H), 4.82-4.73 (m, 1H), 4.79 (t, 2H), 4.19/4.04 (2d, 2H), 3.97/3.86 (2d, 2H), 3.94 (m, 2H), 3.67/3.45 (m+dt, 2H), 3.21/3.06 (2dd, 2H), 2.65 (s, 3H), 2.35 (s, 3H), 2.21/2.06 (2m, 2H), 1.8/1.6 (2m, 2H), 1.02 (t, 3H)

Step 6: Preparation of Example 33

Using General Procedure 12 starting from ethyl[5-chloro-4,31-dimethyl-27,27-dioxo-21,26-dioxa-27$\lambda^6$-thia-1,14,15,16-tetraazahexacyclo[20.5.3.$1^{3,7}$0.$1^{9,13}$0.$0^{12,16}$0.$0^{25,29}$]dotriaconta-3(32),4,6,9(31),10,12,14,22,24,29-decaen-8-yl]acetate (1 eq.) as a reactant, the title compound (white solid, 90% yield) was obtained.

The enantiopure products were obtained by chromatographic separation on chiral column.

EXAMPLE 33a (E1)

HRMS calculated for $C_{29}H_{29}ClN_4O_6S$: 596.1496; $[M+H]^+$ found: 597.1573 (δ=0.7 ppm).

EXAMPLE 33b (E2)

HRMS calculated for $C_{29}H_{29}ClN_4O_6S$: 596.1496; $[M+H]^+$ found: 597.1571 (δ=0.3 ppm).

$^{1}$H-NMR (400 MHz, DMSO-d6) δ ppm: 12.27 (s, 1H), 7.68 (s, 1H), 7.67 (d, 1H), 7.42 (d, 1H), 6.99 (d, 1H), 6.79 (dd, 1H), 6.58 (s, 1H), 5.86 (d, 1H), 4.82-4.72 (m, 3H), 4.18/4.04 (2d, 2H), 3.98/3.85 (d, 2H), 3.66/3.44 (m+dt, 2H), 3.09/2.94 (2dd, 2H), 2.64 (s, 3H), 2.35 (s, 3H), 2.21/2.06 (2m, 2H), 1.81/1.61 (2m, 2H);

EXAMPLE 34: [(2R,8S)-2,4,20,33-tetramethyl-29,29-dioxo-23,28-dioxa-29$\lambda^6$-thia-1,14,15,16,20-pentaazahexacyclo[22.5.3.1$^{3,7}$0.1$^{9,13}$0.0$^{12,16}$0.0$^{27,31}$]tetratriaconta-3(34),4,6,9(33),10,12,14,24,26,31-decaen-8-yl]acetic acid and [(2R,8R)-2,4,20,33-tetramethyl-29,29-dioxo-23,28-dioxa-29$\lambda^6$-thia-1,14,15,16,20-pentaazahexacyclo[22.5.3.1$^{3,7}$0.1$^{9,13}$0.0$^{12,16}$0.0$^{27,31}$]tetratriaconta-3(34),4,6,9(33),10,12,14,24,26,31-decaen-8-yl]acetic acid

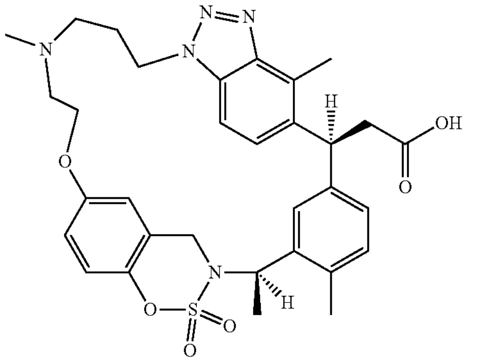

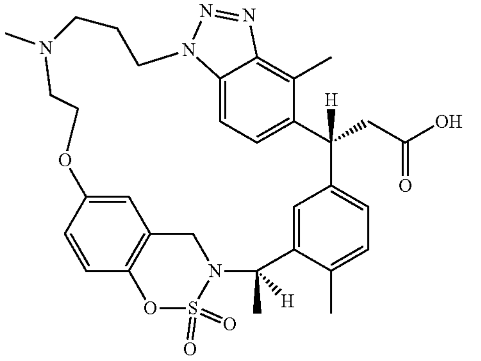

Step A1: Preparation of tert-butyl (3-{[2-(benzyloxy)ethyl](methyl)amino}propyl) carbamate To a solution of [(2-bromoethoxy)methyl]benzene (10 g, 46.5 mmol, 7.35 mL) in MeCN (3 mL/mmol, 139 mL) tert-butyl[3-(methylamino)propyl]carbamate (1 eq., 8.75 g, 46.5 mmol) and $K_2CO_3$ (2 eq., 9.22 g, 93 mmol) were added at RT. The reaction mixture was heated to 50° C. and stirred for 2 h. After completion of the reaction the mixture was diluted with 500 ml of EtOAc, washed with 500 ml of water then with 500 ml of brine. The organic layer was dried over anhydrous $Na_2SO_4$, filtered, concentrated to dryness to give the crude product as a colorless oil, which was used in a next step without further purification (14.5 g, 77% yield).

$^{1}$H-NMR (400 MHz, DMSO-d6) δ ppm: 7.38-7.25 (m, 5H), 6.74 (t, 1H), 4.46 (s, 2H), 3.5 (t, 2H), 2.92 (q, 2H), 2.5 (m, 2H), 2.31 (t, 2H), 2.15 (s, 3H), 1.49 (quint, 2H), 1.37 (s, 9H)

Step A2: Preparation of $N^1$-[2-(benzyloxy)ethyl]-N-methyl-$N^3$-(3-methyl-2-nitrophenyl)propane-1,3-diamine To a solution of tert-butyl (3-{[2-(benzyloxy)ethyl](methyl)amino}propyl)carbamate (14.5 g, 36 mmol) in dioxane (5 mL/mmol, 180 mL) HCl (4N in dioxane) (4 eq., 36 mL) was added at RT. The reaction mixture was stirred overnight at RT. After completion of the reaction the solvent was evaporated to dryness under reduced pressure. The crude $N^1$-[2-(benzyloxy)ethyl]-$N^1$-methylpropane-1,3-diamine hydrochloride (13.3 g, 68% yield) was reacted without further purification with 1-fluoro-3-methyl-2-nitrobenzene using General Procedure 2 STEP 1, resulting the title compound (78% yield).

$^{1}$H-NMR (400 MHz, DMSO-d6) δ ppm: 7.39-7.28 (m, 5H), 7.25 (dd, 1H), 6.78 (d, 1H), 6.58 (d, 1H), 6.55 (m, 1H), 4.5 (s, 2H), 3.67 (t, 2H), 3.22 (q, 2H), 2.98 (m, 2H), 2.82 (quint, 2H), 2.82 (m, 2H), 2.5 (–, 3H), 2.29 (s, 3H)

Step A3: Preparation of $N^1$-[2-(benzyloxy)ethyl]-$N^3$-(4-bromo-3-methyl-2-nitrophenyl)-$N^1$-methyl-propane-1,3-diamine Using General Procedure 2 STEP 2 starting from $N^1$-[2-(benzyloxy)ethyl]-$N^1$-methyl-$N^3$-(3-methyl-2-nitrophenyl)propane-1,3-diamine (1 eq.) as a reactant, the title compound (65% yield) was obtained.

$^{1}$H-NMR (400 MHz, DMSO-d6) δ ppm: 7.5 (d, 1H), 7.3 (m, 5H), 6.7 (d, 1H), 6.55 (t, 1H), 4.45 (s, 2H), 3.52 (t, 2H), 3.15 (q, 2H), 2.55 (t, 2H), 2.45 (t, 2H), 2.22/2.2 (2s, 6H), 1.69 (m, 2H)

Step A4: Preparation of N-[2-(benzyloxy)ethyl]-3-(5-bromo-4-methyl-1H-benzotriazol-1-yl)-N-methyl-propan-1-amine Using General Procedure 2 STEP 3 starting from $N^1$-[2-(benzyloxy)ethyl]-$N^3$-(4-bromo-3-methyl-2-nitrophenyl)-$N^1$-methylpropane-1,3-diamine (1 eq.) as a reactant, $N^1$-(3-{[2-(benzyloxy)ethyl](methyl)amino}propyl)-4-bromo-3-methylbenzene-1,2-diamine (76% yield) was obtained. The crude product was reacted using General Procedure 2 STEP 4 resulting the title compound (quant.).

$^{1}$H-NMR (400 MHz, DMSO-d6) δ ppm: 7.63 (m, 2H), 7.3 (m, 5H), 4.7 (t, 2H), 4.42 (s, 2H), 3.48 (t, 2H), 2.71 (s, 3H), 2.49 (t, 2H), 2.3 (t, 2H), 2.15 (s, 3H), 2.04 (q, 2H)

Step A5: Preparation of ethyl (2E)-3-[1-(3-{[2-(benzyloxy)ethyl](methyl)amino}propyl)-4-methyl-1H-benzotriazol-5-yl]prop-2-enoate Using General Procedure 2 STEP 5 starting from N-[2-(benzyloxy)ethyl]-3-(5-bromo-4-methyl-1H-benzotriazol-1-yl)-N-methylpropan-1-amine (1 eq.) as a reactant, the title compound (92% yield) was obtained.

$^{1}$H-NMR (400 MHz, DMSO-d6) δ ppm: 8.02 (d, 1H), 7.92/7.69 (dd, 2H), 7.36-7.23 (m, 5H), 6.62 (d, 1H), 4.7 (t, 2H), 4.42 (s, 2H), 4.22 (q, 2H), 3.48 (t, 2H), 2.8 (s, 3H), 2.5 (m, 2H), 2.32 (t, 2H), 2.16 (s, 3H), 2.04 (m, 2H), 1.28 (t, 3H)

Step 1: Preparation of ethyl 3-[1-(3-{[2-(benzyloxy)ethyl](methyl)amino}propyl)-4-methyl-1H-benzotriazol-5-yl]-3-{3-[(1S)-1-hydroxyethyl]-4-methylphenyl}propanoate Using General Procedure 6 starting from ethyl (2E)-3-[1-(3-{[2-(benzyloxy)ethyl](methyl)amino}propyl)-4-methyl- 1H-benzotriazol-5-yl]prop-2-enoate (1 eq.) and (1S)-1-[2-methyl-5-(4,4,5,5-tetramethyl-1,3,2-dioxaborolan-2-yl) phenyl]ethanol (1 eq.) as reactants, the title compound (30% yield) was obtained.

$^1$H-NMR (400 MHz, DMSO-d6) δ ppm: 7.57/7.44 (d, 2H), 7.4 (d, 1H), 7.35-7.22 (d, 5H), 7.03 (d, 1H), 6.99 (dd, 1H), 4.98 (d, 1H), 4.82 (m, 1H), 4.82 (m, 1H), 4.63 (m, 2H), 4.4 (s, 2H), 3.92 (q, 2H), 3.49 (t, 2H), 3.11 (m, 2H), 2.77 (s, 3H), 2.5 (m, 2H), 2.32 (m, 2H), 2.17 (s, 3H), 2.17 (s, 3H), 2.01 (quint, 2H), 1.22 (d, 3H), 1 (t, 3H)

Step 2: Preparation of ethyl 3-(3-{(1R)-1-[6-(benzyloxy)-2,2-dioxo-2H-1,2λ$^6$,3-benzoxathiazin-3 (4H)-yl]ethyl}-4-methylphenyl)-3-[1-(3-{[2-(benzyloxy)ethyl](methyl)amino}propyl)-4-methyl-1H-benzotriazol-5-yl]propanoate Using General Procedure 7 starting from ethyl 3-[1-(3-{[2-(benzyloxy)ethyl](methyl)amino}propyl)-4-methyl-1H-benzotriazol-5-yl]-3-{3-[(1S)-1-hydroxyethyl]-4-methylphenyl}propanoate (1 eq.) and 6-(benzyloxy)-3,4-dihydro-2H-1,2λ$^6$,3-benzoxathiazine-2,2-dione (1.1 eq.) as reactants, the title compound (92% yield) was obtained.

$^1$H-NMR (400 MHz, DMSO-d6) δ ppm: 0.97 (td, J=7.06, 4.95 Hz, 2H) 1.41 (d, J=6.97 Hz, 2H) 2.12 (d, J=2.93 Hz, 4H) 2.21-2.32 (m, 4H) 2.76 (d, J=3.79 Hz, 2H) 3.11-3.25 (m, 2H) 3.44 (d, J=4.28 Hz, 1H) 3.92 (d, J=7.09 Hz, 1H) 4.38 (d, J=4.65 Hz, 3H) 4.60 (s, 1H) 4.79-4.95 (m, 1H) 4.98-5.17 (m, 2H) 5.20-5.35 (m, 1H) 6.77-7.65 (m, 14H)

Step 3: Preparation of ethyl 3-{3-[(1R)-1-(6-hydroxy-2,2-dioxo-2H-1,2λ$^6$,3-benzoxathiazin-3(4H)-yl)ethyl]-4-methylphenyl}-3-(1-{3-[(2-hydroxyethyl) (methyl)amino]propyl}-4-methyl-1H-benzotriazol-5-yl)propanoate Using General Procedure 8 starting from ethyl 3-(3-{(1R)-1-[6-(benzyloxy)-2,2-dioxo-2H-1,2λ$^6$,3-benzoxathiazin-3(4H)-yl]ethyl}-4-methylphenyl)-3-[1-(3-{[2-(benzyloxy)ethyl](methyl)amino}propyl)-4-methyl-1H-benzotriazol-5-yl]propanoate (1 eq.) as a reactant, the title compound (white solid, 95% yield) was obtained.

$^1$H-NMR (400 MHz, DMSO-d6) δ ppm: 9.64 (s, 1H), 7.62/7.56 (2d+2d, 2H), 7.46 (2s, 1H), 7.11 (m, 2H), 6.91 (2d, 1H), 6.72 (m, 1H), 6.57 (2d, 1H), 5.25 (q, 1H), 4.87 (q, 1H), 4.66 (t, 2H), 4.36-4.25 (m, 3H), 3.94 (2q, 2H), 3.43 (t, 2H), 3.22 (d, 2H), 2.76 (s, 3H), 2.35 (2t, 2H), 2.31-2.27 (m, 2H), 2.27 (s, 3H), 2.12 (2s, 3H), 2 (q, 2H), 1.42 (2d, 3H), 1 (2t, 3H)

Step 4: Preparation of ethyl 3-(1-{3-[(2-chloroethyl)(methyl)amino]propyl}-4-methyl-1H-benzotriazol-5-yl)-3-{3-[(1R)-1-(6-hydroxy-2,2-dioxo-2H-1, 2)$^6$,3-benzoxathiazin-3(4H)-yl)ethyl]-4-methylphenyl}propanoate hydrochloride Using General Procedure 10 starting from ethyl 3-{3-[(1R)-1-(6-hydroxy-2,2-dioxo-2H-1,2)$^6$,3-benzoxathiazin-3 (4H)-yl)ethyl]-4-methylphenyl}-3-(1-{3-[(2-hydroxyethyl) (methyl)amino]propyl}-4-methyl-1H-benzotriazol-5-yl) propanoate (1 eq.) as a reactant, the title compound (white solid, 90% yield) was obtained.

$^1$H-NMR (400 MHz, DMSO-d6) δ ppm: 10.32 (2s1, 1H), 9.7 (s1, 1H), 7.74-7.62 (d, 2H), 7.5 (s, 1H), 7.13-7.08 (m, 2H), 6.92 (d, 1H), 6.74 (t, 1H), 6.66/6.57 (d, 1H), 5.26 (quint, 1H), 4.89 (q, 1H), 4.75 (q, 2H), 4.35 (d, 2H), 3.96 (q, 4H), 3.94 (t, 2H), 3.54-3.38 (m, 2H), 3.3-3.11 (m, 4H), 2.77 (m, 6H), 2.36-2.26 (m, 2H), 2.3 (s, 3H), 1.43 (t, 3H), 1.04 (2t, 3H)

Step 5: Preparation of ethyl[(2R)-2,4,20,33-tetramethyl-29,29-dioxo-23,28-dioxa-29)$^6$-thia-1,14,15,16, 20-pentaazahexacyclo[22.5.3.1$^{3,7}$0.1$^{9,13}$0.0$^{12,16}$0. 0$^{27,31}$]tetratriaconta-3(34),4,6,9(33),10,12,14,24,26, 31-decaen-8-yl]acetate Using General Procedure 11 starting from ethyl 3-(1-{3-[(2-chloroethyl)(methyl)amino]propyl}-4-methyl-1H-benzotriazol-5-yl)-3-{3-[(1R)-1-(6-hydroxy-2,2-dioxo-2H-1, 2λ$^6$,3-benzoxathiazin-3(4H)-yl)ethyl]-4-methylphenyl}propanoate hydrochloride (1 eq.) as a reactant, the title compound (white solid, 96% yield) was obtained.

$^1$H-NMR (400 MHz, DMSO-d6) δ ppm: 7.85/7.71 (dd, 1H), 7.63/7.06 (dd, 1H), 7.56/6.85 (d, 1H), 7.45/7.31 (dd, 1H), 7.28/7.11 (d, 1H), 7.05/6.98 (d, 1H), 6.91/6.82 (dd, 1H), 6.28/6.06 (d, 1H), 5.34-5.21 (m, 1H), 4.95/4.88 (t, 1H), 4.83-4.53 (m, 2H), 4.12/4.03/3.78/3.66 (2dd, 2H), 4.03-3.73 (m, 2H), 3.91 (q, 2H), 3.4-2.91 (2ddd, 2H), 2.83/2.81 (2s, 3H), 2.72-2.38 (m, 4H), 2.35-2.03 (m, 2H), 2.32/2.3/2.27 (3s, 6H), 1.5/1.15 (2d, 3H), 1.03/1 (2t, 3H)

Step 6: Preparation of Example 34

Using General Procedure 12 starting from ethyl[(2R)-2, 4,20,33-tetramethyl-29,29-dioxo-23,28-dioxa-29λ$^6$-thia-1, 14,15,16,20-pentaazahexacyclo[22.5.3.1$^{3,7}$0.1$^{9,13}$0. 0$^{12,16}$0.0$^{27,31}$]tetratriaconta-3(34),4,6,9(33),10,12,14,24,26, 31-decaen-8-yl]acetate (1 eq.) as a reactant, the title compound (white solid, 68% yield) was obtained.

The diastereo-pure products were obtained by chromatographic separation on chiral column.

EXAMPLE 34a (2R,8S)

HRMS calculated for $C_{32}H_{37}N_5O_6S$: 619.2464; [M+H]$^+$ found: 620.2536 (δ=−0.2 ppm).

$^1$H-NMR (400 MHz, DMSO-d6) δ ppm: 12.1 (m, 1H), 7.83/7.71 (d, 2H), 7.54 (d, 1H), 7.31 (dd, 1H), 7.11 (d, 1H), 7.04 (d, 1H), 6.91 (dd, 1H), 6.28 (d, 1H), 5.31 (q, 1H), 4.85 (t, 1H), 4.82-4.68 (m, 2H), 4.11/3.65 (dd, 2H), 3.99 (t, 2H), 3.22/3.05 (2dd, 2H), 2.85-2.44 (m, 4H), 2.82 (s, 3H), 2.3/2.28 (2s, 6H), 2.12 (m, 2H), 1.49 (d, 3H)

EXAMPLE 34b (2R,8R)

HRMS calculated for $C_{32}H_{37}N_5O_6S$: 619.2464; [M+H]$^+$ found: 620.2536 (δ=−0.2 ppm).

$^1$H-NMR (400 MHz, DMSO-d6) δ ppm: 12.3 (m, 1H), 7.62/7.3 (dd, 1H), 7.46 (dd, 1H), 7.03 (d, 1H), 6.98 (d, 1H), 6.84 (d, 1H), 6.83 (dd, 1H), 6.07 (d, 1H), 5.27 (q, 1H), 4.93 (t, 1H), 4.74/4.58 (2m, 2H), 4.03/3.77 (dd, 2H), 3.88-3.75 (m, 2H), 3.15/2.83 (2dd, 2H), 2.81 (s, 3H), 2.68 (m, 2H), 2.54 (m, 2H), 2.33/2.3 (2s, 3H), 2.2 (m, 2H), 1.15 (d, 3H)

EXAMPLE 35: [4,5-Dimethoxy-31-methyl-27,27-dioxo-21,26-dioxa-27$\lambda^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid enantiomer 2

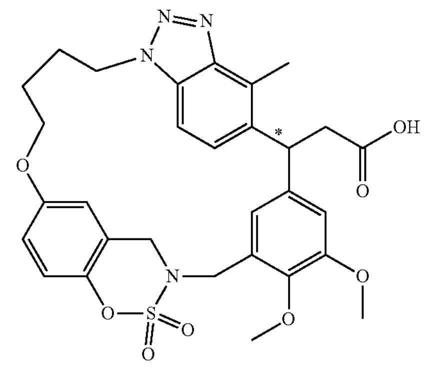

* = RorS enantiomer 1

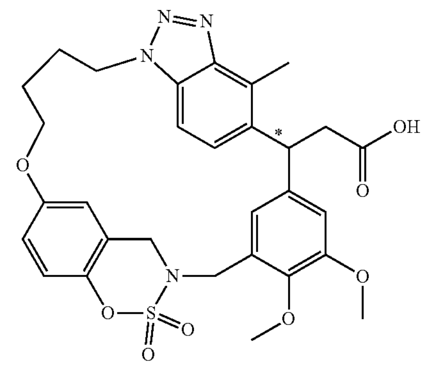

* = RorS

Step B1: Preparation of [2,3-dimethoxy-5-(4,4,5,5-tetramethyl-1,3,2-dioxaborolan-2-yl)phenyl]methanol Using General Procedure 3 starting from (5-bromo-2,3-dimethoxyphenyl)methanol (1 eq., 18.0 g, 72.9 mmol) as a reactant, gave the title compound (11.10 g, 52% yield)

$^1$H-NMR (400 MHz, DMSO-d6) δ ppm: 7.4 (sl, 1H), 7.13 (sl, 1H), 5.04 (t, 1H), 4.5 (d, 2H), 3.81/3.73 (2s, 6H), 1.29 (s, 12H)

Step 1: Preparation of ethyl 3-{1-[4-(benzyloxy)butyl]-4-methyl-1H-benzotriazol-5-yl}-3-[3-(hydroxymethyl)-4,5-dimethoxyphenyl]propanoate Using General Procedure 6 starting from ethyl (2E)-3-{1-[4-(benzyloxy)butyl]-4-methyl-1H-benzotriazol-5-yl}prop-2-enoate (1 eq.) and [2,3-dimethoxy-5-(4,4,5,5-tetramethyl-1,3,2-dioxaborolan-2-yl)phenyl]methanol (1 eq.) as reactants, the title compound (61% yield) was obtained.

$^1$H-NMR (400 MHz, DMSO-d6) δ ppm: 7.6/7.52 (2d, 2H), 7.33-7.23 (m, 5H), 6.95 (d, 1H), 6.88 (d, 1H), 4.93 (t, 1H), 4.83 (t, 1H), 4.66 (t, 2H), 4.42 (d, 2H), 4.4 (m, 2H), 3.93 (q, 2H), 3.77/3.63 (2s, 6H), 3.42 (t, 2H), 3.16 (d, 2H), 2.78 (s, 3H), 1.94 (quint, 2H), 1.5 (quint, 2H), 0.99 (t, 3H)

Step 2: Preparation of ethyl 3-{1-[4-(benzyloxy)butyl]-4-methyl-1H-benzotriazol-5-yl}-3-(3-{[6-(benzyloxy)-2,2-dioxo-2H-1,2$\lambda^6$,3-benzoxathiazin-3(4H)-yl]methyl}-4,5-dimethoxyphenyl)propanoate Using General Procedure 7 starting from ethyl 3-{1-[4-(benzyloxy)butyl]-4-methyl-1H-benzotriazol-5-yl}-3-[3-(hydroxymethyl)-4,5-dimethoxyphenyl]propanoate (1 eq.) and 6-(benzyloxy)-3,4-dihydro-2H-1,2$\lambda^6$,3-benzoxathiazine-2,2-dione (1.1 eq.) as reactants, the title compound (97% yield) was obtained.

$^1$H-NMR (400 MHz, DMSO-d6) δ ppm: 7.6 (d, 1H), 7.52 (d, 1H), 7.48-7.2 (m, 10H), 7.02 (m, 3H), 6.92 (d, 1H), 6.88 (d, 1H), 5.09 (s, 2H), 4.82 (t, 1H), 4.62 (t, 2H), 4.5 (s, 2H), 4.39 (s, 2H), 4.2 (s, 2H), 3.92 (q, 2H), 3.78 (s, 3H), 3.61 (s, 3H), 3.4 (t, 2H), 3.19 (m, 2H), 2.79 (s, 3H), 1.91 (m, 2H), 1.49 (m, 2H), 0.99 (t, 3H)

Step 3: Preparation of ethyl 3-[1-(4-hydroxybutyl)-4-methyl-1H-benzotriazol-5-yl]-3-{3-[(6-hydroxy-2,2-dioxo-2H-1,2$\lambda^6$,3-benzoxathiazin-3(4H)-yl)methyl]-4,5-dimethoxyphenyl}propanoate Using General Procedure 8 starting from ethyl 3-{1-[4-(benzyloxy)butyl]-4-methyl-1H-benzotriazol-5-yl}-3-(3-{[6-(benzyloxy)-2,2-dioxo-2H-1,2$\lambda^6$,3-benzoxathiazin-3(4H)-yl]methyl}-4,5-dimethoxyphenyl)propanoate (1 eq.) as a reactant, the title compound (87% yield) was obtained.

$^1$H-NMR (400 MHz, DMSO-d6) δ ppm: 9.65/4.85 (s+t, 2H), 7.62 (d, 1H), 7.58 (d, 1H), 7.02 (d, 1H), 6.91 (d, 1H), 6.88 (d, 1H), 6.8 (m, 1H), 6.75 (dd, 1H), 4.66 (t, 2H), 4.45 (s, 2H), 4.41 (m, 1H), 4.2 (m, 2H), 3.95 (q, 2H), 3.78 (s, 3H), 3.68 (s, 3H), 3.4 (t, 2H), 3.2 (dd, 2H), 2.8 (s, 3H), 1.91 (m, 2H), 1.39 (m, 2H), 1 (t, 3H)

Step 4: Preparation of ethyl 3-[1-(4-bromobutyl)-4-methyl-1H-benzotriazol-5-yl]-3-{3-[(6-hydroxy-2,2-dioxo-2H-1,2$\lambda^6$,3-benzoxathiazin-3(4H)-yl)methyl]-4,5-dimethoxyphenyl}propanoate Using General Procedure 9 starting from ethyl 3-[1-(4-hydroxybutyl)-4-methyl-1H-benzotriazol-5-yl]-3-{3-[(6-hydroxy-2,2-dioxo-2H-1,2$\lambda^6$,3-benzoxathiazin-3(4H)-yl)methyl]-4,5-dimethoxyphenyl}propanoate (1 eq.) as a reactant, the title compound (white solid, 91% yield) was obtained.

$^1$H-NMR (400 MHz, DMSO-d6) δ ppm: 9.63 (s, 1H), 7.65 (d, 1H), 7.58 (d, 1H), 7.02 (d, 1H), 6.91 (d, 1H), 6.86 (d, 1H), 6.74 (dd, 1H), 6.6 (d, 1H), 4.84 (t, 1H), 4.69 (t, 2H), 4.45 (sl, 2H), 4.2/4.15 (2d, 2H), 3.94 (q, 2H), 3.76 (s, 3H), 3.63 (s, 3H), 3.54 (t, 2H), 3.19 (dd, 2H), 2.79 (s, 3H), 2 (m, 2H), 1.77 (m, 2H), 1 (t, 3H)

Step 5: Preparation of ethyl[4,5-dimethoxy-31-methyl-27,27-dioxo-21,26-dioxa-27$\lambda^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate Using General Procedure 11 starting from ethyl 3-[1-(4-bromobutyl)-4-methyl-1H-benzotriazol-5-yl]-3-{3-[(6-hydroxy-2,2-dioxo-2H-1,2)$^6$,3-benzoxathiazin-3(4H)-yl)

methyl]-4,5-dimethoxyphenyl}propanoate (1 eq.) as a reactant, the title compound (white solid, 70% yield) was obtained.

$^1$H-NMR (400 MHz, DMSO-d6) δ ppm: 7.68 (d, 1H), 7.47 (d, 1H), 7.34 (d, 1H), 6.97 (d, 1H), 6.79 (dd, 1H), 6.11 (d, 1H), 5.85 (d, 1H), 4.83-4.72 (m, 3H), 4.09-3.63 (m, 6H), 3.92 (s, 3H), 3.76 (s, 3H), 3.69/3.47 (2m, 2H), 3.25/3.09 (2dd, 2H), 2.65 (s, 3H), 2.21/2.07 (2m, 2H), 1.81/1.63 (2m, 2H), 1 (t, 3H)

Step 6: Preparation of Example 35

Using General Procedure 12 starting from ethyl[4,5-dimethoxy-31-methyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (1 eq.) as a reactant, the title compound (97% yield) was obtained.

The enantiopure products were obtained by chromatographic separation on chiral column.

EXAMPLE 35a (E2)

HRMS calculated for $C_{30}H_{32}N_4O_8S$: 608.1941; $[M+H]^+$ found: 609.2013 (δ=−0.1 ppm).

EXAMPLE 35b (E1)

HRMS calculated for $C_{30}H_{32}N_4O_8S$: 608.1941; $[M+H]^+$ found: 609.2013 (δ=−0.1 ppm).

$^1$H-NMR (400 MHz, DMSO-d6) δ ppm: 12.15 (m, 1H), 7.7 (d, 1H), 7.49 (d, 1H), 7.38 (d, 1H), 6.99 (d, 1H), 6.8 (dd, 1H), 6.1 (d, 1H), 5.82 (d, 1H), 4.8 (m, 3H), 4.1 (2d, 2H), 3.92/3.75 (2s, 6H), 3.91/3.85 (2d, 2H), 3.7/3.45 (2m, 2H), 3.15/3 (2dd, 2H), 2.65 (s, 3H), 2.2/2.1 (2m, 2H), 1.82/1.65 (2m, 2H)

EXAMPLE 36: [4-Chloro-5,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid enantiomer 1

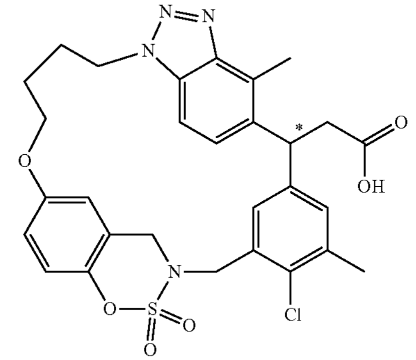

* = RorS

-continued enantiomer 2

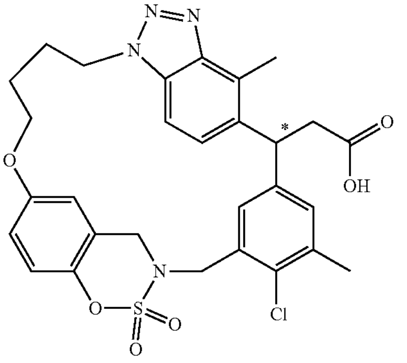

* = RorS

Step B1: Preparation of (5-bromo-2-chloro-3-methylphenyl)methanol

Methyl 5-bromo-2-chloro-3-methylbenzoate (1 eq., 24.0 g, 91 mmol) was dissolved in EtOH (300 mL), then sodium borohydride (3 eq., 10.4 g, 273 mmol) was added to the stirred mixture at 0° C. The mixture was stirred at this temperature for 10 min before addition of calcium chloride (3 eq., 30.3 g, 273 mmol) over 30 min, then was allowed to warm to RT and stirred for 2 h. The reaction mixture was quenched with cold 1M aq. HCl solution, extracted with EtOAc, the organic phase was separated, dried over $MgSO_4$, concentrated under reduced pressure to give the crude product (19.0 g, 88% yield) as white solid, which was used in the next step without further purification.

$^1$H-NMR (400 MHz, DMSO-d6) δ ppm: 7.51 (s, 2H), 5.54 (t, 1H), 4.53 (d, 2H), 2.32 (s, 3H)

Step B2: Preparation of [2-chloro-3-methyl-5-(4,4,5,5-tetramethyl-1,3,2-dioxaborolan-2-yl)phenyl]methanol Using General Procedure 3 starting from (5-bromo-2-chloro-3-methylphenyl)methanol (1 eq., 19.0 g, 80.7 mmol) as a reactant, the title compound (15.15 g, 66% yield) was obtained.

$^1$H-NMR (400 MHz, DMSO-d6) δ ppm: 7.78 (d, 1H), 7.51 (d, 1H), 5.4 (t, 1H), 4.55 (d, 2H), 2.32 (s, 3H), 1.3 (s, 12H)

Step 1: Preparation of ethyl 3-[4-chloro-3-(hydroxymethyl)-5-methylphenyl]-3-(1-{4-[(4-methoxyphenyl)methoxy]butyl}-4-methyl-1H-benzotriazol-5-yl)propanoate Using General Procedure 6 starting from ethyl (2E)-3-(1-{4-[(4-methoxyphenyl)methoxy]butyl}-4-methyl-1H-benzotriazol-5-yl)prop-2-enoate (1 eq.) and [2-chloro-3-methyl-5-(4,4,5,5-tetramethyl-1,3,2-dioxaborolan-2-yl)phenyl]methanol (1.5 eq.) as reactants, the title compound (yellow oil, 50% yield) was obtained.

$^1$H-NMR (400 MHz, DMSO-d6) δ ppm: 7.6 (d, 1H), 7.45 (d, 1H), 7.3/7.25 (2d, 2H), 7.2 (d, 2H), 6.9 (d, 2H), 5.3 (t, 1H), 4.85 (t, 1H), 4.65 (t, 2H), 4.5 (d, 2H), 4.3 (s, 2H), 3.95 (q, 2H), 3.75 (s, 3H), 3.4 (t, 2H), 3.2 (2dd, 2H), 2.8 (s, 3H), 2.3 (s, 3H), 1.9 (quint, 2H), 1.5 (quint, 2H), 1 (t, 3H)

Step 2: Preparation of ethyl 3-(3-{[6-(benzyloxy)-2,2-dioxo-2H-1,2λ$^6$,3-benzoxathiazin-3(4H)-yl]methyl}-4-chloro-5-methylphenyl)-3-(1-{4-[(4-methoxyphenyl)methoxy]butyl}-4-methyl-1H-benzotriazol-5-yl)propanoate Using General Procedure 7 starting from ethyl 3-[4-chloro-3-(hydroxymethyl)-5-methylphenyl]-3-(1-{4-[(4-methoxyphenyl)methoxy]butyl}-4-methyl-1H-benzotriazol-5-yl)propanoate (1 eq.) and 6-(benzyloxy)-3,4-dihydro-2H-1,2λ$^6$,3-benzoxathiazine-2,2-dione (1.1 eq.) as reactants, the title compound (91% yield) was obtained.

$^1$H-NMR (400 MHz, DMSO-d6) δ ppm: 7.6/7.5 (2d, 2H), 7.45 (d1, 2H), 7.4 (t, 2H), 7.35 (m, 3H), 7.2 (d, 2H), 7.1 (d+dd, 2H), 6.95 (d, 1H), 6.85 (d, 2H), 5.1 (s, 2H), 4.9 (t, 1H), 4.6 (t, 2H), 4.55 (s1, 2H), 4.35 (s1, 2H), 4.3 (s, 2H), 3.9 (q, 2H), 3.7 (s, 3H), 3.4 (t, 2H), 3.2 (2dd, 2H), 2.8 (s, 3H), 2.3 (s, 3H), 1.9 (quint, 2H), 1.15 (quint, 2H), 1 (t, 3H)

Step 3: Preparation of ethyl 3-[4-chloro-3-[(6-hydroxy-2,2-dioxo-4H-1,2λ$^6$,3-benzoxathiazin-3-yl)methyl]-5-methyl-phenyl]-3-[1-(4-hydroxybutyl)-4-methyl-benzotriazol-5-yl]propanoate Using General Procedure 8 starting from ethyl 3-(3-{[6-(benzyloxy)-2,2-dioxo-2H-1,2λ$^6$,3-benzoxathiazin-3(4H)-yl]methyl}-4-chloro-5-methylphenyl)-3-(1-{4-[(4-methoxyphenyl)methoxy]butyl}-4-methyl-1H-benzotriazol-5-yl)propanoate (1 eq.) as a reactant, the title compound (97% yield) was obtained.

$^1$H-NMR (400 MHz, DMSO-d6) δ ppm: 9.6 (m, 1H), 7.6 (d, 1H), 7.5 (d, 1H), 7.3 (2d, 2H), 6.95 (d, 1H), 6.8 (dd, 1H), 6.6 (d, 1H), 4.95 (t, 1H), 4.65 (t, 2H), 4.5 (s1, 2H), 4.4 (m, 1H), 4.3 (s1, 2H), 3.95 (q, 2H), 3.4 (m, 2H), 3.2 (m, 2H), 2.8 (s, 3H), 2.3 (s, 3H), 1.9 (quint, 2H), 1.4 (quint, 2H), 1 (t, 3H)

Step 4: Preparation of ethyl 3-[1-(4-bromobutyl)-4-methyl-1H-benzotriazol-5-yl]-3-{4-chloro-3-[(6-hydroxy-2,2-dioxo-2H-1,2)$^6$,3-benzoxathiazin-3(4H)-yl)methyl]-5-methylphenyl}propanoate Using General Procedure 9 starting from ethyl 3-[4-chloro-3-[(6-hydroxy-2,2-dioxo-4H-1,2λ$^6$,3-benzoxathiazin-3-yl)methyl]-5-methyl-phenyl]-3-[1-(4-hydroxybutyl)-4-methyl-benzotriazol-5-yl]propanoate (1 eq.) as a reactant, the title compound (70% yield) was obtained.

$^1$H-NMR (400 MHz, DMSO-d6) δ ppm: 9.66 (s, 1H), 7.65 (d, 1H), 7.53 (d, 1H), 7.33 (2d, 2H), 6.96 (d, 1H), 6.77 (dd, 1H), 6.61 (d, 1H), 4.85 (t, 1H), 4.69 (t, 2H), 4.5 (s, 2H), 4.32 (m, 2H), 3.95 (q, 2H), 3.54 (t, 2H), 3.19 (dd, 2H), 2.78 (s, 3H), 2.28 (s, 3H), 2 (m, 2H), 1.77 (m, 2H), 1.01 (t, 3H)

Step 5: Preparation of ethyl[4-chloro-5,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate Using General Procedure 11 starting from ethyl 3-[1-(4-bromobutyl)-4-methyl-1H-benzotriazol-5-yl]-3-{4-chloro-3-[(6-hydroxy-2,2-dioxo-2H-1,2)$^6$,3-benzoxathiazin-3(4H)-yl)methyl]-5-methylphenyl}propanoate (1 eq.) as a reactant, the title compound (colorless solid, 85% yield) was obtained.

$^1$H-NMR (400 MHz, DMSO-d6) δ ppm: 7.7 (d, 1H), 7.62 (s, 1H), 7.45 (d, 1H), 7 (s, 1H), 6.8 (dd, 1H), 6.7 (s, 1H), 6.6 (s, 1H), 4.8 (t, 2H), 4.8 (t, 1H), 4.25/3.8 (d, 2H), 4.05 (d, 2H), 3.92 (q, 2H), 3.7/3.45 (m, 2H), 3.2/3.1 (dd, 2H), 2.65 (s, 3H), 2.4 (s, 3H), 2.2-2 (m, 2H), 1.8/1.65 (m, 2H), 1 (t, 3H)

Step 6: Preparation of Example 36

Using General Procedure 12 starting from ethyl[4-chloro-5,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (1 eq.) as a reactant, the title compound (78% yield) was obtained.

The enantiopure products were obtained by chromatographic separation on chiral column.

EXAMPLE 36a (E1)

HRMS calculated for $C_{29}H_{29}ClN_4O_6S$: 596.1496; $[M+H]^+$ found: 597.1574 (δ=0.8 ppm).

EXAMPLE 36b (E2)

HRMS calculated for $C_{29}H_{29}ClN_4O_6S$: 596.1496; $[M+H]^+$ found: 597.1573 (δ=0.7 ppm).

$^1$H-NMR (400 MHz, DMSO-d6) δ ppm: 12.3 (m, 1H), 7.7 (d+d, 2H), 7.45 (d, 1H), 7 (d, 1H), 6.8 (dd, 1H), 6.6 (d, 1H), 5.8 (d, 1H), 4.8 (m, 3H), 4.25/4 (d, 2H), 4/3.8 (d, 2H), 3.65/3.4 (m, 2H), 3.1/2.95 (dd, 2H), 2.65 (s1, 3H), 2.4 (s, 3H), 2.2/2.1 (m, 2H), 1.8/1.65 (m, 2H)

EXAMPLE 37: [5-Chloro-4-methoxy-31-methyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid enantiomer 1

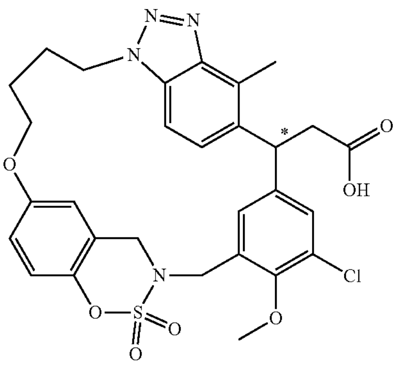

* = RorS

-continued enantiomer 2

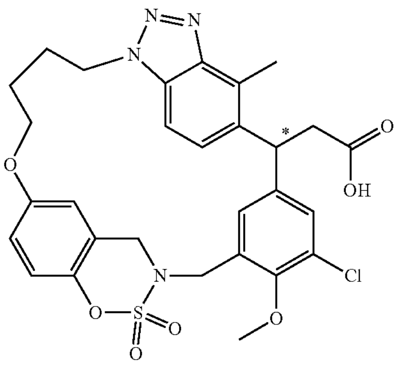

* = RorS

Step B1: Preparation of [3-chloro-2-methoxy-5-(4,4,5,5-tetramethyl-1,3,2-dioxaborolan-2-yl)phenyl]methanol Using General Procedure 3 starting from (5-bromo-3-chloro-2-methoxy-phenyl)methanol (1 eq., 17.0 g, 67.6 mmol) as a reactant, the title compound (11 g, 55% yield) was obtained.

$^1$H-NMR (400 MHz, DMSO-d6) δ ppm: 7.73 (d, 1H), 7.54 (d, 1H), 5.26 (t, 1H), 4.56 (d, 2H), 3.78 (s, 3H), 1.29 (s, 12H)

Step 1: Preparation of ethyl 3-{1-[4-(benzyloxy)butyl]-4-methyl-1H-benzotriazol-5-yl}-3-[3-chloro-5-(hydroxymethyl)-4-methoxyphenyl]propanoate Using General Procedure 6 starting from ethyl (2E)-3-{1-[4-(benzyloxy)butyl]-4-methyl-1H-benzotriazol-5-yl}prop-2-enoate (1 eq.) and [3-chloro-2-methoxy-5-(4,4,5,5-tetramethyl-1,3,2-dioxaborolan-2-yl)phenyl]methanol (1.05 eq.) as reactants, the title compound (60% yield) was obtained.

$^1$H-NMR (400 MHz, DMSO-d6) δ ppm: 7.61 (d, 1H), 7.5 (d, 1H), 7.38-7.2 (m, 7H), 5.18 (t, 1H), 4.82 (t, 1H), 4.68 (t, 2H), 4.49 (d, 2H), 4.4 (s, 2H), 3.92 (q, 2H), 3.7 (s, 3H), 3.41 (t, 2H), 3.18 (m, 2H), 2.77 (s, 3H), 1.95 (m, 2H), 1.5 (m, 2H), 1 (t, 3H)

Step 2: Preparation of ethyl 3-{1-[4-(benzyloxy)butyl]-4-methyl-1H-benzotriazol-5-yl}-3-(3-{[6-(benzyloxy)-2,2-dioxo-2H-1,2λ$^6$,3-benzoxathiazin-3(4H)-yl]methyl}-5-chloro-4-methoxyphenyl)propanoate Using General Procedure 7 starting from ethyl 3-{1-[4-(benzyloxy)butyl]-4-methyl-1H-benzotriazol-5-yl}-3-[3-chloro-5-(hydroxymethyl)-4-methoxyphenyl]propanoate (1 eq.) and 6-(benzyloxy)-3,4-dihydro-2H-1,2λ$^6$,3-benzoxathiazine-2,2-dione (1.1 eq.) as reactants, the title compound (97% yield) was obtained.

$^1$H-NMR (400 MHz, DMSO-d6) δ ppm: 7.62 (d, 1H), 7.54 (d, 1H), 7.45-7.25 (m, 12H), 7.03 (m, 2H), 6.96 (d, 1H), 5.08 (s, 2H), 4.85 (t, 1H), 4.65 (t, 2H), 4.57 (s, 2H), 4.39 (s, 2H), 4.29 (s, 2H), 3.94 (q, 2H), 3.7 (s, 3H), 3.41 (t, 2H), 3.2 (dd, 2H), 2.77 (s, 3H), 1.93 (quint, 2H), 1.49 (quint, 2H), 0.99 (t, 3H)

Step 3: Preparation of ethyl 3-{3-chloro-5-[(6-hydroxy-2,2-dioxo-2H-1,2λ$^6$,3-benzoxathiazin-3(4H)-yl)methyl]-4-methoxyphenyl}-3-[1-(4-hydroxybutyl)-4-methyl-1H-benzotriazol-5-yl]propanoate Using General Procedure 8 starting from ethyl 3-{1-[4-(benzyloxy)butyl]-4-methyl-1H-benzotriazol-5-yl}-3-(3-{[6-(benzyloxy)-2,2-dioxo-2H-1,2λ$^6$,3-benzoxathiazin-3(4H)-yl]methyl}-5-chloro-4-methoxyphenyl)propanoate (1 eq.) as a reactant, the title compound (80% yield) was obtained.

$^1$H-NMR (400 MHz, DMSO-d6) δ ppm: 9.69 (sl, 1H), 7.65 (d, 1H), 7.56 (d, 1H), 7.43/7.35 (2d, 2H), 6.92 (d, 1H), 6.75 (dd, 1H), 6.62 (d, 1H), 4.85 (t, 1H), 4.66 (t, 2H), 4.52 (s, 2H), 4.27 (s, 2H), 3.95 (q, 2H), 3.71 (s, 3H), 3.39 (t, 2H), 3.2 (d, 2H), 2.77 (s, 3H), 1.91 (quint, 2H), 1.37 (quint, 2H), 1.01 (t, 3H)

Step 4: Preparation of ethyl 3-[1-(4-bromobutyl)-4-methyl-1H-benzotriazol-5-yl]-3-{3-chloro-5-[(6-hydroxy-2,2-dioxo-2H-1,2λ$^6$,3-benzoxathiazin-3(4H)-yl)methyl]-4-methoxyphenyl}propanoate Using General Procedure 9 starting from ethyl 3-{3-chloro-5-[(6-hydroxy-2,2-dioxo-2H-1,2λ$^6$,3-benzoxathiazin-3(4H)-yl)methyl]-4-methoxyphenyl}-3-[1-(4-hydroxybutyl)-4-methyl-1H-benzotriazol-5-yl]propanoate (1 eq.) as a reactant, the title compound (89% yield) was obtained.

$^1$H-NMR (400 MHz, DMSO-d6) δ ppm: 9.65 (s, 1H), 7.67 (d, 1H), 7.57 (d, 1H), 7.43/7.35 (2d, 2H), 6.92 (d, 1H), 6.75 (dd, 1H), 6.62 (d, 1H), 4.85 (t, 1H), 4.7 (t, 2H), 4.52/4.27 (2s, 4H), 3.94 (q, 2H), 3.71 (s, 3H), 3.54 (t, 2H), 3.2 (d, 2H), 2.77 (s, 3H), 2 (m, 2H), 1.78 (m, 2H), 1 (t, 3H)

Step 5: Preparation of ethyl[5-chloro-4-methoxy-31-methyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate Using General Procedure 11 starting from ethyl 3-[1-(4-bromobutyl)-4-methyl-1H-benzotriazol-5-yl]-3-{3-chloro-5-[(6-hydroxy-2,2-dioxo-2H-1,2λ$^6$,3-benzoxathiazin-3(4H)-yl)methyl]-4-methoxyphenyl}propanoate (1 eq.) as a reactant, the title compound (61% yield) was obtained.

$^1$H-NMR (400 MHz, DMSO-d6) δ ppm: 7.75 (d, 1H), 7.68 (d, 1H), 7.44 (d, 1H), 6.98 (d, 1H), 6.79 (dd, 1H), 6.63 (d, 1H), 5.93 (d, 1H), 4.79 (m, 3H), 4.14/4.03 (2d, 2H), 4-3.9 (m, 4H), 3.83 (s, 3H), 3.73/3.53 (m+dt, 2H), 3.26/3.07 (2dd, 2H), 2.66 (s, 3H), 2.2/2.06 (2m, 2H), 1.78/1.59 (2m, 2H), 1 (t, 3H)

Step 6: Preparation of Example 37

Using General Procedure 12 starting from ethyl[5-chloro-4-methoxy-31-methyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (1 eq.) as a reactant, the title compound (white solid, quant.) was obtained.

The enantiopure products were obtained by chromatographic separation on chiral column.

EXAMPLE 37a (E1)

HRMS calculated for $C_{29}H_{29}ClN_4O_7S$: 612.1445; $[M+H]^+$ found: 613.1523 (δ=0.8 ppm).

EXAMPLE 37b (E2)

HRMS calculated for $C_{29}H_{29}ClN_4O_7S$: 612.1445; $[M+H]^+$ found: 613.1524 (δ=0.9 ppm).

$^1$H-NMR (400 MHz, DMSO-d6) δ ppm: 12.25 (m, 1H), 7.75 (d, 1H), 7.68 (d, 1H), 7.43 (d, 1H), 7 (d, 1H), 6.8 (dd, 1H), 6.62 (d, 1H), 5.92 (d, 1H), 4.79 (m, 3H), 4.13/4.03 (2d, 2H), 4.02-3.92 (dd, 2H), 3.82 (s, 3H), 3.72/3.52 (m+dt, 2H), 3.12/2.98 (2dd, 2H), 2.65 (s, 3H), 2.21/2.08 (2m, 2H), 1.79/1.6 (2m, 2H)

EXAMPLE 38: [4-Chloro-5-methoxy-31-methyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid enantiomer 1

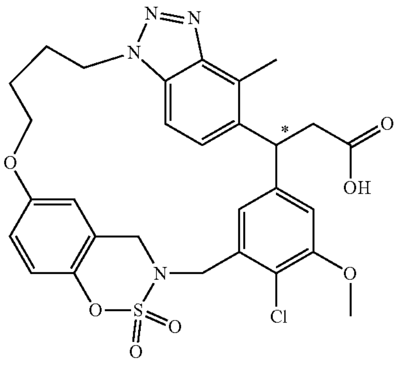

* = RorS enantiomer 2

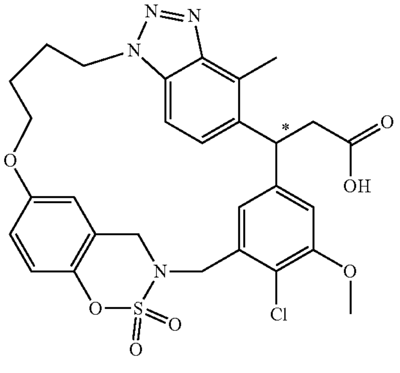

* = RorS

Step B1: Preparation of [2-chloro-3-methoxy-5-(4,4,5,5-tetramethyl-1,3,2-dioxaborolan-2-yl)phenyl]methanol Using General Procedure 3 starting from (5-bromo-2-chloro-3-methoxyphenyl)methanol (1 eq., 20.0 g, 79.5 mmol) as a reactant, gave the title compound (14.6 g, 62% yield).

$^1$H-NMR (400 MHz, DMSO-d6) δ ppm: 7.52 (d, 1H), 7.19 (d, 1H), 5.4 (t, 1H), 4.55 (d, 2H), 3.89 (s, 3H), 1.3 (s, 12H)

Step 1: Preparation of ethyl 3-[4-chloro-3-(hydroxymethyl)-5-methoxyphenyl]-3-(1-{4-[(4-methoxyphenyl)methoxy]butyl}-4-methyl-1H-benzotriazol-5-yl)propanoate Using General Procedure 6 starting from ethyl 3-(1-{4-[(4-methoxyphenyl)methoxy]butyl}-4-methyl-1H-benzotriazol-5-yl)propanoate (1 eq.) and [2-chloro-3-methoxy-5-(4,4,5,5-tetramethyl-1,3,2-dioxaborolan-2-yl)phenyl]methanol (1.5 eq.) as reactants, the title compound (yellow oil, 57% yield) was obtained.

$^1$H-NMR (400 MHz, DMSO-d6) δ ppm: 7.6 (d, 1H), 7.51 (d, 1H), 7.2 (d, 2H), 7.07/7.02 (2d, 2H), 6.88 (d, 2H), 5.28 (t, 1H), 4.89 (t, 1H), 4.63 (t, 2H), 4.47 (d, 2H), 4.3 (s, 2H), 3.92 (q, 2H), 3.81 (s, 3H), 3.71 (s, 3H), 3.39 (t, 2H), 3.2 (d, 2H), 2.79 (s, 3H), 1.91 (m, 2H), 1.49 (m, 2H), 1 (t, 3H)

Step 2: Preparation of ethyl 3-(3-{[6-(benzyloxy)-2,2-dioxo-2H-1,2λ$^6$,3-benzoxathiazin-3(4H)-yl]methyl}-4-chloro-5-methoxyphenyl)-3-(1-{4-[(4-methoxyphenyl)methoxy]butyl}-4-methyl-1H-benzotriazol-5-yl)propanoate Using General Procedure 7 starting from ethyl 3-[4-chloro-3-(hydroxymethyl)-5-methoxyphenyl]-3-(1-{4-[(4-methoxyphenyl)methoxy]butyl}-4-methyl-1H-benzotriazol-5-yl)propanoate (1 eq.) and 6-(benzyloxy)-3,4-dihydro-2H-1,2λ$^6$,3-benzoxathiazine-2,2-dione (1.1 eq.) as reactants, the title compound (89% yield) was obtained.

$^1$H-NMR (400 MHz, DMSO-d6) δ ppm: 7.59 (d, 1H), 7.55 (d, 1H), 7.46-7.32 (m, 5H), 7.18 (d, 2H), 7.14 (d, 1H), 7.1-7.02 (m, 3H), 6.93 (d, 1H), 6.85 (d, 2H), 5.08 (s, 2H), 4.9 (t, 1H), 4.62 (t, 2H), 4.53 (s, 2H), 4.31 (s, 2H), 4.3 (s, 2H), 3.94 (q, 2H), 3.83 (s, 3H), 3.72 (s, 3H), 3.36 (t, 2H), 3.23 (d, 2H), 2.8 (s, 3H), 1.9 (quint, 2H), 1.46 (m, 2H), 1 (t, 3H)

Step 3: Preparation of ethyl 3-{4-chloro-3-[(6-hydroxy-2,2-dioxo-2H-1,2)$^6$,3-benzoxathiazin-3(4H)-yl)methyl]-5-methoxyphenyl}-3-[1-(4-hydroxybutyl)-4-methyl-1H-benzotriazol-5-yl]propanoate Using General Procedure 8 starting from ethyl 3-(3-{[6-(benzyloxy)-2,2-dioxo-2H-1,2λ$^6$,3-benzoxathiazin-3(4H)-yl]methyl}-4-chloro-5-methoxyphenyl)-3-(1-{4-[(4-methoxyphenyl)methoxy]butyl}-4-methyl-1H-benzotriazol-5-yl)propanoate (1 eq.) as a reactant, the title compound (97% yield) was obtained.

$^1$H-NMR (400 MHz, DMSO-d6) δ ppm: 9.67 (s, 2H), 7.62 (d, 1H), 7.57 (d, 1H), 7.12 (d, 1H), 7.01 (dd, 1H), 6.94 (d, 1H), 6.78 (dd, 1H), 6.6 (d, 1H), 4.9 (t, 1H), 4.64 (t, 2H), 4.49 (s, 2H), 4.4 (t, 1H), 4.29 (m, 2H), 3.93 (q, 2H), 3.8 (t, 2H), 3.39 (m, 3H), 3.21 (d, 3H), 2.79 (s, 2H), 1.9 (m, 2H), 1.37 (m, 2H), 1 (t, 3H)

Step 4: Preparation of ethyl 3-[1-(4-bromobutyl)-4-methyl-1H-benzotriazol-5-yl]-3-{4-chloro-3-[(6-hydroxy-2,2-dioxo-2H-1,2)$^6$,3-benzoxathiazin-3(4H)-yl)methyl]-5-methoxyphenyl}propanoate Using General Procedure 9 starting from ethyl 3-{4-chloro-3-[(6-hydroxy-2,2-dioxo-2H-1,2λ$^6$,3-benzoxathiazin-3(4H)-yl)methyl]-5-methoxyphenyl}-3-[1-(4-hydroxybutyl)-4-methyl-1H-benzotriazol-5-yl]propanoate (1 eq.) as a reactant, the title compound (76% yield) was obtained.

$^1$H-NMR (400 MHz, DMSO-d6) δ ppm: 9.66 (s, 1H), 7.65 (d, 1H), 7.59 (d, 1H), 7.14 (d, 1H), 7.02 (d, 1H), 6.95 (d, 1H), 6.76 (dd, 1H), 6.59 (d, 1H), 4.89 (t, 1H), 4.69 (t, 2H), 4.48 (s, 2H), 4.29 (m, 2H), 3.95 (q, 2H), 3.83 (s, 3H), 3.53 (t, 2H), 3.23 (d, 2H), 2.8 (s, 3H), 2 (m, 2H), 1.77 (m, 2H), 1.01 (t, 3H)

Step 5: Preparation of ethyl[4-chloro-5-methoxy-31-methyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate Using General Procedure 11 starting from ethyl 3-[1-(4-bromobutyl)-4-methyl-1H-benzotriazol-5-yl]-3-{4-chloro-3-[(6-hydroxy-2,2-dioxo-2H-1,2)$^6$,3-benzoxathiazin-3(4H)-yl)methyl]-5-methoxyphenyl}propanoate (1 eq.) as a reactant, the title compound (72% yield) was obtained.

$^1$H-NMR (400 MHz, DMSO-d6) δ ppm: 7.69 (d, 1H), 7.47 (d, 1H), 7.44/6.31 (2d, 2H), 6.98 (d, 1H), 6.79 (dd, 1H), 5.81 (d, 1H), 4.85 (m, 1H), 4.77 (m, 2H), 4.23 (d, 4H), 4.07-3.8 (m, 4H), 3.98 (s, 3H), 3.66/3.42 (m+dt, 2H), 3.26/3.11 (2dd, 2H), 2.65 (s, 3H), 2.2/2.08 (2m, 2H), 1.82/1.65 (2m, 2H), 1.01 (t, 3H)

Step 6: Preparation of Example 38

Using General Procedure 12 starting from ethyl[4-chloro-5-methoxy-31-methyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (1 eq.) as a reactant, the title compound (white solid, 66% yield) was obtained.

The enantiopure products were obtained by chromatographic separation on chiral column.

EXAMPLE 38a (E1)

HRMS calculated for $C_{29}H_{29}ClN_4O_7S$: 612.1445; $[M+H]^+$ found: 613.1522 (δ=0.6 ppm).

EXAMPLE 38b (E2)

HRMS calculated for $C_{29}H_{29}ClN_4O_7S$: 612.1445; $[M+H]^+$ found: 613.1522 (δ=0.6 ppm).

$^1$H-NMR (400 MHz, DMSO-d6) δ ppm: 12.3 (m, 1H), 7.7 (d, 1H), 7.5 (m, 2H), 7 (d, 1H), 6.8 (dd, 1H), 6.3 (d, 1H), 5.8 (d, 1H), 4.8 (m, 3H), 4.25/3.95 (2d, 2H), 4.1/3.8 (2d, 2H), 4 (s, 3H), 3.65/3.4 (m, 2H), 3.15/3 (2dd, 2H), 2.7 (s1, 3H), 2.2/2.1 (2m, 2H), 1.85/1.65 (m, 2H)

EXAMPLE 39: [4,26,31-Trimethyl-27,27-dioxo-21-oxa-27λ$^6$-thia-1,14,15,16,26-pentaazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid enantiomer 1

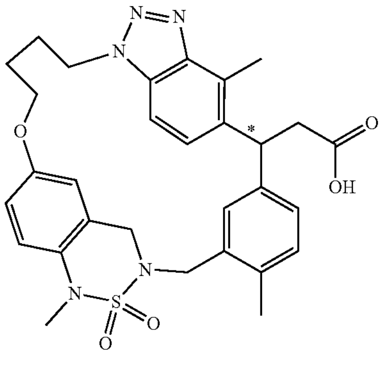

* = RorS

-continued enantiomer 2

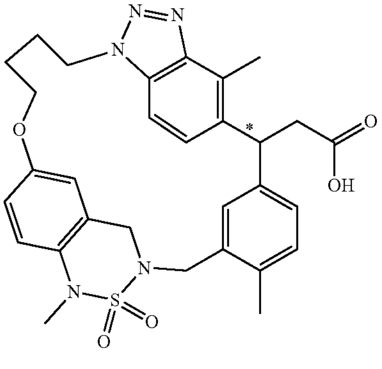

* = RorS

Step C1: Preparation of [5-(benzyloxy)-2-nitrophenyl]methanol 3-(Hydroxymethyl)-4-nitrophenol (1 eq., 4.15 g, 24.5 mmol) was dissolved in DMF (75 mL), NaH (1.1 eq., 1.08 g, 27.0 mmol) was added and the mixture was stirred at RT for 15 min. After cooling to 0° C., (bromomethyl)benzene (1 eq., 2.92 mL, 4.20 g, 24.6 mmol) was added dropwise and the reaction mixture was stirred at RT overnight. After completion of the reaction the mixture was concentrated under reduced pressure, the residue was treated with water, the precipitated solid was filtered, washed with water and dried to give the title compound (5.77 g, 91% yield) as a yellowish solid, which was used in the next step without further purification.

$^1$H-NMR (500 MHz, DMSO-d6) δ ppm: 8.14 (d, 1H), 7.52-7.31 (m, 5H), 7.44 (d, 1H), 7.11 (dd, 1H), 5.59 (t, 1H), 5.26 (s, 2H), 4.85 (d, 2H)

Step C2: Preparation of 2-{[5-(benzyloxy)-2-nitrophenyl]methyl}-1H-isoindole-1,3(2H)-dione

[5-(Benzyloxy)-2-nitrophenyl]methanol (1 eq., 5.76 g, 22.2 mmol) was dissolved in THF (250 mL), 1H-isoindole-1,3(2H)-dione (1 eq., 3.27 g, 22.2 mmol) and $PPh_3$ (2 eq., 11.65 g, 44.42 mmol) were added, and the solution was cooled to 5-10° C. DIAD (2 eq., 8.75 mL, 8.99 g, 44.4 mmol) was added dropwise and the mixture was stirred at RT for 1 h. After concentration under reduced pressure, the residue was purified via normal phase silica gel chromatography using DCM-MeOH (100:0 to 95:5) as eluents to give the title compound (2.89 g, 34% yield) as a yellowish white solid.

$^1$H-NMR (500 MHz, DMSO-d6) δ ppm: 8.21 (d, 1H), 7.95-7.85 (m, 4H), 7.37-7.25 (m, 5H), 7.19 (dd, 1H), 6.87 (d, 1H), 5.17 (s, 2H), 5.09 (s, 2H)

Step C3: Preparation of 1-[5-(benzyloxy)-2-nitrophenyl]methanamine

2-{[5-(Benzyloxy)-2-nitrophenyl]methyl}-1H-isoindole-1,3(2H)-dione (1 eq., 2.89 g, 7.44 mmol) was dissolved in EtOH (6 mL). Hydrazine hydrate (5 eq., 1.81 mL, 1.86 g, 37.38 mmol) was added and the reaction mixture was stirred at 50° C. overnight. After cooling to RT, the solid was filtered off and the mother liquor was concentrated under reduced pressure. The residue was dissolved in DCM, washed with sat. aq. $NaHCO_3$ solution, dried over $MgSO_4$, filtered, concentrated under reduced pressure to give the title compound (1.86 g, 97% yield) as a yellowish oil, which was used in a next step without purification.

$^1$H-NMR (500 MHz, DMSO-d6) δ ppm: 8.05 (d, 1H), 7.5-7.32 (m, 5H), 7.44 (d, 1H), 7.07 (dd, 1H), 5.25 (s, 2H), 3.99 (s, 2H), 1.96 (brs, 2H)

Step C4: Preparation of 2-(aminomethyl)-4-(benzyloxy)aniline

1-[5-(Benzyloxy)-2-nitrophenyl]methanamine (1 eq., 1.86 g, 7.20 mmol) was dissolved in EtOH (27 mL), then water (8 mL), iron powder (10 eq., 4.026 g, 72.09 mmol) and $NH_4Cl$ (0.5 eq., 193 mg, 3.6081 mmol) were added. The reaction mixture was refluxed for 1 h. After cooling to RT, the mixture was filtered through a Celite pad and concentrated under reduced pressure. The residue was dissolved in EtOAc and washed with 1M aq. NaOH solution. The organic phase was dried over $MgSO_4$, filtered, concentrated under reduced pressure to give the title compound (1.427 g, 87% yield) as a brownish oil, which was used in the next step without purification.

$^1$H-NMR (500 MHz, DMSO-d6) δ ppm: 7.44-7.27 (m, 5H), 6.79 (d, 1H), 6.63 (dd, 1H), 6.53 (d, 1H), 4.94 (s, 2H), 3.57 (s, 2H)

Step C5: Preparation of 6-(benzyloxy)-3,4-dihydro-2λ$^6$,1,3-benzothiadiazine-2,2(1H)-dione 2-(Aminomethyl)-4-(benzyloxy)aniline (1 eq., 1.42 g, 6.22 mmol) was dissolved in pyridine (45 mL). Sulfuric diamide (7 eq., 4.18 g, 43.5 mmol) was added and the mixture was refluxed for 2 h. The reaction mixture was concentrated under reduced pressure and the residue was treated with 60 mL 0.5 M aq. HCl solution. The precipitated solid was filtered off, dried in vacuum to give the title compound (1.721 g, 95% yield) as yellowish white solid, which was used in the next step without purification.

$^1$H-NMR (500 MHz, DMSO-d6) δ ppm: 9.82 (s, 1H), 7.45-7.28 (m, 5H), 7.17 (t, 1H), 6.87 (dd, 1H), 6.84 (d, 1H), 6.65 (d, 1H), 5.03 (s, 2H), 4.36 (d, 2H)

Step C6: Preparation of 6-(benzyloxy)-1-methyl-3,4-dihydro-2λ$^6$,1,3-benzothiadiazine-2,2(1H)-dione 6-(Benzyloxy)-3,4-dihydro-2λ$^6$,1,3-benzothiadiazine-2,2(1H)-dione (1 eq., 1.57 g, 5.41 mmol) was dissolved in THF (50 mL). $PPh_3$ (2 eq., 2.83 g, 10.82 mmol) and MeOH (1.1 eq., 0.24 mL, 190 mg, 5.925 mmol) were added. The reaction mixture was cooled to 0° C., and DIAD (2 eq., 2.13 mL, 2.19 g, 10.8 mmol) was added dropwise into the stirred reaction mixture at 0° C., followed by stirring at this temperature for 2 h. The reaction mixture was concentrated under reduced pressure, the residue was purified via flash chromatography using DCM as eluent to give the title compound (690 mg, 42% yield) as a white solid.

$^1$H-NMR (500 MHz, DMSO-d6) δ ppm: 7.69 (brs, 1H), 7.46-7.29 (m, 5H), 6.98 (d, 1H), 6.94 (dd, 1H), 6.87 (d, 1H), 5.07 (s, 2H), 4.38 (s, 2H), 3.12 (s, 3H)

Step 1: Preparation of ethyl 3-{1-[4-(benzyloxy) butyl]-4-methyl-1H-benzotriazol-5-yl}-3-(3-{[6-(benzyloxy)-1-methyl-2,2-dioxo-1,4-dihydro-2λ$^6$,1,3-benzothiadiazin-3(2H)-yl]methyl}-4-methylphenyl)propanoate Using General Procedure 7 starting from ethyl 3-{1-[4-(benzyloxy)butyl]-4-methyl-1H-benzotriazol-5-yl}-3-[3-(hydroxymethyl)-4-methylphenyl]propanoate (1 eq.) and 6-(benzyloxy)-1-methyl-3,4-dihydro-2λ$^6$,1,3-benzothiadiazine-2,2(1H)-dione (1 eq.) as reactants, the title compound (57% yield) was obtained.

$^1$H-NMR (500 MHz, DMSO-d6) δ ppm: 7.57 (d, 1H), 7.47 (d, 1H), 7.45 (d, 2H), 7.39 (t, 2H), 7.33 (t, 1H), 7.3 (t, 2H), 7.25 (d, 2H), 7.24 (t, 1H), 7.19 (dd, 1H), 7.13 (d, 1H), 7.12 (d, 1H), 7.08 (d, 1H), 7.03 (dd, 1H), 6.82 (d, 1H), 5.09 (s, 2H), 4.84 (t, 1H), 4.61 (t, 2H), 4.38 (s, 2H), 4.27 (s, 2H), 4.01 (s, 2H), 3.91 (q, 2H), 3.38 (t, 2H), 3.24 (s, 3H), 3.19/3.14 (dd+dd, 2H), 2.75 (s, 3H), 2.21 (s, 3H), 1.9 (qn, 2H), 1.46 (qn, 2H), 0.97 (t, 3H)

Step 2: Preparation of ethyl 3-[1-(4-hydroxybutyl)-4-methyl-1H-benzotriazol-5-yl]-3-{3-[(6-hydroxy-1-methyl-2,2-dioxo-1,4-dihydro-2λ$^6$,1,3-benzothiadiazin-3(2H)-yl)methyl]-4-methylphenyl}propanoate Using General Procedure 8 starting from ethyl 3-{1-[4-(benzyloxy)butyl]-4-methyl-1H-benzotriazol-5-yl}-3-(3-{[6-(benzyloxy)-1-methyl-2,2-dioxo-1,4-dihydro-2λ$^6$,1,3-benzothiadiazin-3(2H)-yl]methyl}-4-methylphenyl) propanoate (1 eq.) as a reactant, the title compound (quant.) was obtained.

$^1$H-NMR (500 MHz, DMSO-d6) δ ppm: 9.42 (s, 1H), 7.61 (d, 1H), 7.5 (d, 1H), 7.19 (dd, 1H), 7.13 (brs., 1H), 7.12 (d, 1H), 6.96 (d, 1H), 6.76 (dd, 1H), 6.49 (d, 1H), 4.83 (t, 1H), 4.64 (t, 2H), 4.43 (t, 1H), 4.23/4.19 (d+d, 2H), 4.04/3.99 (d+d, 2H), 3.93 (q, 2H), 3.38 (q, 2H), 3.19 (s, 3H), 3.16 (m, 2H), 2.74 (s, 3H), 2.22 (s, 3H), 1.9 (m, 2H), 1.36 (m, 2H), 0.99 (t, 3H)

Step 3: Preparation of ethyl 3-[1-(4-chlorobutyl)-4-methyl-1H-benzotriazol-5-yl]-3-{3-[(6-hydroxy-1-methyl-2,2-dioxo-1,4-dihydro-2)$^6$,1,3-benzothiadiazin-3(2H)-yl)methyl]-4-methylphenyl}propanoate hydrochloride Using General Procedure 10 starting from ethyl 3-[1-(4-hydroxybutyl)-4-methyl-1H-benzotriazol-5-yl]-3-{3-[(6-hydroxy-1-methyl-2,2-dioxo-1,4-dihydro-2λ$^6$,1,3-benzothiadiazin-3(2H)-yl)methyl]-4-methylphenyl}propanoate (1 eq.) as a reactant, the title compound (quant.) was obtained.

$^1$H-NMR (500 MHz, DMSO-d6) δ ppm: 9.43 (br., 1H), 7.64 (d, 1H), 7.51 (d, 1H), 7.19 (dd, 1H), 7.13 (d, 1H), 7.12 (d, 1H), 6.96 (d, 1H), 6.77 (dd, 1H), 6.49 (d, 1H), 4.83 (t, 1H), 4.69 (t, 2H), 4.23/4.19 (d+d, 2H), 4.04/3.99 (d+d, 2H), 3.93 (q, 2H), 3.64 (t, 2H), 3.19 (s, 3H), 3.17 (m, 2H), 2.74 (s, 3H), 2.22 (s, 3H), 1.99 (m, 2H), 1.68 (m, 2H), 0.99 (t, 3H)

Step 4: Preparation of ethyl[4,26,31-trimethyl-27,27-dioxo-21-oxa-27λ$^6$-thia-1,14,15,16,26-pentaazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate Using General Procedure 11 starting from ethyl 3-[1-(4-chlorobutyl)-4-methyl-1H-benzotriazol-5-yl]-3-{3-[(6-hydroxy-1-methyl-2,2-dioxo-1,4-dihydro-2λ$^6$,1,3-benzothiadiazin-3(2H)-yl)methyl]-4-methylphenyl}propanoate hydrochloride (1 eq.) as a reactant, the title compound (quant.) was obtained.

$^1$H-NMR (500 MHz, DMSO-d6) δ ppm: 7.68 (d, 1H), 7.45 (d, 1H), 7.45 (d, 1H), 7.26 (d, 1H), 6.94 (d, 1H), 6.76 (dd, 1H), 6.51 (d, 1H), 5.71 (d, 1H), 4.78 (t, 1H), 4.76 (m, 2H), 3.95/3.76 (d+d, 2H), 3.92 (q, 2H), 3.9/3.76 (d+d, 2H), 3.62/3.42 (m+m, 2H), 3.18 (s, 3H), 3.16/3.05 (dd+dd, 2H), 2.61 (s, 3H), 2.33 (s, 3H), 2.19/2.09 (m+m, 2H), 1.82/1.64 (m+m, 2H), 1 (t, 3H)

Step 5: Preparation of Example 39

Using General Procedure 12 starting from ethyl[4,26,31-trimethyl-27,27-dioxo-21-oxa-27λ$^6$-thia-1,14,15,16,26-pentaazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl] acetate (1 eq.) as a reactant, the title compound (white solid, 55% yield) was obtained.

The enantiopure products were obtained by chromatographic separation on chiral column.

EXAMPLE 39a (E1, Optical Purity>99.9%)

HRMS calculated for $C_{30}H_{33}N_5O_5S$: 575.2202; [M+H]$^+$ found: 576.2273 (δ=−0.4 ppm).

EXAMPLE 39b (E2, optical purity-99.7%)

HRMS calculated for $C_{30}H_{33}N_5O_5S$: 575.2202; [M+H]$^+$ found: 576.2252 (δ=−4.0 ppm).

$^1$H-NMR (500 MHz, DMSO-d6) δ ppm: 7.67 (d, 1H), 7.46 (dd, 1H), 7.43 (d, 1H), 7.26 (d, 1H), 6.94 (d, 1H), 6.76 (dd, 1H), 6.49 (d, 1H), 5.7 (d, 1H), 4.76 (t, 1H), 4.75 (m, 2H), 3.94/3.76 (d+d, 2H), 3.9/3.76 (d+d, 2H), 3.61/3.4 (m+m, 2H), 3.18 (s, 3H), 3.04/2.94 (dd+dd, 2H), 2.6 (s, 3H), 2.33 (s, 3H), 2.2/2.11 (m+m, 2H), 1.82/1.64 (m+m, 2H)

$^{13}$C-NMR (125 MHz, DMSO-d6) δ ppm: 131.2, 130.8, 128.2, 127.4, 118.2, 116.3, 111.8, 108, 67.6, 51.1, 49.6, 48.3, 41.8, 41, 33.6, 26.7, 25.6, 18.6, 13.4

EXAMPLE 40: [(2R,8S)-4-methoxy-2,33-dimethyl-29,29-dioxo-23,28-dioxa-29λ$^6$-thia-1,14,15,16-tetraazahexacyclo[22.5.3.1$^{3,7}$0.1$^{9,13}$0.0$^{12,16}$0.0$^{27,31}$]tetratriaconta-3(34),4,6,9(33),10,12,14,24,26,31-decaen-8-yl]acetic acid and [(2R,8R)-4-methoxy-2,33-dimethyl-29,29-dioxo-23,28-dioxa-29λ$^6$-thia-1,14,15,16-tetraazahexacyclo[22.5.3.1$^{3,7}$0.1$^{9,13}$0.0$^{12,16}$0.0$^{27,31}$]tetratriaconta-3(34),4,6,9(33),10,12,14,24,26,31-decaen-8-yl]acetic acid

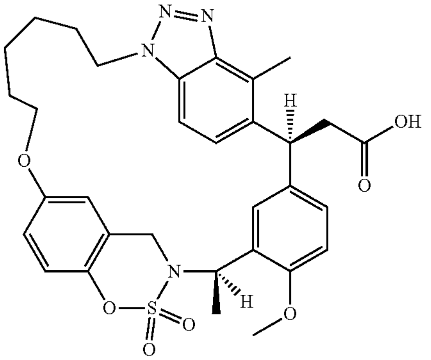

-continued

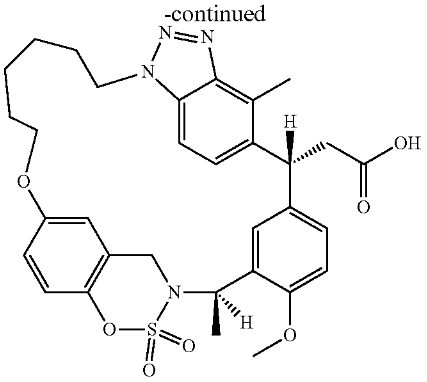

Step 1: Preparation of ethyl 3-{1-[6-(benzyloxy)hexyl]-4-methyl-1H-benzotriazol-5-yl}-3-{3-[(1S)-1-hydroxyethyl]-4-methoxyphenyl}propanoate Using General Procedure 6 starting from ethyl (E)-3-[1-(6-benzyloxy)hexyl)-4-methyl-benzotriazol-5-yl]prop-2-enoate (1 eq.) and (1S)-1-[2-methoxy-5-(4,4,5,5-tetramethyl-1,3,2-dioxaborolan-2-yl)phenyl]ethanol (1.1 eq.) as reactants, the title compound (50% yield) was obtained.

$^1$H-NMR (400 MHz, DMSO-d6) δ ppm: 7.6 (d, 1H), 7.48 (d, 1H), 7.38 (d, 1H), 7.32-7.25 (m, 5H), 7.11 (dd, 1H), 6.81 (d, 1H), 4.9 (d, 1H), 4.9 (m, 1H), 4.8 (m, 1H), 4.62 (t, 2H), 4.4 (s, 2H), 3.91 (q, 2H), 3.71 (s, 3H), 3.38 (t, 2H), 3.1 (d, 2H), 2.78 (s, 3H), 1.88 (m, 2H), 1.5 (m, 2H), 1.35 (m, 2H), 1.2 (m+d, 5H), 1 (t, 3H)

Step 2: Preparation of ethyl 3-(3-{(1R)-1-[6-(benzyloxy)-2,2-dioxo-2H-1,2λ$^6$,3-benzoxathiazin-3(4H)-yl]ethyl}-4-methoxyphenyl)-3-{1-[6-(benzyloxy)hexyl]-4-methyl-1H-benzotriazol-5-yl}propanoate Using General Procedure 7 starting from ethyl 3-{1-[6-(benzyloxy)hexyl]-4-methyl-1H-benzotriazol-5-yl}-3-{3-[(1S)-1-hydroxyethyl]-4-methoxyphenyl}propanoate (1 eq.) and 6-(benzyloxy)-3,4-dihydro-2H-1,2λ$^6$,3-benzoxathiazine-2,2-dione (1.5 eq.) as reactants, the title compound (beige solid, 71% yield) was obtained.

$^1$H-NMR (400 MHz, DMSO-d6) δ ppm: 0.97 (t, J=7.09 Hz, 5H) 1.10-1.26 (m, 7H) 1.29 (br. s., 3H) 1.37-1.53 (m, 7H) 1.75-1.91 (m, 3H) 2.72-2.79 (m, 4H) 3.09-3.21 (m, 3H) 3.33-3.41 (m, 3H) 3.64 (d, J=1.71 Hz, 3H) 3.91 (qd, J=6.95, 2.26 Hz, 2H) 4.38 (d, J=1.47 Hz, 2H) 4.46-4.65 (m, 3H) 4.82 (q, J=8.15 Hz, 1H) 4.86-5.12 (m, 2H) 5.28-5.45 (m, 1H) 6.63-6.82 (m, 2H) 6.82-6.97 (m, 2H) 7.08-7.48 (m, 12H) 7.48-7.55 (m, 1H) 7.57-7.68 (m, 1H)

Step 3: Preparation of ethyl 3-{3-[(1R)-1-(6-hydroxy-2,2-dioxo-2H-1,2λ$^6$,3-benzoxathiazin-3(4H)-yl)ethyl]-4-methoxyphenyl}-3-[1-(6-hydroxyhexyl)-4-methyl-1H-benzotriazol-5-yl]propanoate Using General Procedure 8 starting from ethyl 3-(3-{(1R)-1-[6-(benzyloxy)-2,2-dioxo-2H-1,2λ$^6$,3-benzoxathiazin-3(4H)-yl]ethyl}-4-methoxyphenyl)-3-{11-[6-(benzyloxy)hexyl]-4-methyl-1H-benzotriazol-5-yl}propanoate (1 eq.) as a reactant, the title compound (98% yield) was obtained.

$^1$H-NMR (400 MHz, DMSO-d6) δ ppm: 0.91-1.04 (m, 7H) 1.11-1.47 (m, 23H) 1.87 (quint, J=7.12 Hz, 4H) 2.73-

2.78 (m, 5H) 3.13-3.22 (m, 3H) 3.32-3.36 (m, 3H) 3.57-3.59 (m, 3 H) 3.67 (d, J=0.98 Hz, 6H) 3.94 (q, J=7.46 Hz, 4H) 4.29 (t, J=5.07 Hz, 2H) 4.37-4.57 (m, 3H) 4.63 (t, J=6.91 Hz, 4H) 4.78-4.87 (m, 2H) 5.37 (quint, J=7.06 Hz, 2H) 6.51 (dd, J=12.35, 2.81 Hz, 2H) 6.64 (dd, J=8.80, 2.69 Hz, 2H) 6.76 (d, J=1.22 Hz, 1H) 6.77-6.84 (m, 1H) 7.13 (dd, J=8.56, 1.96 Hz, 1H) 7.42 (dd, J=11.13, 2.08 Hz, 1H) 7.53 (t, J=9.05 Hz, 1H) 7.59-7.66 (m, 1H) 9.52 (d, J=3.55 Hz, 1H)

Step 4: Preparation of ethyl 3-[1-(6-bromohexyl)-4-methyl-1H-benzotriazol-5-yl]-3-{3-[(1R)-1-(6-hydroxy-2,2-dioxo-2H-1,2$\lambda^6$,3-benzoxathiazin-3(4H)-yl)ethyl]-4-methoxyphenyl}propanoate Using General Procedure 9 starting from ethyl 3-{3-[(1R)-1-(6-hydroxy-2,2-dioxo-2H-1,2$\lambda^6$,3-benzoxathiazin-3(4H)-yl)ethyl]-4-methoxyphenyl}-3-[1-(6-hydroxyhexyl)-4-methyl-1H-benzotriazol-5-yl]propanoate (1 eq.) as a reactant, the title compound (77% yield) was obtained.

$^1$H-NMR (400 MHz, DMSO-d6) δ ppm: 9.5 (s, 1H), 7.6 (d, 1H), 7.55 (d, 1H), 7.4 (d, 1H), 7.1 (m, 1H), 6.8 (m, 1H), 6.75 (d, 1H), 6.65 (d, 1H), 6.5 (d, 1H), 5.4 (m, 1H), 4.8 (m, 1H), 4.65 (t, 2H), 4.5 (m, 2H), 3.95 (q, 2H), 3.7 (s, 3H), 3.45 (t, 2H), 3.2 (m, 2H), 2.75 (d, 3H), 1.9 (quint, 2H), 1.75 (quint, 2H), 1.4 (t, 3H), 1.4/1.25 (2m, 4H), 1 (m, 3H)

Step 5: Preparation of ethyl[(2R)-4-methoxy-2,33-dimethyl-29,29-dioxo-23,28-dioxa-29$\lambda^6$-thia-1,14,15,16-tetraazahexacyclo[22.5.3.$1^{3,7}$0.$1^{9,13}$0.$0^{12,16}$0.$0^{27,31}$]tetratriaconta-3(34),4,6,9(33),10,12,14,24,26,31-decaen-8-yl]acetate Using General Procedure 11 starting from ethyl 3-[1-(6-bromohexyl)-4-methyl-1H-benzotriazol-5-yl]-3-{3-[(1R)-1-(6-hydroxy-2,2-dioxo-2H-1,2$\lambda^6$,3-benzoxathiazin-3(4H)-yl)ethyl]-4-methoxyphenyl}propanoate (1 eq.) as a reactant, the title compound (65% yield) was obtained.

$^1$H-NMR (400 MHz, DMSO-d6) δ ppm: 0.93-1.03 (m, 8H) 1.24 (d, J=4.65 Hz, 8H) 1.32-1.67 (m, 15H) 1.96 (d, J=6.85 Hz, 4H) 2.85 (s, 7H) 2.97-3.12 (m, 3H) 3.15-3.22 (m, 3H) 3.39-3.48 (m, 1H) 3.62 (d, J=18.71 Hz, 8H) 3.67-3.78 (m, 2H) 3.91 (qd, J=7.05, 5.01 Hz, 5 H) 4.10-4.27 (m, 2H) 4.24-4.38 (m, 3H) 4.59-4.74 (m, 6H) 4.79-4.90 (m, 3H) 5.42 (q, J=7.17 Hz, 1H) 5.51 (q, J=7.13 Hz, 1H) 5.86 (d, J=2.81 Hz, 1H) 6.24 (d, J=2.81 Hz, 1H) 6.72 (d, J=8.56 Hz, 4H) 6.84 (d, J=8.56 Hz, 1H) 6.90 (dd, J=9.05, 4.16 Hz, 2H) 7.12-7.25 (m, 2H) 7.36 (d, J=8.80 Hz, 1H) 7.46 (dd, J=8.56, 2.08 Hz, 1H) 7.57-7.73 (m, 5H)

Step 6: Preparation of Example 40

Using General Procedure 12 starting from ethyl[(2R)-4-methoxy-2,33-dimethyl-29,29-dioxo-23,28-dioxa-29$\lambda^6$-thia-1,14,15,16-tetraazahexacyclo[22.5.3.$1^{3,7}$0.$1^{9,13}$0.$0^{12,16}$0.$0^{27,31}$]tetratriaconta-3(34),4,6,9(33),10,12,14,24,26,31-decaen-8-yl]acetate (1 eq.) as a reactant, the title compound (white solid, 79% yield) was obtained.

The diastereo-pure products were obtained by chromatographic separation on chiral column.

EXAMPLE 40a (2R,8S)

HRMS calculated for $C_{32}H_{36}N_4O_7S$: 620.2305; $[M+H]^+$ found: 621.2378 (δ=0.1 ppm).

$^1$H-NMR (400 MHz, DMSO-d6) δ ppm: 12.1 (m, 1H), 7.62 (d, 1H), 7.46 (dd, 1H), 7.31 (d, 1H), 7.15 (d, 1H), 6.91 (d, 1H), 6.87 (d, 1H), 6.72 (dd, 1H), 5.87 (d, 1H), 5.42 (q, 1H), 4.84 (t, 1H), 4.67 (m, 2H), 4.16 (dd, 2H), 3.66 (s, 3H), 3.61/3.46 (2m, 2H), 3.01/2.91 (2dd, 2H), 2.85 (s, 3H), 1.97 (m, 2H), 1.68-1.16 (m, 6H), 1.35 (d, 3H)

EXAMPLE 40b (2R,8R)

HRMS calculated for $C_{32}H_{36}N_4O_7S$: 620.2305; $[M+H]^+$ found: 621.2377 (δ=−0.1 ppm).

$^1$H-NMR (400 MHz, DMSO-d6) δ ppm: 12.08 (m, 1H), 7.66 (d, 1H), 7.59 (d, 1H), 7.58 (d, 1H), 7.2 (dd, 1H), 6.9 (d, 1H), 6.73 (d, 1H), 6.72 (dd, 1H), 6.24 (d, 1H), 5.51 (q, 1H), 4.82 (t, 1H), 4.67 (m, 2H), 4.29 (dd, 2H), 3.65 (s, 3H), 3.6/3.5 (2m, 2H), 3.07 (d, 2H), 2.84 (s, 3H), 1.96 (m, 2H), 1.7-1.2 (m, 6H), 1.54 (d, 3H)

EXAMPLE 41: [(2R,8S)-4-Methoxy-2,32-dimethyl-28,28-dioxo-19,22,27-trioxa-28)$^6$-thia-1,14,15,16-tetraazahexacyclo[21.5.3.$1^{3,7}$0.$1^{9,13}$0.$0^{12,16}$0.$0^{26,30}$]tritriaconta-3(33),4,6,9(32),10,12,14,23,25,30-decaen-8-yl]acetic acid and [(2R,8R)-4-methoxy-2,32-dimethyl-28,28-dioxo-19,22,27-trioxa-28)$^6$-thia-1,14,15,16-tetraazahexacyclo[21.5.3.$1^{3,7}$0.$1^{9,13}$0.$0^{12,16}$0.$0^{26,30}$]tritriaconta-3(33),4,6,9(32),10,12,14,23,25,30-decaen-8-yl]acetic acid

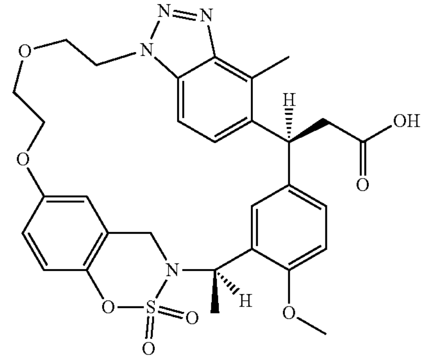

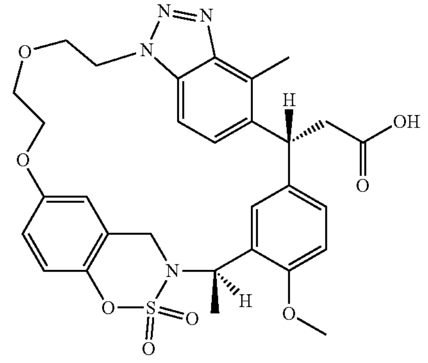

Step 1: Preparation of ethyl 3-(1-{2-[2-(benzyloxy)ethoxy]ethyl}-4-methyl-1H-benzotriazol-5-yl)-3-{3-[(1S)-1-hydroxyethyl]-4-methoxyphenyl}propanoate Using General Procedure 6 starting from ethyl (2E)-3-(1-{2-[2-(benzyloxy)ethoxy]ethyl}-4-methyl-1H-benzotriazol-5-yl)prop-2-enoate (1 eq.) and (1S)-1-[2-methoxy-5-(4,4,5,5-tetramethyl-1,3,2-dioxaborolan-2-yl)phenyl]ethan-1-ol (2 eq.) as reactants, the title compound (colorless oil, 52% yield) was obtained.

$^1$H-NMR (400 MHz, DMSO-d6) δ ppm 7.6 (d, 1H), 7.45 (d, 1H), 7.38 (s, 1H), 7.3-7.2 (t+d, 5H), 7.1 (d, 1H), 6.8 (d, 1H), 4.9 (d, 1H), 4.9 (m, 1H), 4.8 (t, 2H), 4.8 (t, 1H), 4.3 (s, 2H), 3.9 (t, 2H), 3.9 (q, 2H), 3.7 (s, 3H), 3.55/3.45 (t, 4H), 3.1 (m, 2H), 2.75 (s, 3H), 1.2 (d, 3H), 1 (t, 3H)

Step 2: Preparation of ethyl 3-(3-{(1R)-1-[6-(benzyloxy)-2,2-dioxo-2H-1,2λ$^6$,3-benzoxathiazin-3(4H)-yl]ethyl}-4-methoxyphenyl)-3-(1-{2-[2-(benzyloxy)ethoxy]ethyl}-4-methyl-1H-benzotriazol-5-yl)propanoate Using General Procedure 7 starting from ethyl 3-(1-{2-[2-(benzyloxy)ethoxy]ethyl}-4-methyl-1H-benzotriazol-5-yl)-3-{3-[(1R)-1-hydroxyethyl]-4-methoxyphenyl}propanoate (1 eq.) and 6-(benzyloxy)-3,4-dihydro-2H-1,2λ$^6$,3-benzoxathiazine-2,2-dione (1.1 eq.) as reactants, the title compound (67% yield) was obtained.

$^1$H-NMR (400 MHz, DMSO-d6) δ ppm: 7.63-7.45 (dd, 2H), 7.45-7.05 (m, 12H), 6.94-6.71 (m, 4H), 5.36 (m, 1H), 5.08-4.97 (dd, 2H), 4.86-4.75 (m, 3H), 4.54/4.51 (dd, 2H), 4.29 (s, 2H), 3.95-3.84 (m, 4H), 3.63/3.62 (s, 3H), 3.5/3.4 (m, 4H), 3.17-3.1 (m, 2H), 2.75/2.74 (s, 3H), 1.42/1.4 (d, 3H), 0.98 (t, 3H)

Step 3: Preparation of ethyl 3-{3-[(1R)-1-(6-hydroxy-2,2-dioxo-2H-1,2λ$^6$,3-benzoxathiazin-3(4H)-yl)ethyl]-4-methoxyphenyl}-3-{1-[2-(2-hydroxyethoxy)ethyl]-4-methyl-1H-benzotriazol-5-yl}propanoate Using General Procedure 8 starting from ethyl 3-(3-{(1R)-1-[6-(benzyloxy)-2,2-dioxo-2H-1,2λ$^6$,3-benzoxathiazin-3(4H)-yl]ethyl}-4-methoxyphenyl)-3-(1-{12-[2-(benzyloxy)ethoxy]ethyl}-4-methyl-1H-benzotriazol-5-yl) propanoate (1 eq.) as a reactant, the title compound (white solid, 69% yield) was obtained.

$^1$H-NMR (400 MHz, DMSO-d6) δ ppm: 0.96-1.05 (m, 3H) 1.42 (t, J=6.64 Hz, 3H) 2.76 (d, J=5.65 Hz, 3H) 3.11-3.21 (m, 2H) 3.38 (d, J=2.29 Hz, 4H) 3.67 (s, 3H) 3.85-3.91 (m, 2H) 3.94 (qd, J=7.12, 1.22 Hz, 2H) 4.38-4.57 (m, 3H) 4.76-4.88 (m, 3H) 5.37 (quin, J=7.02 Hz, 1H) 6.51 (dd, J=16.02, 2.90 Hz, 1H) 6.65 (dd, J=8.85, 2.90 Hz, 1H) 6.75-6.84 (m, 2H) 7.13 (dd, J=8.54, 1.83 Hz, 1H) 7.43 (dd, J=8.54, 1.98 Hz, 1H) 7.49-7.58 (m, 1H) 7.61-7.68 (m, 1H) 9.53 (br. s., 1H)

Step 4: Preparation of ethyl 3-{1-[2-(2-bromoethoxy)ethyl]-4-methyl-1H-benzotriazol-5-yl}-3-{3-[(1R)-1-(6-hydroxy-2,2-dioxo-2H-1,2λ$^6$,3-benzoxathiazin-3(4H)-yl)ethyl]-4-methoxyphenyl}propanoate Using General Procedure 9 starting from ethyl 3-{3-[(1R)-1-(6-hydroxy-2,2-dioxo-2H-1,2)$^6$,3-benzoxathiazin-3(4H)-yl)ethyl]-4-methoxyphenyl}-3-{11-[2-(2-hydroxyethoxy)ethyl]-4-methyl-1H-benzotriazol-5-yl}propanoate (1 eq.) as a reactant, the title compound (white solid, 94% yield) was obtained.

$^1$H-NMR (400 MHz, DMSO-d6) δ ppm: 1.01 (td, J=7.09, 3.91 Hz, 3H) 1.41 (t, J=6.54 Hz, 3H) 2.75 (d, J=4.77 Hz, 3H) 3.08-3.26 (m, 2H) 3.45 (t, J=5.99 Hz, 2H) 3.64-3.69 (m, 4H) 3.88-3.98 (m, 6H) 4.36-4.59 (m, 2H) 4.76-4.87 (m, 3H) 5.31-5.42 (m, 1H) 6.51 (dd, J=11.13, 2.81 Hz, 1H) 6.65 (dd, J=8.86, 2.87 Hz, 1H) 6.75-6.85 (m, 2H) 7.12 (dd, J=8.50, 1.90 Hz, 1H) 7.42 (dd, J=7.03, 2.02 Hz, 1H) 7.50-7.58 (m, 1H) 7.62-7.68 (m, 1H)

Step 5: Preparation of ethyl[(2R)-4-methoxy-2,32-dimethyl-28,28-dioxo-19,22,27-trioxa-28λ$^6$-thia-1,14,15,16-tetraazahexacyclo[21.5.3.1$^{3,7}$0.1$^{9,13}$0.0$^{12,16}$0.0$^{26,30}$ tritriaconta-3(33),4,6,9(32),10,12,14,23,25,30-decaen-8-yl]acetate Using General Procedure 11 starting from ethyl 3-{1-[2-(2-bromoethoxy)ethyl]-4-methyl-1H-benzotriazol-5-yl}-3-{3-[(1R)-1-(6-hydroxy-2,2-dioxo-2H-1,2λ$^6$,3-benzoxathiazin-3(4H)-yl)ethyl]-4-methoxyphenyl}propanoate (1 eq.) as a reactant, the title compound (white solid, 96% yield) was obtained.

$^1$H-NMR (400 MHz, DMSO-d6) δ ppm: 1.01 (dt, J=17.58, 7.11 Hz, 7H) 1.36 (d, J=7.09 Hz, 3H) 1.61 (d, J=7.09 Hz, 4H) 2.86 (d, J=4.89 Hz, 7H) 2.93-3.12 (m, 3H) 3.12-3.27 (m, 3H) 3.45-3.64 (m, 8H) 3.68-3.85 (m, 8H) 3.86-3.98 (m, 10H) 4.04 (d, J=11.13 Hz, 1H) 4.08-4.26 (m, 3H) 4.53 (d, J=17.85 Hz, 1H) 4.74-4.97 (m, 9H) 5.43 (q, J=6.77 Hz, 1H) 5.56 (q, J=7.21 Hz, 1H) 5.68 (d, J=2.57 Hz, 1H) 6.45 (d, J=2.45 Hz, 1H) 6.54 (d, J=8.56 Hz, 1H) 6.60 (dd, J=8.93, 2.93 Hz, 1H) 6.68-6.78 (m, 2H) 6.85 (dd, J=11.19, 8.99 Hz, 3H) 7.10 (s, 1H) 7.13 (d, J=8.68 Hz, 1H) 7.27 (d, J=8.80 Hz, 1H) 7.45 (d, J=8.44 Hz, 1H) 7.55-7.61 (m, 2H) 7.70 (d, J=8.68 Hz, 1H)

Step 6: Preparation of Example 41

Using General Procedure 12 starting from ethyl[(2R)-4-methoxy-2,32-dimethyl-28,28-dioxo-19,22,27-trioxa-28λ$^6$-thia-1,14,15,16-tetraazahexacyclo[21.5.3.1$^{3,7}$0.1$^{9,13}$0.0$^{12,16}$0.0$^{26,30}$]tritriaconta-3(33),4,6,9(32),10,12,14,23,25,30-decaen-8-yl]acetate (1 eq.) as a reactant, the title compound (white solid, 72% yield) was obtained.

The diastereo-pure products were obtained by chromatographic separation on chiral column.

EXAMPLE 41a (2R,8S)

HRMS calculated for $C_{30}H_{32}N_4O_8S$: 608.1941; $[M+H]^+$ found: 609.2014 (δ=0.1 ppm).

$^1$H-NMR (400 MHz, DMSO-d6) δ ppm: 12.1 (br), 7.7 (d, 1H), 7.6 (s1, 1H), 7.27 (d, 1H), 6.87 (d, 1H), 6.76 (d, 1H), 6.61 (dd, 1H), 6.54 (d, 1H), 6.45 (d, 1H), 5.56 (q, 1H), 4.85/4.52 (2d, 2H), 4.85 (m, 2H), 4.8 (t, 1H), 3.92 (m, 2H), 3.9/3.52 (2m, 2H), 3.76 (m, 2H), 3.57 (s, 3H), 3.18/3.05 (2dd, 2H), 2.85 (s, 3H), 1.6 (d, 3H)

$^{13}$C-NMR (100 MHz, DMSO-d6) δ ppm: 1561, 173.7, 154.8, 146.2, 145.4, 138.3, 135.4, 132.6, 131.5, 127.8, 125.2, 125.2, 124.6, 119.6, 118.1, 114.4, 113, 111, 109.7, 70.4, 68.8, 68.1, 55.6, 51.3, 48.5, 46, 40.6, 39.5, 19.6, 13.5

$^{15}$N-NMR (50 MHz, DMSO-d6) δ ppm: −152.9, −290.5

EXAMPLE 41b (2R,8R)

HRMS calculated for $C_{30}H_{32}N_4O_8S$: 608.1941; $[M+H]^+$ found: 609.2014 (δ=0.1 ppm).

$^1$H-NMR (400 MHz, DMSO-d6) δ ppm: 12.1 (br), 7.59 (d, 1H), 7.46 (d, 1H), 7.1 (d, 1H), 7.08 (s1, 1H), 6.89 (d, 1H), 6.85 (d, 1H), 6.73 (dd, 1H), 5.71 (d, 1H), 5.43 (q, 1H), 4.85 (m, 1H), 4.82 (m, 2H), 4.17/4.12 (m, 2H), 4.06/3.91 (dt+td, 2H), 3.84/3.71 (2m, 2H), 3.72 (s, 3H), 3.62/3.52 (2m, 2H), 2.97/2.84 (2dd, 2H), 2.86 (s, 3H), 1.35 (d, 3H)

$^{13}$C-NMR (100 MHz, DMSO-d6) δ ppm: 173, 155.8, 155.4, 146.7, 145.2, 137.6, 136.1, 132.4, 128.7, 128.3, 127, 126.1, 125.5, 119.4, 118.5, 115, 113.3, 111.3, 108.9, 69.7, 68.7, 68.7, 55.9, 52.4, 48.6, 46.1, 41.3, 40.8, 17.7, 13.3

$^{15}$N-NMR (50 MHz, DMSO-d6) δ ppm: −3.1, −152.9, −290.5

EXAMPLE 42: [4,21,31-Trimethyl-27,27-dioxo-26-oxa-27λ$^6$-thia-1,14,15,16,21-pentaazahexacyclo [20.5.3.1$^{3,7}$0.1$^{9,13}$0.0$^{12,16}$0.0$^{25,29}$]dotriaconta-3(32), 4,6,9(31),10,12,14,22,24,29-decaen-8-yl]acetic acid

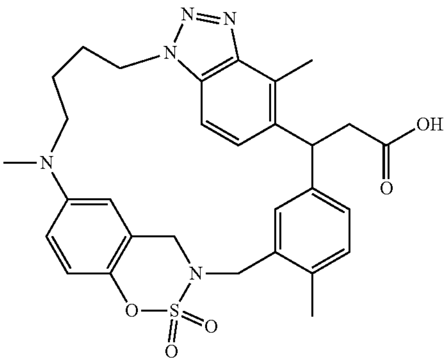 [SMILES: Cc1ccc2cc1CN1Cc3cc(ccc3OS1(=O)=O)N(C)CCCCn1nnc3c(C)c(ccc31)C2CC(=O)O]

Step C1: Preparation of 6-bromo-2H-1,2)$^6$,3-benzoxathiazine-2,2-dione

Using General Procedure 4 STEP 2 starting from 5-bromo-2-hydroxybenzaldehyde (1 eq.) as a reactant, the title compound (white solid, 38% yield) was obtained.

$^1$H-NMR (400 MHz, DMSO-d6) δ ppm: 8.25 (d, 1H), 8.15 (s, 1H), 8.1 (dd, 1H), 7.52 (d, 1H)

Step C2: Preparation of 6-bromo-3,4-dihydro-2H-1,2λ$^6$,3-benzoxathiazine-2,2-dione Using General Procedure 4 STEP 3 starting from 6-bromo-2H-1,2λ$^6$,3-benzoxathiazine-2,2-dione (1 eq.) as a reactant, the title compound (white solid, 57% yield) was obtained.

$^1$H-NMR (400 MHz, DMSO-d6) δ ppm: 8.6 (m, 1H), 7.56 (d, 1H), 7.52 (dd, 1H), 7.05 (d, 1H), 4.58 (s, 2H)

Step 1: Preparation of ethyl 3-{3-[(6-bromo-2,2-dioxo-2H-1,2λ$^6$,3-benzoxathiazin-3(4H)-yl)methyl]-4-methylphenyl}-3-(1-{4-[(4-methoxyphenyl) methoxy]butyl}-4-methyl-1H-benzotriazol-5-yl) propanoate Using General Procedure 7 starting from ethyl 3-[3-(hydroxymethyl)-4-methyl-phenyl]-3-[1-[4-[(4-methoxyphenyl)methoxy]butyl]-4-methyl-benzotriazol-5-yl]propanoate (1 eq.) and 6-bromo-3,4-dihydro-2H-1,2λ$^6$,3-benzoxathiazine-2,2-dione (1.2 eq.) as reactants, the title compound (91% yield) was obtained.

$^1$H-NMR (400 MHz, DMSO-d6) δ ppm: 7.62 (dd, 1H), 7.59/7.48 (2d, 2H), 7.53 (d, 1H), 7.24 (d, 1H), 7.22-7.11 (m, 5H), 6.86 (d, 2H), 4.84 (t, 1H), 4.65 (t, 2H), 4.5 (m, 2H), 4.31 (s, 2H), 4.24 (m, 2H), 3.93 (q, 2H), 3.72 (s, 3H), 3.37 (t, 2H), 3.16 (d, 2H), 2.76 (s, 3H), 2.23 (s, 3H), 1.92 (quint, 2H), 1.48 (quint, 2H), 0.99 (t, 3H)

Step 2: Preparation of ethyl 3-[3-({6-[(tert-butoxycarbonyl)amino]-2,2-dioxo-2H-1,2λ$^6$,3-benzoxathiazin-3(4H)-yl}methyl)-4-methylphenyl]-3-(1-{4-[(4-methoxyphenyl)methoxy]butyl}-4-methyl-1H-benzotriazol-5-yl)propanoate A 25 mL round bottom flask, equipped with drying tube was charged with ethyl 3-{3-[(6-bromo-2,2-dioxo-2H-1, 2λ$^6$,3-benzoxathiazin-3(4H)-yl)methyl]-4-methylphenyl}-3-(1-{4-[(4-methoxyphenyl)methoxy]butyl}-4-methyl-1H-benzotriazol-5-yl)propanoate (1 eq., 100 mg, 0.126 mmol), tert-butyl carbamate (1.2 eq., 17.8 mg, 0.152 mmol), sodium-tert-butoxide (1.5 eq., 18.2 mg, 0.189 mmol), tBuX-Phos (0.2 eq., 10.7 mg, 0.0253 mmol) and $Pd_2(dba)_3$ (0.1 eq., 11.6 mg, 0.0126 mmol) under argon flow. The mixture was suspended in toluene (1 mL) and stirred at RT overnight. The volatiles were evaporated under reduced pressure. The residue was purified by normal phase silica gel chromatography using hexane-EtOAc eluent to give the title compound (27 mg, 20% yield).

$^1$H-NMR (400 MHz, DMSO-d6) δ ppm: 0.98 (t, J=7.09 Hz, 3H) 1.15-1.28 (m, 13H) 1.92 (quint, J=7.24 Hz, 2H) 2.22 (s, 3H) 2.75 (s, 3H) 3.16 (d, J=7.46 Hz, 2H) 3.36 (t, J=6.30 Hz, 3H) 3.72 (s, 3H) 3.86-3.97 (m, 2H) 4.22 (s, 2H) 4.30 (s, 2H) 4.46 (s, 2H) 4.64 (t, J=6.91 Hz, 2H) 4.84 (t, J=8.07 Hz, 1H) 6.12 (br. s., 2H) 6.86 (d, J=8.68 Hz, 2H) 6.92 (s, 1H) 7.06-7.15 (m, 2H) 7.18 (d, J=8.68 Hz, 2H) 7.24 (s, 1H) 7.36 (dd, J=9.05, 2.45 Hz, 1H) 7.46-7.56 (m, 2H) 7.59 (d, J=8.68 Hz, 1H) 9.54 (s, 1H)

Step 3: Preparation of ethyl 3-[3-({6-[(tert-butoxycarbonyl)(methyl)amino]-2,2-dioxo-2H-1,2)$^6$,3-benzoxathiazin-3(4H)-yl}methyl)-4-methylphenyl]-3-(1-{4-[(4-methoxyphenyl)methoxy]butyl}-4-methyl-1H-benzotriazol-5-yl)propanoate In a 100 mL round bottom flask, equipped with drying tube ethyl 3-[3-({6-[(tert-butoxycarbonyl)amino]-2,2-dioxo-2H-1,2λ$^6$,3-benzoxathiazin-3(4H)-yl}methyl)-4-methylphenyl]-3-(1-{4-[(4-methoxyphenyl)methoxy]butyl}-4-methyl-1H-benzotriazol-5-yl)propanoate (1 eq., 260 mg, 0.289 mmol) was dissolved in DMF (2.4 mL). Sodium-hydride (60% in mineral oil (1.5 eq., 17.3 mg, 0.433 mmol) was added portion-wise to the stirred mixture. After stirring for 5 min, iodomethane (1.5 eq., 61.5 mg, 0.027 mL) was added and the stirring was continued overnight at RT. The reaction mixture was poured into water (20 mL) and extracted with EtOAc (2×20 mL). The combined organic layers were washed with brine (20 mL) dried over $Na_2SO_4$, filtered, the resulted filtrate was concentrated to dryness. The residue was purified by normal phase silica gel chromatography using heptane-EtOAc as an eluent to give the title compound (212 mg, 87% yield).

$^1$H-NMR (400 MHz, DMSO-d6) δ ppm: 7.58 (d, 1H), 7.48 (d, 1H), 7.38-7.1 (m, 6H), 7.19 (d, 2H), 6.86 (d, 2H), 4.82 (t, 1H), 4.62 (t, 2H), 4.49 (d, 2H), 4.3 (s, 2H), 4.22 (s, 2H), 3.91 (q, 2H), 3.71 (s, 3H), 3.38 (t, 2H), 3.2 (s, 3H), 3.15 (m, 2H), 2.5 (s, 3H), 2.21 (s, 3H), 1.9 (m, 2H), 1.49 (m, 2H), 1.4 (s, 9H), 0.99 (t, 3H)

Step 4: Preparation of ethyl 3-[3-({6-[(tert-butoxycarbonyl)(methyl)amino]-2,2-dioxo-2H-1,2)$^6$,3-benzoxathiazin-3(4H)-yl}methyl)-4-methylphenyl]-3-[1-(4-hydroxybutyl)-4-methyl-1H-benzotriazol-5-yl] propanoate Into a 25 mL round bottom flask equipped with drying tube ethyl 3-[3-({6-[(tert-butoxycarbonyl)(methyl)amino]-2,2-dioxo-2H-1,2λ$^6$,3-benzoxathiazin-3(4H)-yl}methyl)-4-methylphenyl]-3-(1-{4-[(4-methoxyphenyl)methoxy] butyl}-4-methyl-1H-benzotriazol-5-yl)propanoate (1 eq., 0.262 g, 0.311 mmol), DCM (1.6 mL) and water (0.078 mL) were added.

After addition of DDQ (1.5 eq., 106 mg, 0.467 mmol) the reaction mixture turned black, while additional stirring at RT for 3 h resulted a color change to red. The reaction mixture was diluted with DCM (20 mL), washed with sat. aq. $NaHCO_3$ solution (20 mL) and the aq. layer was extracted with DCM (20 mL). The combined organic layers were dried over $Na_2SO_4$, filtered, the filtrate was concentrated. The residue was purified by normal phase silica gel chromatography using heptane-EtOAc as eluents to give the title compound (202 mg, 90% yield).

$^1$H-NMR (400 MHz, DMSO-d6) δ ppm: 7.6 (d, 1H), 7.45 (d, 1H), 7.32 (dd, 1H), 7.22 (d, 1H), 7.17 (dd, 1H), 7.15 (d, 1H), 7.13 (d, 1H), 4.83 (t, 1H), 4.63 (t, 2H), 4.5 (m, 2H), 4.4 (t), 4.25 (s, 2H), 4.23 (d, 1H), 3.92 (q, 2H), 3.38 (q, 2H), 3.2 (s, 3H), 3.18 (m, 2H), 2.75 (s, 3H), 2.21 (s, 3H), 1.9 (m, 2H), 1.4 (s, 9H), 1.38 (m, 2H), 1 (t, 3H)

Step 5: Preparation of ethyl 3-[1-(4-bromobutyl)-4-methyl-1H-benzotriazol-5-yl]-3-[3-({6-[(tert-butoxycarbonyl)(methyl)amino]-2,2-dioxo-2H-1,2λ$^6$,3-benzoxathiazin-3(4H)-yl}methyl)-4-methylphenyl] propanoate Using General Procedure 9 starting from ethyl 3-[3-({6-[(tert-butoxycarbonyl)(methyl)amino]-2,2-dioxo-2H-1,2λ$^6$, 3-benzoxathiazin-3(4H)-yl}methyl)-4-methylphenyl]-3-[1-(4-hydroxybutyl)-4-methyl-1H-benzotriazol-5-yl] propanoate (1 eq.) as a reactant, the title compound (188 mg, 83% yield) was obtained.

$^1$H-NMR (400 MHz, DMSO-d6) δ ppm: 7.6 (d, 1H), 7.5 (d, 1H), 7.33 (dd, 1H), 7.3-7.1 (m, 5H), 4.82 (t, 1H), 4.68 (t, 2H), 4.5 (m, 2H), 4.22 (m, 2H), 3.92 (q, 2H), 3.52 (t, 2H), 3.19 (s, 3H), 3.18 (m, 2H), 2.75 (s, 3H), 2.2 (s, 3H), 1.99 (m, 2H), 1.78 (m, 2H), 1.4 (s, 9H), 1 (t, 3H)

Step 6: Preparation of ethyl 3-[1-(4-bromobutyl)-4-methyl-1H-benzotriazol-5-yl]-3-(4-methyl-3-{[6-(methylamino)-2,2-dioxo-2H-1,2λ$^6$,3-benzoxathiazin-3(4H)-yl]methyl}phenyl)propanoate In a 100 mL round bottom flask equipped with drying tube ethyl 3-[1-(4-bromobutyl)-4-methyl-1H-benzotriazol-5-yl]-3-[3-({6-[(tert-butoxycarbonyl)(methyl)amino]-2,2-dioxo-2H-1,2λ$^6$,3-benzoxathiazin-3(4H)-yl}methyl)-4-methylphenyl]propanoate (1 eq., 0.181 g, 0.231 mmol) was dissolved in DCM (3.6 mL). TFA (16 eq., 0.282 mL, 0.420 g, 3.7 mmol) was added dropwise, and the mixture was stirred at RT for 9 h. After completion of the reaction, the pH was set to 8-9 using sat. aq. $Na_2CO_3$ solution. The layers were separated, the organic layer was washed with brine (10 mL) and the aq. layer was washed with DCM (10 mL). The combined organic layers were dried over $Na_2SO_4$, filtered, and the filtrate was concentrated to dryness. The residue was purified by normal phase silica gel chromatography using heptane-EtOAc-EtOH (100:0:0 to 100/75/25) as eluents to give the title compound (0.117 g, 70% yield).

$^1$H-NMR (400 MHz, DMSO-d6) δ ppm: 7.62 (d, 1H), 7.51 (d, 1H), 7.21 (s1, 1H), 7.2 (d, 1H), 7.14 (d, 1H), 6.91 (d, 1H), 6.57 (dd, 1H), 6.29 (d, 1H), 5.79 (q), 4.85 (t, 1H), 4.69 (t, 2H), 4.38/4.32 (m, 2H), 4.22/4.15 (m, 2H), 3.93 (q, 2H), 3.53 (t, 2H), 3.17 (m, 2H), 2.76 (s, 3H), 2.66 (d, 3H), 2.22 (s, 3H), 1.98 (m, 2H), 1.77 (m, 2H), 1 (t, 3H)

Step 7: Preparation of ethyl[4,21,31-trimethyl-27,27-dioxo-26-oxa-27λ$^6$-thia-1,14,15,16,21-pentaazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate and ethyl[4,21,31-trimethyl-20,27,27-trioxo-26-oxa-27λ$^6$-thia-1,14,15,16,21-pentaazahexacyclo[20.5.3.1$^{3,7}$0.1$^{9,13}$0.0$^{12,16}$0.0$^{25,29}$] dotriaconta-3(32),4,6,9(31),10,12,14,22,24,29-decaen-8-yl]acetate Into a 100 mL round bottom flask equipped with a reflux condenser and a drying tube ethyl 3-[1-(4-bromobutyl)-4-methyl-1H-benzotriazol-5-yl]-3-(4-methyl-3-{[6-(methylamino)-2,2-dioxo-2H-1,2λ$^6$,3-benzoxathiazin-3(4H)-yl] methyl}phenyl)propanoate (1 eq., 0.11 g, 0.161 mmol) and MeCN (48 mL) were added. Potassium iodide (0.1 eq., 2.667 mg, 0.0161 mmol) and $Cs_2CO_3$ (2 eq., 6.2 g, 0.322 mmol) were added, and the mixture was stirred at 60° C. for 24 h.

After completion of the reaction, the mixture was concentrated under reduced pressure, the residue was diluted with EtOAc (40 mL) and washed with water (40 mL). The layers were separated, the organic layer was washed with brine, the combined aq. layers were washed with EtOAc (20 mL). The combined organic layer was dried over $Na_2SO_4$, then filtered, the filtrate was concentrated to dryness. The residue was purified by reversed-phase chromatography using water-MeCN—HCOOH (1000:25:1 to 25:1000:1) as eluent. The fractions containing of the 2 main products were individually combined and concentrated till water. The resulted aq. mixtures were freeze dried to give the title compounds:

Ethyl[4,21,31-trimethyl-27,27-dioxo-26-oxa-27λ$^6$-thia-1,14,15,16,21-pentaazahexacyclo [20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (28% yield)

$^1$H-NMR (400 MHz, DMSO-d6) δ ppm: 7.66 (d, 1H), 7.43 (dd, 1H), 7.3 (d, 1H), 7.27 (d, 1H), 6.87 (d, 1H), 6.64 (d, 1H), 6.5 (dd, 1H), 5.77 (d, 1H), 4.82/4.72 (m, 2H), 4.72 (m, 1H), 4.24/3.94 (d, 2H), 3.99/3.73 (d, 2H), 3.94 (q, 2H), 3.26/3.02 (dd, 2H), 3.13/2.97 (m, 2H), 2.83 (s, 3H), 2.72 (s, 3H), 2.32 (s, 3H), 2.12/1.81 (m, 2H), 1.47/1.04 (m, 2H), 1.01 (t, 3H) Ethyl[4,21,31-trimethyl-20,27,27-trioxo-26-oxa-27λ$^6$-thia-1,14,15,16,21-pentaazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (42% yield)

$^1$H-NMR (400 MHz, DMSO-d6) δ ppm: 7.6 (d, 1H), 7.5 (dd, 1H), 7.33 (d, 1H), 7.29 (m, 2H), 7.08 (d, 1H), 6.97 (s1, 1H), 6.2 (s1, 1H), 4.87/4.58 (m, 2H), 4.87 (m, 1H), 4.3/3.69 (m, 2H), 4.2 (m, 2H), 3.92 (q, 2H), 3.22/3.1 (2dd, 2H), 3.2 (s, 3H), 2.4/2.03 (m, 2H), 2.3 (s, 3H), 2.2 (s, 3H), 2.02/1.75 (m, 2H), 1 (t, 3H)

Step 8: Preparation of Example 42

Using General Procedure 12 starting from ethyl[4,21,31-trimethyl-27,27-dioxo-26-oxa-27λ$^6$-thia-1,14,15,16,21-pentaazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl] acetate (1 eq., 47 mg, 0.0779 mmol) as a reactant, the title compound (25 mg, 54% yield) was obtained.

HRMS calculated for $C_{30}H_{33}N_5O_5S$: 575.2202; $[M+H]^+$ found: 576.2277 (δ=0.3 ppm).

$^1$H-NMR (400 MHz, DMSO-d6) δ ppm: 12.3 (m, 1H), 7.64 (d, 1H), 7.45 (dd, 1H), 7.27 (d, 1H), 7.26 (d, 1H), 6.87

(d, 1H), 6.63 (d, 1H), 6.49 (dd, 1H), 5.77 (d, 1H), 4.82/4.72 (2m, 2H), 4.78 (m, 1H), 4.25/3.91 (2d, 2H), 3.99/3.73 (2d, 2H), 3.14/2.99 (2dd, 2H), 3.1/2.97 (2m, 2H), 2.83 (s, 3H), 2.72 (s, 3H), 2.32 (s, 3H), 2.12/1.81 (2m, 2H), 1.47/1.04 (2m, 2H).

EXAMPLE 43: [4,21,31-Trimethyl-20,27,27-trioxo-26-oxa-27λ$^6$-thia-1,14,15,16,21-pentaazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid

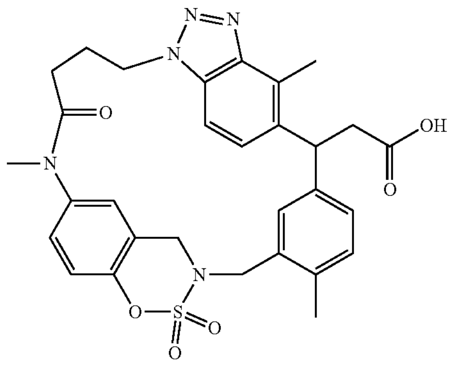 [SMILES: Cc1ccc2cc1CN1Cc3cc(ccc3OS1(=O)=O)N(C)C(=O)CCCn1nnc3c(C)c(ccc31)C2CC(=O)O]

Using General Procedure 12 starting from ethyl[4,21,31-trimethyl-20,27,27-trioxo-26-oxa-2726-thia-1,14,15,16,21-pentaazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl] acetate (1 eq., 71 mg, 0.1149 mmol) as a reactant, the title compound (35 mg, 50% yield) was obtained.

HRMS calculated for $C_{30}H_{31}N_5O_6S$: 589.1995; $[M+H]^+$ found: 590.2074 (δ=1.0 ppm).

$^1$H-NMR (400 MHz, DMSO-d6) δ ppm: 11.8 (m, 1H), 7.6 (d, 1H), 7.53 (dd, 1H), 7.35 (d, 1H), 7.29 (d, 1H), 7.27 (dd, 1H), 7.07 (d, 1H), 6.94 (s1, 1H), 6.2 (s1, 1H), 4.87/4.58 (m, 2H), 4.87 (m, 1H), 4.27/3.69 (m, 2H), 4.19 (m, 2H), 3.21 (s, 3H), 3.13/3 (2dd, 2H), 2.51 (s, 3H), 2.4/2.03 (m, 2H), 2.31 (s, 3H), 2.02/1.75 (m, 2H)

EXAMPLE 44: [(19R)-19-hydroxy-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid

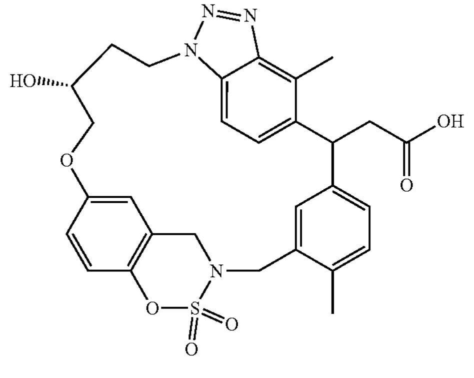 [SMILES: Cc1ccc2cc1CN1Cc3cc(ccc3OS1(=O)=O)OC[C@H](O)CCn1nnc3c(C)c(ccc31)C2CC(=O)O]

Step A1: Preparation of 1-bromo-4-fluoro-2-methyl-3-nitrobenzene

In a 3-necked round bottomed flask equipped with a thermostat 1-fluoro-3-methyl-2-nitrobenzene (1 eq., 50 g, 322.31 mmol) was dissolved in TFA (200 mL, 2.611 mol) and the reaction mixture was cooled to −5° C. Sulphuric acid (100 mL) was added dropwise, followed by addition of 1-bromopyrrolidine-2,5-dione (1 eq., 57.33 g, 322.1 mmol) in small portions. The reaction mixture was stirred at −5° C. overnight, then at 0° C. for 72 hours, and at 5° C. for another night. The mixture was poured to a 1:1 mixture of ice/water, the precipitated solid was filtered out and washed with water. The obtained solid was dissolved in DCM and washed with sat. aq. $NaHCO_3$ solution and brine, dried over $MgSO_4$, evaporated and dried on air at RT overnight to give 47.38 g (63% yield) of the title compound as an off-white solid.

$^1$H-NMR (500 MHz, DMSO-d6) δ ppm: 7.98 (dd, 1H), 7.49 (td, 1H), 2.37 (s, 3H)

Step A2: Preparation of (2R)-4-(4-bromo-3-methyl-2-nitroanilino)butane-1,2-diol

The solution of 1-bromo-4-fluoro-2-methyl-3-nitrobenzene (1 eq., 4 g, 17 mmol), (2R)-4-aminobutane-1,2-diol hydrochloride (1.5 eq., 4.6 mL, 3.6 g, 25 mmol) and DIPEA (2 eq., 6 mL, 4.452 g, 34.45 mmol) in N,N-dimethylacetamide (38 eq., 60 mL, 56.2 g, 645.3 mmol) was stirred at 100° C. overnight. After addition of another 0.74 g (5.22 mmol) of (2R)-4-aminobutane-1,2-diol hydrochloride and 1 ml of DIPEA, the reaction mixture was stirred for additional 6 h at 100° C. The reaction mixture was poured on ice, extracted with EtOAc, and the aq. layer was back-extracted with EtOAc. The combined organic layers were washed with brine, dried over $Na_2SO_4$ and concentrated under reduced pressure. The crude product was purified by normal phase silica gel chromatography using heptane-EtOAc (100:0 to 60:40) as eluents. Collection and evaporation of the fractions containing of the product resulted in the title compound (4.13 g, 76% yield) as an orange solid.

$^1$H-NMR (500 MHz, DMSO-d6) δ ppm: 7.54 (d, 1H), 6.74 (d, 1H), 6.29 (t, 1H), 4.72 (d, 1H), 4.55 (t, 1H), 3.5 (m, 1H), 3.23/3.131 (dd+m, 2H), 3.22 (q, 2H), 2.25 (s, 3H), 1.75/1.45 (m+m, 2H)

Step A3: Preparation of (2R)-4-(4-bromo-3-methyl-2-nitro-anilino)-1-[tert-butyl(dimethyl)silyl]oxy-butan-2-ol (2R)-4-(4-Bromo-3-methyl-2-nitroanilino)butane-1,2-diol (1 eq., 3 g, 9.40 mmol) was dissolved in dry DMF (18 mL) and DIPEA (4.2 mL, 24 mmol) was added. The mixture was cooled to 0° C. prior to the dropwise addition of a solution of tert-butyl(chloro)dimethylsilane (1.5 g, 10 mmol) in DMF (5.5 mL). The temperature was allowed to warm to RT and the mixture was stirred at this temperature overnight. The reaction mixture was poured on sat. $NH_4Cl$ solution and extracted with DCM. The organic phase was washed with brine, dried over $Na_2SO_4$, filtered and concentrated. The residual DMF was removed by evaporation in high vacuo. The crude product was purified by normal phase silica gel chromatography using heptane-EtOAc (100:0 to 75:25) as eluents to give the title compound (3.898 g, 96% yield) as an orange solid.

$^1$H-NMR (500 MHz, DMSO-d6) δ ppm: 7.53 (d, 1H), 6.73 (d, 1H), 6.27 (t, 1H), 4.78 (d, 1H), 3.52 (m, 1H), 3.51/3.36 (m+m, 2H), 3.23 (q, 2H), 2.25 (s, 3H), 1.78/1.44 (m+m, 2H), 0.84 (s, 9H), 0.02 (s, 6H)

Step A4: Preparation of 4-bromo-N-[(3R)-4-{[tert-butyl(dimethyl)silyl]oxy}-3-{[tert-butyl(diphenyl)silyl]oxy}butyl]-3-methyl-2-nitroaniline (2R)-4-(4-Bromo-3-methyl-2-nitro-anilino)-1-[tert-butyl(dimethyl)silyl]oxy-butan-2-ol (1 eq., 3.898 g, 8.994 mmol) was dissolved in dry DMF (45 mL), and imidazole (3 eq., 1.83 g, 26.9 mmol) was added followed by addition of N,N-dimethylpyridin-4-amine (0.113 g, 0.925 mmol). The reaction mixture was cooled to 0° C. and tert-butyl(chloro)diphenylsilane (2 eq., 4.96 g, 18.0 mmol) was added dropwise. The temperature was raised to 50° C. and the mixture was stirred at this temperature overnight. The reaction mixture was poured on sat. $NH_4Cl$ solution and extracted with DCM. The organic phase was washed with sat. $NaHCO_3$ solution, then with brine, dried over $Na_2SO_4$, filtered and evaporated. The residual DMF was removed by evaporation in high vacuo. The crude product was purified by normal phase silica gel chromatography using DCM eluent to give the title compound (5.92 g, 98% yield) as an orange oil.

$^1$H-NMR (500 MHz, DMSO-d6) δ ppm: 7.65-7.35 (m, 10H), 7.44 (d, 1H), 6.52 (d, 1H), 6.06 (t, 1H), 3.82 (m, 1H), 3.46/3.44 (dd+dd, 2H), 3.17/3.13 (m+m, 2H), 2.24 (s, 3H), 1.8/1.7 (m+m, 2H), 0.99 (s, 3H), 0.76 (s, 3H), −0.12/−0.16 (s, 6H)

Step A5: Preparation of 4-bromo-N$^1$- [(3R)-4-{[tert-butyl(dimethyl)silyl]oxy}-3-{[tert-butyl(diphenyl)silyl]oxy}butyl]-3-methylbenzene-1,2-diamine 4-Bromo-N-[(3R)-4-{[tert-butyl(dimethyl)silyl]oxy}-3-{[tert-butyl(diphenyl)silyl]oxy}butyl]-3-methyl-2-nitroaniline (1 eq., 6.0 g, 8.9 mmol) was dissolved in a mixture of dioxane (30 mL) and MeOH (5 mL). Raney nickel catalyst (0.38 g, 4.4 mmol), washed with dioxane was added and the mixture was hydrogenated in a stainless steel autoclave under 10 bar pressure at RT for 3 h. After completion of the reaction the mixture was filtered through a pad of Celite, washed with DCM and the mother liquor was evaporated to dryness to give the title compound (5.63 g, 98% yield) as a brownish thick oil, which was used in a next step without purification.

$^1$H-NMR (500 MHz, DMSO-d6) δ ppm: 7.69-7.37 (m, 10H), 6.65 (d, 1H), 6.1 (d, 1H), 4.55 (s, 2H), 4.52 (t, 1H), 3.87 (m, 1H), 3.48/3.46 (dd+dd, 2H), 3.04/2.97 (m+m, 2H), 2.15 (s, 3H), 1.87/1.79 (m+m, 2H), 1 (s, 9H), 0.77 (s, 3H), −0.11 (s, 3H), −0.14 (s, 3H)

Step A6: Preparation of 5-bromo-1-[(3R)-4-{[tert-butyl(dimethyl)silyl]oxy}-3-{[tert-butyl(diphenyl)silyl]oxy}butyl]-4-methyl-1H-benzotriazole 4-Bromo-N$^1$- [(3R)-4-{[tert-butyl(dimethyl)silyl]oxy}-3-{[tert-butyl(diphenyl)silyl]oxy}butyl]-3-methylbenzene-1,2-diamine (1 eq., 5.0 g, 7.8 mmol) was dissolved in abs. THF (40 mL) and the mixture was cooled to 0° C. TFA (10 mg, 0.0612 mmol) was added to the mixture followed by the dropwise addition of 3-methylbutyl nitrite (1.66 eq., 1.8 mL, 13 mmol) at 0° C. The reaction mixture was stirred for 3 h, while the temperature was allowed to raise to RT. The mixture was diluted with THF and evaporated to Celite. The crude product was purified by normal phase silica gel chromatography using heptane-EtOAc (100:0 to 98:2) as eluents, resulted in a title compound (2.46 g, 48% yield) as a dark orange thick oil.

$^1$H-NMR (500 MHz, DMSO-d6) δ ppm: 7.64 (d, 1H), 7.6-7.31 (m, 10H), 7.43 (d, 1H), 3.75 (m, 1H), 3.74 (t, 2H), 3.47/3.43 (dd+dd, 2H), 2.7 (s, 3H), 2.19/2.04 (m+m, 2H), 0.98 (s, 9H), 0.7 (s, 9H), −0.17/−0.23 (s+s, 6H)

Step A7: Preparation of ethyl (2E)-3-{1-[(3R)-4-{[tert-butyl(dimethyl)silyl]oxy}-3-{[tert-butyl(diphenyl)silyl]oxy}butyl]-4-methyl-1H-benzotriazol-5-yl}prop-2-enoate 5-Bromo-1-[(3R)-4-{[tert-butyl(dimethyl)silyl]oxy}-3-{[tert-butyl(diphenyl)silyl]oxy}butyl]-4-methyl-1H-benzotriazole (1 eq., 2.455 g, 3.76 mmol) was dissolved in abs. DMF (10 mL) in a microwave tube. Ethyl prop-2-enoate (2 eq., 0.805 mL, 7.40 mmol) was added followed by an addition of DIPEA (1.95 mL, 11.375 mmol). The reaction mixture was flushed with $N_2$ prior to the addition of (acetato-κO)({2-[bis(2-methylphenyl)phosphanyl]phenyl}methyl)palladium (0.1 eq., 0.359 g, 0.382 mmol). The mixture was flushed again with $N_2$, the tube was sealed and placed into the microwave reactor for 2 h at 150° C. The mixture was filtered through a pad of celite, the filter cake was washed with DCM and the mother liquor was evaporated to celite. The crude product was purified by normal phase silica gel chromatography using heptane-EtOAc (100:0 to 80:20) as eluents resulting the title compound (2.19 g, 88% yield) as a yellow thick oil.

$^1$H-NMR (500 MHz, DMSO-d6) δ ppm: 8.02 (d, 1H), 7.93 (d, 1H), 7.62-7.31 (m, 10H), 7.46 (d, 1H), 6.66 (d, 1H), 4.74 (t, 2H), 4.22 (q, 2H), 3.78 (m, 1H), 3.49/3.45 (dd+dd, 2H), 2.8 (s, 3H), 2.19/2.05 (m+m, 2H), 1.28 (t, 3H), 0.99 (s, 9H), 0.71 (s, 9H), −0.16/−0.21 (s+s, 6H)

Step 1: Preparation of ethyl 3-{1-[(3R)-4-{[tert-butyl(dimethyl)silyl]oxy}-3-{[tert-butyl(diphenyl)silyl]oxy}butyl]-4-methyl-1H-benzotriazol-5-yl}-3-[3-(hydroxymethyl)-4-methylphenyl]propanoate Ethyl (2E)-3-{11-[(3R)-4-{[tert-butyl(dimethyl)silyl]oxy}-3-{[tert-butyl(diphenyl)silyl]oxy}butyl]-4-methyl-1H-benzotriazol-5-yl}prop-2-enoate (1 eq., 1.43 g, 2.13 mmol) was dissolved in dioxane (10 mL) and [2-methyl-5-(4,4,5,5-tetramethyl-1,3,2-dioxaborolan-2-yl)phenyl]methanol (1.55 eq., 0.81 g, 3.3 mmol) was added followed by addition of TEA (1.4 eq., 0.42 mL, 3.0 mmol) and water (2 mL). The reaction mixture was flushed with $N_2$ prior to the addition of chloro(1,5-cyclooctadiene)rhodium(I) dimer catalyst (0.051 g, 0.10 mmol). After stirring at 80° C. overnight the mixture was filtered through a pad of Celite, the filter cake was washed with DCM, the mother liquor was evaporated and the residue was taken up in heptane.

The mixture was purified by normal phase silica gel chromatography using heptane-EtOAc (100:0 to 60:40) as eluents, resulting the title compound (0.99 g, 59% yield) as a colourless thick oil.

$^1$H-NMR (500 MHz, DMSO-d6) δ ppm: 7.62-7.28 (m, 10H), 7.43 (d, 1H), 7.34 (d, 1H), 7.29/7.27 (d/d, 1H), 7.1/7.08 (dd/dd, 1H), 7.03/7.01 (d/d, 1H), 5/4.99 (t/t, 1H), 4.83 (t, 1H), 4.67 (t, 2H), 4.41/4.4 (d/d, 2H), 3.92 (m, 2H), 3.76 (m, 1H), 3.44 (m, 2H), 3.13 (m, 2H), 2.75 (s, 3H), 2.15 (s, 3H), 2.15/2.02 (m+m, 2H), 1.01/1 (t/t, 3H), 0.97 (s, 9H), 0.7/0.68 (s/s, 9H), −0.18/−0.19/−0.23/−0.26 (s/s/s/s, 6H)

Step 2: Preparation of ethyl 3-(3-{[6-(benzyloxy)-2,2-dioxo-2H-1,2λ$^6$,3-benzoxathiazin-3(4H)-yl]methyl}-4-methylphenyl)-3-{1-[(3R)-4-{[tert-butyl(dimethyl)silyl]oxy}-3-{[tert-butyl(diphenyl)silyl]oxy}butyl]-4-methyl-1H-benzotriazol-5-yl}propanoate Ethyl 3-{1-[(3R)-4-{[tert-butyl(dimethyl)silyl]oxy}-3-{[tert-butyl(diphenyl)silyl]oxy}butyl]-4-methyl-1H-benzotriazol-5-yl}-3-[3-(hydroxymethyl)-4-methylphenyl]propanoate (1 eq., 0.882 g, 1.11 mmol), 6-(benzyloxy)-3,4-dihydro-2H-1,2λ$^6$,3-benzoxathiazine-2,2-dione (0.696 g, 2.39 mmol) and $PPh_3$ (0.57 g, 2.2 mmol) were suspended in dry THF (20 mL) and DIAD (0.27 g, 1.3 mmol) was added in one portion. The reaction mixture was stirred at RT for 24 h. The mixture was diluted with DCM, evaporated to Celite and purified by normal phase silica gel chromatography using heptane-EtOAc (100:0 to 80:20) as eluents, resulting the title compound (0.707 g, 60% yield) as a white solid.

$^1$H-NMR (500 MHz, DMSO-d6) δ ppm: 7.62-7.28 (m, 18H), 7.45 (d, 1H), 7.34 (d, 1H), 7.13 (d, 1H), 7.06 (dd, 1H), 6.96/6.94 (d/d, 1H), 5.09 (s, 2H), 4.86 (t, 1H), 4.66 (m, 2H), 4.43 (m, 2H), 4.2 (s, 2H), 3.92 (m, 2H), 3.76 (m, 1H), 3.42 (m, 2H), 3.18 (m, 2H), 2.76 (s, 3H), 2.22/2.21 (s/s, 3H), 2.15/2 (m+m, 2H), 0.99/0.98 (t/t, 3H), 0.95 (s, 9H), 0.69/0.66 (s/s, 9H), −0.2/−0.22/−0.25/−0.3 (s/s/s/s, 6H)

Step 3: Preparation of ethyl 3-{1-[(3R)-4-{[tert-butyl(dimethyl)silyl]oxy}-3-{[tert-butyl(diphenyl)silyl]oxy}butyl]-4-methyl-1H-benzotriazol-5-yl}-3-{3-[(6-hydroxy-2,2-dioxo-2H-1,2λ$^6$,3-benzoxathiazin-3(4H)-yl)methyl]-4-methylphenyl}propanoate Ethyl 3-(3-{[6-(benzyloxy)-2,2-dioxo-2H-1,2λ$^6$,3-benzoxathiazin-3(4H)-yl]methyl}-4-methylphenyl)-3-{11-[(3R)-4-{[tert-butyl(dimethyl)silyl]oxy}-3-{[tert-butyl(diphenyl)silyl]oxy}butyl]-4-methyl-1H-benzotriazol-5-yl}propanoate (1 eq., 0.577 g, 0.541 mmol) was dissolved in a mixture of dioxane (2 mL) and MeOH (6 mL), and Pd/C (0.05 g, 0.05 mmol) was added to the mixture, which was hydrogenated in a stainless steel autoclave under 2 bars at RT overnight. After completion of the reaction the mixture was filtered through a pad of Celite, the filter cake was washed with DCM, the mother liquor was concentrated, the residue was dried in high vacuo at RT to yield the title compound (0.485 g, 92% yield) as a white foamy material. The product was used in a next step without purification.

$^1$H-NMR (500 MHz, DMSO-d6) δ ppm: 9.7 (s, 1H), 7.61-7.08 (m, 13H), 7.47 (d, 1H), 7.36 (d, 1H), 6.99 (d, 1H), 6.79 (dd, 1H), 6.61 (d, 1H), 4.85 (t, 1H), 4.68 (m, 2H), 4.41/4.36 (d+d, 2H), 4.21/4.16 (d+d, 2H), 3.93 (m, 2H), 3.74 (m, 1H), 3.43 (m, 2H), 3.17 (m, 2H), 2.75 (s, 3H), 2.22/2.21 (s/s, 3H), 2.16/2.02 (m+m, 2H), 1.01/1 (t/t, 3H), 0.96 (s, 9H), 0.69/0.66 (s/s, 9H), −0.2/−0.21/−0.25/−0.29 (s/s/s/s, 6H)

Step 4: Preparation of ethyl 3-{1-[(3R)-3-{[tert-butyl(diphenyl)silyl]oxy}-4-hydroxybutyl]-4-methyl-1H-benzotriazol-5-yl}-3-{3-[(6-hydroxy-2,2-dioxo-2H-1,2λ$^6$,3-benzoxathiazin-3(4H)-yl)methyl]-4-methylphenyl}propanoate Ethyl 3-{11-[(3R)-4-{[tert-butyl(dimethyl)silyl]oxy}-3-{[tert-butyl(diphenyl)silyl]oxy}butyl]-4-methyl-1H-benzotriazol-5-yl}-3-{3-[(6-hydroxy-2,2-dioxo-2H-1,2λ$^6$,3-benzoxathiazin-3(4H)-yl)methyl]-4-methylphenyl}propanoate (1 eq., 0.47 g, 0.48 mmol) was dissolved in EtOH (30 mL). 2M aq. hydrochloric acid (0.5 mL, 1 mmol) was added and the mixture was stirred at RT for 3 h. After completion of the reaction the mixture was cooled to 0° C. and neutralized with 0.15 ml of TEA. The mixture was diluted with DCM, evaporated to Celite and purified by normal phase silica gel chromatography using DCM-MeOH (100:0 to 80:20) as eluents, resulting the title compound (0.335 g, 81% yield) as a white solid.

$^1$H-NMR (500 MHz, DMSO-d6) δ ppm: 9.7 (s, 1H), 7.61-7.09 (m, 13H), 7.47 (d, 1H), 7.36 (d, 1H), 6.99 (d, 1H), 6.79 (dd, 1H), 6.62/6.61 (d, 1H), 4.84 (t, 1H), 4.74 (t, 1H), 4.66 (t, 2H), 4.41/4.36 (d+d, 2H), 4.22/4.17 (d+d, 2H), 3.93 (m, 2H), 3.74 (m, 1H), 3.38 (m, 2H), 3.17 (m, 2H), 2.76/2.75 (s/s, 3H), 2.22/2.21 (s/s, 3H), 2.15/2.02 (m+m, 2H), 1.01/1 (t/t, 3H), 0.96 (s, 9H)

Step 5: Preparation of ethyl 3-{1-[(3R)-3-{[tert-butyl(diphenyl)silyl]oxy}-4-chlorobutyl]-4-methyl-1H-benzotriazol-5-yl}-3-{3-[(6-hydroxy-2,2-dioxo-2H-1,2λ$^6$,3-benzoxathiazin-3(4H)-yl)methyl]-4-methylphenyl}propanoate Using General Procedure 10 starting from ethyl 3-{1-[(3R)-3-{[tert-butyl(diphenyl)silyl]oxy}-4-hydroxybutyl]-4-methyl-1H-benzotriazol-5-yl}-3-{3-[(6-hydroxy-2,2-dioxo-2H-1,2λ$^6$,3-benzoxathiazin-3(4H)-yl)methyl]-4-methylphenyl}propanoate (1 eq.) as a reactant, the title compound (colorless oil, 33% yield) was obtained.

$^1$H-NMR (500 MHz, DMSO-d6) δ ppm: 9.72 (brs, 1H), 7.54-7.11 (m, 15H), 6.99 (d, 1H), 6.79 (dd, 1H), 6.6 (d, 1H), 4.85 (t, 1H), 4.63 (t, 2H), 4.4/4.36 (d+d, 2H), 4.21/4.17 (d+d, 2H), 3.93 (q, 2H), 3.93 (dd, 1H), 3.67 (d, 2H), 3.18 (m, 2H), 2.76/2.75 (s, 3H), 2.22 (s, 3H), 2.2/2.11 (m+m, 2H), 1.0/0.99 (t/t, 3H), 0.96/0.95 (s/s, 9H)

Step 6: Preparation of ethyl [(19R)-19-{[tert-butyl(diphenyl)silyl]oxy}-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate Using General Procedure 11 starting from ethyl 3-{1-[(3R)-3-{[tert-butyl(diphenyl)silyl]oxy}-4-chlorobutyl]-4-methyl-1H-benzotriazol-5-yl}-3-{3-[(6-hydroxy-2,2-dioxo-2H-1,2λ$^6$,3-benzoxathiazin-3(4H)-yl)methyl]-4-methylphenyl}propanoate (1 eq.) as a reactant, the title compound (39% yield) was obtained.

$^1$H-NMR (500 MHz, DMSO-d6) δ ppm: 7.75-7.25 (m, 12H), 7.51/7.48 (d/d, 1H), 7.31/7.29 (d/d, 1H), 6.92/6.85 (d/d, 1H), 6.55/6.52 (d/d, 1H), 6.43/6.3 (dd/dd, 1H), 5.36/5.28 (d/d, 1H), 4.92/4.64 (m+m, 2H), 4.8 (m, 1H), 4.32/4.16 (m/m, 1H), 4.29/3.72 (d+d, 2H), 4.01/3.61 (d+d, 2H), 3.94/3.92 (q/q, 2H), 3.41/3.14 (dd+m, 2H), 3.12 (m, 2H), 2.59/2.52 (s/s, 3H), 2.5/2.36 (m+m, 2H), 2.33/2.32 (s/s, 3H), 1.07 (s, 9H), 1.03 (t, 3H)

Step 7: Preparation of ethyl [(19R)-19-hydroxy-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate Ethyl[(19R)-19-{[tert-butyl(diphenyl)silyl]oxy}-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (1 eq., 30 mg, 0.03550 mmol) was dissolved in THF (2 mL) and 1 M tetrabutylammonium-fluoride in THF (1.5 eq., 0.053 mL, 0.053 mmol) was added. The reaction mixture was stirred at RT for 24 h. The mixture was diluted with DMF, and purified via preparative reversed-phase $C_{18}$ column chromatography by direct injection, resulting in 15 mg (70% yield) of the title compound as a white solid foam.

$^1$H-NMR (500 MHz, DMSO-d6) δ ppm: 7.66/7.65 (d, 1H), 7.49/7.4 (d, 1H), 7.48 (dd, 1H), 7.3/7.27 (d, 1H), 7.02/7 (d, 1H), 6.84/6.83 (dd, 1H), 6.57/6.46 (d, 1H), 6.03/5.74 (d, 1H), 5.33/5.28 (brs, 1H), 4.94-4.7 (m, 2H), 4.78 (m, 1H), 4.24-3.75 (d+d, 4H), 3.93 (q, 2H), 3.85/3.69 (m, 1H), 3.57/3.34 (m, 2H), 3.24-2.99 (dd+dd, 2H), 2.61/2.6 (s, 3H), 2.41/2.26 (m+m, 2H), 2.33/2.32 (s, 3H), 1.01 (t, 3H)

Step 8: Preparation of Example 44

Using General Procedure 12 starting from ethyl[(19R)-19-hydroxy-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (1 eq.) as reactant, the title compound (white solid, 92% yield) was obtained.

HRMS calculated for $C_{29}H_{30}N_4O_7S$: 578.1835; $[M+H]^+$ found: 579.1906 (δ=−0.3 ppm).

$^1$H-NMR (500 MHz, DMSO-d6) δ ppm: 7.6/7.58 (d/d, 1H), 7.54/7.51 (brd/brd., 1H), 7.41/7.35 (d/d, 1H), 7.24/7.21 (d/d, 1H), 7/6.99 (d/d, 1H), 6.83/6.82 (dd/dd, 1H), 6.37/6.31 (d/d, 1H), 5.94/5.7 (brd/d, 1H), 5.46/5.29 (brd/d, 1H), 4.9-4.68 (m, 2H), 4.8 (m, 1H), 4.07-3.87 (m, 2H), 3.99/3.87 (d+d, 2H), 3.86/3.72 (br/br., 1H), 3.55-3.24 (m, 2H), 2.59-2.34 (m, 2H), 2.56/2.55 (s/s, 3H), 2.4/2.3 (m+m, 2H), 2.31/2.3 (s/s, 3H)

$^{13}$C-NMR (125 MHz, DMSO-d6) δ ppm: 173.4, 155.9, 144.5, 131.3, 131.1/131, 129.1, 128.2, 119.7/119.5, 117.6/117.3, 116.9, 111.3/11.1, 107.4/107.3, 73/72.4, 65.9/65.8, 52.2/51.8, 48.8/48.6, 46.9, 43.9/43.6, 43.5/43, 32.9, 18.5/18.4, 13.5

EXAMPLE 45: [(19R)-4,19,31-Trimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid diastereoisomer 1

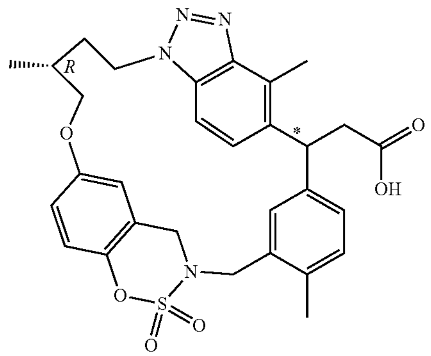

* = RorS

-continued diastereoisomer 2

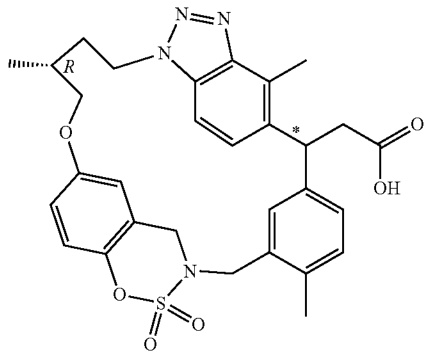

* = RorS

Step A1: Preparation of ethyl (2E)-3-(4-fluoro-2-methyl-3-nitrophenyl)prop-2-enoate The mixture of 1-bromo-4-fluoro-2-methyl-3-nitrobenzene (1 eq., 50 g, 213.66 mmol), ethyl (2E)-3-(4,4,5,5-tetramethyl-1,3,2-dioxaborolan-2-yl)prop-2-enoate (1.15 eq., 55.55 g, 245.71 mmol), sodium carbonate (2.5 eq., 56.61 g, 534.14 mmol) dissolved in THF (250 mL) and water (250 mL) was purged with $N_2$ prior to the addition of A$^{ta}$phos·$PdCl_2$ (0.02 eq., 1.9 g, 4.2731 mmol). The reaction mixture was heated at reflux for 2 h under $N_2$ atmosphere. 500 ml EtOAc and 250 ml water were added. The layers were separated, the aq. layer was extracted with 2×20 ml EtOAc, the combined organic layers were dried over $MgSO_4$, filtered and evaporated under reduced pressure. The residue was purified by filtration through 250 g silica gel in a glass filter with 4 L heptane-EtOAc (90:10). The fractions containing of the product were collected and evaporated under reduced pressure. The residue was taken up in 30 ml heptane and crystallised by sonication. The precipitated solid was filtered and dried in vacuo at 40° C. overnight to yield 48.48 g (89.6% yield) of the title compound as a white solid.

$^1$H-NMR (500 MHz, DMSO-d6) δ ppm: 8.06 (dd, 1H), 7.8 (d, 1H), 7.52 (t, 1H), 6.64 (d, 1H), 4.21 (q, 2H), 2.36 (s, 3H), 1.27 (t, 3H)

Step 1: Preparation of 6-(benzyloxy)-3-[(5-bromo-2-methylphenyl)methyl]-3,4-dihydro-2H-1,2λ$^6$,3-benzoxathiazine-2,2-dione Using General Procedure 7 starting from (5-bromo-2-methylphenyl)methanol (1 eq.) and 6-(benzyloxy)-3,4-dihydro-2H-1,2λ$^6$,3-benzoxathiazine-2,2-dione (0.83 eq.) as reactants, the title compound (65% yield) was obtained as a white solid.

$^1$H-NMR (500 MHz, DMSO-d6) δ ppm: 7.47 (d, 1H), 7.46 (dd, 1H), 7.44 (d, 2H), 7.4 (t, 2H), 7.34 (t, 1H), 7.21 (d, 1H), 7.13 (d, 1H), 7.06 (d, 1H), 7.05 (dd, 1H), 5.08 (s, 2H), 4.57 (s, 2H), 4.29 (s, 2H), 2.24 (s, 3H)

Step 2: Preparation of 6-(benzyloxy)-3-{[2-methyl-5-(4,4,5,5-tetramethyl-1,3,2-dioxaborolan-2-yl)phenyl]methyl}-3,4-dihydro-2H-1,2λ$^6$,3-benzoxathiazine-2,2-dione Using General Procedure 3 starting from 6-(benzyloxy)-3-[(5-bromo-2-methylphenyl)methyl]-3,4-dihydro-2H-1, 226,3-benzoxathiazine-2,2-dione (1 eq.) as a reactant, the title compound (56% yield) was obtained as a white solid.

$^1$H-NMR (500 MHz, DMSO-d6) δ ppm: 7.58 (d, 1H), 7.54 (s, 1H), 7.47-7.31 (m, 5H), 7.27 (d, 1H), 7.15 (d, 1H), 7.05 (dd, 1H), 7.04 (d, 1H), 5.07 (s, 2H), 4.5 (s, 2H), 4.29 (s, 2H), 2.29 (s, 3H), 1.29 (s, 12H)

Step 3: Preparation of ethyl 3-(3-{[6-(benzyloxy)-2,2-dioxo-2H-1,2λ$^6$,3-benzoxathiazin-3(4H)-yl]methyl}-4-methylphenyl)-3-(4-fluoro-2-methyl-3-nitrophenyl)propanoate Using General Procedure 6 starting from ethyl (2E)-3-(4-fluoro-2-methyl-3-nitrophenyl)prop-2-enoate (1 eq.) and 6-(benzyloxy)-3-{[2-methyl-5-(4,4,5,5-tetramethyl-1,3,2-dioxaborolan-2-yl)phenyl]methyl}-3,4-dihydro-2H-1,2λ$^6$,3-benzoxathiazine-2,2-dione (1.15 eq.) as reactants, the title compound (white solid, 51% yield) was obtained.

$^1$H-NMR (500 MHz, DMSO-d6) δ ppm: 7.69 (dd, 1H), 7.47-7.31 (m, 5H), 7.42 (m, 1H), 7.2 (d, 1H), 7.17 (d, 1H), 7.15 (dd, 1H), 7.14 (d, 1H), 7.07 (dd, 1H), 6.96 (d, 1H), 5.09 (s, 2H), 4.67 (t, 1H), 4.44 (s, 2H), 4.22 (s, 2H), 3.97 (q, 2H), 3.2/3.1 (dd+dd, 2H), 2.27 (s, 3H), 2.23 (s, 3H), 1.04 (t, 3H)

Step 4: Preparation of ethyl 3-(3-{[6-(benzyloxy)-2,2-dioxo-2H-1,2λ$^6$,3-benzoxathiazin-3(4H)-yl]methyl}-4-methylphenyl)-3-(4-{[(3R)-4-hydroxy-3-methylbutyl]amino}-2-methyl-3-nitrophenyl)propanoate To a solution of ethyl 3-(3-{[6-(benzyloxy)-2,2-dioxo-2H-1,2λ$^6$,3-benzoxathiazin-3(4H)-yl]methyl}-4-methylphenyl)-3-(4-fluoro-2-methyl-3-nitrophenyl)propanoate (1 eq., 2.57 g, 3.96 mmol) and DIPEA (3 eq., 1.54 g, 11.9 mmol, 2.07 mL) in DMSO (13 mL) (2R)-4-amino-2-methylbutan-1-ol (1.3 eq., 0.531 g, 5.15 mmol) was added. The reaction mixture was stirred at 80° C. for 18 h. The reaction mixture was poured into brine (150 ml), and the aq. layer was extracted with EtOAc (150 ml). The organic layer was dried over $MgSO_4$, filtered and evaporated. The residue was purified by normal phase silica gel chromatography using heptane-EtOAc eluents to give the title compound (1.90 g, 62% yield)

$^1$H-NMR (500 MHz, DMSO-d6) δ ppm: 7.5-7.3 (m, 5H), 7.33 (d, 1H), 7.15 (d, 1H), 7.15 (d, 1H), 7.14 (d, 1H), 7.1 (dd, 1H), 7.07 (dd, 1H), 6.98 (d, 1H), 6.7 (d, 1H), 5.68 (t, 1H), 5.1 (s, 2H), 4.53 (t, 1H), 4.46 (t, 1H), 4.44 (s, 2H), 4.23/4.2 (d+d, 2H), 3.96 (q, 2H), 3.22/3.19 (m+m, 2H), 3.11/3.07 (m+m, 2H), 3.05/3.002 (dd+dd, 2H), 2.22 (s, 3H), 2.13 (s, 3H), 1.58/1.24 (m+m, 2H), 1.52 (m, 1H), 1.04 (t, 3H), 0.83 (d, 3H)

Step 5: Preparation of ethyl 3-(3-amino-4-{[(3R)-4-hydroxy-3-methylbutyl]amino}-2-methylphenyl)-3-(3-{[6-(benzyloxy)-2,2-dioxo-2H-1,2λ$^6$,3-benzoxathiazin-3(4H)-yl]methyl}-4-methylphenyl)propanoate To a solution of ethyl 3-(3-{[6-(benzyloxy)-2,2-dioxo-2H-1,2λ$^6$,3-benzoxathiazin-3(4H)-yl]methyl}-4-methylphenyl)-3-(4-{[(3R)-4-hydroxy-3-methylbutyl]amino}-2-methyl-3-nitrophenyl)propanoate (1 eq., 1.58 g, 2.16 mmol) in 1,2-dichloroethane (15 mL) and IPA (15 mL) Raney nickel catalyst (1.5 g) was added. To the suspension hydrazine hydrate (5 eq., 5.40 g, 10.8 mmol, 5.24 mL) was added dropwise over 3 min. The reaction mixture was stirred at RT for 90 min. The reaction mixture was filtered through a pad of Celite, and the Celite was washed with DCM (3×20 ml). The filtrate was evaporated to give the title compound (1.4 g, 92% yield).

$^1$H-NMR (500 MHz, DMSO-d6) δ ppm: 7.49-7.31 (m, 5H), 7.14 (d, 1H), 7.1 (d, 1H), 7.07 (dd, 1H), 7.06 (d, 1H), 7.02 (dd, 1H), 6.98 (d, 1H), 6.48 (d, 1H), 6.31 (d, 1H), 5.11 (s, 2H), 4.52 (t, 1H), 4.44 (t, 1H), 4.41 (s, 2H), 4.21/4.14 (d+d, 2H), 3.95 (m, 2H), 3.27/3.22 (m+m, 2H), 3/2.94 (m+m, 2H), 2.9 (m, 2H), 2.21 (s, 3H), 1.96 (s, 3H), 1.66/1.32 (m+m, 2H), 1.64 (m, 1H), 1.05 (t, 3H), 0.86 (d, 3H)

Step 6: Preparation of ethyl 3-(3-{[6-(benzyloxy)-2,2-dioxo-2H-1,2λ$^6$,3-benzoxathiazin-3(4H)-yl]methyl}-4-methylphenyl)-3-{1-[(3R)-4-hydroxy-3-methylbutyl]-4-methyl-3a,7a-dihydro-1H-benzotriazol-5-yl}propanoate To a solution of ethyl 3-(3-amino-4-{[(3R)-4-hydroxy-3-methylbutyl]amino}-2-methylphenyl)-3-(3-{[6-(benzyloxy)-2,2-dioxo-2H-1,2λ$^6$,3-benzoxathiazin-3(4H)-yl]methyl}-4-methylphenyl)propanoate (1 eq., 1.10 g, 1.6 mmol) in DCM (25 mL) 3-methylbutyl nitrite (3 eq., 550 mg, 4.7 mmol, 0.63 mL) was added in one portion. The reaction mixture was stirred at RT for 1 day. The reaction mixture was diluted with DCM (100 ml) and washed with brine (100 ml). The organic layer was dried over $MgSO_4$, filtered and evaporated. The residue was purified by normal phase silica gel chromatography using heptane-EtOAc eluents to give the title compound (560 mg, 50% yield).

$^1$H-NMR (500 MHz, DMSO-d6) δ ppm: 7.51 (d, 1H), 7.49 (d, 1H), 7.48-7.32 (m, 5H), 7.24 (m, 1H), 7.19 (dd, 1H), 7.14 (d, 1H), 7.14 (d, 1H), 7.07 (dd, 1H), 6.97 (d, 1H), 5.1 (s, 2H), 4.84 (t, 1H), 4.65 (m, 2H), 4.48 (t, 1H), 4.44 (s, 2H), 4.22 (s, 2H), 3.92 (q, 2H), 3.22 (m, 2H), 3.18 (m, 2H), 2.76 (s, 3H), 2.21 (s, 3H), 1.98/1.59 (m+m, 2H), 1.39 (m, 1H), 0.98 (t, 3H), 0.86 (d, 3H)

Step 7: Preparation of ethyl 3-{3-[(6-hydroxy-2,2-dioxo-2H-1,2λ$^6$,3-benzoxathiazin-3(4H)-yl)methyl]-4-methylphenyl}-3-{1-[(3R)-4-hydroxy-3-methylbutyl]-4-methyl-3a,7a-dihydro-1H-benzotriazol-5-yl}propanoate Using General Procedure 8 starting from ethyl 3-(3-{[6-(benzyloxy)-2,2-dioxo-2H-1,2λ$^6$,3-benzoxathiazin-3(4H)-yl]methyl}-4-methylphenyl)-3-{1-[(3R)-4-hydroxy-3-methylbutyl]-4-methyl-3a,7a-dihydro-1H-benzotriazol-5-yl}propanoate (1 eq., 560 mg, 0.7856 mmol) as a reactant, the title compound (460 mg, 94% yield) was obtained.

$^1$H-NMR (500 MHz, DMSO-d6) δ ppm: 9.7 (s, 1H), 7.61 (d, 1H), 7.51 (d, 1H), 7.22 (d, 1H), 7.2 (dd, 1H), 7.13 (d, 1H), 6.99 (d, 1H), 6.79 (dd, 1H), 6.61 (d, 1H), 4.84 (t, 1H), 4.68 (t, 2H), 4.5 (brs, 1H), 4.38 (s, 2H), 4.21/4.17 (d+d, 2H), 3.93 (q, 2H), 3.24 (m, 2H), 3.19/3.15 (dd+dd, 2H), 2.75 (s, 3H), 2.22 (s, 3H), 2/1.61 (m+m, 2H), 1.42 (m, 1H), 1 (t, 3H), 0.88 (d, 3H)

Step 8: Preparation of ethyl 3-{1-[(3R)-4-chloro-3-methylbutyl]-4-methyl-3a,7a-dihydro-1H-benzotriazol-5-yl}-3-{3-[(6-hydroxy-2,2-dioxo-2H-1,2)$^6$,3-benzoxathiazin-3(4H)-yl)methyl]-4-methylphenyl}propanoate Using General Procedure 10 starting from ethyl 3-{3-[(6-hydroxy-2,2-dioxo-2H-1,2λ$^6$,3-benzoxathiazin-3(4H)-yl)methyl]-4-methylphenyl}-3-{11-[(3R)-4-hydroxy-3-methylbutyl]-4-methyl-3a,7a-dihydro-1H-benzotriazol-5- yl}propanoate (1 eq., 460 mg, 0.7387 mmol) as a reactant, the title compound (470 mg, 99% yield) was obtained.

$^{1}$H-NMR (500 MHz, DMSO-d6) δ ppm: 9.71 (s, 1H), 7.63 (d, 1H), 7.52 (d, 1H), 7.22 (d, 1H), 7.2 (dd, 1H), 7.13 (d, 1H), 6.99 (d, 1H), 6.79 (dd, 1H), 6.6 (d, 1H), 4.84 (t, 1H), 4.71 (t, 2H), 4.38 (s, 2H), 4.21/4.17 (d+d, 2H), 3.93 (q, 2H), 3.63/3.6 (dd+dd, 2H), 3.17 (d, 2H), 2.76 (s, 3H), 2.22 (s, 3H), 2.04/1.77 (m+m, 2H), 1.74 (m, 1H), 1.01 (d, 3H), 0.99 (t, 3H)

Step 9: Preparation of ethyl[(19R)-4,19,31-trimethyl-27,27-dioxo-21,26-dioxa-27$\lambda^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate Using General Procedure 11 starting from ethyl 3-{1-[(3R)-4-chloro-3-methylbutyl]-4-methyl-3a,7a-dihydro-1H-benzotriazol-5-yl}-3-{3-[(6-hydroxy-2,2-dioxo-2H-1,2$\lambda^6$,3-benzoxathiazin-3(4H)-yl)methyl]-4-methylphenyl}propanoate (1 eq., 470 mg, 0.7330 mmol) as a reactant, the title compound (110 mg, 25% yield) was obtained.

$^{1}$H-NMR (500 MHz, DMSO-d6, mixture of diastereomers) 6 ppm: 7.68/7.65 (d/d, 1H), 7.5/7.35 (d/d, 1H), 7.48 (dd, 1H), 7.3/7.28 (d/d, 1H), 7/6.98 (d/d, 1H), 6.81 (dd, 1H), 6.56/6.53 (d/d, 1H), 5.83/5.77 (d/d, 1H), 4.83/4.79/4.75 (m+m/m, 2H), 4.8/4.79 (t/t, 1H), 4.18/4.09/4/3.87 (d/d+d/d, 2H), 4.03/3.94/3.89/3.75 (d/d+d/d, 2H), 3.92 (m, 2H), 3.67/3.42/3.36 (m/dd+dd, 2H), 3.22/3.14/3.06/3.02 (dd+dd/dd+dd, 2H), 2.64/2.59 (s/s, 3H), 2.33/2.11/2.02/1.95 (m+m/m+m, 2H), 2.32 (s, 3H), 2.11/1.6 (m/m, 1H), 1.1/1.04 (d/d, 3H), 1.01/1 (t/t, 3H)

Step 10: Preparation of Example 45

Using General Procedure 12 starting from ethyl[(19R)-4,19,31-trimethyl-27,27-dioxo-21,26-dioxa-27$\lambda^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (1 eq., 110 mg, 0.1819 mmol) as a reactant, the title compound (90 mg, 86% yield) was obtained.

The diastereoisomers were obtained by chromatographic separation on chiral column.

EXAMPLE 45a (19R, dia1)

$^{1}$H-NMR (500 MHz, DMSO-d6) δ ppm: 12.22 (br., 1H), 7.64 (d, 1H), 7.49 (d, 1H), 7.49 (d, 1H), 7.28 (d, 1H), 7 (d, 1H), 6.81 (dd, 1H), 6.54 (d, 1H), 5.75 (d, 1H), 4.82/4.74 (dm+m, 2H), 4.75 (t, 1H), 4.17/3.87 (d+d, 2H), 4.04/3.75 (d+d, 2H), 3.35 (m, 2H), 3.03/2.95 (dd+dd, 2H), 2.58 (s, 3H), 2.32 (s, 3H), 2.12/2.03 (m+m, 2H), 2.12 (m, 1H), 1.1 (d, 3H)

$^{13}$C-NMR (125 MHz, DMSO-d6) δ ppm: 173.2, 131.2, 131.2, 128.8, 127.4, 119.5, 117.4, 111.1, 107.7, 72.4, 51.8, 48.7, 46.2, 42, 41, 33.8, 32.3, 18.4, 17.1, 13.4

EXAMPLE 45b (19R, dia2)

HRMS calculated for $C_{30}H_{32}N_4O_6S$: 576.2042; $[M+H]^+$ found: 577.212 (δ=0.8 ppm).

$^{1}$H-NMR (500 MHz, DMSO-d6) δ ppm: 12.2 (br., 1H), 7.68 (d, 1H), 7.49 (dd, 1H), 7.34 (d, 1H), 7.3 (d, 1H), 6.99 (d, 1H), 6.81 (dd, 1H), 6.51 (d, 1H), 5.83 (d, 1H), 4.79 (m, 2H), 4.78 (m, 1H), 4.1/4 (d+d, 2H), 3.95/3.89 (d+d, 2H), 3.67/3.41 (dd+dd, 2H), 3.11/2.91 (dd+dd, 2H), 2.63 (s, 3H), 2.34/1.96 (m+m, 2H), 2.32 (s, 3H), 1.61 (m, 1H), 1.04 (d, 3H)

$^{13}$C-NMR (125 MHz, DMSO-d6) δ ppm: 173.3, 131.6, 131.3, 128.1, 127.4, 119.5, 116.8, 112, 108.2, 72.8, 51.8, 48.6, 45.9, 41.3, 40.7, 31.5, 29.9, 18.4, 16.6, 13.4

EXAMPLE 46: [(2R,8RS,19S)-19-Hydroxy-2,4,31-trimethyl-27,27-dioxo-21,26-dioxa-27$\lambda^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid and [(2R,8RS,19S)-19-hydroxy-2,4,31-trimethyl-27,27-dioxo-21,26-dioxa-27$\lambda^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid

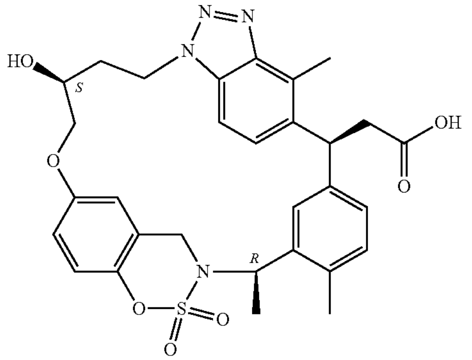

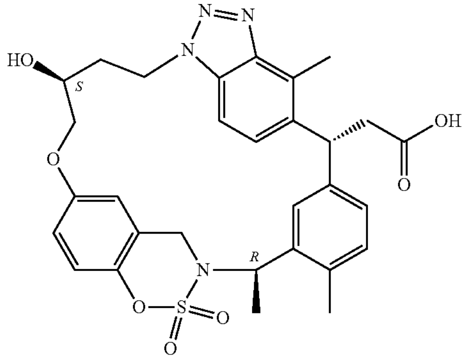

Step A1: Preparation of (2S)-4-(4-bromo-3-methyl-2-nitroanilino)butane-1,2-diol

A mixture of 1-bromo-4-fluoro-2-methyl-3-nitrobenzene (1 eq., 6 g, 26 mmol), (2S)-4-aminobutane-1,2-diol hydrochloride (1.5 eq., 6.9 mL, 5.40 g, 38 mmol) and DIPEA (2 eq., 9 mL, 6.68 g, 51.67 mmol) was stirred in N,N-dimethylacetamide (120 mL) at 100° C. over the weekend. The reaction mixture was poured on crushed ice, extracted with EtOAc, and the aq. layer was washed with EtOAc. The combined organic layers were washed with brine, dried over $Na_2SO_4$, concentrated under reduced pressure. The residue was purified by normal phase silica gel chromatography using DCM-MeOH eluents to give the title compound (7.47 g, 91% yield).

$^{1}$H-NMR (500 MHz, DMSO-d6) δ ppm: 7.54 (d, 1H), 6.74 (d, 1H), 6.29 (t, 1H), 4.72 (d, 1H), 4.55 (t, 1H), 3.5 (m, 1H), 3.23/3.131 (dd+m, 2H), 3.22 (q, 2H), 2.25 (s, 3H), 1.75/1.45 (m+m, 2H)

Step A2: Preparation of (2S)-4-(4-bromo-3-methyl-2-nitroanilino)-1-{[tert-butyl(dimethyl)silyl]oxy}butan-2-ol (2S)-4-(4-Bromo-3-methyl-2-nitroanilino)butane-1,2-diol (1 eq., 7.29 g, 22.8 mmol) was dissolved in dry DMF (44 mL) and DIPEA (2.51 eq., 10 mL, 7.42 g, 57.41 mmol, 2.51 equiv) was added. The reaction mixture was cooled to 0° C. prior to the dropwise addition of tert-butyl(chloro)dimethylsilane (1.06 eq., 4.2 mL, 3.65 g, 24.2 mmol), dissolved in dry DMF (13 mL). The temperature was allowed to raise to RT, and the mixture was stirred at this temperature overnight. The reaction mixture was poured on sat. $NH_4Cl$ solution, extracted with EtOAc, and the aq. layer was washed with EtOAc. The combined organic layers were washed with brine, dried over $Na_2SO_4$, concentrated. The residue was purified by normal phase silica gel chromatography using heptane-EtOAc eluents to give the title compound (8.30 g, 84% yield).

$^1$H-NMR (500 MHz, DMSO-d6) δ ppm: 7.53 (d, 1H), 6.73 (d, 1H), 6.27 (t, 1H), 4.78 (d, 1H), 3.52 (m, 1H), 3.51/3.36 (m+m, 2H), 3.23 (q, 2H), 2.25 (s, 3H), 1.78/1.44 (m+m, 2H), 0.84 (s, 9H), 0.02 (s, 6H)

Step A3: Preparation of 4-bromo-N-[(3S)-4-{[tert-butyl(dimethyl)silyl]oxy}-3-{[tert-butyl(diphenyl)silyl]oxy}butyl]-3-methyl-2-nitroaniline (2S)-4-(4-Bromo-3-methyl-2-nitroanilino)-1-{[tert-butyl(dimethyl)silyl]oxy}butan-2-ol (1 eq., 8.24 g, 19.0 mmol) was dissolved in dry DMF (95 mL) and imidazole (3 eq., 3.87 g, 56.8 mmol) was added followed by the addition of N,N-dimethylpyridin-4-amine (0.1 eq., 0.238 g, 1.95 mmol). The reaction mixture was cooled to 0° C. prior to the dropwise addition of tert-butyl-chloro-diphenyl-silane (2 eq., 10.5 g, 38.2 mmol). The temperature was allowed to raise to RT and the mixture was stirred at this temperature overnight. The reaction mixture was poured on cooled sat. $NH_4Cl$ solution, extracted with DCM. The combined organic layers were washed with brine, dried over $Na_2SO_4$, concentrated under reduced pressure. The residue was purified by normal phase silica gel chromatography using heptane-EtOAc as eluents to give the title compound (13.37 g, quant.).

$^1$H-NMR (500 MHz, DMSO-d6) δ ppm: 7.65-7.35 (m, 10H), 7.44 (d, 1H), 6.52 (d, 1H), 6.06 (t, 1H), 3.82 (m, 1H), 3.46/3.44 (dd+dd, 2H), 3.17/3.13 (m+m, 2H), 2.24 (s, 3H), 1.8/1.7 (m+m, 2H), 0.99 (s, 3H), 0.76 (s, 3H), −0.12/−0.16 (s, 6H)

Step A4: Preparation of 4-bromo-N$^1$-[(3S)-4-{[tert-butyl(dimethyl)silyl]oxy}-3-{[tert-butyl(diphenyl)silyl]oxy}butyl]-3-methylbenzene-1,2-diamine 4-Bromo-N-[(3S)-4-{[tert-butyl(dimethyl)silyl]oxy}-3-1{[tert-butyl(diphenyl)silyl]oxy}butyl]-3-methyl-2-nitroaniline (1 eq., 13.0 g, 19.35 mmol) was dissolved in dioxane (10 mL) and MeOH (50 mL). Raney nickel catalyst (0.5 eq., 0.8 g, 9.00 mmol)—washed with dioxane—was added to the mixture, which was hydrogenated in a stainless steel autoclave under 10 bar pressure at RT for 3 h. After completion of the reaction the mixture was filtered through a Celite pad, the Celite was washed with DCM, the mother liquor was concentrated. The residue was purified by normal phase silica gel chromatography using heptane-EtOAc eluents to give the title compound (10.90 g, 88% yield).

$^1$H-NMR (500 MHz, DMSO-d6) δ ppm: 7.69-7.37 (m, 10H), 6.65 (d, 1H), 6.1 (d, 1H), 4.55 (s, 2H), 4.52 (t, 1H), 3.87 (m, 1H), 3.48/3.46 (dd+dd, 2H), 3.04/2.97 (m+m, 2H), 2.15 (s, 3H), 1.87/1.79 (m+m, 2H), 1 (s, 9H), 0.77 (s, 3H), −0.11 (s, 3H), −0.14 (s, 3H)

Step A5: Preparation of 5-bromo-1-[(3S)-4-{[tert-butyl(dimethyl)silyl]oxy}-3-{[tert-butyl(diphenyl)silyl]oxy}butyl]-4-methyl-1H-benzotriazole 4-Bromo-N$^1$-[(3S)-4-{[tert-butyl(dimethyl)silyl]oxy}-3-1{[tert-butyl(diphenyl)silyl]oxy}butyl]-3-methylbenzene-1,2-diamine (1 eq., 8.50 g, 13 mmol) was dissolved in abs. THF (40 mL) and the mixture was cooled to 0° C. 2,2,2-trichloroacetic acid (0.01 eq., 17.4 mg, 0.106 mmol) was added to the mixture followed by the dropwise addition of 3-methylbutyl nitrite (1.8 eq., 3.13 mL, 2.73 g, 13 mmol). The reaction mixture was stirred for 3 h, while the temperature was allowed to warm to RT. The mixture was diluted with THF and evaporated to celite. The crude product was purified by normal phase silica gel chromatography using heptane-EtOAc eluents to give the title compound (4.67 g, 54% yield).

$^1$H-NMR (500 MHz, DMSO-d6) δ ppm: 7.64 (d, 1H), 7.6-7.31 (m, 10H), 7.43 (d, 1H), 3.75 (m, 1H), 3.74 (t, 2H), 3.47/3.43 (dd+dd, 2H), 2.7 (s, 3H), 2.19/2.04 (m+m, 2H), 0.98 (s, 9H), 0.7 (s, 9H), −0.17/−0.23 (s+s, 6H)

Step A6: Preparation of ethyl (2E)-3-{1-[(3S)-4-{[tert-butyl(dimethyl)silyl]oxy}-3-{[tert-butyl(diphenyl)silyl]oxy}butyl]-4-methyl-1H-benzotriazol-5-yl}prop-2-enoate 5-Bromo-1-[(3S)-4-{[tert-butyl(dimethyl)silyl]oxy}-3-{[tert-butyl(diphenyl)silyl]oxy}butyl]-4-methyl-1H-benzotriazole (1 eq., 5.09 g, 7.80 mmol) was dissolved in abs. DMF (10 mL). Ethyl prop-2-enoate (2 eq., 1.70 mL 1.56 g, 15.6 mmol) and DIPEA (3 eq., 4.07 mL, 3.02 g, 23.4 mmol) were added, and the reaction mixture was flushed with $N_2$. Acetoxy-[[2-(bis-o-tolylphosphanyl)phenyl]methyl]palladium (0.1 eq., 731 mg, 0.780 mmol) catalyst was added and the mixture was heated at 150° C. in a microwave reactor for 7 h. The mixture was filtered through a pad of Celite and the filtrate was purified by reversed-phase chromatography to give the title compound (2.58 g, 49% yield).

$^1$H-NMR (500 MHz, DMSO-d6) δ ppm: 8.02 (d, 1H), 7.93 (d, 1H), 7.62-7.31 (m, 10H), 7.46 (d, 1H), 6.66 (d, 1H), 4.74 (t, 2H), 4.22 (q, 2H), 3.78 (m, 1H), 3.49/3.45 (dd+dd, 2H), 2.8 (s, 3H), 2.19/2.05 (m+m, 2H), 1.28 (t, 3H), 0.99 (s, 9H), 0.71 (s, 9H), −0.16/−0.21 (s+s, 6H)

Step 1: Preparation of 6-(benzyloxy)-3-[(1R)-1-(5-bromo-2-methylphenyl)ethyl]-3,4-dihydro-2H-1,2λ$^6$,3-benzoxathiazine-2,2-dione Using General Procedure 7 starting from (1R)-1-(5-bromo-2-methylphenyl)ethan-1-ol (1.4 eq., 30.08 g, 139.8 mmol) and 6-(benzyloxy)-3,4-dihydro-2H-1,2λ$^6$,3-benzoxathiazine-2,2-dione (1 eq., 29.10 g, 99.9 mmol) as reactants, the title compound (41.6 g, 85% yield) was obtained as a white solid.

$^1$H-NMR (500 MHz, DMSO-d6) δ ppm: 7.6 (d, 1H), 7.47-7.31 (m, 5H), 7.44 (dd, 1H), 7.2 (d, 1H), 7.03 (d, 1H), 7.03 (d, 1H), 6.97 (dd, 1H), 5.27 (q, 1H), 5.09/5.06 (d+d, 2H), 4.5 (s, 2H), 2.33 (s, 3H), 1.42 (d, 3H)

Step 2: Preparation of 6-(benzyloxy)-3-{(1R)-1-[2-methyl-5-(4,4,5,5-tetramethyl-1,3,2-dioxaborolan-2-yl)phenyl]ethyl}-3,4-dihydro-2H-1,2)[6],3-benzoxathiazine-2,2-dione Using General Procedure 3 starting from 6-(benzyloxy)-3-[(1R)-1-(5-bromo-2-methylphenyl)ethyl]-3,4-dihydro-2H-1,2λ[6],3-benzoxathiazine-2,2-dione (1 eq., 60 g, 122.9 mmol) as a reactant, the title compound (60.7 g, 92% yield) was obtained.

$^1$H-NMR (500 MHz, DMSO-d6) δ ppm: 7.62 (d, 1H), 7.58 (dd, 1H), 7.43 (d, 2H), 7.39 (t, 2H), 7.33 (t, 1H), 7.27 (d, 1H), 7.04 (d, 1H), 7.02 (d, 1H), 6.98 (dd, 1H), 5.3 (q, 1H), 5.07/5.03 (d+d, 2H), 4.4 (s, 2H), 2.39 (s, 3H), 1.44 (d, 3H), 1.3 (s, 6H), 1.29 (s, 6H)

Step 3: Preparation of ethyl 3-(3-{(1R)-1-[6-(benzyloxy)-2,2-dioxo-2H-1,2λ[6],3-benzoxathiazin-3(4H)-yl]ethyl}-4-methylphenyl)-3-{1-[(3S)-4-{[tert-butyl(dimethyl)silyl]oxy}-3-{[tert-butyl(diphenyl)silyl]oxy}butyl]-4-methyl-1H-benzotriazol-5-yl}propanoate Using General Procedure 6 starting from ethyl (2E)-3-{1-[(3S)-4-{[tert-butyl(dimethyl)silyl]oxy}-3-{[tert-butyl(diphenyl)silyl]oxy}butyl]-4-methyl-1H-benzotriazol-5-yl}prop-2-enoate (1 eq., 2.87 g, 4.28 mmol) and 6-(benzyloxy)-3-{(1R)-1-[2-methyl-5-(4,4,5,5-tetramethyl-1,3,2-dioxaborolan-2-yl)phenyl]ethyl}-3,4-dihydro-2H-1,2λ[6],3-benzoxathiazine-2,2-dione (1.2 eq., 2.75 g, 5.13 mmol) as reactants, the title compound (3.34 g, 72% yield) was obtained.

$^1$H-NMR (500 MHz, DMSO-d6, mixture of diastereomers) 6 ppm: 7.61-7.06 (m, 20H), 7.06/7.05 (d/d, 1H), 7.01/6.99 (dd/dd, 1H), 6.9/6.85 (d/d, 1H), 5.27 (m, 1H), 5.09/5.06 (d+d, 2H), 4.88/4.87 (t/t, 1H), 4.66 (m, 2H), 4.53-4.31 (m, 2H), 3.92/3.91 (q/q, 2H), 3.73 (m, 1H), 3.46-3.36 (m, 2H), 3.23 (m, 2H), 2.77 (s, 3H), 2.28/2.27 (s/s, 3H), 2.15/2 (m+m, 2H), 1.42 (d, 3H), 0.99/0.98 (t/t, 3H), 0.96/0.94 (s/s, 9H), 0.68/0.66 (s/s, 9H), −0.2/−0.21/−0.25/−0.29 (s/s/s/s, 6H)

Step 4: Preparation of ethyl 3-{1-[(3S)-3-{[tert-butyl(diphenyl)silyl]oxy}-4-hydroxybutyl]-4-methyl-1H-benzotriazol-5-yl}-3-{3-[(1R)-1-(6-hydroxy-2,2-dioxo-2H-1,2λ[6],3-benzoxathiazin-3(4H)-yl)ethyl]-4-methylphenyl}propanoate Using General Procedure 8 starting from ethyl 3-(3-{(1R)-1-[6-(benzyloxy)-2,2-dioxo-2H-1,2λ[6],3-benzoxathiazin-3(4H)-yl]ethyl}-4-methylphenyl)-3-{1-[(3S)-4-{[tert-butyl(dimethyl) silyl]oxy}-3-{[tert-butyl(diphenyl)silyl]oxy}butyl]-4-methyl-1H-benzotriazol-5-yl}propanoate (1 eq., 3.56 g, 3.29 mmol) as a reactant, the crude ethyl 3-{1-[(3S)-4-{[tert-butyl(dimethyl)silyl]oxy}-3-{[tert-butyl(diphenyl)silyl]oxy}butyl]-4-methyl-1H-benzotriazol-5-yl}-3-{3-[(1R)-1-(6-hydroxy-2,2-dioxo-2H-1,2λ[6],3-benzoxathiazin-3(4H)-yl)ethyl]-4-methylphenyl}propanoate (3.23 g) was obtained. The crude product (1 eq.) was dissolved in EtOH (200 mL) and hydrogen chloride (1M, aq.) (2 eq., 7.18 mL, 7.18 mmol) was added. The mixture was stirred at RT for 24 h, then the mixture was neuralised with TEA (20 mmol, 2.8 mL) and the solvent was evaporated. The crude product was purified by reversed-phase chromatography using aq. 5 mM $NH_4HCO_3$ solution-MeCN as eluents to give the title compound (1.97 g, 62% yield).

$^1$H-NMR (500 MHz, DMSO-d6, mixture of diastereomers) 6 ppm: 9.66/9.64 (s/s, 1H), 7.61-7.02 (m, 15H), 6.92 (d, 1H), 6.73 (dd, 1H), 6.61/6.57 (d/d, 1H), 5.26 (q, 1H), 4.89/4.87 (t/t, 1H), 4.75/4.66 (t/t, 2H), 4.44-4.25 (m, 2H), 3.94 (q, 2H), 3.73 (m, 1H), 3.38 (m, 2H), 3.23 (m, 2H), 2.8/2.77 (s/s, 3H), 2.28/2.27 (s/s, 3H), 2.26/2.15/2.02/1.84 (m/m+m/m, 2H), 1.43/1.41 (d/d, 3H), 1.01 (t, 3H), 0.96/0.95/0.87/0.82 (s/s+s/s, 9H)

Step 5: Preparation of ethyl[(2R,19S)-19-hydroxy-2,4,31-trimethyl-27,27-dioxo-21,26-dioxa-27λ[6]-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate Using General Procedure 10 starting from ethyl 3-{1-[(3S)-3-{[tert-butyl(diphenyl)silyl]oxy}-4-hydroxybutyl]-4-methyl-1H-benzotriazol-5-yl}-3-{3-[(1R)-1-(6-hydroxy-2,2-dioxo-2H-1,2λ[6],3-benzoxathiazin-3(4H)-yl)ethyl]-4-methylphenyl}propanoate (1 eq., 1.97 g, 2.24 mmol) as a reactant, the crude ethyl 3-{1-[(3S)-3-{[tert-butyl(diphenyl)silyl]oxy}-4-chlorobutyl]-4-methyl-1H-benzotriazol-5-yl}-3-{3-[(1R)-1-(6-hydroxy-2,2-dioxo-2H-1,2λ[6],3-benzoxathiazin-3(4H)-yl)ethyl]-4-methylphenyl}propanoate (2.01 g) was obtained. This was reacted without further purification using General Procedure 11 to give the title compound (77 mg, 4% yield).

$^1$H-NMR (500 MHz, DMSO-d6, mixture of diastereomers) 6 ppm: 7.89/7.44 (d/d, 1H), 7.7/7.69 (d/d, 1H), 7.44-6.68 (m, 3H), 7/6.94 (d/d, 1H), 6.84/6.76 (dd/dd, 1H), 5.97/5.93 (d/brd, 1H), 5.39/5.14 (d/d, 1H), 5.25/5.23 (q/q, 1H), 4.94/4.74 (t/t, 2H), 4.92/4.81 (t/t, 1H), 4.04/4.02/3.41/3.31 (d+d/d+d, 2H), 3.98/3.25 (m/m, 1H), 3.95/3.94 (q/q, 2H), 3.81/3.6/3.57/3.53 (d+d/d+d, 2H), 3.41/3.33/3.12/3.01 (dd+dd/dd+dd, 2H), 2.81/2.69 (s/s, 3H), 2.43/1.99/1.98 (m+m/m, 2H), 2.32/2.29 (s/s, 3H), 1.28/1.08 (d/d, 3H), 1.03/1.02 (t/t, 3H)

Step 6: Preparation of Example 46

Using General Procedure 12 starting from ethyl[(2R,19S)-19-hydroxy-2,4,31-trimethyl-27,27-dioxo-21,26-dioxa-27λ[6]-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (1 eq., 69 mg, 0.1112 mmol) as a reactant, the title compound (38 mg, 58% yield) was obtained.

The enantiopure products were obtained by chromatographic separation on chiral column.

EXAMPLE 46a (2R,8S,19S)

HRMS calculated for $C_{30}H_{32}N_4O_7S$: 592.1992; $[M+H]^+$ found: 593.2056 (δ=−1.4 ppm).

$^1$H-NMR (500 MHz, DMSO-d6) δ ppm: 7.86 (d, 1H), 7.67 (d, 1H), 7.43 (dd, 1H), 7.18 (d, 1H), 7.13 (brs., 1H), 7 (d, 1H), 6.84 (dd, 1H), 5.91 (d, 1H), 5.4 (br., 1H), 5.23 (q, 1H), 4.8 (m, 2H), 4.78 (t, 1H), 4.03/3.3 (d+d, 2H), 3.98 (m, 1H), 3.6/3.52 (dd+dd, 2H), 3.15/2.93 (dd+dd, 2H), 2.65 (s, 3H), 2.28 (s, 3H), 2 (m, 2H), 1.25 (d, 3H)

$^{13}$C-NMR (125 MHz, DMSO-d6) δ ppm: 131.2, 129.5, 126.2, 125.7, 119.7, 118.5, 109.2, 107.6, 72.8, 66, 55.5, 45, 44, 42.7, 42.2, 35.3, 18.5, 14.4, 13.4

EXAMPLE 46b (2R,8R,19S)

HRMS calculated for $C_{30}H_{32}N_4O_7S$: 592.1992; $[M+H]^+$ found: 593.2051 (δ=−2.3 ppm).

$^{1}$H-NMR (500 MHz, DMSO-d6) δ ppm: 7.67 (d, 1H), 7.46 (d, 1H), 7.28 (d, 1H), 7.06 (d, 1H), 6.94 (d, 1H), 6.76 (dd, 1H), 6.68 (brs., 1H), 5.95 (brs., 1H), 5.22 (q, 1H), 5.15 (br., 1H), 4.94/4.72 (dd+dd, 2H), 4.91 (br., 1H), 4.05/3.42 (d+d, 2H), 3.82/3.6 (d+d, 2H), 3.26 (br., 1H), 3.26/2.81 (br+br., 2H), 2.8 (brs., 3H), 2.43/2 (br+br., 2H), 2.31 (s, 3H), 1.07 (d, 3H)

$^{13}$C-NMR (125 MHz, DMSO-d6) δ ppm: 131.4, 128.4, 128.1, 125.8, 119.9, 118, 109.2, 108.7, 73.1, 64.2, 55.3, 44.9, 44.4, 40.6, 39.7, 31.1, 18.5, 14.2, 13.3

EXAMPLE 47: [4-Methoxy-21,34-dimethyl-30,30-dioxo-24,29-dioxa-30)$^{6}$-thia-1,14,15,16,21-pentaaza-hexacyclo[23.5.3.1$^{3,7}$0.1$^{9,13}$0.0$^{12,16}$0.0$^{28,32}$]penta-triaconta-3(35),4,6,9(34),10,12,14,25,27,32-decaen-8-yl]acetic acid

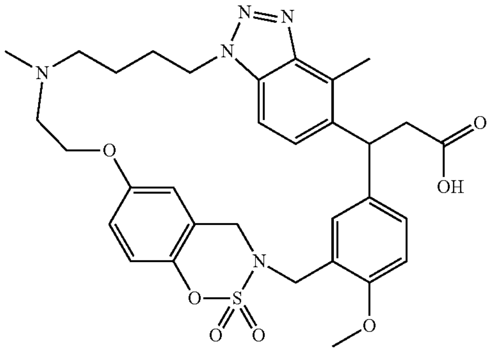 [SMILES: COc1ccc2cc1CN1Cc3cc(ccc3OS1(=O)=O)OCCN(C)CCCCn1nnc3c(C)c(ccc31)C2CC(=O)O]

Step 1: Preparation of ethyl 3-[1-(4-chlorobutyl)-4-methyl-1H-benzotriazol-5-yl]-3-{3-[(6-hydroxy-2,2-dioxo-2H-1,2λ$^{6}$,3-benzoxathiazin-3(4H)-yl)methyl]-4-methoxyphenyl}propanoate hydrochloride Using General Procedure 10 starting from ethyl 3-[1-(4-hydroxybutyl)-4-methyl-1H-benzotriazol-5-yl]-3-{3-[(6-hydroxy-2,2-dioxo-2H-1,2λ$^{6}$,3-benzoxathiazin-3(4H)-yl)methyl]-4-methoxyphenyl}propanoate (1 eq.) as a reactant, the title compound (yellow solid foam, quant.) was obtained.

$^{1}$H-NMR (500 MHz, DMSO-d6) δ ppm: 7.65 (d, 1H), 7.51 (d, 1H), 7.26 (d, 1H), 7.23 (dd, 1H), 6.89 (d, 1H), 6.83 (d, 1H), 6.72 (dd, 1H), 6.6 (d, 1H), 4.82 (t, 1H), 4.7 (t, 2H), 4.47 (s, 2H), 4.19 (s, 2H), 3.93 (q, 2H), 3.69 (s, 3H), 3.64 (t, 2H), 3.14 (d, 2H), 2.75 (s, 3H), 1.99 (m, 2H), 1.68 (m, 2H), 1 (t, 3H)

Step 2: Preparation of ethyl 3-(1-{4-[benzyl(methyl)amino]butyl}-4-methyl-1H-benzotriazol-5-yl)-3-{3-[(6-hydroxy-2,2-dioxo-2H-1,2λ$^{6}$,3-benzoxathiazin-3(4H)-yl)methyl]-4-methoxyphenyl}propanoate To a stirred solution of ethyl 3-[1-(4-chlorobutyl)-4-methyl-1H-benzotriazol-5-yl]-3-{3-[(6-hydroxy-2,2-dioxo-2H-1,2λ$^{6}$,3-benzoxathiazin-3(4H)-yl)methyl]-4-methoxyphenyl}propanoate hydrochloride (1 eq., 1.2 g, 1.9 mmol) in MeCN (10 mL)N-methyl-1-phenylmethanamine (3 eq., 0.68 g, 5.6 mmol) was added at RT and the mixture was heated at 80° C. overnight. The crude product was purified by reversed-phase chromatography using aq. 5 mM $NH_4HCO_3$ solution-MeCN as eluents to give the title compound as a beige solid foam (0.82 g, 61% yield).

$^{1}$H-NMR (500 MHz, DMSO-d6) δ ppm: 9.63 (s, 1H), 7.6 (d, 1H), 7.49 (d, 1H), 7.29-7.18 (m, 5H), 7.26 (d, 1H), 7.25 (dd, 1H), 6.88 (d, 1H), 6.83 (d, 1H), 6.7 (dd, 1H), 6.58 (d, 1H), 4.82 (t, 1H), 4.64 (t, 2H), 4.47 (s, 2H), 4.19 (s, 2H), 3.93 (q, 2H), 3.69 (s, 3H), 3.37 (s, 2H), 3.14 (d, 2H), 2.75 (s, 3H), 2.3 (t, 2H), 2.01 (s, 3H), 1.9 (qn, 2H), 1.41 (qn, 2H), 1 (t, 3H)

Step 3: Preparation of ethyl 3-{3-[(6-hydroxy-2,2-dioxo-2H-1,2λ$^{6}$,3-benzoxathiazin-3(4H)-yl)methyl]-4-methoxyphenyl}-3-{4-methyl-1-[4-(methylamino)butyl]-1H-benzotriazol-5-yl}propanoate Using General Procedure 8 starting from ethyl 3-(1-{4-[benzyl(methyl)amino]butyl}-4-methyl-1H-benzotriazol-5-yl)-3-{3-[(6-hydroxy-2,2-dioxo-2H-1,2λ$^{6}$,3-benzoxathiazin-3(4H)-yl)methyl]-4-methoxyphenyl}propanoate (1 eq., 0.83 g, 1.13 mmol) as a reactant, the title compound (white solid foam, 0.4 g, 56% yield) was obtained.

$^{1}$H-NMR (500 MHz, DMSO-d6) δ ppm: 7.63 (d, 1H), 7.5 (d, 1H), 7.25 (d, 1H), 7.24 (dd, 1H), 6.89 (d, 1H), 6.83 (d, 1H), 6.7 (dd, 1H), 6.57 (d, 1H), 4.81 (t, 1H), 4.64 (t, 2H), 4.47 (s, 2H), 4.2/4.17 (d+d, 2H), 3.94 (q, 2H), 3.69 (s, 3H), 3.14 (d, 2H), 2.75 (s, 3H), 2.42 (t, 2H), 2.19 (s, 3H), 1.89 (qn, 2H), 1.33 (qn, 2H), 1.01 (t, 3H)

Step 4: Preparation of ethyl[4-methoxy-21,34-dimethyl-30,30-dioxo-24,29-dioxa-30)$^{6}$-thia-1,14,15,16,21-pentaazahexacyclo[23.5.3.1$^{3,7}$0.1$^{9,13}$0.0$^{12,16}$0.0$^{28,32}$]pentatriaconta-3(35),4,6,9(34),10,12,14,25,27,32-decaen-8-yl]acetate To a stirred solution of ethyl 3-{3-[(6-hydroxy-2,2-dioxo-2H-1,2λ$^{6}$,3-benzoxathiazin-3(4H)-yl)methyl]-4-methoxyphenyl}-3-{4-methyl-1-[4-(methylamino)butyl]-1H-benzotriazol-5-yl}propanoate (1 eq., 0.286 g, 0.448 mmol) in MeCN (6 mL) $Cs_2CO_3$ (5 eq., 0.73 g, 2.24 mmol) and 1,2-dibromoethane (5 eq., 0.193 mL, 2.24 mmol) were added at RT and the mixture was heated at 80° C. for 5 h. The crude product was purified by reversed-phase chromatography using aq. 5 mM $NH_4HCO_3$ solution-MeCN eluents to give the title compound as a white solid (0.045 g, 15% yield).

$^{1}$H-NMR (500 MHz, DMSO-d6) δ ppm: 7.63 (d, 1H), 7.55 (d, 1H), 7.44 (dd, 1H), 7.14 (d, 1H), 7.07 (d, 1H), 7 (dd, 1H), 6.96 (d, 1H), 6.47 (d, 1H), 4.8 (t, 1H), 4.76/4.69 (m+m, 2H), 4.37/3.96 (d+d, 2H), 4.27/3.92 (d+d, 2H), 4.12/4.05 (m+m, 2H), 3.89 (q, 2H), 3.77 (s, 3H), 3.14/3.07 (dd+dd, 2H), 2.76 (s, 3H), 2.73/2.7 (m+m, 2H), 2.59/2.42 (m+m, 2H), 2.22 (s, 3H), 1.96 (qn, 2H), 1.63 (m, 2H), 0.98 (t, 3H)

Step 5: Preparation of Example 47

Using General Procedure 12 starting from ethyl[4-methoxy-21,34-dimethyl-30,30-dioxo-24,29-dioxa-30λ$^{6}$-thia-1,14,15,16,21-pentaazahexacyclo[23.5.3.1$^{3,7}$0.1$^{9,13}$0.0$^{12,16}$0.0$^{28,32}$]pentatriaconta-3(35),4,6,9(34),10,12,14,25,27,32-decaen-8-yl]acetate (1 eq., 41 mg, 0.0617 mmol) as a reactant, the title compound (white solid, 35 mg, 89% yield) was obtained.

HRMS calculated for $C_{32}H_{37}N_5O_7S$: 635.2414; $[M+H]^+$ found=636.2479 (δ=−1.2 ppm).

$^{1}$H-NMR (500 MHz, DMSO-d6) δ ppm 12.42 (brs, 1H), 7.64 (d, 1H), 7.54 (d, 1H), 7.45 (dd, 1H), 7.11 (d, 1H), 7.07 (d, 1H), 7 (dd, 1H), 6.96 (d, 1H), 6.45 (d, 1H), 4.78 (t, 1H), 4.76/4.7 (m+m, 2H), 4.36/3.97 (d+d, 2H), 4.27/3.91 (d+d, 2H), 4.13/4.05 (m+m, 2H), 3.77 (s, 3H), 3.03/2.98 (dd+dd, 2H), 2.75 (s, 3H), 2.74/2.69 (m+m, 2H), 2.6/2.43 (m+m, 2H), 2.23 (s, 3H), 1.96 (m, 2H), 1.63 (m, 2H)

$^{13}$C-NMR (125 MHz, DMSO-d6) δ ppm: 131.2, 130.9, 126.8, 119.1, 114.5, 114.4, 111.7, 108, 66.7, 56.6, 56.2, 56.2, 48.6, 48.6, 47.5, 42.6, 41, 41, 27.3, 23.4, 13.3

EXAMPLE 48: [(8R)-11-Bromo-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid

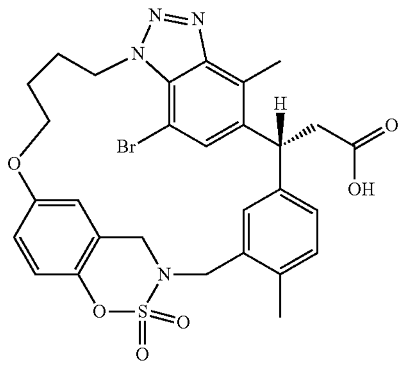 [SMILES: Cc1ccc2cc1CN1Cc3cc(ccc3OS1(=O)=O)OCCCCn1nnc3c(C)c(cc(Br)c31)[C@@H]2CC(=O)O]

Step 1: Preparation of ethyl[(8R)-11-bromo-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate To a stirred solution of ethyl[(8R)-4,31-dimethyl-27,27-dioxo-21,26-dioxa-27λ$^6$-thia-1,14,15,16-tetraazahexacyclo [20.5.3.1$^{3,7}$0.1$^{9,13}$0.0$^{12,16}$0.0$^{25,29}$]dotriaconta-3(32),4,6,9 (31),10,12,14,22,24,29-decaen-8-yl]acetate (1 eq., 1.47 g, 2.49 mmol) in nitromethane (15 mL) potassium peroxymonosulfate (3 eq., 3.595 g, 7.466 mmol) and potassium bromide (0.77 eq., 0.23 g, 1.93 mmol) were added at RT, then the mixture was stirred at 60° C. for 2 days. The reaction mixture was taken up in EtOAc (150 ml) and the organic layer was washed with 10% aq. $Na_2S2O_3$ solution (150 ml). The organic layer was dried over anhydrous $MgSO_4$, filtered and concentrated under reduced pressure. The residue was purified by normal phase silica gel chromatography using heptane-EtOAc gradient elution to give the title compound as a white solid (0.63 g, 38% yield).

$^1$H-NMR (500 MHz, DMSO-d6) δ ppm: 7.63 (s, 1H), 7.49 (dd, 1H), 7.3 (d, 1H), 7 (d, 1H), 6.81 (dd, 1H), 6.5 (d, 1H), 5.73 (d, 1H), 5.18/4.82 (dm+m, 2H), 4.74 (m, 1H), 4.27/3.83 (d+d, 2H), 4.04/3.76 (d+d, 2H), 3.95 (m, 2H), 3.58/3.12 (dt+m, 2H), 3.11 (m, 2H), 2.59 (s, 3H), 2.33 (s, 3H), 2.27/2.17 (m+m, 2H), 1.91/1.68 (m+m, 2H), 1.03 (t, 3H)

Step 2: Preparation of Example 48

Using General Procedure 12 starting from ethyl[(8R)-11-bromo-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24, 29-decaen-8-yl]acetate (1 eq., 308 mg, 0.46 mmol) as a reactant, the title compound (white solid, 144 mg, 49% yield) was obtained.

$^1$H-NMR (500 MHz, DMSO-d6) δ ppm: 12.28 (brs, 1H), 7.6 (s, 1H), 7.5 (dd, 1H), 7.3 (d, 1H), 7 (d, 1H), 6.81 (dd, 1H), 6.49 (d, 1H), 5.73 (d, 1H), 5.19/4.82 (m+m, 2H), 4.82 (t, 1H), 4.26/3.84 (d+d, 2H), 4.03/3.77 (d+d, 2H), 3.58/3.13 (m+m, 2H), 3 (d, 2H), 2.59 (s, 3H), 2.33 (s, 3H), 2.27/2.18 (m+m, 2H), 1.91/1.69 (qn+qn, 2H)

EXAMPLE 49: [(8R)-4,31-Dimethyl-27,27-dioxo-11-phenyl-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid diastereoisomer 1

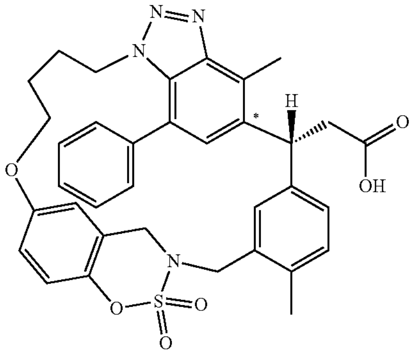

* = RorS

Step 1: Preparation of ethyl[(8R)-4,31-dimethyl-27,27-dioxo-11-phenyl-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate A mixture of ethyl[(8R)-11-bromo-4,31-dimethyl-27,27-dioxo-21,26-dioxa-27λ$^6$-thia-1,14,15,16-tetraazahexacyclo [20.5.3.1$^{3,7}$0.1$^{9,13}$0.0$^{12,16}$0.0$^{25,29}$]dotriaconta-3(32),4,6,9 (31),10,12,14,22,24,29-decaen-8-yl]acetate (1 eq., 300 g, 0.448 mmol), phenylboronic acid (3 eq., 164 mg, 1.344 mmol), $Cs_2CO_3$ (3 eq., 438 mg, 1.344 mmol), $A^{ta}$phos·$PdCl_2$ catalyst (0.1 eq., 20 mg, 0.0448 mmol), THF (4 mL) and water (4 mL) was heated in a microwave reactor at 100° C. for 1 h under nitrogene atmosphere. After the mixture was cooled down, the layers were separated, the aq. layer was extracted with further 2×5 ml of EtOAc. The combined organic layer was dried over $MgSO_4$, evaporated under reduced pressure. The crude product contains the mixture of 2 atropisomers (ratio: 94:6). The residue was purified by reversed-phase chromatography using aq. 5 mM $NH_4HCO_3$ solution-MeCN eluents to give the title compound as a white solid (diastereomer1, 232 mg, 78% yield).

$^1$H-NMR (500 MHz, DMSO-d6) δ ppm: 7.49 (dd, 1H), 7.47 (t, 1H), 7.45 (t, 2H), 7.31 (s, 1H), 7.28 (d, 1H), 7.21 (br., 2H), 7.08 (d, 1H), 6.83 (d, 1H), 6.8 (dd, 1H), 5.82 (d, 1H), 4.79 (t, 1H), 4.77/4.32 (dd+dt, 2H), 4.39/3.95 (d+d, 2H), 4.13/3.83 (d+d, 2H), 3.86 (q, 2H), 3.35/2.95 (m+m, 2H), 3.06 (d, 2H), 2.72 (s, 3H), 2.35 (s, 3H), 1.43/1.1 (m+m, 2H), 1.35/1.1 (m+m, 2H), 0.9 (t, 3H)

Step 2: Preparation of Example 49

Using General Procedure 12 starting from ethyl[(8R)-4,31-dimethyl-27,27-dioxo-11-phenyl-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (1 eq., 228 mg, 0.342 mmol) as a reactant, the title compound (white solid, 193 mg, 88% yield) was obtained.

HRMS calculated for $C_{35}H_4O_6S$: 638.2199; $[M+H]^+$ found: 639.2263 (δ=−1.4 ppm).

$^1$H-NMR (500 MHz, DMSO-d6) δ ppm: 12.11 (brs, 1H), 7.49 (dd, 1H), 7.47 (t, 1H), 7.45 (t, 2H), 7.29 (s, 1H), 7.28 (d, 1H), 7.22 (br, 2H), 7.08 (d, 1H), 6.82 (d, 1H), 6.79 (dd, 1H), 5.83 (d, 1H), 4.77/4.33 (m+m, 2H), 4.77 (t, 1H), 4.38/3.97 (d+d, 2H), 4.12/3.85 (d+d, 2H), 3.34/2.97 (m+m, 2H), 2.96 (d, 2H), 2.73 (s, 3H), 2.35 (s, 3H), 1.43/1.08 (m+m, 2H), 1.34/1.08 (m+m, 2H) $^{13}$C-NMR (125 MHz, DMSO-d6) δ ppm: 173.1, 155.9, 147.3, 144.4, 141.7, 137.8, 136.8, 136.4, 132, 131.3, 131.3, 129.3, 129, 128.8, 128.6, 127.9, 127, 123.8, 119.6, 117.8, 117.1, 110.2, 67.4, 52.4, 50.5, 48.8, 41.6, 41.2, 25.6, 24.1, 18.6, 13.3

EXAMPLE 50: [(8R)-11-Chloro-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid

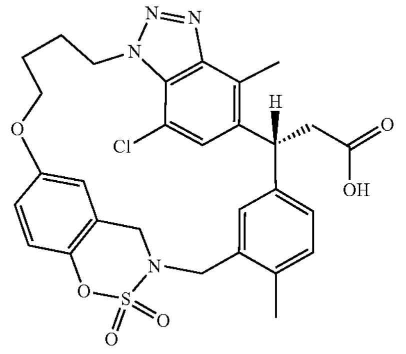 [SMILES: Cc1ccc2cc1CN1Cc3cc(ccc3OS1(=O)=O)OCCCCn1nnc3c(C)c(cc(Cl)c31)[C@@H]2CC(=O)O]

Step 1: Preparation of ethyl[(8R)-11-chloro-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate and ethyl[(8R)-11,30-dichloro-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate and ethyl[(8R)-11,23-dichloro-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate To a stirred solution of ethyl[(8R)-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (1 eq., 0.5 g, 0.846 mmol) in nitromethane (10 mL) potassium peroxymonosulfate (3 eq., 1.223 g, 2.54 mmol) and potassium chloride (1.5 eq., 95 mg, 1.269 mmol) were added at RT, then the mixture was stirred at 60° C. for 24 h. The reaction mixture was diluted with DCM (20 ml) and the organic layer was washed with water (20 ml). The organic layer was dried over anhydrous $MgSO_4$, filtered and evaporated under reduced pressure. The residue was purified by reversed-phase chromatography using aq. 5 mM HCOOH solution-MeCN eluents to give the 3 title compounds:

Ethyl[(8R)-11-chloro-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (61 mg, 12% yield), $^1$H-NMR (500 MHz, DMSO-d6) δ ppm: 7.52 (s, 1H), 7.49 (dd, 1H), 7.3 (d, 1H), 7 (d, 1H), 6.82 (dd, 1H), 6.53 (d, 1H), 5.76 (d, 1H), 5.1/4.89 (m+m, 2H), 4.75 (t, 1H), 4.3/3.83 (d+d, 2H), 4.05/3.76 (d+d, 2H), 3.95 (q, 2H), 3.61/3.17 (t+t, 2H), 3.12 (dd, 2H), 2.61 (s, 3H), 2.33 (s, 3H), 2.22/2.14 (m, 2H), 1.9/1.67 (m, 2H), 1.03 (t, 3H)

Ethyl[(8R)-11,30-dichloro-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (74 mg), $^1$H-NMR (500 MHz, DMSO-d6) δ ppm: 7.48 (dd, 1H), 7.34 (s, 1H), 7.33 (d, 1H), 7.11 (d, 1H), 7.05 (d, 1H), 6.43 (d, 1H), 5.07/4.85 (dm+m, 2H), 4.74 (dd, 1H), 4.27/4 (d+d, 2H), 4.09/3.87 (d+d, 2H), 4.04/3.78 (m+m, 2H), 3.91 (q, 2H), 3.27/3.09 (dd+dd, 2H), 2.62 (s, 3H), 2.43/2.12 (m+m, 2H), 2.34 (s, 3H), 1.74/1.43 (m+m, 2H), 0.98 (t, 3H)

Ethyl[(8R)-11,23-dichloro-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (42 mg).

$^1$H-NMR (500 MHz, DMSO-d6) δ ppm: 7.57 (s, 1H), 7.48 (dd, 1H), 7.36 (s, 1H), 7.27 (d, 1H), 6.66 (d, 1H), 6.02 (s, 1H), 5.09/4.93 (m+m, 2H), 4.73 (t, 1H), 4.44/3.78 (d+d, 2H), 4.09/3.65 (d+d, 2H), 3.97/3.93 (m+m, 2H), 3.6/3.04 (m+m, 2H), 3.15/3.04 (dd+dd, 2H), 2.62 (s, 3H), 2.32 (s, 3H), 2.28/2.08 (m+m, 2H), 1.9/1.67 (m+m, 2H), 1.03 (t, 3H)

Step 2: Preparation of Example 50

Using General Procedure 12 starting from ethyl[(8R)-11-chloro-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (1 eq., 54 mg, 0.086 mmol) as a reactant, the title compound (white solid, 26 mg, 50% yield) was obtained.

HRMS calculated for $C_{29}H_{29}ClN_4O_6S$: 596.1496; $[M+H]^+$ found: 597.156 (δ=−1.5 ppm).

$^1$H-NMR (500 MHz, DMSO-d6) δ ppm: 7.5 (dd, 1H), 7.49 (s, 1H), 7.29 (d, 1H), 7 (d, 1H), 6.81 (dd, 1H), 6.5 (d, 1H), 5.74 (d, 1H), 5.09/4.87 (m+m, 2H), 4.72 (t, 1H), 4.28/3.83 (d+d, 2H), 4.04/3.76 (d+d, 2H), 3.6/3.17 (dm+dm, 2H), 3.02/2.98 (dd+dd, 2H), 2.6 (s, 3H), 2.33 (s, 3H), 2.22/2.15 (m+m, 2H), 1.9/1.68 (m+m, 2H)

$^{13}$C-NMR (125 MHz, DMSO-d6) δ ppm: 131.4, 131.1, 129, 127.6, 119.5, 117.1, 111.3, 67.9, 51.9, 50, 48.7, 41.6, 40.8, 26.5, 26.3, 18.5, 13.3

EXAMPLE 51: [(8R)-11,30-Dichloro-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid

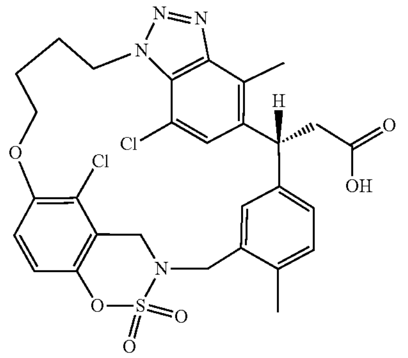 [SMILES: Cc1ccc2cc1CN1Cc3c(ccc(c3Cl)OCCCCn3nnc4c(C)c(cc(Cl)c43)[C@@H]2CC(=O)O)OS1(=O)=O]

Using General Procedure 12 starting from ethyl[(8R)-11,30-dichloro-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (1 eq., 69 mg, 0.1046 mmol) as a reactant, the title compound (white solid, 57 mg, 86% yield) was obtained.

HRMS calculated for $C_{29}H_{28}Cl_2N_4O_6S$: 630.1107; $[M+H]^+$ found: 631.1179 (δ=−0.1 ppm).

$^1$H-NMR (500 MHz, DMSO-d6) δ ppm: 7.49 (dd, 1H), 7.32 (d, 1H), 7.3 (s, 1H), 7.11 (d, 1H), 7.04 (d, 1H), 6.43 (d, 1H), 5.07/4.85 (dm+m, 2H), 4.72 (t, 1H), 4.27/4 (d+d, 2H), 4.09/3.87 (d+d, 2H), 4.03/3.76 (m+m, 2H), 3.17/2.96 (dd+dd, 2H), 2.62 (s, 3H), 2.44/2.13 (m+m, 2H), 2.34 (s, 3H), 1.74/1.45 (m+m, 2H)

$^{13}$C-NMR (125 MHz, DMSO-d6) δ ppm: 131.5, 131.5, 127.7, 127.6, 117.6, 117.6, 70.3, 52.6, 49.9, 47.4, 40.3, 39.8, 27.2, 26.7, 18.5, 13.2

EXAMPLE 52: [(8R)-11,23-Dichloro-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid

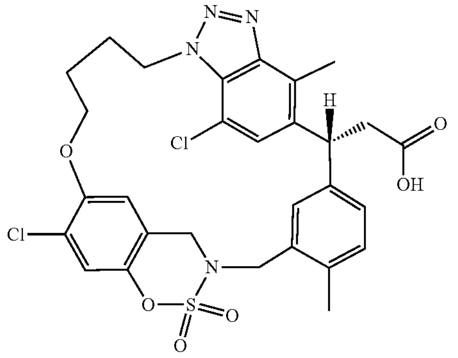 [SMILES: Cc1ccc2cc1CN1Cc3cc(c(Cl)cc3OS1(=O)=O)OCCCCn1nnc3c(C)c(cc(Cl)c31)[C@@H]2CC(=O)O]

Using General Procedure 12 starting from ethyl[(8R)-11,23-dichloro-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (1 eq., 38 mg, 0.0576 mmol) as a reactant, the title compound (white solid, 23 mg, 63% yield) was obtained.

HRMS calculated for $C_{29}H_{28}Cl_2N_4O_6S$: 630.1107; $[M+H]^+$ found: 631.1173 (δ=−1.0 ppm).

$^1$H-NMR (500 MHz, DMSO-d6) δ ppm: 7.55 (s, 1H), 7.49 (dd, 1H), 7.36 (s, 1H), 7.27 (d, 1H), 6.64 (d, 1H), 6.01 (s, 1H), 5.09/4.93 (m+m, 2H), 4.71 (t, 1H), 4.43/3.78 (d+d, 2H), 4.09/3.66 (d+d, 2H), 3.6/3.04 (m+m, 2H), 3.04/2.94 (dd+dd, 2H), 2.61 (s, 3H), 2.32 (s, 3H), 2.28/2.08 (m+m, 2H), 1.9/1.66 (m+m, 2H)

$^{13}$C-NMR (125 MHz, DMSO-d6) δ ppm: 151.4, 131.3, 131.1, 129.3, 127.5, 120, 111.4, 68.5, 52, 49.8, 48.7, 41.9, 40.8, 26.2, 26, 18.5, 13.4

EXAMPLE 53: [4-Methoxy-39-methyl-35,35-dioxo-21,29,34-trioxa-35λ$^6$-thia-1,14,15,16-tetraazaheptacyclo[28.5.3.1$^{3,7}$0.1$^{9,13}$0.0$^{12,16}$0.0$^{22,27}$0.0$^{33,37}$]tetraconta-3(40),4,6,9(39),10,12,14,22,24,26,30,32,37-tridecaen-8-yl]acetic acid enantiomer 1

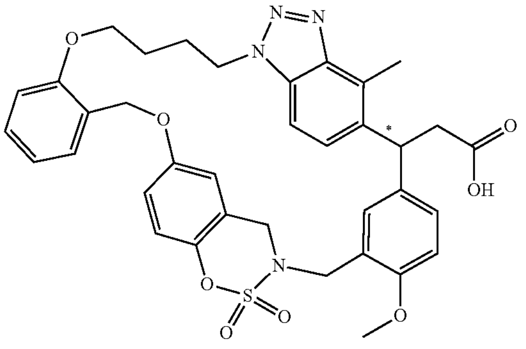

* = RorS enantiomer 2

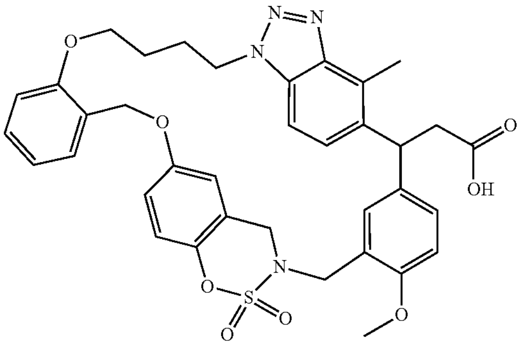

* = RorS

Step 1: Preparation of ethyl 3-{1-[4-(2-formylphenoxy)butyl]-4-methyl-1H-benzotriazol-5-yl}-3-{3-[(6-hydroxy-2,2-dioxo-2H-1,2λ$^6$,3-benzoxathiazin-3(4H)-yl)methyl]-4-methoxyphenyl}propanoate Ethyl 3-[1[-(4-chlorobutyl)-4-methyl-1H-benzotriazol-5-yl]-3-{3-[(6-hydroxy-2,2-dioxo-2H-1,2λ$^6$,3-benzoxathiazin-3(4H)-yl)methyl]-4-methoxyphenyl}propanoate hydrochloride (1 eq., 0.5 g, 0.78 mmol) was dissolved in dry DMF (8 mL) and 2-hydroxybenzaldehyde (24 eq., 2 mL, 19 mmol) was added followed by addition of $Cs_2CO_3$ (0.50 g, 1.5 mmol). The reaction mixture was stirred at 120° C. for 1 h under $N_2$ atmosphere. After 1 h an additional 0.5 g (1.5 mmol) of $Cs_2CO_3$ was added and the mixture was stirred for additional 2 h at 120° C. The mixture was cooled to RT, poured on ice and extracted with DCM. The collected organic layer was dried over $Na_2SO_4$, filtered and evaporated under reduced pressure. The crude product was purified by normal phase silica gel chromatography using DCM-MeOH (100:0 to 97.5:2.5) as eluents resulted in 0.426 g (75% yield) of the title compound as a light brown foamy material.

$^1$H-NMR (500 MHz, DMSO-d6) δ ppm: 10.32 (s, 1H), 9.62 (s, 1H), 7.66 (d, 1H), 7.66 (dd, 1H), 7.6 (ddd, 1H), 7.5 (d, 1H), 7.26 (d, 1H), 7.23 (dd, 1H), 7.16 (d, 1H), 7.04 (t, 1H), 6.89 (d, 1H), 6.83 (d, 1H), 6.7 (dd, 1H), 6.58 (d, 1H), 4.81 (t, 1H), 4.75 (t, 2H), 4.48 (s, 2H), 4.21/4.17 (d+d, 2H), 4.13 (t, 2H), 3.94 (q, 2H), 3.69 (s, 3H), 3.14 (d, 2H), 2.75 (s, 3H), 2.1 (m, 2H), 1.74 (m, 2H), 1.01 (t, 3H)

Step 2: Preparation of ethyl 3-{3-[(6-hydroxy-2,2-dioxo-2H-1,2)$^6$,3-benzoxathiazin-3(4H)-yl)methyl]-4-methoxyphenyl}-3-(1-{4-[2-(hydroxymethyl)phenoxy]butyl}-4-methyl-1H-benzotriazol-5-yl) propanoate Ethyl 3-{11-[4-(2-formylphenoxy)butyl]-4-methyl-1H-benzotriazol-5-yl}-3-{3-[(6-hydroxy-2,2-dioxo-2H-1,2λ$^6$, 3-benzoxathiazin-3(4H)-yl)methyl]-4-methoxyphenyl}propanoate (1 eq., 0.350 g, 0.480 mmol) was dissolved in EtOH (2 mL) and sodium borohydride (2.75 eq., 50 mg, 1.322 mmol) was added. The reaction mixture was stirred at RT for 1 h. The mixture was poured on crushed ice and evaporated under reduced pressure. The residue was partitioned between water and EtOAc, the phases were separated and the aq. phase was extracted with additional portions of EtOAc. The combined organic phase was dried over $Na_2SO_4$, filtered and evaporated to Celite. The crude product was purified by normal phase silica gel chromatography using DCM-MeOH (100:0 to 95.2:4.8) as an eluent, resulting in 0.33 g (94% yield) of the title compound as an off-white foamy material.

$^1$H-NMR (500 MHz, DMSO-d6) δ ppm: 9.62 (s, 1H), 7.66 (d, 1H), 7.51 (d, 1H), 7.35 (d, 1H), 7.26 (d, 1H), 7.23 (dd, 1H), 7.15 (t, 1H), 6.9 (t, 1H), 6.89 (d, 1H), 6.87 (d, 1H), 6.84 (d, 1H), 6.71 (dd, 1H), 6.59 (d, 1H), 4.94 (t, 1H), 4.82 (t, 1H), 4.73 (t, 2H), 4.6 (d, 2H), 4.48 (s, 2H), 4.19 (s, 2H), 3.96 (t, 2H), 3.94 (q, 2H), 3.69 (s, 3H), 3.15 (d, 2H), 2.76 (s, 3H), 2.06 (m, 2H), 1.68 (m, 2H), 1.01 (t, 3H)

Step 3: Preparation of ethyl 3-(1-{4-[2-(chloromethyl)phenoxy]butyl}-4-methyl-1H-benzotriazol-5-yl)-3-{3-[(6-hydroxy-2,2-dioxo-2H-1,2λ$^6$,3-benzoxathiazin-3(4H)-yl)methyl]-4-methoxyphenyl}propanoate Ethyl 3-{3-[(6-hydroxy-2,2-dioxo-2H-1,2λ$^6$,3-benzoxathiazin-3(4H)-yl)methyl]-4-methoxyphenyl}-3-(1-{4-[2-(hydroxymethyl)phenoxy]butyl}-4-methyl-1H-benzotriazol-5-yl)propanoate (1 eq., 0.330 g, 0.452 mmol) was dissolved in dry DCM (2 mL) and the mixture was cooled to 0° C. Thionyl chloride (70 L, 0.95965 mmol) was added and the reaction mixture was stirred at 0° C. for 30 minutes. After completion of the reaction the volatiles were evaporated to dryness, the excess of the reagent was removed by evaporation of DCM from the residue. Drying of the crude product in high vacuo at RT resulted in 0.441 g (quant.) of a title compound as an off-white foamy material.

$^1$H-NMR (500 MHz, DMSO-d6) δ ppm: 9.66 (brs, 1H), 7.66 (d, 1H), 7.5 (d, 1H), 7.35 (dm, 1H), 7.29 (m, 1H), 7.26 (d, 1H), 7.23 (dd, 1H), 6.97 (dm, 1H), 6.9 (m, 1H), 6.89 (d, 1H), 6.84 (d, 1H), 6.71 (dd, 1H), 6.59 (d, 1H), 4.82 (t, 1H), 4.75 (t, 2H), 4.64 (s, 2H), 4.48 (s, 2H), 4.19 (s, 2H), 4.04 (t, 2H), 3.93 (q, 2H), 3.69 (s, 3H), 3.15 (d, 2H), 2.75 (s, 3H), 2.1 (m, 2H), 1.71 (m, 2H), 1 (t, 3H)

Step 4: Preparation of ethyl[4-methoxy-39-methyl-35,35-dioxo-21,29,34-trioxa-35λ$^6$-thia-1,14,15,16-tetraazaheptacyclo[28.5.3.1$^{3,7}$0.1$^{9,13}$0.0$^{12,16}$0.0$^{22,27}$0.0$^{33,37}$]tetraconta-3(40),4,6,9(39),10,12,14,22,24,26,30,32,37-tridecaen-8-yl]acetate Using General Procedure 11 starting from ethyl 3-(1-{4-[2-(chloromethyl)phenoxy]butyl}-4-methyl-1H-benzotriazol-5-yl)-3-{3-[(6-hydroxy-2,2-dioxo-2H-1,2λ$^6$,3-benzoxathiazin-3(4H)-yl)methyl]-4-methoxyphenyl}propanoate (1 eq.) as a reactant, the title compound (white solid, 48% yield) was obtained.

$^1$H-NMR (500 MHz, DMSO-d6) δ ppm: 7.67 (d, 1H), 7.57 (d, 1H), 7.44 (dd, 1H), 7.34 (dd, 1H), 7.29 (td, 1H), 7.26 (d, 1H), 7.01 (d, 1H), 7 (dd, 1H), 6.95 (t, 1H), 6.87 (d, 1H), 6.77 (d, 1H), 6.64 (d, 1H), 5.03 (s, 2H), 4.81 (t, 1H), 4.77 (t, 2H), 4.41/4.34 (d+d, 2H), 4.3/4.2 (d+d, 2H), 4.13/4.06 (m+m, 2H), 3.91 (qd, 2H), 3.73 (s, 3H), 3.2/3.15 (dd+dd, 2H), 2.8 (s, 3H), 2.21/2.02 (m+m, 2H), 1.84 (m, 2H), 1 (t, 3H)

Step 5: Preparation of Example 53

Using General Procedure 12 starting from ethyl[4-methoxy-39-methyl-35,35-dioxo-21,29,34-trioxa-35λ$^6$-thia-1,14,15,16-tetraazaheptacyclo[28.5.3.1$^{3,7}$0.1$^{9,13}$0.0$^{12,16}$0.0$^{22,27}$0.0$^{33,37}$]tetraconta-3(40),4,6,9(39),10,12,14,22,24,26,30,32,37-tridecaen-8-yl]acetate (1 eq.) as a reactant, the title compound (80% yield) was obtained.

The enantiopure products were obtained by chromatographic separation on chiral column.

EXAMPLE 53a (E1)

HRMS calculated for $C_{36}H_{36}N_4O_8S$: 684.2254; $[M+H]^+$ found: 685.2315 (δ=−1.7 ppm).

EXAMPLE 53b (E2)

HRMS calculated for $C_{36}H_{36}N_4O_8S$: 684.2254; $[M+H]^+$ found: 685.2317 (δ=−1.4 ppm).

$^1$H-NMR (500 MHz, DMSO-d6) δ ppm: 7.67 (d, 1H), 7.55 (d, 1H), 7.34 (dd, 1H), 7.29 (t, 1H), 7.23 (d, 1H), 7.14 (d, 1H), 7.01 (d, 1H), 7 (dd, 1H), 6.95 (t, 1H), 6.88 (d, 1H), 6.78 (d, 1H), 6.63 (d, 1H), 5.03 (s, 2H), 4.79 (t, 1H), 4.77 (t, 2H), 4.4/4.33 (d+d, 2H), 4.3/4.2 (d+d, 2H), 4.14/4.06 (m+m, 2H), 3.73 (s, 3H), 3.09/3.05 (dd+dd, 2H), 2.8 (s, 3H), 2.21/2.03 (m+m, 2H), 1.84 (qn, 2H)

$^{13}$C-NMR (125 MHz, DMSO-d6) δ ppm: 173.2, 156.4, 156.3, 155.6, 146.4, 144.6, 137.7, 136.1, 131.5, 130.1, 129.7, 129.3, 129.1, 127, 126.6, 124.8, 121.9, 120.7, 119, 118.2, 116.3, 112.9, 111.9, 111.5, 108.2, 67.5, 65.1, 56.1, 49.8, 48.5, 48.1, 40.8, 40.4, 27.1, 26.4, 13.3

EXAMPLE 54: [4-Methoxy-39-methyl-35,35-dioxo-29,34-dioxa-21,35)$^6$-dithia-1,14,15,16-tetraazaheptacyclo[28.5.3.1$^{3,7}$0.1$^{9,13}$0.0$^{12,16}$0.0$^{22,27}$0.0$^{33,37}$] tetraconta-3(40),4,6,9(39),10,12,14,22,24,26,30,32,37-tridecaen-8-yl]acetic acid enantiomer 1

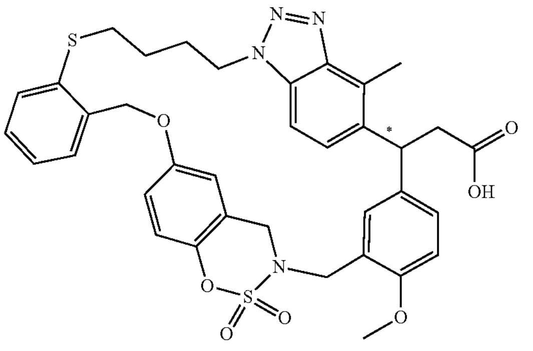

* = RorS enantiomer 2

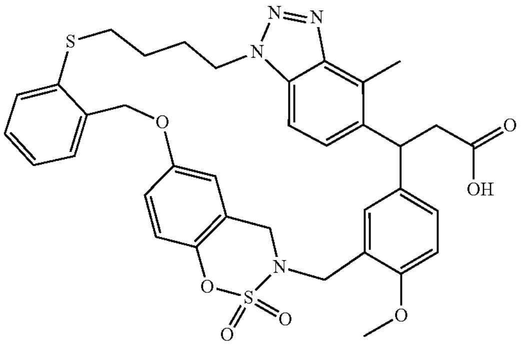

* = RorS

Step 1: Preparation of ethyl 3-{3-[(6-hydroxy-2,2-dioxo-2H-1,2λ$^6$,3-benzoxathiazin-3(4H)-yl)methyl]-4-methoxyphenyl}-3-[1-(4-{[2-(hydroxymethyl) phenyl]sulfanyl}butyl)-4-methyl-1H-benzotriazol-5-yl]propanoate Ethyl 3-[1-(4-chlorobutyl)-4-methyl-1H-benzotriazol-5-yl]-3-{3-[(6-hydroxy-2,2-dioxo-2H-1,2λ$^6$,3-benzoxathiazin-3(4H)-yl)methyl]-4-methoxyphenyl}propanoate (1 eq., 1 g, 1.55 mmol) and (2-sulfanylphenyl)methanol (1.2 eq., 262 mg, 1.87 mmol) were dissolved in DMF (5 mL) and $K_2CO_3$ (2 eq., 430 mg, 3.11 mmol) was added. The reaction mixture was stirred at RT for 2 h. After completion of the reaction, the mixture was poured into 10 ml of water and extracted with 2×30 ml of DCM. The organic layer was separated and dried over $MgSO_4$. After filtration the mother liquor was evaporated to dryness to give a yellow crystalline product (1.15 g, 99% yield).

$^1$H-NMR (500 MHz, DMSO-d6) δ ppm: 7.63 (d, 1H), 7.5 (d, 1H), 7.41 (dm, 1H), 7.27 (d, 1H), 7.23 (dd, 1H), 7.22 (d, 1H), 7.15 (td, 1H), 7.12 (td, 1H), 6.89 (d, 1H), 6.84 (d, 1H), 6.7 (dd, 1H), 6.58 (d, 1H), 4.82 (t, 1H), 4.67 (t, 2H), 4.48 (s, 2H), 4.48 (s, 2H), 4.21/4.17 (d+d, 2H), 3.93 (q, 2H), 3.69 (s, 3H), 3.15 (d, 2H), 2.94 (t, 2H), 2.75 (s, 3H), 2.01/1.51 (m+m, 4H), 1 (t, 3H)

Step 2: Preparation of ethyl 3-[1-(4-{[2-(chloromethyl)phenyl]sulfanyl}butyl)-4-methyl-1H-benzotriazol-5-yl]-3-{3-[(6-hydroxy-2,2-dioxo-2H-1,2)$^6$,3-benzoxathiazin-3(4H)-yl)methyl]-4-methoxyphenyl}propanoate Using General Procedure 10 starting from ethyl 3-{3-[(6-hydroxy-2,2-dioxo-2H-1,2λ$^6$,3-benzoxathiazin-3(4H)-yl) methyl]-4-methoxyphenyl}-3-[1-(4-{[2-(hydroxymethyl) phenyl]sulfanyl}butyl)-4-methyl-1H-benzotriazol-5-yl] propanoate (1 eq.) as a reactant, the title compound (98% yield) was obtained.

$^1$H-NMR (500 MHz, DMSO-d6) δ ppm: 7.62 (d, 1H), 7.5 (d, 1H), 7.39 (dd, 1H), 7.34 (dd, 1H), 7.27 (d, 1H), 7.24 (td, 1H), 7.23 (dd, 1H), 7.16 (td, 1H), 6.89 (d, 1H), 6.84 (d, 1H), 6.71 (dd, 1H), 6.59 (d, 1H), 4.82 (t, 1H), 4.74/4.7 (d+d, 2H), 4.67 (t, 2H), 4.48 (s, 2H), 4.21/4.17 (d+d, 2H), 3.93 (q, 2H), 3.69 (s, 3H), 3.15 (d, 2H), 3 (t, 2H), 2.75 (s, 3H), 2.01/1.51 (m+m, 4H), 1 (t, 3H)

Step 3: Preparation of ethyl[4-methoxy-39-methyl-35,35-dioxo-29,34-dioxa-21,35)$^6$-dithia-1,14,15,16-tetraazaheptacyclo[28.5.3.1$^{3,7}$0.1$^{9,13}$0.0$^{12,16}$0.0$^{22,27}$0.0$^{33,37}$]tetraconta-3(40),4,6,9(39),10,12,14,22,24,26,30,32,37-tridecaen-8-yl]acetate Using General Procedure 11 starting from ethyl 3-[1-(4-{[2-(chloromethyl)phenyl]sulfanyl}butyl)-4-methyl-1H-benzotriazol-5-yl]-3-{3-[(6-hydroxy-2,2-dioxo-2H-1,2λ$^6$,3-benzoxathiazin-3(4H)-yl)methyl]-4-methoxyphenyl}propanoate (1 eq.) as a reactant, the title compound (yellow crystals, 21% yield) was obtained.

The enantiopure final intermediates were obtained by chromatographic separation on chiral column.

$^1$H-NMR (500 MHz, DMSO-d6) δ ppm: 7.58 (d, 1H), 7.53 (d, 1H), 7.51 (d, 1H), 7.38 (t, 1H), 7.34 (d, 1H), 7.34 (dd, 1H), 7.31 (d, 1H), 7.24 (t, 1H), 6.86 (d, 1H), 6.79 (dd, 1H), 6.74 (d, 1H), 6.72 (d, 1H), 4.99/4.92 (d+d, 2H), 4.82 (t, 1H), 4.65 (t, 2H), 4.47/4.4 (d+d, 2H), 4.34/4.26 (d+d, 2H), 3.9 (qd, 2H), 3.72 (s, 3H), 3.16/3.07 (m+m, 2H), 3.14 (m, 2H), 2.81 (s, 3H), 2.04/1.9 (m+m, 2H), 1.62 (m, 2H), 0.99 (t, 3H)

Step 4: Preparation of Example 54

Using General Procedure 12 starting from ethyl[4-methoxy-39-methyl-35,35-dioxo-29,34-dioxa-21,35λ$^6$-dithia-1,14,15,16-tetraazaheptacyclo[28.5.3.1$^{3,7}$0.1$^{9,13}$0.0$^{12,16}$0.0$^{22,27}$0.0$^{33,37}$]tetraconta-3(40),4,6,9(39),10,12,14,22,24,26,30,32,37-tridecaen-8-yl]acetate E1 (1 eq.) or E2 (1 eq.) as reactants, the title compounds (18%-73% yields respectively) were obtained.

EXAMPLE 54a (E1)

HRMS calculated for $C_{36}H_{36}N_4O_7S_2$: 700.2025; $[M+H]^+$ found: 701.2100 (δ=0.3 ppm).

EXAMPLE 54b (E2)

HRMS calculated for $C_{36}H_{36}N_4O_7S_2$: 700.2025; $[M+H]^+$ found: 701.2101 (δ=0.4 ppm).

$^1$H-NMR (500 MHz, DMSO-d6) δ ppm: 7.57 (d, 1H), 7.53-7.21 (m, 4H), 7.49 (d, 1H), 7.33 (dd, 1H), 7.26 (d, 1H), 6.85 (d, 1H), 6.79 (dd, 1H), 6.76 (d, 1H), 6.71 (d, 1H), 4.98/4.91 (d+d, 2H), 4.81 (t, 1H), 4.64 (t, 2H), 4.46/4.39

(d+d, 2H), 4.33/4.26 (d+d, 2H), 3.72 (s, 3H), 3.16/3.06 (m+m, 2H), 2.97 (d, 2H), 2.8 (s, 3H), 2.04/1.9 (m+m, 2H), 1.61 (m, 2H)

$^{13}$C-NMR (125 MHz, DMSO-d6) δ ppm: 130.3, 129.5, 127.2, 119, 116.4, 112.7, 111.4, 107.9, 68.4, 56, 49.9, 48.6, 47.4, 41.4, 41.1, 32.4, 28.5, 25.1, 13.4

EXAMPLE 55a: [(8R)-4,31-Dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]($^2$H$_2$)acetic acid

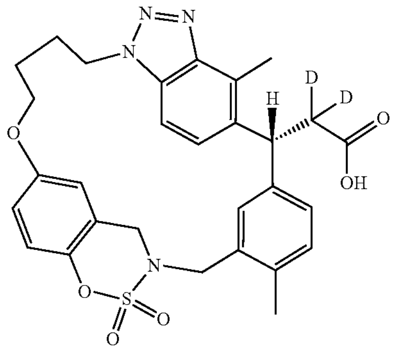 [SMILES: [2H]C([2H])(C(=O)O)[C@@H]1c2ccc(C)c(c2)CN2Cc3cc(ccc3OS2(=O)=O)OCCCCn2nnc3c(C)c1ccc32]

To a stirred solution of ethyl[(8R)-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (1 eq., 100 mg, 0.1693 mmol) in methanol-d4 (tetradeutero-methanol, ($^2$H$_3$)methan($^2$H)ol) (2 mL) NaH (60% in mineral oil, 10 eq., 68 mg, 1.6936 mmol) was added slowly at RT. After the mixture was stirred for 5 min, the reaction vessel was closed and the mixture was stirred at 65° C. for 18 h. The reaction mixture was neutralised with 2 ml 1M aq. HCl solution, the white precipitate was filtered off, washed with 2×5 ml water, dried in vacuo. The crude product was purified by reversed-phase chromatography using aq. 5 mM HCOOH solution-MeCN as an eluent to give the title compound (beige solid, 82 mg, 86% yield).

HRMS calculated for $C_{29}D_2H_{28}N_4O_6S$: 564.2012; [M+H]$^+$ found: 565.2086 (δ=0.3 ppm).

$^1$H-NMR (500 MHz, DMSO-d6) δ ppm: 12.19 (br., 1H), 7.68 (d, 1H), 7.49 (dd, 1H), 7.43 (d, 1H), 7.29 (d, 1H), 6.99 (d, 1H), 6.79 (dd, 1H), 6.54 (d, 1H), 5.85 (d, 1H), 4.77 (m, 2H), 4.74 (s, 1H), 4.13/3.94 (d+d, 2H), 3.99/3.84 (d+d, 2H), 3.64/3.42 (m+m, 2H), 2.62 (s, 3H), 2.32 (s, 3H), 2.21/2.06 (m+m, 2H), 1.82/1.62 (m+m, 2H)

$^{13}$C-NMR (125 MHz, DMSO-d6) δ ppm: 173.3, 131.3, 131.3, 128.6, 127.3, 119.5, 117.5, 111.2, 108, 67.8, 51.9, 48.8, 48.2, 41.6, 40.1, 26.7, 25.5, 18.5, 13.4

EXAMPLE 55b: [(8S)-4,31-Dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]($^2$H$_2$)acetic acid

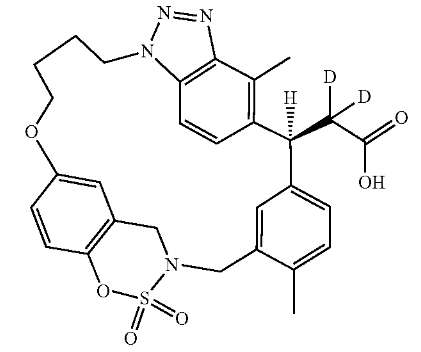 [SMILES: [2H]C([2H])(C(=O)O)[C@H]1c2ccc(C)c(c2)CN2Cc3cc(ccc3OS2(=O)=O)OCCCCn2nnc3c(C)c1ccc32]

To a stirred solution of ethyl[(8R)-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (1 eq., 200 mg, 0.338 mmol) in methanol-d4 (tetradeutero-methanol, ($^2$H$_3$)methan($^2$H)ol) (4 mL) NaH (60% in mineral oil, 10 eq., 135 mg, 3.38 mmol) was added at RT slowly. After the mixture was stirred for 5 min, the reaction vessel was closed and the mixture was stirred at 65° C. overnight. The reaction mixture was neutralised with 2 ml 1M aq. HCl solution, the white precipitate was filtered off, washed with 2×5 ml water, dried in vacuo. The crude product was purified by reversed-phase chromatography using aq. 5 mM HCOOH solution-MeCN as an eluent to give the title compound (white solid, 82 mg, 43% yield).

HRMS calculated for $C_{29}D_2H_{28}N_4O_6S$: 564.2012; [M+H]$^+$ found: 565.2081 (δ=−0.6 ppm).

$^1$H-NMR (500 MHz, DMSO-d6) δ ppm: 12.19 (br., 1H), 7.68 (d, 1H), 7.49 (dd, 1H), 7.43 (d, 1H), 7.29 (d, 1H), 6.99 (d, 1H), 6.79 (dd, 1H), 6.54 (d, 1H), 5.85 (d, 1H), 4.77 (m, 2H), 4.74 (s, 1H), 4.13/3.94 (d+d, 2H), 3.99/3.84 (d+d, 2H), 3.64/3.42 (m+m, 2H), 2.62 (s, 3H), 2.32 (s, 3H), 2.21/2.06 (m+m, 2H), 1.82/1.62 (m+m, 2H)

$^{13}$C-NMR (125 MHz, DMSO-d6) δ ppm: 173.3, 131.3, 131.3, 128.6, 127.3, 119.5, 117.5, 111.2, 108, 67.8, 51.9, 48.8, 48.2, 41.6, 40.1, 26.7, 25.5, 18.5, 13.4

EXAMPLE 56: [(2R,8R)-2,4,32-Trimethyl-28,28-dioxo-19,22,27-trioxa-28λ$^6$-thia-1,14,15,16-tetraazahexacyclo[21.5.3.1$^{3,7}$0.1$^{9,13}$0.0$^{12,16}$0.0$^{26,30}$]tritriaconta-3(33),4,6,9(32),10,12,14,23,25,30-decaen-8-yl]($^2$H$_2$)acetic acid

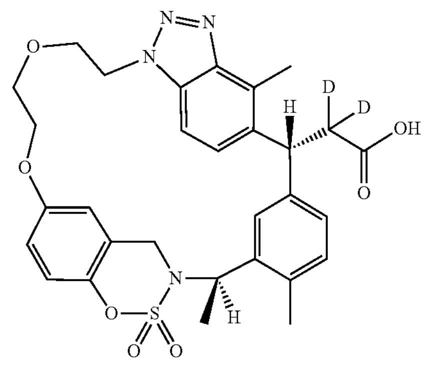 [SMILES: [2H]C([2H])(C(=O)O)[C@@H]1c2ccc(C)c(c2)[C@@H](C)N2Cc3cc(ccc3OS2(=O)=O)OCCOCCn2nnc3c(C)c1ccc32]

To a stirred solution of ethyl[(2R,8R)-2,4,32-trimethyl-28,28-dioxo-19,22,27-trioxa-28λ$^6$-thia-1,14,15,16-tetraaza-hexacyclo[21.5.3.1$^{3,7}$0.1$^{9,13}$0.0$^{12,16}$0.0$^{26,30}$]tritriaconta-3(33),4,6,9(32),10,12,14,23,25,30-decaen-8-yl]acetate (1 eq., 150 mg, 0.2417 mmol) in methanol-d4 (tetradeutero-methanol, ($^2H_3$)methan($^2$H)ol) (3 mL) NaH (60% in mineral oil, 10 eq., 97 mg, 2.417 mmol) was added slowly at RT. After the mixture was stirred for 5 min, the reaction vessel was closed and the mixture was stirred at 65° C. for 18 h. The reaction mixture was neutralized with 2.5 ml 1M aq. HCl solution, the white precipitate was filtered off, washed with 2×5 ml water, dried in vacuo. The crude product was purified by reversed-phase chromatography using aq. 5 mM HCOOH solution-MeCN as an eluent to give the title compound (beige solid, 82 mg, 86%)

HRMS calculated for $C_{30}D_2H_{34}O_7S$: 594.2117; [M+H]$^+$ found: 595.2192 (δ=0.3 ppm).

$^1$H-NMR (500 MHz, DMSO-d6) δ ppm: 12.23 (brs, 1H), 7.65 (d, 1H), 7.46 (dd, 1H), 7.29 (d, 1H), 7.12 (d, 1H), 6.94 (d, 1H), 6.9 (d, 1H), 6.8 (dd, 1H), 6.01 (d, 1H), 5.25 (q, 1H), 4.9 (s, 1H), 4.82 (t, 2H), 4.15/3.79 (d+d, 2H), 4.11/4.03 (dt+dt, 2H), 3.95/3.8 (m+m, 2H), 3.7/3.68 (m+m, 2H), 2.79 (s, 3H), 2.33 (s, 3H), 1.16 (d, 3H)

$^{13}$C-NMR (125 MHz, DMSO-d6) δ ppm: 173.4, 155.5, 146.5, 145, 141.5, 137.7, 135.9, 135.5, 132.3, 131.6, 128.3, 127.9, 127, 126.6, 120, 119, 115.4, 114.1, 108.6, 69.3, 69.1, 68.5, 55.4, 48.8, 45.1, 41.1, 39.4, 18.6, 15.6, 13.4

EXAMPLE 57: [4,38-Dimethyl-34,34-dioxo-20,28,33-trioxa-34λ$^6$-thia-1,14,15,16-tetraazaheptacyclo[27.5.3.1$^{3,7}$0.1$^{9,13}$0.0$^{12,16}$0.0$^{21,26}$0.0$^{32,36}$]nonatriaconta-3(39),4,6,9(38),10,12,14,21,23,25,29,31,36-tridecaen-8-yl]acetic acid enantiomer 1

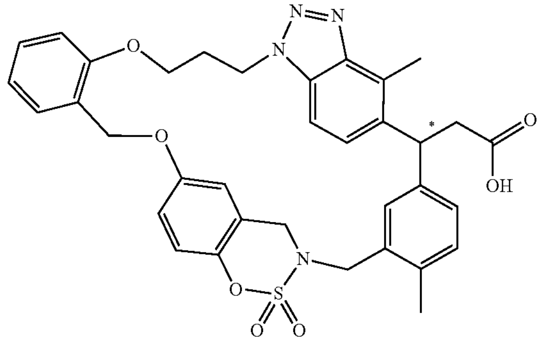

* = RorS enantiomer 2

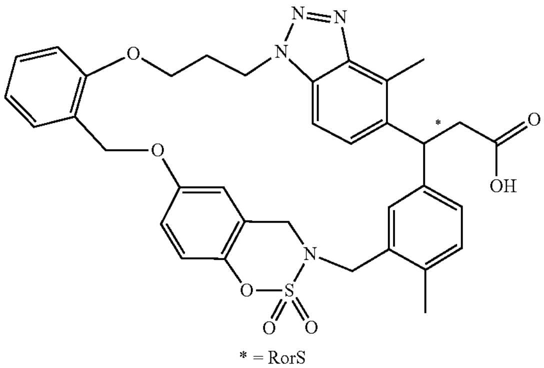

* = RorS

Step A1: Preparation of 3-(4-bromo-3-methyl-2-nitroanilino)propan-1-ol

1-Bromo-4-fluoro-2-methyl-3-nitrobenzene (1 eq., 90 g, 385 mmol) was taken up in 3-aminopropan-1-ol (2.2 eq, 64 g, 847 mmol) under $N_2$ at RT. The mixture was heated at 80° C. for 1 h. After completion of the reaction, the mixture was cooled to Rt and diluted with DCM. This solution was washed with water. The organic layer was dried over $MgSO_4$, filtered and evaporated to dryness to get the crude product, which was purified by trituration with petroleum ether (104 g, 94% yield).

$^1$H-NMR (500 MHz, DMSO-d6) δ ppm: 7.54 (d, 1H), 6.74 (d, 1H), 6.24 (t, 1H), 4.61 (t, 1H), 3.47 (q, 2H), 3.19 (q, 2H), 2.25 (s, 3H), 1.67 (m, 2H)

Step A2: Preparation of 3-(2-amino-4-bromo-3-methylanilino)propan-1-ol

To the stirred solution of 3-(4-bromo-3-methyl-2-nitroanilino)propan-1-ol (1 eq., 104 g, 360 mmol) in EtOH (1000 mL) and water (200 mL), $NH_4Cl$ (5 eq., 97.2 g, 1800 mmol) and iron powder (5 eq., 100.8 g, 1800 mmol) were added and the mixture was heated at 90° C. overnight. After completion of the reaction, the mixture was cooled to RT and filtered through a Celite pad. The filtrate was evaporated till water and extracted with EtOAc. The organic layer was separated and dried over $Na_2SO_4$. Filtration and evaporation of the mother liquor gave the crude product, which was purified by normal phase silica gel chromatography using EtOAc-petroleum ether (0:100 to 50:50%) as an eluent (80 g, 86% yield).

$^1$H-NMR (500 MHz, DMSO-d6) δ ppm: 6.71 (d, 1H), 6.26 (d, 1H), 4.58 (br, 3H), 4.48 (br, 1H), 3.52 (q, 2H), 3.04 (q, 2H), 2.16 (s, 3H), 1.73 (m, 2H)

Step A3: Preparation 3-(5-bromo-4-methyl-1H-benzotriazol-1-yl)propan-1-ol

To the stirred solution of 3-(2-amino-4-bromo-3-methylanilino)propan-1-ol (1 eq., 10 g, 0.038 mol) in THF (150 mL) and AcOH (15 mL), 3-methylbutyl nitrite (3 eq., 13.6 g, 0.115 mol) was added at RT. The reaction mixture was stirred for 1 h at RT. After completion of the reaction, the mixture was poured into ice-water. Extraction with EtOAc, drying of the organic layer over $MgSO_4$, filtration and evaporation to dryness afforded the crude product, which was purified by normal phase silica gel chromatography using EtOAc-petroleum ether (0:100 to 40:60%) to give the title compound (4 g, 38% yield).

$^1$H-NMR (500 MHz, DMSO-d6) δ ppm: 7.70 (d, 2H), 7.68 (d, 2H), 4.74 (t, 2H), 4.67 (t, 1H), 3.40 (q, 2H), 2.72 (s, 3H), 2.05 (m, 2H)

Step A4: Preparation of ethyl (2E)-3-[1-(3-hydroxypropyl)-4-methyl-1H-benzotriazol-5-yl]prop-2-enoate To the stirred solution of 3-(5-bromo-4-methyl-1H-benzotriazol-1-yl)propan-1-ol (1 eq., 8 g, 0.029 mol) in a mixture of THF (120 mL) and water (20 mL) $Na_2CO_3$ (2.5 eq., 7.85 g, 0.079 mol) and ethyl (2E)-3-(4,4,5,5-tetramethyl-1,3,2-dioxaborolan-2-yl)prop-2-enoate (1.2 eq., 8.04 g, 0.035 mol) were added and the mixture was degassed with $N_2$ for 30 min. Finally A$^{ta}$phos·$PdCl_2$ catalyst (0.02 eq., 0.52 g, 0.0007 mol) was added and the mixture was heated at 70° C. for 2 h. After completion of the reaction the mixture was poured into ice-water and extracted with EtOAc. The organic phase was dried and evaporated. The received crude product was purified by trituration with $Et_2O$ to give the title compound (12.6 g, 47% yield).

$^1$H-NMR (500 MHz, DMSO-d6) δ ppm: 8.03 (d, 1H), 7.98 (d, 1H), 7.71 (d, 1H), 6.66 (d, 1H), 4.75 (t, 2H), 4.68 (t, 1H), 4.22 (q, 2H), 3.39 (q, 2H), 2.81 (s, 3H), 2.04 (m, 2H), 1.28 (t, 3H)

Step 1: Preparation of ethyl 3-(3-{[6-(benzyloxy)-2,2-dioxo-2H-1,2λ$^6$,3-benzoxathiazin-3(4H)-yl]methyl}-4-methylphenyl)-3-[1-(3-hydroxypropyl)-4-methyl-1H-benzotriazol-5-yl]propanoate Using General Procedure 6 starting from ethyl (2E)-3-[1-(3-hydroxypropyl)-4-methyl-1H-benzotriazol-5-yl]prop-2-enoate (1 eq.) and 6-(benzyloxy)-3-{[2-methyl-5-(4,4,5,5-tetramethyl-1,3,2-dioxaborolan-2-yl)phenyl]methyl}-3,4-dihydro-2H-1,2λ$^6$,3-benzoxathiazine-2,2-dione (2 eq.) as reactants, the title compound (yellow solid foam, 77% yield) was obtained.

$^1$H-NMR (500 MHz, DMSO-d6) δ ppm: 7.58 (d, 1H), 7.49-7.31 (m, 5H), 7.49 (d, 1H), 7.23 (d, 1H), 7.19 (dd, 1H), 7.13 (d, 1H), 7.13 (d, 1H), 7.07 (dd, 1H), 6.97 (d, 1H), 5.11 (s, 2H), 4.85 (t, 1H), 4.65 (t, 2H), 4.65 (t, 1H), 4.44 (s, 2H), 4.22 (s, 2H), 3.92 (q, 2H), 3.36 (m, 2H), 3.19/3.15 (dd+dd, 2H), 2.77 (s, 3H), 2.21 (s, 3H), 1.99 (m, 2H), 0.99 (t, 3H)

Step 2: Preparation of ethyl 3-{3-[(6-hydroxy-2,2-dioxo-2H-1,2λ$^6$,3-benzoxathiazin-3(4H)-yl)methyl]-4-methylphenyl}-3-[1-(3-hydroxypropyl)-4-methyl-1H-benzotriazol-5-yl]propanoate Using General Procedure 8 starting from ethyl 3-(3-{[6-(benzyloxy)-2,2-dioxo-2H-1,2λ$^6$,3-benzoxathiazin-3(4H)-yl]methyl}-4-methylphenyl)-3-[1-(3-hydroxypropyl)-4-methyl-1H-benzotriazol-5-yl]propanoate (1 eq.) as a reactant, the title compound (white solid foam, 93% yield) was obtained.

$^1$H-NMR (500 MHz, DMSO-d6) δ ppm: 9.71 (brs., 1H), 7.6 (d, 1H), 7.5 (d, 1H), 7.22 (d, 1H), 7.19 (dd, 1H), 7.13 (d, 1H), 6.99 (d, 1H), 6.79 (dd, 1H), 6.6 (d, 1H), 4.84 (t, 1H), 4.68 (t, 2H), 4.67 (br., 1H), 4.4/4.36 (d+d, 2H), 4.21/4.17 (d+d, 2H), 3.94 (q, 2H), 3.38 (t, 2H), 3.19/3.15 (dd+dd, 2H), 2.76 (s, 3H), 2.22 (s, 3H), 2.01 (m, 2H), 1 (t, 3H)

Step 3: Preparation of ethyl 3-[1-(3-chloropropyl)-4-methyl-1H-benzotriazol-5-yl]-3-{3-[(6-hydroxy-2,2-dioxo-2H-1,2λ$^6$,3-benzoxathiazin-3(4H)-yl)methyl]-4-methylphenyl}propanoate Using General Procedure 10 starting from ethyl 3-{3-[(6-hydroxy-2,2-dioxo-2H-1,2λ$^6$,3-benzoxathiazin-3(4H)-yl)methyl]-4-methylphenyl}-3-[1-(3-hydroxypropyl)-4-methyl-1H-benzotriazol-5-yl]propanoate (1 eq.) as a reactant, the title compound (yellow solid foam, 97% yield) was obtained.

$^1$H-NMR (500 MHz, DMSO-d6) δ ppm: 9.72 (brs., 1H), 7.62 (d, 1H), 7.53 (d, 1H), 7.22 (d, 1H), 7.2 (dd, 1H), 7.13 (d, 1H), 6.99 (d, 1H), 6.79 (dd, 1H), 6.6 (d, 1H), 4.84 (t, 1H), 4.77 (t, 2H), 4.39/4.35 (d+d, 2H), 4.21/4.17 (d+d, 2H), 3.94 (q, 2H), 3.61 (m, 2H), 3.19/3.15 (dd+dd, 2H), 2.76 (s, 3H), 2.34 (m, 2H), 2.22 (s, 3H), 1 (t, 3H)

Step 4: Preparation of ethyl 3-{1-[3-(2-formylphenoxy)propyl]-4-methyl-1H-benzotriazol-5-yl}-3-{3-[(6-hydroxy-2,2-dioxo-2H-1,2λ$^6$,3-benzoxathiazin-3(4H)-yl)methyl]-4-methylphenyl}propanoate Ethyl 3-[1-(3-chloropropyl)-4-methyl-1H-benzotriazol-5-yl]-3-{3-[(6-hydroxy-2,2-dioxo-2H-1,2λ$^6$,3-benzoxathiazin-3(4H)-yl)methyl]-4-methylphenyl}propanoate (1 eq., 0.65 g, 1.1 mmol) was dissolved in dry N,N-dimethylacetamide (5 mL) and 2-hydroxybenzaldehyde (34 eq., 4 mL, 37.536 mmol) was added followed by addition of $Cs_2CO_3$ (5.55 eq., 2.0 g, 6.1 mmol). The solution was heated at 1200 for 2 h. The crude product was purified by normal phase silica gel chromatography using DCM-MeOH (100:0 to 95:5) as eluents resulted in 0.49 g (66% yield) of the title compound as a light orange solid.

$^1$H-NMR (500 MHz, DMSO-d6) δ ppm: 10.12 (d, 1H), 9.7 (brs, 1H), 7.63 (d, 1H), 7.62 (d, 1H), 7.58 (t, 1H), 7.45 (d, 1H), 7.2 (d, 1H), 7.16 (dd, 1H), 7.12 (d, 1H), 7.1 (d, 1H), 7.03 (t, 1H), 6.99 (d, 1H), 6.78 (dd, 1H), 6.6 (d, 1H), 4.89 (t, 2H), 4.82 (t, 1H), 4.39/4.35 (d+d, 2H), 4.21/4.16 (d+d, 2H), 4.11 (t, 2H), 3.93 (q, 2H), 3.17/3.11 (dd+dd, 2H), 2.73 (s, 3H), 2.41 (qn, 2H), 2.22 (s, 3H), 1 (t, 3H)

Step 5: Preparation of ethyl 3-{3-[(6-hydroxy-2,2-dioxo-2H-1,2)$^6$,3-benzoxathiazin-3(4H)-yl)methyl]-4-methylphenyl}-3-(1-{3-[2-(hydroxymethyl)phenoxy]propyl}-4-methyl-1H-benzotriazol-5-yl)propanoate Ethyl 3-{11-[3-(2-formylphenoxy)propyl]-4-methyl-1H-benzotriazol-5-yl}-3-{3-[(6-hydroxy-2,2-dioxo-2H-1,2λ$^6$,3-benzoxathiazin-3(4H)-yl)methyl]-4-methylphenyl}propanoate (1 eq., 0.48 g, 0.69 mmol) was dissolved in dry EtOH (5 mL), and sodium borohydride (3.77 eq., 0.10 g, 2.6 mmol) was added. The solution was stirred at RT for 2 h. The reaction mixture was poured on crushed ice and concentrated. The residue was partitioned between water and EtOAc, the phases were separated and the aq. phase was extracted with additional portions of EtOAc. The collected organic phases were dried over $Na_2SO_4$, filtered and evaporated. Drying of the residue in high vacuo at RT resulted in 0.466 g (97% yield) of a title compound as an off-white foamy material.

$^1$H-NMR (500 MHz, DMSO-d6) δ ppm: 9.56 (brs, 1H), 7.61 (d, 1H), 7.48 (d, 1H), 7.36 (d, 1H), 7.2 (d, 1H), 7.17 (dd, 1H), 7.14 (t, 1H), 7.13 (d, 1H), 6.96 (d, 1H), 6.91 (t, 1H), 6.82 (d, 1H), 6.76 (dd, 1H), 6.56 (d, 1H), 4.84 (t, 1H), 4.83 (t, 2H), 4.52 (s, 2H), 4.35 (s, 2H), 4.2/4.16 (d+d, 2H), 3.94 (m, 2H), 3.93 (q, 2H), 3.17/3.13 (dd+dd, 2H), 2.75 (s, 3H), 2.33 (qn, 2H), 2.22 (s, 3H), 1 (t, 3H)

Step 6: Preparation of ethyl[4,38-dimethyl-34,34-dioxo-20,28,33-trioxa-34)$^6$-thia-1,14,15,16-tetraazaheptacyclo[27.5.3.1$^{3,7}$0.1$^{9,13}$0.0$^{12,16}$0.0$^{21,26}$0.0$^{32,36}$]nonatriaconta-3(39),4,6,9(38),10,12,14,21,23,25,29,31,36-tridecaen-8-yl]acetate Ethyl 3-{3-[(6-hydroxy-2,2-dioxo-2H-1,2λ$^6$,3-benzoxathiazin-3(4H)-yl)methyl]-4-methylphenyl}-3-(1-{3-[2-(hydroxymethyl)phenoxy]propyl}-4-methyl-1H-benzotriazol-5-yl)propanoate (1 eq., 0.66 mmol, 0.46 g) was dissolved in dry THF (40 mL) and $PPh_3$ (3 eq., 0.52 g, 2 mmol) was added followed by addition of DIAD (3 eq., 0.40 g, 2.0 mmol) while cooling. The reaction mixture was stirred at RT for 1.5 h. The solvent was evaporated and the crude product was purified by normal phase silica gel chromatography using heptane-EtOAc (100:0 to 30:70) as eluents resulted in 0.187 g (42% yield) of the title compound as a white foamy material.

The enantiopure final intermediates were obtained by chromatographic separation on chiral column. (ee-99.9%)

$^1$H-NMR (500 MHz, DMSO-d6) δ ppm: 7.63 (d, 1H), 7.58 (d, 1H), 7.58 (dm, 1H), 7.36 (dd, 1H), 7.35 (d, 1H), 7.33 (m, 1H), 7.22 (dd, 1H), 7.17 (d, 1H), 7.15 (d, 1H), 7.06 (dm, 1H), 7.02 (m, 1H), 6.91 (d, 1H), 5.27 (s, 2H), 4.9/4.82 (m+m, 2H), 4.85 (t, 1H), 4.43/4.09 (d+d, 2H), 4.29/4.02 (d+d, 2H), 4.18/4.02 (m+m, 2H), 3.88 (m, 2H), 3.19/3.11 (dd+dd, 2H), 2.81 (s, 3H), 2.37/2.27 (m+m, 2H), 2.28 (s, 3H), 0.96 (t, 3H)

Step 7: Preparation of Example 57

Using General Procedure 12 starting from ethyl[4,38-dimethyl-34,34-dioxo-20,28,33-trioxa-34λ$^6$-thia-1,14,15,16-tetraazaheptacyclo[27.5.3.1$^{3,7}$0.1$^{9,13}$0.0$^{12,16}$0.0$^{21,26}$0.0$^{32,36}$]nonatriaconta-3(39),4,6,9(38),10,12,14,21,23,25,29,31,36-tridecaen-8-yl]acetate E1 (1 eq.) or E2 (1 eq.) as reactants, the title compounds (75%-83% yields respectively) were obtained.

EXAMPLE 57a (E1)

HRMS calculated for $C_{35}H_{34}N_4O_7S$: 654.2148; [M+H]$^+$ found: 655.2224 (δ=0.5 ppm).

EXAMPLE 57b (E2)

HRMS calculated for $C_{35}H_{34}N_4O_7S$: 654.2148; [M+H]$^+$ found: 655.2231 (δ=1.5 ppm).

$^1$H-NMR (500 MHz, DMSO-d6) δ ppm: 12.07 (brs, 1H), 7.63 (d, 1H), 7.58 (d, 1H), 7.57 (s, 1H), 7.36 (dd, 1H), 7.34 (t, 1H), 7.33 (d, 1H), 7.21 (dd, 1H), 7.16 (d, 1H), 7.15 (d, 1H), 7.07 (d, 1H), 7.02 (t, 1H), 6.91 (d, 1H), 5.27 (s, 2H), 4.9/4.82 (m+m, 2H), 4.83 (t, 1H), 4.43/4.1 (d+d, 2H), 4.28/4.03 (d+d, 2H), 4.17/4.05 (m+m, 2H), 3.07/3.03 (dd+dd, 2H), 2.81 (s, 3H), 2.37/2.28 (m+m, 2H), 2.28 (s, 3H)

$^{13}$C-NMR (125 MHz, DMSO-d6) δ ppm: 173.2, 156.1, 156.1, 146.2, 144.8, 142.2, 137.4, 136.2, 132.4, 131.8, 131.2, 130.1, 129.9, 129.4, 129.3, 127.3, 126.8, 125, 120.9, 119.6, 118.3, 117, 112.4, 111.8, 107.7, 65.4, 64, 51.9, 49.1, 44.3, 41.1, 40.8, 30.1, 18.3, 13.3

EXAMPLE 58: [4,32-Dimethyl-28,28-dioxo-19-phenyl-22,27-dioxa-28λ$^6$-thia-1,14,15,16,19-pentaazahexacyclo[21.5.3.1$^{3,7}$0.1$^{9,13}$0.0$^{12,16}$0.0$^{26,30}$]tritriaconta-3(33),4,6,9(32),10,12,14,23,25,30-decaen-8-yl]acetic acid enantiomer 1

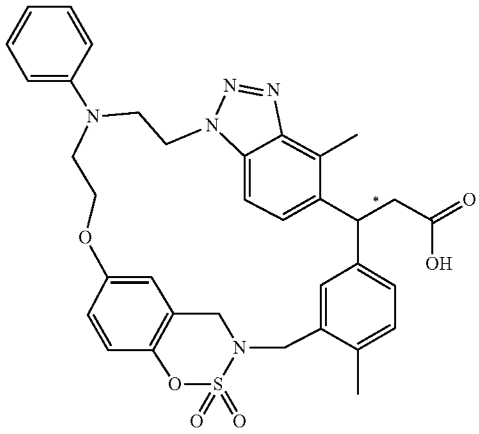

* = RorS enantiomer 2

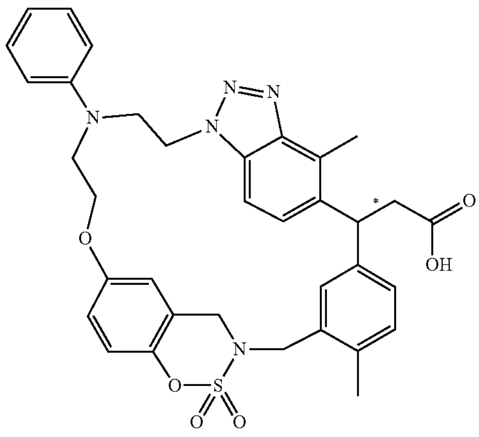

* = RorS

Step A1: Preparation of 2-(4-bromo-3-methyl-2-nitroanilino)ethan-1-ol

1-Bromo-4-fluoro-2-methyl-3-nitrobenzene (1 eq., 600 g, 2.56 mol) was taken up in ethanolamine (2.5 eq, 332 g, 5.45 mol) under $N_2$ at RT. After heating at 95° C. for 1.5 h, the reaction mixture was cooled to Rt and diluted with DCM. The solution was washed with water. The organic layer was dried over $MgSO_4$ and evaporated to dryness to get the crude product, which was purified by trituration with petroleum ether to give the title compound (630 g, 89% yield).

$^1$H-NMR (500 MHz, DMSO-d6) δ ppm: 7.59 (d, 1H), 6.79 (d, 1H), 6.09 (t, 1H), 4.84 (t, 1H), 3.54 (q, 2H), 3.19 (q, 2H), 2.27 (s, 3H)

Step A2: Preparation of 2-(2-amino-4-bromo-3-methylanilino)ethan-1-ol

To the stirred solution of 2-(4-bromo-3-methyl-2-nitroanilino)ethan-1-ol (1 eq., 630 g, 2.29 mol) in EtOH (500 mL)

and water (100 mL), $NH_4Cl$ (5 eq., 611 g, 11.45 mol) and zinc powder (5 eq., 744 g, 11.45 mol) were added and the mixture was heated at 95° C. for 12 h. After completion of the reaction, the mixture was filtered through a pad of Celite. The filtrate was evaporated and the residue was stirred for 3 h in 2 L water. The precipitated product was filtered off, dried and purified by trituration with pentane. (430 g, 77% yield)

$^1$H-NMR (500 MHz, DMSO-d6) δ ppm: 6.72 (d, 1H), 6.28 (d, 1H), 4.67 (t, 1H), 4.58 (s, 2H), 4.51 (t, 1H), 3.59 (q, 2H), 3.06 (q, 2H), 2.17 (s, 3H)

Step A3: Preparation of 2-(5-bromo-4-methyl-1H-benzotriazol-1-yl)ethan-1-ol

To the stirred solution of 2-(2-amino-4-bromo-3-methyl-anilino)ethan-1-ol (1 eq., 160 g, 0.652 mol) and tetrafluoroboric acid (2 eq., 160 mL, 1.3 mol) in MeCN (1500 mL), 3-methylbutyl nitrite (1.5 eq., 114.7 g, 0.979 mol) and tetrafluoroboric acid (2 eq., 160 mL, 1.3 mol) in MeCN were added within 2.5 h. The internal temperature must remain under 5° C. during this process. After completion of the reaction, the mixture was poured into ice-water, basified with 10% NaOH solution and extracted with EtOAc. The organic layer was dried over $MgSO_4$ and evaporated to dryness. The crude product was purified by column chromatography (90 g, 48% yield).

$^1$H-NMR (500 MHz, DMSO-d6) δ ppm: 7.67 (s, 2H), 4.98 (t, 1H), 4.74 (t, 2H), 3.86 (q, 2H), 2.72 (s, 3H)

Step A4: Preparation of ethyl (2E)-3-[1-(2-hydroxy-ethyl)-4-methyl-1H-benzotriazol-5-yl]prop-2-enoate To the stirred solution of 2-(5-bromo-4-methyl-1H-benzotriazol-1-yl)ethan-1-ol (1 eq., 50 g, 0.19 mol) in a mixture of THF (450 mL) and water (50 mL), $Na_2CO_3$ (2.5 eq., 51.2 g, 0.48 mol) and ethyl (2E)-3-(4,4,5,5-tetramethyl-1,3,2-dioxaborolan-2-yl)prop-2-enoate (1.2 eq., 53 g, 0.23 mol) were added and the mixture was degassed with $N_2$ for 30 min. $A^{ta}$phos·$PdCl_2$ catalyst (0.02 eq., 2.76 g, 0.04 mol) was added and the mixture was heated at 70° C. for 8 h. After completion of the reaction the mixture was poured into ice-water and extracted with EtOAc. The organic phase was dried and evaporated. The received crude product was purified by trituration with $Et_2O$ (46 g, 86% yield).

$^1$H-NMR (500 MHz, DMSO-d6) δ ppm: 8.03 (d, 1H), 7.95 (d, 1H), 7.70 (d, 1H), 6.65 (d, 1H), 4.98 (t, 1H), 4.74 (t, 2H), 4.22 (q, 2H), 3.87 (q, 2H), 2, 82 (s, 3H), 1.28 (t, 3H)

Step 1: Preparation of ethyl 3-(3-{[6-(benzyloxy)-2,2-dioxo-2H-1,2λ$^6$,3-benzoxathiazin-3(4H)-yl]methyl}-4-methylphenyl)-3-[1-(2-hydroxyethyl)-4-methyl-1H-benzotriazol-5-yl]propanoate Using General Procedure 6 starting from ethyl (2E)-3-[1-(2-hydroxyethyl)-4-methyl-1H-benzotriazol-5-yl]prop-2-enoate (1 eq.) and 6-(benzyloxy)-3-{[2-methyl-5-(4,4,5,5-tetramethyl-1,3,2-dioxaborolan-2-yl)phenyl]methyl}-3,4-dihydro-2H-1,2λ$^6$,3-benzoxathiazine-2,2-dione (1.3 eq.) as reactants, the title compound (yellow solid foam, 82% yield) was obtained.

$^1$H-NMR (500 MHz, DMSO-d6) δ ppm: 7.58 (d, 1H), 7.47 (m, 2H), 7.47 (d, 1H), 7.41 (tm, 2H), 7.35 (tm, 1H), 7.24 (d, 1H), 7.18 (dd, 1H), 7.14 (d, 1H), 7.13 (d, 1H), 7.07 (dd, 1H), 6.97 (d, 1H), 5.11 (s, 2H), 4.95 (t, 1H), 4.85 (t, 1H), 4.64 (t, 2H), 4.46/4.42 (d+d, 2H), 4.24/4.2 (d+d, 2H), 3.93 (q, 2H), 3.81 (q, 2H), 3.2/3.15 (dd+dd, 2H), 2.77 (s, 3H), 2.21 (s, 3H), 1.01 (t, 3H)

Step 2: Preparation of ethyl 3-(3-{[6-(benzyloxy)-2,2-dioxo-2H-1,2λ$^6$,3-benzoxathiazin-3(4H)-yl]methyl}-4-methylphenyl)-3-[1-(2-chloroethyl)-4-methyl-1H-benzotriazol-5-yl]propanoate Using General Procedure 10 starting from ethyl 3-(3-{[6-(benzyloxy)-2,2-dioxo-2H-1,2λ$^6$,3-benzoxathiazin-3(4H)-yl]methyl}-4-methylphenyl)-3-[1-(2-hydroxyethyl)-4-methyl-1H-benzotriazol-5-yl]propanoate (1 eq.) as a reactant, the title compound (beige solid foam, 88% yield) was obtained. The product was used in the next step without further purification.

$^1$H-NMR (500 MHz, DMSO-d6) δ ppm: 7.65 (d, 1H), 7.52 (d, 1H), 7.46 (d, 2H), 7.44 (t, 2H), 7.35 (t, 1H), 7.25 (d, 1H), 7.2 (dd, 1H), 7.14 (d, 1H), 7.14 (d, 1H), 7.07 (dd, 1H), 6.96 (d, 1H), 5.1 (s, 2H), 4.99 (t, 2H), 4.85 (t, 1H), 4.46/4.42 (d+d, 2H), 4.23/4.2 (d+d, 2H), 4.12 (t, 2H), 3.93 (q, 2H), 3.2/3.16 (dd+dd, 2H), 2.78 (s, 3H), 2.21 (s, 3H), 0.98 (t, 3H)

Step 3: Preparation of ethyl 3-(3-{[6-(benzyloxy)-2,2-dioxo-2H-1,2λ$^6$,3-benzoxathiazin-3(4H)-yl]methyl}-4-methylphenyl)-3-(1-{2-[(2-hydroxyethyl)(phenyl)amino]ethyl}-4-methyl-1H-benzotriazol-5-yl)propanoate Ethyl 3-(3-{[6-(benzyloxy)-2,2-dioxo-2H-1,2λ$^6$,3-benzoxathiazin-3(4H)-yl]methyl}-4-methylphenyl)-3-[1-(2-chloroethyl)-4-methyl-1H-benzotriazol-5-yl]propanoate (1 eq., 1 g, 1.378 mmol) was dissolved in 2-anilinoethanol (20 eq., 3.78 g, 27.56 mmol). The reaction mixture was heated at 130° C. for 13 h. After cooling to Rt, the mixture was diluted with water and extracted with EtOAc. The organic phase was dried over $MgSO_4$, filtered and concentrated to dryness to give the crude product, which was purified via normal phase silica gel chromatography using heptane-AcOEt (0 to 50:50) as an eluent to give the title compound (643 mg, white solid, 59% yield).

$^1$H-NMR (500 MHz, DMSO-d6) δ ppm: 7.48 (s, 1H), 7.48 (s, 1H), 7.48-7.31 (m, 5H), 7.22 (d, 1H), 7.17 (dd, 1H), 7.15-6.55 (m, 5H), 7.14 (d, 1H), 7.14 (d, 1H), 7.07 (dd, 1H), 6.96 (d, 1H), 5.1 (s, 2H), 4.84 (t, 1H), 4.78 (t, 2H), 4.65 (t, 1H), 4.46/4.42 (d+d, 2H), 4.23/4.2 (d+d, 2H), 3.92 (q, 2H), 3.84 (m, 2H), 3.36 (m, 2H), 3.16 (m, 2H), 3.09 (m, 2H), 2.75 (s, 3H), 2.21 (s, 3H), 0.99 (t, 3H)

Step 4: Preparation of ethyl 3-{3-[(6-hydroxy-2,2-dioxo-2H-1,2λ$^6$,3-benzoxathiazin-3(4H)-yl)methyl]-4-methylphenyl}-3-(1-{2-[(2-hydroxyethyl)(phenyl)amino]ethyl}-4-methyl-1H-benzotriazol-5-yl)propanoate Ethyl 3-(3-{[6-(benzyloxy)-2,2-dioxo-2H-1,2λ$^6$,3-benzoxathiazin-3(4H)-yl]methyl}-4-methylphenyl)-3-(1-{12-[(2-hydroxyethyl)(phenyl)amino]ethyl}-4-methyl-1H-benzotriazol-5-yl)propanoate (1 eq., 637 mg, 0.806 mmol) and Pd/C catalyst (230 mg) were suspensed in EtOH (25 mL) and dioxane (5 mL). The mixture was hydrogenated in a stainless steel reaction vessel under 2 bar pressure at RT for 18 hours. Filtration through a Celite pad and evaporation to dryness resulted in the crude product, which was triturated with $Et_2O$ then dissolved in EtOH and evaporated to give the title compound (530 mg, white solid, 94% yield).

$^{1}$H-NMR (500 MHz, DMSO-d6) δ ppm: 9.7 (s, 1H), 7.6 (d, 1H), 7.5 (d, 1H), 7.21 (d, 1H), 7.17 (dd, 1H), 7.13-6.59 (m, 5H), 7.13 (d, 1H), 6.99 (d, 1H), 6.79 (dd, 1H), 6.61 (d, 1H), 4.83 (t, 1H), 4.81 (t, 2H), 4.66 (t, 1H), 4.4/4.36 (d+d, 2H), 4.21/4.17 (d+d, 2H), 3.93 (q, 2H), 3.85 (m, 2H), 3.38 (q, 2H), 3.17 (d, 2H), 3.11 (t, 2H), 2.74 (s, 3H), 2.22 (s, 3H), 1 (t, 3H)

Step 5: Preparation of ethyl[4,32-dimethyl-28,28-dioxo-19-phenyl-22,27-dioxa-28)$^{6}$-thia-1,14,15,16,19-pentaazahexacyclo[21.5.3.1$^{3,7}$0.1$^{9,13}$0.0$^{12,16}$0.0$^{26,30}$]tritriaconta-3(33),4,6,9(32),10,12,14,23,25,30-decaen-8-yl]acetate Ethyl 3-{3-[(6-hydroxy-2,2-dioxo-2H-1,2λ$^{6}$,3-benzoxathiazin-3(4H)-yl)methyl]-4-methylphenyl}-3-(1-{12-[(2-hydroxyethyl)(phenyl)amino]ethyl}-4-methyl-1H-benzotriazol-5-yl)propanoate (1 eq., 248 mg, 0.3540 mmol) was dissolved in THF (50 mL) and $PPh_3$ (4 eq., 371 mg, 1.416 mmol) was added. The mixture was cooled to −5° C. and DIAD (4 eq., 286 mg, 1.416 mmol) was added dropwise. The mixture was heated at reflux temperature for 1 h. After completion of the reaction the solvent was evaporated, the crude product was purified via normal phase silica gel chromatography using heptane-AcOEt (60:40) as an eluent to give the title compound (157 mg, white solid, 65% yield).

The enantiopure final intermediates were obtained by chromatographic separation on chiral column.

$^{1}$H-NMR (500 MHz, DMSO-d6) δ ppm: 7.67 (d, 1H), 7.46 (d, 1H), 7.45 (dd, 1H), 7.26 (d, 1H), 7.25-6.67 (m, 5H), 7.07 (d, 1H), 6.9 (dd, 1H), 6.88 (d, 1H), 6.1 (d, 1H), 4.89/4.85 (m+m, 2H), 4.82 (t, 1H), 4.13 (s, 2H), 4.13/3.94 (m+m, 2H), 4.01/3.93 (d+d, 2H), 3.9 (q, 2H), 3.8/3.58 (m+m, 2H), 3.67/3.42 (m+m, 2H), 3.1/3.03 (dd+dd, 2H), 2.72 (s, 3H), 2.32 (s, 3H), 0.99 (t, 3H)

Step 6: Preparation of Example 58

Using General Procedure 12 starting from ethyl[4,32-dimethyl-28,28-dioxo-19-phenyl-22,27-dioxa-28λ$^{6}$-thia-1,14,15,16,19-pentaazahexacyclo[21.5.3.1$^{3,7}$0.1$^{9,13}$0.0$^{12,16}$0.0$^{26,30}$]tritriaconta-3(33),4,6,9(32),10,12,14,23,25,30-decaen-8-yl]acetate E1 (1 eq.) or E2 (1 eq.) as reactants, the title compounds (68%-82% yields respectively) were obtained.

EXAMPLE 58a (E1)

HRMS calculated for $C_{35}H_{35}N_5O_6S$: 653.2308; $[M+H]^+$ found: 654.236 (δ=−3.2 ppm).

EXAMPLE 58b (E2)

HRMS calculated for $C_{35}H_{35}N_5O_6S$: 653.2308; $[M+H]^+$ found: 654.2359 (δ=−3.3 ppm).

$^{1}$H-NMR (500 MHz, DMSO-d6) δ ppm: 12.13 (brs, 1H), 7.66 (d, 1H), 7.46 (dd, 1H), 7.43 (d, 1H), 7.27 (d, 1H), 7.23 (t, 2H), 7.06 (d, 1H), 6.89 (dd, 1H), 6.86 (d, 2H), 6.84 (d, 1H), 6.71 (t, 1H), 6.07 (d, 1H), 4.88/4.86 (m+m, 2H), 4.8 (t, 1H), 4.17/4.09 (d+d, 2H), 4.15/3.95 (m+m, 2H), 3.99/3.96 (d+d, 2H), 3.77/3.55 (m+m, 2H), 3.65/3.4 (m+m, 2H), 3.02/2.91 (dd+dd, 2H), 2.72 (s, 3H), 2.32 (s, 3H)

$^{13}$C-NMR (125 MHz, DMSO-d6) δ ppm: 173.2, 155.6, 147.9, 146.4, 144.9, 141.8, 137.3, 136.3, 132, 132, 131.6, 131.3, 129.8, 128.5, 127.5, 127.3, 119.5, 117.5, 117.4, 116.4, 113.2, 112.5, 108.1, 66.6, 51.9, 50.6, 49.8, 48.5, 46.2, 41.3, 41, 18.4, 13.4

EXAMPLE 59: [4-Methoxy-32-methyl-28,28-dioxo-19,22,27-trioxa-28λ$^{6}$-thia-1,14,15,16-tetraazahexacyclo[21.5.3.1$^{3,7}$0.1$^{9,13}$0.0$^{12,16}$0.0$^{26,30}$]tritriaconta-3(33),4,6,9(32),10,12,14,23,25,30-decaen-8-yl]acetic acid enantiomer 1

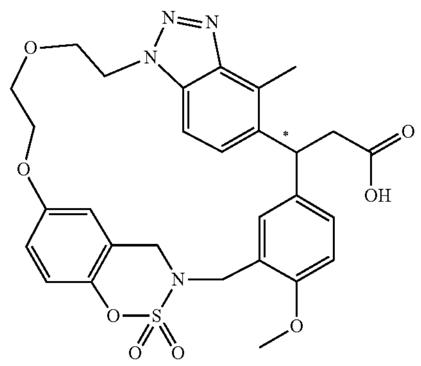

* = RorS enantiomer 2

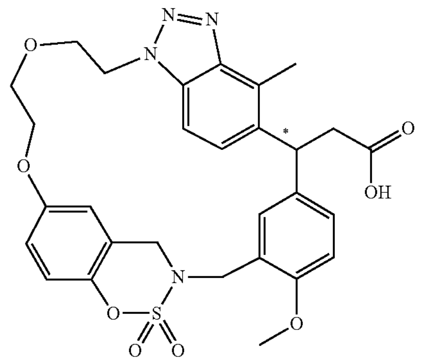

* = RorS

Step 1: Preparation of 6-(benzyloxy)-3-[(5-bromo-2-methoxyphenyl)methyl]-3,4-dihydro-2H-1,2λ$^{6}$,3-benzoxathiazine-2,2-dione Using General Procedure 7 starting from (5-bromo-2-methoxyphenyl)methanol (1 eq.) and 6-(benzyloxy)-3,4-dihydro-2H-1,2λ$^{6}$,3-benzoxathiazine-2,2-dione (0.77 eq.) as reactants, the title compound (82% yield) was obtained as a white solid.

$^{1}$H-NMR (500 MHz, DMSO-d6) δ ppm: 7.49 (dd, 1H), 7.48-7.29 (m, 5H), 7.45 (d, 1H), 7.06 (m, 1H), 7.01 (m, 1H), 7.01 (m, 1H), 6.96 (d, 1H), 5.08 (s, 2H), 4.65 (s, 2H), 4.26 (s, 2H), 3.72 (s, 3H)

Step 2: Preparation of 6-(benzyloxy)-3-{[2-methoxy-5-(4,4,5,5-tetramethyl-1,3,2-dioxaborolan-2-yl)phenyl]methyl}-3,4-dihydro-2H-1,2λ$^{6}$,3-benzoxathiazine-2,2-dione Using General Procedure 3 starting from 6-(benzyloxy)-3-[(5-bromo-2-methoxyphenyl)methyl]-3,4-dihydro-2H-1,2λ$^{6}$,3-benzoxathiazine-2,2-dione (1 eq.) as a reactant, the title compound (87% yield) was obtained as a beige solid.

$^1$H-NMR (500 MHz, DMSO-d6) δ ppm: 7.66 (dd, 1H), 7.6 (d, 1H), 7.44 (d, 2H), 7.4 (t, 2H), 7.34 (t, 1H), 7.08 (d, 1H), 7.02 (dd, 1H), 7.02 (d, 1H), 7 (d, 1H), 5.07 (s, 2H), 4.59 (s, 2H), 4.26 (s, 2H), 3.75 (s, 3H), 1.28 (s, 12H)

Step 3: Preparation of ethyl 3-(3-{[6-(benzyloxy)-2,2-dioxo-2H-1,2λ$^6$,3-benzoxathiazin-3(4H)-yl]methyl}-4-methoxyphenyl)-3-(1-{2-[2-(benzyloxy)ethoxy]ethyl}-4-methyl-1H-benzotriazol-5-yl)propanoate Using General Procedure 6 starting from ethyl (2E)-3-(1-{2-[2-(benzyloxy)ethoxy]ethyl}-4-methyl-1H-benzotriazol-5-yl)prop-2-enoate (1 eq.) and 6-(benzyloxy)-3-{[2-methoxy-5-(4,4,5,5-tetramethyl-1,3,2-dioxaborolan-2-yl)phenyl]methyl}-3,4-dihydro-2H-1,2λ$^6$,3-benzoxathiazine-2,2-dione (1.3 eq.) as reactants, the title compound (52% yield) was obtained.

$^1$H-NMR (500 MHz, DMSO-d6) δ ppm: 7.62 (d, 1H), 7.47-7.14 (m, 12H), 7.42 (d, 1H), 6.98 (dd, 1H), 6.96 (d, 1H), 6.92 (d, 1H), 6.84 (d, 1H), 5.07 (s, 2H), 4.81 (m, 2H), 4.81 (t, 1H), 4.52 (s, 2H), 4.3 (s, 2H), 4.19 (s, 2H), 3.92 (q, 2H), 3.88 (t, 2H), 3.64 (s, 3H), 3.51 (m, 2H), 3.41 (m, 2H), 3.13/3.09 (dd+dd, 2H), 2.75 (s, 3H), 1 (t, 3H)

Step 4: Preparation of ethyl 3-{3-[(6-hydroxy-2,2-dioxo-2H-1,2λ$^6$,3-benzoxathiazin-3(4H)-yl)methyl]-4-methoxyphenyl}-3-{1-[2-(2-hydroxyethoxy)ethyl]-4-methyl-1H-benzotriazol-5-yl}propanoate Using General Procedure 8 starting from ethyl 3-(3-{[6-(benzyloxy)-2,2-dioxo-2H-1,2λ$^6$,3-benzoxathiazin-3(4H)-yl]methyl}-4-methoxyphenyl)-3-(1-{12-[2-(benzyloxy)ethoxy]ethyl}-4-methyl-1H-benzotriazol-5-yl)propanoate (1 eq.) as a reactant, the title compound (white solid, quant.) was obtained.

$^1$H-NMR (500 MHz, DMSO-d6) δ ppm: 9.62 (s, 1H), 7.64 (d, 1H), 7.48 (d, 1H), 7.26 (d, 1H), 7.23 (dd, 1H), 6.89 (d, 1H), 6.85 (d, 1H), 6.71 (dd, 1H), 6.59 (d, 1H), 4.82 (t, 1H), 4.81 (t, 2H), 4.55 (m, 1H), 4.48 (s, 2H), 4.21/4.17 (d+d, 2H), 3.94 (q, 2H), 3.89 (t, 2H), 3.69 (s, 3H), 3.38 (m, 4H), 3.14 (m, 2H), 2.75 (s, 3H), 1.02 (t, 3H)

Step 5: Preparation of ethyl 3-{1-[2-(2-chloroethoxy)ethyl]-4-methyl-1H-benzotriazol-5-yl}-3-{3-[(6-hydroxy-2,2-dioxo-2H-1,2λ$^6$,3-benzoxathiazin-3(4H)-yl)methyl]-4-methoxyphenyl}propanoate hydrochloride Using General Procedure 10 starting from ethyl 3-{3-[(6-hydroxy-2,2-dioxo-2H-1,2λ$^6$,3-benzoxathiazin-3(4H)-yl)methyl]-4-methoxyphenyl}-3-{11-[2-(2-hydroxyethoxy)ethyl]-4-methyl-1H-benzotriazol-5-yl}propanoate (1 eq.) as a reactant, the title compound (solid foam, 96% yield) was obtained.

$^1$H-NMR (500 MHz, DMSO-d6) δ ppm: 9.64 (brs, 1H), 7.64 (d, 1H), 7.49 (d, 1H), 7.26 (d, 1H), 7.22 (dd, 1H), 6.89 (d, 1H), 6.84 (d, 1H), 6.71 (dd, 1H), 6.59 (d, 1H), 4.83 (t, 2H), 4.81 (t, 1H), 4.47 (s, 2H), 4.2/4.17 (d+d, 2H), 3.94 (q, 2H), 3.93 (t, 2H), 3.69 (s, 3H), 3.6 (t, 2H), 3.59 (t, 2H), 3.14 (d, 2H), 2.75 (s, 3H), 1.02 (t, 3H)

Step 6: Preparation of ethyl[4-methoxy-32-methyl-28,28-dioxo-19,22,27-trioxa-28λ$^6$-thia-1,14,15,16-tetraazahexacyclo[21.5.3.1$^{3,7}$0.1$^{9,13}$0.0$^{12,16}$0.0$^{26,30}$]tritriaconta-3(33),4,6,9(32),10,12,14,23,25,30-decaen-8-yl]acetate Using General Procedure 11 starting from ethyl 3-{1-[2-(2-chloroethoxy)ethyl]-4-methyl-1H-benzotriazol-5-yl}-3-{3-[(6-hydroxy-2,2-dioxo-2H-1,2λ$^6$,3-benzoxathiazin-3(4H)-yl)methyl]-4-methoxyphenyl}propanoate hydrochloride (1 eq.) as a reactant, the title compound (59% yield) was obtained.

The enantiopure final intermediates were obtained by chromatographic separation on chiral column.

$^1$H-NMR (500 MHz, DMSO-d6) δ ppm: 7.71 (d, 1H), 7.38 (dd, 1H), 7.35 (d, 1H), 6.96 (d, 1H), 6.95 (d, 1H), 6.94 (d, 1H), 6.82 (dd, 1H), 6.46 (d, 1H), 4.86/4.83 (m+m, 2H), 4.79 (t, 1H), 4.4/4.23 (d+d, 2H), 4.18 (s, 2H), 3.99/3.94 (m+m, 2H), 3.94 (m, 2H), 3.89 (m, 2H), 3.81/3.68 (m+m, 2H), 3.76 (s, 3H), 3.09/3.04 (dd+dd, 2H), 2.7 (s, 3H), 0.98 (t, 3H)

Step 7: Preparation of Example 59

Using General Procedure 12 starting from ethyl[4-methoxy-32-methyl-28,28-dioxo-19,22,27-trioxa-28λ$^6$-thia-1,14,15,16-tetraazahexacyclo[21.5.3.1$^{3,7}$0.1$^{9,13}$0.0$^{12,}$$_{16}$0.0$^{26,30}$]tritriaconta-3(33),4,6,9(32),10,12,14,23,25,30-decaen-8-yl]acetate E1 (1 eq.) or E2 (1 eq.) as reactants, the title compounds (91%-93% yields respectively) were obtained.

EXAMPLE 59a (E1)

HRMS calculated for $C_{29}H_{30}N_4O_8S$: 594.1784; $[M+H]^+$ found: 595.1843 (δ=−2.4 ppm).

EXAMPLE 59b (E2)

HRMS calculated for $C_{29}H_{30}N_4O_8S$: 594.1784; $[M+H]^+$ found: 595.1849 (δ=−1.4 ppm).

$^1$H-NMR (500 MHz, DMSO-d6) δ ppm: 12.05 (brs, 1H), 7.71 (d, 1H), 7.4 (dd, 1H), 7.34 (d, 1H), 6.96 (d, 1H), 6.95 (d, 1H), 6.92 (d, 1H), 6.82 (dd, 1H), 6.44 (d, 1H), 4.84 (m, 2H), 4.77 (t, 1H), 4.39/4.22 (d+d, 2H), 4.18 (s, 2H), 4/3.95 (m+m, 2H), 3.94 (m, 2H), 3.81/3.68 (m+m, 2H), 3.77 (s, 3H), 2.96 (d, 2H), 2.7 (s, 3H)

$^{13}$C-NMR (125 MHz, DMSO-d6) δ ppm: 173.2, 157, 155.6, 146.5, 145.2, 136.7, 135.7, 132.5, 131, 131, 127.1, 126.6, 121.3, 118.7, 118.2, 115, 114.4, 111.8, 109.2, 69.9, 68.6, 68.3, 56.1, 48.9, 48.8, 48.5, 41.3, 41.1, 13.3

EXAMPLE 60: [4,36-Dimethyl-30,30-dioxo-24,29-dioxa-30λ$^6$-thia-1,14,15,16,19-pentaazaheptacyclo[23.5.3.2$^{19,22}$0.1$^{3,7}$0.1$^{9,13}$0.0$^{12,16}$0.0$^{28,32}$]heptatriaconta-3(37),4,6,9(36),10,12,14,25,27,32-decaen-8-yl]acetic acid enantiomer 1

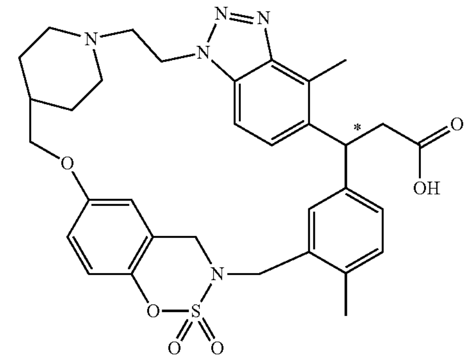

* = RorS

-continued enantiomer 2

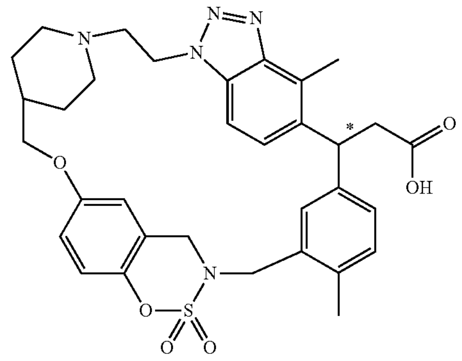

* = RorS

Step 1: Preparation of ethyl 3-{3-[(6-hydroxy-2,2-dioxo-2H-1,2λ$^6$,3-benzoxathiazin-3(4H)-yl)methyl]-4-methylphenyl}-3-[1-(2-hydroxyethyl)-4-methyl-1H-benzotriazol-5-yl]propanoate Using General Procedure 8 starting from ethyl 3-(3-{[6-(benzyloxy)-2,2-dioxo-2H-1,2λ$^6$,3-benzoxathiazin-3(4H)-yl]methyl}-4-methylphenyl)-3-[1-(2-hydroxyethyl)-4-methyl-1H-benzotriazol-5-yl]propanoate (1 eq.) as a reactant, the title compound (white solid, 94% yield) was obtained.

$^1$H-NMR (500 MHz, DMSO-d6) δ ppm: 9.71 (s, 1H), 7.6 (d, 1H), 7.49 (d, 1H), 7.23 (d, 1H), 7.18 (dd, 1H), 7.13 (d, 1H), 7 (d, 1H), 6.79 (dd, 1H), 6.62 (d, 1H), 4.96 (t, 1H), 4.84 (t, 1H), 4.67 (t, 2H), 4.41/4.36 (d+d, 2H), 4.21/4.17 (d+d, 2H), 3.94 (q, 2H), 3.84 (q, 2H), 3.19/3.15 (dd+dd, 2H), 2.76 (s, 3H), 2.22 (s, 3H), 1.03 (t, 3H)

Step 2: Preparation of ethyl 3-[1-(2-chloroethyl)-4-methyl-1H-benzotriazol-5-yl]-3-{3-[(6-hydroxy-2,2-dioxo-2H-1,2λ$^6$,3-benzoxathiazin-3(4H)-yl)methyl]-4-methylphenyl}propanoate hydrochloride Using General Procedure 10 starting from ethyl 3-{3-[(6-hydroxy-2,2-dioxo-2H-1,2)$^6$,3-benzoxathiazin-3(4H)-yl) methyl]-4-methylphenyl}-3-[1-(2-hydroxyethyl)-4-methyl-1H-benzotriazol-5-yl]propanoate (1 eq.) as a reactant, the title compound (off-white solid foam, 96% yield) was obtained. The product was used in the next step without further purification.

$^1$H-NMR (500 MHz, DMSO-d6) δ ppm: 9.72 (br., 1H), 7.67 (d, 1H), 7.53 (d, 1H), 7.24 (d, 1H), 7.2 (dd, 1H), 7.13 (d, 1H), 6.99 (d, 1H), 6.79 (dd, 1H), 6.61 (d, 1H), 5.02 (t, 2H), 4.84 (t, 1H), 4.4/4.36 (d+d, 2H), 4.22/4.17 (d+d, 2H), 4.15 (t, 2H), 3.93 (q, 2H), 3.18 (d, 2H), 2.77 (s, 3H), 2.22 (s, 3H), 1 (t, 3H)

Step 3: Preparation of ethyl 3-{3-[(6-hydroxy-2,2-dioxo-2H-1,2λ$^6$,3-benzoxathiazin-3(4H)-yl)methyl]-4-methylphenyl}-3-(1-{2-[4-(hydroxymethyl)piperidin-1-yl]ethyl}-4-methyl-1H-benzotriazol-5-yl) propanoate To a stirred mixture of ethyl 3-[1-(2-chloroethyl)-4-methyl-1H-benzotriazol-5-yl]-3-{3-[(6-hydroxy-2,2-dioxo-2H-1,2λ$^6$,3-benzoxathiazin-3(4H)-yl)methyl]-4-methylphenyl}propanoate hydrochloride (1 eq., 0.8 g, 1.335 mmol) in DMF (8 mL) (piperidin-4-yl)methanol (10 eq., 1.538 g, 13.35 mmol) was added at RT. The reaction mixture was heated to 80° C. and stirred at this temperature for 24 h. After completion of the reaction the mixture was cooled to RT and it was directly injected to a C18 column and purified by reversed-phase chromatography using aq. 5 mM $NH_4HCO_3$ solution-MeCN gradient elution to give the title compound (393 mg, white solid, 43% yield).

$^1$H-NMR (500 MHz, DMSO-d6) δ ppm: 9.73 (brs, 1H), 7.62 (d, 1H), 7.5 (d, 1H), 7.22 (d, 1H), 7.19 (dd, 1H), 7.13 (d, 1H), 6.99 (d, 1H), 6.79 (dd, 1H), 6.6 (d, 1H), 4.83 (t, 1H), 4.74 (t, 2H), 4.56/0.96 (m+m, 4H), 4.4/4.35 (d+d, 2H), 4.37 (brs, 1H), 4.22/4.17 (d+d, 2H), 3.93 (q, 2H), 3.17 (d, 2H), 3.17 (d, 2H), 2.9/2.85/1.92 (d/d+t, 4H), 2.77 (t, 2H), 2.75 (s, 3H), 2.22 (s, 3H), 1.27 (m, 1H), 0.99 (t, 3H)

Step 4: Preparation of ethyl[4,36-dimethyl-30,30-dioxo-24,29-dioxa-30)$^6$-thia-1,14,15,16,19-pentaaza-heptacyclo[23.5.3.2$^{19,22}$0.1$^{3,7}$0.1$^{9,13}$0.0$^{12,16}$0.0$^{28,32}$] heptatriaconta-3(37),4,6,9(36),10,12,14,25,27,32-decaen-8-yl]acetate Ethyl 3-{3-[(6-hydroxy-2,2-dioxo-2H-1,2λ$^6$,3-benzoxathiazin-3(4H)-yl)methyl]-4-methylphenyl}-3-(1-{12-[4-(hydroxymethyl)piperidin-1-yl]ethyl}-4-methyl-1H-benzotriazol-5-yl)propanoate (1 eq., 287 mg, 0.4237 mmol) was dissolved in THF (60 mL) and $PPh_3$ (4 eq., 444 mg, 1.694 mmol) was added. The mixture was cooled to −5° C. and DIAD (4 eq., 343 mg, 1.694 mmol) was added dropwise. After heating at reflux temperature for 1.5 h. the solvent was evaporated, the crude product was dissolved in DMF and the mixture was directly injected to a C18 column and purified by reversed-phase chromatography using aq. 5 mM $NH_4HCO_3$ solution-MeCN gradient elution to give the title compound (100 mg, 36% yield).

The enantiopure final intermediates were obtained by chromatographic separation on chiral column.

$^1$H-NMR (500 MHz, DMSO-d6) δ ppm: 7.68 (d, 1H), 7.61 (d, 1H), 7.42 (dd, 1H), 7.25 (d, 1H), 7.04 (d, 1H), 7.01 (d, 1H), 6.99 (d, 1H), 6.96 (dd, 1H), 4.84/4.61 (td+dd, 2H), 4.8 (t, 1H), 4.35/4.24 (d+d, 2H), 4.24/4.12 (d+d, 2H), 4.07/3.93 (dd+dd, 2H), 3.88 (q, 2H), 3.14/2.99 (dd+dd, 2H), 3.02/2.76 (t+dd, 2H), 3.01/2.64/2.06/1.72 (dd+t+dd+t, 4H), 2.67 (s, 3H), 2.33 (s, 3H), 1.57 (m, 1H), 1.47/1.42/1.28/1.12 (d+dd+d+dd, 4H), 0.97 (t, 3H)

Step 5: Preparation of Example 60

Using General Procedure 12 starting from ethyl[4,36-dimethyl-30,30-dioxo-24,29-dioxa-30λ$^6$-thia-1,14,15,16,19-pentaazaheptacyclo[23.5.3.2$^{1922}$0.1$^{3,7}$0.1$^{9,13}$0.0$^{12,16}$0.0$^{28,32}$]heptatriaconta-3(37),4,6,9(36),10,12,14,25,27,32-decaen-8-yl]acetate E1 (1 eq.) or E2 (1 eq.) as reactants, the title compounds (48%-44% yields respectively) were obtained.

EXAMPLE 60a (E1)

HRMS calculated for $C_{33}H_{37}N_5O_6S$: 631.2464; $[M+H]^+$ found: 632.2538 (δ=0.1 ppm).

EXAMPLE 60b (E2)

HRMS calculated for $C_{33}H_{37}N_5O_6S$: 631.2464; $[M+H]^+$ found: 632.2542 (δ=0.7 ppm).

$^1$H-NMR (500 MHz, DMSO-d6) δ ppm: 12.29 (brs, 1H), 7.69 (d, 1H), 7.6 (d, 1H), 7.43 (dd, 1H), 7.25 (d, 1H), 7.04

(d, 1H), 7.01 (d, 1H), 6.97 (d, 1H), 6.95 (dd, 1H), 4.84/4.6 (dd+d, 2H), 4.78 (t, 1H), 4.34/4.24 (d+d, 2H), 4.25/4.11 (d+d, 2H), 4.06/3.93 (dd+dd, 2H), 3.04/2.77 (t+dd, 2H), 3.03/2.9 (dd+dd, 2H), 3.01/2.64/2.07/1.72 (dd+t+dd+t, 4H), 2.66 (s, 3H), 2.34 (s, 3H), 1.57 (m, 1H), 1.47/1.43/1.28/1.12 (d+dd+d+dd, 4H)

$^{13}$C-NMR (125 MHz, DMSO-d6) δ ppm: 173, 157.1, 146.4, 144.4, 141.9, 136.6, 136.2, 132.7, 132.5, 131.6, 129.9, 129.8, 126.9, 126.6, 119.2, 118.1, 116.1, 113.7, 109.2, 71.5, 57.9, 53.4/51.9, 52.3, 49.2, 46, 42.2, 41.7, 36.5, 28.9/28.2, 18.9, 13.3

EXAMPLE 61: [(17E)-4,36-dimethyl-32,32-dioxo-26,31-dioxa-32λ$^6$-thia-1,14,15,16-tetraazaheptacyclo[25.5.3.1$^{3,7}$0.1$^{9,13}$0.0$^{12,16}$0.0$^{19,24}$0.0$^{30,34}$]heptatriaconta-3(37),4,6,9(36),10,12,14,17,19,21,23,27,29,34-tetradecaen-8-yl]acetic acid enantiomer 1

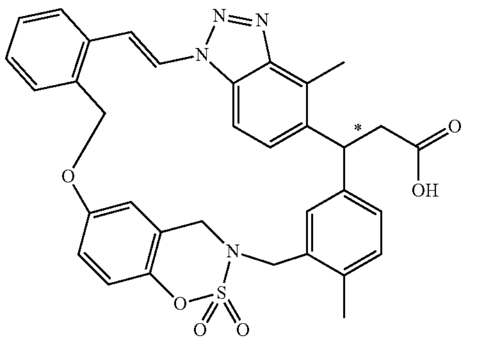

* = RorS enantiomer 2

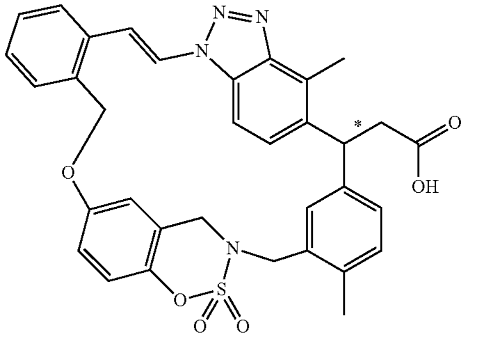

* = RorS

Step 1: Preparation of ethyl 3-(1-ethenyl-4-methyl-1H-benzotriazol-5-yl)-3-{3-[(6-hydroxy-2,2-dioxo-2H-1,2λ$^6$,3-benzoxathiazin-3(4H)-yl)methyl]-4-methylphenyl}propanoate To the stirred solution of ethyl 3-[1-(2-chloroethyl)-4-methyl-benzotriazol-5-yl]-3-[3-[(6-hydroxy-2,2-dioxo-4H-1,2λ$^6$,3-benzoxathiazin-3-yl)methyl]-4-methyl-phenyl]propanoate hydrochloride (1 eq., 1.5 g, 2.36 mmol) in MeCN (25 mL) $Cs_2CO_3$ (3 eq., 2.31 g, 7.08 mmol) was added and the mixture was stirred overnight at 80° C. After the completion of the reaction the solvent was evaporated under reduced pressure. The residue was partitioned between 50 mL DCM/50 mL water, the layers were separated, the aq. layer was extracted with further 2×30 mL DCM. The combined organic layer was dried over $MgSO_4$, filtered and the filtrate was concentrated to dryness. The crude product was purified by reversed-phase chromatography using aq. 5 mM $NH_4HCO_3$ solution-MeCN gradient elution to give the title compound (848 mg, 64% yield).

$^1$H-NMR (500 MHz, DMSO-d6) δ ppm: 9.7 (s, 1H), 7.82 (d, 1H), 7.82 (dd, 1H), 7.62 (d, 1H), 7.23 (d, 1H), 7.2 (dd, 1H), 7.14 (d, 1H), 6.99 (d, 1H), 6.78 (dd, 1H), 6.61 (d, 1H), 5.97/5.29 (dd+dd, 2H), 4.85 (t, 1H), 4.41/4.36 (d+d, 2H), 4.22/4.17 (d+d, 2H), 3.94 (q, 2H), 3.19 (d, 2H), 2.79 (s, 3H), 2.22 (s, 3H), 1.01 (t, 3H)

Step 2: Preparation of ethyl 3-{3-[(6-hydroxy-2,2-dioxo-2H-1,2λ$^6$,3-benzoxathiazin-3(4H)-yl)methyl]-4-methylphenyl}-3-(1-{(E)-2-[2-(hydroxymethyl)phenyl]ethenyl}-4-methyl-1H-benzotriazol-5-yl)propanoate To the stirred solution of ethyl 3-(1-ethenyl-4-methyl-1H-benzotriazol-5-yl)-3-{3-[(6-hydroxy-2,2-dioxo-2H-1,2λ$^6$,3-benzoxathiazin-3(4H)-yl)methyl]-4-methylphenyl}propanoate (1 eq., 0.844 g, 1.5 mmol) in MeCN (8 mL) TEA (38 eq., 8 mL, 57.4 mmol), (2-iodophenyl)methanol (2 eq., 702 mg, 3 mmol), $PPh_3$ (0.2 eq., 79 mg, 0.3 mmol) and palladium(II) acetate catalyst (0.1 eq., 34 mg, 0.15 mmol) were added. The mixture was flushed with nitrogene and heated in a microwave reactor at 110° C. for 4 h. After completion of the reaction the solvent was evaporated under reduced pressure. The residue was partitioned between 50 mL DCM/50 mL water, the layers were separated, then the aq. layer was extracted with 50 mL DCM. The combined organic layer was dried over $MgSO_4$, filtered and the filtrate was concentrated to dryness. The crude product was purified by normal phase silica gel chromatography using DCM-MeOH (100:0 to 99:1) as an eluent to give the title compound (808 mg, 81% yield).

$^1$H-NMR (500 MHz, DMSO-d6) δ ppm: 9.69 (s, 1H), 8.29 (d, 1H), 7.94 (d, 1H), 7.86 (dd, 1H), 7.76 (d, 1H), 7.65 (d, 1H), 7.43 (dd, 1H), 7.36 (td, 1H), 7.33 (td, 1H), 7.26 (d, 1H), 7.21 (dd, 1H), 7.15 (d, 1H), 6.99 (d, 1H), 6.79 (dd, 1H), 6.61 (d, 1H), 5.3 (t, 1H), 4.87 (t, 1H), 4.66 (d, 2H), 4.42/4.38 (d+d, 2H), 4.23/4.19 (d+d, 2H), 3.95 (q, 2H), 3.21 (d, 2H), 2.81 (s, 3H), 2.23 (s, 3H), 1.02 (t, 3H)

Step 3: Preparation of ethyl 3-(1-{(E)-2-[2-(chloromethyl)phenyl]ethenyl}-4-methyl-1H-benzotriazol-5-yl)-3-{3-[(6-hydroxy-2,2-dioxo-2H-1,2λ$^6$,3-benzoxathiazin-3(4H)-yl)methyl]-4-methylphenyl}propanoate hydrochloride Using General Procedure 10 starting from ethyl 3-{3-[(6-hydroxy-2,2-dioxo-2H-1,2λ$^6$,3-benzoxathiazin-3(4H)-yl)methyl]-4-methylphenyl}-3-(1-{(E)-2-[2-(hydroxymethyl)phenyl]ethenyl}-4-methyl-1H-benzotriazol-5-yl)propanoate (1 eq.) as a reactant, the title compound (yellow solid foam, quant.) was obtained. The product was used in the next step without further purification.

$^1$H-NMR (500 MHz, DMSO-d6) δ ppm: 9.71 (brs, 1H), 8.39 (d, 1H), 7.98 (d, 1H), 7.96 (dm, 1H), 7.78 (d, 1H), 7.68 (d, 1H), 7.51 (dm, 1H), 7.46 (m, 1H), 7.36 (m, 1H), 7.27 (d, 1H), 7.22 (dd, 1H), 7.15 (d, 1H), 6.99 (d, 1H), 6.79 (dd, 1H), 6.61 (d, 1H), 5 (s, 2H), 4.87 (t, 1H), 4.41/4.38 (d+d, 2H), 4.23/4.18 (d+d, 2H), 3.95 (q, 2H), 3.21 (d, 2H), 2.82 (s, 3H), 2.23 (s, 3H), 1.02 (t, 3H)

Step 4: Preparation of ethyl[(17E)-4,36-dimethyl-32,32-dioxo-26,31-dioxa-32λ$^6$-thia-1,14,15,16-tetraazaheptacyclo[25.5.3.1$^{3,7}$0.1$^{9,13}$0.0$^{12,16}$0.0$^{19,24}$0.0$^{30,34}$]heptatriaconta-3(37),4,6,9(36),10,12,14,17,19,21,23,27,29,34-tetradecaen-8-yl] acetate Using General Procedure 11 starting from ethyl 3-(1-{(E)-2-[2-(chloromethyl)phenyl]ethenyl}-4-methyl-1H-benzotriazol-5-yl)-3-{3-[(6-hydroxy-2,2-dioxo-2H-1,2λ$^6$,3-benzoxathiazin-3(4H)-yl)methyl]-4-methylphenyl}propanoate hydrochloride (1 eq.) as a reactant, the title compound (13% yield) was obtained.

The enantiopure final intermediates were obtained by chromatographic separation on chiral column.

$^1$H-NMR (500 MHz, DMSO-d6) δ ppm: 8.42 (d, 1H), 8 (d, 1H), 7.83 (d, 1H), 7.66 (d, 1H), 7.64 (d, 1H), 7.55 (d, 1H), 7.51 (t, 1H), 7.45 (dd, 1H), 7.41 (t, 1H), 7.24 (dd, 1H), 7.23 (d, 1H), 7.21 (d, 1H), 7.02 (d, 1H), 6.92 (d, 1H), 5.26/5.16 (d+d, 2H), 4.89 (dd, 1H), 4.32/4.11 (d+d, 2H), 4.28/4.08 (d+d, 2H), 3.89 (q, 2H), 3.23/3.08 (dd+dd, 2H), 2.8 (s, 3H), 2.31 (s, 3H), 0.96 (t, 3H)

Step 5: Preparation of Example 61

Using General Procedure 12 starting from ethyl[(17E)-4,36-dimethyl-32,32-dioxo-26,31-dioxa-32λ$^6$-thia-1,14,15,16-tetraazaheptacyclo[25.5.3.1$^{3,7}$0.1$^{9,13}$0.0$^{12,16}$0.0$^{19,24}$0.0$^{30,34}$]heptatriaconta-3(37),4,6,9(36),10,12,14,17,19,21,23,27,29,34-tetradecaen-8-yl]acetate E1 (1 eq.) or E2 (1 eq.) as reactants, the title compounds (89%-73% yields respectively) were obtained.

EXAMPLE 61a (E1)

HRMS calculated for $C_4H_3N_4O_6S$: 622.1886; [M+H]$^+$ found: 623.1956 (δ=−0.5 ppm).

EXAMPLE 61b (E2)

HRMS calculated for $C_4H_3N_4O_6S$: 622.1886; [M+H]$^+$ found: 623.1955 (δ=−0.6 ppm).

$^1$H-NMR (500 MHz, DMSO-d6) δ ppm: 8.42 (d, 1H), 8 (d, 1H), 7.81 (d, 1H), 7.63 (d, 1H), 7.6 (d, 1H), 7.55 (d, 1H), 7.51 (t, 1H), 7.44 (dd, 1H), 7.41 (t, 1H), 7.24 (dd, 1H), 7.22 (d, 1H), 7.2 (d, 1H), 6.99 (d, 1H), 6.92 (d, 1H), 5.26/5.15 (d+d, 2H), 4.87 (t, 1H), 4.34/4.11 (d+d, 2H), 4.28/4.09 (d+d, 2H), 3.09/2.94 (dd+dd, 2H), 2.8 (s, 3H), 2.31 (s, 3H)

$^{13}$C-NMR (125 MHz, DMSO-d6) δ ppm: 173.4, 156, 146.9, 145.5, 141.7, 138.3, 136.2, 135, 134.4, 132.1, 131.3, 131.3, 130.5, 129.9, 129.6, 129.2, 128.9, 128.8, 128.2, 126.3, 125.6, 119.9, 119.5, 118.6, 116.1, 115.4, 109.4, 70.8, 52, 48.7, 41.9, 40.9, 18.5, 13.3

EXAMPLE 62: [4,36-Dimethyl-32,32-dioxo-26,31-dioxa-32λ$^6$-thia-1,14,15,16-tetraazaheptacyclo[25.5.3.1$^{3,7}$0.1$^{9,13}$0.0$^{12,16}$0.0$^{19,24}$0.0$^{30,34}$]heptatriaconta-3(37),4,6,9(36),10,12,14,19,21,23,27,29,34-tridecaen-8-yl]acetic acid enantiomer 1

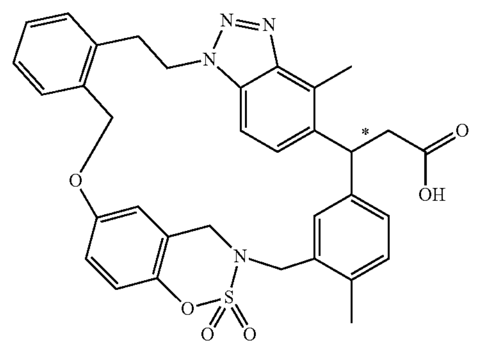

* = RorS enantiomer 2

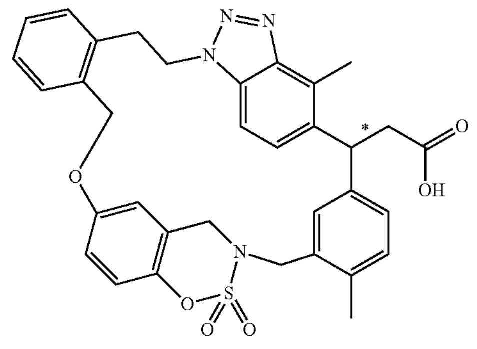

* = RorS

Ethyl[(17E)-4,36-dimethyl-32,32-dioxo-26,31-dioxa-32λ$^6$-thia-1,14,15,16-tetraazaheptacyclo[25.5.3.1$^{3,7}$0.1$^{9,13}$0.0$^{12,16}$0.0$^{19,24}$0.0$^{30,34}$]heptatriaconta-3(37),4,6,9(36),10,12,14,17,19,21,23,27,29,34-tetradecaen-8-yl]acetate (1 eq., 49 mg, 0.075 mmol) and Pd/C catalyst (0.1 eq., 4 mg) were suspended in dioxane (5 mL) and hydrogenated in a stainless steel reaction vessel under atmospheric pressure at RT for 3.5 h. The mixture was filtered through a Celite pad and evaporated to dryness. The crude product was reacted using General Procedure 12 to give the title compound (white solid, 61% yield).

The enantiopure products were obtained by chromatographic separation on chiral column.

EXAMPLE 62a (E1)

HRMS calculated for $C_{34}H_{32}N_4O_6S$: 624.2042; [M+H]$^+$ found: 625.2141 (δ=4.1 ppm).

EXAMPLE 62b (E2)

HRMS calculated for $C_{34}H_{32}N_4O_6S$: 624.2042; [M+H]$^+$ found: 625.2128 (δ=2.0 ppm).

$^1$H-NMR (500 MHz, DMSO-d6) δ ppm: 7.75 (d, 1H), 7.62 (d, 1H), 7.48 (d, 1H), 7.48 (d, 1H), 7.46 (t, 1H), 7.38 (d, 1H), 7.33 (t, 1H), 7.27 (d, 1H), 7.1 (d, 1H), 7.03 (dd, 1H), 6.71 (brs., 1H), 6.53 (d, 1H), 4.92 (m, 2H), 4.83 (t, 1H), 4.74/4.69 (d+d, 2H), 4.3/3.96 (d+d, 2H), 4.18/4.02 (d+d, 2H), 3.43/3.16 (m+m, 2H), 3.11/2.85 (dd+dd, 2H), 2.71 (s, 3H), 2.33 (s, 3H) $^{13}$C-NMR (125 MHz, DMSO-d6) δ ppm: 131.5, 131.3, 130.5, 130.2, 129.5, 128.4, 127.8, 127.3, 119.6, 116, 112.8, 108, 69.2, 52, 48.8, 48.8, 41.4, 40.9, 32.2, 18.4, 13.3

EXAMPLE 63: [4,32-Dimethyl-28,28-dioxo-22,27-dioxa-19,28λ$^6$-dithia-1,14,15,16-tetraazahexacyclo[21.5.3.1$^{3,7}$0.1$^{9,13}$0.0$^{12,16}$0.0$^{26,30}$]tritriaconta-3(33),4,6,9(32),10,12,14,23,25,30-decaen-8-yl]acetic acid enantiomer 1

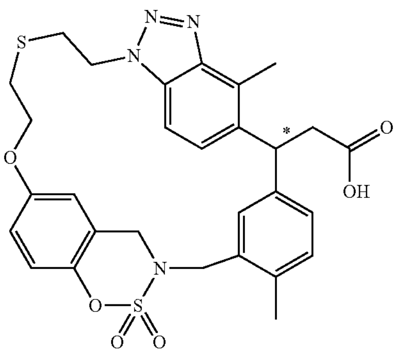

* = RorS enantiomer 2

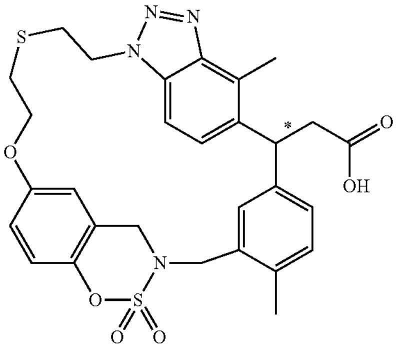

* = RorS

Step 1: Preparation of ethyl 3-{3-[(6-hydroxy-2,2-dioxo-2H-1,2λ$^6$,3-benzoxathiazin-3(4H)-yl)methyl]-4-methylphenyl}-3-(1-{2-[(2-hydroxyethyl)sulfanyl]ethyl}-4-methyl-1H-benzotriazol-5-yl)propanoate Ethyl 3-[1-(2-chloroethyl)-4-methyl-1H-benzotriazol-5-yl]-3-{3-[(6-hydroxy-2,2-dioxo-2H-1,2λ$^6$,3-benzoxathiazin-3(4H)-yl)methyl]-4-methylphenyl}propanoate hydrochloride (1 eq., 0.836 g, 1.395 mmol) and $K_2CO_3$ (2.2 eq., 424 mg, 3.070 mmol) were suspended in EtOH (50 mL). Potassium iodide (0.1 eq., 23 mg, 0.1395 mmol) and 2-sulfanylethan-1-ol (15 eq., 1.64 g, 20.93 mmol) were added at RT and the mixture was heated at 60° C. for 6 days. After cooling to Rt, the reaction mixture was filtered and concentrated to dryness to give the crude product, which was purified via normal phase silica gel chromatography using DCM-MeOH (100:0 to 95:5) as eluents to give the title compound (yellow oil, 400 mg, 45% yield).

$^1$H-NMR (500 MHz, DMSO-d6) δ ppm: 9.71 (s, 1H), 7.65 (d, 1H), 7.51 (d, 1H), 7.23 (d, 1H), 7.19 (dd, 1H), 7.13 (d, 1H), 6.99 (d, 1H), 6.79 (dd, 1H), 6.6 (d, 1H), 4.86 (t, 1H), 4.84 (dd, 1H), 4.83 (t, 2H), 4.4/4.36 (d+d, 2H), 4.22/4.17 (d+d, 2H), 3.94 (q, 2H), 3.52 (q, 2H), 3.19/3.15 (dd+dd, 2H), 3.09 (t, 2H), 2.76 (s, 3H), 2.58 (t, 2H), 2.22 (s, 3H), 1.01 (t, 3H)

Step 2: Preparation of ethyl[4,32-dimethyl-28,28-dioxo-22,27-dioxa-19,28λ$^6$-dithia-1,14,15,16-tetraazahexacyclo[21.5.3.1$^{3,7}$0.1$^{9,13}$0.0$^{12,16}$0.0$^{26,30}$]tritriaconta-3(33),4,6,9(32),10,12,14,23,25,30-decaen-8-yl]acetate Ethyl 3-{3-[(6-hydroxy-2,2-dioxo-2H-1,2λ$^6$,3-benzoxathiazin-3(4H)-yl)methyl]-4-methylphenyl}-3-(1-{12-[(2-hydroxyethyl)sulfanyl]ethyl}-4-methyl-1H-benzotriazol-5-yl)propanoate (1 eq., 400 mg, 0.624 mmol) was dissolved in THF (20 mL). $PPh_3$ (4 eq., 655 mg, 2.497 mmol) was added and the mixture was cooled to −5° C. DIAD (4 eq., 504.9 mg, 2.497 mmol) was added dropwise and the mixture was stirred at RT for 2 h. After completion of the reaction the mixture was concentrated to dryness to give the crude product, which was purified via preparative reversed-phase chromatography using 5 mM aq. $NH_4HCO_3$ solution-MeCN as eluents to give the title compound (215 mg, white solid, 55% yield).

The enantiopure final intermediates were obtained by chromatographic separation on chiral column.

$^1$H-NMR (500 MHz, DMSO-d6) δ ppm: 7.72 (d, 1H), 7.65 (d, 1H), 7.45 (dd, 1H), 7.23 (d, 1H), 7.12 (d, 1H), 7.07 (d, 1H), 6.99 (dd, 1H), 6.11 (d, 1H), 5.04/4.84 (m+m, 2H), 4.81 (t, 1H), 4.36/3.99 (m+m, 2H), 4.35/3.94 (d+d, 2H), 4.14/3.68 (d+d, 2H), 3.88 (q, 2H), 3.41/3.14 (m+m, 2H), 3.36/2.85 (m+m, 2H), 3.12/3.08 (dd+dd, 2H), 2.74 (s, 3H), 2.31 (s, 3H), 0.98 (t, 3H)

Step 3: Preparation of [4,32-dimethyl-28,28-dioxo-22,27-dioxa-19,28λ$^6$-dithia-1,14,15,16-tetraazahexacyclo[21.5.3.1$^{3,7}$0.1$^{9,13}$0.0$^{12,16}$0.0$^{26,30}$]tritriaconta-3(33),4,6,9(32),10,12,14,23,25,30-decaen-8-yl]acetic acid Using General Procedure 12 starting from ethyl[4,32-dimethyl-28,28-dioxo-22,27-dioxa-19,28)$^6$-dithia-1,14,15,16-tetraazahexacyclo[21.5.3.1$^{3,7}$0.0$^{9,13}$0.0$^{12,16}$0.0$^{26,30}$]tritriaconta-3(33),4,6,9(32),10,12,14,23,25,30-decaen-8-yl]acetate E1 (1 eq.) or E2 (1 eq.) as reactants, the title compounds (77%-74% yields respectively) were obtained.

EXAMPLE 63a (E1)

HRMS calculated for $C_{29}H_{30}N_4O_6S_2$: 594.1607; [M+H]$^+$ found: 595.1686 (δ=1.1 ppm).

EXAMPLE 63b (E2)

HRMS calculated for $C_{29}H_{30}N_4O_6S_2$: 594.1607; [M+H]$^+$ found: 595.1681 (δ=0.2 ppm).

$^1$H-NMR (500 MHz, DMSO-d6) δ ppm: 12.08 (br., 1H), 7.72 (d, 1H), 7.62 (d, 1H), 7.44 (dd, 1H), 7.23 (d, 1H), 7.11 (d, 1H), 7.04 (d, 1H), 6.98 (dd, 1H), 6.11 (d, 1H), 5.03/4.84 (m+m, 2H), 4.78 (t, 1H), 4.33/3.96 (d+d, 2H), 4.33/3.97 (m+m, 2H), 4.13/3.71 (d+d, 2H), 3.4/3.16 (m+m, 2H), 3.33/2.85 (m+m, 2H), 3 (d, 2H), 2.73 (s, 3H), 2.31 (s, 3H)

$^{13}$C-NMR (125 MHz, DMSO-d6) δ ppm: 131.4, 131.2, 129.3, 127, 119.2, 114.9, 114.3, 108.2, 71.5, 51.8, 48.4, 47.2, 41.6, 41.2, 31.3, 28.8, 18.3, 13.3

EXAMPLE 64: [(2R,8S)-4-chloro-2,31-dimethyl-27,27-dioxo-21,26-dioxa-$27\lambda^6$-thia-1,14,15,16-tetraazahexacyclo[20.5.3.$1^{3,7}$0.$1^{9,13}$0.$0^{12,16}$0.$0^{25,29}$]dotriaconta-3(32),4,6,9(31),10,12,14,22,24,29-decaen-8-yl]acetic acid and [(2R,8R)-4-chloro-2,31-dimethyl-27,27-dioxo-21,26-dioxa-$27\lambda^6$-thia-1,14,15,16-tetraazahexacyclo[20.5.3.$1^{3,7}$0.$1^{9,13}$0.$0^{12,16}$0.$0^{25,29}$]dotriaconta-3(32),4,6,9(31),10,12,14,22,24,29-decaen-8-yl]acetic acid

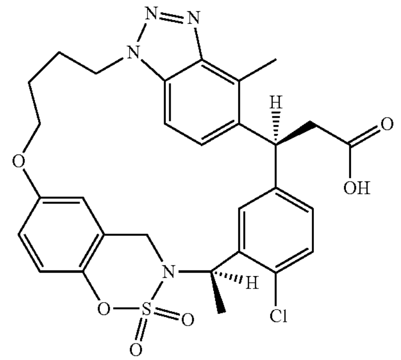

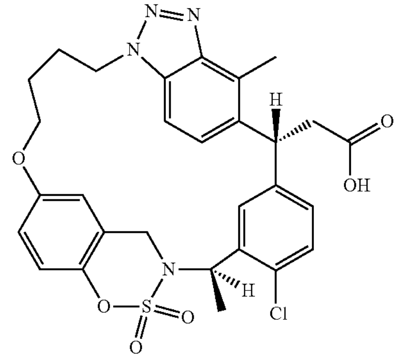

Step B1: Preparation of (1S)-1-[2-chloro-5-(4,4,5,5-tetramethyl-1,3,2-dioxaborolan-2-yl)phenyl]ethan-1-ol Using General Procedure 3 starting from (1S)-1-(5-bromo-2-chlorophenyl)ethan-1-ol (1 eq., 7.8 g, 33.1 mmol) as a reactant, gave the title compound (7.1 g, 76% yield).

$^1$H-NMR (400 MHz, DMSO-d6) δ ppm: 7.98 (d, 1H), 7.5 (dd, 1H), 7.38 (dd, 1H), 5.4 (d, 1H), 5.01 (m, 1H), 1.3 (d+s, 15H)

Step 1: Preparation of ethyl 3-{1-[4-(benzyloxy)butyl]-4-methyl-1H-benzotriazol-5-yl}-3-{4-chloro-3-[(1S)-1-hydroxyethyl]phenyl}propanoate Using General Procedure 6 starting from ethyl (2E)-3-{1-[4-(benzyloxy)butyl]-4-methyl-1H-benzotriazol-5-yl}prop-2-enoate (1 eq.) and (1S)-1-[2-chloro-5-(4,4,5,5-tetramethyl-1,3,2-dioxaborolan-2-yl)phenyl]ethan-1-ol (2 eq.) as reactants, the title compound (87% yield) was obtained.

$^1$H-NMR (400 MHz, DMSO-d6) δ ppm: 7.61/7.47 (2dd, 2H), 7.56/7.33-7.19 (s+m, 8H), 5.32/5.3 (2d, 1H), 4.94 (m, 1H), 4.86 (m, 1H), 4.66 (2t, 2H), 4.4 (s, 2H), 3.93 (q, 2H), 3.42 (t, 2H), 3.17 (m, 2H), 2.77/2.76 (2s, 3H), 1.94 (quint, 2H), 1.5 (quint, 2H), 1.27/1.24 (2d, 3H), 1 (t, 3H)

Step 2: Preparation of ethyl 3-{1-[4-(benzyloxy)butyl]-4-methyl-1H-benzotriazol-5-yl}-3-(3-{(1R)-1-[6-(benzyloxy)-2,2-dioxo-2H-1,$2\lambda^6$,3-benzoxathiazin-3(4H)-yl]ethyl}-4-chlorophenyl)propanoate Using General Procedure 7 starting from ethyl 3-{1-[4-(benzyloxy)butyl]-4-methyl-1H-benzotriazol-5-yl}-3-{4-chloro-3-[(1S)-1-hydroxyethyl]phenyl}propanoate (1 eq.) and 6-(benzyloxy)-3,4-dihydro-2H-1,$2\lambda^6$,3-benzoxathiazine-2,2-dione (1.1 eq.) as reactants, the title compound (82% yield) was obtained.

$^1$H-NMR (400 MHz, DMSO-d6) δ ppm: 0.93-1.01 (m, 3H) 1.40-1.54 (m, 5H) 1.86-1.98 (m, 2H) 2.77 (s, 3H) 3.19-3.26 (m, 2H) 3.36-3.45 (m, 2H) 3.85-3.98 (m, 2H) 4.36-4.41 (m, 2H) 4.43-4.60 (m, 2H) 4.60-4.70 (m, 2H) 4.84-4.95 (m, 1H) 5.03-5.13 (m, 2H) 5.35-5.43 (m, 1H) 6.81-6.94 (m, 1H) 6.98-7.07 (m, 1H) 7.17-7.31 (m, 5H) 7.36 (s, 1H) 7.37-7.47 (m, 5H) 7.51-7.57 (m, 1H) 7.62 (d, J=8.56 Hz, 1H)

Step 3: Preparation of ethyl 3-{4-chloro-3-[(1R)-1-(6-hydroxy-2,2-dioxo-2H-1,$2\lambda^6$,3-benzoxathiazin-3(4H)-yl)ethyl]phenyl}-3-[1-(4-hydroxybutyl)-4-methyl-1H-benzotriazol-5-yl]propanoate Using General Procedure 8 starting from ethyl 3-{1-[4-(benzyloxy)butyl]-4-methyl-1H-benzotriazol-5-yl}-3-(3-{(1R)-1-[6-(benzyloxy)-2,2-dioxo-2H-1,$2\lambda^6$,3-benzoxathiazin-3(4H)-yl]ethyl}-4-chlorophenyl)propanoate (1 eq.) as a reactant, the title compound (48% yield) was obtained.

$^1$H-NMR (400 MHz, DMSO-d6) δ ppm: 9.6 (s, 1H), 7.65 (m, 2H), 7.6 (d, 1H), 7.35 (d, 1H), 7.2 (dd, 1H), 6.9 (d, 1H), 6.7 (dd, 1H), 6.6 (d, 1H), 5.4 (m, 1H), 4.9 (m, 1H), 4.65 (t, 2H), 4.45 (m, 3H), 3.95 (q, 2H), 3.4 (q, 2H), 3.25 (d, 2H), 2.8 (s, 3H), 1.9 (m, 2H), 1.5 (m, 3H), 1.4 (m, 2H), 1 (2t, 3H)

Step 4: Preparation of ethyl 3-[1-(4-bromobutyl)-4-methyl-1H-benzotriazol-5-yl]-3-{4-chloro-3-[(1R)-1-(6-hydroxy-2,2-dioxo-2H-1,$2\lambda^6$,3-benzoxathiazin-3(4H)-yl)ethyl]phenyl}propanoate Using General Procedure 9 starting from ethyl 3-{4-chloro-3-[(1R)-1-(6-hydroxy-2,2-dioxo-2H-1,$2\lambda^6$,3-benzoxathiazin-3(4H)-yl)ethyl]phenyl}-3-[1-(4-hydroxybutyl)-4-methyl-1H-benzotriazol-5-yl]propanoate (1 eq.) as a reactant, the title compound (yellow oil, 70% yield) was obtained.

$^1$H-NMR (400 MHz, DMSO-d6) δ ppm: 9.63/9.62 (2m, 1H), 7.67 (d, 1H), 7.66/7.58 (dd, 2H), 7.36 (d, 1H), 7.25 (dd, 1H), 6.9 (d, 1H), 6.72 (m, 1H), 6.62/6.59 (d, 1H), 5.37 (m, 1H), 4.94-4.87 (m, 1H), 4.7 (t, 2H), 4.51-4.39 (m, 2H), 3.94 (q, 2H), 3.54 (q, 2H), 3.25 (d, 2H), 2.77 (s, 3H), 2 (m, 2H), 1.77 (m, 2H), 1.46 (m, 3H), 1 (t, 3H)

Step 5: Preparation of ethyl[(2R)-4-chloro-2,31-dimethyl-27,27-dioxo-21,26-dioxa-$27\lambda^6$-thia-1,14,15,16-tetraazahexacyclo[20.5.3.$1^{3,7}$0.$1^{9,13}$0.$0^{12,16}$0.$0^{25,29}$]dotriaconta-3(32),4,6,9(31),10,12,14,22,24,29-decaen-8-yl]acetate Using General Procedure 11 starting from ethyl 3-[1-(4-bromobutyl)-4-methyl-1H-benzotriazol-5-yl]-3-{4-chloro-3-[(1R)-1-(6-hydroxy-2,2-dioxo-2H-1,226,3-benzoxathiazin-3(4H)-yl)ethyl]phenyl}propanoate (1 eq.) as a reactant, the title compound (white solid, 98% yield) was obtained.

$^1$H-NMR (400 MHz, DMSO-d6) δ ppm: 0.96-1.08 (m, 5H) 1.14 (d, J=6.85 Hz, 2H) 1.29 (d, J=6.97 Hz, 4H)

1.55-1.77 (m, 2H) 1.77-1.90 (m, 1H) 1.92-2.27 (m, 3H) 2.61-2.86 (m, 5H) 2.98-3.20 (m, 2H) 3.34-3.53 (m, 4H) 3.59-3.80 (m, 2H) 3.86-4.03 (m, 3H) 4.03-4.17 (m, 2H) 4.66-4.80 (m, 3H) 4.86 (t, J=7.95 Hz, 1H) 4.95 (t, J=7.76 Hz, 1H) 5.28-5.47 (m, 2H) 5.72 (d, J=2.81 Hz, 1H) 5.85 (br. s., 1H) 6.66-6.80 (m, 2H) 6.87-6.98 (m, 2H) 7.15 (d, J=8.80 Hz, 1H) 7.31 (d, J=1.96 Hz, 1H) 7.48 (d, J=8.19 Hz, 1H) 7.57-7.63 (m, 2H) 7.71 (d, J=8.68 Hz, 1H) 7.78 (d, J=8.68 Hz, 1H) 7.91 (d, J=8.80 Hz, 1H)

Step 6: Preparation of Example 64

Using General Procedure 12 starting from ethyl[(2R)-4-chloro-2,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (1 eq.) as a reactant, the title compound (white solid, quant.) was obtained.

The diastereo-pure products were obtained by chromatographic separation on chiral column.

EXAMPLE 64a (2R,8S)

HRMS calculated for $C_{29}H_{29}ClN_4O_6S$: 596.1496; $[M+H]^+$ found: 597.1572 (δ=0.5 ppm).

$^1$H-NMR (400 MHz, DMSO-d6) δ ppm: 12.16 (m, 1H), 7.9 (d, 1H), 7.78 (d, 1H), 7.61 (dd, 1H), 7.49 (d, 1H), 7.27 (d, 1H), 6.94 (d, 1H), 6.75 (dd, 1H), 5.69 (d, 1H), 5.4 (m, 1H), 4.83 (m, 1H), 4.82-4.68 (m, 2H), 4.1/3.38 (dd, 2H), 3.67/3.47 (2m, 2H), 3.24/3.05 (2dd, 2H), 2.66 (s, 3H), 2.18/2.1 (2m, 2H), 1.86/1.74 (2m, 2H), 1.28 (d, 3H)

EXAMPLE 64b (2R,8R)

HRMS calculated for $C_{29}H_{29}ClN_4O_6S$: 596.1496; $[M+H]^+$ found: 597.1573 (δ=0.7 ppm).

$^1$H-NMR (400 MHz, DMSO-d6) δ ppm: 12.33 (m, 1H), 7.71 (d, 1H), 7.6/6.9 (2s, 3H), 7.11 (d, 1H), 6.92 (d, 1H), 6.73 (dd, 1H), 5.86 (d, 1H), 5.36 (q, 1H), 4.93 (m, 1H), 4.76 (m, 2H), 4.1/3.49 (dd, 2H), 3.76/3.65 (2m, 2H), 3.28/2.91 (2dd, 2H), 2.66 (s, 3H), 2.21/2.04 (2m, 2H), 1.66/1.32 (2m, 2H), 1.14 (d, 3H)

EXAMPLE 65: {4,31-Dimethyl-27,27-dioxo-18-[4-(trifluoromethyl)phenyl]-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl}acetic acid

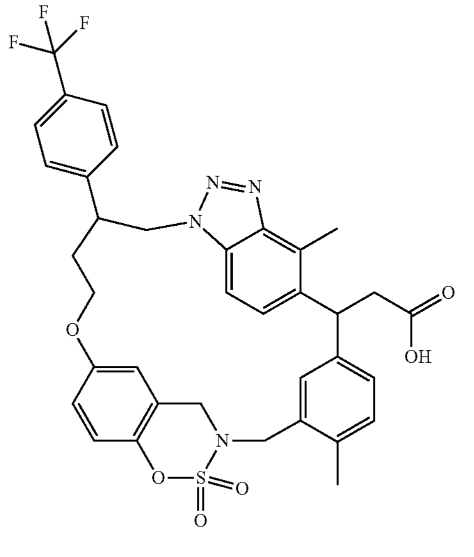 [SMILES: Cc1ccc2cc1CN1Cc3cc(ccc3OS1(=O)=O)OCCC(c1ccc(C(F)(F)F)cc1)Cn1nnc3c(C)c(ccc31)C2CC(=O)O]

Step 1: Preparation of ethyl 3-(3-{[6-(benzyloxy)-2,2-dioxo-2H-1,2λ$^6$,3-benzoxathiazin-3(4H)-yl]methyl}-4-methylphenyl)-3-[4-({4-hydroxy-2-[4-(trifluoromethyl)phenyl]butyl}amino)-2-methyl-3-nitrophenyl]propanoate Ethyl 3-(3-{[6-(benzyloxy)-2,2-dioxo-2H-1,2λ$^6$,3-benzoxathiazin-3(4H)-yl]methyl}-4-methylphenyl)-3-(4-fluoro-2-methyl-3-nitrophenyl)propanoate (1 eq., 2 g, 3.1 mmol) and 4-amino-3-[4-(trifluoromethyl) phenyl]butan-1-ol (1.5 eq., 1.078 g, 4.622 mmol) were dissolved in N,N-dimethylacetamide (5 mL). DIPEA (1.85 eq., 1 mL, 5.741 mmol) was added and the mixture was stirred under $N_2$ atmosphere at 100° C. overnight. Excess of 4-amino-3-[4-(trifluoromethyl)phenyl]butan-1-ol (0.25 g, 1.072 mmol) was added followed by addition of DIPEA (0.3 mL, 1.72 mmol), and the mixture was stirred at 100° C. for additional 24 h. After cooling, pouring on chilled brine and extraction with DCM, the collected organic phases were dried over $Na_2SO_4$ and evaporated to Celite. The crude product was purified by normal phase silica gel chromatography using DCM-MeOH (100:0 to 95.2:4.8) eluents resulted in 2.334 g (88% yield) of the title compound after drying in high vacuo at RT.

$^1$H-NMR (500 MHz, DMSO-d6) δ ppm: 7.63/7.62 (d/d, 2H), 7.43 (d, 2H), 7.41 (d/d, 2H), 7.39 (t, 2H), 7.34 (t, 1H), 7.33 (d, 1H), 7.16 (db, 1H), 7.15 (d, 1H), 7.14 (d, 1H), 7.11 (dd, 1H), 7.07 (dd, 1H), 6.99/6.98 (d/d, 1H), 6.75 (d, 1H), 5.62 (t, 1H), 5.09 (s, 2H), 4.53 (t, 1H), 4.46/4.42 (d+d, 2H), 4.45 (t, 1H), 4.24/4.23/4.19/4.19 (d+d/d+d, 2H), 3.97/3.95 (q/q, 2H), 3.39/3.27 (m+m, 2H), 3.28/3.27/3.18/3.16 (m+m/m+m, 2H), 3.13 (m, 1H), 3.05/3.04/3.01/3 (dd+dd/dd+dd, 2H), 2.22/2.21 (s/s, 3H), 2.11 (s, 3H), 1.88/1.7 (m+m, 2H), 1.04/1.03 (t/t, 3H)

Step 2: Preparation of ethyl 3-[3-amino-4-({4-hydroxy-2-[4-(trifluoromethyl)phenyl]butyl}amino)-2-methylphenyl]-3-(3-{[6-(benzyloxy)-2,2-dioxo-2H-1,2λ$^6$,3-benzoxathiazin-3(4H)-yl]methyl}-4-methylphenyl)propanoate To a solution of ethyl 3-(3-{[6-(benzyloxy)-2,2-dioxo-2H-1,2λ$^6$,3-benzoxathiazin-3(4H)-yl]methyl}-4-methylphenyl)-3-[4-({4-hydroxy-2-[4-(trifluoromethyl)phenyl]butyl}amino)-2-methyl-3-nitrophenyl]propanoate (1 eq., 2.327 g, 2.7 P mmol) in 1,2-dichloroethane (7 mL) and IPA (7 mL) Raney-nickel catalyst (0.65 g, 7.6 mmol) was added. Hydrazine hydrate (0.8109 g, 0.7858 mL, 8.100 mmol) was added dropwise over a period of 60 minutes (exothermic reaction!) and the reaction mixture was stirred at RT for further 30 min. The reaction mixture was filtered through a pad of Celite, the Celite was washed with DCM (3×15 mL) and THF (2×15 mL). The filtrate was evaporated to yield 2.267 g (quant.) of the title compound as a light yellow foamy material.

$^1$H-NMR (500 MHz, DMSO-d6) δ ppm: 7.63 (m, 2H), 7.48-7.3 (m, 5H), 7.46 (m, 2H), 7.14 (d, 1H), 7.09 (d, 1H), 7.07 (dd, 1H), 7.06 (d, 1H), 7.02/7.01 (dd, 1H), 6.98 (d, 1H), 6.35 (d, 1H), 5.1 (s, 2H), 4.51 (t, 1H), 4.43 (t, 1H), 4.42 (s, 2H), 4.32 (t, 1H), 4.21/4.14 (d+d, 2H), 4.12 (s, 2H), 3.96/3.93 (m+m, 2H), 3.48 (d, 1H), 3.29/3.19 (m+m, 2H), 3.23/3.16 (m+m, 2H), 3.15 (m, 1H), 2.9 (d, 2H), 2.2 (s, 3H), 1.98-1.72 (m+m, 2H), 1.94 (s, 3H), 1.05 (t, 3H)

Step 3: Preparation of ethyl 3-(3-{[6-(benzyloxy)-2,2-dioxo-2H-1,2λ$^6$,3-benzoxathiazin-3(4H)-yl]methyl}-4-methylphenyl)-3-(1-{4-hydroxy-2-[4-(trifluoromethyl)phenyl]butyl}-4-methyl-1H-benzotriazol-5-yl)propanoate Ethyl 3-[3-amino-4-({4-hydroxy-2-[4-(trifluoromethyl)phenyl]butyl}amino)-2-methylphenyl]-3-(3-{[6-(benzyloxy)-2,2-dioxo-2H-1,2λ$^6$,3-benzoxathiazin-3(4H)-yl]methyl}-4-methylphenyl) propanoate (1 eq., 2.24 g, 2.69 mmol) was dissolved in a mixture of THF (15 mL) and AcOH (1.5 mL). To this clear solution 3-methylbutyl nitrite (3 eq., 0.946 g, 1.09 mL, 8.08 mmol) was added dropwise at 0° C. and the mixture was stirred at RT for 3 h. The mixture was poured on sat. $NaHCO_3$ solution and extracted with EtOAc. The aq. layer was washed with further EtOAc portions, the combined organic layer was dried over $Na_2SO_4$, filtered and evaporated under reduced pressure. The crude product was purified by preparative HPLC on reversed-phase C18 column using aq. $NH_4HCO_3$-MeCN (100:0 to 30:70) as an eluent to give 0.80 g (40% yield) of the title compound as a light yellow foamy material.

$^1$H-NMR (500 MHz, DMSO-d6) δ ppm: 7.53 (d, 2H), 7.47 (d, 1H), 7.46 (m, 2H), 7.44/7.43 (d/d, 1H), 7.41 (m, 2H), 7.4 (m, 2H), 7.34 (tm, 1H), 7.22 (brs., 1H), 7.17/7.11 (dd/m, 1H), 7.14 (d, 1H), 7.11 (m, 1H), 7.07 (dd, 1H), 6.96/6.95 (d/d, 1H), 5.11/5.08 (d+d, 2H), 4.89 (m, 2H), 4.8 (t, 1H), 4.48/4.47 (t/t, 1H), 4.44 (m, 2H), 4.21 (m, 2H), 3.92/3.89 (q/q, 2H), 3.58 (m, 1H), 3.27/3.14 (m+m, 2H), 3.14 (m, 2H), 2.7 (s, 3H), 2.21 (s, 3H), 1.82 (m, 2H), 0.96/0.92 (t/t, 3H)

Step 4: Preparation of ethyl 3-{3-[(6-hydroxy-2,2-dioxo-2H-1,2λ$^6$,3-benzoxathiazin-3(4H)-yl)methyl]-4-methylphenyl}-3-(1-{4-hydroxy-2-[4-(trifluoromethyl)phenyl]butyl}-4-methyl-1H-benzotriazol-5-yl)propanoate Using General Procedure 8 starting from ethyl 3-(3-{[6-(benzyloxy)-2,2-dioxo-2H-1,2λ$^6$,3-benzoxathiazin-3(4H)-yl]methyl}-4-methylphenyl)-3-(1-{4-hydroxy-2-[4-(trifluoromethyl) phenyl]butyl}-4-methyl-1H-benzotriazol-5-yl) propanoate (1 eq.) as a reactant, the title compound (white foamy material, 96% yield) was obtained.

$^1$H-NMR (500 MHz, DMSO-d6) δ ppm: 9.71 (s, 1H), 7.55 (d, 2H), 7.5/7.48 (d/d, 1H), 7.45 (d, 1H), 7.43 (d, 2H), 7.21 (brs., 1H), 7.17/7.11 (d/d, 1H), 7.12 (m, 1H), 7 (d, 1H), 6.79 (dd, 1H), 6.61/6.6 (d/d, 1H), 4.92 (m, 2H), 4.79 (t, 1H), 4.38 (s, 2H), 4.21/4.17 (d+d, 2H), 3.91 (m, 2H), 3.6 (m, 1H), 3.28/3.15 (m+m, 2H), 3.14 (m, 2H), 2.7/2.69 (s/s, 3H), 2.22 (s, 3H), 1.83 (m, 2H), 0.97/0.94 (t/t, 3H)

Step 5: Preparation of ethyl 3-(1-{4-chloro-2-[4-(trifluoromethyl)phenyl]butyl}-4-methyl-1H-benzotriazol-5-yl)-3-{3-[(6-hydroxy-2,2-dioxo-2H-1,2λ$^6$,3-benzoxathiazin-3(4H)-yl)methyl]-4-methylphenyl}propanoate Using General Procedure 10 starting from ethyl 3-{3-[(6-hydroxy-2,2-dioxo-2H-1,2λ$^6$,3-benzoxathiazin-3(4H)-yl)methyl]-4-methylphenyl}-3-(1-{4-hydroxy-2-[4-(trifluoromethyl)phenyl]butyl}-4-methyl-1H-benzotriazol-5-yl) propanoate (1 eq.) as a reactant, the title compound (yellow solid foam, quant.) was obtained. The product was used in the next step without further purification.

$^1$H-NMR (500 MHz, DMSO-d6) δ ppm: 9.72 (br., 1H), 7.58 (d, 2H), 7.5/7.49 (d/d, 1H), 7.47/7.45 (d/d, 1H), 7.4 (d, 2H), 7.21 (brs., 1H), 7.17/7.11 (d/d, 1H), 7.12 (m, 1H), 6.99 (d, 1H), 6.79 (dd, 1H), 6.61 (brs., 1H), 4.97 (m, 2H), 4.79 (t, 1H), 4.38 (s, 2H), 4.21/4.17 (d+d, 2H), 3.91 (m, 2H), 3.66 (m, 1H), 3.53/3.31 (m+m, 2H), 3.14 (m, 2H), 2.69 (s/s, 3H), 2.24/2.12 (m+m, 2H), 2.22 (s, 3H), 0.97/0.93 (t/t, 3H)

Step 6: Preparation of ethyl {4,31-dimethyl-27,27-dioxo-18-[4-(trifluoromethyl)phenyl]-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl}acetate Ethyl 3-(1-{4-chloro-2-[4-(trifluoromethyl)phenyl]butyl}-4-methyl-1H-benzotriazol-5-yl)-3-{3-[(6-hydroxy-2,2-dioxo-2H-1,2λ$^6$,3-benzoxathiazin-3(4H)-yl)methyl]-4-methylphenyl}propanoate (1 eq., 0.55 g, 0.71 mmol) was dissolved in N,N-dimethylacetamide (5 mL). $Cs_2CO_3$ (1.7 eq., 0.50 g, 1.5 mmol) was added and the mixture was stirred at 120° C. for 3 h. After completion of the reaction the mixture was filtered through a pad of Celite, which was washed with DCM. The mother liquor was evaporated and the crude product was purified by reversed-phase C18 column chromatography using aq. $NH_4HCO_3$-MeCN (100:0 to 0:100), resulted in 0.23 g (44% yield) of the desired compound as a yellowish foamy material.

$^1$H-NMR (500 MHz, DMSO-d6, mixture of diastereomers) 6 ppm: 7.87/7.84 (d/d, 1H), 7.8/7.78 (s/d, 2H), 7.8/7.67 (s/d, 2H), 7.58/7.5 (d/d, 1H), 7.51/7.49 (dd/dd, 1H), 7.31/7.29 (d/d, 1H), 7 (d, 1H), 6.79/6.77 (dd/dd, 1H), 6.61/6.55 (d/d, 1H), 6.02/5.82 (d/d, 1H), 5.16/5.04/4.86/4.77 (dd/dd+dd/dd, 2H), 4.8 (t, 1H), 4.22/4.15/3.97/3.87 (d/d+d/d, 2H), 4.08/4.04/3.85/3.82 (d/d+d/d, 2H), 3.93/3.92 (q/q, 2H), 3.78/3.6 (m/m, 1H), 3.61/3.53/3.53/3.06 (m/m+m/m, 2H), 3.22-3.03 (m, 2H), 2.64/2.62 (s/s, 3H), 2.35-2 (m, 2H), 2.34/2.33 (s/s, 3H), 1.02/1.01 (t/t, 3H)

Step 7: Preparation of Example 65

Using General Procedure 12 starting from ethyl {4,31-dimethyl-27,27-dioxo-18-[4-(trifluoromethyl)phenyl]-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl}acetate (1 eq.) as a reactant, the title compound (white solid, 29% yield) was obtained.

HRMS calculated for $C_{36}H_{33}F_3N_4O_6S$: 706.2073; $[M+H]^+$ found: 707.2142 (δ=−0.5 ppm).

$^1$H-NMR (500 MHz, DMSO-d6, mixture of diastereomers) 6 ppm: 12.13 (br., 1H), 7.86/7.84 (d/d, 1H), 7.8/7.68 (s/d, 2H), 7.8/7.78 (s/d, 2H), 7.56/7.5 (d/d, 1H), 7.52/7.5 (dd/dd, 1H), 7.31/7.3 (d/d, 1H), 6.99 (d, 1H), 6.79/6.77 (dd/dd, 1H), 6.59/6.53 (d/d, 1H), 6/5.81 (d/d, 1H), 5.15/5.04/4.85/4.77 (dd/dd+dd/dd, 2H), 4.78 (t, 1H), 4.22/4.14/3.98/3.87 (d/d+d/d, 2H), 4.07/4.04/3.86/3.82 (d/d+d/d, 2H), 3.78/3.63 (m/m, 1H), 3.67-3.02 (m, 2H), 3.06/2.99 (m+m, 2H), 2.63/2.62 (s/s, 3H), 2.38-2.02 (m, 2H), 2.34/2.33 (s/s, 3H) $^{13}$C-NMR (125 MHz, DMSO-d6) δ ppm: 173.2, 131.4/131.3, 131.1, 129.5/129.2, 128.8, 127.6/127.4, 126.1, 119.6/119.4, 117.7/117.3, 111.7/111.3, 108.3/108, 66.5/66.3, 54/52.5, 51.9, 48.8/48.7, 43.7/41.2, 41.9/41.8, 40.9, 34.2/32.7, 18.5/18.4, 13.5/13.4

EXAMPLE 66: [30-Chloro-4,31-dimethyl-27,27-dioxo-21,26-dioxa-27λ$^6$-thia-1,14,15,16-tetraaza-hexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid enantiomer 1

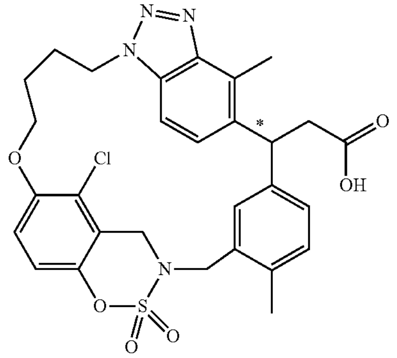

* = RorS enantiomer 2

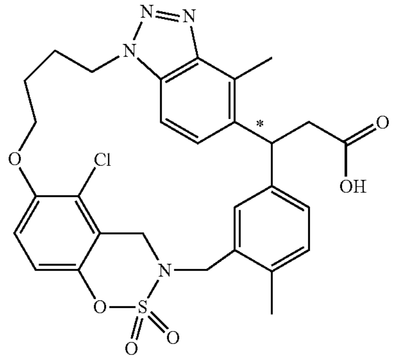

* = RorS

Step 1: Preparation of 6-(benzyloxy)-3-[(5-bromo-2-methylphenyl)methyl]-5-chloro-3,4-dihydro-2H-1,2λ$^6$,3-benzoxathiazine-2,2-dione 6-(Benzyloxy)-3-[(5-bromo-2-methylphenyl)methyl]-3,4-dihydro-2H-1,2λ$^6$,3-benzoxathiazine-2,2-dione (1 eq., 2 g, 4.2 mmol) was dissolved in nitromethane (40 mL), then Oxone® (3 eq., 7.78 g, 12.7 mmol) and potassium chloride (1.8 eq., 5.66 g, 7.5921 mmol) were added. The reaction mixture was stirred at 60° C. for 2 days. After concentration under reduced pressure, the residue was dissolved in DCM and the solution was washed with water. The organic phase was dried over $MgSO_4$, filtered and concentrated under reduced pressure to give 2.078 g of the crude product, which was purified via flash chromatography using heptane-EtOAc as eluents to give the title compound (1.404 g, 2.759 mmol, 65% yield) as a yellowish oil.

$^1$H-NMR (500 MHz, DMSO-d6) δ ppm: 7.51-7.32 (m, 5H), 7.5 (d, 1H), 7.47 (dd, 1H), 7.34 (d, 1H), 7.22 (d, 1H), 7.21 (d, 1H), 5.25 (s, 2H), 4.59 (s, 2H), 4.36 (s, 2H), 2.26 (s, 3H)

Step 2: Preparation of 6-(benzyloxy)-5-chloro-3-{[2-methyl-5-(4,4,5,5-tetramethyl-1,3,2-dioxaborolan-2-yl)phenyl]methyl}-3,4-dihydro-2H-1,2λ$^6$,3-benzoxathiazine-2,2-dione Using General Procedure 3 starting from 6-(benzyloxy)-3-[(5-bromo-2-methylphenyl)methyl]-5-chloro-3,4-dihydro-2H-1,2λ$^6$,3-benzoxathiazine-2,2-dione (1 eq., 1.40 g, 2.75 mmol) as a reactant, the title compound (1.33 g, 87% yield) was obtained.

$^1$H-NMR (500 MHz, DMSO-d6) δ ppm: 7.58 (dd, 1H), 7.51 (d, 1H), 7.49-7.33 (m, 5H), 7.35 (s, 1H), 7.28 (d, 1H), 7.22 (d, 1H), 5.25 (s, 2H), 4.5 (s, 2H), 4.34 (s, 2H), 2.33 (s, 3H), 1.28 (s, 12H)

Step 3: Preparation of ethyl 3-{1-[4-(benzyloxy)butyl]-4-methyl-1H-benzotriazol-5-yl}-3-(3-{[6-(benzyloxy)-5-chloro-2,2-dioxo-2H-1,2λ$^6$,3-benzoxathiazin-3(4H)-yl]methyl}-4-methylphenyl)propanoate Using General Procedure 6 starting from ethyl (2E)-3-{1-[4-(benzyloxy)butyl]-4-methyl-1H-benzotriazol-5-yl}prop-2-enoate (1 eq., 0.92 g, 2.34 mmol) and 6-(benzyloxy)-5-chloro-3-{[2-methyl-5-(4,4,5,5-tetramethyl-1,3,2-dioxaborolan-2-yl)phenyl]methyl}-3,4-dihydro-2H-1,2λ$^6$,3-benzoxathiazine-2,2-dione (1 eq., 1.30 g, 2.34 mmol) as reactants, the title compound (638 mg, 33% yield) was obtained.

$^1$H-NMR (500 MHz, DMSO-d6) δ ppm: 7.56 (d, 1H), 7.51-7.21 (m, 10H), 7.46 (d, 1H), 7.33 (d, 1H), 7.25 (m, 1H), 7.24 (m, 1H), 7.2 (d, 1H), 7.16 (d, 1H), 5.24 (s, 2H), 4.84 (t, 1H), 4.63 (t, 2H), 4.39 (s, 2H), 4.37 (s, 2H), 4.26 (s, 2H), 3.91 (q, 2H), 3.38 (t, 2H), 3.15 (d, 2H), 2.76 (s, 3H), 2.25 (s, 3H), 1.91 (m, 2H), 1.47 (m, 2H), 0.97 (t, 3H)

Step 4: Preparation of ethyl 3-{3-[(5-chloro-6-hydroxy-2,2-dioxo-2H-1,2λ$^6$,3-benzoxathiazin-3(4H)-yl)methyl]-4-methylphenyl}-3-[1-(4-hydroxybutyl)-4-methyl-1H-benzotriazol-5-yl]propanoate Using General Procedure 8 starting from ethyl 3-{1-[4-(benzyloxy)butyl]-4-methyl-1H-benzotriazol-5-yl}-3-(3-{[6-(benzyloxy)-5-chloro-2,2-dioxo-2H-1,2λ$^6$,3-benzoxathiazin-3(4H)-yl]methyl}-4-methylphenyl)propanoate (1 eq., 755 mg, 0.9169 mmol) as a reactant, the title compound (423 mg, 72% yield) was obtained.

$^1$H-NMR (500 MHz, DMSO-d6) δ ppm: 10.5 (br., 1H), 7.58 (d, 1H), 7.48 (d, 1H), 7.24 (m, 1H), 7.24 (m, 1H), 7.16 (d, 1H), 7.04 (d, 1H), 7.02 (d, 1H), 4.84 (t, 1H), 4.64 (t, 2H), 4.43 (br., 1H), 4.36 (s, 2H), 4.26/4.22 (d+d, 2H), 3.92 (q, 2H), 3.38 (t, 2H), 3.15 (d, 2H), 2.76 (s, 3H), 2.24 (s, 3H), 1.9 (m, 2H), 1.36 (m, 2H), 0.99 (t, 3H)

Step 5: Preparation of ethyl 3-[1-(4-chlorobutyl)-4-methyl-1H-benzotriazol-5-yl]-3-{3-[(5-chloro-6-hydroxy-2,2-dioxo-2H-1,2λ$^6$,3-benzoxathiazin-3(4H)-yl)methyl]-4-methylphenyl}propanoate Using General Procedure 10 starting from ethyl 3-{3-[(5-chloro-6-hydroxy-2,2-dioxo-2H-1,2)$^6$,3-benzoxathiazin-3(4H)-yl)methyl]-4-methylphenyl}-3-[1-(4-hydroxybutyl)-4-methyl-1H-benzotriazol-5-yl]propanoate (1 eq., 420 mg, 0.6530 mmol) as a reactant, the title compound (444 mg, 99% yield) was obtained.

$^1$H-NMR (500 MHz, DMSO-d6) δ ppm: 10.52 (s, 1H), 7.6 (d, 1H), 7.49 (d, 1H), 7.24 (dd, 1H), 7.23 (d, 1H), 7.16

(d, 1H), 7.04 (d, 1H), 7.02 (d, 1H), 4.84 (t, 1H), 4.68 (t, 2H), 4.35 (s, 2H), 4.25/4.22 (d+d, 2H), 3.92 (q, 2H), 3.64 (t, 2H), 3.15 (d, 2H), 2.75 (s, 3H), 2.24 (s, 3H), 1.99/1.68 (m+m, 4H), 0.98 (t, 3H)

Step 6: Preparation of ethyl[30-chloro-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate Using General Procedure 11 starting from ethyl 3-[1-(4-chlorobutyl)-4-methyl-1H-benzotriazol-5-yl]-3-{3-[(5-chloro-6-hydroxy-2,2-dioxo-2H-1,2)$^6$,3-benzoxathiazin-3(4H)-yl)methyl]-4-methylphenyl}propanoate (1 eq., 432 mg, 0.6530 mmol) as a reactant, the title compound (372 mg, 91% yield) was obtained.

$^1$H-NMR (500 MHz, DMSO-d6) δ ppm: 7.55 (d, 1H), 7.5 (dd, 1H), 7.31 (d, 1H), 7.31 (d, 1H), 7.15 (d, 1H), 7.06 (d, 1H), 6.41 (d, 1H), 4.78/4.73 (dm+dm, 2H), 4.78 (t, 1H), 4.12/4.01 (d+d, 2H), 4.1/4.01 (m+m, 2H), 4.05/3.98 (d+d, 2H), 3.9 (m, 2H), 3.23/3.01 (dd+dd, 2H), 2.6 (s, 3H), 2.33 (s, 3H), 2.23/2.06 (m+m, 2H), 1.67/1.53 (m+m, 2H), 0.97 (t, 3H)

Step 7: Preparation of Example 66

Using General Procedure 12 starting from ethyl[30-chloro-4,31-dimethyl-27,27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (1 eq., 370 mg, 0.5919 mmol) as a reactant, the title compound (221 mg, 63% yield) was obtained.

The enantiopure products were obtained by chromatographic separation on chiral column.

EXAMPLE 66a (E1)

HRMS calculated for $C_{29}H_{29}ClN_4O_6S$: 596.1496; $[M+H]^+$ found: 597.1565 (δ=−0.7 ppm).

EXAMPLE 66b (E2)

HRMS calculated for $C_{29}H_{29}ClN_4O_6S$: 596.1496; $[M+H]^+$ found: 597.1567 (δ=−0.4 ppm).

$^1$H-NMR (500 MHz, DMSO-d6) δ ppm: 7.55 (d, 1H), 7.51 (d, 1H), 7.31 (d, 1H), 7.29 (d, 1H), 7.15 (d, 1H), 7.05 (d, 1H), 6.39 (s, 1H), 4.79/4.71 (m+m, 2H), 4.79/4.71 (d+d, 2H), 4.76 (t, 1H), 4.12/4.01 (d+d, 2H), 4.09/4.01 (m+m, 2H), 3.1/2.88 (dd+dd, 2H), 2.6 (s, 3H), 2.33 (s, 3H), 2.24/2.07 (m+m, 2H), 1.67/1.52 (m+m, 2H)

$^{13}$C-NMR (125 MHz, DMSO-d6) δ ppm: 131.4, 131.3, 128.4, 127, 118, 117.7, 108.5, 71.4, 52.7, 48, 48, 41.1, 41.1, 27.2, 26.5, 18.5, 13.3

EXAMPLE 67: [4,38-Dimethyl-34,34-dioxo-28,33-dioxa-20,34λ$^6$-dithia-1,14,15,16-tetraazaheptacyclo[27.5.3.1$^{3,7}$0.1$^{9,13}$0.0$^{12,16}$0.0$^{21,26}$0.0$^{32,36}$]nonatriaconta-3(39),4,6,9(38),10,12,14,21,23,25,29,31,36-tridecaen-8-yl]acetic acid enantiomer 1

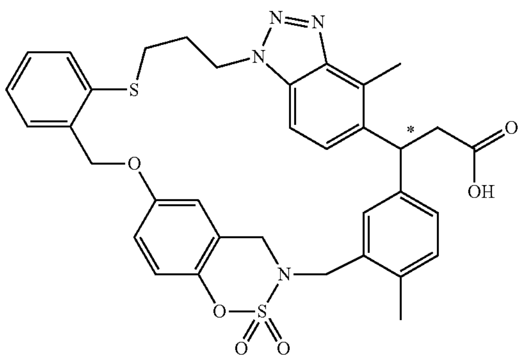

* = RorS enantiomer 2

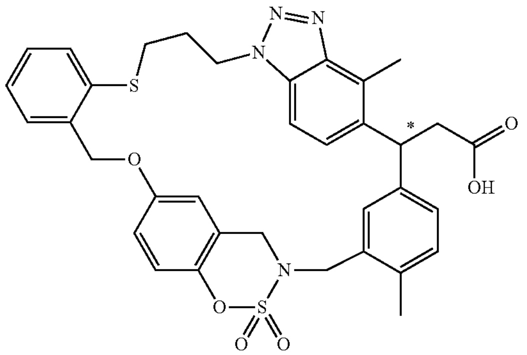

* = RorS

Step A1: Preparation of ethyl (2E)-3-(4-methyl-1-{3-[(oxan-2-yl)oxy]propyl}-1H-benzotriazol-5-yl)prop-2-enoate To a solution of ethyl (2E)-3-[1-(3-hydroxypropyl)-4-methyl-1H-benzotriazol-5-yl]prop-2-enoate (1 eq., 4.34 g, 15 mmol) in DCM (50 mL) at 0° C. 4-methylbenzene-1-sulfonic acid monohydrate (0.01 eq., 38 mg, 0.15 mmol) was added followed by addition of 3,4-dihydro-2H-pyran (1.1 equiv., 1.39 g, 16.5 mmol). The reaction mixture was allowed to warm to RT and was stirred for 1 h before quenching with saturated $NaHCO_3$ (30 mL). The phases were separated. The aq. phase was extracted with DCM (30 mL), and the combined organic phases were dried over $MgSO_4$. The solvent was removed under reduced pressure to give the title compound (5.5 g, 98% yield).

$^1$H-NMR (500 MHz, DMSO-d6) δ ppm: 8.02 (d, 1H), 7.97 (d, 1H), 7.71 (d, 1H), 6.65 (d, 1H), 4.77 (t, 2H), 4.47 (dd, 1H), 4.22 (q, 2H), 3.65/3.36 (m+m, 2H), 3.62/3.29 (m+m, 2H), 2.81 (s, 3H), 2.16 (m, 2H), 1.71-1.32 (m, 6H), 1.28 (t, 3H)

Step 1: Preparation of ethyl 3-[3-(hydroxymethyl)-4-methylphenyl]-3-(4-methyl-1-{3-[(oxan-2-yl)oxy]propyl}-1H-benzotriazol-5-yl)propanoate Ethyl (2E)-3-(4-methyl-1-{3-[(oxan-2-yl)oxy]propyl}-1H-benzotriazol-5-yl)prop-2-enoate (1 eq., 5.5 g, 0.015 mol) was added to dioxane (90 mL) and water (45 mL) and the suspension was degassed with nitrogene. [2-methyl-5-(4,4,5,5-tetramethyl-1,3,2-dioxaborolan-2-yl)phenyl]methanol (1.5 equiv., 5.5 g, 0.022 mol) and TEA (1.6 eq., 2.4 g, 0.024 mol) were added prior to the addition of chloro(1,5-cyclooctadiene)rhodium(I) dimer catalyst (0.05 equiv., 0.36 g, 0.00074 mol). The reaction mixture was heated at 80° C. for 30 minutes, then stirred at RT overnight. After the reaction was completed, the mixture was diluted with water (50 mL). The solution was extracted with EtOAc (2×50 mL). The combined organic layer was washed with brine (50 mL), and dried over $MgSO_4$. The solvent was evaporated to give a dark oil, which was purified by flash chromatography using heptane/EtOAc (50:50) as an eluent to give the title compound (7.3 g, quant.)

$^1$H-NMR (500 MHz, DMSO-d6) δ ppm: 7.6 (d, 1H), 7.47 (d, 1H), 7.26 (d, 1H), 7.1 (dd, 1H), 7.02 (d, 1H), 4.99 (t, 1H), 4.83 (t, 1H), 4.71 (t, 2H), 4.45 (dd, 1H), 4.4 (d, 2H), 3.92 (q, 2H), 3.62/3.33 (m+m, 2H), 3.59/3.26 (m+m, 2H), 3.13 (m, 2H), 2.76 (s, 3H), 2.15 (s, 3H), 2.13 (m, 2H), 1.7-1.3 (m, 6H), 1.01 (t, 3H)

Step 2: Preparation of ethyl 3-(3-{[6-(benzyloxy)-2,2-dioxo-2H-1,2λ$^6$,3-benzoxathiazin-3(4H)-yl]methyl}-4-methylphenyl)-3-(4-methyl-1-{3-[(oxan-2-yl)oxy]propyl}-1H-benzotriazol-5-yl)propanoate Ethyl 3-[3-(hydroxymethyl)-4-methylphenyl]-3-(4-methyl-1-{3-[(oxan-2-yl)oxy]propyl}-1H-benzotriazol-5-yl)propanoate (1 eq., 3.0 g, 6.1 mmol) was dissolved in THF (20 mL), then 6-(benzyloxy)-3,4-dihydro-2H-1,2λ$^6$,3-benzoxathiazine-2,2-dione (1 eq., 1.80 g, 6.18 mmol) and $PPh_3$ (2 eq., 3.20 g, 12.2 mmol) were added. The mixture was cooled to 5° C., DIAD (2 eq., 2.40 g, 11.9 mmol) was added dropwise and the reaction mixture was stirred at RT for 2 h. The solvent was evaporated to dryness. The crude product was purified by normal phase silica gel chromatography using heptane-EtOAc (100:0 to 50:50) as an eluent to give the title compound (2.8 g, 60% yield).

$^1$H-NMR (500 MHz, DMSO-d6) δ ppm: 7.58 (d, 1H), 7.49-7.31 (m, 5H), 7.49 (d, 1H), 7.22 (d, 1H), 7.19 (dd, 1H), 7.13 (d, 1H), 7.13 (d, 1H), 7.07 (dd, 1H), 6.96 (d, 1H), 5.1 (s, 2H), 4.85 (t, 1H), 4.68 (t, 2H), 4.43 (s, 2H), 4.42 (dd, 1H), 4.21 (s, 2H), 3.92 (q, 2H), 3.6/3.31 (m+m, 2H), 3.57/3.24 (m+m, 2H), 3.2/3.15 (dd+dd, 2H), 2.77 (s, 3H), 2.22 (s, 3H), 2.11 (m, 2H), 1.69-1.26 (m, 6H), 0.99 (t, 3H)

Step 3: Preparation of ethyl 3-{3-[(6-hydroxy-2,2-dioxo-2H-1,2λ$^6$,3-benzoxathiazin-3(4H)-yl)methyl]-4-methylphenyl}-3-(4-methyl-1-{3-[(oxan-2-yl)oxy]propyl}-1H-benzotriazol-5-yl)propanoate Ethyl 3-(3-{[6-(benzyloxy)-2,2-dioxo-2H-1,2λ$^6$,3-benzoxathiazin-3(4H)-yl]methyl}-4-methylphenyl)-3-(4-methyl-1-{3-[(oxan-2-yl)oxy]propyl}-1H-benzotriazol-5-yl)propanoate (1 eq., 2.80 g, 3.6 mmol) was dissolved in THF (45 mL) in an oven-dried vessel equipped with a PTFE-coated magnetic stir bar. Pd/C was added and the mixture was hydrogenated under 4 bar pressure at RT for 12 h. After completion of the reaction the catalyst was filtered off. The mother liquid was evaporated to dryness to give the title compound (2.45 g, 99% yield).

$^1$H-NMR (500 MHz, DMSO-d6) δ ppm: 9.7 (s, 1H), 7.6 (d, 1H), 7.51 (d, 1H), 7.21 (d, 1H), 7.19 (dd, 1H), 7.13 (d, 1H), 6.99 (d, 1H), 6.79 (dd, 1H), 6.6 (d, 1H), 4.84 (t, 1H), 4.71 (t, 2H), 4.43 (m, 1H), 4.38 (s, 2H), 4.21/4.17 (d+d, 2H), 3.93 (q, 2H), 3.61/3.33 (m+m, 2H), 3.59/3.27 (m+m, 2H), 3.19/3.15 (dd+dd, 2H), 2.75 (s, 3H), 2.22 (s, 3H), 2.14 (qn, 2H), 1.66-1.31 (m, 6H), 1 (t, 3H)

Step 4: Preparation of ethyl 3-{3-[(6-hydroxy-2,2-dioxo-2H-1,2λ$^6$,3-benzoxathiazin-3(4H)-yl)methyl]-4-methylphenyl}-3-[1-(3-hydroxypropyl)-4-methyl-1H-benzotriazol-5-yl]propanoate Ethyl 3-{3-[(6-hydroxy-2,2-dioxo-2H-1,2λ$^6$,3-benzoxathiazin-3(4H)-yl)methyl]-4-methylphenyl}-3-(4-methyl-1-{3-[(oxan-2-yl)oxy]propyl}-1H-benzotriazol-5-yl)propanoate (1 eq., 2.40 g, 3.60 mmol) was dissolved in EtOH (25.0 mL) and the 4-methylbenzene-1-sulfonic acid pyridine complex (0.05 eq., 45.3 mg, 0.180 mmol) was added. The reaction mixture was stirred at 55° C. for 2 h. The reaction mixture was concentrated, the residue was dissolved in DCM, washed with 2×20 ml of $NaHCO_3$, then with 20 ml brine, dried over $MgSO_4$, filtered and evaporated to dryness to give the title compound (1.90 g, 88% yield).

$^1$H-NMR (500 MHz, DMSO-d6) δ ppm: 9.71 (brs., 1H), 7.6 (d, 1H), 7.5 (d, 1H), 7.22 (d, 1H), 7.19 (dd, 1H), 7.13 (d, 1H), 6.99 (d, 1H), 6.79 (dd, 1H), 6.6 (d, 1H), 4.84 (t, 1H), 4.68 (t, 2H), 4.67 (br., 1H), 4.4/4.36 (d+d, 2H), 4.21/4.17 (d+d, 2H), 3.94 (q, 2H), 3.38 (t, 2H), 3.19/3.15 (dd+dd, 2H), 2.76 (s, 3H), 2.22 (s, 3H), 2.01 (m, 2H), 1 (t, 3H)

Step 5: Preparation of ethyl 3-[1-(3-chloropropyl)-4-methyl-1H-benzotriazol-5-yl]-3-{3-[(6-hydroxy-2,2-dioxo-2H-1,2λ$^6$,3-benzoxathiazin-3(4H)-yl)methyl]-4-methylphenyl}propanoate Using General Procedure 10 starting from ethyl 3-{3-[(6-hydroxy-2,2-dioxo-2H-1,2)$^6$,3-benzoxathiazin-3(4H)-yl)methyl]-4-methylphenyl}-3-[1-(3-hydroxypropyl)-4-methyl-1H-benzotriazol-5-yl]propanoate (1 eq.) as a reactant, the title compound (97% yield) was obtained.

$^1$H-NMR (500 MHz, DMSO-d6) δ ppm: 9.76 (brs, 1H), 7.63 (d, 1H), 7.53 (d, 1H), 7.22 (d, 1H), 7.2 (dd, 1H), 7.13 (d, 1H), 6.99 (d, 1H), 6.8 (dd, 1H), 6.6 (d, 1H), 4.84 (t, 1H), 4.77 (t, 2H), 4.37 (s, 2H), 4.21/4.17 (d+d, 2H), 3.93 (q, 2H), 3.61 (t, 2H), 3.19/3.15 (dd+dd, 2H), 2.76 (s, 3H), 2.33 (qn, 2H), 2.22 (s, 3H), 1 (t, 3H)

Step 6: Preparation of ethyl 3-{3-[(6-hydroxy-2,2-dioxo-2H-1,2λ$^6$,3-benzoxathiazin-3(4H)-yl)methyl]-4-methylphenyl}-3-[1-(3-{[2-(hydroxymethyl)phenyl]sulfanyl}propyl)-4-methyl-1H-benzotriazol-5-yl]propanoate Ethyl 3-[1-(3-chloropropyl)-4-methyl-1H-benzotriazol-5-yl]-3-{3-[(6-hydroxy-2,2-dioxo-2H-1,2λ$^6$,3-benzoxathiazin-3(4H)-yl)methyl]-4-methylphenyl}propanoate (1 eq., 1.61 g, 2.63 mmol) and (2-sulfanylphenyl)methanol (1.2 eq., 442 mg, 3.15 mmol) were dissolved in DMF (9 mL) and $K_2CO_3$, (2 eq., 726 mg, 5.25 mmol) was added. The reaction mixture was stirred at RT for 2 h. After pouring into 10 ml of water, the mixture was extracted with 2×30 mL of DCM. The combined organic layer was dried over $MgSO_4$, filtered and evaporated to dryness to give a yellow crystalline product (1.5 g, 79% yield).

$^1$H-NMR (500 MHz, DMSO-d6) δ ppm: 9.7 (s, 1H), 7.59 (d, 1H), 7.51 (d, 1H), 7.43 (d, 1H), 7.22 (d, 1H), 7.19 (dd, 1H), 7.19 (d, 1H), 7.17 (t, 1H), 7.13 (d, 1H), 7.12 (t, 1H), 6.99 (d, 1 H), 6.79 (dd, 1H), 6.6 (d, 1H), 5.22 (t, 1H), 4.84 (t, 1H), 4.76 (t, 2H), 4.52 (d, 2H), 4.4/4.35 (d+d, 2H), 4.21/4.17 (d+d, 2H), 3.93 (q, 2H), 3.19/3.13 (dd+dd, 2H), 2.9 (t, 2H), 2.76 (s, 3H), 2.22 (s, 3H), 2.13 (qn, 2H), 1 (t, 3H)

Step 7: Preparation of ethyl 3-[1-(3-{[2-(chloromethyl)phenyl]sulfanyl}propyl)-4-methyl-1H-benzotriazol-5-yl]-3-{3-[(6-hydroxy-2,2-dioxo-2H-1,2)$^6$,3-benzoxathiazin-3(4H)-yl)methyl]-4-methylphenyl}propanoate Using General Procedure 10 starting from ethyl 3-{3-[(6-hydroxy-2,2-dioxo-2H-1,2λ$^6$,3-benzoxathiazin-3(4H)-yl) methyl]-4-methylphenyl}-3-[1-(3-{[2-(hydroxymethyl)phenyl]sulfanyl}propyl)-4-methyl-1H-benzotriazol-5-yl] propanoate (1 eq.) as a reactant, the title compound (98% yield) was obtained.

HRMS calculated for $C_{37}H_{39}ClN_4O_6S_2$: 734.2000; $[M+H]^+$ found: 735.2057 (δ=−2.1 ppm).

Step 8: Preparation of ethyl[4,38-dimethyl-34,34-dioxo-28,33-dioxa-20,34λ$^6$-dithia-1,14,15,16-tetraazaheptacyclo[27.5.3.1$^{3,7}$0.1$^{9,13}$0.0$^{12,16}$0.0$^{21,26}$0.0$^{32,36}$]nonatriaconta-3(39),4,6,9(38),10,12,14,21,23,25,29,31,36-tridecaen-8-yl]acetate Using General Procedure 11 starting from ethyl 3-[1-(3-{[2-(chloromethyl)phenyl]sulfanyl}propyl)-4-methyl-1H-benzotriazol-5-yl]-3-{3-[(6-hydroxy-2,2-dioxo-2H-1,2λ$^6$,3-benzoxathiazin-3(4H)-yl)methyl]-4-methylphenyl}propanoate (1 eq., 1.56 g, 2.12 mmol) as a reactant, the title compound (1.375 g, yellow crystals, 93% yield) was obtained.

HRMS calculated for $C_{37}H_{38}N_4O_6S_2$: 698.2233; $[M+H]^+$ found: 699.229 (δ=−2.2 ppm).

Step 9: Preparation of Example 67

Using General Procedure 12 starting from ethyl[4,38-dimethyl-34,34-dioxo-28,33-dioxa-20,34λ$^6$-dithia-1,14,15,16-tetraazaheptacyclo[27.5.3.1$^{3,7}$0.1$^{9,13}$0.0$^{12,16}$0.0$^{21,26}$0.0$^{32,36}$]nonatriaconta-3(39),4,6,9(38),10,12,14,21,23,25,29,31,36-tridecaen-8-yl]acetate (1 eq.) as a reactant, the title compound (white solid, 22% yield) was obtained.

The enantiopure products were obtained by chromatographic separation on chiral column.

EXAMPLE 67a (E1)

HRMS calculated for $C_{35}H_4O_6S_2$: 670.1920; $[M+H]^+$ found: 671.1992 (δ=−0.1 ppm).

EXAMPLE 67b (E2)

HRMS calculated for $C_{35}H_4O_6S_2$: 670.1920; $[M+H]^+$ found: 671.1992 (δ=−0.1 ppm).

$^1$H-NMR (500 MHz, DMSO-d6) δ ppm: 12.12 (br., 1H), 7.61 (dd, 1H), 7.57 (dd, 1H), 7.54 (d, 1H), 7.46 (d, 1H), 7.41 (td, 1H), 7.36 (dd, 1H), 7.33 (td, 1H), 7.18 (d, 1H), 7.15 (m, 1H), 7.15 (m, 1H), 7.15 (d, 1H), 6.77 (brs., 1H), 5.26/5.14 (d+d, 2H), 4.81 (t, 1H), 4.64 (m, 2H), 4.34/4.17 (d+d, 2H), 4.25/4.11 (d+d, 2H), 3.04 (m, 2H), 3.01 (m, 2H), 2.75 (s, 3H), 2.29 (s, 3H), 2.24/2.14 (m+m, 2H)

$^{13}$C-NMR (125 MHz, DMSO-d6) δ ppm: 173.2, 131.3, 131.2, 130.2, 130, 129.7, 129.2, 127.3, 127.1, 119.6, 116.4, 113.4, 107.8, 68.9, 51.8, 49.2, 45.8, 41.3, 40.8, 30.6, 28.6, 18.4, 13.3

EXAMPLE 68: [(2R)-2,4,31-Trimethyl-27,27-dioxo-27λ$^6$-spiro[21,26-dioxa-27-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaene-18,4'-oxan]-8-yl]acetic acid

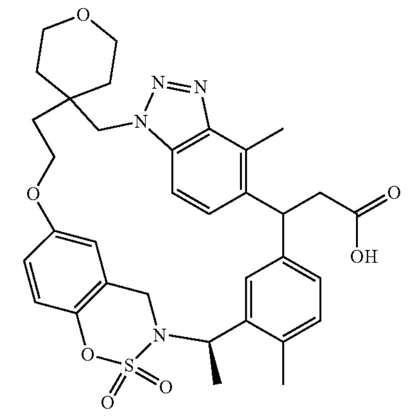 [SMILES: Cc1ccc2cc1[C@@H](C)N1Cc3cc(ccc3OS1(=O)=O)OCCC1(CCOCC1)Cn1nnc3c(C)c(ccc31)C2CC(=O)O]

Step A1: Preparation of 4-[2-(benzyloxy)ethyl]oxane-4-carbonitrile

To a solution of oxane-4-carbonitrile (1 eq., 10 g, 90 mmol) in abs. THF (20 mL/g, 200 mL) lithium bis(trimethylsilyl)amide (1.2 eq., 1 M in THF, 108 mL, 108 mmol) was added dropwise at −78° C. while continuous stirring and the mixture was stirred at this temperature for additional 2 h. [(2-Iodoethoxy)methyl]benzene (1 eq., 23.58 g, 90 mmol) dissolved in 100 mL of THF was added dropwise at −78° C. The reaction mixture was allowed to warm to RT and the stirring at Rt was continued over a week-end. After completion of the reaction the mixture was quenched with 100 mL water. 500 mL of EtOAc was added and the layers were separated. The organic layer was washed with further 300 mL of brine, dried over anhydrous $Na_2SO_4$, filtered and concentrated to dryness to give the crude product, which was purified by normal phase silica gel chromatography using heptane-EtOAc (0 to 60:40) as an eluent to give the title compound (12.3 g, 56% yield).

$^1$H-NMR (400 MHz, DMSO-d6) δ ppm: 7.3 (m, 5H), 4.49 (s, 2H), 3.84/3.49 (m, 4H), 3.62 (t, 2H), 1.9 (t, 2H), 1.83/1.6 (2m, 4H)

Step A2: Preparation of 1-{4-[2-(benzyloxy)ethyl]oxan-4-yl}methanamine

Lithium aluminium hydride (1.5 eq., 2.85 g, 75 mmol) was placed into a round bottom flask. After addition of abs. THF (10 mL/g, 123 ml) the mixture was cooled to 10° C. A solution of 4-[2-(benzyloxy)ethyl]oxane-4-carbonitrile (1 eq., 12.3 g, 50 mmol) in abs. THF (10 mL/g, 123 mL) was added dropwise over a period of 20 min at 10° C. while continuous stirring. The reaction mixture was allowed to warm to RT and was stirred for further 5 h. After completion of the reaction the mixture was cooled to 0° C., quenched with aq. NaOH, then with aq. $Na_2SO_4$ solution. After stirring overnight at RT, the mixture was filtered, washed with EtOAc and the mother liquor was concentrated to dryness to give the title compound (12.1 g, 90% yield).

$^1$H-NMR (400 MHz, DMSO-d6) δ ppm: 7.37-7.23 (m, 4H), 4.44 (s, 2H), 3.57-3.49 (m, 4H), 3.48 (t, 2H), 2.48 (s, 2H), 1.66 (t, 2H), 1.41-1.26 (m, 4H)

Step A3: Preparation of N-({4-[2-(benzyloxy)ethyl]oxan-4-yl}methyl)-3-methyl-2-nitroaniline Using General Procedure 2 STEP 1 starting from 1-{4-[2-(benzyloxy)ethyl]oxan-4-yl}methanamine (1 eq.) as a reactant, the title compound (orange oil, 52% yield) was obtained.

$^1$H-NMR (400 MHz, DMSO-d6) δ ppm: 7.38-7.24 (m, 5H), 7.27 (m, 1H), 6.82 (d, 1H), 6.59 (d, 1H), 6.46 (t, 1H), 4.42 (s, 2H), 3.57 (t, 2H), 3.52-3.47 (m, 4H), 3.33 (dt, 2H), 2.31 (s, 3H), 1.79 (quint, 2H)

Step A4: Preparation of N-({4-[2-(benzyloxy)ethyl]oxan-4-yl}methyl)-4-bromo-3-methyl-2-nitroaniline Using General Procedure 2 STEP 2 starting from N-({4-[2-(benzyloxy)ethyl]oxan-4-yl}methyl)-3-methyl-2-nitroaniline (1 eq.) as a reactant, the title compound (78% yield) was obtained.

$^1$H-NMR (400 MHz, DMSO-d6) δ ppm: 7.49 (d, 1H), 7.35-7.22 (m, 5H), 6.91 (d, 1H), 5.99 (t, 1H), 4.43 (s, 2H), 3.62-3.5 (m, 4H), 3.51 (t, 2H), 3.19 (g, 2H), 2.28 (s, 3H), 2.28 (t, 2H), 1.45/1.33 (m, 4H)

Step A5: Preparation of $N^1$—({4-[2-(benzyloxy)ethyl]oxan-4-yl}methyl)-4-bromo-3-methylbenzene-1,2-diamine Using General Procedure 2 STEP 3 starting from N-({4-[2-(benzyloxy)ethyl]oxan-4-yl}methyl)-4-bromo-3-methyl-2-nitroaniline (1 eq.) as a reactant, the title compound (97% yield) was obtained.

$^1$H-NMR (400 MHz, DMSO-d6) δ ppm: 7.29 (m, 5H), 6.7 (d, 1H), 6.35 (d, 1H), 4.7 (m, 2H), 4.4 (s, 2H), 4.1 (m, 1H), 3.6 (m, 4H), 3.5 (t, 2H), 2.99 (s, 2H), 2.2 (s, 3H), 1.87 (t, 2H), 1.6-1.4 (m, 4H)

Step A6: Preparation of 1-({4-[2-(benzyloxy)ethyl]oxan-4-yl}methyl)-5-bromo-4-methyl-1H-benzotriazole Using General Procedure 2 STEP 4 starting from $N^1$—({4-[2-(benzyloxy)ethyl]oxan-4-yl}methyl)-4-bromo-3-methylbenzene-1,2-diamine (1 eq.) as a reactant, the title compound (brown solid, 80% yield) was obtained.

$^1$H-NMR (400 MHz, DMSO-d6) δ ppm: 7.69 (m, 2H), 7.4-7.3 (m, 5H), 4.7 (s, 2H), 4.48 (s, 2H), 3.68/3.52 (m, 4H), 3.61 (t, 2H), 2.71 (s, 3H), 1.71 (t, 2H), 1.45 (m, 4H)

Step A7: Preparation of ethyl (2E)-3-[1-({4-[2-(benzyloxy)ethyl]oxan-4-yl}methyl)-4-methyl-1H-benzotriazol-5-yl]prop-2-enoate The mixture of 1-({4-[2-(benzyloxy)ethyl]oxan-4-yl}methyl)-5-bromo-4-methyl-1H-benzotriazole (1 eq., 3 g, 6.75 mmol), ethyl (2E)-3-(4,4,5,5-tetramethyl-1,3,2-dioxaborolan-2-yl)prop-2-enoate (1.1 eq., 1.68 g, 7.43 mmol), sodium carbonate (2.5 eq., 1.79 g, 16.9 mmol), $A^{ta}$phos·$PdCl_2$ catalyst (0.05 eq., 149 mg, 0.3375 mmol), THF (5 mL/mmol, 34 mL) and water (5 mL/mmol, 34 mL) was heated at reflux temperature for 2 h under nitrogene atmosphere. After the completion of the reaction the solvent was evaporated under reduced pressure. The residue was purified by normal phase silica gel chromatography using heptane-EtOAc (0 to 50:50) as an eluent to give the title compound (2.61 g, 79% yield).

$^1$H-NMR (400 MHz, DMSO-d6) δ ppm: 8.01 (d, 1H), 7.96 (d, 1H), 7.7 (d, 1H), 7.3 (m, 5H), 6.64 (d, 1H), 4.7 (s, 2H), 4.48 (s, 2H), 4.21 (q, 2H), 3.65/3.53 (m, 4H), 3.63 (t, 2H), 2.8 (s, 3H), 1.72 (t, 2H), 1.45 (m, 4H), 1.29 (t, 3H)

Step 1: Preparation of ethyl 3-[1-({4-[2-(benzyloxy)ethyl]oxan-4-yl}methyl)-4-methyl-1H-benzotriazol-5-yl]-3-{3-[(1S)-1-hydroxyethyl]-4-methylphenyl}propanoate Using General Procedure 6 starting from ethyl (2E)-3-[1-({4-[2-(benzyloxy)ethyl]oxan-4-yl}methyl)-4-methyl-1H-benzotriazol-5-yl]prop-2-enoate (1 eq.) and (1S)-1-[2-methyl-5-(4,4,5,5-tetramethyl-1,3,2-dioxaborolan-2-yl)phenyl]ethan-1-ol (2 eq.) as reactants, the title compound (30% yield) was obtained.

$^1$H-NMR (400 MHz, DMSO-d6) δ ppm: 7.6 (d, 1H), 7.45 (d, 1H), 7.4 (d, 1H), 7.3 (m, 5H), 7.05 (dd, 1H), 7 (d, 1H), 5 (d, 1H), 4.8 (m, 2H), 4.65 (s, 2H), 4.5 (s, 2H), 3.9 (q, 2H), 3.65/3.5 (m, 4H), 3.1 (m, 2H), 2.8 (d, 3H), 2.65 (m, 2H), 2.2 (s, 3H), 1.7 (t, 2H), 1.4 (m, 4H), 1.25 (d, 3H), 1 (t, 3H)

Step 2: Preparation of ethyl 3-(3-{(1R)-1-[6-(benzyloxy)-2,2-dioxo-2H-1,2λ$^6$,3-benzoxathiazin-3(4H)-yl]ethyl}-4-methylphenyl)-3-[1-({4-[2-(benzyloxy)ethyl]oxan-4-yl}methyl)-4-methyl-1H-benzotriazol-5-yl]propanoate Using General Procedure 7 starting from ethyl 3-[1-({4-[2-(benzyloxy)ethyl]oxan-4-yl}methyl)-4-methyl-1H-benzotriazol-5-yl]-3-{3-[(1S)-1-hydroxyethyl]-4-methylphenyl}propanoate (1 eq.) and 6-(benzyloxy)-3,4-dihydro-2H-1,2λ$^6$,3-benzoxathiazine-2,2-dione (1.1 eq.) as reactants, the title compound (48% yield) was obtained.

$^1$H-NMR (400 MHz, DMSO-d6) δ ppm: 7.59 (d, 1H), 7.52 (d, 1H), 7.46/7.24 (m, 11H), 7.13 (m, 2H), 7.04 (m, 1H), 7 (m, 1H), 6.89/6.82 (d, 1H), 5.26 (q, 1H), 5.07 (m, 2H), 4.87 (m, 1H), 4.6 (s1, 2H), 4.44 (s1, 2H), 4.41/4.32 (d, 2H), 3.92 (q, 2H), 3.64/3.52 (m, 4H), 3.61 (m, 2H), 3.2 (m, 2H), 2.77 (s, 3H), 2.28 (s, 3H), 1.68 (m, 2H), 1.44-1.37 (m, 3H), 1.4 (d, 4H), 0.96 (t, 3H)

Step 3: Preparation of ethyl 3-{3-[(1R)-1-(6-hydroxy-2,2-dioxo-2H-1,2λ$^6$,3-benzoxathiazin-3(4H)-yl)ethyl]-4-methylphenyl}-3-(1-{[4-(2-hydroxyethyl)oxan-4-yl]methyl}-4-methyl-1H-benzotriazol-5-yl)propanoate Using General Procedure 8 starting from ethyl 3-(3-{(1R)-1-[6-(benzyloxy)-2,2-dioxo-2H-1,2λ$^6$,3-benzoxathiazin-3(4H)-yl]ethyl}-4-methylphenyl)-3-[1-({4-[2-(benzyloxy)ethyl]oxan-4-yl}methyl)-4-methyl-1H-benzotriazol-5-yl]propanoate (1 eq.) as a reactant, the title compound (96% yield) was obtained.

$^1$H-NMR (400 MHz, DMSO-d6) δ ppm: 10.6 (s, 1H), 7.65 (d, 1H), 7.6 (d, 1H), 7.5 (d, 1H), 7.15 (m, 2H), 6.9 (d, 1H), 6.7 (m, 1H), 6.6 (d, 1H), 5.3 (m, 1H), 4.9 (m, 1H), 4.6 (s, 2H), 4.5 (t, 1H), 4.4/4.3 (s+d, 2H), 3.95 (q, 2H), 3.65/3.5 (m, 6H), 3.2 (d, 2H), 2.8 (s, 3H), 2.3 (s, 3H), 1.6 (t, 2H), 1.4 (m, 7H), 1 (t, 3H)

Step 4: Preparation of ethyl 3-(1-{[4-(2-chloroethyl)oxan-4-yl]methyl}-4-methyl-1H-benzotriazol-5-yl)-3-{3-[(1R)-1-(6-hydroxy-2,2-dioxo-2H-1,2)$^{6}$,3-benzoxathiazin-3(4H)-yl)ethyl]-4-methylphenyl}propanoate Using General Procedure 10 starting from ethyl 3-{3-[(1R)-1-(6-hydroxy-2,2-dioxo-2H-1,2λ$^{6}$,3-benzoxathiazin-3(4H)-yl)ethyl]-4-methylphenyl}-3-(1-{[4-(2-hydroxyethyl)oxan-4-yl]methyl}-4-methyl-1H-benzotriazol-5-yl) propanoate (1 eq.) as a reactant, the title compound (17% yield) was obtained.

$^{1}$H-NMR (400 MHz, DMSO-d6) δ ppm: 9.65 (s, 1H), 7.68 (d, 1H), 7.6 (d, 1H), 7.45 (d, 1H), 7.15 (m, 2H), 6.91 (d, 1H), 6.71 (m, 1H), 6.6 (d, 1H), 5.25 (m, 1H), 4.89 (m, 1H), 4.68 (s, 2H), 4.4/4.3 (s+d, 2H), 3.91 (q, 2H), 3.81 (t, 2H), 3.69/3.55 (m, 4H), 3.21 (d, 2H), 2.79 (s, 3H), 2.29 (s, 3H), 1.85 (t, 2H), 1.5-1.3 (m+d, 7H), 1 (2t, 3H)

Step 5: Preparation of ethyl[(2R)-2,4,31-trimethyl-27,27-dioxo-27λ$^{6}$-spiro[21,26-dioxa-27-thia-1,14,15,16-tetraazahexacyclo[20.5.3.1$^{3,7}$0.1$^{9,13}$0.0$^{12,}$$_{16}$0.0$^{25,29}$]dotriaconta-3(32),4,6,9(31),10,12,14,22,24,29-decaene-18,4'-oxan]-8-yl]acetate Using General Procedure 11 starting from ethyl 3-(1-{[4-(2-chloroethyl)oxan-4-yl]methyl}-4-methyl-1H-benzotriazol-5-yl)-3-{3-[(1R)-1-(6-hydroxy-2,2-dioxo-2H-1,2λ$^{6}$,3-benzoxathiazin-3(4H)-yl)ethyl]-4-methylphenyl}propanoate (1 eq.) as a reactant, the title compound (91% yield) was obtained.

$^{1}$H-NMR (400 MHz, DMSO-d6) δ ppm: 0.91-1.12 (m, 23H) 1.15-1.33 (m, 11H) 1.37-1.51 (m, 13H) 1.58-1.74 (m, 25H) 1.73-2.08 (m, 8H) 2.19-2.39 (m, 22H) 2.63-2.85 (m, 24H) 2.92-3.24 (m, 11H) 3.36-3.49 (m, 15H) 3.57-3.81 (m, 22H) 3.83-4.02 (m, 19H) 4.26-4.40 (m, 8H) 4.55-4.66 (m, 11H) 4.70-4.92 (m, 13H) 5.06 (dd, J=10.76, 5.99 Hz, 4H) 5.26 (t, J=6.66 Hz, 7H) 5.57 (br. s., 1H) 5.68 (s, 1H) 5.72 (d, J=6.85 Hz, 2H) 6.49-6.79 (m, 8H) 6.84-6.99 (m, 7H) 7.05-7.23 (m, 12H) 7.26-7.50 (m, 7H) 7.52-7.66 (m, 8H) 7.73 (d, J=8.68 Hz, 1H) 7.80 (d, J=8.68 Hz, 1H) 7.90 (d, J=8.68 Hz, 1H)

Step 6: Preparation of Example 68

Using General Procedure 12 starting from ethyl[(2R)-2,4,31-trimethyl-27,27-dioxo-27λ$^{6}$-spiro[21,26-dioxa-27-thia-1,14,15,16-tetraazahexacyclo[20.5.3.1$^{3,7}$0.1$^{9,13}$0.0$^{12,}$$_{16}$0.0$^{25,29}$]dotriaconta-3(32),4,6,9(31),10,12,14,22,24,29-decaene-18,4'-oxan]-8-yl]acetate (1 eq.) as a reactant, the title compound (59% yield) was obtained.

HRMS calculated for $C_{34}H_{38}N_4O_7S$: 646.2461; $[M+H]^+$ found: 647.2535 (δ=0.2 ppm).

$^{1}$H-NMR (400 MHz, DMSO-d6) δ ppm: 1.16 (d, J=6.36 Hz, 2H) 1.24 (d, J=6.72 Hz, 4H) 1.52-1.77 (m, 7H) 1.78-1.96 (m, 5H) 1.98-2.11 (m, 2H) 2.29 (s, 4H) 2.31-2.36 (m, 3H) 2.62-2.69 (m, 5H) 2.81 (d, J=15.53 Hz, 4H) 2.95 (dd, J=16.20, 6.66 Hz, 2H) 3.14-3.23 (m, 3H) 3.43 (d, J=17.85 Hz, 3H) 3.59-3.82 (m, 8H) 3.83-3.93 (m, 2H) 4.06-4.17 (m, 2H) 4.52-4.72 (m, 3H) 4.73-4.82 (m, 3H) 4.93 (br. s., 1H) 5.26 (q, J=6.44 Hz, 3H) 5.53 (d, J=2.69 Hz, 2H) 6.60-6.76 (m, 3H) 6.85-6.96 (m, 4H) 7.14 (s, 2H) 7.19 (d, J=7.82 Hz, 2H) 7.31 (d, J=7.95 Hz, 1H) 7.39-7.50 (m, 2H) 7.73 (d, J=8.80 Hz, 1H) 7.78 (d, J=8.68 Hz, 1H) 7.85-7.93 (m, 1H) 12.28 (br. s., 1H)

EXAMPLE 69: [4,31-Dimethyl-19,27,27-trioxo-26-oxa-27λ$^{6}$-thia-1,14,15,16,20-pentaazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetic acid

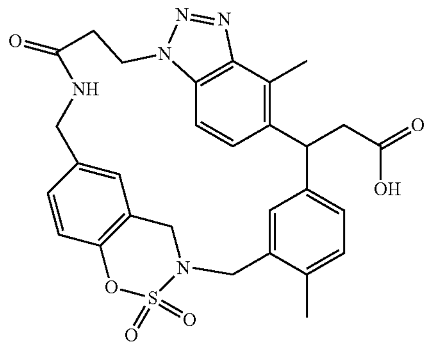 [SMILES: Cc1ccc2cc1CN1Cc3cc(ccc3OS1(=O)=O)CNC(=O)CCn1nnc3c(C)c(ccc31)C2CC(=O)O]

Step A1: Preparation of 3-{5-[(1E)-3-ethoxy-3-oxoprop-1-en-1-yl]-4-methyl-1H-benzotriazol-1-yl}propanoic acid Ethyl (2E)-3-[1-(3-hydroxypropyl)-4-methyl-1H-benzotriazol-5-yl]prop-2-enoate (1 eq., 2 g, 6.91 mmol) was dissolved in MeCN (10 mL) and water (10 mL), then 3-iodo-1,2-phenylene diacetate (2.2 eq., 4.90 g, 15.2 mmol) and (2,2,6,6-tetramethylpiperidin-1-yl)oxidanyl (0.2 eq., 0.216 g, 1.38 mmol) were added and the mixture was stirred at RT for 1 h. After the completion of the reaction the mixture was quenched with aq. $Na_2S_2O_3$ solution, and aq. $Na_2CO_3$ solution (25-25 mL), then washed with EtOAc. The layers were separated and the pH of the aq. phase was adjusted with citric acid to 3-4. The mixture was extracted with EtOAc, the layers were separated, the organic layer was dried over $MgSO_4$, filtered and concentrated under reduced pressure. The solid residue was treated with water, the precipitate was filtered-off and dried to give the title compound (1.731 g, 83% yield).

$^{1}$H-NMR (400 MHz, DMSO-d6) δ ppm: 12.6 (m, 1H), 8 (d, 1H), 7.95 (d, 1H), 7.7 (d, 1H), 6.65 (d, 1H), 4.9 (t, 2H), 4.2 (q, 2H), 3 (t, 2H), 2.8 (s1, 3H), 1.3 (t, 3H)

Step A2: Preparation of ethyl (2E)-3-{1-[3-(benzyloxy)-3-oxopropyl]-4-methyl-1H-benzotriazol-5-yl}prop-2-enoate 3-{15-[(1E)-3-Ethoxy-3-oxoprop-1-en-1-yl]-4-methyl-1H-benzotriazol-1-yl}propanoic acid (1 eq., 1.724 g, 5.684 mmol) was dissolved in DCM (70 mL) under argon atm., then DMF (0.2 eq., 0.09 mL, 1.1 mmol) was added to the solution. The mixture was cooled to 0° C., then oxalyl chloride (9 eq., 6.49 g, 4.33 mL, 51.1 mmol) was added. The reaction mixture was stirred at 0° C. for 15 min, then at RT for further 1 h. The reaction mixture was concentrated and the residue was suspended in DCM (15 mL). Phenylmethanol (1.2 eq., 0.74 g, 0.71 mL, 6.82 mmol) was dissolved in DCM (20 mL) under argon atm. The suspension of the acyl chloride in DCM was added dropwise and the reaction mixture was stirred at RT overnight. The mixture was washed with water, then with brine. The organic phase was separated and dried over $MgSO_4$, filtered and concentrated under reduced pressure. The residue was purified by normal phase silica gel chromatography using heptane-EtOAc as eluents to give the title compound (1.607 g, 72% yield).

$^1$H-NMR (400 MHz, DMSO-d6) δ ppm: 8.05 (d, 1H), 7.95 (d, 1H), 7.7 (d, 1H), 7.25 (2m, 5H), 6.65 (d, 1H), 5 (s, 2H), 4.9 (t, 2H), 4.2 (q, 2H), 3.2 (t, 2H), 2.8 (s, 3H), 1.3 (t, 3H)

Step 1: Preparation of ethyl 3-{1-[3-(benzyloxy)-3-oxopropyl]-4-methyl-1H-benzotriazol-5-yl}-3-[3-(hydroxymethyl)-4-methylphenyl]propanoate Using General Procedure 6 starting from ethyl (2E)-3-{1-[3-(benzyloxy)-3-oxopropyl]-4-methyl-1H-benzotriazol-5-yl}prop-2-enoate (1 eq., 0.859 g, 2.18 mmol) and [2-methyl-5-(4,4,5,5-tetramethyl-1,3,2-dioxaborolan-2-yl)phenyl] methanol (1.1 eq., 0.596 g, 2.40 mmol) as a reactant, the title compound (0.729 g, 62% yield) was obtained.

$^1$H-NMR (400 MHz, DMSO-d6) δ ppm: 7.6 (d, 1H), 7.5 (d, 1H), 7.3/7.2 (m, 5H), 7.3 (d, 1H), 7.1 (dd, 1H), 7 (d, 1H), 5.05 (s, 2H), 5 (t, 1H), 4.85 (t, 3H), 4.4 (d, 2H), 3.9 (q, 2H), 3.1 (m, 4H), 2.8 (s, 3H), 2.2 (s, 3H), 1 (t, 3H)

Step C1: Preparation of tert-butyl 6-cyano-2,2-dioxo-2H-1,2λ$^6$,3-benzoxathiazine-3(4H)-carboxylate 6-Bromo-3,4-dihydro-2H-1,2λ$^6$,3-benzoxathiazine-2,2-dione (1 eq., 5.95 g, 22.5 mmol) was dissolved in DCM (225 mL), then TEA (1.1 eq., 2.51 g, 3.45 mL, 24.8 mmol), N,N-dimethylpyridin-4-amine (0.1 eq., 275 mg, 2.25 mmol) and di-tert-butyl dicarbonate (1.1 eq., 5.41 g, 24.8 mmol) were added. The reaction mixture was stirred at RT for 2 h. The mixture was poured into 500 mL 0.1 M HCl solution. The organic phase was separated, washed with 500 mL 0.1 M HCl solution (2×), dried over $MgSO_4$, filtered and concentrated to give tert-butyl 6-bromo-2,2-dioxo-2H-1,2λ$^6$,3-benzoxathiazine-3(4H)-carboxylate (quant.). The crude product (1 eq., 5 g, 13.73 mmol) was dissolved in N,N-dimethylacetamide (80 mL), then zinc (0.5 eq., 449 mg, 6.86 mmol) and zinc cyanide (1 eq., 1.612 g, 13.73 mmol) were added. The mixture was degassed with argon, then bis(tri-tert-butylphosphine)palladium(0) catalyst (0.1 eq., 424 mg, 1.73 mmol) was added. The reaction mixture was stirred at 80° C. for 4 h. The mixture was filtered, the filtered solid was washed with EtOAc, the filtrate was concentrated under high vacuum. The residue was dissolved in EtOAc, then washed with brine. The organic phase was dried over $MgSO_4$, filtered and concentrated under reduced pressure to give the crude product, which was purified by normal phase silica gel chromatography using heptane-EtOAc as eluents to give the title compound (2.704 g, 63% yield).

$^1$H-NMR (400 MHz, DMSO-d6) δ ppm: 8.15 (d, 1H), 8 (dd, 1H), 7.6 (d, 1H), 5.2 (s, 2H), 1.5 (s, 9H)

Step C2: Preparation of benzyl[(2,2-dioxo-3,4-dihydro-2H-1,2λ$^6$,3-benzoxathiazin-6-yl)methyl]carbamate Tert-butyl 6-cyano-2,2-dioxo-2H-1,2λ$^6$,3-benzoxathiazine-3(4H)-carboxylate (1 eq., 1 g, 3.22 mmol) was dissolved in 7M $NH_3$ solution in MeOH (10 mL), and Raney nickel catalyst (5 eq., 945 mg, 16.11 mmol) was added. The reaction mixture was hydrogenated under atmospheric pressure for 4 h. After the completion of the reaction the mixture was filtered, the filtrate was concentrated to give the crude 6-(aminomethyl)-3,4-dihydro-2H-1,2λ$^6$,3-benzoxathiazine-2,2-dione (66% yield), which was dissolved in THF (2.5 mL). $NaHCO_3$ (1.1 eq.) was added followed by a dropwise addition of benzyl chloroformate (1.1 eq.) and the mixture was stirred at RT for 2 h. The mixture was diluted with water and EtOAc, the separated organic phase was washed with brine, dried over $MgSO_4$, filtered, concentrated to give a crude product, which was purified by normal phase silica gel chromatography using heptane-EtOAc as eluents to give the title compound (46% yield).

$^1$H-NMR (400 MHz, DMSO-d6) δ ppm: 8.5 (m, 1H), 7.8 (t, 1H), 7.35 (m, 5H), 7.2 (dd, 1H), 7.15 (d, 1H), 7 (d, 1H), 5.05 (s, 2H), 4.5 (s, 2H), 4.2 (d, 2H)

Step 2: Preparation of ethyl 3-(3-{[6-({[(benzyloxy) carbonyl]amino}methyl)-2,2-dioxo-2H-1,2λ$^6$,3-benzoxathiazin-3(4H)-yl]methyl}-4-methylphenyl)-3-{1-[3-(benzyloxy)-3-oxopropyl]-4-methyl-1H-benzotriazol-5-yl}propanoate Using General Procedure 7 starting from benzyl[(2,2-dioxo-3,4-dihydro-2H-1,2λ$^6$,3-benzoxathiazin-6-yl)methyl] carbamate (1 eq., 571 mg, 1.64 mmol) and ethyl 3-{1-[3-(benzyloxy)-3-oxopropyl]-4-methyl-1H-benzotriazol-5-yl}-3-[3-(hydroxymethyl)-4-methylphenyl]propanoate (1.1 eq., 930 mg, 1.80 mmol) as reactants, the title compound (1.017 g, 73% yield) was obtained.

$^1$H-NMR (400 MHz, DMSO-d6) δ ppm: 7.85 (t, 1H), 7.6 (d, 1H), 7.5 (d, 1H), 7.4-7.1 (m, 16H), 5.05/5 (2s, 4H), 4.9 (t, 2H), 4.85 (m, 1H), 4.5 (2d, 2H), 4.2 (m, 4H), 3.9 (q, 2H), 3.2 (d, 2H), 3.1 (t, 1H), 2.8 (s, 3H), 2.2 (s, 3H), 1 (t, 3H)

Step 3: Preparation of 3-{5-[1-(3-{[6-(aminomethyl)-2,2-dioxo-2H-1,2)$^6$,3-benzoxathiazin-3(4H)-yl]methyl}-4-methylphenyl)-3-ethoxy-3-oxopropyl]-4-methyl-1H-benzotriazol-1-yl}propanoic acid Using General Procedure 8 starting from ethyl 3-(3-{[6-({[(benzyloxy)carbonyl]amino}methyl)-2,2-dioxo-2H-1,2λ$^6$,3-benzoxathiazin-3(4H)-yl]methyl}-4-methylphenyl)-3-{11-[3-(benzyloxy)-3-oxopropyl]-4-methyl-1H-benzotriazol-5-yl}propanoate (1 eq., 1.01 g, 1.19 mmol) as a reactant, the title compound (844 mg, 97% yield) was obtained.

$^1$H-NMR (400 MHz, DMSO-d6) δ ppm: 7.8 (d, 1H), 7.5 (d, 1H), 7.4 (dd, 1H), 7.3 (dd, 1H), 7.2 (m, 4H), 4.8 (m, 3H), 4.3/4.15 (2d, 2H), 4.25 (m, 2H), 4/3.8 (2d, 2H), 3.95 (q, 2H), 3.2 (d, 2H), 2.8/2.65 (s+2m, 5H), 2.2 (s1, 3H), 1 (t, 3H)

Step 4: Preparation of Example 69

3-{15-[1-(3-{[6-(Aminomethyl)-2,2-dioxo-2H-1,2λ$^6$,3-benzoxathiazin-3(4H)-yl]methyl}-4-methylphenyl)-3-ethoxy-3-oxopropyl]-4-methyl-1H-benzotriazol-1-yl}propanoic acid (1 eq., 830 mg, 1.13 mmol) was dissolved in DCM (340 mL), then TEA (5 eq., 574 mg, 0.791 mL, 5.67 mmol), 1H-benzotriazol-1-ol (1.5 eq., 256 mg, 1.7 mmol) and 3-{[(ethylimino)methylidene]amino}-N,N-dimethylpropan-1-amine hydrochloride (1.5 eq., 326 mg, 1.7 mmol) were added. The reaction mixture was stirred at RT overnight. The mixture was concentrated to 50 mL, and was washed with aq. sat. $NaHCO_3$ and brine. The aq. phases were extracted with DCM. The combined organic phases were washed with 10% aq. citric acid solution, with water, then with brine. The organic layer was dried over $MgSO_4$, filtered, concentrated to give the crude ethyl[4,31-dimethyl-19,27,27-trioxo-26-oxa-27λ$^6$-thia-1,14,15,16,20-pentaazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]acetate (53% yield), which was reacted using General Procedure 12 to give the title compound as a racemic mixture (45 mg, 13%).

HRMS calculated for $C_{29}H_{29}N_5O_6S$: 575.1838; $[M+H]^+$ found: 576.1913 (δ=0.3 ppm).

$^1$H-NMR (400 MHz, DMSO-d6) δ ppm: 12.1 (m, 1H), 8.35 (m, 1H), 7.65/7.6 (d, 2H), 7.45 (dd, 1H), 7.25 (d+dd, 2H), 7.1 (d, 1H), 6.75 (d, 1H), 6.3 (d, 1H), 5.05/4.95 (m, 2H), 4.8 (t, 1H), 4.7/4 dd, 2H), 4.3/3.9 (2d, 2H), 4.1/3.7 (d, 2H), 3/2.8 (m, 2H), 3 (m, 2H), 2.6 (s, 3H), 2.3 (s1, 3H)

EXAMPLE 70: [4,36-Dimethyl-32,32-dioxo-26,31-dioxa-32λ$^6$-thia-1,14,15,16,19-pentaazaheptacyclo [25.5.3.1$^{3,7}$0.1$^{9,13}$0.0$^{12,16}$0.0$^{20,25}$0.0$^{30,34}$]heptatriaconta-3(37),4,6,9(36),10,12,14,20,22,24,27,29,34-tridecaen-8-yl]acetic acid enantiomer 1

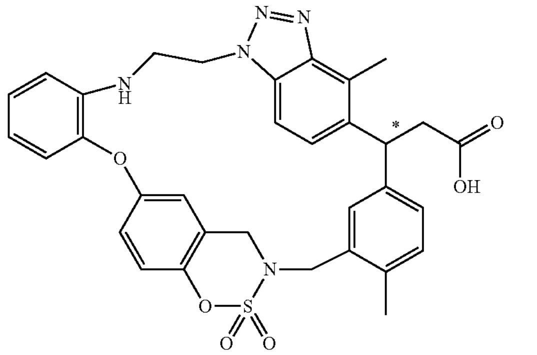

* = RorS enantiomer 2

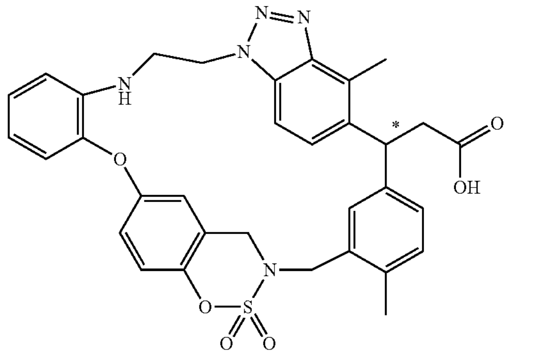

* = RorS

Step C1: Preparation of 1-(4-methoxyphenoxy)-2-nitrobenzene

4-Methoxyphenol (1 eq., 6.207 g, 50 mmol) and 1-fluoro-2-nitrobenzene (1 eq., 7.055 g, 0.05 mol) were dissolved in dioxane (50 mL) and $K_2CO_3$ (2 eq., 13.821 g, 0.1 mol) was added to the solution. The mixture was stirred at 100° C. for 23 h. After completion of the reaction the mixture was cooled to RT and the organic salts were filtered out. The filtrate was concentrated under reduced pressure and the residue was purified by trituration with heptane to afford the title compound (yellow crystals, 11.96 g, 98% yield).

$^1$H-NMR (500 MHz, DMSO-d6) δ ppm: 8.02 (dd, 1H), 7.63 (t, 1H), 7.29 (t, 1H), 7.07 (m, 2H), 7.00 (m, 3H), 3.76 (s, 3H)

Step C2: Preparation of 4-(2-nitrophenoxy)phenol 1-(4-Methoxyphenoxy)-2-nitrobenzene (1 eq., 11.96 g, 0.04878 mol) was dissolved in DCM (300 mL, 4.680 mol) at 0° C. The solution of tribromoborane (1.2 eq., 14.66 g, 0.05853 mol) in 20 mL DCM was added dropwise. The reaction mixture was stirred overnight at RT. The mixture was poured into water (100 mL). The organic layer was washed with brine, dried over $MgSO_4$, filtered and concentrated under reduced pressure. The residue was diluted with EtOAc and was purified by normal phase silica gel chromatography using heptane-EtOAc (100:0 to 66:33) as an eluent to give the title compound (11.11 g, yellow crystals, 98% yield).

$^1$H-NMR (500 MHz, DMSO-d6) δ ppm: 9.52 (s, 1H), 7.99 (dd, 1H), 7.61 (m, 1H), 7.24 (t, 1H), 6.96 (m, 3H), 6.82 (m, 2H)

Step C3: Preparation of 2-hydroxy-5-(2-nitrophenoxy)benzaldehyde 4-(2-Nitrophenoxy)phenol (1 eq., 11.11 g, 0.04805 mol) was dissolved in 1,2-dichloroethane (150 mL), then magnesium dichloride (5 eq., 22.88 g, 0.2403 mol) and TEA (6 eq., 29.18 g, 0.2883 mol, 40.19 mL) were added. Paraformaldehyde (10 eq., 14.42 g, 0.4805 mol) was added and the mixture was stirred at 40° C. for an hour, then at 70° C. for 12 h. The cooled mixture was diluted with DCM (300 mL) and washed with 3x50 mL 1M aq. HCl solution. The organic layer was dried over $MgSO_4$, filtered and evaporated to give the title compound as brownish crystals (11.89 g, 95% yield).

$^1$H-NMR (500 MHz, DMSO-d6) δ ppm: 10.8 (br., 1H), 10.24 (s, 1H), 8.04 (dd, 1H), 7.66 (ddd, 1H), 7.36 (dd, 1H), 7.33 (td, 1H), 7.27 (d, 1H), 7.09 (d, 1H), 7.09 (dd, 1H)

Step C4: Preparation of 6-(2-nitrophenoxy)-2H-1,2)$^6$,3-benzoxathiazine-2,2-dione Chlorosulfonyl isocyanate (4 eq., 25.20 g, 15.50 mL, 0.1781 mol) was cooled to 0° C. and HCOOH (4 eq., 8.196 g, 6.72 mL, 0.1781 mol) was added dropwise at 0° C. over 30 minutes. A white precipitate was formed. The reaction mixture was allowed to warm to RT in 30 minutes and was stirred at RT for 1 h. The mixture was cooled again to 0° C. and the solution of 2-hydroxy-5-(2-nitrophenoxy)benzaldehyde (1 eq., 11.54 g, 0.04452 mol) in NMP (75 mL) was added dropwise. The mixture was stirred overnight at RT. Pouring carefully into 100 mL cc. $NH_4Cl$ solution, an orange precipitate was formed, which after filtration and drying in vacuum gave the title compound as orange crystals (6.71 g, 47% yield).

$^1$H-NMR (500 MHz, DMSO-d6) δ ppm: 9.15 (s, 1H), 8.15 (dd, 1H), 7.78 (td, 1H), 7.71 (d, 1H), 7.69 (dd, 1H), 7.63 (d, 1H), 7.48 (td, 1H), 7.36 (dd, 1H)

Step C5: Preparation of 6-(2-nitrophenoxy)-3,4-dihydro-2H-1,2λ$^6$,3-benzoxathiazine-2,2-dione 6-(2-Nitrophenoxy)-2H-1,2λ$^6$,3-benzoxathiazine-2,2-dione (1 eq., 7.65 g, 23.9 mmol) was dissolved in EtOH (250 mL) and sodium cyanoborohydride (1.2 eq., 1.8 g, 28.7 mmol) was added portionwise to the solution at 0° C. The mixture was stirred at RT for 30 min. The solvent was evaporated to dryness. The yellowish oil was partitioned between EtOAc and water. The organic layer was separated and the aqueous phase was extracted with EtOAc (2x30 mL). The combined organic phases were dried over $MgSO_4$, filtered and concentrated. The residue was purified by normal phase flash chromatography on silica gel column with heptane-EtOAc (100:0 to 50:50) as an eluent to give the title compound as a yellowish oil (1.25 g, 16% yield).

$^1$H-NMR (500 MHz, DMSO-d6) δ ppm: 8.54 (t, 1H), 8.08 (dm, 1H), 7.71 (m, 1H), 7.39 (m, 1H), 7.18 (dm, 1H), 7.16 (d, 1H), 7.09 (dd, 1H), 7.07 (d, 1H), 4.55 (d, 2H)

Step A1: Preparation of ethyl (2E)-3-(4-methyl-1-{2-[(oxan-2-yl)oxy]ethyl}-1H-benzotriazol-5-yl) prop-2-enoate To a solution of 6-(2-nitrophenoxy)-3,4-dihydro-2H-1,2λ$^6$,3-benzoxathiazine-2,2-dione (1 eq., 1.38 g, 5 mmol) in DCM (25 mL) at 0° C. 4-methylbenzene-1-sulfonic acid monohydrate (0.01 eq., 9.5 mg, 0.05 mmol) was added followed by addition of 3,4-dihydro-2H-pyran (1.1 equiv., 0.463 g, 5.5 mmol). The reaction mixture was allowed to warm to RT and stirred for 1 h. The mixture was quenched with saturated $NaHCO_3$ (30 mL) and the phases were separated. The aq. phase was extracted with DCM (30 mL), and the combined organic phases were dried over $MgSO_4$, filtered and evaporated under reduced pressure to give the title compound (1.7 g, 95% yield).

$^1$H-NMR (500 MHz, DMSO-d6) δ ppm: 8.01 (d, 1H), 7.96 (d, 1H), 7.72 (d, 1H), 6.64 (d, 1H), 4.93/4.88 (m+m, 2H), 4.53 (dd, 1H), 4.21 (q, 2H), 4.05/3.84 (m+m, 2H), 3.36/3.29 (m+m, 2H), 2.8 (s, 3H), 1.58-1.19 (m, 6H), 1.27 (t, 3H)

Step 1: Preparation of 3-[3-(hydroxymethyl)-4-methylphenyl]-3-(4-methyl-1-{2-[(oxan-2-yl)oxy] ethyl}-1H-benzotriazol-5-yl)propanoic acid The suspension of ethyl (2E)-3-(4-methyl-1-{2-[(oxan-2-yl)oxy]ethyl}-1H-benzotriazol-5-yl)prop-2-enoate (1 eq., 4.85 g, 13.5 mmol) in dioxane (80 mL) and water (40 mL) was degassed with $N_2$, then [2-methyl-5-(4,4,5,5-tetramethyl-1,3,2-dioxaborolan-2-yl)phenyl]methanol (1.4 eq., 4.69 g, 18.9 mmol) and TEA (1.6 eq., 2.18 g, 21.6 mmol) were added. Chloro(1,5-cyclooctadiene)rhodium(I) dimer catalyst (0.05 eq., 0.333 g, 0.675 mmol) was added and the reaction mixture was heated at 80° C. for 30 min, then at RT overnight. The reaction mixture was diluted with water and EtOAc, the organic phase was separated, dried over $MgSO_4$, filtered and concentrated to dryness to give the crude product, which was purified via normal phase silica gel chromatography using heptane-EtOAc (50:50) as an eluent to give the title compound (dark oil, 5.11 g, 79% yield).

$^1$H-NMR (500 MHz, DMSO-d6) δ ppm: 7.62 (d, 1H), 7.47 (d, 1H), 7.25 (brs., 1H), 7.09/7.07 (dd/dd, 1H), 7.02/7.01 (d/d, 1H), 4.99/4.98 (t/t, 1H), 4.9-4.78 (m, 2H), 4.83 (m, 1H), 4.51 (dm, 1H), 4.4 (d, 2H), 4.01/3.82 (m+m, 2H), 3.92 (q, 2H), 3.33-3.2 (m, 2H), 3.13 (d, 2H), 2.74 (s, 3H), 2.15 (s, 3H), 1.54-1.18 (m, 6H), 1 (t, 3H)

Step 2: Preparation of ethyl 3-(4-methyl-3-{[6-(2-nitrophenoxy)-2,2-dioxo-2H-1,2λ$^6$,3-benzoxathiazin-3(4H)-yl]methyl}phenyl)-3-(4-methyl-1-{2-[(oxan-2-yl)oxy]ethyl}-1H-benzotriazol-5-yl) propanoate 3-[3-(Hydroxymethyl)-4-methylphenyl]-3-(4-methyl-1-{12-[(oxan-2-yl)oxy]ethyl}-1H-benzotriazol-5-yl)propanoic acid (1 eq., 3.277 g, 6.804 mmol) was dissolved in THF (30 mL). To this solution 6-(2-nitrophenoxy)-3,4-dihydro-2H-1,2λ$^6$,3-benzoxathiazine-2,2-dione (1.39 eq., 3.04 g, 9.43 mmol) dissolved in THF (10 mL) and $PPh_3$ (2 eq., 3.570 g, 13.61 mmol) were added. The mixture was cooled to −5° C., DIAD (2 eq., 2.897 g, 2.821 mL, 13.61 mmol) was added dropwise and the mixture was heated at 45° C. for 1 h. The reaction mixture was concentrated to dryness to give the crude product, which was purified via normal phase silica gel chromatography using DCM-MeOH (99:1) as an eluent to give the title compound (orange solid, 5.3 g, 99% yield).

$^1$H-NMR (500 MHz, DMSO-d6) δ ppm: 8.09 (dd, 1H), 7.72 (td, 1H), 7.58 (d, 1H), 7.48 (d, 1H), 7.38 (t, 1H), 7.27 (dd, 1H), 7.25 (m, 1H), 7.24 (dm, 1H), 7.17 (d, 1H), 7.16 (m, 1H), 7.12 (d, 1H), 7.11 (m, 1H), 4.82 (m, 1H), 4.82 (m, 2H), 4.48 (m, 2H), 4.48 (m, 1H), 4.26/4.23 (d+d, 2H), 3.99/3.8 (m+m, 2H), 3.89 (q, 2H), 3.23 (m, 2H), 3.15 (d, 2H), 2.73/2.72 (s/s, 3H), 2.22 (s, 3H), 1.5-1.13 (m, 6H), 0.97 (t, 3H)

Step 3: Preparation of ethyl 3-[1-(2-hydroxyethyl)-4-methyl-1H-benzotriazol-5-yl]-3-(4-methyl-3-{[6-(2-nitrophenoxy)-2,2-dioxo-2H-1,2λ$^6$,3-benzoxathiazin-3(4H)-yl]methyl}phenyl)propanoate Ethyl 3-(4-methyl-3-{[6-(2-nitrophenoxy)-2,2-dioxo-2H-1,2λ$^6$,3-benzoxathiazin-3(4H)-yl]methyl}phenyl)-3-(4-methyl-1-{12-[(oxan-2-yl)oxy]ethyl}-1H-benzotriazol-5-yl)propanoate (1 eq., 3.091 g, 3.933 mmol) was dissolved in THF (16 mL) and EtOH (2 mL). Phosphotungstic acid hydrate (0.1 eq., 0.1368 g, 0.3933 mmol) was added and the reaction mixture was stirred at RT for 24 h. After completion of the reaction the mixture was concentrated to dryness. The crude solid product was partitioned between EtOAc and water. The separated organic layer was washed twice with sodium bicarbonate solution, dried over $MgSO_4$, filtered and evaporated to dryness to give the title compound (brown solid, 2.8 g, quant.).

$^1$H-NMR (500 MHz, DMSO-d6) δ ppm: 8.09 (dd, 1H), 7.71 (td, 1H), 7.53 (d, 1H), 7.45 (d, 1H), 7.38 (td, 1H), 7.27 (d, 1H), 7.27 (d, 1H), 7.24 (dd, 1H), 7.18 (dd, 1H), 7.17 (dd, 1H), 7.12 (d, 1H), 7.12 (d, 1H), 4.94 (t, 1H), 4.83 (t, 1H), 4.64 (t, 2H), 4.48 (s, 2H), 4.26 (s, 2H), 3.91 (q, 2H), 3.81 (q, 2H), 3.15 (m, 2H), 2.74 (s, 3H), 2.22 (s, 3H), 1 (t, 3H)

Step 4: Preparation of ethyl 3-[1-(2-chloroethyl)-4-methyl-1H-benzotriazol-5-yl]-3-(4-methyl-3-{[6-(2-nitrophenoxy)-2,2-dioxo-2H-1,2λ$^6$,3-benzoxathiazin-3(4H)-yl]methyl}phenyl)propanoate Ethyl 3-[1[-(2-hydroxyethyl)-4-methyl-1H-benzotriazol-5-yl]-3-(4-methyl-3-[6-(2-nitrophenoxy)-2,2-dioxo-2H-1,2λ$^6$,3-benzoxathiazin-3(4H)-yl]methyl}phenyl)propanoate (1 eq., 2.8 g, 4.0 mmol) was dissolved in DCM (30 mL). Thionyl chloride (3 eq., 1.4 g, 12 mmol) was added slowly at RT. The reaction mixture was heated at 45° C. for 1.5 h. After completion of the reaction the mixture was concentrated to dryness. The crude product was partitioned between EtOAc and water, the organic phase was washed twice with sat. aq. sodium bicarbonate solution, dried over $MgSO_4$, filtered and evaporated to dryness to give the title compound (2.9 g, brown solid, 97% yield).

$^1$H-NMR (500 MHz, DMSO-d6) δ ppm: 8.09 (dm, 1H), 7.71 (m, 1H), 7.62 (d, 1H), 7.5 (d, 1H), 7.38 (m, 1H), 7.28 (d, 1H), 7.27 (d, 1H), 7.24 (dm, 1H), 7.19 (dd, 1H), 7.18 (dd, 1H), 7.13 (d, 1H), 7.11 (d, 1H), 4.99 (t, 2H), 4.83 (t, 1H), 4.48 (s, 2H), 4.26 (s, 2H), 4.12 (t, 2H), 3.9 (q, 2H), 3.16 (d, 2H), 2.76 (s, 3H), 2.23 (s, 3H), 0.97 (t, 3H)

Step 5: Preparation of ethyl 3-(3-{[6-(2-aminophenoxy)-2,2-dioxo-2H-1,2λ$^6$,3-benzoxathiazin-3(4H)-yl]methyl}-4-methylphenyl)-3-[1-(2-chloroethyl)-4-methyl-1H-benzotriazol-5-yl]propanoate The mixture of ethyl 3-[1-(2-chloroethyl)-4-methyl-1H-benzotriazol-5-yl]-3-(4-methyl-3-{[6-(2-nitrophenoxy)-2,2-dioxo-2H-1,2λ$^6$,3-benzoxathiazin-3(4H)-yl]methyl}phenyl) propanoate (1 eq., 2.78 g, 3.86 mmol), iron powder (10 eq., 2160 mg, 38.6 mmol) and $NH_4Cl$ (0.5 eq., 103 mg, 1.93 mmol), dissolved in EtOH (10 mL) and water (3 mL) was heated at 80° C. for 1.5 h.

After cooling to RT, the mixture was filtered and concentrated under reduced pressure. The residue was dissolved in EtOAc, washed with sat. aq. $Na_2CO_3$ solution, dried over $MgSO_4$, filtered, evaporated under reduced pressure, and dried in vacuo overnight to give the title compound (2.314 g, brown solid, 87% yield).

$^1$H-NMR (500 MHz, DMSO-d6) δ ppm: 7.63 (d, 1H), 7.52 (d, 1H), 7.25 (d, 1H), 7.18 (dd, 1H), 7.16 (d, 1H), 7.12 (d, 1H), 6.93 (m, 1H), 6.92 (dd, 1H), 6.85 (d, 1H), 6.84 (dm, 1H), 6.81 (dm, 1H), 6.56 (m, 1H), 5 (t, 2H), 4.97 (s, 2H), 4.83 (t, 1H), 4.45 (s, 2H), 4.23 (s, 2H), 4.13 (t, 2H), 3.91 (q, 2H), 3.16 (d, 2H), 2.76 (s, 3H), 2.22 (s, 3H), 0.99 (t, 3H)

Step 6: Preparation of ethyl[4,36-dimethyl-32,32-dioxo-26,31-dioxa-32λ$^6$-thia-1,14,15,16,19-pentaazaheptacyclo[25.5.3.1$^{3,7}$0.1$^{9,13}$0.0$^{12,16}$0.0$^{20,25}$0.0$^{30,34}$]heptatriaconta-3(37),4,6,9(36),10,12,14,20,22,24,27,29,34-tridecaen-8-yl]acetate Ethyl 3-(3-{[6-(2-aminophenoxy)-2,2-dioxo-2H-1,2λ$^6$,3-benzoxathiazin-3(4H)-yl]methyl}-4-methylphenyl)-3-[1-(2-chloroethyl)-4-methyl-1H-benzotriazol-5-yl]propanoate (1 eq., 1.12 g, 1.62 mmol) was dissolved in propanenitrile (50 mL) and sodium iodide (5 eq., 1.22 g, 8.11 mmol) was added at RT. The reaction mixture was heated at 100° C. for 35 h. The mixture was concentrated to dryness then partitioned between water and EtOAc. The organic phase was separated and dried over $MgSO_4$, filtered and concentrated to dryness to give the crude product, which was purified via preparative reversed-phase chromatography using aq. TFA solution-MeCN as eluents to give the title compound (360 mg, yellow powder, 34% yield).

The enantiopure final intermediates were obtained by chromatographic separation on chiral column.

$^1$H-NMR (500 MHz, DMSO-d6) δ ppm: 7.39 (d, 1H), 7.37 (dd, 1H), 7.34 (d, 1H), 7.21 (d, 1H), 7.16 (d, 1H), 7.06 (dd, 1H), 7 (t, 1H), 6.9 (d, 1H), 6.86 (d, 1H), 6.69 (d, 1H), 6.56 (t, 1H), 6.37 (d, 1H), 5.47 (dd, 1H), 4.95/4.83 (dt+dt, 2H), 4.8 (t, 1H), 4.27/4.1 (d+d, 2H), 4.21/4.15 (d+d, 2H), 3.87 (q, 2H), 3.79/3.68 (m+m, 2H), 3.08/2.99 (dd+dd, 2H), 2.7 (s, 3H), 2.3 (s, 3H), 0.95 (t, 3H)

Step 7: Preparation of Example 70

Using General Procedure 12 starting from ethyl[4,36-dimethyl-32,32-dioxo-26,31-dioxa-32λ$^6$-thia-1,14,15,16,19-pentaazaheptacyclo[25.5.3.1$^{3,7}$0.1$^{9,13}$0.0$^{12,16}$0.0$^{20,25}$0.0$^{30,34}$]heptatriaconta-3(37),4,6,9(36),10,12,14,20,22,24,27,29,34-tridecaen-8-yl]acetate E1 (1 eq.) or E2 (1 eq.) as reactants, the title compounds (58%-92% yields respectively) were obtained.

EXAMPLE 70a (E1)

HRMS calculated for $C_{33}H_{31}N_5O_6S$: 625.1995; [M+H]$^+$ found: 626.2062 (δ=–0.9 ppm).

EXAMPLE 70b (E2)

HRMS calculated for $C_{33}H_{31}N_5O_6S$: 625.1995; [M+H]$^+$ found: 626.2062 (δ=–0.9 ppm).

$^1$H-NMR (500 MHz, DMSO-d6) δ ppm: 12.07 (brs, 1H), 7.38 (dd, 1H), 7.38 (d, 1H), 7.32 (d, 1H), 7.21 (d, 1H), 7.16 (d, 1H), 7.06 (dd, 1H), 7 (t, 1H), 6.9 (d, 1H), 6.84 (d, 1H), 6.69 (d, 1H), 6.56 (t, 1H), 6.37 (d, 1H), 5.47 (brs, 1H), 4.95/4.82 (t+d, 2H), 4.77 (t, 1H), 4.27/4.09 (d+d, 2H), 4.2/4.14 (d+d, 2H), 3.79/3.68 (t+d, 2H), 2.99/2.87 (dd+dd, 2H), 2.7 (s, 3H), 2.3 (s, 3H)

$^{13}$C-NMR (125 MHz, DMSO-d6) δ ppm: 173.1, 155, 146.3, 146.2, 143.8, 141.6, 140.2, 136.4, 136.1, 133.1, 132.1, 131.4, 130.2, 129, 127.2, 127.1, 125.4, 120.1, 119.7, 119.3, 118.6, 117, 116.1, 111.8, 108.1, 51.9, 48.8, 47.6, 44.3, 41.2, 41.2, 18.6, 13.3

EXAMPLE 71: [4,37-Dimethyl-33,33-dioxo-27,32-dioxa-33λ$^6$-thia-1,14,15,16,20-pentaazaheptacyclo[26.5.3.1$^{3,7}$0.1$^{9,13}$0.0$^{12,16}$0.0$^{21,26}$0.0$^{31,35}$]octatriaconta-3(38),4,6,9(37),10,12,14,21,23,25,28,30,35-tridecaen-8-yl]acetic acid enantiomer 1

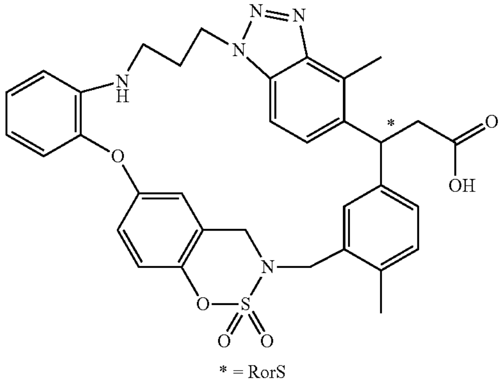

* = RorS enantiomer 2

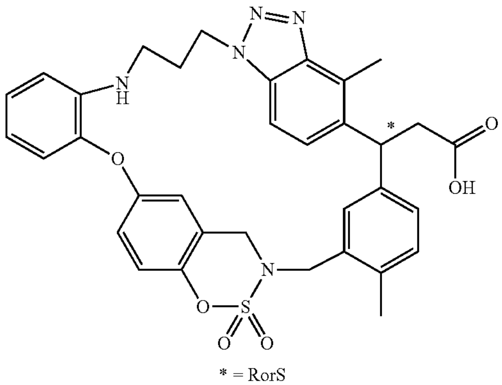

* = RorS

Step 1: Preparation of ethyl 3-[4-methyl-3-[[6-(2-nitrophenoxy)-2,2-dioxo-4H-1,2λ$^6$,3-benzoxathiazin-3-yl]methyl]phenyl]-3-[4-methyl-1-(3-tetrahydropyran-2-yloxypropyl)benzotriazol-5-yl]propanoate Ethyl 3-[3-(hydroxymethyl)-4-methylphenyl]-3-(4-methyl-1-{3-[(oxan-2-yl)oxy]propyl}-1H-benzotriazol-5-yl)propanoate (1 eq., 1890 mg, 3.81 mmol) was dissolved in THF (25 mL), then 6-(2-nitrophenoxy)-3,4-dihydro-2H-1,2λ$^6$,3-benzoxathiazine-2,2-dione (1.5 eq., 1.8 g, 5.58 mmol) and $PPh_3$ (3.2 eq., 3.2 g, 12.2 mmol) were added. The mixture was cooled to 5° C. under inert atmosphere ($N_2$) and DIAD (3.11 eq., 2.4 g, 11.9 mmol) was added dropwise. The reaction mixture was stirred at RT for 2 h. After completion of the reaction the solvent was evaporated under reduced pressure, the crude product was purified by normal phase flash chromatography on silica gel with heptane-EtOAc (50:50) as eluents to obtain the title compound as yellowish solid (2.04 g, 67% yield).

$^1$H-NMR (500 MHz, DMSO-d6) δ ppm: 8.09 (dd, 1H), 7.71 (td, 1H), 7.54 (d, 1H), 7.48 (d, 1H), 7.42 (m, 1H), 7.38 (td, 1H), 7.27 (d, 1H), 7.25 (d, 1H), 7.24 (dd, 1H), 7.18 (dd, 1H), 7.18 (dd, 1H), 7.12 (d, 1H), 7.1 (d, 1H), 4.83 (t, 1H), 4.68 (t, 2H), 4.47 (s, 2H), 4.25 (s, 2H), 3.9 (q, 2H), 3.6/3.31 (m+m, 2H), 3.57/3.24 (m+m, 2H), 3.15 (d, 2H), 2.74 (s, 3H), 2.23 (s, 3H), 2.11 (m, 2H), 1.67-1.29 (m, 6H), 0.98 (t, 3H)

Step 2: Preparation of ethyl 3-[1-(3-hydroxypropyl)-4-methyl-1H-benzotriazol-5-yl]-3-(4-methyl-3-{[6-(2-nitrophenoxy)-2,2-dioxo-2H-1,2λ$^6$,3-benzoxathiazin-3(4H)-yl]methyl}phenyl)propanoate Ethyl 3-[4-methyl-3-[[6-(2-nitrophenoxy)-2,2-dioxo-4H-1,2λ$^6$,3-benzoxathiazin-3-yl]methyl]phenyl]-3-[4-methyl-1-(3-tetrahydropyran-2-yloxypropyl)benzotriazol-5-yl]propanoate (1 eq., 2.03 g, 2.54 mmol) was dissolved in EtOH (40 mL) and THF (25 mL), then pyridinium p-toluenesulfonate (0.1 eq., 64 mg, 0.127 mmol) was added to the solution. The reaction mixture was stirred at 55° C. overnight. After completion of the reaction, the solvents were evaporated, the mixture was diluted with DCM and washed with sat. aq. $NaHCO_3$. The layers were separated, the organic layer was dried over $MgSO_4$. After filtration the filtrate was concentrated to obtain the title compound as white solid (1.8 g, quant.).

$^1$H-NMR (500 MHz, DMSO-d6) δ ppm: 8.09 (dd, 1H), 7.71 (td, 1H), 7.54 (d, 1H), 7.47 (d, 1H), 7.38 (td, 1H), 7.27 (d, 1H), 7.25 (d, 1H), 7.24 (dd, 1H), 7.18 (dd, 1H), 7.18 (dd, 1H), 7.12 (d, 1H), 7.1 (d, 1H), 4.82 (t, 1H), 4.65 (t, 1H), 4.65 (m, 2H), 4.47 (s, 2H), 4.25 (s, 2H), 3.9 (q, 2H), 3.35 (q, 2H), 3.15 (m, 2H), 2.74 (s, 3H), 2.23 (s, 3H), 1.98 (m, 2H), 0.98 (t, 3H)

Step 3: Preparation of ethyl 3-[1-(3-chloropropyl)-4-methyl-1H-benzotriazol-5-yl]-3-(4-methyl-3-{[6-(2-nitrophenoxy)-2,2-dioxo-2H-1,2λ$^6$,3-benzoxathiazin-3(4H)-yl]methyl}phenyl)propanoate Using General Procedure 10 starting from ethyl 3-[1-(3-hydroxypropyl)-4-methyl-1H-benzotriazol-5-yl]-3-(4-methyl-3-{[6-(2-nitrophenoxy)-2,2-dioxo-2H-1,2λ$^6$,3-benzoxathiazin-3(4H)-yl]methyl}phenyl)propanoate (1 eq., 1.8 g, 2.5 mmol) as a reactant, the title compound (1.8 g, quant., brown oil) was obtained.

$^1$H-NMR (500 MHz, DMSO-d6) δ ppm: 8.09 (dd, 1H), 7.71 (td, 1H), 7.56 (d, 1H), 7.5 (d, 1H), 7.38 (td, 1H), 7.27 (d, 1H), 7.27 (d, 1H), 7.24 (dd, 1H), 7.18 (dd, 1H), 7.18 (dd, 1H), 7.13 (d, 1H), 7.1 (d, 1H), 4.82 (t, 1H), 4.74 (t, 2H), 4.48 (s, 2H), 4.26 (s, 2H), 3.9 (q, 2H), 3.58 (t, 2H), 3.15 (d, 2H), 2.75 (s, 3H), 2.31 (quint., 2H), 2.23 (s, 3H), 0.98 (t, 3H)

Step 4: Preparation of ethyl 3-(3-{[6-(2-aminophenoxy)-2,2-dioxo-2H-1,2λ$^6$,3-benzoxathiazin-3(4H)-yl]methyl}-4-methylphenyl)-3-[1-(3-chloropropyl)-4-methyl-1H-benzotriazol-5-yl]propanoate Using General Procedure 1 STEP 3 starting from ethyl 3-[1-(3-chloropropyl)-4-methyl-1H-benzotriazol-5-yl]-3-(4-methyl-3-{[6-(2-nitrophenoxy)-2,2-dioxo-2H-1,2λ$^6$,3-benzoxathiazin-3(4H)-yl]methyl}phenyl)propanoate (1 eq., 1.8 g, 2.5 mmol) as a reactant, the title compound (1.41 g, 82% yield, brown solid) was obtained.

HRMS calculated for $C_{36}H_{38}ClN_5O6S$: 703.2231; $[M+H]^+$ found: 704.2301 (δ=−0.4 ppm).

Step 5: Preparation of ethyl[4,37-dimethyl-33,33-dioxo-27,32-dioxa-33λ$^6$-thia-1,14,15,16,20-pentaazaheptacyclo[26.5.3.1$^{3,7}$0.1$^{9,13}$0.0$^{12,16}$0.0$^{21,26}$0.0$^{31,35}$]octatriaconta-3(38),4,6,9(37),10,12,14,21,23,25,28,30,35-tridecaen-8-yl]acetate Ethyl 3-(3-{[6-(2-aminophenoxy)-2,2-dioxo-2H-1,2λ$^6$,3-benzoxathiazin-3(4H)-yl]methyl}-4-methylphenyl)-3-[1-(3-chloropropyl)-4-methyl-1H-benzotriazol-5-yl]propanoate (1 eq., 500 mg, 0.7100 mmol) was dissolved in propanenitrile (25 mL) and sodium iodide (2 eq., 213 mg, 1.420 mmol) was added at RT. The mixture was heated to 100° C. and refluxed for 5 h. $K_2CO_3$ (2 eq., 196 mg, 1.420 mmol) was added and the mixture was stirred at 100° C. for 6 h. The solvent was evaporated under reduced pressure and the residue was partitioned between DCM and water. The organic layer was separated and washed with 1M aq. HCl solution, then with sat. aq.

$NaHCO_3$ solution. The organic phase was dried over $MgSO_4$, and after filtration evaporated under reduced pressure. The crude product was purified by reversed-phase chromatography using water-MeCN as eluents to give the title compound as white solid (125 mg, 0.187 mmol, 26% yield).

$^1$H-NMR (500 MHz, DMSO-d6) δ ppm: 7.6 (d, 1H), 7.4 (dd, 1H), 7.36 (d, 1H), 7.2 (d, 1H), 7.13 (d, 1H), 7.04 (t, 1H), 6.91 (d, 1H), 6.89 (dd, 1H), 6.88 (d, 1H), 6.86 (d, 1H), 6.85 (d, 1H), 6.64 (t, 1H), 5.05 (brt, 1H), 4.85 (t, 1H), 4.74/4.56 (dt+dt, 2H), 4.29/4.11 (d+d, 2H), 4.21/4.09 (d+d, 2H), 3.9 (q, 2H), 3.29/3.01 (m+m, 2H), 3.16 (d, 2H), 2.69 (s, 3H), 2.27 (s, 3H), 2.19 (qn, 2H), 0.99 (t, 3H)

Step 6: Preparation of Example 71

Using General Procedure 12 starting from ethyl[4,37-dimethyl-33,33-dioxo-27,32-dioxa-33λ$^6$-thia-1,14,15,16,20-pentaazaheptacyclo[26.5.3.1$^{3,7}$0.1$^{9,13}$0.0$^{12,16}$0.0$^{21,26}$0.0$^{31,35}$]octatriaconta-3(38),4,6,9(37),10,12,14,21,23,25,28,30,35-tridecaen-8-yl]acetate (1 eq., 170 mg, 0.25 mmol) as a reactant, the title compound (135 mg, 83% yield, white solid) was obtained.

The enantiopure products were obtained by the chromatographic separation on chiral column.

EXAMPLE 71a (E1, optical purity: 97.9%)

HRMS calculated for $C_{34}H_{33}N_5O_6S$: 639.2151; $[M+H]^+$ found: 640.2231 (δ=1.0 ppm).

EXAMPLE 71b (E2, Optical Purity>99.9%)

HRMS calculated for $C_{34}H_{33}N_5O_6S$: 639.2151; $[M+H]^+$ found: 640.2226 (δ=0.3 ppm).

$^1$H-NMR (500 MHz, DMSO-d6) δ ppm: 12.32 (brs, 1H), 7.56 (d, 1H), 7.39 (dd, 1H), 7.34 (d, 1H), 7.17 (d, 1H), 7.12 (d, 1H), 7.04 (t, 1H), 6.88 (dd, 1H), 6.87 (d, 1H), 6.86 (d, 1H), 6.85 (d, 1H), 6.82 (d, 1H), 6.63 (t, 1H), 5.04 (t, 1H), 4.84 (t, 1H), 4.73/4.55 (dt+dt, 2H), 4.28/4.14 (d+d, 2H), 4.2/4.09 (d+d, 2H), 3.28/3.02 (m+m, 2H), 2.96 (m, 2H), 2.68 (s, 3H), 2.27 (s, 3H), 2.19 (qn, 2H)

$^{13}$C-NMR (125 MHz, DMSO-d6) δ ppm: 154.7, 146.5, 146.1, 143.1, 142.4, 140.4, 137, 135.7, 132, 131.7, 131.3, 129.8, 129.3, 127.7, 127.3, 126, 120.1, 119.5, 118.9, 118.1, 117.2, 116.7, 113, 107.3, 51.5, 49.1, 45, 42.5, 41.6, 39.6, 28.3, 18.4, 13.3

EXAMPLE 72: [4-Methyl-10,25,25-trioxo-19,24-dioxa-25λ$^6$-thia-1,9,12,13,14-pentaazapentacyclo[18.5.3.1$^{3,7}$0.1$^{11,14}$0.0$^{23,27}$]triaconta-3(30),4,6,11(29),12,20,22,27-octaen-8-yl]acetic acid enantiomer 1

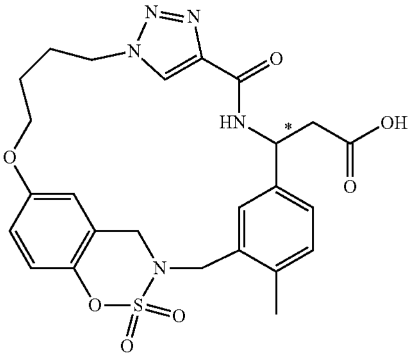

* = RorS enantiomer 2

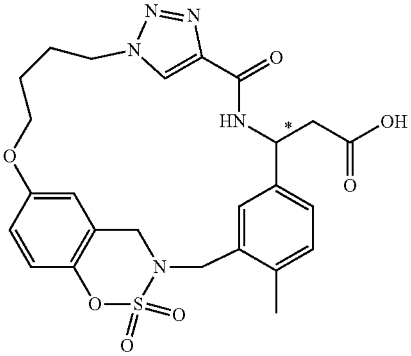

* = RorS

Step 1: Preparation of [(5-bromo-2-methylphenyl)methoxy](tert-butyl)diphenylsilane A mixture of (5-bromo-2-methylphenyl)methanol (1 eq., 20 g, 99 mmol), imidazole (3 eq., 20 g, 297 mmol) and DCM (250 mL) was stirred at 10° C. Tert-butyl(chloro)diphenylsilane was added and the mixture was stirred for 1 h at this temperature. After completion of the reaction, the mixture was quenched with water (300 mL), the resulted mixture was extracted with DCM, the layers were separated. The organic layer was dried over anhydrous $Na_2SO_4$, filtered and the filtrate was evaporated under reduced pressure. The crude product was purified by normal phase silica gel chromatography using heptane-DCM (100:0 to 50:50) as eluents. The title compound was obtained as colorless solid (44 g, quant.).

$^1$H-NMR (400 MHz, DMSO-d6) δ ppm: 7.63 (m, 4H), 7.55 (d, 1H), 7.44 (m, 6H), 7.37 (dd, 1H), 7.11 (d, 1H), 4.73 (s, 2H), 2.09 (s, 3H), 1.04 (s, 9H)

Step 2: Preparation of 1-[3-({[tert-butyl(diphenyl)silyl]oxy}methyl)-4-methylphenyl]ethan-1-one To a stirred solution of [(5-bromo-2-methylphenyl)methoxy](tert-butyl)diphenylsilane (1 eq., 20 g, 45.5 mmol) in THF (364 mL, 8 mL/mmol) butyllithium (2.6 M, 2 eq., 35 mL, 91 mmol) was added dropwise at −78° C. under inert atmosphere and the mixture was stirred overnight at this temperature. N,N-dimethylacetamide (3 eq., 14.1 g, 137 mmol) was added dropwise at −78° C. and the mixture was stirred for additional 1 h at −78° C. The mixture was allowed to warm to RT and stirred overnight. After completion of the reaction, the mixture was quenched with water, extracted with EtOAc, the layers were separated. The organic layer was dried over $Na_2SO_4$, filtered and the filtrate was evaporated under reduced pressure. The crude product was purified by normal phase silica gel chromatography using heptane-EtOAc-EtOH (100:0:0 to 70:22.5:7.5) as eluents. The title compound was obtained as a colorless solid (9.5 g, 47% yield).

$^1$H-NMR (400 MHz, $CDCl_3$) δ ppm: 8.1 (d, 1H), 7.8 (dd, 1H), 7.7 (dd, 4H), 7.4 (td+d, 6H), 7.2 (d, 1H), 4.8 (s, 2H), 2.6 (s, 3H), 2.2 (s, 3H), 1.1 (q, 9H)

Step 3: Preparation of methyl 3-[3-({[tert-butyl(diphenyl)silyl]oxy}methyl)-4-methylphenyl]-3-oxopropanoate To a stirred solution of 1-[3-({[tert-butyl(diphenyl)silyl]oxy}methyl)-4-methylphenyl]ethan-1-one (1 eq., 9.5 g, 23.6 mmol) in dimethyl carbonate (11 eq., 23.4 g, 259.6 mmol) NaH (2 eq., 1.88 g, 12 mmol, 47.2 mmol, 60 wt % in mineral oil) was added at RT. The mixture was heated at 95° C. for 4 h. After completion of the reaction, the mixture was cooled to RT, diluted with water, the resulted mixture was extracted with EtOAc. The layers were separated, the organic layer was dried over $Na_2SO_4$, filtered and the filtrate was evaporated under reduced pressure.

The crude product was purified by normal phase silica gel chromatography using heptane-DCM (100:0 to 0:100) as eluents. The title compound was obtained as a colorless oil (7.9 g, 73% yield).

$^1$H-NMR (400 MHz, DMSO-d6) δ ppm: 8.05 (d, 1H), 7.8 (dd, 1H), 7.65 (m, 4H), 7.51-7.4 (m, 6H), 7.33 (d, 1H), 4.8 (s, 2H), 4.13 (s, 2H), 3.64 (s, 3H), 2.22 (s, 3H), 1.05 (s, 9H)

Step 4: Preparation of methyl 3-amino-3-[3-({[tert-butyl(diphenyl)silyl]oxy}methyl)-4-methylphenyl]propanoate The mixture of methyl 3-[3-({[tert-butyl(diphenyl)silyl]oxy}methyl)-4-methylphenyl]-3-oxopropanoate (1 eq., 7.9 g, 17 mmol), ammonium acetate (5 eq., 6.6 g, 86 mmol) and MeOH (86 mL, 5 mL/mmol) was stirred at reflux temperature overnight. After completion of the reaction, the solvent was evaporated under reduced pressure to give methyl 3-[3-({[tert-butyl(diphenyl)silyl]oxy}methyl)-4-methylphenyl]-3-iminopropanoate as an oil. The crude product was dissolved in AcOH (43 mL, 2.5 mL/mmol) and sodium borohydride was added slowly to the mixture at 10° C. The mixture was allowed to warm to RT and stirred overnight. The mixture was quenched with sat. aq. $K_2CO_3$ solution, the resulted mixture was extracted with EtOAc. The layers were separated, the organic layer was dried over $Na_2SO_4$, filtered and the filtrate was evaporated under reduced pressure. The crude product was used in a next step without further purification (7.4 g oil, 75% yield).

$^1$H-NMR (400 MHz, DMSO-d6) δ ppm: 7.65 (dd, 4H), 7.4 (m, 7H), 7.2 (dd, 1H), 7.1 (d, 1H), 4.7 (s, 2H), 4.25 (m, 1H), 3.55 (s, 3H), 2.65 (2dd, 2H), 2.15 (s, 3H), 1 (s, 9H)

Step 5: Preparation of methyl 3-[(tert-butoxycarbonyl)amino]-3-[3-({[tert-butyl(diphenyl)silyl]oxy}methyl)-4-methylphenyl]propanoate To a stirred solution of methyl 3-amino-3-[3-({[tert-butyl(diphenyl)silyl]oxy}methyl)-4-methylphenyl]propanoate (1 eq., 4 g, 7.02 mmol) in DCM (56 mL, 8 mL/mmol) TEA (1.2 eq., 2.5 mL, 18 mmol) and di-tert-butyl-dicarbonate (1.2 eq., 1.84 g, 8.42 mmol) were added at RT. The mixture was stirred at RT for 4 h. After completion of the reaction the mixture was diluted with water, then extracted with EtOAc. The organic layer was separated and dried over anhydrous $Na_2SO_4$, filtered, concentrated to dryness. The crude product was purified by normal phase silica gel chromatography using heptane-EtOAc-EtOH (100:0:0 to 70:22.5:7.5) as eluents. The title compound was obtained as a colorless oil (3.7 g, 92% yield).

$^1$H-NMR (400 MHz, DMSO-d6) δ ppm: 7.65 (m, 4H), 7.4 (m, 9H), 7.1 (dd+d, 2H), 4.9 (m, 1H), 4.7 (s, 2H), 3.55 (s, 3H), 2.7 (2dd, 2H), 2.1 (s, 3H), 1.3 (m, 9H), 1 (s, 9H)

Step 6: Preparation of methyl 3-[(tert-butoxycarbonyl)amino]-3-[3-(hydroxymethyl)-4-methylphenyl]propanoate The mixture of methyl 3-[(tert-butoxycarbonyl)amino]-3-[3-({[tert-butyl(diphenyl)silyl]oxy}methyl)-4-methylphenyl]propanoate (1 eq., 16.4 g, 29.3 mmol), tetrabutylammonium fluoride (1 eq., 26.4 g, 29.3 mmol) and THF (234 mL, 8 mL/mmol) was stirred at RT for 1 h. After completion of the reaction, the mixture was quenched with sat. aq. $NaHCO_3$ solution, the resulted mixture was extracted with EtOAc. The layers were separated, the organic layer was dried over $Na_2SO_4$, filtered and evaporated under reduced pressure. The crude product was purified by normal phase silica gel chromatography using heptane-EtOAc (80:20 to 30:70) as eluents. The title compound was obtained as a colorless oil (8.55 g, 90% yield).

$^1$H-NMR (400 MHz, DMSO-d6) δ ppm: 7.42 (d, 1H), 7.29 (s, 1H), 7.08-7.02 (m, 2H), 5.05 (t, 1H), 4.88 (m, 1H), 4.45 (d, 2H), 3.55 (s, 3H), 2.73/2.62 (2dd, 2H), 2.19 (s, 3H), 1.35 (s, 9H)

Step 7: Preparation of methyl 3-(3-{[6-(benzyloxy)-2,2-dioxo-2H-1,2λ$^6$,3-benzoxathiazin-3(4H)-yl]methyl}-4-methylphenyl)-3-[(tert-butoxycarbonyl)amino]propanoate Using General Procedure 7 starting from methyl 3-[(tert-butoxycarbonyl)amino]-3-[3-(hydroxymethyl)-4-methylphenyl]propanoate (1 eq.) and 6-(benzyloxy)-3,4-dihydro-2H-1,2λ$^6$,3-benzoxathiazine-2,2-dione (1.1 eq.) as reactants, the title compound (9 g, 81% yield) was obtained.

$^1$H-NMR (400 MHz, DMSO-d6) δ ppm: 7.45 (d, 1H), 7.45 (d, 2H), 7.42 (t, 2H), 7.38 (t, 1H), 7.2 (m, 3H), 7.18 (d, 1H), 7.1 (dd, 1H), 7 (d, 1H), 5.09 (s, 2H), 4.9 (m, 1H), 4.48 (s, 2H), 4.22 (m, 2H), 3.55 (s, 3H), 2.76/2.7 (2dd, 2H), 2.23 (s, 3H), 1.38 (s, 9H)

Step 8: Preparation of methyl 3-(3-{[6-(4-bromobutoxy)-2,2-dioxo-2H-1,2λ$^6$,3-benzoxathiazin-3(4H)-yl]methyl}-4-methylphenyl)-3-[(tert-butoxycarbonyl)amino]propanoate Using General Procedure 8 starting from methyl 3-(3-{[6-(benzyloxy)-2,2-dioxo-2H-1,2λ$^6$,3-benzoxathiazin-3(4H)-yl]methyl}-4-methylphenyl)-3-[(tert-butoxycarbonyl)amino]propanoate (1 eq.) as a reactant, methyl 3-[(tert-butoxycarbonyl)amino]-3-{3-[(6-hydroxy-2,2-dioxo-2H-1,2λ$^6$,3-benzoxathiazin-3(4H)-yl)methyl]-4-methylphenyl}propanoate (4.3 g, 62% yield) was obtained. To the solution of the crude product (0.5 g, 1 mmol, 7.35 mL) in MeCN (10 mL/mmol, 10 mL) 1,4-dibromobutane (1.5 eq., 0.2 mL, 46.5 mmol) and $Cs_2CO_3$ (3 eq., 0.6 g, 3 mmol) were added at RT and the mixture was stirred overnight. After completion of the reaction the solvent was evaporated. The crude product was purified by reversed-phase chromatography using water-MeCN gradient elution (59:41 to 5:95) to give the title compound (345 mg white solid, 50% yield).

$^1$H-NMR (400 MHz, DMSO-d6) δ ppm: 7.45 (d, 1H), 7.25-7.15 (m, 3H), 7.11 (d, 1H), 7 (dd, 1H), 6.89 (d, 1H), 4.88 (m, 1H), 4.45/4.2 (s+m, 4H), 4 (t, 2H), 3.6 (t, 2H), 3.55 (s, 3H), 2.77/2.68 (2dd, 2H), 2.22 (s, 3H), 1.95 (m, 2H), 1.8 (m, 2H), 1.35 (s, 9H)

Step 9: Preparation of methyl 3-(3-{[6-(4-azidobutoxy)-2,2-dioxo-2H-1,2λ$^6$,3-benzoxathiazin-3(4H)-yl]methyl}-4-methylphenyl)-3-[(tert-butoxycarbonyl)amino]propanoate The mixture of methyl 3-(3-{[6-(4-bromobutoxy)-2,2-dioxo-2H-1,2λ$^6$,3-benzoxathiazin-3(4H)-yl]methyl}-4-methylphenyl)-3-[(tert-butoxycarbonyl)amino]propanoate (1 eq., 345 mg, 0.538 mmol), sodium azide (2.3 eq., 80 mg, 1.23 mmol) and DMF (10 mL) was stirred overnight at RT. After completion of the reaction, the mixture was quenched with ice cold water, the resulted mixture was extracted with EtOAc. The layers were separated, the organic layer was dried over $Na_2SO_4$ and filtered. The solvent was evaporated under reduced pressure. The crude product was purified by reversed-phase chromatography using water-MeCN gradient elution (100:0 to 0:100) to give the title compound (290 mg white solid, 50% yield).

$^1$H-NMR (400 MHz, DMSO-d6) δ ppm: 7.42 (d, 1H), 7.25-7.15 (m, 3H), 7.12 (d, 1H), 6.99 (dd, 1H), 6.9 (d, 1H), 4.88 (m, 1H), 4.45 (s, 2H), 4.2 (2d, 2H), 4 (t, 2H), 3.57 (s, 3H), 3.4 (t, 2H), 2.77/2.68 (2dd, 2H), 2.25 (s, 3H), 1.8-1.65 (m, 4H), 1.35 (s, 9H)

Step 10: Preparation of tert-butyl 1-[4-({3-[(5-{1-[(tert-butoxycarbonyl)amino]-3-methoxy-3-oxopropyl}-2-methylphenyl)methyl]-2,2-dioxo-3,4-dihydro-2H-1,2λ$^6$,3-benzoxathiazin-6-yl}oxy)butyl]-1H-1,2,3-triazole-4-carboxylate To a stirred solution of methyl 3-(3-{[6-(4-azidobutoxy)-2,2-dioxo-2H-1,2λ$^6$,3-benzoxathiazin-3(4H)-yl]methyl}-4- methylphenyl)-3-[(tert-butoxycarbonyl)amino]propanoate (1 eq., 225 mg, 0.372 mmol) in tert-butanol (1.86 mL, 5 mL/mmol) and water (0.75 mL, 2 mL/mmol) tert-butyl prop-2-ynoate (1 eq., 47 mg, 0.372 mmol), copper sulfate (0.06 eq., 3.6 mg, 0.022 mmol) and sodium ascorbate (0.2 eq., 15 mg, 0.075 mmol) were added at RT and the mixture was stirred for 24 h. The reaction was quenched with 0.1 M aq. HCl, the resulted mixture was extracted with EtOAc. The layers were separated, the organic layer was dried over $Na_2SO_4$ and filtered. The solvent was evaporated under reduced pressure. The crude product was purified by normal phase silica gel chromatography using DCM-EtOAc (100:0 to 80:20) as eluents. The title compound was obtained as a colorless gum (263 mg, 96% yield).

$^1$H-NMR (400 MHz, DMSO-d6) δ ppm: 8.68 (s, 1H), 7.45 (d, 1H), 7.2 (m, 3H), 7.15 (d, 1H), 7 (dd, 1H), 6.9 (d, 1H), 4.9 (m, 1H), 4.5 (t, 2H), 4.45 (s, 2H), 4.2 (m, 2H), 3.98 (t, 2H), 3.55 (s, 3H), 2.7 (m, 2H), 2.25 (s, 3H), 2 (m, 2H), 1.7 (m, 2H), 1.5 (s, 9H), 1.3 (s, 9H)

Step 11: Preparation of 1-{4-[(3-{[5-(1-amino-3-methoxy-3-oxopropyl)-2-methylphenyl]methyl}-2,2-dioxo-3,4-dihydro-2H-1,2λ$^6$,3-benzoxathiazin-6-yl)oxy]butyl}-1H-1,2,3-triazole-4-carboxylic acid hydrochloride To a solution of tert-butyl 1-[4-({3-[(5-{1-[(tert-butoxycarbonyl)amino]-3-methoxy-3-oxopropyl}-2-methylphenyl)methyl]-2,2-dioxo-3,4-dihydro-2H-1,2λ$^6$,3-benzoxathiazin-6-yl}oxy)butyl]-1H-1,2,3-triazole-4-carboxylate (1 eq., 200 mg, 0.274 mmol) in dioxane (10 mL/mmol, 2.74 mL) HCl (4M in dioxane) (5.5 eq., 0.377 mL) was added at 0° C. The reaction mixture was allowed to warm to RT and stirred at RT for 4 h. After completion of the reaction the volatiles were evaporated to dryness under reduced pressure. The crude product was used without further purification (174 mg, quant.).

$^1$H-NMR (400 MHz, DMSO-d6) δ ppm: 8.8-8.4 (m, 3H), 8.71 (s, 1H), 7.4 (dd+d, 2H), 7.3 (d, 1H), 7.15 (d, 1H), 7 (dd+d, 2H), 4.62 (t, 1H), 4.52 (s, 2H), 4.5 (t, 2H), 4.25 (m, 2H), 4 (t, 2H), 3.6 (s, 3H), 3.12/2.98 (2dd, 2H), 2.3 (s, 3H), 2.02 (m, 2H), 1.7 (m, 2H)

Step 12: Preparation of methyl[4-methyl-10,25,25-trioxo-19,24-dioxa-25λ$^6$-thia-1,9,12,13,14-pentaazapentacyclo[18.5.3.1$^{3,7}$0.1$^{11,14}$0.0$^{23,27}$]triaconta-3(30),4,6,11(29),12,20,22,27-octaen-8-yl]acetate 1-{4-[(3-{[5-(1-Amino-3-methoxy-3-oxopropyl)-2-methylphenyl]methyl}-2,2-dioxo-3,4-dihydro-2H-1,226,3-benzoxathiazin-6-yl)oxy]butyl}-1H-1,2,3-triazole-4-carboxylic acid hydrochloride (1 eq., 154 mg, 0.252 mmol) was dissolved in DCM (126 mL, 500 mL/mmol), then TEA (5 eq., 0.176 mL, 1.262 mmol), benzotriazol-1-ol (1.2 eq., 41 mg, 0.303 mmol) and N-(3-dimethylaminopropyl)-N$^1$-ethylcarbodiimide hydrochloride (1.2 eq., 58 mg, 0.303 mmol) were added. The mixture was stirred at RT overnight, quenched with 30 mL water and extracted with DCM. The organic phase was separated, washed with brine, dried over $Na_2SO_4$, filtered and concentrated to give the crude product, which was purified by reversed-phase chromatography using water-MeCN gradient elution (64:36 to 28:72) to give the title compound (43 mg white solid, 31% yield).

$^1$H-NMR (400 MHz, DMSO-d6) δ ppm: 8.2 (d, 1H), 8.11 (s, 1H), 7.21 (m, 2H), 6.98 (d, 1H), 6.91 (d, 1H), 6.75 (dd, 1H), 6 (d, 1H), 5.61 (m, 1H), 4.7/4.38 (2m, 2H), 4.3 (2d, 2H), 4.18/4.05 (2d, 2H), 4/3.61 (2m, 2H), 3.65 (s, 3H), 3.2/3.1 (2m, 2H), 2.45 (s, 3H), 2.4-1.9 (m, 4H)

Step 13: Preparation of Example 72

Using General Procedure 12 starting from methyl[4-methyl-10,25,25-trioxo-19,24-dioxa-25λ$^6$-thia-1,9,12,13,14-pentaazapentacyclo[18.5.3.1$^{3,7}$0.1$^{11,14}$0.0$^{23,27}$]triaconta-3(30),4,6,11(29),12,20,22,27-octaen-8-yl]acetate (1 eq.) as a reactant, the title compound (white solid, quant.) was obtained.

The enantiopure products were obtained by chromatographic separation on chiral column.

EXAMPLE 72a (E1)

HRMS calculated for $C_{25}H_{27}N_5O_7S$: 541.1631; $[M+H]^+$ found: 542.1709 (δ=0.9 ppm).

EXAMPLE 72b (E2)

HRMS calculated for $C_{25}H_{27}N_5O_7S$: 541.1631; $[M+H]^+$ found: 542. 1708 (δ=0.7 ppm).

$^1$H-NMR (400 MHz, DMSO-d6) δ ppm: 12.3 (m, 1H), 9.15 (d, 1H), 8.66 (s, 1H), 7.31 (dd, 1H), 7.25 (d, 1H), 7.11 (d, 1H), 7.06 (d, 1H), 6.86 (dd, 1H), 6.2 (d, 1H), 5.41 (m, 1H), 4.53 (m, 2H), 4.53/3.99 (dd, 2H), 4.39/3.77 (dd, 2H), 3.39/2.81 (2m, 2H), 2.84/2.72 (2dd, 2H), 2.35 (s, 3H), 2.16-1.7 (m, 4H)

EXAMPLE 73: [4,10,14-Trimethyl-29,29-dioxo-17,23,28-trioxa-29λ$^6$-thia-1,12,13,14-tetraazahexacyclo[22.5.3.1$^{3,7}$0.1$^{9,16}$0.0$^{11,15}$0.0$^{27,31}$]tetratriaconta-3(34),4,6,9(33),10,12,15,24,26,31-decaen-8-yl]acetic acid enantiomer 1

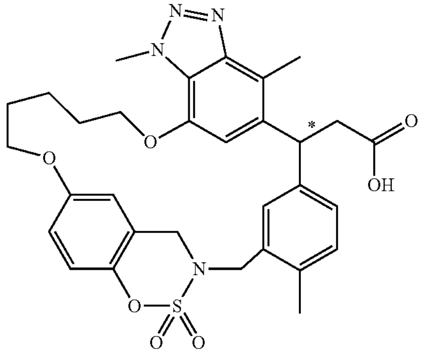

* = RorS enantiomer 2

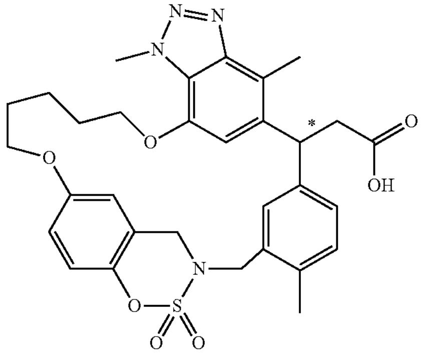

* = RorS

Step A1: Preparation of methyl 3-(1,4-dimethyl-1H-benzotriazol-5-yl)-3-[3-(hydroxymethyl)-4-methylphenyl]propanoate Using General Procedure 6 starting from methyl (2E)-3-(1,4-dimethyl-1H-benzotriazol-5-yl)prop-2-enoate (1 eq.) and [2-methyl-5-(4,4,5,5-tetramethyl-1,3,2-dioxaborolan-2-yl)phenyl]methanol (1.3 eq.) as reactants, the title compound (orange oil, 88% yield) was obtained.

$^1$H-NMR (500 MHz, DMSO-d6) δ ppm: 7.57 (d, 1H), 7.47 (d, 1H), 7.24 (d, 1H), 7.1 (dd, 1H), 7.02 (d, 1H), 4.99 (t, 1H), 4.84 (t, 1H), 4.4 (d, 2H), 4.23 (s, 3H), 3.48 (s, 3H), 3.18/3.13 (dd+dd, 2H), 2.75 (s, 3H), 2.15 (s, 3H)

Step 1: Preparation of methyl 3-(3-{[6-(benzyloxy)-2,2-dioxo-2H-1,2λ$^6$,3-benzoxathiazin-3(4H)-yl]methyl}-4-methylphenyl)-3-(1,4-dimethyl-1H-benzotriazol-5-yl)propanoate Using General Procedure 7 starting from methyl methyl 3-(1,4-dimethyl-1H-benzotriazol-5-yl)-3-[3-(hydroxymethyl)-4-methylphenyl]propanoate (1 eq.) and 6-(benzyloxy)-3,4-dihydro-2H-1,2)$^6$,3-benzoxathiazine-2,2-dione (1.2 eq.) as reactants, the title compound (beige solid foam, 84% yield) was obtained.

$^1$H-NMR (500 MHz, DMSO-d6) δ ppm: 7.56 (d, 1H), 7.49 (d, 1H), 7.48-7.32 (m, 5H), 7.21 (d, 1H), 7.18 (dd, 1H), 7.13 (d, 1H), 7.13 (d, 1H), 7.07 (dd, 1H), 6.94 (d, 1H), 5.1 (s, 2H), 4.85 (t, 1H), 4.42 (s, 2H), 4.22/4.19 (d+d, 2H), 4.2 (s, 3H), 3.48 (s, 3H), 3.22/3.17 (dd+dd, 2H), 2.75 (s, 3H), 2.22 (s, 3H)

Step 2: Preparation of methyl 3-(3-{[6-(benzyloxy)-2,2-dioxo-2H-1,2λ$^6$,3-benzoxathiazin-3(4H)-yl]methyl}-4-methylphenyl)-3-(7-bromo-1,4-dimethyl-1H-benzotriazol-5-yl)propanoate Methyl 3-(3-{[6-(benzyloxy)-2,2-dioxo-2H-1,2λ$^6$,3-benzoxathiazin-3(4H)-yl]methyl}-4-methylphenyl)-3-(1,4-dimethyl-1H-benzotriazol-5-yl)propanoate (1 eq., 1 g, 1.59 mmol) was dissolved in nitromethane (20 mL), then Oxone® (3 eq., 2.31 g, 4.79 mmol) and potassium bromide (1.2 eq., 0.23 g, 1.92 mmol) were added. The reaction mixture was stirred overnight at 60° C., diluted with DCM (30 mL) and washed with water (50 mL). The organic phase was dried over $MgSO_4$, filtered and concentrated under reduced pressure to give the crude product, which was purified by preparative reversed-phase chromatography using 5 mM aq. $NH_4HCO_3$-MeCN gradient elution (95:5 to 0:100) to give the title compound (35% yield).

$^1$H-NMR (500 MHz, DMSO-d6) δ ppm: 7.68 (s, 1H), 7.49-7.31 (m, 5H), 7.25 (d, 1H), 7.21 (dd, 1H), 7.16 (d, 1H), 7.13 (d, 1H), 7.06 (dd, 1H), 6.96 (d, 1H), 5.1 (s, 2H), 4.83 (t, 1H), 4.47/4.42 (d+d, 2H), 4.41 (s, 3H), 4.22 (s, 2H), 3.49 (s, 3H), 3.24 (d, 2H), 2.73 (s, 3H), 2.23 (s, 3H)

Step 3: Preparation of methyl 3-(3-{[6-(benzyloxy)-2,2-dioxo-2H-1,2λ$^6$,3-benzoxathiazin-3(4H)-yl]methyl}-4-methylphenyl)-3-(7-{[5-(benzyloxy)pentyl]oxy}-1,4-dimethyl-1H-benzotriazol-5-yl)propanoate Methyl 3-(3-{[6-(benzyloxy)-2,2-dioxo-2H-1,2λ$^6$,3-benzoxathiazin-3(4H)-yl]methyl}-4-methylphenyl)-3-(7-bromo-1,4-dimethyl-1H-benzotriazol-5-yl)propanoate (1 eq., 391 mg, 0.554 mmol) was dissolved in toluene (20 mL), then 5-benzyloxypentan-1-ol (10 eq., 1.07 g, 5.54 mmol), $Cs_2CO_3$ (10 eq., 1.81 g, 5.54 mmol), 2-(di-tert-butylphosphino)-1,1'-binapthyl (0.1 eq., 22 mg, 0.055 mmol) and palladium diacetate catalyst (0.08 eq., 10 mg, 0.044 mmol) were added. The reaction mixture was stirred for 3 days at 70° C. under inert atmosphere. The solvent was evaporated, then the mixture was diluted with EtOAc (20 mL) and water (20 mL). The organic phase was separated, the aq. phase was extracted with further 3×20 mL EtOAc. The combined organic phase was dried over $MgSO_4$, filtered, concentrated under reduced pressure to give the crude product, which was purified by preparative reversed-phase chromatography using 5 mM aq. $NH_4HCO_3$-MeCN gradient elution (95:5 to 0:100) to give the title compound (colorless oil, 11% yield).

$^1$H-NMR (500 MHz, DMSO-d6) δ ppm: 7.47-7.19 (m, 12H), 7.13 (d, 1H), 7.13 (d, 1H), 7.06 (dd, 1H), 6.93 (d, 1H), 6.88 (s, 1H), 5.08 (s, 2H), 4.8 (t, 1H), 4.47/4.42 (d+d, 2H), 4.42 (s, 2H), 4.29 (s, 3H), 4.24/4.19 (d+d, 2H), 4.15/4.06 (m+m, 2H), 3.49 (s, 3H), 3.43 (t, 2H), 3.22 (m, 2H), 2.62 (s, 3H), 2.21 (s, 3H), 1.84-1.03 (m, 6H)

Step 4: Preparation of methyl 3-{3-[(6-hydroxy-2,2-dioxo-2H-1,2λ$^6$,3-benzoxathiazin-3(4H)-yl)methyl]-4-methylphenyl}-3-{7-[(5-hydroxypentyl)oxy]-1,4-dimethyl-1H-benzotriazol-5-yl}propanoate Using General Procedure 8 starting from methyl 3-(3-{[6-(benzyloxy)-2,2-dioxo-2H-1,2λ$^6$,3-benzoxathiazin-3(4H)-yl]methyl}-4-methylphenyl)-3-(7-{[5-(benzyloxy)pentyl]oxy}-1,4-dimethyl-1H-benzotriazol-5-yl)propanoate (1 eq.) as a reactant, the title compound (white solid foam, 82% yield) was obtained.

$^1$H-NMR (500 MHz, DMSO-d6) δ ppm: 9.69 (s, 1H), 7.24 (d, 1H), 7.21 (dd, 1H), 7.13 (d, 1H), 6.99 (d, 1H), 6.88 (s, 1H), 6.78 (dd, 1H), 6.58 (d, 1H), 4.79 (t, 1H), 4.42/4.36 (d+d, 2H), 4.39 (brs, 1H), 4.35 (s, 3H), 4.23/4.16 (d+d, 2H), 4.16/4.07 (m+m, 2H), 3.51 (s, 3H), 3.42 (m, 2H), 3.23/3.19 (m+m, 2H), 2.61 (s, 3H), 2.22 (s, 3H), 1.85-1.43 (m, 6H)

Step 5: Preparation of methyl 3-{7-[(5-chloropentyl)oxy]-1,4-dimethyl-1H-benzotriazol-5-yl}-3-{3-[(6-hydroxy-2,2-dioxo-2H-1,2λ$^6$,3-benzoxathiazin-3(4H)-yl)methyl]-4-methylphenyl}propanoate hydrochloride Using General Procedure 10 starting from methyl 3-{3-[(6-hydroxy-2,2-dioxo-2H-1,2)$^6$,3-benzoxathiazin-3(4H)-yl)methyl]-4-methylphenyl}-3-{17-[(5-hydroxypentyl)oxy]-1,4-dimethyl-1H-benzotriazol-5-yl}propanoate (1 eq.) as a reactant, the title compound (off-white solid foam, quant.) was obtained.

$^1$H-NMR (500 MHz, DMSO-d6) δ ppm: 9.71 (brs, 1H), 7.24 (d, 1H), 7.21 (dd, 1H), 7.13 (d, 1H), 6.99 (d, 1H), 6.89 (s, 1H), 6.79 (dd, 1H), 6.58 (d, 1H), 4.79 (t, 1H), 4.42/4.37 (d+d, 2H), 4.35 (s, 3H), 4.23/4.17 (d+d, 2H), 4.17/4.07 (m+m, 2H), 3.66 (t, 2H), 3.51 (s, 3H), 3.24/3.19 (dd+dd, 2H), 2.61 (s, 3H), 2.22 (s, 3H), 1.81 (m, 2H), 1.79 (m, 2H), 1.59 (m, 2H)

Step 6: Preparation of methyl[4,10,14-trimethyl-29,29-dioxo-17,23,28-trioxa-29)$^6$-thia-1,12,13,14-tetraazahexacyclo[22.5.3.1$^{3,7}$0.1$^{9,16}$0.0$^{11,15}$0.0$^{27,31}$]tetratriaconta-3(34),4,6,9(33),10,12,15,24,26,31-decaen-8-yl]acetate Using General Procedure 11 starting from methyl 3-{7-[(5-chloropentyl)oxy]-1,4-dimethyl-1H-benzotriazol-5-yl}-3-{3-[(6-hydroxy-2,2-dioxo-2H-1,2λ$^6$,3-benzoxathiazin-3

(4H)-yl)methyl]-4-methylphenyl}propanoate hydrochloride (1 eq.) as a reactant, the title compound (beige solid, 19%) was obtained.

$^1$H-NMR (500 MHz, DMSO-d6) δ ppm: 7.4 (dd, 1H), 7.2 (d, 1H), 7.1 (s, 1H), 7.07 (m, 1H), 7.07 (d, 1H), 6.97 (m, 1H), 6.96 (m, 1H), 4.77 (t, 1H), 4.42/4.26 (d+d, 2H), 4.35 (s, 3H), 4.29/4.07 (m+m, 2H), 4.18 (t, 2H), 4.11/4.05 (d+d, 2H), 3.49 (s, 3H), 3.32/3.18 (dd+dd, 2H), 2.52 (s, 3H), 2.31 (s, 3H), 2.1-1.58 (m, 6H)

Step 7: Preparation of Example 73

Using General Procedure 12 starting from methyl[4,10,14-trimethyl-29,29-dioxo-17,23,28-trioxa-29$\lambda^6$-thia-1,12,13,14-tetraazahexacyclo[22.5.3.1$^{3,7}$0.1$^{9,16}$0.0$^{11,15}$0.0$^{27,31}$]tetratriaconta-3(34),4,6,9(33),10,12,15,24,26,31-decaen-8-yl]acetate (1 eq.) as a reactant, the title compound (white solid, 72% yield) was obtained.

The enantiopure products were obtained by chromatographic separation on chiral column.

EXAMPLE 73a (E1)

HRMS calculated for $C_{31}H_{34}N_4O_7S$: 606.2148; $[M+H]^+$ found: 607.2223 (δ=0.3 ppm).

EXAMPLE 73b (E2)

HRMS calculated for $C_{31}H_{34}N_4O_7S$: 606.2148; $[M+H]^+$ found: 607.2223 (δ=0.3 ppm).

$^1$H-NMR (500 MHz, DMSO-d6) δ ppm 7.4 (d, 1H), 7.19 (d, 1H), 7.13 (s, 1H), 7.06 (d, 1H), 7.02 (d, 1H), 6.99 (d, 1H), 6.96 (dd, 1H), 4.73 (t, 1H), 4.41/4.29 (d+d, 2H), 4.35 (s, 3H), 4.28/4.08 (m+m, 2H), 4.17 (t, 2H), 4.14/3.99 (d+d, 2H), 3.16/3.02 (dd+dd, 2H), 2.5 (s, 3H), 2.31 (s, 3H), 2/1.92 (m+m, 2H), 1.9/1.74 (m+m, 2H), 1.73/1.63 (m+m, 2H)

$^{13}$C-NMR (125 MHz, DMSO-d6) δ ppm: 173.5, 155.7, 148.3, 144.8, 143.6, 142.3, 137.6, 136.4, 132.8, 131.2, 129.9, 129.8, 123.9, 119.4, 118.1, 117.9, 117.6, 113.8, 107, 68.3, 68.1, 51.9, 49.8, 42.2, 41.7, 36.9, 27.4, 26.7, 21.1, 18.7, 12.8

EXAMPLE 74: 2-[4,31-Dimethyl-27,27-dioxo-21,26-dioxa-27$\lambda^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]-2-methylpropanoic acid enantiomer 1

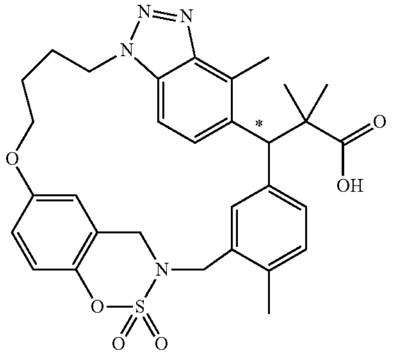

* = RorS

-continued enantiomer 2

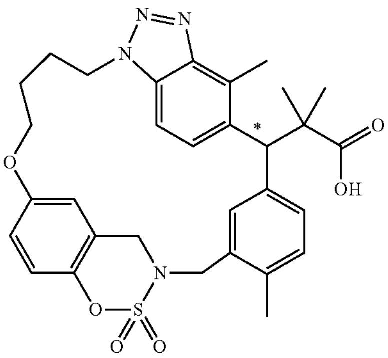

* = RorS

Step 1: Preparation of 2-[(5-bromo-2-methylphenyl)methoxy]oxane

To a solution of (5-bromo-2-methylphenyl)methanol (1 eq., 7.05 g, 35.1 mmol) in DCM (50 mL) at 0° C. 4-methylbenzene-1-sulfonic acid monohydrate (0.01 equiv., 0.07 g, 0.351 mmol) was added followed by addition of 3,4-dihydro-2H-pyran (1.1 equiv., 3.52 mL, 38.6 mmol). The reaction mixture was warmed to RT and stirred for 1 h before quenching with saturated $NaHCO_3$ (30 mL). The phases were separated. The aq. phase was extracted with DCM (30 mL), the combined organic phases were dried over $MgSO_4$ and filtered. The solvent was removed under reduced pressure to give the title compound (10 g, quant.).

$^1$H-NMR (500 MHz, DMSO-d6) δ ppm: 7.49 (d, 1H), 7.38 (dd, 1H), 7.15 (d, 1H), 4.7 (t, 1H), 4.66/4.42 (d+d, 2H), 3.77/3.49 (m+m, 2H), 2.22 (s, 3H), 1.82-1.41 (m, 6H)

Step 2: Preparation of 4-methyl-3-{[(oxan-2-yl)oxy]methyl}benzaldehyde

To a stirred solution of 2-[(5-bromo-2-methylphenyl)methoxy]oxane (1 eq., 5 g, 18 mmol) in THF (40 mL) N$^1$,N$^1$,N$^2$,N$^2$-tetramethylethane-1,2-diamine (1.5 eq., 3.1 g, 26 mmol) was added. The mixture was cooled to −75° C., butyllithium (1.5 eq., 26 mmol) was added dropwise and the mixture was stirred at −75° C. for further 30 min. DMF (2 eq., 2.6 g, 35 mmol) was added dropwise, the temperature was allowed to warm to RT and the mixture was stirred for further 1 h at Rt. After completion of the reaction the mixture was poured into 80 ml of water and extracted with EtOAc. The separated organic layer was dried over $MgSO_4$, filtered and evaporated to dryness. The crude oil was purified by normal phase silica gel chromatography using heptane-EtOAc (100:0 to 0:100) as an eluent to give the title compound (4 g, 97% yield).

$^1$H-NMR (500 MHz, DMSO-d6) δ ppm: 9.97 (s, 1H), 7.87 (d, 1H), 7.75 (dd, 1H), 7.42 (d, 1H), 4.76/4.51 (d+d, 2H), 4.73 (dd, 1H), 3.79/3.5 (m+m, 2H), 2.36 (s, 3H), 1.83-1.41 (m, 6H)

Step 3: Preparation of {1-[4-(benzyloxy)butyl]-4-methyl-1H-benzotriazol-5-yl}(4-methyl-3-{[(oxan-2-yl)oxy]methyl}phenyl)methanol 1-[4-(Benzyloxy)butyl]-5-bromo-4-methyl-1H-benzotriazole (1 eq., 1.04 g, 2.78 mmol) was dissolved in THF (40 mL) and $N^1$,$N^1$,$N^2$,$N^2$-tetramethylethane-1,2-diamine (1.5 eq., 484 mg, 4.17 mmol) was added. The mixture was cooled to −75° C., butyllithium (3 eq., 8.34 mmol) was added dropwise and the mixture was stirred at −75° C. for 30 min. 4-methyl-3-{[(oxan-2-yl)oxy]methyl}benzaldehyde (2 eq., 1.3 g, 5.5 mmol) dissolved in THF (10 mL) was added and the reaction mixture was stirred at RT for 2 h. After completion of the reaction the mixture was poured into 100 ml of water, extracted with 2×50 ml of EtOAc, the combined organic layer was dried over $MgSO_4$, filtered, evaporated under reduced pressure to dryness. The crude oil was purified by normal phase silica gel chromatography using heptane-EtOAc (100:0 to 0:100) as an eluent to give the title compound (0.4 g, 27% yield).

$^1$H-NMR (500 MHz, DMSO-d6) δ ppm: 7.61 (d, 1H), 7.59 (d, 1H), 7.35-7.23 (m, 5H), 7.25 (d, 1H), 7.17 (dd, 1H), 7.09 (d, 1H), 6.05 (d, 1H), 5.89 (d, 1H), 4.67 (t, 2H), 4.61/4.37 (d+d, 2H), 4.59 (dd, 1H), 4.4 (s, 2H), 3.67/3.37 (m+m, 2H), 3.42 (t, 2H), 2.67/2.66 (s, 3H), 2.21 (s, 3H), 1.94 (m, 2H), 1.7-1.3 (m, 6H), 1.49 (m, 2H)

Step 4: Preparation of methyl 3-{1-[4-(benzyloxy) butyl]-4-methyl-1H-benzotriazol-5-yl}-2,2-dimethyl-3-(4-methyl-3-{[(oxan-2-yl)oxy] methyl}phenyl)propanoate {1-[4-(Benzyloxy)butyl]-4-methyl-1H-benzotriazol-5-yl}(4-methyl-3-{[(oxan-2-yl)oxy]methyl}phenyl)methanol (1 eq., 4.04 g, 7.62 mmol) was dissolved in MeCN (50 mL) and 2,2,2-trichloroacetonitrile (2 eq., 2.2 g, 15.25 mmol) and 2,3,4,6,7,8,9,10-octahydropyrimido[1,2-a]azepine (0.05 eq., 58.06 mg, 0.38 mmol) were added. The mixture was stirred at RT for 45 min, then [(1-methoxy-2-methylprop-1-en-1-yl)oxy](trimethyl)silane (2.5 eq., 3.32 g, 19.07 mmol) and 1,1,1-trifluoro-N-(trifluoromethanesulfonyl)-methanesulfonamide (0.1 eq., 0.21 g, 0.76 mmol) were added. The reaction mixture was stirred at RT for 2 h. After completion of the reaction 40 ml of sat. aq. $NaHCO_3$ was added—and the layers were separated. The aq. layer was extracted with 2×50 mL of EtOAc, the combined organic layer was dried over $MgSO_4$, filtered and evaporated under reduced pressure to give the title compound (4.6 g, 98% yield).

$^1$H-NMR (500 MHz, DMSO-d6) δ ppm: 7.61-7.54 (d, 1H), 7.61-7.54 (d, 1H), 7.35-7.23 (m, 5H), 7.22 (d, 1H), 7.13 (dd, 1H), 7.06 (d, 1H), 4.77 (s, 1H), 4.66 (t, 2H), 4.58/4.38 (d+d, 2H), 4.57 (m, 1H), 4.4 (s, 2H), 3.67/3.35 (m+m, 2H), 3.43 (s, 3H), 3.42 (t, 2H), 2.7/2.69 (s, 3H), 2.19 (s, 3H), 1.94 (m, 2H), 1.75-1.31 (m, 6H), 1.52 (m, 2H), 1.3 (s, 3H), 1.23 (s, 3H)

Step 5: Preparation of methyl 3-{1-[4-(benzyloxy) butyl]-4-methyl-1H-benzotriazol-5-yl}-3-[3-(hydroxymethyl)-4-methylphenyl]-2,2-dimethylpropanoate Methyl 3-{11-[4-(benzyloxy)butyl]-4-methyl-1H-benzotriazol-5-yl}-2,2-dimethyl-3-(4-methyl-3-{[(oxan-2-yl)oxy] methyl}phenyl)propanoate (1 eq., 4.6 g, 7.49 mmol) was dissolved in MeOH (80 mL) and 4-methylbenzenesulfonic acid pyridine complex (0.05 eq., 94.2 mg, 0.375 mmol) was added. After stirring at 55° C. for 2 h the reaction mixture was cooled to RT, evaporated to dryness under reduced pressure, dissolved in DCM, extracted with 2×50 mL of sat. aq. $NaHCO_3$, then with 50 ml of brine. The organic layer was dried over $MgSO_4$, filtered and evaporated under reduced pressure to give the title compound (3.93 g, 99% yield).

$^1$H-NMR (500 MHz, DMSO-d6) δ ppm: 7.61 (d, 1H), 7.59 (d, 1H), 7.36-7.23 (m, 5H), 7.28 (d, 1H), 7.09 (dd, 1H), 7.01 (d, 1H), 5.01 (t, 1H), 4.76 (s, 1H), 4.66 (t, 2H), 4.41 (d, 2H), 4.4 (s, 2H), 3.43 (t, 2H), 3.42 (s, 3H), 2.7 (s, 3H), 2.15 (s, 3H), 1.95 (m, 2H), 1.52 (m, 2H), 1.3 (s, 3H), 1.24 (s, 3H)

Step 6: Preparation of methyl 3-{1-[4-(benzyloxy) butyl]-4-methyl-1H-benzotriazol-5-yl}-3-(3-{[6-(benzyloxy)-2,2-dioxo-2H-1,2λ$^6$,3-benzoxathiazin-3 (4H)-yl]methyl}-4-methylphenyl)-2,2-dimethylpropanoate Using General Procedure 7 starting from methyl 3-{1-[4-(benzyloxy)butyl]-4-methyl-1H-benzotriazol-5-yl}-3-[3-(hydroxymethyl)-4-methylphenyl]-2,2-dimethylpropanoate (1 eq.) and 6-(benzyloxy)-3,4-dihydro-2H-1,2λ$^6$,3-benzoxathiazine-2,2-dione (1 eq.) as reactants, the title compound (62% yield) was obtained.

$^1$H-NMR (500 MHz, DMSO-d6) δ ppm: 7.59 (d, 1H), 7.57 (d, 1H), 7.46 (dm, 2H), 7.41 (tm, 2H), 7.34 (tm, 1H), 7.3 (tm, 2H), 7.25 (tm, 1H), 7.25 (dm, 2H), 7.23 (d, 1H), 7.19 (dd, 1H), 7.14 (d, 1H), 7.12 (d, 1H), 7.08 (dd, 1H), 6.89 (d, 1H), 5.1 (s, 2H), 4.77 (s, 1H), 4.63 (t, 2H), 4.42 (s, 2H), 4.38 (s, 2H), 4.28/4.17 (d+d, 2H), 3.44 (s, 3H), 3.4 (t, 2H), 2.71 (s, 3H), 2.22 (s, 3H), 1.93 (m, 2H), 1.49 (m, 2H), 1.29/1.25 (s+s, 6H)

Step 7: Preparation of methyl 3-[1-(4-hydroxybutyl)-4-methyl-1H-benzotriazol-5-yl]-3-{3-[(6-hydroxy-2,2-dioxo-2H-1,2λ$^6$,3-benzoxathiazin-3 (4H)-yl)methyl]-4-methylphenyl}-2,2-dimethylpropanoate Using General Procedure 8 starting from methyl 3-{1-[4-(benzyloxy)butyl]-4-methyl-1H-benzotriazol-5-yl}-3-(3-{ [6-(benzyloxy)-2,2-dioxo-2H-1,2λ$^6$,3-benzoxathiazin-3 (4H)-yl]methyl}-4-methylphenyl)-2,2-dimethylpropanoate (1 eq.) as a reactant, the title compound (99% yield) was obtained.

$^1$H-NMR (500 MHz, DMSO-d6) δ ppm: 9.71 (s, 1H), 7.61 (m, 1H), 7.61 (m, 1H), 7.21 (d, 1H), 7.19 (dd, 1H), 7.13 (d, 1H), 7 (d, 1H), 6.8 (dd, 1H), 6.57 (d, 1H), 4.76 (s, 1H), 4.65 (t, 2H), 4.44 (brs, 1H), 4.37 (s, 2H), 4.26/4.15 (d+d, 2H), 3.45 (s, 3H), 3.39 (t, 2H), 2.71 (s, 3H), 2.23 (s, 3H), 1.91 (qn, 2H), 1.38 (qn, 2H), 1.3 (s, 3H), 1.25 (s, 3H)

Step 8: Preparation of methyl 3-[1-(4-chlorobutyl)-4-methyl-1H-benzotriazol-5-yl]-3-{3-[(6-hydroxy-2, 2-dioxo-2H-1,2λ$^6$,3-benzoxathiazin-3(4H)-yl) methyl]-4-methylphenyl}-2,2-dimethylpropanoate Using General Procedure 10 starting from methyl 3-[1-(4-hydroxybutyl)-4-methyl-1H-benzotriazol-5-yl]-3-{3-[(6-hydroxy-2,2-dioxo-2H-1,2)$^6$,3-benzoxathiazin-3(4H)-yl) methyl]-4-methylphenyl}-2,2-dimethylpropanoate (1 eq.) as a reactant, the title compound (98% yield) was obtained.

$^1$H-NMR (500 MHz, DMSO-d6) δ ppm: 9.6 (brs, 1H), 7.65 (d, 1H), 7.62 (d, 1H), 7.21 (d, 1H), 7.2 (dd, 1H), 7.13 (d, 1H), 7.01 (d, 1H), 6.81 (dd, 1H), 6.58 (d, 1H), 4.77 (s, 1H), 4.7 (t, 2H), 4.37 (s, 2H), 4.27/4.15 (d+d, 2H), 3.65 (t, 2H), 3.45 (s, 3H), 2.71 (s, 3H), 2.23 (s, 3H), 2.01 (qn, 2H), 1.71 (qn, 2H), 1.3 (s, 3H), 1.26 (s, 3H)

Step 9: Preparation of methyl 2-[4,31-dimethyl-27, 27-dioxo-21,26-dioxa-27λ$^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]-2-methylpropanoate Using General Procedure 11 starting from methyl 3-[1-(4-chlorobutyl)-4-methyl-1H-benzotriazol-5-yl]-3-{3-[(6- hydroxy-2,2-dioxo-2H-1,2)$^6$,3-benzoxathiazin-3(4H)-yl) methyl]-4-methylphenyl}-2,2-dimethylpropanoate (1 eq., 3.2 g, 4.99 mmol) as a reactant, the title compound (2.95 g, 97% yield) was obtained.

$^1$H-NMR (500 MHz, DMSO-d6) δ ppm: 7.6 (d, 1H), 7.5 (d, 1H), 7.38 (dd, 1H), 7.27 (d, 1H), 7.01 (d, 1H), 6.81 (dd, 1H), 6.67 (d, 1H), 5.85 (br., 1H), 4.81 (s, 1H), 4.8/4.73 (m+m, 2H), 4.35/3.84 (brd+brd, 2H), 4.08/3.65 (d+d, 2H), 3.7/3.43 (br+m, 2H), 3.43 (s, 3H), 2.63 (s, 3H), 2.33 (s, 3H), 2.21/2.06 (m+m, 2H), 1.84/1.64 (m+m, 2H), 1.27/1.13 (s+s, 6H)

Step 10: Preparation of Example 74

Using General Procedure 12 starting from methyl 2-[4,31-dimethyl-27,27-dioxo-21,26-dioxa-2726-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]-2-methylpropanoate as a reactant, the title compound was obtained.

The enantiopure products were obtained by chromatographic separation on chiral column.

EXAMPLE 74a (E1)

HRMS calculated for $C_{31}H_{34}N_4O_6S$: 590.2199; $[M+H]^+$ found: 591.2272 (δ=0.0 ppm).

EXAMPLE 74b (E2)

HRMS calculated for $C_{31}H_{34}N_4O_6S$: 590.2199; $[M+H]^+$ found: 591.2277 (δ=0.9 ppm).

$^1$H-NMR (500 MHz, DMSO-d6) δ ppm: 12.34 (brs, 1H), 7.61 (d, 1H), 7.53 (d, 1H), 7.46 (dd, 1H), 7.26 (d, 1H), 7 (d, 1H), 6.81 (dd, 1H), 6.61 (brs, 1H), 5.85 (brs, 1H), 4.84 (s, 1H), 4.79/4.73 (m+m, 2H), 4.27/3.87 (brd+brd, 2H), 4.06/3.71 (brd+brd, 2H), 3.71/3.43 (m+m, 2H), 2.62 (s, 3H), 2.33 (s, 3H), 2.22/2.08 (m+m, 2H), 1.83/1.64 (m+m, 2H), 1.25 (s, 3H), 1.07 (s, 3H)

$^{13}$C-NMR (125 MHz, DMSO-d6) δ ppm: 133.3, 130.9, 130.6, 128.3, 119.6, 117.6, 111.1, 107.2, 67.9, 52, 51.6, 48.7, 48.2, 26.6, 25.6, 25.3, 24.7, 18.5, 14.2

EXAMPLE 75: [24-Chloro-4,32-dimethyl-28,28-dioxo-19,22,27-trioxa-28λ$^6$-thia-1,14,15,16-tetraazahexacyclo[21.5.3.1$^{3,7}$0.1$^{9,13}$0.0$^{12,16}$0.0$^{26,30}$]tritriaconta-3(33),4,6,9(32),10,12,14,23,25,30-decaen-8-yl]acetic acid

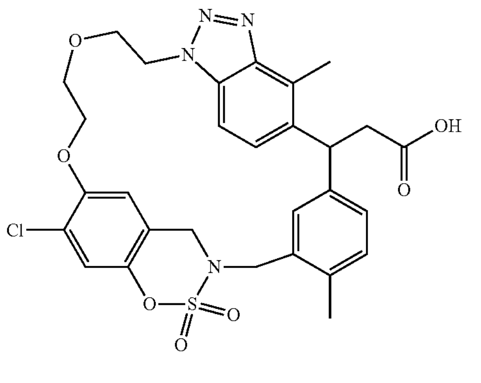 [SMILES: Cc1ccc2cc1CN1Cc3cc(c(Cl)cc3OS1(=O)=O)OCCOCCn1nnc3c(C)c(ccc31)C2CC(=O)O]

Step 1: Preparation of ethyl 3-(1-{2-[2-(benzyloxy) ethoxy]ethyl}-4-methyl-1H-benzotriazol-5-yl)-3-[3-(hydroxymethyl)-4-methylphenyl]propanoate Using General Procedure 6 starting from ethyl (2E)-3-(1-{2-[2-(benzyloxy)ethoxy]ethyl}-4-methyl-1H-benzotriazol-5-yl)prop-2-enoate (1 eq.) and [2-methyl-5-(4,4,5,5-tetramethyl-1,3,2-dioxaborolan-2-yl)phenyl]methanol (1.3 eq.) as reactants, the title compound (yellow oil, 71% yield) was obtained.

$^1$H-NMR (500 MHz, DMSO-d6) δ ppm: 7.61 (d, 1H), 7.4 (d, 1H), 7.33-7.17 (m, 5H), 7.26 (d, 1H), 7.08 (dd, 1H), 7.01 (d, 1H), 4.99 (t, 1H), 4.82 (t, 1H), 4.81 (t, 2H), 4.39 (d, 2H), 4.32 (s, 2H), 3.92 (q, 2H), 3.89 (t, 2H), 3.52 (m, 2H), 3.43 (m, 2H), 3.12/3.07 (dd+dd, 2H), 2.75 (s, 3H), 2.14 (s, 3H), 1.01 (t, 3H)

Step 2: Preparation of ethyl 3-(3-{[6-(benzyloxy)-7-chloro-2,2-dioxo-2H-1,2λ$^6$,3-benzoxathiazin-3(4H)-yl]methyl}-4-methylphenyl)-3-(1-{2-[2-(benzyloxy) ethoxy]ethyl}-4-methyl-1H-benzotriazol-5-yl) propanoate Using General Procedure 7 starting from ethyl 3-(1-{2-[2-(benzyloxy)ethoxy]ethyl}-4-methyl-1H-benzotriazol-5-yl)-3-[3-(hydroxymethyl)-4-methylphenyl]propanoate (1 eq.) and 6-(benzyloxy)-7-chloro-3,4-dihydro-2H-1,2λ$^6$,3-benzoxathiazine-2,2-dione (0.83 eq.) as reactants, the title compound (off-white solid, 95% yield) was obtained.

$^1$H-NMR (500 MHz, DMSO-d6) δ ppm: 7.6 (d, 1H), 7.51-7.13 (m, 10H), 7.46 (s, 1H), 7.43 (d, 1H), 7.26 (s, 1H), 7.25 (d, 1H), 7.17 (dd, 1H), 7.11 (d, 1H), 5.16 (s, 2H), 4.84 (t, 1H), 4.8 (t, 2H), 4.48/4.44 (d+d, 2H), 4.28 (s, 2H), 4.24/4.19 (d+d, 2H), 3.91 (q, 2H), 3.87 (t, 2H), 3.5 (m, 2H), 3.4 (m, 2H), 3.18/3.12 (dd+dd, 2H), 2.76 (s, 3H), 2.19 (s, 3H), 0.97 (t, 3H)

Step 3: Preparation of ethyl 3-{3-[(7-chloro-6-hydroxy-2,2-dioxo-2H-1,2λ$^6$,3-benzoxathiazin-3(4H)-yl)methyl]-4-methylphenyl}-3-{1-[2-(2-hydroxyethoxy)ethyl]-4-methyl-1H-benzotriazol-5-yl}propanoate Using General Procedure 8 starting from ethyl 3-(3-{[6-(benzyloxy)-7-chloro-2,2-dioxo-2H-1,2λ$^6$,3-benzoxathiazin-3(4H)-yl]methyl}-4-methylphenyl)-3-(1-{12-[2-(benzyloxy)ethoxy]ethyl}-4-methyl-1H-benzotriazol-5-yl) propanoate (1 eq.) as a reactant, the title compound (white solid foam, quant.) was obtained.

$^1$H-NMR (500 MHz, DMSO-d6) δ ppm: 10.48 (s, 1H), 7.62 (d, 1H), 7.5 (d, 1H), 7.31 (s, 1H), 7.28 (d, 1H), 7.18 (dd, 1H), 7.13 (d, 1H), 6.85 (s, 1H), 4.83 (t, 1H), 4.8 (t, 2H), 4.54 (m, 1H), 4.46/4.41 (d+d, 2H), 4.25/4.2 (d+d, 2H), 3.93 (q, 2H), 3.88 (t, 2H), 3.37 (m, 2H), 3.37 (m, 2H), 3.17 (d, 2H), 2.76 (s, 3H), 2.22 (s, 3H), 1 (t, 3H)

Step 4: Preparation of ethyl[24-chloro-4,32-dimethyl-28,28-dioxo-19,22,27-trioxa-28)$^6$-thia-1,14,15,16-tetraazahexacyclo[21.5.3.1$^{3,7}$0.1$^{9,13}$0.0$^{12,16}$0.0$^{26,30}$]tritriaconta-3(33),4,6,9(32),10,12,14,23,25,30-decaen-8-yl]acetate Ethyl 3-{3-[(7-chloro-6-hydroxy-2,2-dioxo-2H-1,2λ$^6$,3-benzoxathiazin-3(4H)-yl)methyl]-4-methylphenyl}-3-{11-[2-(2-hydroxyethoxy)ethyl]-4-methyl-1H-benzotriazol-5-yl}propanoate (1 eq., 855 mg, 1.3 mmol) was dissolved in THF (80 mL) and $PPh_3$ (3 eq., 1020 mg, 3.89 mmol) was added. DIAD (3 eq., 787 mg, 3.89 mmol) was added dropwise at RT and the mixture was stirred at RT for further 1.5 h. After completion of the reaction the solvent was evaporated, the crude product was purified via normal phase silica gel chromatography using heptane-AcOEt (100:0 to 35:65) as an eluent to give the title compound (white solid, quant.).

$^1$H-NMR (500 MHz, DMSO-d6) δ ppm: 7.65 (d, 1H), 7.46 (d, 1H), 7.42 (dd, 1H), 7.42 (s, 1H), 7.23 (d, 1H), 7.13 (d, 1H), 6.61 (s, 1H), 4.86 (m, 2H), 4.78 (t, 1H), 4.36/4.08 (d+d, 2H), 4.21/3.9 (d+d, 2H), 4.01/3.94 (m+m, 2H), 3.97/3.86 (m+m, 2H), 3.86 (q, 2H), 3.85/3.62 (m+m, 2H), 3.09/3.02 (dd+dd, 2H), 2.74 (s, 3H), 2.3 (s, 3H), 0.96 (t, 3H)

Step 5: Preparation of Example 75

Using General Procedure 12 starting from ethyl[24-chloro-4,32-dimethyl-28,28-dioxo-19,22,27-trioxa-2826-thia-1,14,15,16-tetraazahexacyclo[21.5.3.1$^{3,7}$0.1$^{9,13}$0.0$^{12,16}$0.0$^{26,30}$]tritriaconta-3(33),4,6,9(32),10,12,14,23,25,30-decaen-8-yl]acetate (1 eq.) as a reactant, the title compound (white solid, 93% yield) was obtained.

HRMS calculated for $C_{29}H_{29}ClN_4O_7S$: 612.1445; $[M+H]^+$ found: 613.1505 (δ=−2.2 ppm).

$^1$H-NMR (500 MHz, DMSO-d6) δ ppm: (m, 6H), 12.08 (brs., 1H), 7.65 (d, 1H), 7.45 (d, 1H), 7.43 (d, 1H), 7.42 (s, 1H), 7.23 (d, 1H), 7.1 (s, 1H), 6.6 (s, 1H), 4.86 (m, 2H), 4.76 (t, 1H), 4.35/4.1 (d+d, 2H), 4.2/3.9 (d+d, 2H), 2.95 (d, 2H), 2.74 (s, 3H), 2.31 (s, 3H)

$^{13}$C-NMR (125 MHz, DMSO-d6) δ ppm: 173.1, 131.2, 130.8, 129.4, 126.8, 119.8, 116, 108.9, 71.3/69.9/68.3, 52, 48.6, 48.4, 41.7, 41.1, 18.6, 13.4

EXAMPLE 76 [31-Chloro-4,32-dimethyl-28,28-dioxo-19,22,27-trioxa-28λ$^6$-thia-1,14,15,16-tetraazahexacyclo[21.5.3.1$^{3,7}$0.1$^{9,13}$0.0$^{12,16}$0.0$^{26,30}$]tritriaconta-3(33),4,6,9(32),10,12,14,23,25,30-decaen-8-yl]acetic acid enantiomer 1

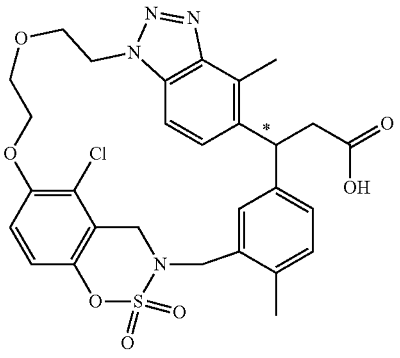

* = RorS

-continued enantiomer 2

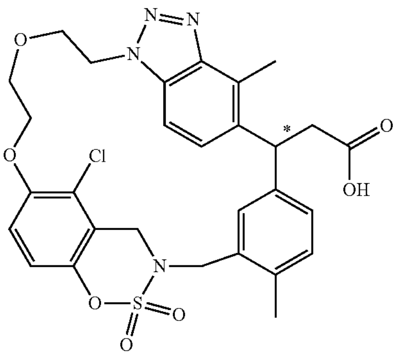

* = RorS

Step 1: Preparation of ethyl 3-(3-{[6-(benzyloxy)-5-chloro-2,2-dioxo-2H-1,2λ$^6$,3-benzoxathiazin-3(4H)-yl]methyl}-4-methylphenyl)-3-(1-{2-[2-(benzyloxy)ethoxy]ethyl}-4-methyl-1H-benzotriazol-5-yl)propanoate Using General Procedure 6 starting from ethyl (E)-3-[1-[2-(2-benzyloxyethoxy)ethyl]-4-methyl-benzotriazol-5-yl]prop-2-enoate (1 eq.) and 6-benzyloxy-5-chloro-3-[[2-methyl-5-(4,4,5,5-tetramethyl-1,3,2-dioxaborolan-2-yl)phenyl]methyl]-4H-1,2λ$^6$,3-benzoxathiazine 2,2-dioxide (1.2 eq.) as reactants, the title compound (white solid foam, 27% yield) was obtained.

$^1$H-NMR (500 MHz, DMSO-d6) δ ppm: 7.59 (d, 1H), 7.51-7.12 (m, 10H), 7.42 (d, 1H), 7.34 (d, 1H), 7.24 (d, 1H), 7.21 (dd, 1H), 7.21 (d, 1H), 7.14 (d, 1H), 5.25 (s, 2H), 4.83 (t, 1H), 4.78 (t, 2H), 4.4 (s, 2H), 4.28 (s, 2H), 4.24 (s, 2H), 3.9 (q, 2H), 3.87 (t, 2H), 3.5 (m, 2H), 3.4 (m, 2H), 3.12 (m, 2H), 2.75 (s, 3H), 2.23 (s, 3H), 0.98 (t, 3H)

Step 2: Preparation of ethyl 3-{3-[(5-chloro-6-hydroxy-2,2-dioxo-2H-1,2λ$^6$,3-benzoxathiazin-3(4H)-yl)methyl]-4-methylphenyl}-3-{1-[2-(2-hydroxyethoxy)ethyl]-4-methyl-1H-benzotriazol-5-yl}propanoate Using General Procedure 8 starting from ethyl 3-(3-{[6-(benzyloxy)-5-chloro-2,2-dioxo-2H-1,2λ$^6$,3-benzoxathiazin-3(4H)-yl]methyl}-4-methylphenyl)-3-(1-{12-[2-(benzyloxy)ethoxy]ethyl}-4-methyl-1H-benzotriazol-5-yl)propanoate (1 eq.) as a reactant, the title compound (white solid foam, quant.) was obtained.

$^1$H-NMR (500 MHz, DMSO-d6) δ ppm: 10.51 (s, 1H), 7.6 (d, 1H), 7.47 (d, 1H), 7.25 (d, 1H), 7.24 (dd, 1H), 7.16 (d, 1H), 7.05 (d, 1H), 7.02 (d, 1H), 4.84 (t, 1H), 4.8 (t, 2H), 4.54 (m, 1H), 4.37 (s, 2H), 4.24 (s, 2H), 3.92 (q, 2H), 3.88 (t, 2H), 3.38 (m, 2H), 3.38 (m, 2H), 3.15 (m, 2H), 2.76 (s, 3H), 2.24 (s, 3H), 1 (t, 3H)

Step 3: Preparation of ethyl[31-chloro-4,32-dimethyl-28,28-dioxo-19,22,27-trioxa-28λ$^6$-thia-1,14,15,16-tetraazahexacyclo[21.5.3.1$^{3,7}$0.1$^{9,13}$0.0$^{12,16}$0.0$^{26,30}$]tritriaconta-3(33),4,6,9(32),10,12,14,23,25,30-decaen-8-yl]acetate Ethyl 3-{3-[(5-chloro-6-hydroxy-2,2-dioxo-2H-1,2λ$^6$,3-benzoxathiazin-3(4H)-yl)methyl]-4-methylphenyl}-3-{11-

[2-(2-hydroxyethoxy)ethyl]-4-methyl-1H-benzotriazol-5-yl}propanoate (1 eq., 385 mg, 0.584 mmol) was dissolved in THF (10 mL) and $PPh_3$ (3 eq., 460 mg, 1.75 mmol) was added. DIAD (3 eq., 354 mg, 1.75 mmol) was added dropwise at RT and the mixture was stirred at this temperature for further 1.5 h. After completion of the reaction the solvent was evaporated, the crude product was purified via normal phase silica gel chromatography using heptane-AcOEt (100:0 to 35:65) as an eluent to give the title compound (white solid foam, 64% yield).

$^1$H-NMR (500 MHz, DMSO-d6) δ ppm: 7.59 (d, 1H), 7.47 (dd, 1H), 7.32 (d, 1H), 7.29 (d, 1H), 7.09 (d, 1H), 7.07 (d, 1H), 6.61 (d, 1H), 4.83 (m, 2H), 4.78 (t, 1H), 4.28/3.9 (d+d, 2H), 4.21/4.03 (d+d, 2H), 4.17-3.98 (m, 4H), 3.9 (m, 2H), 3.76 (m, 2H), 3.04/2.99 (dd+dd, 2H), 2.59 (s, 3H), 2.34 (s, 3H), 0.99 (t, 3H)

Step 4: Preparation of Example 76

Using General Procedure 12 starting from ethyl[31-chloro-4,32-dimethyl-28,28-dioxo-19,22,27-trioxa-28$\lambda^6$-thia-1,14,15,16-tetraazahexacyclo[21.5.3.$1^{3,7}$0.$1^{9,13}$0.$0^{12,16}$0.$0^{26,30}$]tritriaconta-3(33),4,6,9(32),10,12,14,23,25,30-decaen-8-yl]acetate (1 eq.) as a reactant, the title compound (white solid, 86% yield) was obtained.

The enantiopure products were obtained by chromatographic separation on chiral column.

EXAMPLE 76a (E1)

HRMS calculated for $C_{29}H_{29}ClN_4O_7S$: 612.1445; $[M+H]^+$ found: 613.1499 (δ=−3.1 ppm).

EXAMPLE 76b (E2)

HRMS calculated for $C_{29}H_{29}ClN_4O_7S$: 612.1445; $[M+H]^+$ found: 613. 1515 (δ=−0.5 ppm).

$^1$H-NMR (500 MHz, DMSO-d6) δ ppm: 11.83 (brs, 1H), 7.59 (d, 1H), 7.49 (dd, 1H), 7.33 (d, 1H), 7.29 (d, 1H), 7.1 (d, 1H), 7.07 (d, 1H), 6.58 (d, 1H), 4.85/4.8 (m+m, 2H), 4.75 (t, 1H), 4.26/3.89 (d+d, 2H), 4.2/4.03 (d+d, 2H), 4.14/4.09 (m+m, 2H), 4.09/4.01 (m+m, 2H), 3.77 (m, 2H), 2.88/2.82 (dd+dd, 2H), 2.58 (s, 3H), 2.34 (s, 3H)

$^{13}$C-NMR (125 MHz, DMSO-d6) δ ppm: 131.6, 130.7, 129.5, 126.8, 117.1, 114.4, 108.5, 69.5, 68.9, 68.3, 52.2, 48.8, 47.4, 42.1, 41.9, 18.5, 13.3

EXAMPLE 77: [4,29-Dimethyl-25,25-dioxo-19,24-dioxa-25$\lambda^6$-thia-1,14,15,16-tetraazahexacyclo [18.5.3.$1^{3,7}$0.$1^{9,13}$0.$0^{12,16}$0.$0^{23,27}$]triaconta-3(30),4,6,9(29),10,12,14,20,22,27-decaen-8-yl]acetic acid enantiomer 1

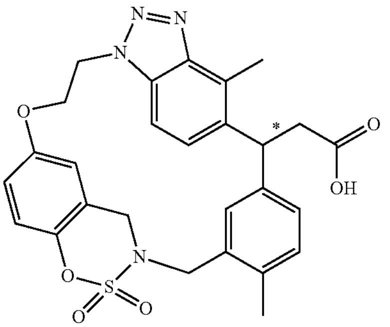

* = RorS

-continued enantiomer 2

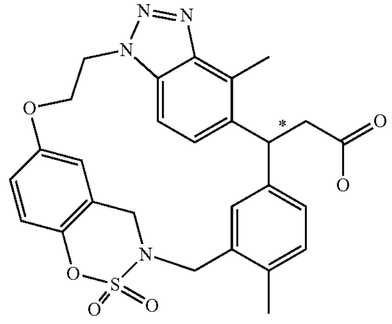

* = RorS

Step 1: Preparation of ethyl[4,29-dimethyl-25,25-dioxo-19,24-dioxa-25$\lambda^6$-thia-1,14,15,16-tetraazahexacyclo[18.5.3.$1^{3,7}$0.$1^{9,13}$0.$0^{12,16}$0.$0^{23,27}$]triaconta-3(30),4,6,9(29),10,12,14,20,22,27-decaen-8-yl]acetate Ethyl 3-{3-[(6-hydroxy-2,2-dioxo-2H-1,2$\lambda^6$,3-benzoxathiazin-3(4H)-yl)methyl]-4-methylphenyl}-3-[1-(2-hydroxyethyl)-4-methyl-1H-benzotriazol-5-yl]propanoate (1 eq., 320 mg, 0.5512 mmol) was dissolved in THF (60 mL) and $PPh_3$ (2 eq., 289 mg, 1.10 mmol) was added. DIAD (2 eq., 0.217 mL, 222.86 mg, 1.1 mmol) was added to the stirred solution and the reaction mixture was stirred at 70° C. for 2 h. The mixture was concentrated under reduced pressure and the residue was purified by reversed-phase chromatography using 5 mM aq.

$NH_4HCO_3$-MeCN gradient elution to give the title compound (230 mg, 74% yield) as a white solid foam.

$^1$H-NMR (500 MHz, DMSO-d6) δ ppm: 7.79 (d, 1H), 7.51 (dd, 1H), 7.36 (d, 1H), 7.3 (d, 1H), 6.92 (d, 1H), 6.87 (dd, 1H), 5.89 (d, 1H), 5.88 (d, 1H), 5.15/5.04 (m+m, 2H), 4.79 (dd, 1H), 4.68/4.33 (m+m, 2H), 4.15/3.54 (d+d, 2H), 3.98/3.69 (d+d, 2H), 3.94/3.91 (m+m, 2H), 3.43/3.04 (dd+dd, 2H), 2.61 (s, 3H), 2.29 (s, 3H), 0.99 (t, 3H)

Step 2: Preparation of Example 77

Using General Procedure 12 starting from ethyl[4,29-dimethyl-25,25-dioxo-19,24-dioxa-25$\lambda^6$-thia-1,14,15,16-tetraazahexacyclo[18.5.3.$1^{3,7}$0.$1^{9,13}$0.$0^{12,16}$0.$0^{23,27}$]triaconta-3(30),4,6,9(29),10,12,14,20,22,27-decaen-8-yl] acetate (1 eq., 265 mg, 0.4710 mmol) as a reactant, gave the title compound (175 mg, 69% yield).

The enantiopure products were obtained by chromatographic separation on chiral column.

EXAMPLE 77a (E1)

HRMS calculated for $C_{27}H_{26}N_4O_6S$: 534.1573; $[M+H]^+$ found: 535.1646 (δ=0.0 ppm).

EXAMPLE 77b (E2)

HRMS calculated for $C_{27}H_{26}N_4O_6S$: 534.1573; $[M+H]^+$ found: 535.1646 (δ=0.0 ppm).

$^1$H-NMR (500 MHz, DMSO-d6) δ ppm: 12.21 (brs, 1H), 7.79 (d, 1H), 7.51 (dd, 1H), 7.34 (d, 1H), 7.3 (d, 1H), 6.92 (d, 1H), 6.87 (dd, 1H), 5.88 (d, 1H), 5.88 (d, 1H), 5.15/5.03

(m+m, 2H), 4.77 (t, 1H), 4.67/4.34 (m+m, 2H), 4.14/3.55 (d+d, 2H), 3.97/3.7 (d+d, 2H), 3.31/2.94 (dd+dd, 2H), 2.6 (s, 3H), 2.29 (s, 3H)

$^{13}$C-NMR (125 MHz, DMSO-d6) δ ppm: 132.2, 131.2, 127.8, 127.1, 118.9, 116.4, 115.7, 109.8, 69.8, 51.6, 49.2, 48, 40.1, 40, 18.1, 13.1

EXAMPLE 78: [4,32-Dimethyl-28,28-dioxo-19,22,27-trioxa-28λ$^6$-thia-1,14,15,16-tetraazahexacyclo[21.5.3.1$^{3,7}$0.1$^{9,13}$0.0$^{12,16}$0.0$^{26,30}$]tritriaconta-3(33),4,6,9(32),10,12,14,23,25,30-decaen-8-yl]acetic acid enantiomer 1

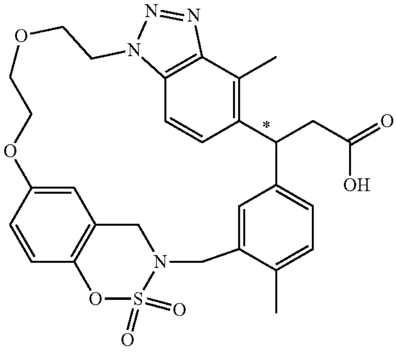

* = RorS enantiomer 2

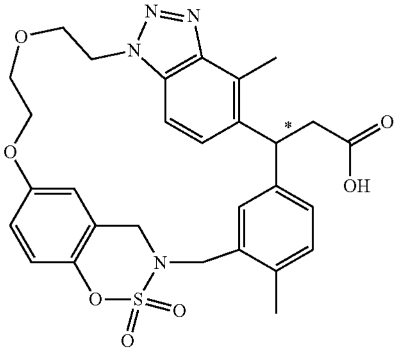

* = RorS

Step 1: Preparation of ethyl 3-(3-{[6-(benzyloxy)-2,2-dioxo-2H-1,2λ$^6$,3-benzoxathiazin-3(4H)-yl]methyl}-4-methylphenyl)-3-(1-{2-[2-(benzyloxy)ethoxy]ethyl}-4-methyl-1H-benzotriazol-5-yl)propanoate Using General Procedure 7 starting from ethyl 3-(1-{2-[2-(benzyloxy)ethoxy]ethyl}-4-methyl-1H-benzotriazol-5-yl)-3-[3-(hydroxymethyl)-4-methylphenyl]propanoate (1 eq., 2.19 g, 4.12 mmol) and 6-(benzyloxy)-3,4-dihydro-2H-1,2λ$^6$,3-benzoxathiazine-2,2-dione (1.2 eq., 1.44 g, 4.94 mmol) as reactants, the title compound (2.604 g, 79% yield) was obtained.

$^1$H-NMR (500 MHz, DMSO-d6) δ ppm: (m, 5H), (m, 5H), 7.6 (d, 1H), 7.43 (d, 1H), 7.21 (d, 1H), 7.16 (dd, 1H), 7.14 (d, 1H), 7.11 (d, 1H), 7.07 (dd, 1H), 6.95 (d, 1H), 5.1 (s, 2H), 4.83 (t, 1H), 4.78 (t, 2H), 4.43/4.39 (d+d, 2H), 4.28 (s, 2H), 4.21/4.18 (d+d, 2H), 3.91 (q, 2H), 3.86 (t, 2H), 3.49 (m, 2H), 3.4 (m, 2H), 3.17/3.11 (dd+dd, 2H), 2.75 (s, 3H), 2.2 (s, 3H), 0.98 (t, 3H)

Step 2: Preparation of ethyl 3-{3-[(6-hydroxy-2,2-dioxo-2H-1,2λ$^6$,3-benzoxathiazin-3(4H)-yl)methyl]-4-methylphenyl}-3-{1-[2-(2-hydroxyethoxy)ethyl]-4-methyl-1H-benzotriazol-5-yl}propanoate Using General Procedure 8 starting from ethyl 3-(3-{[6-(benzyloxy)-2,2-dioxo-2H-1,2λ$^6$,3-benzoxathiazin-3(4H)-yl]methyl}-4-methylphenyl)-3-(1-{12-[2-(benzyloxy)ethoxy]ethyl}-4-methyl-1H-benzotriazol-5-yl)propanoate (1 eq., 2.60 mg, 3.23 mmol) as a reactant, the title compound (2.604 g, 79% yield) was obtained.

$^1$H-NMR (500 MHz, DMSO-d6) δ ppm: 9.71 (s, 1H), 7.63 (d, 1H), 7.49 (d, 1H), 7.23 (d, 1H), 7.19 (dd, 1H), 7.13 (d, 1H), 6.99 (d, 1H), 6.79 (dd, 1H), 6.61 (d, 1H), 4.84 (t, 1H), 4.8 (t, 2H), 4.54 (m, 1H), 4.4/4.36 (d+d, 2H), 4.22/4.17 (d+d, 2H), 3.94 (q, 2H), 3.88 (t, 2H), 3.38 (m, 2H), 3.37 (m, 2H), 3.17 (m, 2H), 2.76 (s, 3H), 2.22 (s, 3H), 1.01 (t, 3H)

Step 3: Preparation of ethyl[4,32-dimethyl-28,28-dioxo-19,22,27-trioxa-28λ$^6$-thia-1,14,15,16-tetraazahexacyclo[21.5.3.1$^{3,7}$0.1$^{9,13}$0.0$^{12,16}$0.0$^{26,30}$]tritriaconta-3(33),4,6,9(32),10,12,14,23,25,30-decaen-8-yl]acetate Using General Procedure 7 starting from ethyl 3-{3-[(6-hydroxy-2,2-dioxo-2H-1,2λ$^6$,3-benzoxathiazin-3(4H)-yl)methyl]-4-methylphenyl}-3-{11-[2-(2-hydroxyethoxy)ethyl]-4-methyl-1H-benzotriazol-5-yl}propanoate (1 eq., 2.10 mg, 3.36 mmol) as a reactant in 120 mL/mmol THF, the title compound (1.65 g, 81% yield) was obtained.

$^1$H-NMR (500 MHz, DMSO-d6) δ ppm: (m, 6H), 7.73 (d, 1H), 7.44 (d, 1H), 7.43 (dd, 1H), 7.25 (d, 1H), 7.06 (d, 1H), 6.92 (dd, 1H), 6.81 (d, 1H), 6.46 (d, 1H), 4.84 (m, 2H), 4.81 (t, 1H), 4.27/4.06 (d+d, 2H), 4.15/4.07 (d+d, 2H), 3.88 (q, 2H), 3.08/3.03 (dd+dd, 2H), 2.67 (s, 3H), 2.32 (s, 3H), 0.97 (t, 3H)

Step 4: Preparation of Example 78

Using General Procedure 12 starting from ethyl[4,32-dimethyl-28,28-dioxo-19,22,27-trioxa-28λ$^6$-thia-1,14,15,16-tetraazahexacyclo[21.5.3.1$^{3,7}$0.1$^{9,13}$0.0$^{12,16}$0.0$^{26,30}$]tritriaconta-3(33),4,6,9(32),10,12,14,23,25,30-decaen-8-yl]acetate (1 eq., 1.645 g, 2.72 mmol) as a reactant, the title compound was obtained (83% yield).

The enantiopure products were obtained by chromatographic separation on chiral column.

EXAMPLE 78a (E1)

HRMS calculated for $C_{29}H_{30}N_4O_7S$: 578.1835; $[M+H]^+$ found: 579.1915 (δ=1.2 ppm).

EXAMPLE 78b (E2)

HRMS calculated for $C_{29}H_{30}N_4O_7S$: 578.1835; $[M+H]^+$ found: 579.1917 (δ=1.6 ppm).

$^1$H-NMR (500 MHz, DMSO-d6) δ ppm: 12.28 (brs, 1H), 7.72 (d, 1H), 7.43 (dd, 1H), 7.42 (d, 1H), 7.25 (d, 1H), 7.06 (d, 1H), 6.92 (dd, 1H), 6.78 (d, 1H), 6.44 (d, 1H), 4.85/4.82 (m+m, 2H), 4.79 (t, 1H), 4.25/4.05 (d+d, 2H), 4.15/4.06 (d+d, 2H), 4.03/3.98 (m+m, 2H), 4 (m, 2H), 3.8/3.74 (m+m, 2H), 2.93 (d, 2H), 2.66 (s, 3H), 2.32 (s, 3H)

$^{13}$C-NMR (125 MHz, DMSO-d6) δ ppm: 131.4, 130.7, 129.4, 127.2, 118.9, 115.3, 114.7, 109, 69.8, 68.5, 68.4, 51.8, 49, 48.4, 41.8, 41.7, 18.5, 13.3

EXAMPLE 79: 2-[(8R)-4,31-Dimethyl-27,27-dioxo-21,26-dioxa-27$\lambda^6$-thia-1,14,15,16-tetraazahexacyclo[20.5.3.$1^{3,7}$0.$1^{9,13}$0.$0^{12,16}$0.$0^{25,29}$]dotriaconta-3(32),4,6,9(31),10,12,14,22,24,29-decaen-8-yl]-N-(pyrimidin-5-yl)acetamide and 2-[(8S)-4,31-dimethyl-27,27-dioxo-21,26-dioxa-27$\lambda^6$-thia-1,14,15,16-tetraazahexacyclo[20.5.3.$1^{3,7}$0.$1^{9,13}$0.$0^{12,16}$0.$0^{25,29}$]dotriaconta-3(32),4,6,9(31),10,12,14,22,24,29-decaen-8-yl]-N-(pyrimidin-5-yl)acetamide

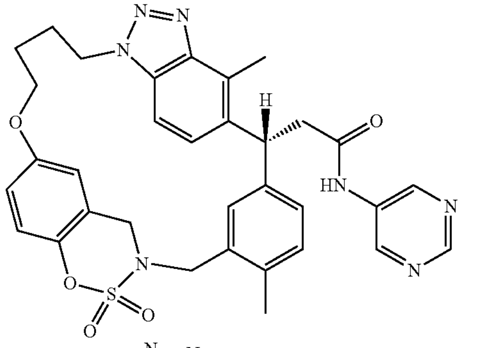

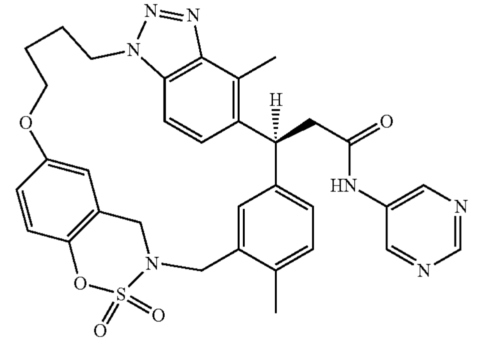

To a stirred solution of [(8R)-4,31-dimethyl-27,27-dioxo-21,26-dioxa-27$\lambda^6$-thia-1,14,15,16-tetraazahexacyclo[20.5.3.$1^{3,7}$0.$1^{9,13}$0.$0^{12,16}$0.$0^{25,29}$]dotriaconta-3(32),4,6,9(31),10,12,14,22,24,29-decaen-8-yl]acetic acid or [(8S)-4,31-dimethyl-27,27-dioxo-21,26-dioxa-27$\lambda^6$-thia-1,14,15,16-tetraazahexacyclo[20.5.3.$1^{3,7}$0.$1^{9,13}$0.$0^{12,16}$0.$0^{25,29}$]dotriaconta-3(32),4,6,9(31),10,12,14,22,24,29-decaen-8-yl]acetic acid (1 eq., 250 mg, 0.444 mmol) in dry DMF (3 mL) 1-[bis(dimethylamino)methylene]-1H-1,2,3-triazolo[4,5-b]pyridinium 3-oxide hexafluorophosphate (1.48 eq., 250 mg, 0.657 mmol) and DIPEA (3.2 eq., 0.25 mL, 1.4 mmol) were added at RT. The mixture was stirred at RT for 3 min, then pyrimidin-5-amine (2.37 eq., 100 mg, 1.05 mmol) was added and the mixture was stirred overnight at RT. After completion of the reaction the mixture was filtered, the filtrate was diluted with DMF and purified by reversed-phase chromatography using aq. 25 mM $NH_4HCO_3$ solution-MeCN as eluents to give the title compound (white solids, 48% yield).

EXAMPLE 79a (8R)

HRMS calculated for $C_{33}H_{33}N_7O_5S$: 639.2264; $[M+H]^+$ found: 640.2335 (δ=−0.3 ppm).

EXAMPLE 79b (8S)

HRMS calculated for $C_{33}H_{33}N_7O_5S$: 639.2264; $[M+H]^+$ found: 640.2332 (δ=−0.7 ppm).

$^1$H-NMR (500 MHz, DMSO-d6) δ ppm: 10.45 (s, 1H), 8.88 (s, 2H), 8.83 (s, 1H), 7.68 (d, 1H), 7.52 (dd, 1H), 7.43 (d, 1H), 7.31 (d, 1H), 7 (d, 1H), 6.8 (dd, 1H), 6.54 (d, 1H), 5.82 (d, 1H), 4.94 (t, 1H), 4.78/4.73 (m+m, 2H), 4.11/3.98 (d+d, 2H), 3.99/3.87 (d+d, 2H), 3.61/3.4 (m+m, 2H), 3.24/3.11 (dd+dd, 2H), 2.63 (s, 3H), 2.33 (s, 3H), 2.2/2.08 (m+m, 2H), 1.82/1.62 (m+m, 2H)

$^{13}$C-NMR (125 MHz, DMSO-d6) δ ppm: 153.5, 147.4, 131.5, 131.3, 128.4, 127.4, 119.6, 117.5, 111.2, 108.1, 67.9, 51.9, 48.8, 48.3, 42.7, 41.7, 26.7, 25.5, 18.5, 13.5

EXAMPLE 80: 2-[(8S)-4,31-Dimethyl-27,27-dioxo-21,26-dioxa-27$\lambda^6$-thia-1,14,15,16-tetraazahexacyclo[20.5.3.$1^{3,7}$0.$1^{9,13}$0.$0^{12,16}$0.$0^{25,29}$]dotriaconta-3(32),4,6,9(31),10,12,14,22,24,29-decaen-8-yl]-N-(pyridin-3-yl)acetamide and 2-[(8R)-4,31-dimethyl-27,27-dioxo-21,26-dioxa-27$\lambda^6$-thia-1,14,15,16-tetraazahexacyclo[20.5.3.$1^{3,7}$0.$1^{9,13}$0.$0^{12,16}$0.$0^{25,29}$]dotriaconta-3(32),4,6,9(31),10,12,14,22,24,29-decaen-8-yl]-N-(pyridin-3-yl)acetamide

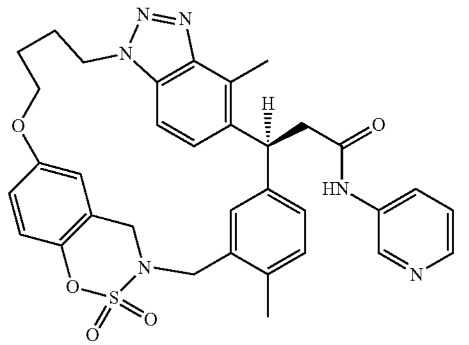

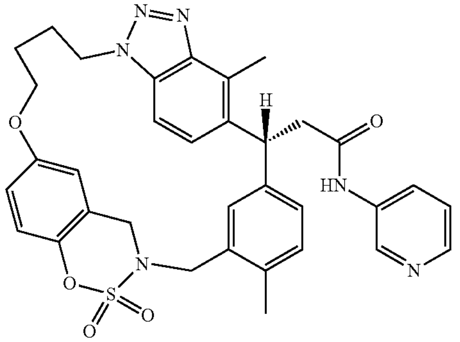

To a stirred solution of [(8S)-4,31-dimethyl-27,27-dioxo-21,26-dioxa-27$\lambda^6$-thia-1,14,15,16-tetraazahexacyclo[20.5.3.$1^{3,7}$0.$1^{9,13}$0.$0^{12,16}$0.$0^{25,29}$]dotriaconta-3(32),4,6,9(31),10,12,14,22,24,29-decaen-8-yl]acetic acid or [(8R)-4,31-dimethyl-27,27-dioxo-21,26-dioxa-27$\lambda^6$-thia-1,14,15,16-tetraazahexacyclo[20.5.3.$1^{3,7}$0.$1^{9,13}$0.$0^{12,16}$0.$0^{25,29}$]dotriaconta-3(32),4,6,9(31),10,12,14,22,24,29-decaen-8-yl]acetic acid (1 eq., 250 mg, 0.444 mmol) in dry DMF (3 mL) 1-[bis(dimethylamino)methylene]-1H-1,2λ6,3-triazolo[4,5-b]pyridinium 3-oxide hexafluorophosphate (1.48 eq., 250 mg, 0.657 mmol) and DIPEA (3.2 eq., 0.25 mL, 1.4 mmol) were added at RT. The mixture was stirred at RT for 3 min, then pyridin-3-amine (2.39 eq., 100 mg, 1.06 mmol) was added and the mixture was stirred overnight at RT. After completion of the reaction the mixture was filtered, the filtrate was diluted with DMF and purified by reversed-phase chromatography using aq. 25 mM $NH_4HCO_3$ solution-MeCN as eluents to give the title compound (white solids, 44% yield).

EXAMPLE 80a (8S)

HRMS calculated for $C_{34}H_{34}N_6O_5S$: 638.2311; $[M+H]^+$ found: 639.2382 (δ=−0.3 ppm).

EXAMPLE 80b (8R)

HRMS calculated for $C_{34}H_{34}N_6O_5S$: 638.2311; $[M+H]^+$ found: 639.2381 (δ=−0.5 ppm).

$^1$H-NMR (500 MHz, DMSO-d6) δ ppm: 10.22 (s, 1H), 8.6 (s, 1H), 8.2 (dd, 1H), 7.91 (dm, 1H), 7.68 (d, 1H), 7.53 (dd, 1H), 7.42 (d, 1H), 7.31 (d, 1H), 7.27 (m, 1H), 7 (d, 1H), 6.8 (dd, 1H), 6.53 (d, 1H), 5.83 (d, 1H), 4.94 (t, 1H), 4.77/4.74 (m+m, 2H), 4.1/3.98 (d+d, 2H), 3.99/3.88 (d+d, 2H), 3.62/3.41 (m+m, 2H), 3.21/3.08 (dd+dd, 2H), 2.63 (s, 3H), 2.33 (s, 3H), 2.2/2.07 (m+m, 2H), 1.82/1.62 (m+m, 2H)

$^{13}$C-NMR (125 MHz, DMSO-d6) δ ppm 144.6, 141, 131.4, 131.3, 128.4, 127.4, 126.4, 124.1, 119.5, 117.5, 111.2, 108, 67.8, 51.9, 48.8, 48.3, 42.8, 41.7, 26.7, 25.5, 18.5, 13.4

EXAMPLE 81: 2-[4,31-Dimethyl-27,27-dioxido-21,26-dioxa-27-thia-1,14,15,16-tetraazahexacyclo $[20.5.3.1^{3,7}0.1^{9,13}0.0^{12,16}0.0^{25,29}]$dotriaconta-3(32),4,6,9(31),10,12,14,22,24,29-decaen-8-yl]-2-methyl-N-(pyrimidin-5-yl)propanamide enantiomer 1

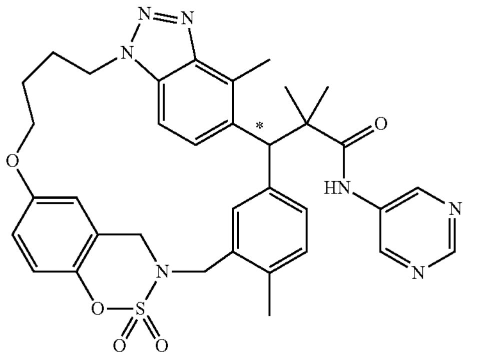

* = RorS enantiomer 2

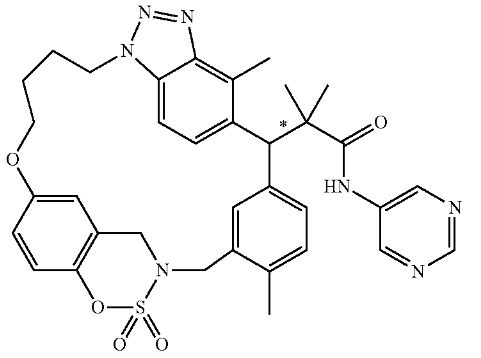

* = RorS

The stirred solution of 2-[4,31-dimethyl-27,27-dioxido-21,26-dioxa-27-thia-1,14,15,16-tetraazahexacyclo $[20.5.3.1^{3,7}0.1^{9,13}0.0^{12,16}0.0^{25,29}]$dotriaconta-3(32),4,6,9(31),10,12,14,22,24,29-decaen-8-yl]-2-methylpropanoic acid E1 (1 eq., 261 mg, 0.442 mmol) or E2 (1 eq.) in thionyl chloride (310 eq., 16.3 g, 10 mL, 0.137 mol) was heated under $N_2$ atmosphere at 80° C. for 1 day. After completion of the reaction, the mixture was evaporated to dryness and used without further purification. The crude acyl chloride was dissolved in THF (5 mL), then DIPEA (44 mg, 0.442 mmol) and pyrimidin-5-amine (42 mg, 0.442 mmol) were added and the mixture was stirred overnight at RT. After completion of the reaction the mixture was purified directly by reversed-phase chromatography using aq. 5 mM $NH_4HCO_3$ solution-MeCN as eluents to give the title compound (white solids, 14%-15% yields respectively).

EXAMPLE 81a (E1)

HRMS calculated for $C_{35}H_{37}N_7O_5S$: 667.2577; $[M+H]^+$ found: 668.2657 (δ=1.1 ppm).

EXAMPLE 81b (E2)

HRMS calculated for $C_{35}H_{37}N_7O_5S$: 667.2577; $[M+H]^+$ found: 668.2654 (δ=0.7 ppm).

$^1$H-NMR (500 MHz, DMSO-d6) δ ppm: 9.71 (brs., 1H), 8.81 (s, 1H), 8.76 (s, 2H), 7.63 (d, 1H), 7.57 (d, 1H), 7.46 (brd., 1H), 7.29 (d, 1H), 7.01 (d, 1H), 6.81 (dd, 1H), 6.67 (brs., 1H), 5.75 (brs., 1H), 5.03 (s, 1H), 4.76/4.7 (dm+dm, 2H), 4.43/3.75 (brd+brd, 2H), 4.13/3.57 (brd+brd, 2H), 3.66/3.35 (br+m, 2H), 2.65 (brs., 3H), 2.34 (s, 3H), 2.18/2.06 (m+m, 2H), 1.83/1.67 (m+m, 2H), 1.38/1.23 (s+s, 6H)

$^{13}$C-NMR (125 MHz, DMSO-d6) δ ppm: 176.9, 153.8, 149, 133.2, 131.2, 130.8, 128, 119.6, 117.7, 110.8, 107, 67.9, 52, 52, 48.8, 48.2, 47, 26.8, 26.2/24.1, 25.6, 18.5, 14.2

EXAMPLE 82: 2-[4,31-Dimethyl-27,27-dioxo-21,26-dioxa-27$\lambda^6$-thia-1,14,15,16-tetraazahexacyclo $[20.5.3.1^{3,7}0.1^{9,13}0.0^{12,16}0.0^{25,29}]$dotriaconta-3(32),4,6,9(31),10,12,14,22,24,29-decaen-8-yl]-2-methyl-N-(pyridin-3-yl)propanamide enantiomer 1

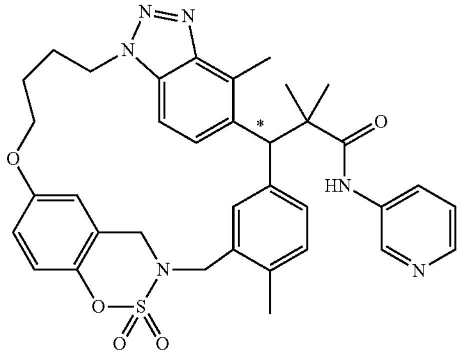

* = RorS

-continued enantiomer 2

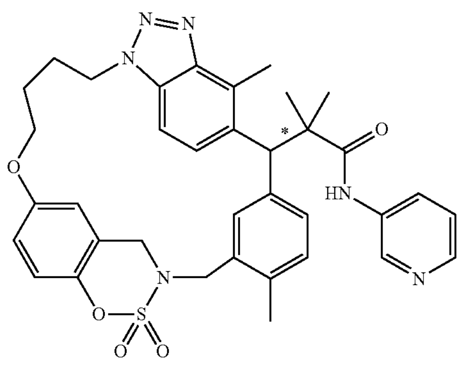

* = RorS

The stirred solution of 2-[4,31-dimethyl-27,27-dioxo-21,26-dioxa-27$\lambda^6$-thia-1,14,15,16-tetraazahexacyclo[20.5.3.1$^{3,7}$0.1$^{9,13}$0.0$^{12,16}$0.0$^{25,29}$]dotriaconta-3(32),4,6,9(31),10,12,14,22,24,29-decaen-8-yl]-2-methylpropanoic acid E1 (1 eq., 261 mg, 0.442 mmol) or E2 (1 eq.) in thionyl chloride (310 eq., 16.3 g, 10 mL, 0.137 mol) was heated under $N_2$ atmosphere at 80° C. for 1 day. After completion of the reaction, the mixture was evaporated to dryness and used without further purification. The crude acyl chloride was dissolved in THF (5 mL), then DIPEA (44 mg, 0.442 mmol) and pyridin-3-amine (42 mg, 0.443 mmol) were added and the mixture was stirred overnight at RT. After completion of the reaction the mixture was purified directly by reversed-phase chromatography using aq. 5 mM $NH_4HCO_3$ solution-MeCN eluents to give the title compound (white solids, 41%-46% yields respectively).

EXAMPLE 82a (E1)

HRMS calculated for $C_{36}H_{38}N_6O_5S$: 666.2625; $[M+H]^+$ found: 667.2697 (δ=0.0 ppm).

EXAMPLE 82b (E2)

HRMS calculated for $C_{36}H_{38}N_6O_5S$: 666.2625; $[M+H]^+$ found: 667.2700 (δ=0.4 ppm).

$^1$H-NMR (500 MHz, DMSO-d6) δ ppm: 9.48 (s, 1H), 8.51 (d, 1H), 8.18 (d, 1H), 7.75 (d, 1H), 7.63 (d, 1H), 7.57 (d, 1H), 7.47 (d, 1H), 7.29 (d, 1H), 7.24 (dd, 1H), 7.01 (d, 1H), 6.81 (dd, 1H), 6.65 (br, 1H), 5.74 (br, 1H), 5.05 (s, 1H), 4.75/4.71 (m+m, 2H), 4.43/3.74 (d+d, 2H), 4.13/3.57 (d+d, 2H), 3.66/3.34 (m+m, 2H), 2.65 (s, 3H), 2.34 (s, 3H), 2.18/2.07 (m+m, 2H), 1.83/1.67 (m+m, 2H), 1.37 (s, 3H), 1.22 (s, 3H) $^{13}$C-NMR (125 MHz, DMSO-d6) δ ppm: 176.4, 156, 146.6, 144.9, 144.6, 142.8, 139.4, 136.4, 135.9, 135.6, 133.3, 131.8, 131.8, 131.2, 130.7, 128.7, 128.3, 128.1, 123.8, 119.6, 117.7, 117.1, 110.8, 107, 67.9, 52.1, 51.8, 48.8, 48.2, 46.9, 26.8, 26.3, 25.6, 24, 18.6, 14.2

EXAMPLE 83: HEPG2—GENE REPORTER ASSAY

Nrf2 transcription factor will activate protective genes from oxidative damage through the binding on the Antioxidant Response Elements (ARE). We used the transfection factor property of Nrf2 to develop a gene reporter assay, based on the activation of the betalactamase reporter gene under the control of the ARE and Nrf2 activation.

The CellSensor® ARE-bla HepG2 cell line (Ref.K1208, Invitrogen) containing a beta-lactamase reporter gene under control of the Antioxidant Response Element (ARE) was stably integrated into HepG2 cells.

CellSensor® ARE-bla HepG2 cells were grown to confluence in DMEM GlutaMAX™ (Ref.61965-026, Thermo Fisher), 10% dialyzed FBS (Ref.P30-193306, PanBiotech), 12 mM Hepes (Ref.15630-056, Gibco), 0.1 mM Non-Essential Amino Acid (NEAA) Cell Culture Supplement (Ref.11140-35, Gibco), 1% Na-pyruvate (Ref.S8636, Sigma), 2.5 μg/ml Blasticidine (Ref.210-01, Invitrogen), 1% Pénicilline/streptomycine (15070-063, Gibco) in collagen I (50 μg/mL, Ref.A10483-1, Life Technologies) coated flasks, 37° C., 5% $CO_2$. Eighteen hours before the experiment, cells were harvested using Tryple Xpress (Ref.126905, Bibco) for 10 min at 37° C., resuspended in DMEM GlutaMAX™ (Ref.61965-026, Thermo Fisher), 1% dialyzed FBS (Ref.P30-193306, PanBiotech), 25 mM Hepes (Ref.15630-056, Gibco), 0.1 mM NEAA (Ref.11140-35, Gibco), 1% Na-pyruvate (Ref.S8636, Sigma), 2.5 μg/ml Blasticidine (Ref.210-01, Invitrogen), 1% Pénicilline/streptomycine (15070-063, Gibco) then plated into 384 wells Cell culture microclear plates (Ref.781091, Greiner) at the density of 30 000 cells/well in 32 μl. Cell are stored at 37° C., 5% $CO_2$ until used.

Compounds in 100% DMSO (0.315 μl/well) were resuspended in 20 μl DMEM GlutaMAX™, 1% dialyzed FBS, 25 mM Hepes, 0.1 mM NEAA, 1% Na-pyruvate (Ref.S8636, Sigma), 2.5 μg/ml Blasticidine, 3.4% DMSO, 1% Pénicilline/streptomycine (15070-063, Gibco)). Compounds and andrographolide (10 μM final concentration; Ref.365645-500MG, Aldrich)) as positive control, were dispensed on cell, 8 μl/well, and then incubated for 16 h at 37° C. and 5% $CO_2$. The day after Live Blazer reagent (Live Blazer FRET B/G (CCF4-AM), Ref.K1089, Invitrogen), was dispensed on cells (8 μl/well) and incubated for 2 h at room temperature in the dark.

Then, Fluorescence Resonance Energy Transfer (FRET) signal was measured using multimodal reader (Ex 409 nM/Em 460 nM and 530 nM; Envision, Perkin Elmer). Data were normalized between 1% DMSO (basal signal) and 10 μM andrographolide (positive signal) and analyzed using Activity Base software.

EXAMPLE 84: U2OS—TRANSLOCATION ASSAY

U2OS cell have been stably transduced using MMLV-derived retroviral vector, to overexpress Nrf2-Enzyme Donor fusion protein, and Acceptor Enzyme in the nucleus (PathHunter® U2OS Keap1-NRF2 Nuclear Translocation Cell Line, Ref.93-0821C3, DiscoverX).

PathHunter U2OS cells were grown in Minimum Essential Medium (MEM) (Ref.30-2003, ATCC), 10% FBS (Ref.P30-193306, PanBiotech), 500 μg/ml Geneticine, 250 μg/ml hygromycine, 0.25 μg/ml puromycine (10131-027, 10687-010 and Ref.A1113802 respectively, Life Technologies).

The night before experiment, cells were harvested using Tryple Xpress (Ref.126905, Bibco) for 5 min at 37° C., resuspended in Opti-MEM™ (Ref.31985-047, Gibco), 1% FBS (Ref.P30-193306, PanBiotech) and then plated into 384 wells plates (Ref.6007680, Perkin Elmer) at the density of 7 500 cells/well in 20 μl. Cell are stored over night at 37° C., 5% $CO_2$ until used. Compounds in 100% DMSO (0.315 μl/well) were resuspended in 20 μl MEM, 1% FBS, 3.4% DMSO. Compounds and andrographolide (10 μM final concentration; Ref.365645-500MG, Aldrich)) as positive control, were dispensed on cell, 5 µl /well, and then incubated for 3 h at 37° C. and 5% $CO_2$. After incubation, Path hunter reagents were dispensed on cells (12 µl /well, Ref.93-0001, DiscoverX) and incubated for 60 min at room temperature in the dark.

Then, luminescence signal was measured using multimodal reader (Pherastar, BMG Labtech). Data were normalized between 1% DMSO (basal signal) and 10 µM andrographolide (positive signal) and analyzed using Activity Base software.

| EXAMPLE | CELLULAR U2OS EC50 (nM) |
|---|---|
| 1a | 10.1 |
| 1b | 735 |
| 2 | 830 |
| 3a | 79.5 |
| 3b | 10.6 |
| 4 | 3470 |
| 5 | 1810 |
| 6 | 1330 |
| 7a | 23 |
| 7b | 290 |
| 8a | 986 |
| 8b | 516 |
| 9a | 48.2 |
| 9b | 845 |
| 10a | 58.1 |
| 10b | 369 |
| 11a | 109 |
| 11b | 13.1 |
| 12a | 3160 |
| 12b | >3160 |
| 13a | 232 |
| 13b | 26.7 |
| 14 | 582 |
| 15a | 57.9 |
| 15b | 381 |
| 16a | 871 |
| 16b | 108 |
| 17a | 1660 |
| 17b | 89 |
| 18a | 1140 |
| 18b | 91.3 |
| 19a | 73.6 |
| 19b | 2.76 |
| 20a | 1.99 |
| 20b | 131 |
| 21a | 10.9 |
| 21b | 166 |
| 22a | 17.2 |
| 22b | 111 |
| 23a | 3160 |
| 23b | 344 |
| 24a | 7.28 |
| 24b | 2.45 |
| 24c | 60 |
| 24d | 36.4 |
| 25a | 14 |
| 25b | 56.8 |
| 26a | 11.3 |
| 26b | 88.8 |
| 27a | 93.1 |
| 27b | 16.2 |
| 28a | 611 |
| 28b | 15.3 |
| 28c | >3160 |
| 28d | 879 |
| 29a | 440 |
| 29b | 68.4 |
| 30a | 555 |
| 30b | 2360 |
| 31a | 1430 |
| 31b | 27.4 |
| 31c | >3160 |
| 31d | 326 |

-continued

| EXAMPLE | CELLULAR U2OS EC50 (nM) |
|---|---|
| 32a | 20 |
| 32b | 150 |
| 33a | 94.5 |
| 33b | 894 |
| 34a | 2.66 |
| 34b | 31.1 |
| 35a | >3160 |
| 35b | >3160 |
| 36a | 126 |
| 36b | 1260 |
| 37a | 1300 |
| 37b | >3160 |
| 38a | 2080 |
| 38b | >3160 |
| 39a | 14.2 |
| 39b | 79.5 |
| 40a | 9.72 |
| 40b | 353 |
| 41a | 716 |
| 41b | >3160 |
| 42 | 21.4 |
| 43 | 570 |
| 44 | 292 |
| 45a | 11.8 |
| 45b | 144 |
| 46a | 228 |
| 46b | 792 |
| 47 | 288 |
| 48 | 198 |
| 49 | 1620 |
| 50 | 139 |
| 51 | 103 |
| 52 | 180 |
| 53a | 369 |
| 53b | 899 |
| 54a | 1290 |
| 54b | 2270 |
| 55a | 183 |
| 55b | 15.8 |
| 56 | 214 |
| 57a | 496 |
| 57b | 2820 |
| 58a | 90.4 |
| 58b | 427 |
| 59a | 311 |
| 59b | 1760 |
| 60a | 265 |
| 60b | >3160 |
| 61a | 717 |
| 61b | >3160 |
| 62a | 177 |
| 62b | >3160 |
| 63a | 57.1 |
| 63b | 1220 |
| 64a | 24 |
| 64b | 231 |
| 65 | 699 |
| 66a | 3.44 |
| 66b | 17.9 |
| 67a | 554 |
| 67b | >3160 |
| 68 | 38.3 |
| 69 | >3160 |
| 70a | 306 |
| 70b | >3160 |
| 71a | 42 |
| 71b | 570 |
| 72a | >3160 |
| 72b | >3160 |
| 73a | 63.4 |
| 73b | 707 |
| 74a | 6.11 |
| 74b | 756 |
| 75 | 59.6 |
| 76a | 7.5 |
| 76b | 26.2 |

-continued

| EXAMPLE | CELLULAR U2OS EC50 (nM) |
|---|---|
| 77a | 1750 |
| 77b | >3160 |
| 78a | 69 |
| 78b | 873 |
| 79a | 1120 |
| 79b | 296 |
| 80a | 596 |
| 80b | 2700 |
| 81a | 275 |
| 81b | >3160 |
| 82a | 635 |
| 82b | >3160 |

EXAMPLE 85: SURFACE PLASMON RESONANCE

Binding assay to Kelch domain of KEAP1 was performed by Surface Plasmon Resonance (SPR) on a Biacore T200 (GE Healthcare) at 25° C. using CM5 chip. His-Thromb-KEAP1(A321-C624) acquired from Novalix (batch PU-P01) was immobilized covalently by amine coupling using standard wizard protocol, at a concentration of 20 µg/mL in sodium acetate pH 5.5. The ligand was captured until 1250 RU was reached. Amine blank is used as the reference flow cell. Binding of analyte to the ligand was monitored in real time with associations of 180 seconds and a dissociation of 720 seconds. Association ($k_a$) and dissociation ($k_d$) rates were fitted with a simple 1:1 kinetic interaction model using Biacore T200 Evaluation Software (GE Healthcare). The equilibrium constant ($K_D=k_d/k_a$) was calculated from these fitted parameters. In the experiment, a half-log dilution of the compound was injected over KEAP1 in Single Cycle Kinetics (SCK) with 5 increasing concentrations of 0.316, 1, 3.16, 10 and 31.6 nM per cycle. The Biacore binding assay was performed with a flowrate of 50 µL/min using a running buffer of 10 mM HEPES (pH 7.4), 150 mM NaCl, 3 mM EDTA, 1 mM TCEP, 0.05% P20,5% DMSO. Double subtraction was used by subtracting both reference flow cell and previous blank cycle (with running buffer). Solvent correction was applied to correct DMSO bulk effect.

| EXAMPLE | Keap1 (A321-C624) (h) direct/SPR (KD) [M] |
|---|---|
| 1a | 1.8100E−10 |
| 1b | 3.9700E−09 |
| 2 | 3.5200E−08 |
| 3a | 7.6400E−09 |
| 3b | 1.0500E−09 |
| 4 | 2.5500E−07 |
| 5 | 1.3100E−07 |
| 6 | 3.3700E−08 |
| 7a | 1.0700E−09 |
| 7b | 4.8600E−09 |
| 8a | 6.2200E−08 |
| 8b | 1.2400E−08 |
| 9a | 2.1200E−09 |
| 9b | 9.9900E−09 |
| 10a | 3.5400E−09 |
| 10b | 1.5100E−08 |
| 11a | 2.4200E−09 |
| 11b | 7.7800E−10 |
| 12a | 3.0700E−06 |
| 12b | 2.9200E−06 |
| 13a | 1.6200E−08 |

-continued

| EXAMPLE | Keap1 (A321-C624) (h) direct/SPR (KD) [M] |
|---|---|
| 13b | 4.1500E−09 |
| 14 | 1.4200E−08 |
| 15a | 1.9200E−09 |
| 15b | 4.4100E−09 |
| 16a | 4.0300E−09 |
| 16b | 1.7300E−09 |
| 17a | 2.5700E−08 |
| 17b | 5.5500E−09 |
| 18a | 3.6700E−09 |
| 18b | 1.0100E−09 |
| 19a | 1.3400E−09 |
| 19b | 6.4600E−10 |
| 20a | 5.4900E−10 |
| 20b | 2.3000E−09 |
| 21a | 2.5500E−09 |
| 21b | 2.0800E−08 |
| 22a | 6.3100E−10 |
| 22b | 2.1100E−09 |
| 23a | 5.0500E−08 |
| 23b | 8.8000E−09 |
| 24a | 1.1000E−09 |
| 24b | 1.2300E−09 |
| 24c | 5.0000E−09 |
| 24d | 4.3200E−09 |
| 25a | 5.6200E−10 |
| 25b | 1.1600E−09 |
| 26a | 3.4000E−09 |
| 26b | 1.2200E−08 |
| 27a | 1.4200E−08 |
| 27b | 3.5600E−09 |
| 28a | 2.3400E−08 |
| 28b | 3.2500E−09 |
| 32a | 6.4500E−10 |
| 32b | 2.0200E−09 |
| 33a | 4.5500E−09 |
| 33b | 9.2900E−09 |
| 34a | 4.9000E−10 |
| 34b | 1.8500E−09 |
| 35a | 3.3600E−05 |
| 35b | 7.4500E−06 |
| 36a | 9.0200E−09 |
| 36b | 3.2500E−08 |
| 37a | 7.5100E−08 |
| 37b | 5.2900E−07 |
| 38b | 6.0400E−07 |
| 39a | 1.3700E−10 |
| 39b | 6.8500E−10 |
| 40a | 5.5100E−09 |
| 40b | 2.2300E−08 |
| 42 | 1.5700E−09 |
| 43 | 2.9200E−09 |
| 44 | 1.4600E−10 |
| 45a | 5.9400E−10 |
| 45b | 2.3500E−09 |
| 50 | 5.9700E−09 |
| 51 | 2.0300E−09 |
| 52 | 8.8600E−09 |
| 53a | 4.7700E−08 |
| 53b | 1.7600E−07 |
| 54a | 9.0500E−08 |
| 54b | 3.9100E−07 |
| 55a | 2.0000E−09 |
| 55b | 2.5000E−09 |
| 56 | 1.2600E−08 |
| 57a | 5.8900E−08 |
| 57b | 4.9800E−07 |
| 58a | 4.6600E−09 |
| 58b | 1.2500E−08 |
| 59a | 5.0700E−09 |
| 62a | 3.0000E−09 |
| 63a | 4.3900E−09 |
| 64a | 1.9500E−10 |
| 66a | 6.7800E−10 |
| 66b | 8.3300E−10 |
| 68 | 8.9600E−09 |
| 71a | 1.9300E−08 |

-continued

| EXAMPLE | Keap1 (A321-C624) (h) direct/SPR (KD) [M] |
|---|---|
| 72a | 2.3600E−08 |
| 72b | 7.3000E−07 |
| 73a | 6.2300E−09 |
| 73b | 1.7600E−08 |

EXAMPLE 86: TARGET ENGAGEMENT STUDY

Target engagement was assessed in fed db/db mice (8 week-old, Janvier Labs). Compounds were orally administered at the doses of 30 and/or 100 mg/kg (10 mL/kg in HEC 1%) or vehicle. After mouse anesthesia, blood and liver samples were taken 4, 6 and 24 hours after administration. Compound concentration was determined both in plasma and liver at each time point. Activation of NRF2 by compounds was measured by the increase of Nqo1 gene expression in liver of treated mice versus controlled mice.

EXAMPLE 87: ORAL GLUCOSE TOLERANCE TEST STUDY (OGTT)

The efficacy of compounds on glucose tolerance was assessed in ob/ob mice (10-wk, Janvier Labs). Compounds were administered at 30 and/or 100 mg/kg (10 mL/kg in HEC 1%) for 10 days. Immediately after the last administration, mice were fasted for 4 hours. An oral glucose tolerance test was then performed with the measurement of blood glucose and plasma insulin levels before and at different time points after glucose administration (1.5 g/kg, 10 mL/kg in water). Mice were then provided with food ad libitum. On the day after OGTT, mice were sacrificed and the liver taken. Target engagement was then confirmed by measuring the increase of Ngo1 gene expression in the liver of compound-treated mice versus controlled mice.

EXAMPLE 88: EFFICACY STUDY IN NASH USING MCD MODEL

The efficacy of compounds in NASH was addressed using the murine model of NASH induced by Methionine and Choline Deficient (MCD) diet. Treatment with compound and NASH induction by the diet started concomitantly. Mice were placed under MCD diet and treatment with compounds started immediately for 14 days. Mice were weighed and orally administered with compounds (10 mL/kg in HEC 1%). After 14 days of treatment and diet, 4 hr-fasted mice were euthanized. Blood samples were obtained for hepatic enzyme determination (Alanine aminotransferase (ALT) and Aspartate aminotransferase (AST)). Liver were taken for NASH analysis and target engagement measurement. Hepatic triglyceride content was quantified. NASH was determined by the measurement of steatosis, inflammation and by the quantification of the NAFLD Activity Score (NAS). Target engagement was then confirmed by measuring the increase of Ngo1 gene expression in the liver of compound-treated mice versus controlled mice.

EXAMPLE 89: EFFICACY STUDY IN ADPKD

In order to assess the efficacy of Nrf2 activators, we use conditional and inducible Pkd1 gene deficient mice as initially described (Lantinga-van Leeuwen et al, Hum Mol Genet. 2007, 16(24), 3188-96). Upon tamoxifen injection to 10 d-old mice (p10), Pkd1 gene is specifically deleted in renal epithelium. This leads to quick progression of cyst formation in the distal segment of the nephron. Mice then receive either tested molecule (3 to 30 mg/kg/d) or vehicle (HydroxyEthylCellulose 1%) for 2 to 3 weeks by gavage. At the end of the treatment, all the mice are sacrificed and both plasma and kidneys are collected. Plasma samples are used to monitor drug exposure at the end of the study. Efficacy is determined by quantifying the impact of the treatment on kidney size, kidney weight, kidney weight to body weight ratio, cystic index (determined by histological analysis) and urea volume as a proxy of kidney function as previously described (Lu et al., Sci. Transl. Med. 12, eaba3613 (2020) 29 Jul. 2020 "Activation of NRF2 ameliorates oxidative stress and cystogenesis in autosomal dominant polycystic kidney disease"). Nrf2 target engagement can be monitored either by measuring Nrf2 target gene activation such as Nqo1 or by directly quantifying Reactive Oxygen Species (ROS) in the kidney using standard assay kits.

EXAMPLE 90: PHARMACEUTICAL COMPOSITION

Formulation for the preparation of 1000 tablets each containing 10 mg:

| | |
|---|---|
| Compound of one of Examples 1 to 82 | 10 g |
| Hydroxypropylcellulose | 2 g |
| Wheat starch | 10 g |
| Lactose | 100 g |
| Magnesium stearate | 3 g |
| Talc | 3 g |

The invention claimed is:

1. A compound of formula ($IA_1$):

($IA_1$)

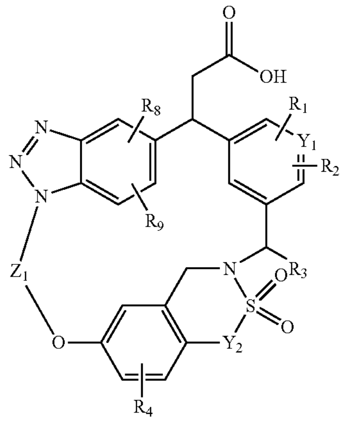

wherein $Z_1$ is —$(CH_2)_{n1}$—$(CH_2)_{n1}$—O— $(CH_2)_{n2}$— $(CH_2)_{n1}$—S— $(CH_2)_{n2}$,—$(CH_2)_{n1}$—NR—$(CH_2)_{n2}$—$(CH_2)_{n1}$—CHR'—$(CH_2)_{n2}$,—$(CH_2)_{n1}$—$Ar_1$—$(CH_2)_{n2}$—$(CH_2)_{n1}$—$Ar_1$—O— $(CH_2)_{n2}$— $(CH_2)_{n1}$—$Ar_1$—S—$(CH_2)_{n2}$, —$(CH_2)_{n1}$—$Ar_1$—CHR'—$(CH_2)_{n2}$,—$Ar_1$—NR—$(CH_2)_{n1}$, or $Z_1$ is

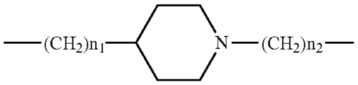

or

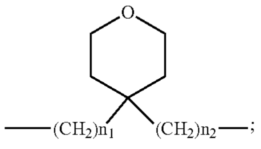

$Y_1$ is C;

$Y_2$ is O or NR';

$Ar_1$ is optionally substituted aryl or optionally substituted heteroaryl;

R is hydrogen, linear or branched $C_1$-$C_3$ alkyl or optionally substituted aryl;

R' is hydrogen, hydroxyl, optionally substituted aryl or linear or branched $C_1$-$C_3$ alkyl optionally substituted by alkoxy or by one to three halogen atoms;

$n_1$ and $n_2$ each independently represent an integer from 1 to 6;

$R_1$, $R_2$, $R_4$, $R_8$, $R_9$, which may be identical or different, each represent hydrogen, halo, cyano, linear or branched $C_1$-$C_3$ alkyl optionally substituted by one to three halogen atoms, linear or branched $C_1$-$C_3$ alkoxy or optionally substituted aryl;

$R_3$ is hydrogen or linear or branched $C_1$-$C_3$ alkyl optionally substituted by one to three halogen atoms;

or $R_2$ and $R_3$, together with the atoms bearing them, form a ring;

its optical isomers, or addition salts thereof with a pharmaceutically acceptable base.

2. The compound according to claim 1, wherein $Z_1$ is $-(CH_2)_{n1}$, $-(CH_2)_{n1}-O-(CH_2)_{n2}$ or $-(CH_2)_{n1}-S-(CH_2)_{n2}$.

3. The compound according to claim 1, wherein $Y_2$ is O or $NCH_3$.

4. The compound according to claim 1, which is selected from the group consisting of:

[4,32-dimethyl-28,28-dioxo-22,27-dioxa-28λ$^6$-thia-1,14, 15, 16-tetraazahexacyclo [21.5.3.1$^{3,7}$.1$^{9,13}$.0$^{12,16}$. 0$^{26,30}$]tritriaconta-3 (33),4,6,9 (32), 10,12, 14,23,25, 30-decaen-8-yl]acetic acid, its optical isomers, and addition salts thereof with a pharmaceutically acceptable base;

[2,4,31-trimethyl-27,27-dioxo-21,26-dioxa-27λ$^6$-thia-1, 14,15, 16-tetraazahexacyclo [20.5.3.1$^{3,7}$. 1$^{9,13}$.0$^{12,16}$. 0$^{25,29}$]dotriaconta-3 (32),4,6,9 (31), 10,12,14,22,24,29-decaen-8-yl]acetic acid, its optical isomers, and addition salts thereof with a pharmaceutically acceptable base;

[4,31-dimethyl-27,27-dioxo-21,26-dioxa-27λ$^6$-thia-1,14, 15, 16-tetraazahexacyclo [20.5.3.1$^{3,7}$. 1$^{9,13}$.0$^{12,16}$. 0$^{25,29}$]dotriaconta-3 (32),4,6,9 (31), 10,12, 14,22,24, 29-decaen-8-yl]acetic acid, its optical isomers, and addition salts thereof with a pharmaceutically acceptable base;

[4-chloro-31-methyl-27,27-dioxo-21,26-dioxa-27λ$^6$-thia-1,14,15,16-tetraazahexacyclo [20.5.3.1$^{3,7}$. 1$^{9,13}$.0$^{12,16}$. 0$^{25,29}$]dotriaconta-3 (32),4,6,9 (31), 10, 12,14,22,24, 29-decaen-8-yl]acetic acid, its optical isomers, and addition salts thereof with a pharmaceutically acceptable base;

[4-methoxy-31-methyl-27,27-dioxo-21,26-dioxa-27λ$^6$-thia-1,14, 15,16-tetraazahexacyclo [20.5.3.1$^{3,7}$. 1$^{9,13}$.0$^{12,16}$. 0$^{25,29}$]dotriaconta-3 (32) ,4,6,9 (31) , 10, 12,14,22,24,29-decaen-8-yl]acetic acid, its optical isomers, and addition salts thereof with a pharmaceutically acceptable base;

[4,33-dimethyl-29,29-dioxo-23,28-dioxa-29λ$^6$-thia-1,14, 15, 16-tetraazahexacyclo [22.5.3.1$^{3,7}$. 1$^{9,13}$ 0$^{12,16}$. 0$^{27,31}$]tetratriaconta-3 (34),4,6,9 (33),10,12,14,24,26, 31-decaen-8-yl]acetic acid, its optical isomers, and addition salts thereof with a pharmaceutically acceptable base;

[2,4,32-trimethyl-28,28-dioxo-19,22,27-trioxa-28λ$^6$-thia-1,14, 15, 16-tetraazahexacyclo [21.5.3.1$^{3,7}$. 1$^{9,13}$. 0$^{12,16}$.0$^{26,30}$]tritriaconta-3 (33),4,6,9 (32), 10,12, 14,23, 25,30-decaen-8-yl]acetic acid, its optical isomers, and addition salts thereof with a pharmaceutically acceptable base;

[2,4,33-trimethyl-29,29-dioxo-23,28-dioxa-29λ$^6$-thia-1, 14,15,16-tetraazahexacyclo [22.5.3.1$^{3,7}$.1$^{9,13}$. 0$^{12,16}$.0$^{27,31}$]tetratriaconta-3 (34),4,6,9 (33),10,12,14, 24,26,31-decaen-8-yl]acetic acid, its optical isomers, and addition salts thereof with a pharmaceutically acceptable base;

[23-chloro-4,31-dimethyl-27,27-dioxo-21,λ$^6$-dioxa-27) 6-thia-1,14, 15,16-tetraazahexacyclo [20.5.3.1$^{3,7}$. 1$^{9,13}$.0$^{12,16}$.0$^{25,29}$]dotriaconta-3 (32),4,6,9 (31),10,12, 14,22,24,29-decaen-8-yl]acetic acid, its optical isomers, and addition salts thereof with a pharmaceutically acceptable base;

[23-methoxy-4,31-dimethyl-27,27-dioxo-21,λ$^6$-dioxa-27λ$^6$-thia-1,14,15,16-tetraazahexacyclo [20.5.3.1$^{3,7}$. 1$^{9,13}$.0$^{12,16}$.0$^{25,29}$]dotriaconta-3 (32),4,6,9 (31), 10,12, 14,22,24,29-decaen-8-yl]acetic acid, its optical isomers, and addition salts thereof with a pharmaceutically acceptable base;

[23-fluoro-4,31-dimethyl-27,27-dioxo-21,λ$^6$-dioxa-27λ$^6$-thia-1,14,15,16-tetraazahexacyclo [20.5.3.1$^{3,7}$. 1$^{9,13}$0.$^{12,16}$.0$^{25,29}$]dotriaconta-3 (32),4,6,9 (31), 10,12, 14,22,24,29-decaen-8-yl]acetic acid, its optical isomers, and addition salts thereof with a pharmaceutically acceptable base;

[4,26,31-trimethyl-27,27-dioxo-21-oxa-27) 6-thia-1,14, 15, 16,λ$^6$-pentaazahexacyclo [20.5.3.1$^{3,7}$. 1$^{9,13}$. 0$^{12,16}$.0$^{25,29}$]dotriaconta-3 (32) ,4,6,9 (31) , 10,12,14, 22,24,29-decaen-8-yl]acetic acid, its optical isomers, and addition salts thereof with a pharmaceutically acceptable base;

[4,32-dimethyl-28,28-dioxo-22,27-dioxa-19,28λ$^6$-dithia-1,14,15, 16-tetraazahexacyclo [21.5.3.1$^{3,7}$. 1$^{9,13}$. 0$^{12,16}$.0$^{26,30}$]tritriaconta-3 (33),4,6,9 (32), 10,12, 14,23, 25,30-decaen-8-yl]acetic acid, its optical isomers, and addition salts thereof with a pharmaceutically acceptable base;

[30-chloro-4,31-dimethyl-27,27-dioxo-21,λ$^6$-dioxa-27λ$^6$-thia-1,14, 15,16-tetraazahexacyclo [20.5.3.1$^{3,7}$. 1$^{9,13}$.0$^{12,16}$.0$^{25,29}$]dotriaconta-3 (32) ,4,6,9 (31) ,10,12, 14,22,24,29-decaen-8-yl]acetic acid, its optical isomers, and addition salts thereof with a pharmaceutically acceptable base;

[4,32-dimethyl-28,28-dioxo-19,22,27-trioxa-28λ$^6$-thia-1, 14,15, 16-tetraazahexacyclo [21.5.3.1$^{3,7}$. 1$^{9,13}$. 0$^{12,16}$.0$^{26,30}$]tritriaconta-3 (33),4,6,9 (32), 10,12,14,23, 25,30-decaen-8-yl]acetic acid, its optical isomers, and addition salts thereof with a pharmaceutically acceptable base.

5. A pharmaceutical composition comprising the compound according to claim 1, in combination with one or more inert, non-toxic, pharmaceutically acceptable excipients or carriers.

* * * * *